US008461176B2

(12) United States Patent
Soll et al.

(10) Patent No.: US 8,461,176 B2
(45) Date of Patent: *Jun. 11, 2013

(54) ENANTIOMERICALLY ENRICHED ARYLOAZOL-2-YL CYANOETHYLAMINO COMPOUNDS, METHOD OF MAKING AND METHOD OF USING THEREOF

(75) Inventors: Mark David Soll, Alpharetta, GA (US); Loic Patrick Le Hir de Fallois, Chapel Hill, NC (US); Scot Kevin Huber, Raleigh, NC (US); Hyoung Ik Lee, Cary, NC (US); Douglas Edward Wilkinson, Wake Forest, NC (US); Robert Toms Jacobs, Wake Forest, NC (US); Brent Christopher Beck, Apex, NC (US)

(73) Assignee: Merial Limited, Duluth, GA (US)

( * ) Notice: Subject to any disclaimer, the term of this patent is extended or adjusted under 35 U.S.C. 154(b) by 513 days.

This patent is subject to a terminal disclaimer.

(21) Appl. No.: 12/618,308

(22) Filed: Nov. 13, 2009

(65) Prior Publication Data

US 2010/0125089 A1    May 20, 2010

Related U.S. Application Data

(60) Provisional application No. 61/114,665, filed on Nov. 14, 2008, provisional application No. 61/114,656, filed on Nov. 14, 2008, provisional application No. 61/176,136, filed on May 7, 2009.

(51) Int. Cl.
*C07D 513/02* (2006.01)
*C07D 515/02* (2006.01)
*A61K 31/44* (2006.01)

(52) U.S. Cl.
USPC ............ 514/300; 514/303; 546/117; 546/119

(58) Field of Classification Search
USPC .......................... 514/303, 300; 546/119, 117
See application file for complete search history.

(56) References Cited

U.S. PATENT DOCUMENTS

| | | | | |
|---|---|---|---|---|
| 4,683,324 | A | 7/1987 | Gastrock et al. | 558/354 |
| 6,289,077 | B1 | 5/2001 | Ducray et al. | 504/312 |
| 6,346,649 | B1 | 2/2002 | Kremer | 562/585 |
| 7,052,707 | B2 | 5/2006 | Ducray et al. | 424/405 |
| 7,183,443 | B2 | 2/2007 | Dassen et al. | 568/467 |
| 7,446,219 | B2 | 11/2008 | Ducray et al. | 558/391 |
| 8,088,801 | B2 * | 1/2012 | Soll et al. | 514/359 |
| 2005/0033081 | A1 | 2/2005 | Ducray et al. | 558/392 |
| 2005/0059736 | A1 | 3/2005 | Ducray et al. | 514/521 |
| 2005/0203148 | A1 | 9/2005 | Ducray et al. | 514/342 |
| 2005/0203178 | A1 | 9/2005 | Ducray et al. | 514/521 |
| 2005/0272935 | A1 | 12/2005 | Ducray et al. | 548/257 |
| 2006/0025466 | A1 | 2/2006 | Ducray et al. | 514/406 |
| 2008/0261999 | A1 | 10/2008 | Martin et al. | 514/256 |

FOREIGN PATENT DOCUMENTS

| | | |
|---|---|---|
| EP | 0953565 A2 | 11/1999 |
| EP | 1445251 A1 | 8/2004 |
| EP | 1445251 A9 | 8/2004 |
| WO | WO 02/49641 A2 | 6/2002 |
| WO | WO 02/50052 A1 | 6/2002 |
| WO | WO 02/060257 A1 | 8/2002 |
| WO | WO 02/092552 A2 | 11/2002 |
| WO | WO 02/102155 A1 | 12/2002 |
| WO | WO 03/031393 A2 | 4/2003 |
| WO | WO 03/031394 A1 | 4/2003 |
| WO | WO 03/042184 A1 | 5/2003 |
| WO | WO 03/048112 A1 | 6/2003 |
| WO | WO 03/059868 A1 | 7/2003 |

(Continued)

OTHER PUBLICATIONS

"Efficacy of the Amino-acetonitrile Derivative, Monepantel, Against Experimental and Natural Adult Stage Gastro-Intestinal Nematode Infections in Sheep," Sager et al, Veterinary Parasitology, 2009, 159, 49-54. Published Jan. 22, 2009.

(Continued)

*Primary Examiner* — Niloofar Rahmani
(74) *Attorney, Agent, or Firm* — Judy Jarecki-Black; John Ezcurra; Merial Limited

(57) ABSTRACT

The present invention relates to novel aryloazol-2-yl-cyanoethylamino derivatives substantially enriched in an enantiomer of formula (I):

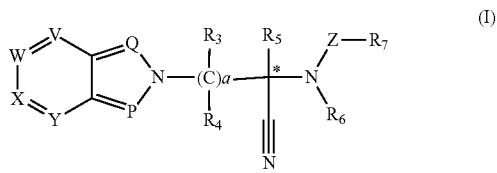

and compounds of formula (IH)

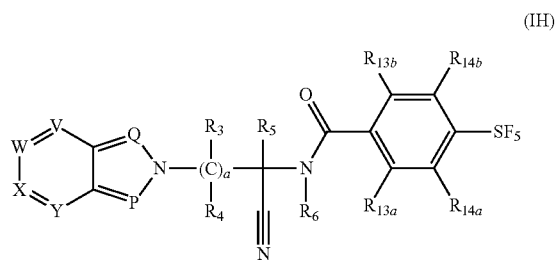

wherein $R_3$, $R_4$, $R_5$, $R_6$, $R_7$, $R_{13a}$, $R_{13b}$, $R_{14a}$, $R_{14b}$, P, Q, V, W, X, Y, Z and a are as defined in the description, compositions thereof, processes for their preparation and their uses as pesticides.

30 Claims, 2 Drawing Sheets

FOREIGN PATENT DOCUMENTS

| | | |
|---|---|---|
| WO | WO 03/080577 A2 | 10/2003 |
| WO | WO 03/097036 A1 | 11/2003 |
| WO | WO 03/097585 A2 | 11/2003 |
| WO | WO 03/104187 A1 | 12/2003 |
| WO | WO 03/104202 A1 | 12/2003 |
| WO | WO2004/000793 A2 | 12/2003 |
| WO | WO2004/000798 A1 | 12/2003 |
| WO | WO2004/024704 A1 | 3/2004 |
| WO | WO2005/016892 | 2/2005 |
| WO | WO2005/044784 A1 | 5/2005 |
| WO | WO2005/058802 A1 | 6/2005 |
| WO | WO2005/121075 A1 | 12/2005 |
| WO | WO2006/043654 A1 | 4/2006 |
| WO | WO2006/050887 A1 | 5/2006 |
| WO | WO2007/017088 A1 | 2/2007 |
| WO | WO2008/062005 A1 | 5/2008 |
| WO | WO2008/064891 A1 | 6/2008 |
| WO | WO2008/096231 A1 | 8/2008 |
| WO | WO2008/096232 A1 | 8/2008 |
| WO | WO2008/144275 A1 | 11/2008 |

OTHER PUBLICATIONS

"Pharmacokinetics of Monepantel and Its Sulfone Metabolite, Monepantel Sulfone, After Intravenous and Oral Administration in Sheep," D. Karadzovska et al., J. Vet Pharmacol. Therap., 2009, 32, 359-367. Published on-line May 6, 2009.

"A New Class of Anthelmintics Effective Against drug-Resistant Nematodes," R. Kaminsky et al., Nature, 2008, 452 (13), 176-181.

"Identification of the Amino-Acetonitrile Derivative Monepantel (AAD 1566) As a New Anthelmintic Drug Development Candidate," R. Kaminsky et al., Parasitol Res., 2008, 103,931.

"Dose Determination Studies for Monepantel, an Amino-Acetonitrile Derivative, Against Fourth Stage Gastro-Intestinal Nematode Larvae Infecting Sheep," B.C. Hosking et al., Veterinary Parasitology, 2008, 157, 72-80.

"Discovery of Amino-Acetonitrile Derivatives, a New Class of Synthetic Anthelmintic Compounds," P. Ducray et al., Bioorganic & Medicinal Chemistry Letters, 2008, 18, 2935-2938.

"Synthesis of the dopamine agonist (−)-Quinpirole", J. M. Schaus et al., *Synthetic Communication.*, 1990, 20, 3553-3562.

"A Novel and Efficient Synthesis of 2-Aryl-2H-indazoles via SnCl2-Mediated Cyclization of 2-Nitrobenzylamines", Synthesis of 2-Aryl-2H-indazoles Da-Qing Shi et al., *Synlett*, 2007, 16, 2509-25120.

"Efficient and Regioselective Synthesis of 2-Alkyl-2H-indazoles", M. Cheung et al., *J. Org. Chem.*, 2003, 68, 4093-4095.

"Claimed 2,1-Benzisoxazoles Are Indazalones", M. J. Kurth et al., *J. Org. Chem.*, 2005, 70, 1060-1062.

"N,N-Bond-Forming Heterocyclization: Synthesis of 3-Alkoxy-2H-indazoles", A. D. Mills et al., *J. Org. Chem.*, 2006, 71, 2687-2689.

"Regioselective Protection at N-2 and Derivatization at C-3 of Indazoles", Guanglin Luo et al., *J. Org. Chem.*, 2006, 71, 5392-5395.

"A Concise Synthesis of (S)-N-Ethoxycarbonyl-α-methylvaline", J. T. Kuethe et al., *J. Org. Chem.*, 2007, 72, 7469-7472.

"Indazoles: Regioselective Protection and Subsequent Amine Coupling Reactions", D. J. Slade et al., *J. Org. Chem.*, 2009, 74, 6331-6334 Published on-line Jul. 21, 2009.

"Synthesis of a Library of 2-Alkyl-3-alkyloxy-2H-indazole-6-carboxamides", A. D. Mills et al., *J. Comb. Chem.*, 2007, 9, 171-177.

"Preparation of Polyfunctional Indazoles and Heteroarylazo Compounds Using Highly Functionalized Zinc Reagents", B. Haag et al., *Org. Lett.*, 2009, 11, 4270-4273 Published on-line Aug. 31, 2009.

"Synthesis and activity of 1H-benzimidazole and 1H-benzotriazole derivatives as inhibitors of *Acanthamoeba castellanii*", K. Kopaska et al., *Bioorganic & Medicinal Chemistry*, 2004, 12, 2617-2624.

"Indazole N-oxide derivatives as antiprotozoal agents: Synthesis, biological evaluation and mechanism of action studies", A. Gerpe et al., *Bioorganic & Medicinal Chemistry*, 2006, 14, 3467-3480.

"Inhibition of Neuronal Nitric Oxide Synthase by 7-Methoxyindazole and Related Substituted Indazoles", P. Schumann et al., *Bioorganic & Medicinal Chemistry Letters*, 2001, 11, 1153-1156.

"4-Substituted indazoles as new inhibitors of neuronal nitric oxide synthase", M. Boulouard et al., *Bioorganic & Medicinal Chemistry Letters*, 2007, 17, 3177-3180.

"2-Substituted Indazoles From Electrogenerated Orho-nitrosobenzylamines", B. A. Frontana-Uribe et al., *Tetrahedron*, 1998, 54, 3197-3206.

"A Mild Method for the Conversion of Activated Aryl Methyl group to Carboxaldehydes via the Catalyzed Periodate Cleavage of Enamines", M. G.Vetelino et al., *Tetrahedron Letters*, 1994, 35, 219-222.

"Preparation of various enantiomerically pure (benzotriazol-1-yl)- and (benzotriazol-2-yl)-alkan-2-ols", B. K. Pchelka et al., *Tetrahedron: Asymmetry*, 2006, 17, 2516-2530.

"Discovery of 2-{4-[(3S)-Piperidin-3-yl]phenyl}-2H-indazole-7-carboxamide (MK-4827): A Novel Oral Poly(ADP-ribose)polymerase (PARP) Inhibitor Efficacious in BRCA-1 and -2 Mutant Tumors", P. Jones et al., *J. Med. Chem.*, 2009, 52, 7170-7185.

\* cited by examiner

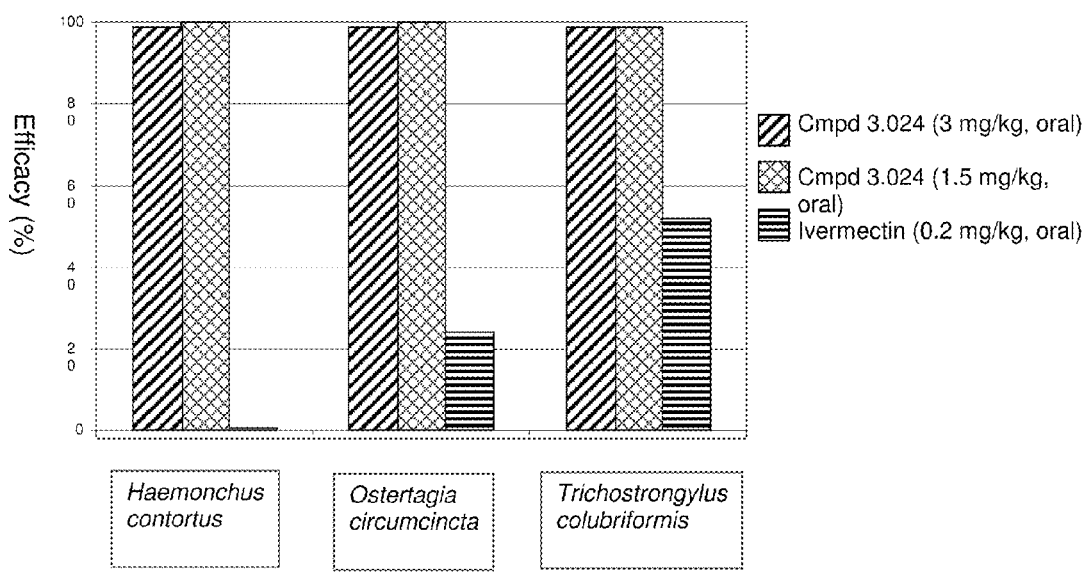
Figure 1: Efficacy Against Ivermectin-Resistant Parasites

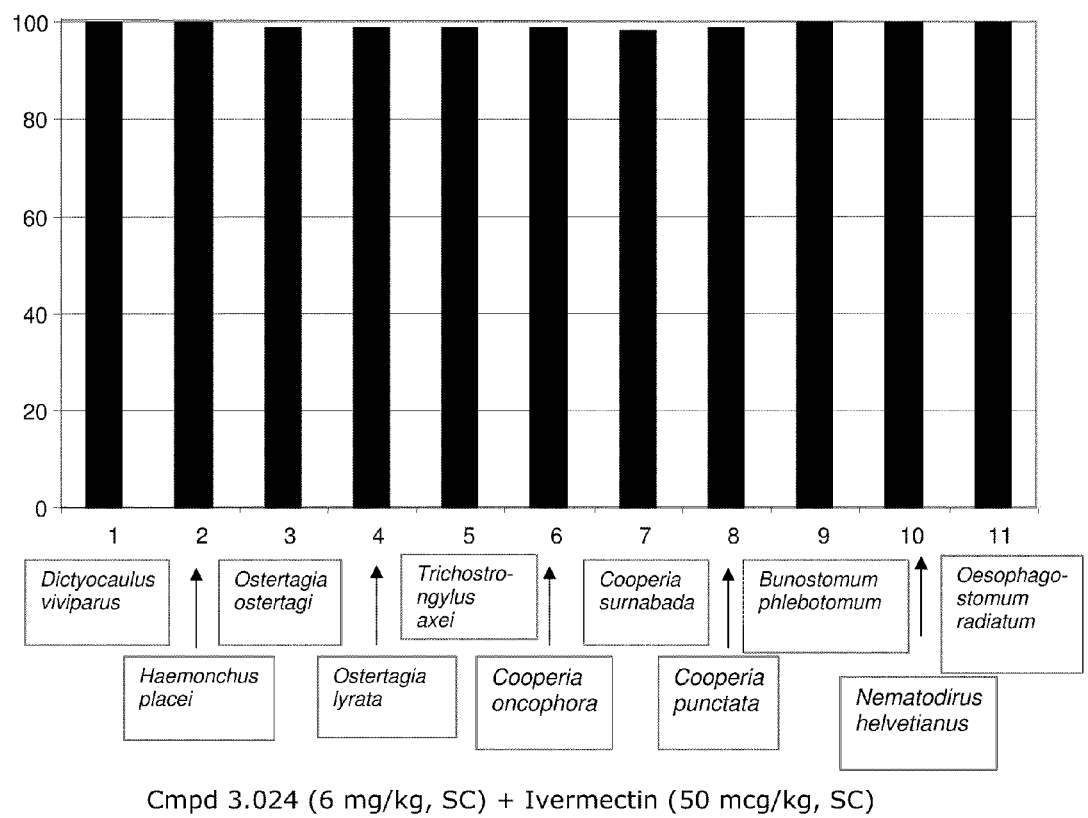
Figure 2: Efficacy of a Combination of aryloazol-2-yl-cyanoethylamino with Ivermectin
Cmpd 3.024 (6 mg/kg, SC) + Ivermectin (50 mcg/kg, SC)

ENANTIOMERICALLY ENRICHED ARYLOAZOL-2-YL CYANOETHYLAMINO COMPOUNDS, METHOD OF MAKING AND METHOD OF USING THEREOF

CROSS REFERENCE TO RELATED APPLICATIONS

This application claims the benefit of priority to U.S. Provisional Patent Application Nos. 61/114,665 and 61/114,656, both filed on Nov. 14, 2008; and 61/176,136, filed on May 7, 2009, the disclosures of which are incorporated herein by reference in their entirety.

INCORPORATION BY REFERENCE

Reference is made to U.S. patent application Ser. No. 12/119,150 filed May 12, 2008, which was published as US 2008/0312272 on Dec. 18, 2008, and claims priority to U.S. provisional patent application Ser. No. 60/930,485 filed May 15, 2007.

The foregoing applications and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to novel paraciticidal aryloazol-2-yl-cyanoethylamino derivatives of formula (I) having a stereocenter present at the carbon bearing the cyano group and $R_5$ identified by an asterisk symbol:

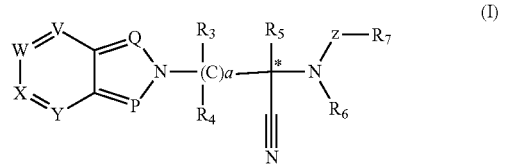

wherein, $R_3$, $R_4$, $R_5$, $R_6$, $R_7$, P, Q, V, W, X, Y, Z, and a are as defined in the description, compositions thereof, processes for their preparation and their uses as pesticides.

BACKGROUND OF THE INVENTION

International Patent Publications WO 2002/049641, WO 2003/097036, WO 2003/097585, WO 2003/104187, WO 2004/000793, WO 2005/05802, WO 2005/121075, WO 2004/024704 (U.S. Pat. No. 7,084,280), WO 2005/044784, WO 2005/121075 and WO 2006/043654 as well as EP 953565 (U.S. Pat. No. 6,239,077) and EP 1445251 are generally concerned with the control of parasites, particularly endoparasites, by means of active agents which may have a cyanoethylamino group.

However none of the foregoing publications describe compounds of formula (I), or enantiomers thereof, that possess activity as pesticides, particularly for controlling endoparasites or ectoparasites in or on animals.

Citation or identification of any document in this application is not an admission that such document is available as prior art to the present invention.

SUMMARY OF THE INVENTION

The present invention is based, in part, on unexpected results that a compound enriched with one enantiomer of the novel aryloazol-2-yl-cyanoethylamino derivatives of formula (I) displays significant in vitro and in vivo activity (the eutomer) with a favorable toxicity profile whereas a compound enriched with the other corresponding enantiomer displays significantly far less in vitro and in vivo activity (the distomer).

This invention provides novel arylo-azol-2-yl-cyanoethylamino derivatives of formula (I) which are substantially enriched in an enantiomer:

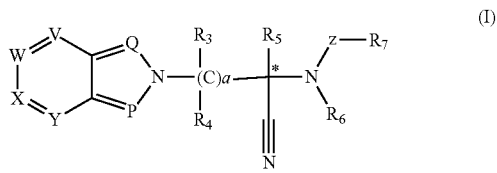

P is C—$R_1$ or N;
Q is C—$R_2$ or N;
V is C—$R_8$ or N;
W is C—$R_9$ or N;
X is C—$R_{10}$ or N;
Y is C—$R_{11}$ or N;
$R_1$, $R_2$, $R_8$, $R_9$, $R_{10}$ and $R_{11}$ are independently of one another hydrogen, amino, amido, cyano, nitro, halogen, alkyl, alkenyl, alkynyl, cycloalkyl, hydroxyalkyl, haloalkyl, alkylthio, haloalkylthio, arylthio, alkoxy, phenoxy, alkoxyalkoxy, cycloalkyloxy, haloalkoxy, alkylcarbonyl, haloalkylcarbonyl, alkoxycarbonyl, haloalkoxycarbonyl, alkylsulfinyl, haloalkylsulfinyl, $SF_5$, alkylsulfonyl, haloalkylsulfonyl, alkylamino, di(alkyl)amino, alkylcarbonylamino, alkylaminoalkoxy, dialkylaminoalkoxy, alkylaminoalkyl, dialkylaminoalkyl, aminoalkyl, formyl, —C(O)OH, unsubstituted or substituted aryl, unsubstituted or substituted arylthio, unsubstituted or substituted aryloxy, or unsubstituted or substituted heteroaryl, wherein the substituents, independent of one another, may be one or more of cyano, nitro, halogen, alkyl, haloalkyl, alkylthio, haloalkylthio, arylthio, alkoxy, haloalkoxy, alkylcarbonyl, haloalkylcarbonyl, alkoxycarbonyl, haloalkoxycarbonyl, alkylsulfinyl, haloalkylsulfinyl, alkylsulfonyl, haloalkylsulfonyl, $SF_5$ or methylthioamino;

$R_3$, $R_4$ and $R_5$ are independently of one another hydrogen, halogen, alkyl, hydroxyalkyl, alkylthioalkyl, haloalkyl, alkyloxyalkyl, alkylsulfinylalkyl, alkylsulfonylalkyl, alkylsulfonyloxyalkyl; unsubstituted or substituted cycloalkyl, wherein the substituents may each be independently halogen and alkyl; unsubstituted or substituted aryl, unsubstituted or substituted heteroaryl, wherein the substituents may each be independent of one another cyano, nitro, halogen, alkyl, haloalkyl, alkylthio, haloalkylthio, arylthio, alkoxy, haloalkoxy, alkylcarbonyl, haloalkylcarbonyl, alkoxycarbonyl, haloalkoxycarbonyl, alkylsulfinyl, haloalkylsulfinyl, alkylsulfonyl, haloalkylsulfonyl, $SF_5$, alkylamino, or di(alkyl)amino; or R$_4$ and R$_5$ together with the carbon to which they are attached form a cycloalkyl ring;

R$_6$ is hydrogen, alkyl, alkoxyalkyl, alkylcarbonyl, haloalkylcarbonyl, alkoxycarbonyl, haloalkoxycarbonyl, alkylthiocarbonyl or unsubstituted or substituted benzyl, wherein the substituents may each be independent of one another cyano, nitro, halogen, alkyl, haloalkyl, alkylthio, haloalkylthio, arylthio, alkoxy, haloalkoxy, alkylcarbonyl, haloalkylcarbonyl, alkoxycarbonyl, haloalkoxycarbonyl, alkylsulfinyl, haloalkylsulfinyl, alkylsulfonyl, haloalkylsulfonyl, SF$_5$, alkylamino, or di(alkyl)amino;

R$_7$ is hydrogen, alkyl, cylcoalkyl, haloalkyl, alkoxyalkyl, alkylcarbonyl, haloalkylcarbonyl, alkoxycarbonyl, haloalkoxycarbonyl, alkylthiocarbonyl, heterocyclyl; unsubstituted or substituted aryl, wherein the substituents may each be independent of one another cyano, nitro, halogen, alkyl, cycloalkyl, haloalkyl, unsubstituted or substituted aryl, unsubstituted or substituted aryloxy, unsubstituted or substituted heteroaryl, unsubstituted or substituted arylthio, alkylthio, haloalkylthio, alkoxy, cycloalkyloxy, haloalkoxy, alkylcarbonyl, haloalkylcarbonyl, alkoxycarbonyl, haloalkoxycarbonyl, alkylsulfinyl, haloalkylsulfinyl, alkylsulfonyl, haloalkylsulfonyl, amino, alkylamino, di(alkyl)amino, SF$_5$, methylthioamino; or unsubstituted or substituted heteroaryl, wherein the substituents may each be independent of one another cyano, nitro, halogen, alkyl, cycloalkyl, haloalkyl, unsubstituted or substituted aryl, unsubstituted or substituted aryloxy, unsubstituted or substituted heteroaryl, unsubstituted or substituted arylthio, alkylthio, haloalkylthio, alkoxy, cycloalkyloxy, haloalkoxy, alkylcarbonyl, haloalkylcarbonyl, alkoxycarbonyl, haloalkoxycarbonyl, alkylsulfinyl, haloalkylsulfinyl, alkylsulfonyl, haloalkylsulfonyl, amino, alkylamino, di(alkyl)amino, SF$_5$, methylthioamino;

Z is a direct bond, C(O), C(S) or S(O)$_p$;

a is 1, 2 or 3; and p is 0, 1 or 2.

The present invention also provides novel aryloazol-2-yl-cyanoethylamino pentafluorothiobenzamide derivatives of formula (IH) that are either in racemic form or are enriched in an enantiomer:

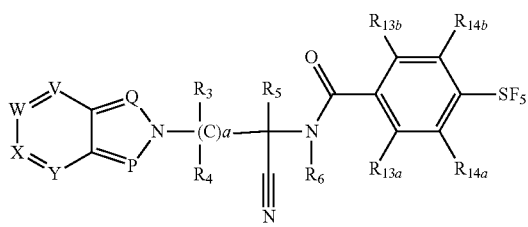

(IH)

Wherein:

P, Q, V, W, X, Y, R$_3$, R$_4$, R$_5$, R$_6$, and a are as defined above for formula (I); and R$_{13a}$, R$_{13b}$, R$_{14a}$ and R$_{14b}$ are each, independently of one another, cyano, nitro, halogen, alkyl, cycloalkyl, haloalkyl, unsubstituted or substituted aryl, unsubstituted or substituted heteroaryl, unsubstituted or substituted aryloxy including phenoxy, unsubstituted or substituted arylthio, alkylthio, haloalkylthio, alkoxy, cycloalkyloxy, haloalkoxy, alkylcarbonyl, haloalkylcarbonyl, alkoxycarbonyl, haloalkoxycarbonyl, alkylsulfinyl, haloalkylsulfinyl, alkylsulfonyl, haloalkylsulfonyl, SF$_5$, amino, alkylamino, di(alkyl)amino, or methylthioamino.

It is an object of the present invention to provide new paraciticidal compounds of the aryloazol-2-yl-cyanoethylamino family substantially enriched in an enantiomer, that display significant in vitro and in vivo activity (the eutomer), together with processes for their preparation. In an especially advantageous embodiment of the present invention, the compounds are (+)-N-[1-Cyano-1-methyl-2-(4,5,7-trichloro-2H-benzotriazol-2-yl)-ethyl]-4-trifluoromethoxybenzamide (compound No 1.096) and (+)-N-[2-(6-Bromo-2H-pyrazolo[4,3-b]pyridin-2-yl)-1-cyano-1-methylethyl]-4-trifluoromethoxybenzamide (compound No 3.024).

A second object of the present invention is to provide paraciticidal compositions comprising one or more compounds of the invention and a pharmaceutically acceptable or veterinarily acceptable carrier, and methods of use of the paraciticidal aryloazol-2-yl-cyanoethylamino compounds in the field of pest control, in particular for controlling endo- and ectoparasites which that are harmful to mammals, fish and birds. The compounds of the invention are well tolerated by warm-blooded species, fish and plants.

Another object of the invention is to provide compositions comprising one or more of the compounds in the invention in combination with one or more paraciticidally active compounds. Methods using the compositions comprising combinations of active agents are also provided.

Another object of the present invention is to provide compounds substantially enriched in an enantiomer with high activity and improved safety to the user and the environment.

The compounds of the invention are intended to encompass racemic mixtures, specific stereoisomers and tautomeric forms of the compound. Another aspect of the invention is a salt form of the compound of the invention.

Another aspect of the invention are solid state forms of the compounds of the invention which consists of crystalline forms including single crystals, nanocrystals, co-crystals, molecular complexes, hydrates, anhydrates, solvates, desolvates, clathrates and inclusion complexes and non-crystalline forms including non-crystalline glass and non-crystalline amorphous forms.

It is further noted that the invention does not intend to encompass within the scope of the invention any previously disclosed product, process of making the product or method of using the product, which meets the written description and enablement requirements of the USPTO (35 U.S.C. 112, first paragraph) or the EPO (Article 83 of the EPC), such that applicant(s) reserve the right and hereby disclose a disclaimer of any previously described product, method of making the product or process of using the product.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are apparent from and encompassed by, the following Detailed Description.

BRIEF DESCRIPTION OF THE FIGURES

FIG. 1 shows the % efficacy of compound 3.024 against ivermectin-resistant endoparasites in sheep.

FIG. 2 shows the % efficacy of a combination of compound 3.024 and ivermectin against a range of endoparasites in cattle.

DETAILED DESCRIPTION OF THE INVENTION

The novel and inventive aryloazol-2-yl-cyanoethylamino compounds of the invention have been found to have superior activity against pests, particularly endoparasites and ectoparasites. It has been surprisingly been found that a single enantiomer of the aryloazol-2-yl-cyanoethylamino compounds is significantly more active in vitro and in vivo than the other enantiomer, while exhibiting a favorable toxicity profile. Accordingly, it has been shown that enantiomerically enriched aryloazol-2-yl-cyanoethylamino compounds are useful for preventing and treating a parasitic infestation/infection in an animal. The present invention provides novel and inventive aryloazol-2-yl-cyanoethylamino compounds and compositions comprising the compounds. Furthermore, the invention provides methods for preventing and/or treating a parasitic infestation or infection in an animal, and the use of the compounds in treating a parasitic infestation or infection in an animal or the use in the manufacture of a medicament for treating a parasitic infestation or infection in an animal.

A first aspect of the invention provides novel aryloazol-2-yl-cyanoethylamino derivatives of formula (I), or pharmaceutically or veterinarily acceptable salts thereof, that are substantially enriched in an enantiomer:

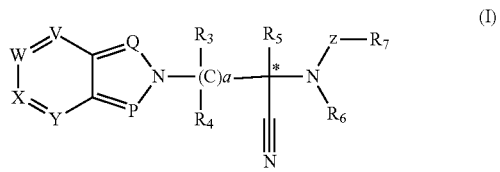

wherein:
P is C—$R_1$ or N;
Q is C—$R_2$ or N;
V is C—$R_8$ or N;
W is C—$R_9$ or N;
X is C—$R_{10}$ or N;
Y is C—$R_{11}$ or N;
$R_1$, $R_2$, $R_8$, $R_9$, $R_{10}$ and $R_{11}$ are independently of one another hydrogen, amino, amido, cyano, nitro, halogen, alkyl, alkenyl, alkynyl, cycloalkyl, hydroxyalkyl, haloalkyl, alkylthio, haloalkylthio, arylthio, alkoxy, phenoxy, alkoxyalkoxy, cycloalkyloxy, haloalkoxy, alkylcarbonyl, haloalkylcarbonyl, alkoxycarbonyl, haloalkoxycarbonyl, alkylsulfinyl, haloalkylsulfinyl, $SF_5$, alkylsulfonyl, haloalkylsulfonyl, alkylamino, di(alkyl)amino, alkylcarbonylamino, alkylaminoalkoxy, dialkylaminoalkoxy, alkylaminoalkyl, dialkylaminoalkyl, aminoalkyl, formyl, —C(O)OH, unsubstituted or substituted aryl, unsubstituted or substituted arylthio, unsubstituted or substituted aryloxy, or unsubstituted or substituted heteroaryl, wherein the substituents, independent of one another, may be one or more of cyano, nitro, halogen, alkyl, haloalkyl, alkylthio, haloalkylthio, arylthio, alkoxy, haloalkoxy, alkylcarbonyl, haloalkylcarbonyl, alkoxycarbonyl, haloalkoxycarbonyl, alkylsulfinyl, haloalkylsulfinyl, alkylsulfonyl, haloalkylsulfonyl, $SF_5$ or methylthioamino;

$R_3$, $R_4$ and $R_5$ are independently of one another hydrogen, halogen, alkyl, hydroxyalkyl, alkylthioalkyl, haloalkyl, alkyloxyalkyl, alkylsulfinylalkyl, alkylsulfonylalkyl, alkylsulfonyloxyalkyl; unsubstituted or substituted cycloalkyl, wherein the substituents may each be independently halogen and alkyl; unsubstituted or substituted aryl, unsubstituted or substituted heteroaryl, wherein the substituents may each be independent of one another cyano, nitro, halogen, alkyl, haloalkyl, alkylthio, haloalkylthio, arylthio, alkoxy, haloalkoxy, alkylcarbonyl, haloalkylcarbonyl, alkoxycarbonyl, haloalkoxycarbonyl, alkylsulfinyl, haloalkylsulfinyl, alkylsulfonyl, haloalkylsulfonyl, $SF_5$, alkylamino, or di(alkyl)amino; or $R_4$ and $R_5$ together with the carbon to which they are attached form a cycloalkyl ring;

$R_6$ is hydrogen, alkyl, alkoxyalkyl, alkylcarbonyl, haloalkylcarbonyl, alkoxycarbonyl, haloalkoxycarbonyl, alkylthiocarbonyl or unsubstituted or substituted benzyl, wherein the substituents may each be independent of one another cyano, nitro, halogen, alkyl, haloalkyl, alkylthio, haloalkylthio, arylthio, alkoxy, haloalkoxy, alkylcarbonyl, haloalkylcarbonyl, alkoxycarbonyl, haloalkoxycarbonyl, alkylsulfinyl, haloalkylsulfinyl, alkylsulfonyl, haloalkylsulfonyl, SF5, alkylamino, or di(alkyl)amino;

$R_7$ is hydrogen, alkyl, cylcoalkyl, haloalkyl, alkoxyalkyl, alkylcarbonyl, haloalkylcarbonyl, alkoxycarbonyl, haloalkoxycarbonyl, alkylthiocarbonyl, heterocyclyl; unsubstituted or substituted aryl, wherein the substituents may each be independent of one another cyano, nitro, halogen, alkyl, cycloalkyl, haloalkyl, unsubstituted or substituted aryl, unsubstituted or substituted aryloxy, unsubstituted or substituted heteroaryl, unsubstituted or substituted arylthio, alkylthio, haloalkylthio, alkoxy, cycloalkyloxy, haloalkoxy, alkylcarbonyl, haloalkylcarbonyl, alkoxycarbonyl, haloalkoxycarbonyl, alkylsulfinyl, haloalkylsulfinyl, alkylsulfonyl, haloalkylsulfonyl, amino, alkylamino, di(alkyl) amino, $SF_5$, methylthioamino; or unsubstituted or substituted heteroaryl, wherein the substituents may each be independent of one another cyano, nitro, halogen, alkyl, cycloalkyl, haloalkyl, unsubstituted or substituted aryl, unsubstituted or substituted aryloxy, unsubstituted or substituted heteroaryl, unsubstituted or substituted arylthio, alkylthio, haloalkylthio, alkoxy, cycloalkyloxy, haloalkoxy, alkylcarbonyl, haloalkylcarbonyl, alkoxycarbonyl, haloalkoxycarbonyl, alkylsulfinyl, haloalkylsulfinyl, alkylsulfonyl, haloalkylsulfonyl, amino, alkylamino, di(alkyl)amino, $SF_5$, methylthioamino;

Z is a direct bond, C(O), C(S) or $S(O)_p$;
a is 1, 2 or 3; and
p is 0, 1 or 2.

In one embodiment of formula (I), P is N and Q is C—$R_2$, and V, W, X, Y, $R_2$, $R_3$, $R_4$, $R_5$, $R_6$, $R_7$, Z and a are as defined for formula (I) above. In another embodiment, P is N and Q is N, and V, W, X, Y, $R_3$, $R_4$, $R_5$, $R_6$, $R_7$, Z and a are as defined for formula (I) above.

In another embodiment, P and Q are N, V is N, and W, X, Y, $R_3$, $R_4$, $R_5$, $R_6$, $R_7$, Z and a are as defined for formula (I) above. In still another embodiment of formula (I), P is N, Q is C—$R_2$, V is N, and W, X, Y, $R_2$, $R_3$, $R_4$, $R_5$, $R_6$, $R_7$, Z and a are as defined for formula (I) above.

In another embodiment of formula (I), P and Q are N, W is N, and V, X, Y, $R_3$, $R_4$, $R_5$, $R_6$, $R_7$, Z and a are as defined for formula (I) above. In yet another embodiment of formula (I), P is N, Q is C—$R_2$, W is N, and V, X, Y, $R_2$, $R_3$, $R_4$, $R_5$, $R_6$, $R_7$, Z and a are as defined for formula (I) above.

In another embodiment of formula (I), P and Q are N, X is N, and V, W, Y, $R_3$, $R_4$, $R_5$, $R_6$, $R_7$, Z and a are as defined for formula (I) above. In another embodiment, P is N, Q is $CR_2$, X is N, and V, W, Y, $R_2$, $R_3$, $R_4$, $R_5$, $R_6$, $R_7$, Z and a are as defined for formula (I) above.

In another embodiment of formula (I), P and Q are N, Y is N, and V, W, X, $R_3$, $R_4$, $R_5$, $R_6$, $R_7$, Z and a are as defined for formula (I) above. In another embodiment, P is N, Q is $CR_2$, Y is N, and V, W, X, $R_2$, $R_3$, $R_4$, $R_5$, $R_6$, $R_7$, Z and a are as defined for formula (I) above.

In one embodiment, the invention provides a compound of formula (I), or a pharmaceutically or veterinarily acceptable salt thereof, wherein $R_7$ is unsubstituted or substituted phenyl, and P, Q, V, W, X, Y, $R_3$, $R_4$, $R_5$, $R_6$, Z and a are as defined for formula (I) above.

In one embodiment, the first aspect of the invention provides novel aryloazol-2-yl-cyanoethylamino derivatives of the formula (I), wherein $R_1$, $R_2$, $R_8$, $R_9$, $R_{10}$ and $R_{11}$ either together or independently of one another, are hydrogen, amino, amido, cyano, nitro, halogen, $C_1$-$C_6$-alkyl, $C_2$-$C_6$-alkenyl, $C_2$-$C_6$-akynyl, $C_3$-$C_7$-cycloalkyl, hydroxy-$C_1$-$C_6$-alkyl, halo-$C_1$-$C_6$-alkyl, $C_1$-$C_6$-alkylthio, halo-$C_1$-$C_6$-alkylthio, $C_1$-$C_6$-alkoxy, $C_3$-$C_7$-cycloalkyloxy, phenoxy, $C_1$-$C_6$-alkoxy-$C_1$-$C_6$-alkoxy, $C_3$-$C_7$-cycloalkyloxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $C_1$-$C_6$-alkylamino, di($C_1$-$C_6$-alkyl)amino, $C_1$-$C_6$-alkylcarboxylamino, $C_1$-$C_6$-alkylamino-$C_1$-$C_6$-alkoxy, di-$C_1$-$C_6$-alkylamino-$C_1$-$C_6$-alkoxy, $C_1$-$C_6$-alkylamino $C_1$-$C_6$-alkyl, di-$C_1$-$C_6$-alkylamino $C_1$-$C_6$-alkyl, amino-$C_1$-$C_6$-alkyl, formyl, —C(O)OH, unsubstituted or substituted aryl, unsubstituted or substituted aryloxy including phenoxy, unsubstituted or substituted arylthio, unsubstituted or substituted heteroaryl whereby the substituents may each be, independent of one another, cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, or halo-$C_1$-$C_6$-alkylsulfonyl;

$R_3$, $R_4$ and $R_5$ are, independently of one another, hydrogen, halogen, $C_1$-$C_6$-alkyl, hydroxy-$C_1$-$C_6$-alkyl, $C_1$-$C_6$-alkylthio-$C_1$-$C_6$-alkyl, halo-$C_1$-$C_6$-alkyl, $C_1$-$C_6$-alkoxy-$C_1$-$C_6$-alkyl, $C_1$-$C_6$-alkylsulfinyl $C_1$-$C_6$-alkyl, $C_1$-$C_6$-alkylsulfonyl-$C_1$-$C_6$-alkyl, $C_1$-$C_6$-alkylsulfonyloxy-$C_1$-$C_6$-alkyl; unsubstituted or substituted $C_3$-$C_7$-cycloalkyl, wherein the substituents may each be, independent of one another, halogen or $C_1$-$C_6$-alkyl; unsubstituted or substituted phenyl, whereby the substituents may each be, independent of one another, cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $C_1$-$C_6$-alkylamino, or di($C_1$-$C_6$-alkyl)amino; or $R_4$ and $R_5$ together with the carbon to which they are attached form a cycloalkyl ring;

$R_6$ is hydrogen, $C_1$-$C_6$-alkyl, $C_1$-$C_6$-alkoxy-$C_1$-$C_6$-alkyl, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylthiocarbonyl or unsubstituted or substituted benzyl, whereby the substituents may each be, independent of one another, cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $C_1$-$C_6$-alkylamino, or di($C_1$-$C_6$-alkyl)amino;

$R_7$ is hydrogen, $C_1$-$C_6$-alkyl, $C_1$-$C_6$-alkoxy-$C_1$-$C_6$-alkyl, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylthiocarbonyl or unsubstituted or substituted aryl including phenyl and naphthyl, wherein the substituents may each be, independent of one another, cyano, nitro, halogen, $SF_5$, $C_1$-$C_6$-alkyl, $C_3$-$C_7$-cycloalkyl, halo-$C_1$-$C_6$-alkyl, phenyl, phenoxy, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, alkylsulfinyl, halo-$C_1$-$C_6$-alkylsulfinyl, $C_1$-$C_6$-alkylsulfonyl, halo-$C_1$-$C_6$-alkylsulfonyl, amino, $C_1$-$C_6$-alkylamino, or di($C_1$-$C_6$-alkyl)amino; unsubstituted or substituted heteroaryl including quinolyl, wherein the substituents may each be, independent of one another, cyano, nitro, halogen, $C_1$-$C_6$-alkyl, halo-$C_1$-$C_6$-alkyl, $C_3$-$C_7$-cycloalkyl, $C_1$-$C_6$-alkylthio, halo-$C_1$-$C_6$-alkylthio, arylthio, $C_1$-$C_6$-alkoxy, $C_3$-$C_7$-cycloalkyloxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, amino, $C_1$-$C_6$-alkylamino, or di($C_1$-$C_6$-alkyl)amino;

Z is a direct bond, C(O), C(S) or $S(O)_p$;

a is 1, 2 or 3; and p is 0, 1 or 2.

In another embodiment of the first aspect of the invention, compounds of formula (I) above are compounds wherein:

P and Q are N;

V is C—$R_8$;

W is C—$R_9$;

X is C—$R_{10}$;

Y is C—$R_{11}$;

$R_3$, $R_4$ and $R_6$ are H;

$R_8$, $R_9$, $R_{10}$ and $R_{11}$ are independently hydrogen, amino, amido, cyano, nitro, halogen, $C_1$-$C_6$-alkyl, $C_2$-$C_6$-alkenyl, $C_2$-$C_6$-akynyl, $C_3$-$C_7$-cycloalkyl, hydroxy-$C_1$-$C_6$-alkyl, halo-$C_1$-$C_6$-alkyl, $C_1$-$C_6$-alkylthio, halo-$C_1$-$C_6$-alkylthio, phenoxy, $C_1$-$C_6$-alkoxy-$C_1$-$C_6$-alkoxy, $C_3$-$C_7$-cycloalkyloxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $C_1$-$C_6$-alkylamino, di($C_1$-$C_6$-alkyl)amino, $C_1$-$C_6$-alkylcarboxylamino, $C_1$-$C_6$-alkylamino-$C_1$-$C_6$-alkoxy, di-$C_1$-$C_6$-alkylamino-$C_1$-$C_6$-alkoxy, $C_1$-$C_6$-alkylamino $C_1$-$C_6$-alkyl, di-$C_1$-$C_6$-alkylamino $C_1$-$C_6$-alkyl, amino-$C_1$-$C_6$-alkyl, formyl, —C(O)OH, unsubstituted or substituted aryl, unsubstituted or substituted arylthio, or unsubstituted or substituted aryloxy including phenoxy, whereby the substituents may each be, independent of one another, cyano, nitro, halogen, $SF_5$, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, or halo-$C_1$-$C_6$-alkylsulfonyl;

$R_5$ is methyl or $C_1$-$C_3$-alkyl;

$R_7$ is hydrogen, $C_1$-$C_6$-alkyl, $C_1$-$C_6$-alkoxy $C_1$-$C_6$-alkyl, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylthiocarbonyl or unsubstituted or substituted phenyl, wherein the substituents may each be, independent of one another, cyano, nitro, halogen, $SF_5$, $C_1$-$C_6$-alkyl, halo-$C_1$-$C_6$-alkyl, phenyl, phenoxy, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl $C_1$-$C_6$-alkylamino, or di($C_1$-$C_6$-alkyl)amino; unsubstituted or substituted heteroaryl, wherein the substituents may each be, independent of one another, cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $C_1$-$C_6$-alkylamino, or di($C_1$-$C_6$-alkyl)amino; or unsubstituted or substituted naphthyl or quinolyl, wherein the substituents may each be, independent of one another, cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $C_1$-$C_6$-alkylamino, or di($C_1$-$C_6$-alkyl)amino;

Z is a direct bond, C(O), C(S) or S(O)$_p$;

a is 1;

p is 0 or 1.

In yet another embodiment of the first aspect of the invention, compounds of formula (I) above are compounds wherein:

P and Q are N;

V is C—$R_8$;

W is C—$R_9$;

X is C—$R_{10}$;

Y is C—$R_{11}$;

$R_8$, $R_9$, $R_{10}$ and $R_{11}$ are independently of one another hydrogen, amino, amido, cyano, nitro, halogen, $C_1$-$C_6$-alkyl, $C_2$-$C_6$-alkenyl, $C_2$-$C_6$-akynyl, $C_3$-$C_7$-cycloalkyl, hydroxy-$C_1$-$C_6$-alkyl, halo-$C_1$-$C_6$-alkyl, $C_1$-$C_6$-alkylthio, halo-$C_1$-$C_6$-alkylthio, $C_1$-$C_6$-alkoxy, phenoxy, $C_1$-$C_6$-alkoxy- $C_1$-$C_6$-alkoxy, $C_3$-$C_7$-cycloalkyloxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $C_1$-$C_6$-alkylamino, di($C_1$-$C_6$-alkyl)amino, $C_1$-$C_6$-alkylcarboxylamino, $C_1$-$C_6$-alkylamino-$C_1$-$C_6$-alkoxy, di-$C_1$-$C_6$-alkylamino-$C_1$-$C_6$-alkoxy, $C_1$-$C_6$-alkylamino-$C_1$-$C_6$-alkyl, di-$C_1$-$C_6$-alkylamino-$C_1$-$C_6$-alkyl, amino-$C_1$-$C_6$-alkyl, formyl, —C(O)OH, unsubstituted or substituted aryl, unsubstituted or substituted arylthio, or unsubstituted or substituted aryloxy including phenoxy, whereby the substituents are each be, independent of one another, cyano, nitro, halogen, $C_1$-$C_6$-alkyl, halo-$C_1$-$C_6$-alkyl, $C_1$-$C_6$-alkylthio, halo-$C_1$-$C_6$-alkylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, alkylsulfonyl, or halo-$C_1$-$C_6$-alkylsulfonyl;

$R_3$, $R_4$ and $R_6$ are H;

$R_5$ is methyl or $C_1$-$C_3$-alkyl;

$R_7$ is hydrogen, $C_1$-$C_6$-alkyl, $C_1$-$C_6$-alkoxy- $C_1$-$C_6$-alkyl, $C_1$-$C_6$-alkylcarbonyl, $C_1$-$C_6$-alkoxycarbonyl, $C_1$-$C_6$-alkylthiocarbonyl or unsubstituted or substituted phenyl, wherein the substituents may each be independent of one another cyano, nitro, halogen, SF$_5$, $C_1$-$C_6$-alkyl, halo-$C_1$-$C_6$-alkyl, phenyl, phenoxy, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, halo-$C_1$-$C_6$-alkylsulfinyl, $C_1$-$C_6$-alkylsulfonyl, halo-$C_1$-$C_6$-alkylsulfonyl $C_1$-$C_6$-alkylamino, di($C_1$-$C_6$-alkyl)amino; unsubstituted or substituted heteroaryl, wherein the substituents may each be independently cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $C_1$-$C_6$-alkylamino, or di($C_1$-$C_6$-alkyl)amino;

Z is C(O); and a is 1.

In still another embodiment of the first aspect of the invention, compounds of formula (I) above are compounds wherein:

P and Q are N;

V is C—$R_8$;

W is C—$R_9$;

X is C—$R_{10}$;

Y is C—$R_{11}$;

$R_8$, $R_9$, $R_{10}$ and $R_{11}$ either together or independently of one another, are hydrogen, amino, amido, cyano, nitro, halogen, $C_1$-$C_6$-alkyl, $C_2$-$C_6$-alkenyl, $C_2$-$C_6$-akynyl, $C_3$-$C_7$-cycloalkyl, hydroxy-$C_1$-$C_6$-alkyl, halo-$C_1$-$C_6$-alkylthio, halo-$C_1$-$C_6$-alkylthio, $C_1$-$C_6$-alkoxy, phenoxy, $C_1$-$C_6$-alkoxy-$C_1$-$C_6$-alkoxy, $C_3$-$C_7$-cycloalkyloxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $C_1$-$C_6$-alkylamino, di($C_1$-$C_6$-alkyl)amino, $C_1$-$C_6$-alkylcarboxylamino, $C_1$-$C_6$-alkylamino-$C_1$-$C_6$-alkoxy, di-$C_1$-$C_6$-alkylamino-$C_1$-$C_6$-alkoxy, $C_1$-$C_6$-alkylamino-$C_1$-$C_6$-alkyl, di-$C_1$-$C_6$-alkylamino-$C_1$-$C_6$-alkyl, amino-$C_1$-$C_6$-alkyl, formyl, —C(O)OH, unsubstituted or substituted aryl, unsubstituted or substituted arylthio, or unsubstituted or substituted aryloxy including phenoxy, whereby the substituents are each independently of one another cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, or halo-$C_1$-$C_6$-alkylsulfonyl;

$R_3$, $R_4$ and $R_6$ are H;

$R_5$ is methyl $R_7$ is unsubstituted or substituted phenyl, wherein the substituents are independently of one another cyano, nitro, halogen, SF$_5$, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $C_1$-$C_6$-alkylamino, di($C_1$-$C_6$-alkyl)amino; unsubstituted or substituted heteroaryl, wherein the substituents may each be independent of one another and are cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $C_1$-$C_6$-alkylamino, di($C_1$-$C_6$-alkyl)amino;

Z is C(O); and a is 1.

In still another embodiment of the first aspect of the invention, compounds of formula (I) above are compounds wherein:

P and Q are N;

V is C—$R_8$;

W is C—$R_9$;

X is C—$R_{10}$;

Y is C—$R_{11}$;

$R_3$, $R_4$ and $R_6$ are hydrogen;

R₅ is hydrogen, alkyl, haloalkyl, hydroxyalkyl, alkylthioalkyl, alkyloxyalkyl, or alkylsulfonyloxyalkyl;

R$_7$ is unsubstituted phenyl or phenyl substituted by one or more of alkyl, haloalkyl, halogen, cyano SF$_5$, phenyl, phenyloxy, alkoxy, haloalkoxy, alkylthio, haloalkylthio, alkylsulfinyl, haloalkylsulfinyl, alkylsulfonyl or haloalkylsulfonyl;

R$_8$, R$_9$, R$_{10}$ and R$_{11}$ are each, independently of one another, hydrogen, halogen, alkyl, haloalkyl, cyano, alkoxy, haloalkoxy, alkenyl, alkylamino, hydroxyalkyl, formyl, alkylaminoalkyl, dialkylaminoalkyl, aminoalkyl, —C(O)OH, alkoxycarbonyl, alkylcarbonyl, formyl or unsubstituted or substituted phenyl wherein the substituents are alkyl or haloalkyl;

Z is C(O); and a is 1.

In still another embodiment of the first aspect of the invention, compounds of formula (I) above are compounds wherein:

P and Q are N;

V is C—R$_8$;

W is C—R$_9$;

X is C—R$_{10}$;

Y is C—R$_{11}$;

R$_3$, R$_4$ and R$_6$ are hydrogen;

R$_5$ is hydrogen, C$_1$-C$_6$-alkyl, halo-C$_1$-C$_6$-alkyl, hydroxy-C$_1$-C$_6$-alkyl, C$_1$-C$_6$-alkylthio-C$_1$-C$_6$-alkyl, C$_1$-C$_6$-alkyloxy-C$_1$-C$_6$-alkyl, or C$_1$-C$_6$-alkylsulfonyloxy-C$_1$-C$_6$-alkyl;

R$_7$ is unsubstituted phenyl or phenyl substituted by one or more of halogen, cyano, SF$_5$, C$_1$-C$_6$-alkyl, halo-C$_1$-C$_6$-alkyl, phenyl, phenyloxy, C$_1$-C$_6$-alkoxy, halo-C$_1$-C$_6$-alkoxy, C$_1$-C$_6$-alkylthio, halo-C$_1$-C$_6$-alkylthio, halo-C$_1$-C$_6$-alkylsulfinyl or halo-C$_1$-C$_6$-alkylsulfonyl;

R$_8$, R$_9$, R$_{10}$ and R$_{11}$ independently of one another, are hydrogen, halogen, C$_1$-C$_6$-alkyl, halo-C$_1$-C$_6$-alkyl, cyano, C$_1$-C$_6$-alkoxy, halo-C$_1$-C$_6$-alkoxy, C$_2$-C$_6$-alkenyl, C$_1$-C$_6$-alkylamino, hydroxy-C$_1$-C$_6$-alkyl, formyl, C$_1$-C$_6$-alkylamino-C$_1$-C$_6$-alkyl, —C(O)OH, alkylcarbonyl, alkoxycarbonyl, or unsubstituted or substituted phenyl wherein the substituents are C$_1$-C$_6$-alkyl or halo-C$_1$-C$_6$-alkyl;

Z is C(O); and a is 1.

In still another embodiment of the first aspect of the invention, compounds of formula (I) above are compounds wherein:

P and Q are N;

V is C—R$_8$;

W is C—R$_9$;

X is C—R$_{10}$;

Y is C—R$_{11}$;

R$_3$, R$_4$ and R$_6$ are hydrogen;

R$_5$ is methyl, ethyl, butyl, CH$_2$OH, CH$_2$OCH$_3$, CH$_2$SCH$_3$, or CH$_2$OSO$_2$CH$_3$, R$_7$ is a phenyl substituted with one or more of halogen, cyano, SF$_5$, butyl, CF$_3$, phenyl, phenoxy, OCF$_3$, SCF$_3$, SOCF$_3$, or SO$_2$CF$_3$;

R$_8$, R$_9$, R$_{10}$ and R$_{11}$ either, independently of one another, is hydrogen, methyl, CH$_2$NH$_2$, CH$_2$N(CH$_3$)$_2$, vinyl, CH$_2$OH, CH(OH)CH$_2$OH, CO$_2$H, CO$_2$CH$_3$, Ph-CF$_3$, F, Cl, Br, CF$_3$, OCF$_3$ or CN;

Z is C(O); and a is 1.

In another embodiment, the invention provides compounds of formula (I) wherein:

P is N;

Q is C—R$_2$;

V is C—R$_9$;

W is C—R$_9$;

X is C—R$_{10}$;

Y is C—R$_{11}$;

R$_3$, R$_4$ and R$_6$ are H;

R$_2$, R$_8$, R$_9$, R$_{10}$ and R$_{11}$ are independently hydrogen, amino, amido, cyano, nitro, halogen, C$_1$-C$_6$-alkyl, C$_2$-C$_6$-alkenyl, C$_2$-C$_6$-akynyl, C$_3$-C$_7$-cycloalkyl, hydroxy-C$_1$-C$_6$-alkyl, halo-C$_1$-C$_6$-alkyl, C$_1$-C$_6$-alkylthio, halo-C$_1$-C$_6$-alkylthio, C$_1$-C$_6$-alkoxy, phenoxy, C$_1$-C$_6$-alkoxy-C$_1$-C$_6$-alkoxy, C$_3$-C$_7$-cycloalkyloxy, halo-C$_1$-C$_6$-alkoxy, C$_1$-C$_6$-alkylcarbonyl, halo-C$_1$-C$_6$-alkylcarbonyl, C$_1$-C$_6$-alkoxycarbonyl, halo-C$_1$-C$_6$-alkoxycarbonyl, C$_1$-C$_6$-alkylsulfinyl, halo-C$_1$-C$_6$-alkylsulfinyl, C$_1$-C$_6$-alkylsulfonyl, halo-C$_1$-C$_6$-alkylsulfonyl C$_1$-C$_6$-alkylamino, di(C$_1$-C$_6$-alkyl)amino, C$_1$-C$_6$-alkylcarboxylamino, C$_1$-C$_6$-alkylamino-C$_1$-C$_6$-alkoxy, di-C$_1$-C$_6$-alkylamino-C$_1$-C$_6$-alkoxy, C$_1$-C$_6$-alkylamino-C$_1$-C$_6$-alkyl, di-C$_1$-C$_6$-alkylamino-C$_1$-C$_6$-alkyl, amino-C$_1$-C$_6$-alkyl, formyl, —C(O)OH, unsubstituted or substituted aryl, unsubstituted or substituted arylthio, or unsubstituted or substituted aryloxy including phenoxy, wherein the substituents are independently cyano, nitro, halogen, SF$_5$, halo-C$_1$-C$_6$-alkylthio, arylthio, C$_1$-C$_6$-alkoxy, halo-C$_1$-C$_6$-alkoxy, C$_1$-C$_6$-alkylcarbonyl, halo-C$_1$-C$_6$-alkylcarbonyl, C$_1$-C$_6$-alkoxycarbonyl, halo-C$_1$-C$_6$-alkoxycarbonyl, C$_1$-C$_6$-alkylsulfinyl, halo-C$_1$-C$_6$-alkylsulfinyl, C$_1$-C$_6$-alkylsulfonyl or halo-C$_1$-C$_6$-alkylsulfonyl;

R$_5$ is methyl or C$_1$-C$_3$-alkyl;

R$_7$ is hydrogen, C$_1$-C$_6$-alkyl, C$_1$-C$_6$-alkoxy-C$_1$-C$_6$-alkyl, C$_1$-C$_6$-alkylcarbonyl, C$_1$-C$_6$-alkylthiocarbonyl, unsubstituted phenyl, or phenyl substituted by one or more substituents, wherein the substituents may be independently cyano, nitro, halogen, SF$_5$, C$_1$-C$_6$-alkyl, halo-C$_1$-C$_6$-alkyl, phenyl, phenoxy, C$_1$-C$_6$-alkylthio, halo-C$_1$-C$_6$-alkylthio, arylthio, C$_1$-C$_6$-alkoxy, halo-C$_1$-C$_6$-alkoxy, C$_1$-C$_6$-alkylcarbonyl, halo-C$_1$-C$_6$-alkylcarbonyl, C$_1$-C$_6$-alkylsulfinyl, halo-C$_1$-C$_6$-alkylsulfinyl, C$_1$-C$_6$-alkylsulfonyl, halo-C$_1$-C$_6$-alkylsulfonyl, C$_1$-C$_6$-alkylamino, or di(C$_1$-C$_6$-alkyl)amino; unsubstituted or substituted heteroaryl, wherein the substituents are independently cyano, nitro, halogen, SF$_5$, C$_1$-C$_6$-alkyl, halo-C$_1$-C$_6$-alkyl, C$_1$-C$_6$-alkylthio, halo-C$_1$-C$_6$-alkylthio, arylthio, C$_1$-C$_6$-alkoxy, halo-C$_1$-C$_6$-alkoxy, C$_1$-C$_6$-alkylcarbonyl, halo-C$_1$-C$_6$-alkylcarbonyl, C$_1$-C$_6$-alkoxycarbonyl, halo-C$_1$-C$_6$-alkoxycarbonyl, halo-C$_1$-C$_6$-alkylsulfinyl, C$_1$-C$_6$-alkylsulfonyl, halo-C$_1$-C$_6$-alkylsulfonyl, C$_1$-C$_6$-alkylamino, or di(C$_1$-C$_6$-alkyl)amino; or unsubstituted or substituted naphthyl or quinolyl, wherein the substituents may each be independently cyano, nitro, halogen, SF$_5$, halo-C$_1$-C$_6$-alkylthio, arylthio, C$_1$-C$_6$-alkoxy, halo-C$_1$-C$_6$-alkoxy, C$_1$-C$_6$-alkylcarbonyl, halo-C$_1$-C$_6$-alkylcarbonyl, C$_1$-C$_6$-alkoxycarbonyl, halo-C$_1$-C$_6$-alkoxycarbonyl, C$_1$-C$_6$-alkylsulfinyl, halo-C$_1$-C$_6$-alkylsulfinyl, C$_1$-C$_6$-alkylsulfonyl, halo-C$_1$-C$_6$-alkylsulfonyl, C$_1$-C$_6$-alkylamino, or di(C$_1$-C$_6$-alkyl)amino;

Z is a direct bond, C(O), C(S) or S(O)$_p$;

a is 1; and p is 0 or 1.

In another embodiment, compounds of formula (I) above are compounds wherein:

P is N;

Q is C—R$_2$;

V is C—R$_8$;

W is C—R$_9$;

X is C—R$_{10}$;

Y is C—R$_{11}$;

R$_2$ is hydrogen, halogen, alkyl, haloalkyl, alkoxy, haloalkoxy, alkoxyalkoxy, alkylaminoalkoxy, or dialkylaminoalkoxy;

R$_3$, R$_4$ and R$_6$ are hydrogen;

$R_5$ is hydrogen, alkyl, or haloalkyl;

$R_7$ is unsubstituted phenyl or phenyl substituted by one or more of halogen, cyano, $SF_5$, alkyl, haloalkyl, alkoxy, haloalkoxy, alkylthio, haloalkylthio, haloalkylsulfinyl or haloalkylsulfonyl;

$R_8$, $R_9$, $R_{10}$ and $R_{11}$ are each independently of one another hydrogen, halogen, alkyl, haloalkyl, nitro, amino, amido, alkylcarbonyl, alkoxycarbonyl, or alkylcarbonylamino;

Z is C(O); and a is 1.

In another embodiment of the invention, compounds of formula (I) above are compounds wherein:

P is N;

Q is C—$R_2$;

V is C—$R_8$;

W is C—$R_9$;

X is C—$R_{10}$;

Y is C—$R_{11}$;

$R_2$ is hydrogen, halogen, $C_1$-$C_6$-alkyl, halo-$C_1$-$C_6$-alkyl, $C_1$-$C_6$-alkoxy, halo-$C_1$-$C_6$-alkoxy, $C_1$-$C_6$-alkoxy-$C_1$-$C_6$-alkoxy, or $C_1$-$C_6$-alkylamino-$C_1$-$C_6$-alkoxy;

$R_3$, $R_4$ and $R_6$ are hydrogen;

$R_5$ is hydrogen, $C_1$-$C_6$-alkyl, or halo-$C_1$-$C_6$-alkyl;

$R_7$ is unsubstituted phenyl or phenyl substituted by one or more of halogen, cyano, $SF_5$, $C_1$-$C_6$-alkyl, halo-$C_1$-$C_6$-alkyl, $C_1$-$C_6$-alkoxy, halo-$C_1$-$C_6$-alkoxy, $C_1$-$C_6$-alkylthio, halo-$C_1$-$C_6$-alkylthio, halo-$C_1$-$C_6$-alkylsulfinyl or halo-$C_1$-$C_6$-alkylsulfonyl;

$R_8$, $R_9$, $R_{10}$ and $R_{11}$ are independently of one another, hydrogen, halogen, $C_1$-$C_6$-alkyl, halo-$C_1$-$C_6$-alkyl, nitro, amino, amido, $C_1$-$C_6$-alkylcarbonyl, $C_1$-$C_6$-alkoxycarbonyl, or $C_1$-$C_6$-alkylcarbonylamino;

Z is C(O); and a is 1.

In still another embodiment, compounds of formula (I) above are compounds wherein:

P is N;

Q is C—$R_2$;

V is C—$R_8$;

W is C—$R_9$;

X is C—$R_{10}$;

Y is C—$R_{11}$;

$R_2$ is hydrogen, Cl, methyl, methoxy, ethoxy, propoxy, butoxy, $O(CH_2)_2OCH_3$, or $O(CH_2)_2N(CH_3)_2$;

$R_3$, $R_4$ and $R_6$ are hydrogen;

$R_5$ is methyl;

$R_7$ is phenyl substituted by one or more of halogen, cyano, $OCF_3$, phenoxy, $SF_5$ or $SCF_3$;

$R_8$, $R_9$, $R_{10}$ and $R_{11}$ are each, independently of one another, hydrogen, Cl, Br, $C_1$-$C_6$-alkyl, $CF_3$, nitro, amino, amido, —$CO_2CH_3$, or —$NHCOCH_3$;

Z is C(O); and a is 1.

In another embodiment of the invention, compounds of formula (I) above are compounds wherein:

P is N;

Q is C—$R_2$ or N;

V is N;

W is C—$R_9$;

X is C—$R_{10}$;

Y is C—$R_{11}$;

$R_3$, $R_4$ and $R_6$ are H;

$R_2$, $R_9$, $R_{10}$ and $R_{11}$ are each, independently of one another, hydrogen, amino, amido, cyano, nitro, halogen, $C_1$-$C_6$-alkyl, $C_2$-$C_6$-alkenyl, $C_2$-$C_6$-akynyl, $C_3$-$C_7$-cycloalkyl, hydroxy-$C_1$-$C_6$-alkyl, halo-$C_1$-$C_6$-alkyl, $C_1$-$C_6$-alkylthio, halo-$C_1$-$C_6$-alkylthio, $C_1$-$C_6$-alkoxy, phenoxy, $C_1$-$C_6$-alkoxy-$C_1$-$C_6$-alkoxy, cycloalkyloxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $C_1$-$C_6$-alkylamino, di($C_1$-$C_6$-alkyl)amino, $C_1$-$C_6$-alkylcarboxylamino, $C_1$-$C_6$-alkylamino-$C_1$-$C_6$-alkoxy, di-$C_1$-$C_6$-alkylamino-$C_1$-$C_6$-alkoxy, $C_1$-$C_6$-alkylamino $C_1$-$C_6$-alkyl, di-$C_1$-$C_6$-alkylamino $C_1$-$C_6$-alkyl, amino-$C_1$-$C_6$-alkyl, formyl, —C(O)OH, —unsubstituted or substituted aryl, unsubstituted or substituted arylthio, unsubstituted or substituted heteroaryl, or unsubstituted or substituted aryloxy including phenoxy, wherein the substituents are each independently cyano, nitro, halogen, $SF_5$, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, or halo-$C_1$-$C_6$-alkylsulfonyl;

$R_5$ is methyl or $C_1$-$C_3$-alkyl;

$R_7$ is hydrogen, $C_1$-$C_6$-alkyl, $C_1$-$C_6$-alkoxy- $C_1$-$C_6$-alkylcarbonyl, $C_1$-$C_6$-alkylthiocarbonyl, or unsubstituted or substituted phenyl wherein the substituents may be independently cyano, nitro, halogen, $SF_5$, $C_1$-$C_6$-alkyl, halo-$C_1$-$C_6$-alkyl, phenyl, phenoxy, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $C_1$-$C_6$-alkylamino, or di($C_1$-$C_6$-alkyl)amino; unsubstituted or substituted heteroaryl, wherein the substituents may each be independent of one another cyano, nitro, halogen, $SF_5$, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $C_1$-$C_6$-alkylamino, or di($C_1$-$C_6$-alkyl)amino; or unsubstituted or substituted naphthyl or quinolyl, wherein the substituents may each be independently cyano, nitro, halogen, $SF_5$, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $C_1$-$C_6$-alkylamino, or di($C_1$-$C_6$-alkyl)amino;

Z is a direct bond, C(O), C(S) or $S(O)_p$;

a is 1; and p is 0 or 1.

In another embodiment, the invention provides compounds of formula (I), wherein:

P is N;

Q is C—$R_2$ or N;

V is N;

W is C—$R_9$;

X is C—$R_{10}$;

Y is C—$R_{11}$;

$R_2$ is hydrogen, halogen, alkyl, alkoxy, or haloalkoxy;

$R_3$, $R_4$ and $R_6$ are hydrogen;

$R_5$ is hydrogen, alkyl, or haloalkyl;

$R_7$ is unsubstituted phenyl or phenyl substituted by one or more of halogen, cyano, $SF_5$, alkyl, haloalkyl, alkoxy, haloalkoxy, alkylthio, haloalkylthio, haloalkylsulfinyl or haloalkylsulfonyl;

$R_9$, $R_{10}$ and $R_{11}$ either together or independently of one another, are hydrogen, halogen, alkyl, or haloalkyl;

Z is C(O); and a is 1.

In another embodiment, compounds of formula (I) above are compounds wherein:
P is N;
Q is C—$R_2$ or N;
V is N;
W is C—$R_9$;
X is C—$R_{10}$;
Y is C—$R_{11}$;
$R_2$ is hydrogen, halogen, $C_1$-$C_6$-alkyl, $C_1$-$C_6$-alkoxy, or halo-$C_1$-$C_6$-alkoxy;
$R_3$, $R_4$ and $R_6$ are hydrogen;
$R_5$ is hydrogen, $C_1$-$C_6$-alkyl, or halo-$C_1$-$C_6$-alkyl;
$R_7$ is unsubstituted phenyl or phenyl substituted by one or more of halogen, cyano, $SF_5$, $C_1$-$C_6$-alkyl, halo-$C_1$-$C_6$-alkyl, $C_1$-$C_6$-alkoxy, halo-$C_1$-$C_6$-alkoxy, $C_1$-$C_6$-alkylthio, halo-$C_1$-$C_6$-alkylthio, halo-$C_1$-$C_6$-alkylsulfinyl or halo-$C_1$-$C_6$-alkylsulfonyl;
$R_9$, $R_{10}$ and $R_{11}$ either, independently of one another, are hydrogen, halogen, $C_1$-$C_6$-alkyl, or halo-$C_1$-$C_6$-alkyl;
Z is C(O); and
a is 1.

In still another embodiment, compounds of formula (I) are provided wherein:
P is N;
Q is C—$R_2$ or N;
V is N;
W is C—$R_9$;
X is C—$R_{10}$;
Y is C—$R_{11}$;
$R_2$ is hydrogen, Cl, Br, methoxy;
$R_3$, $R_4$ and $R_6$ are hydrogen;
$R_5$ is methyl;
$R_7$ is phenyl substituted by one or more of halogen, cyano, $SF_5$, $OCF_3$ or $SCF_3$;
$R_9$, $R_{10}$ and $R_{11}$ either, independently of one another, are hydrogen, Cl, Br, I or methyl;
Z is C(O); and
a is 1.

In another embodiment, compounds of formula (I) above are compounds wherein:
P is N;
Q is C—$R_2$ or N;
V is C—$R_9$ or N;
W is C—$R_9$;
X is C—$R_{10}$;
Y is C—$R_{11}$;
$R_2$ is hydrogen, Cl, Br, methyl or methoxy;
$R_3$, $R_4$ and $R_6$ are H;
$R_5$ is methyl;
$R_7$ is phenyl optionally substituted with one or more of halogen, cyano, $SF_5$, $OCF_3$, $SCF_3$ or $CHFCF_3$;
$R_8$, $R_9$, $R_{10}$ and $R_{11}$, are each independently of one another H, Cl, Br, I, methyl, $CF_3$ or CN;
Z is C(O); and
a is 1.

In another embodiment, compounds of formula (I) above are compounds wherein:
P is N;
Q is C—$R_2$ or N;
V is C—$R_9$ or N;
W is C—$R_9$;
X is C—$R_{10}$;
Y is C—$R_{11}$;
$R_2$ is hydrogen, Cl, Br, methyl or methoxy;
$R_3$, $R_4$ and $R_6$ are H;
$R_5$ is methyl;
$R_7$ is phenyl substituted with one or more of halogen, cyano, $SF_5$, $OCF_3$, $SCF_3$ or $CHFCF_3$;
$R_8$ is H, Cl, Br, F or CN;
$R_9$ is H, Cl or Br;
$R_{10}$ is H, Cl, Br, I or $CF_3$;
$R_{11}$ is H, Cl, Br or methyl;
Z is C(O); and
a is 1.

In yet another embodiment of the invention, compounds of formula (I) above are compounds wherein:
P is N;
Q is C—$R_2$ or N;
V is N;
W is C—$R_9$;
X is C—$R_{10}$;
Y is C—$R_{11}$;
$R_2$ is hydrogen, Cl, Br or methoxy;
$R_3$, $R_4$ and $R_6$ are H;
$R_5$ is methyl;
$R_7$ is phenyl substituted with one or more of halogen, cyano, $OCF_3$ or $SCF_3$;
$R_9$ is H;
$R_{10}$ is Cl, Br or I;
$R_{11}$ is H;
Z is C(O); and
a is 1.

In another embodiment of the invention, compounds of formula (I) above are compounds wherein:
P is N;
Q is N or C—$R_2$;
V is C—$R_8$;
W is N;
X is C—$R_{10}$;
Y is C—$R_{11}$;
$R_3$, $R_4$ and $R_6$ are H;
$R_2$, $R_8$, $R_{10}$ and $R_{11}$ are independently of one another hydrogen, amino, amido, cyano, nitro, halogen, $C_1$-$C_6$-alkyl, $C_2$-$C_6$-alkenyl, $C_2$-$C_6$-akynyl, $C_3$-$C_7$-cycloalkyl, hydroxy-$C_1$-$C_6$-alkyl, halo-$C_1$-$C_6$-alkyl, $C_1$-$C_6$-alkylthio, halo-$C_1$-$C_6$-alkylthio, $C_1$-$C_6$-alkoxy, phenoxy, $C_1$-$C_6$-alkoxy-$C_1$-$C_6$-alkoxy, $C_3$-$C_7$-cycloalkyloxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $C_1$-$C_6$-alkylamino, di($C_1$-$C_6$-alkyl)amino, $C_1$-$C_6$-alkylcarboxylamino, $C_1$-$C_6$-alkylamino-$C_1$-$C_6$-alkoxy, di-$C_1$-$C_6$-alkylamino-$C_1$-$C_6$-alkoxy, $C_1$-$C_6$-alkylamino $C_1$-$C_6$-alkyl, di-$C_1$-$C_6$-alkylamino-$C_1$-$C_6$-alkyl, amino-$C_1$-$C_6$-alkyl, formyl, —C(O)OH, unsubstituted or substituted aryl, unsubstituted or substituted arylthio, or unsubstituted or substituted aryloxy including phenoxy, wherein the substituents may each be independent of one another cyano, nitro, halogen, $SF_5$, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, or halo-$C_1$-$C_6$-alkylsulfonyl;
$R_5$ is methyl or $C_1$-$C_3$-alkyl;
$R_7$ is hydrogen, $C_1$-$C_6$-alkyl, $C_1$-$C_6$-alkoxy- $C_1$-$C_6$-alkyl, $C_1$-$C_6$-alkylcarbonyl, $C_1$-$C_6$-alkylthiocarbonyl or unsubstituted or substituted phenyl wherein the substituents may each be, independent of one another, cyano, nitro, halogen, $SF_5$, $C_1$-$C_6$-alkyl, halo-$C_1$-$C_6$-alkyl, phenyl, phenoxy, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $C_1$-$C_6$-alkylamino, or di($C_1$-$C_6$-alkyl)amino; unsubstituted or substituted heteroaryl, wherein the substituents may each be, independent of one another, cyano, nitro, halogen, $SF_5$, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $C_1$-$C_6$-alkylamino, or di($C_1$-$C_6$-alkyl)amino; or unsubstituted or substituted naphthyl or quinolyl, wherein the substituents may each be, independent of one another, cyano, nitro, halogen, $SF_5$, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $C_1$-$C_6$-alkylamino, di($C_1$-$C_6$-alkyl)amino;

Z is a direct bond, C(O), C(S) or S(O)$_p$;
a is 1; and
p is 0 or 1.

In another embodiment, the invention provides compounds of formula (I), wherein:
P is N;
Q is N or C—$R_2$;
V is C—$R_8$;
W is N;
X is C—$R_{10}$;
Y is C—$R_{11}$;
$R_2$ is hydrogen, halogen, alkyl, alkoxy, or haloalkoxy;
$R_3$, $R_4$ and $R_6$ are hydrogen;
$R_5$ is hydrogen, alkyl, or haloalkyl;
$R_7$ is unsubstituted phenyl or phenyl substituted by one or more of halogen, cyano, $SF_5$, alkyl, haloalkyl, alkoxy, haloalkoxy, alkylthio, haloalkylthio, haloalkylsulfinyl or haloalkylsulfonyl;
$R_8$, $R_{10}$ and $R_{11}$ either together or independently of one another, are hydrogen, halogen, alkyl, or haloalkyl;
Z is C(O); and
a is 1.

In another embodiment, compounds of formula (I) above are compounds wherein:
P is N;
Q is N or C—$R_2$;
V is C—$R_8$;
W is N;
X is C—$R_{10}$;
Y is C—$R_{11}$;
$R_2$ is hydrogen, halogen, $C_1$-$C_6$-alkyl, $C_1$-$C_6$-alkoxy, or halo-$C_1$-$C_6$-alkoxy;
$R_3$, $R_4$ and $R_6$ are hydrogen;
$R_5$ is hydrogen, $C_1$-$C_6$-alkyl, or halo-$C_1$-$C_6$-alkyl;
$R_7$ is unsubstituted phenyl or phenyl substituted by one or more of halogen, cyano, $SF_5$, $C_1$-$C_6$-alkyl, halo-$C_1$-$C_6$-alkyl, $C_1$-$C_6$-alkoxy, halo-$C_1$-$C_6$-alkoxy, $C_1$-$C_6$-alkylthio, halo-$C_1$-$C_6$-alkylthio, halo-$C_1$-$C_6$-alkylsulfinyl or halo-$C_1$-$C_6$-alkylsulfonyl;
$R_8$, $R_{10}$ and $R_{11}$ are independently of one another hydrogen, halogen, $C_1$-$C_6$-alkyl, or halo-$C_1$-$C_6$-alkyl;
Z is C(O); and
a is 1.

In still another embodiment, compounds of formula (I) above are compounds wherein:
P is N;
Q is N or C—$R_2$;
V is C—$R_8$;
W is N;
X is C—$R_{10}$;
Y is C—$R_{11}$;
$R_2$ is hydrogen, Cl, Br, methoxy;
$R_3$, $R_4$ and $R_6$ are hydrogen;
$R_5$ is methyl;
$R_7$ is phenyl substituted by one or more of halogen, cyano, $SF_5$, $OCF_3$ or $SCF_3$;
$R_8$, $R_{10}$ and $R_{11}$ are independently of one another hydrogen, Cl, Br, I or methyl;
Z is C(O); and
a is 1.

In another embodiment of the invention, compounds of formula (I) above are compounds wherein:
P is N;
Q is N or C—$R_2$;
V is C—$R_8$;
W is C—$R_9$;
X is N;
Y is C—$R_{11}$;
$R_3$, $R_4$ and $R_6$ are H;
$R_2$, $R_8$, $R_9$ and $R_{11}$ either together or independently of one another, are hydrogen, amino, amido, cyano, nitro, halogen, $C_1$-$C_6$-alkyl, $C_2$-$C_6$-alkenyl, $C_2$-$C_6$-akynyl, $C_3$-$C_7$-cycloalkyl, hydroxy-$C_1$-$C_6$-alkyl, halo-$C_1$-$C_6$-alkylthio, $C_1$-$C_6$-alkoxy, phenoxy, $C_1$-$C_6$-alkoxy-$C_1$-$C_6$-alkoxy, $C_3$-$C_7$-cycloalkyloxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $C_1$-$C_6$-alkylamino, di($C_1$-$C_6$-alkyl)amino, $C_1$-$C_6$-alkylcarboxylamino, $C_1$-$C_6$-alkylamino-$C_1$-$C_6$-alkoxy, di-$C_1$-$C_6$-alkylamino-$C_1$-$C_6$-alkoxy, $C_1$-$C_6$-alkylamino-$C_1$-$C_6$-alkyl, di-$C_1$-$C_6$-alkylamino-$C_1$-$C_6$-alkyl, amino-$C_1$-$C_6$-alkyl, formyl, —C(O)OH, unsubstituted or substituted aryl, unsubstituted or substituted arylthio, or unsubstituted or substituted aryloxy including phenoxy, wherein the substituents may each be independent of one another cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, or halo-$C_1$-$C_6$-alkylsulfonyl;
$R_5$ is methyl or $C_1$-$C_3$-alkyl;
$R_7$ is hydrogen, $C_1$-$C_6$-alkyl, $C_1$-$C_6$-alkoxy-$C_1$-$C_6$-alkyl, $C_1$-$C_6$-alkylcarbonyl, $C_1$-$C_6$-alkylthiocarbonyl, unsubstituted or substituted phenyl wherein the substituents may each be, independent of one another, cyano, nitro, halogen, $SF_5$, $C_1$-$C_6$-alkyl, halo-$C_1$-$C_6$-alkyl, phenyl, phenoxy, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $C_1$-$C_6$-alkylamino, or di($C_1$-$C_6$-alkyl)amino; unsubstituted or substituted heteroaryl, wherein the substituents may each be, independent of one another, cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $C_1$-$C_6$-alkylamino, di($C_1$-$C_6$-alkyl)amino; or
unsubstituted or substituted naphthyl or quinolyl, wherein the substituents may each be, independent of one another, cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-

$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $C_1$-$C_6$-alkylamino, di($C_1$-$C_6$-alkyl)amino;

Z is a direct bond, C(O), C(S) or S(O)$_p$;
a is 1; and
p is 0 or 1.

In another embodiment, the invention provides compounds of formula (I), wherein:
P is N;
Q is N or C—$R_2$;
V is C—$R_8$;
W is C—$R_9$;
X is N;
Y is C—$R_{11}$;
$R_2$ is hydrogen, halogen, alkyl, alkoxy, or haloalkoxy;
$R_3$, $R_4$ and $R_6$ are hydrogen;
$R_5$ is hydrogen, alkyl, or haloalkyl;
$R_7$ is unsubstituted phenyl or phenyl substituted by one or more of halogen, cyano, $SF_5$, alkyl, haloalkyl, alkoxy, haloalkoxy, alkylthio, haloalkylthio, haloalkylsulfinyl or haloalkylsulfonyl;
$R_8$, $R_9$ and $R_{11}$ are independently hydrogen, halogen, alkyl, or haloalkyl;
Z is C(O); and
a is 1.

In another embodiment, compounds of formula (I) above are compounds wherein:
P is N;
Q is N or C—$R_2$;
V is C—$R_8$;
W is C—$R_9$;
X is N;
Y is C—$R_{11}$;
$R_2$ is hydrogen, halogen, $C_1$-$C_6$-alkyl, $C_1$-$C_6$-alkoxy, or halo-$C_1$-$C_6$-alkoxy;
$R_3$, $R_4$ and $R_6$ are hydrogen;
$R_5$ is hydrogen, $C_1$-$C_6$-alkyl, or halo-$C_1$-$C_6$-alkyl;
$R_7$ is unsubstituted phenyl or phenyl substituted by one or more of halogen, cyano, $SF_5$, $C_1$-$C_6$-alkyl, halo-$C_1$-$C_6$-alkyl, $C_1$-$C_6$-alkoxy, halo-$C_1$-$C_6$-alkoxy, $C_1$-$C_6$-alkylthio, halo-$C_1$-$C_6$-alkylthio, halo-$C_1$-$C_6$-alkylsulfinyl or halo-$C_1$-$C_6$-alkylsulfonyl;
$R_8$, $R_9$ and $R_{11}$ are independently hydrogen, halogen, $C_1$-$C_6$-alkyl, or halo-$C_1$-$C_6$-alkyl;
Z is C(O); and
a is 1.

In still another embodiment, compounds of formula (I) above are compounds wherein:
P is N;
Q is N or C—$R_2$;
V is C—$R_8$;
W is C—$R_9$;
X is N;
Y is C—$R_{11}$;
$R_2$ is hydrogen, Cl, Br, or methoxy;
$R_3$, $R_4$ and $R_6$ are hydrogen;
$R_5$ is methyl;
$R_7$ is phenyl substituted by one or more of halogen, cyano, $SF_5$, $OCF_3$ or $SCF_3$;
$R_8$, $R_9$ and $R_{11}$ are independently hydrogen, Cl, Br, I or methyl;
Z is C(O); and
a is 1.

In another embodiment of the invention, compounds of formula (I) above are compounds wherein:
P is N;
Q is N or C—$R_2$;
V is C—$R_9$;
W is C—$R_9$;
X is C—$R_{10}$;
Y is N;
$R_3$, $R_4$ and $R_6$ are H;
$R_2$, $R_8$, $R_9$ and $R_{10}$ are independently of one another hydrogen, amino, amido, cyano, nitro, halogen, $C_1$-$C_6$-alkyl, $C_2$-$C_6$-alkenyl, $C_2$-$C_6$-akynyl, $C_3$-$C_7$-cycloalkyl, hydroxy-$C_1$-$C_6$-alkyl, halo-$C_1$-$C_6$-alkyl, $C_1$-$C_6$-alkylthio, halo-$C_1$-$C_6$-alkylthio arylthio, $C_1$-$C_6$-alkoxy, phenoxy, $C_1$-$C_6$-alkoxy-$C_1$-$C_6$-alkoxy, $C_3$-$C_7$-cycloalkyloxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $C_1$-$C_6$-alkylamino, di($C_1$-$C_6$-alkyl)amino, $C_1$-$C_6$-alkylcarboxylamino, $C_1$-$C_6$-alkylamino-$C_1$-$C_6$-alkoxy, di-$C_1$-$C_6$-alkylamino-$C_1$-$C_6$-alkoxy, $C_1$-$C_6$-alkylamino-$C_1$-$C_6$-alkyl, di-$C_1$-$C_6$-alkylamino-$C_1$-$C_6$-alkyl, amino-$C_1$-$C_6$-alkyl, formyl, —C(O)OH, —C(O)OC1-C6-alkyl, unsubstituted or substituted aryl or unsubstituted or substituted phenoxy, wherein the substituents may each be independent of one another cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, alkoxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl;

$R_5$ is methyl or $C_1$-$C_3$-alkyl;
$R_7$ is hydrogen, $C_1$-$C_6$-alkyl, $C_1$-$C_6$-alkoxy-$C_1$-$C_6$-alkyl, $C_1$-$C_6$-alkylcarbonyl, $C_1$-$C_6$-alkylthiocarbonyl or unsubstituted or substituted phenyl wherein the substituents may each be, independent of one another, cyano, nitro, halogen, $SF_5$, $C_1$-$C_6$-alkyl, halo-$C_1$-$C_6$-alkyl, phenyl, phenoxy, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $C_1$-$C_6$-alkylamino, or di($C_1$-$C_6$-alkyl)amino; unsubstituted or substituted heteroaryl, wherein the substituents may each be independent of one another cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $C_1$-$C_6$-alkylamino, or di($C_1$-$C_6$-alkyl)amino; or unsubstituted or substituted naphthyl or quinolyl, wherein the substituents may each be, independent of one another, cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $C_1$-$C_6$-alkylamino, or di($C_1$-$C_6$-alkyl)amino;

Z is a direct bond, C(O), C(S) or S(O)$_p$;
a is 1; and
p is 0 or 1.

In another embodiment, the invention provides compounds of formula (I), wherein:

P is N;
Q is N or C—R$_2$;
V is C—R$_8$;
W is C—R$_9$;
X is C—R$_{10}$;
Y is N;
R$_2$ is hydrogen, halogen, alkyl, alkoxy, or haloalkoxy;
R$_3$, R$_4$ and R$_6$ are hydrogen;
R$_5$ is hydrogen, alkyl, or haloalkyl;
R$_7$ is unsubstituted phenyl or phenyl substituted by one or more of halogen, cyano, SF$_5$, alkyl, haloalkyl, alkoxy, haloalkoxy, alkylthio, haloalkylthio, haloalkylsulfinyl or haloalkylsulfonyl;
R$_8$, R$_9$ and R$_{10}$ are independently of one another hydrogen, halogen, alkyl, or haloalkyl;
Z is C(O); and
a is 1.

In another embodiment, compounds of formula (I) above are compounds wherein:

P is N;
Q is N or C—R$_2$;
V is C—R$_8$;
W is C—R$_9$;
X is C—R$_{10}$;
Y is N;
R$_2$ is hydrogen, halogen, C$_1$-C$_6$-alkyl, C$_1$-C$_6$-alkoxy, or halo-C$_1$-C$_6$-alkoxy;
R$_3$, R$_4$ and R$_6$ are hydrogen;
R$_5$ is hydrogen, C$_1$-C$_6$-alkyl, or halo-C$_1$-C$_6$-alkyl;
R$_7$ is unsubstituted phenyl or phenyl substituted by one or more of halogen, cyano, SF$_5$, C$_1$-C$_6$-alkyl, halo-C$_1$-C$_6$-alkyl, C$_1$-C$_6$-alkoxy, halo-C$_1$-C$_6$-alkoxy, C$_1$-C$_6$-alkylthio, halo-C$_1$-C$_6$-alkylthio, halo-C$_1$-C$_6$-alkylsulfinyl or halo-C$_1$-C$_6$-alkylsulfonyl;
R$_8$, R$_9$ and R$_{10}$ are independently hydrogen, halogen, C$_1$-C$_6$-alkyl, or halo-C$_1$-C$_6$-alkyl;
Z is C(O); and
a is 1.

In still another embodiment, compounds of formula (I) above are compounds wherein:

P is N;
Q is N or C—R$_2$;
V is C—R$_8$;
W is C—R$_9$;
X is C—R$_{10}$;
Y is N;
R$_2$ is hydrogen, Cl, Br, methoxy;
R$_3$, R$_4$ and R$_6$ are hydrogen;
R$_5$ is methyl;
R$_7$ is phenyl substituted by one or more of halogen, cyano, SF$_5$, OCF$_3$ or SCF$_3$;
R$_8$, R$_9$ and R$_{10}$ are independently hydrogen, Cl, Br, I or methyl;
Z is C(O); and
a is 1.

In another embodiment, the invention provides a compound of formula (IA) substantially enriched in an enantiomer, or a pharmaceutically or veterinarily acceptable salt thereof:

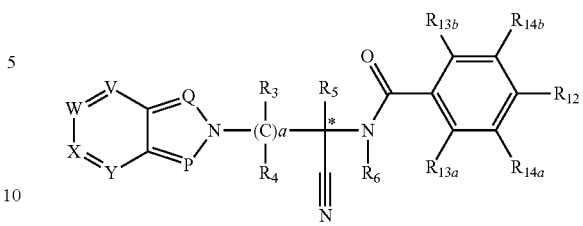

(IA)

wherein:
P, Q, V, W, X, Y and a are as defined for formula (I) above;
R$_3$, R$_4$, R$_5$ are each independently hydrogen, alkyl, or haloalkyl;
R$_6$ is hydrogen, alkyl, alkylcarbonyl, haloalkylcarbonyl, alkoxycarbonyl, haloalkoxycarbonyl, or benzyl that is unsubstituted or independently substituted by one or more of cyano, nitro, halogen, C$_1$-C$_6$-alkyl, C$_3$-C$_7$-cycloalkyl, halo-C$_1$-C$_6$-alkyl, C$_1$-C$_6$-alkylthio, halo-C$_1$-C$_6$-alkylthio, arylthio, C$_1$-C$_6$-alkoxy, C$_3$-C$_7$-cycloalkyloxy, halo-C$_1$-C$_6$-alkoxy, C$_1$-C$_6$-alkylcarbonyl, halo-C$_1$-C$_6$-alkylcarbonyl, C$_1$-C$_6$-alkoxycarbonyl, halo-C$_1$-C$_6$-alkoxycarbonyl, C$_1$-C$_6$-alkylsulfinyl, halo-C$_1$-C$_6$-alkylsulfinyl, C$_1$-C$_6$-alkylsulfonyl, halo-C$_1$-C$_6$-alkylsulfonyl, C$_1$-C$_6$-alkylamino, or di(C$_1$-C$_6$-alkyl)amino; and
R$_{12}$, R$_{13a}$, R$_{13b}$, R$_{14a}$ and R$_{14b}$ are each, independently of one another, cyano, nitro, halogen, alkyl, cycloalkyl, haloalkyl, unsubstituted or substituted aryl, unsubstituted or substituted heteroaryl, unsubstituted or substituted phenoxy, alkylthio, haloalkylthio, arylthio, alkoxy, cycloalkyloxy, haloalkoxy, alkylcarbonyl, haloalkylcarbonyl, alkoxycarbonyl, haloalkoxycarbonyl, alkylsulfinyl, haloalkylsulfinyl, alkylsulfonyl, haloalkylsulfonyl, SF$_5$, amino, alkylamino, di(alkyl)amino, or methylthioamino.

In one embodiment of formula (IA), P is N.
In another embodiment of formula (IA), Q is N.
In still another embodiment of formula (IA), P is N; V is C—R$_8$; W is CR$_9$; X is C—R$_{10}$ and Y is CR$_{11}$.
In yet another embodiment of formula (IA), P and V are each N; W is CR$_9$; X is C—R$_{10}$ and Y is CR$_{11}$.
In another embodiment of formula (IA), the invention provides a compound wherein:

P is N;
Q is N or C—R$_2$;
V is N or C—R$_8$;
W is N or C—R$_9$;
X is N or C—R$_{10}$;
Y is N or C—R$_{11}$;
R$_3$, R$_4$ and R$_6$ are H;
R$_2$, R$_8$, R$_9$, R$_{10}$ and R$_{11}$ are each independently hydrogen, amino, amido, cyano, nitro, halogen, C$_1$-C$_6$-alkyl, C$_2$-C$_6$-alkenyl, C$_2$-C$_6$-akynyl, C$_3$-C$_7$-cycloalkyl, hydroxy-C$_1$-C$_6$-alkyl, halo-C$_1$-C$_6$-alkyl, C$_1$-C$_6$-alkylthio, halo-C$_1$-C$_6$-alkylthio, C$_1$-C$_6$-alkoxy, phenoxy, C$_1$-C$_6$-alkoxy-C$_1$-C$_6$-alkoxy, C$_3$-C$_7$-cycloalkyloxy, halo-C$_1$-C$_6$-alkoxy, C$_1$-C$_6$-alkylcarbonyl, halo-C$_1$-C$_6$-alkylcarbonyl, C$_1$-C$_6$-alkoxycarbonyl, halo-C$_1$-C$_6$-alkoxycarbonyl, C$_1$-C$_6$-alkylsulfinyl, halo-C$_1$-C$_6$-alkylsulfinyl, C$_1$-C$_6$-alkylsulfonyl, halo-C$_1$-C$_6$-alkylsulfonyl, C$_1$-C$_6$-alkylamino, di(C$_1$-C$_6$-alkyl)amino, C$_1$-C$_6$-alkylcarboxylamino, C$_1$-C$_6$-alkylamino-C$_1$-C$_6$-alkoxy, di-C$_1$-C$_6$-alkylamino-C$_1$-C$_6$-alkoxy, C$_1$-C$_6$-alkylamino C$_1$-C$_6$-alkyl, di-C$_1$-C$_6$-alkylamino C$_1$-C$_6$-alkyl, amino-C$_1$-C$_6$-alkyl, formyl, —C(O)OH, unsubstituted or substituted aryl, unsubstituted or substituted arylthio, or unsubstituted or substituted aryloxy including phenoxy, wherein the substituents are independently cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, or halo-$C_1$-$C_6$-alkylsulfonyl;

$R_5$ is methyl or $C_1$-$C_3$-alkyl;

$R_{12}$ is cyano, nitro, halogen, alkyl, cycloalkyl, haloalkyl, unsubstituted or substituted aryl, unsubstituted or substituted heteroaryl, unsubstituted or substituted phenoxy, alkylthio, haloalkylthio, arylthio, alkoxy, cycloalkyloxy, haloalkoxy, alkylcarbonyl, haloalkylcarbonyl, alkylsulfinyl, haloalkylsulfinyl, alkylsulfonyl, haloalkylsulfonyl, $SF_5$, amino, alkylamino, di(alkyl)amino, or methylthioamino;

$R_{13a}$, $R_{13b}$, $R_{14a}$, and $R_{14b}$ are each independently hydrogen, cyano, nitro, halogen, $SF_5$, $C_1$-$C_6$-alkyl, halo-$C_1$-$C_6$-alkyl, $C_1$-$C_6$-alkoxy, $C_1$-$C_6$-alkylthio, halo-$C_1$-$C_6$-alkoxy, or halo-$C_1$-$C_6$-alkylthio; and a is 1.

In another embodiment, the invention provides a compound of formula (IA), wherein:
P is N;
$R_3$, $R_4$ and $R_6$ are each hydrogen;
$R_5$ is methyl;
$R_{12}$ is halogen, cyano, $SF_5$, $OCF_3$ or $SCF_3$; and
$R_{14a}$ and $R_{14b}$ are H or halogen.

In another embodiment, the invention provides a compound of formula (IA), wherein:
P is N;
$R_3$, $R_4$ and $R_6$ are each H;
$R_5$ is methyl;
$R_{12}$ is halogen, cyano, $SF_5$, $OCF_3$ or $SCF_3$;
$R_{13a}$ and $R_{13b}$ are hydrogen; and
$R_{14a}$ and $R_{14b}$ are H or halogen.

In another embodiment, the invention provides a compound of formula (IB) substantially enriched in an enantiomer, or a pharmaceutically or veterinarily acceptable salt thereof:

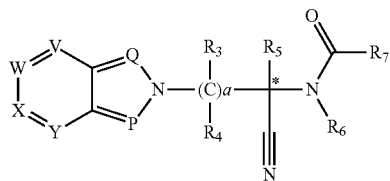

(IB)

wherein:
P, Q, V, W, X, Y and a are as defined for formula (I) above;
$R_3$, $R_4$, $R_5$ are each independently hydrogen, alkyl, or haloalkyl;
$R_6$ is hydrogen, alkyl, cycloalkyl, alkylcarbonyl, haloalkylcarbonyl, alkoxycarbonyl, haloalkoxycarbonyl, or benzyl that is unsubstituted or substituted independently by one or more of cyano, nitro, halogen, $C_1$-$C_6$-alkyl, $C_3$-$C_7$-cycloalkyl, halo-$C_1$-$C_6$-alkyl, $C_1$-$C_6$-alkylthio, halo-$C_1$-$C_6$-alkylthio, arylthio, $C_1$-$C_6$-alkoxy, $C_3$-$C_7$-cycloalkyloxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, amino, $C_1$-$C_6$-alkylamino, or di($C_1$-$C_6$-alkyl)amino;

$R_7$ is a unsubstituted or substituted heterocyclyl or unsubstituted or substituted heteroaryl group, wherein the substituted heterocyclyl or substituted heteroaryl groups are independently substituted by one or more of cyano, nitro, halogen, alkyl, cycloalkyl, unsubstituted or substituted aryl, unsubstituted or substituted heteroaryl, unsubstituted or substituted phenoxy, haloalkyl, alkylthio, haloalkylthio, arylthio, alkoxy, cycloalkyloxy, haloalkoxy, alkylcarbonyl, haloalkylcarbonyl, alkoxycarbonyl, haloalkoxycarbonyl, alkylsulfinyl, haloalkylsulfinyl, alkylsulfonyl, haloalkylsulfonyl, $SF_5$, amino, alkylamino, di(alkyl)amino, or methylthioamino.

In one embodiment of formula (IB), P is N.
In another embodiment of formula (IB), Q is N.
In still another embodiment of formula (IB), P is N; V is C—$R_8$; W is $CR_9$; X is C—$R_{10}$ and Y is $CR_{11}$.
In yet another embodiment of formula (IB), P and V are each N; W is $CR_9$; X is C—$R_{10}$ and Y is $CR_{11}$.
In another embodiment of formula (IB), the invention provides a compound wherein:
P is N;
Q is N or C—$R_2$;
V is N or C—$R_8$;
W is N or C—$R_9$;
X is N or C—$R_{10}$;
Y is N or C—$R_{11}$;
$R_3$, $R_4$ and $R_6$ are H;
$R_2$, $R_8$, $R_9$, $R_{10}$ and $R_{11}$ are independently hydrogen, amino, amido, cyano, nitro, halogen, $C_1$-$C_6$-alkyl, $C_2$-$C_6$-alkenyl, $C_2$-$C_6$-akynyl, $C_3$-$C_7$-cycloalkyl, hydroxy-$C_1$-$C_6$-alkyl, halo-$C_1$-$C_6$-alkyl, $C_1$-$C_6$-alkylthio, halo-$C_1$-$C_6$-alkylthio, $C_1$-$C_6$-alkoxy, phenoxy, $C_1$-$C_6$-alkoxy-$C_1$-$C_6$-alkoxy, $C_3$-$C_7$-cycloalkyloxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $C_1$-$C_6$-alkylamino, di($C_1$-$C_6$-alkyl)amino, $C_1$-$C_6$-alkylcarboxylamino, $C_1$-$C_6$-alkylamino-$C_1$-$C_6$-alkoxy, di-$C_1$-$C_6$-alkylamino-$C_1$-$C_6$-alkoxy, $C_1$-$C_6$-alkylamino-$C_1$-$C_6$-alkyl, di-$C_1$-$C_6$-alkylamino-$C_1$-$C_6$-alkyl, amino-$C_1$-$C_6$-alkyl, formyl, —C(O)OH, unsubstituted or substituted aryl, unsubstituted or substituted arylthio, or unsubstituted or substituted aryloxy including phenoxy, wherein the substituents may each be independent of one another cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, or halo-$C_1$-$C_6$-alkylsulfonyl;

$R_5$ is methyl or $C_1$-$C_3$-alkyl;

$R_7$ is unsubstituted or substituted pyridyl, piridazinyl, pyrimidinyl, triazinyl, pyrrolyl, quinolinyl, isoquinolinyl, quinazolinyl, quinoxalinnyl, furanyl, furyl, imidazolyl, oxazolyl, isoxazolyl, isothiazolyl, pyrazolyl, benzofuranyl, benzothienyl, pyrrolidinyl, oxetanyl, pyrazolinyl, imidazolinyl, imidazolidinyl, oxazolidinyl, isoxazolinyl, thiazolyl, thiadiazolyl, thiazolidinyl, isothiazolidinyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, indolyl, benzothiazolyl, benzoxazolyl, benzodioxolyl, benzothienyl, quinuclidinyl, tetra-hydroisoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), or tetrahydroquinolinyl; and a is 1.

In another embodiment, the invention provides a compound of formula (IB), wherein:

P is N;

Q is N or C—$R_2$;

V is N or C—$R_8$;

W is N or C—$R_9$;

X is N or C—$R_{10}$;

Y is N or C—$R_{11}$;

$R_3$, $R_4$ and $R_6$ are each H;

$R_5$ is methyl;

$R_7$ is pyridyl, piridazinyl, pyrimidinyl, triazinyl, pyrrolyl, quinolinyl, isoquinolinyl, quinazolinyl, quinoxalinnyl, furanyl, thienyl, furyl, imidazolyl, oxazolyl, isoxazolyl, isothiazolyl, pyrazolyl, benzofuranyl, or benzothienyl; and $R_2$, $R_8$, $R_9$, $R_{10}$ and $R_{11}$ are independently of one another hydrogen, amino, amido, cyano, nitro, halogen, $C_1$-$C_6$-alkyl, halo-$C_1$-$C_6$-alkylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, amino, $C_1$-$C_6$-alkylamino, or di($C_1$-$C_6$-alkyl)amino.

In another embodiment, the invention provides a compound of formula (IB), wherein:

P is N;

Q is N or C—$R_2$;

V is N or C—$R_8$;

W is N or C—$R_9$;

X is N or C—$R_{10}$;

Y is N or C—$R_{11}$;

$R_3$, $R_4$ and $R_6$ are each H;

$R_5$ is methyl;

$R_7$ is pyrrolidinyl, oxetanyl, pyrazolinyl, imidazolinyl, imidazolidinyl, oxazolidinyl, isoxazolinyl, thiazolyl, thiadiazolyl, thiazolidinyl, isothiazolidinyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, or triazolyl; and $R_2$, $R_8$, $R_9$, $R_{10}$ and $R_{11}$ are independently of one another hydrogen, amino, amido, cyano, nitro, halogen, $C_1$-$C_6$-alkyl, $C_1$-$C_6$-alkenyl, halo-$C_1$-$C_6$-alkyl, $C_1$-$C_6$-alkylthio, halo-$C_1$-$C_6$-alkylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, amino, $C_1$-$C_6$-alkylamino, or di($C_1$-$C_6$-alkyl)amino.

In still another embodiment, the invention provides a compound of formula (IC) substantially enriched in an enantiomer, or a pharmaceutically or veterinarily acceptable salt thereof:

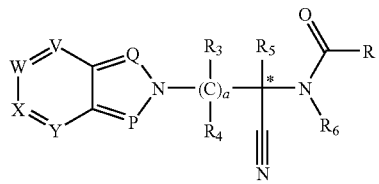

(IC)

wherein:

P, Q, V, W, X, Y and a are as defined for formula (I) above;

$R_3$, $R_4$, $R_5$ are each independently hydrogen, alkyl, or haloalkyl;

$R_6$ is hydrogen, alkyl, cycloalkyl, alkylcarbonyl, haloalkylcarbonyl, alkoxycarbonyl, haloalkoxycarbonyl, or benzyl that is unsubstituted or substituted independently by one or more of cyano, nitro, halogen, $C_1$-$C_6$-alkyl, $C_3$-$C_7$-cycloalkyl, halo-$C_1$-$C_6$-alkyl, $C_1$-$C_6$-alkylthio, halo-$C_1$-$C_6$-alkylthio, arylthio, $C_1$-$C_6$-alkoxy, $C_3$-$C_7$-cycloalkyloxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $C_1$-$C_6$-alkylamino, or di($C_1$-$C_6$-alkyl)amino; and R is unsubstituted or substituted alkyl, unsubstituted or substituted cycloalkyl, unsubstituted or substituted alkenyl, unsubstituted or substituted alkynyl, haloalkyl, or halocycloalkyl.

In one embodiment of formula (IC), P is N.

In another embodiment of formula (IC), Q is N.

In still another embodiment of formula (IC), P is N; V is C—$R_8$; W is $CR_9$; X is C—$R_{10}$ and Y is $CR_{11}$.

In yet another embodiment of formula (IC), P and V are each N; W is $CR_9$; X is C—$R_{10}$ and Y is $CR_{11}$.

In another embodiment of formula (IC), the invention provides a compound wherein:

P is N;

Q is N or C—$R_2$;

V is N or C—$R_8$;

W is N or C—$R_9$;

X is N or C—$R_{10}$;

Y is N or C—$R_{11}$;

$R_3$, $R_4$ and $R_6$ are H;

$R_2$, $R_8$, $R_9$, $R_{10}$ and $R_{11}$ either together or independently of one another, are hydrogen, amino, amido, cyano, nitro, halogen, $C_1$-$C_6$-alkyl, $C_2$-$C_6$-alkenyl, $C_2$-$C_6$-akynyl, $C_3$-$C_7$-cycloalkyl, hydroxy-$C_1$-$C_6$-alkyl, halo-$C_1$-$C_6$-alkyl, $C_1$-$C_6$-alkylthio, halo-$C_1$-$C_6$-alkylthio, $C_1$-$C_6$-alkoxy, phenoxy, $C_1$-$C_6$-alkoxy-$C_1$-$C_6$-alkoxy, $C_3$-$C_7$-cycloalkyloxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $C_1$-$C_6$-alkylamino, di($C_1$-$C_6$-alkyl)amino, $C_1$-$C_6$-alkylcarboxylamino, $C_1$-$C_6$-alkylamino-$C_1$-$C_6$-alkoxy, di-$C_1$-$C_6$-alkylamino-$C_1$-$C_6$-alkoxy, $C_1$-$C_6$-alkylamino $C_1$-$C_6$-alkyl, di-$C_1$-$C_6$-alkylamino-$C_1$-$C_6$-alkyl, amino-$C_1$-$C_6$-alkyl, formyl, —C(O)OH, unsubstituted or substituted aryl, unsubstituted or substituted arylthio, or unsubstituted or substituted aryloxy including phenoxy, wherein the substituents may each be independent of one another cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, or halo-$C_1$-$C_6$-alkylsulfonyl;

$R_5$ is methyl or $C_1$-$C_3$-alkyl;

R is unsubstituted or substituted $C_1$-$C_6$-alkyl, unsubstituted or substituted $C_3$-$C_7$-cycloalkyl, unsubstituted or substituted $C_2$-$C_6$-alkenyl, unsubstituted or substituted $C_2$-$C_6$-alkynyl, halo-$C_1$-$C_6$-alkyl, or halo-$C_3$-$C_8$-cycloalkyl; and a is 1.

In another embodiment, the invention provides a compound of formula (IC), wherein:

P is N;
Q is N or C—$R_2$;
V is N or C—$R_8$;
W is N or C—$R_9$;
X is N or C—$R_{10}$;
Y is N or C—$R_{11}$;
$R_3$, $R_4$ and $R_6$ are each H;
$R_5$ is methyl;
R is methyl, ethyl, propyl, butyl, sec-butyl, cyclopropyl, cyclobutyl, cyclopentyl, $CF_3$, or $C_2F_5$; and $R_2$, $R_8$, $R_9$, $R_{10}$ and $R_{11}$ are independently of one another hydrogen, amino, amido, cyano, nitro, halogen, $C_1$-$C_6$-alkyl, halo-$C_1$-$C_6$-alkylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, amino, $C_1$-$C_6$-alkylamino, or di($C_1$-$C_6$-alkyl)amino.

In another embodiment, the invention provides a compound of formula (ID) substantially enriched in an enantiomer, or a pharmaceutically or veterinarily acceptable salt thereof:

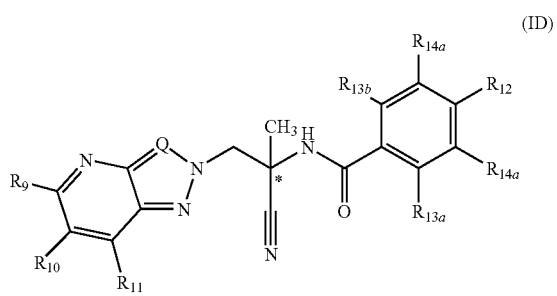

wherein:

Q, $R_9$, $R_{10}$ and $R_{11}$ are as defined for formula (I) above, and $R_{12}$, $R_{13a}$, $R_{13b}$, $R_{14a}$ and $R_{14b}$ are each, independently of one another, cyano, nitro, halogen, alkyl, cycloalkyl, haloalkyl, unsubstituted or substituted aryl, unsubstituted or substituted heteroaryl, unsubstituted or substituted aryloxy, unsubstituted or substituted arylthio, alkylthio, haloalkylthio, alkoxy, cycloalkyloxy, haloalkoxy, alkylcarbonyl, haloalkylcarbonyl, alkoxycarbonyl, haloalkoxycarbonyl, alkylsulfinyl, haloalkylsulfinyl, alkylsulfonyl, haloalkylsulfonyl, $SF_5$, amino, alkylamino, di(alkyl)amino, or methylthioamino.

In one embodiment of formula (ID), Q is N.

In another embodiment of formula (ID), Q is C—$R_2$.

In another embodiment of formula (ID), the invention provides a compound wherein:

$R_2$, $R_9$, $R_{10}$ and $R_{11}$ either together or independently of one another, are hydrogen, amino, amido, cyano, nitro, halogen, $C_1$-$C_6$-alkyl, $C_1$-$C_6$-alkenyl, halo-$C_1$-$C_6$-alkyl, $C_1$-$C_6$-alkylthio, halo-$C_1$-$C_6$-alkylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, amino, $C_1$-$C_6$-alkylamino, or di($C_1$-$C_6$-alkyl)amino;

$R_{12}$ is cyano, nitro, halogen, alkyl, cycloalkyl, haloalkyl, unsubstituted or substituted aryl, unsubstituted or substituted heteroaryl, unsubstituted or substituted phenoxy, alkylthio, haloalkylthio, arylthio, alkoxy, cycloalkyloxy, haloalkoxy, alkylcarbonyl, haloalkylcarbonyl, alkoxycarbonyl, haloalkoxycarbonyl, alkylsulfinyl, haloalkylsulfinyl, alkylsulfonyl, haloalkylsulfonyl, $SF_5$, amino, alkylamino, di(alkyl)amino, or methylthioamino; and $R_{13a}$, $R_{13b}$, $R_{14a}$, and $R_{14b}$ are each independently hydrogen, cyano, nitro, halogen, $SF_5$, $C_1$-$C_6$-alkyl, halo-$C_1$-$C_6$-alkyl, $C_1$-$C_6$-alkoxy, $C_1$-$C_6$-alkylthio, halo-$C_1$-$C_6$-alkoxy, or halo-$C_1$-$C_6$-alkylthio; and a is 1.

In another embodiment, the invention provides a compound of formula (ID), wherein:

Q is C—$R_2$;

$R_2$, $R_9$, $R_{10}$ and $R_{11}$ either together or independently of one another, are hydrogen, amino, amido, cyano, nitro, halogen, $C_1$-$C_6$-alkyl, $C_1$-$C_6$-alkenyl, halo-$C_1$-$C_6$-alkyl, $C_1$-$C_6$-alkylthio, halo-$C_1$-$C_6$-alkylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, amino, $C_1$-$C_6$-alkylamino, or di($C_1$-$C_6$-alkyl)amino;

$R_{12}$ is halogen, cyano, $SF_5$, $OCF_3$ or $SCF_3$;

$R_{13a}$ and $R_{13b}$ are hydrogen or halogen; and $R_{14a}$ and $R_{14b}$ are hydrogen.

In another embodiment, the invention provides a compound of formula (ID), wherein:

Q is N;

$R_9$, $R_{10}$ and $R_{11}$ either together or independently of one another, are hydrogen, amino, amido, cyano, nitro, halogen, $C_1$-$C_6$-alkyl, $C_1$-$C_6$-alkenyl, halo-$C_1$-$C_6$-alkyl, $C_1$-$C_6$-alkylthio, halo-$C_1$-$C_6$-alkylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, amino, $C_1$-$C_6$-alkylamino, or di($C_1$-$C_6$-alkyl)amino;

$R_{12}$ is halogen, cyano, $SF_5$, $OCF_3$ or $SCF_3$;

$R_{13a}$ and $R_{13b}$ are hydrogen; and $R_{14a}$ and $R_{14b}$ are H or halogen.

In another embodiment, the invention provides a compound of formula (IE) substantially enriched in an enantiomer, or a pharmaceutically or veterinarily acceptable salt thereof:

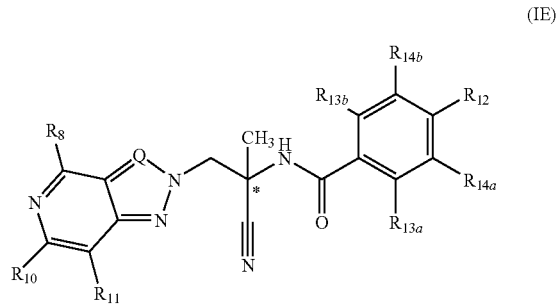

wherein:

Q, $R_9$, $R_{10}$ and $R_{11}$ are as defined for formula (I) above, and $R_{12}$, $R_{13a}$, $R_{13b}$, $R_{14a}$ and $R_{14b}$ are each, independently of one another, cyano, nitro, halogen, alkyl, cycloalkyl, haloalkyl, unsubstituted or substituted aryl, unsubstituted or substituted heteroaryl, unsubstituted or substituted aryloxy, unsubstituted or substituted arylthio, alkylthio, haloalkylthio, alkoxy, cycloalkyloxy, haloalkoxy, alkylcarbonyl, haloalkylcarbonyl, alkoxycarbonyl, haloalkoxycarbonyl, alkylsulfinyl, haloalkylsulfinyl, alkylsulfonyl, haloalkylsulfonyl, $SF_5$, amino, alkylamino, di(alkyl)amino, or methylthioamino.

In one embodiment of formula (IE), Q is N.

In another embodiment of formula (IE), Q is C—$R_2$.

In another embodiment of formula (IE), the invention provides a compound wherein:

$R_2$, $R_8$, $R_{10}$ and $R_{11}$ either together or independently of one another, are hydrogen, amino, amido, cyano, nitro, halogen, $C_1$-$C_6$-alkyl, $C_1$-$C_6$-alkenyl, halo-$C_1$-$C_6$-alkyl, $C_1$-$C_6$-alkylthio, halo-$C_1$-$C_6$-alkylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, amino, $C_1$-$C_6$-alkylamino, or di($C_1$-$C_6$-alkyl)amino;

$R_{12}$ is cyano, nitro, halogen, alkyl, cycloalkyl, haloalkyl, unsubstituted or substituted aryl, unsubstituted or substituted heteroaryl, unsubstituted or substituted phenoxy, alkylthio, haloalkylthio, arylthio, alkoxy, cycloalkyloxy, haloalkoxy, alkylcarbonyl, haloalkylcarbonyl, alkoxycarbonyl, haloalkoxycarbonyl, alkylsulfinyl, haloalkylsulfinyl, alkylsulfonyl, haloalkylsulfonyl, $SF_5$, amino, alkylamino, di(alkyl)amino, or methylthioamino; and $R_{13a}$, $R_{13b}$, $R_{14a}$, and $R_{14b}$ are each independently hydrogen, cyano, nitro, halogen, $SF_5$, $C_1$-$C_6$-alkyl, halo-$C_1$-$C_6$-alkyl, $C_1$-$C_6$-alkoxy, $C_1$-$C_6$-alkylthio, halo-$C_1$-$C_6$-alkoxy, or halo-$C_1$-$C_6$-alkylthio; and a is 1.

In another embodiment, the invention provides a compound of formula (IE), wherein:

Q is C—$R_2$, $R_2$, $R_8$, $R_{10}$ and $R_{11}$ are each independently of one another, hydrogen, amino, amido, cyano, nitro, halogen, $C_1$-$C_6$-alkyl, $C_1$-$C_6$-alkenyl, halo-$C_1$-$C_6$-alkyl, $C_1$-$C_6$-alkylthio, halo-$C_1$-$C_6$-alkylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, amino, $C_1$-$C_6$-alkylamino, or di($C_1$-$C_6$-alkyl)amino;

$R_{12}$ is halogen, cyano, $SF_5$, $OCF_3$ or $SCF_3$;

$R_{13a}$ and $R_{13b}$ are independently hydrogen or halogen; and $R_{14a}$ and $R_{14b}$ are hydrogen.

In another embodiment, the invention provides a compound of formula (IE), wherein:

Q is N;

$R_8$, $R_{10}$ and $R_{11}$ are independently of one another hydrogen, amino, amido, cyano, nitro, halogen, $C_1$-$C_6$-alkyl, $C_1$-$C_6$-alkenyl, halo-$C_1$-$C_6$-alkyl, $C_1$-$C_6$-alkylthio, halo-$C_1$-$C_6$-alkylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, amino, $C_1$-$C_6$-alkylamino, or di($C_1$-$C_6$-alkyl)amino;

$R_{12}$ is halogen, cyano, $SF_5$, $OCF_3$ or $SCF_3$;

$R_{13a}$ and $R_{13b}$ are hydrogen; and $R_{14a}$ and $R_{14b}$ are independently hydrogen or halogen.

In another embodiment, the invention provides a compound of formula (IF) substantially enriched in an enantiomer, or a pharmaceutically or veterinarily acceptable salt thereof:

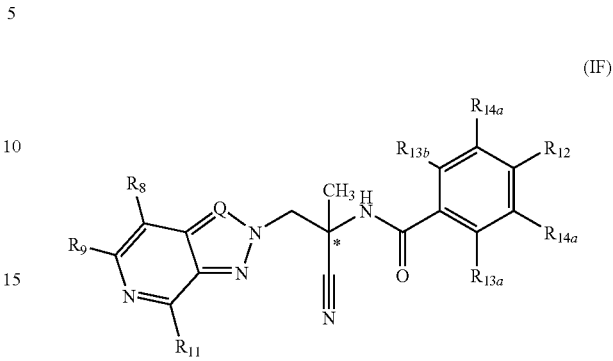

(IF)

wherein:

Q, $R_8$, $R_9$ and $R_{11}$ are as defined for formula (I) above, and $R_{12}$, $R_{13a}$, $R_{13b}$, $R_{14a}$ and $R_{14b}$ are each, independently of one another, cyano, nitro, halogen, alkyl, cycloalkyl, haloalkyl, unsubstituted or substituted aryl, unsubstituted or substituted heteroaryl, unsubstituted or substituted aryloxy, unsubstituted or substituted arylthio, alkylthio, haloalkylthio, alkoxy, cycloalkyloxy, haloalkoxy, alkylcarbonyl, haloalkylcarbonyl, alkoxycarbonyl, haloalkoxycarbonyl, alkylsulfinyl, haloalkylsulfinyl, alkylsulfonyl, haloalkylsulfonyl, $SF_5$, alkylamino, amino, di(alkyl)amino, or methylthioamino.

In one embodiment of formula (IF), Q is N.

In another embodiment of formula (IF), Q is C—$R_2$.

In another embodiment of formula (IF), the invention provides a compound wherein:

$R_2$, $R_8$, $R_9$ and $R_{11}$ either together or independently of one another, are hydrogen, amino, amido, cyano, nitro, halogen, $C_1$-$C_6$-alkyl, $C_1$-$C_6$-alkenyl, halo-$C_1$-$C_6$-alkyl, $C_1$-$C_6$-alkylthio, halo-$C_1$-$C_6$-alkylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, amino, $C_1$-$C_6$-alkylamino, or di($C_1$-$C_6$-alkyl)amino;

$R_{12}$ is cyano, nitro, halogen, alkyl, cycloalkyl, haloalkyl, unsubstituted or substituted aryl, unsubstituted or substituted heteroaryl, unsubstituted or substituted phenoxy, alkylthio, haloalkylthio, arylthio, alkoxy, cycloalkyloxy, haloalkoxy, alkylcarbonyl, haloalkylcarbonyl, alkoxycarbonyl, haloalkoxycarbonyl, alkylsulfinyl, haloalkylsulfinyl, alkylsulfonyl, haloalkylsulfonyl, $SF_5$, amino, alkylamino, amino, di(alkyl)amino, or methylthioamino;

$R_{13a}$, $R_{13b}$, $R_{14a}$, and $R_{14b}$ are each independently hydrogen, cyano, nitro, halogen, $SF_5$, $C_1$-$C_6$-alkyl, halo-$C_1$-$C_6$-alkyl, $C_1$-$C_6$-alkoxy, $C_1$-$C_6$-alkylthio, halo-$C_1$-$C_6$-alkoxy, or halo-$C_1$-$C_6$-alkylthio; and a is 1.

In another embodiment, the invention provides a compound of formula (IF), wherein:

Q is C—$R_2$;

$R_2$, $R_8$, $R_9$ and $R_{11}$ either together or independently of one another, are hydrogen, amino, amido, cyano, nitro, halogen, $C_1$-$C_6$-alkyl, $C_1$-$C_6$-alkenyl, halo-$C_1$-$C_6$-alkyl, $C_1$-$C_6$-alkylthio, halo-$C_1$-$C_6$-alkylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$- alkylsulfinyl, halo-$C_1$-$C_6$-alkylsulfinyl, $C_1$-$C_6$-alkylsulfonyl, halo-$C_1$-$C_6$-alkylsulfonyl, amino, $C_1$-$C_6$-alkylamino, or di($C_1$-$C_6$-alkyl)amino;

$R_{12}$ is halogen, cyano, $SF_5$, $OCF_3$ or $SCF_3$;

$R_{13a}$ and $R_{13b}$ are independently hydrogen or halogen; and $R_{14a}$ and $R_{14b}$ are hydrogen.

In another embodiment, the invention provides a compound of formula (IF), wherein:

Q is N;

$R_8$, $R_9$ and $R_{11}$ are independently of one another hydrogen, amino, amido, cyano, nitro, halogen, $C_1$-$C_6$-alkyl, $C_1$-$C_6$-alkenyl, halo-$C_1$-$C_6$-alkyl, $C_1$-$C_6$-alkylthio, halo-$C_1$-$C_6$-alkylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, amino, $C_1$-$C_6$-alkylamino, or di($C_1$-$C_6$-alkyl)amino;

$R_{12}$ is halogen, cyano, $SF_5$, $OCF_3$ or $SCF_3$;

$R_{13a}$ and $R_{13b}$ are hydrogen; and $R_{14a}$ and $R_{14b}$ are independently hydrogen or halogen.

In yet another embodiment, the invention provides a compound of formula (IG) substantially enriched in an enantiomer, or a pharmaceutically or veterinarily acceptable salt thereof:

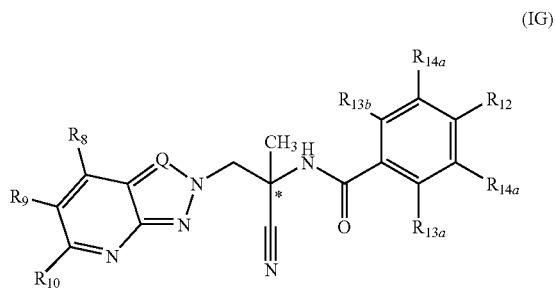

(IG)

wherein:

Q, $R_8$, $R_9$ and $R_{10}$ are as defined for formula (I) above, and $R_{12}$, $R_{13a}$, $R_{13b}$, $R_{14a}$ and $R_{14b}$ are each, independently of one another, cyano, nitro, halogen, alkyl, cycloalkyl, haloalkyl, unsubstituted or substituted aryl, unsubstituted or substituted heteroaryl, unsubstituted or substituted aryloxy, unsubstituted or substituted arylthio, alkylthio, haloalkylthio, alkoxy, cycloalkyloxy, haloalkoxy, alkylcarbonyl, haloalkylcarbonyl, alkoxycarbonyl, haloalkoxycarbonyl, alkylsulfinyl, haloalkylsulfinyl, alkylsulfonyl, haloalkylsulfonyl, $SF_5$, amino, alkylamino, di(alkyl)amino, or methylthioamino.

In one embodiment of formula (IG), Q is N.

In another embodiment of formula (IG), Q is C—$R_2$.

In another embodiment of formula (IG), the invention provides a compound wherein:

$R_2$, $R_8$, $R_9$ and $R_{10}$ either together or independently of one another, are hydrogen, amino, amido, cyano, nitro, halogen, $C_1$-$C_6$-alkyl, $C_1$-$C_6$-alkenyl, halo-$C_1$-$C_6$-alkyl, $C_1$-$C_6$-alkylthio, halo-$C_1$-$C_6$-alkylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, amino, $C_1$-$C_6$-alkylamino, or di($C_1$-$C_6$-alkyl)amino;

$R_{12}$ is cyano, nitro, halogen, alkyl, cycloalkyl, haloalkyl, unsubstituted or substituted aryl, unsubstituted or substituted heteroaryl, unsubstituted or substituted phenoxy, alkylthio, haloalkylthio, arylthio, alkoxy, cycloalkyloxy, haloalkoxy, alkylcarbonyl, haloalkylcarbonyl, alkoxycarbonyl, haloalkoxycarbonyl, alkylsulfinyl, haloalkylsulfinyl, alkylsulfonyl, haloalkylsulfonyl, $SF_5$, amino, alkylamino, di(alkyl)amino, or methylthioamino;

$R_{13a}$, $R_{13b}$, $R_{14a}$, and $R_{14b}$ are each independently hydrogen, cyano, nitro, halogen, $SF_5$, $C_1$-$C_6$-alkyl, halo-$C_1$-$C_6$-alkyl, $C_1$-$C_6$-alkoxy, $C_1$-$C_6$-alkylthio, halo-$C_1$-$C_6$-alkoxy, or halo-$C_1$-$C_6$-alkylthio; and a is 1.

In another embodiment, the invention provides a compound of formula (IG), wherein:

Q is C—$R_2$, $R_2$, $R_8$, $R_9$ and $R_{10}$ either together or independently of one another, are hydrogen, amino, amido, cyano, nitro, halogen, $C_1$-$C_6$-alkyl, $C_1$-$C_6$-alkenyl, halo-$C_1$-$C_6$-alkyl, $C_1$-$C_6$-alkylthio, halo-$C_1$-$C_6$-alkylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, amino, $C_1$-$C_6$-alkylamino, or di($C_1$-$C_6$-alkyl)amino;

$R_{12}$ is halogen, cyano, $SF_5$, $OCF_3$ or $SCF_3$;

$R_{13a}$ and $R_{13b}$ are hydrogen or halogen; and $R_{14a}$ and $R_{14b}$ are hydrogen.

In another embodiment, the invention provides a compound of formula (IG), wherein:

Q is N;

$R_8$, $R_9$ and $R_{10}$ either together or independently of one another, are hydrogen, amino, amido, cyano, nitro, halogen, $C_1$-$C_6$-alkyl, halo-$C_1$-$C_6$-alkylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, amino, $C_1$-$C_6$-alkylamino, or di($C_1$-$C_6$-alkyl)amino;

$R_{12}$ is halogen, cyano, $SF_5$, $OCF_3$ or $SCF_3$;

$R_{13a}$ and $R_{13b}$ are hydrogen; and $R_{14a}$ and $R_{14b}$ are H or halogen.

A second aspect of the invention provides novel aryloazol-2-yl-cyanoethylamino pentafluorothiobenzamide derivatives of formula (IH) either enriched in an enantiomer or in racemic form:

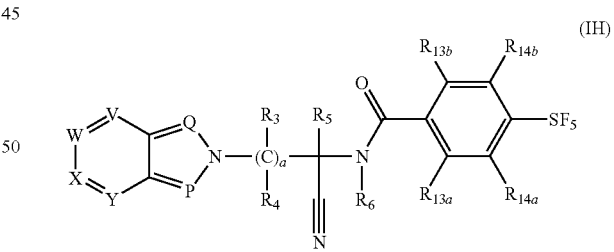

(IH)

Wherein:

P, Q, V, W, X, Y, $R_3$, $R_4$, $R_5$, $R_6$, and a are as defined above for formula (I); and $R_{13a}$, $R_{13b}$, $R_{14a}$ and $R_{14b}$ are each, independently of one another, cyano, nitro, halogen, alkyl, cycloalkyl, haloalkyl, unsubstituted or substituted aryl, unsubstituted or substituted heteroaryl, unsubstituted or substituted aryloxy including phenoxy, unsubstituted or substituted arylthio, alkylthio, haloalkylthio, alkoxy, cycloalkyloxy, haloalkoxy, alkylcarbonyl, haloalkylcarbonyl, alkoxycarbonyl, haloalkoxycarbonyl, alkylsulfinyl, haloalkylsulfinyl, alkylsulfonyl, haloalkylsulfonyl, $SF_5$, amino, alkylamino, di(alkyl)amino, or methylthioamino.

In one embodiment of formula (IH), P is N and Q is C—$R_2$ and V, W, X, Y, $R_2$, $R_3$, $R_4$, $R_5$, $R_6$, and a are as defined for formula (I) above. In another embodiment, P is N and Q is N, and V, W, X, Y, $R_3$, $R_4$, $R_5$, $R_6$, and a are as defined for formula (I) above.

In another embodiment of formula (IH), P and Q are N, V is N, and W, X, Y, $R_3$, $R_4$, $R_5$, $R_6$, and a are as defined for formula (I) above. In still another embodiment of formula (I), P is N, Q is C—$R_2$, V is N, and W, X, Y, $R_2$, $R_3$, $R_4$, $R_5$, $R_6$, and a are as defined for formula (I) above.

In another embodiment of formula (IH), P and Q are N, W is N, and V, X, Y, $R_3$, $R_4$, $R_5$, $R_6$, and a are as defined for formula (I) above. In yet another embodiment of formula (I), P is N, Q is C—$R_2$, W is N, and V, X, Y, $R_2$, $R_3$, $R_4$, $R_5$, $R_6$, and a are as defined for formula (I) above.

In another embodiment of formula (IH), P and Q are N, X is N, and V, W, Y, $R_3$, $R_4$, $R_5$, $R_6$, and a are as defined for formula (I) above. In another embodiment of formula (IH), P is N, Q is $CR_2$, X is N, and V, W, Y, $R_2$, $R_3$, $R_4$, $R_5$, $R_6$, and a are as defined for formula (I) above.

In another embodiment of formula (IH), P and Q are N, Y is N, and V, W, X, $R_3$, $R_4$, $R_5$, $R_6$, and a are as defined for formula (I) above. In another embodiment of formula (IH), P is N, Q is $CR_2$, Y is N, and V, W, X, $R_2$, $R_3$, $R_4$, $R_5$, $R_6$, and a are as defined for formula (I) above.

In another embodiment of formula (IH), the invention provides a compound wherein:

$R_2$, $R_8$, $R_9$, $R_{10}$ and $R_{11}$ are independently of one another hydrogen, amino, amido, cyano, nitro, halogen, $C_1$-$C_6$-alkyl, $C_3$-$C_7$-cycloalkyl, $C_1$-$C_6$-alkenyl, halo-$C_1$-$C_6$-alkyl, $C_1$-$C_6$-alkylthio, halo-$C_1$-$C_6$-alkylthio, $C_1$-$C_6$-alkoxy, $C_3$-$C_7$-cycloalkyloxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, amino, $C_1$-$C_6$-alkylamino, or di($C_1$-$C_6$-alkyl)amino;

$R_{13a}$, $R_{13b}$, $R_{14a}$, and $R_{14b}$ are each independently hydrogen, cyano, nitro, halogen, $SF_5$, $C_1$-$C_6$-alkyl, halo-$C_1$-$C_6$-alkyl, $C_1$-$C_6$-alkoxy, $C_1$-$C_6$-alkylthio, halo-$C_1$-$C_6$-alkoxy, or halo-$C_1$-$C_6$-alkylthio; and a is 1.

In another embodiment of formula (IH), the invention provides a compound of formula (IH), wherein:

Q is C—$R_2$;

$R_2$, $R_8$, $R_9$, $R_{10}$ and $R_{11}$ are independently of one another hydrogen, amino, amido, cyano, nitro, halogen, $C_1$-$C_6$-alkyl, $C_3$-$C_7$-cycloalkyl, halo-$C_1$-$C_6$-alkylthio, $C_1$-$C_6$-alkoxy, $C_3$-$C_7$-cycloalkyloxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, amino, $C_1$-$C_6$-alkylamino, or di($C_1$-$C_6$-alkyl)amino;

$R_{13a}$ and $R_{13b}$ are independently hydrogen or halogen; and $R_{14a}$ and $R_{14b}$ are hydrogen.

In another embodiment, the invention provides a compound of formula (IH), wherein:

Q is N;

$R_8$, $R_9$, $R_{10}$ and $R_{11}$ either together or independently of one another, are hydrogen, amino, amido, cyano, nitro, halogen, $C_1$-$C_6$-alkyl, $C_3$-$C_7$-cycloalkyl, $C_1$-$C_6$-alkenyl, halo-$C_1$-$C_6$-alkyl, $C_1$-$C_6$-alkylthio, halo-$C_1$-$C_6$-alkylthio, $C_3$-$C_7$-cycloalkyloxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, amino, $C_1$-$C_6$-alkylamino, or di($C_1$-$C_6$-alkyl)amino;

$R_{13a}$ and $R_{13b}$ are hydrogen; and $R_{14a}$ and $R_{14b}$ are H or halogen.

In one embodiment, the invention provides a compound of formula (IH), or a pharmaceutically or veterinarily acceptable salt thereof, wherein $R_5$ is hydrogen, $C_1$-$C_3$-alkyl, or halo-$C_1$-$C_3$alkyl.

In another embodiment of formula (IH), the invention provides compounds wherein:

P and Q are N;

V is C—$R_8$;

W is C—$R_9$;

X is C—$R_{10}$;

Y is C—$R_{11}$;

$R_8$, $R_9$, $R_{10}$ and $R_{11}$, independently of one another, are cyano, nitro, halogen, $C_1$-$C_6$-alkyl, $C_3$-$C_7$-cycloalkyl, halo-$C_1$-$C_6$-alkyl, $C_1$-$C_6$-alkylthio, halo-$C_1$-$C_6$-alkylthio, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $SF_5$, $C_1$-$C_6$-alkoxy, $C_3$-$C_7$-cycloalkyloxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, amino, $C_1$-$C_6$-alkylamino, di($C_1$-$C_6$-alkyl)amino, unsubstituted or substituted aryl, unsubstituted or substituted arylthio, unsubstituted or substituted heteroaryl, or unsubstituted or substituted aryloxy including phenoxy, wherein the substituents may each be independently cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, alkylsulfinyl, halo-$C_1$-$C_6$-alkylsulfinyl, $C_1$-$C_6$-alkylsulfonyl, halo-$C_1$-$C_6$-alkylsulfonyl, $SF_5$, or methylthioamino;

$R_3$, $R_4$ and $R_6$ are H;

$R_5$ is methyl or $C_1$-$C_3$-alkyl; and a is 1.

In yet another embodiment, compounds of formula (IH) are provided wherein:

P is N;

Q is N or C—$R_2$;

V is C—$R_8$;

W is C—$R_9$;

X is C—$R_{10}$;

Y is C—$R_{11}$;

$R_2$, $R_8$, $R_9$, $R_{10}$ and $R_{11}$, independently of one another, are cyano, nitro, halogen, $C_1$-$C_6$-alkyl, $C_3$-$C_7$-cycloalkyl, halo-$C_1$-$C_6$-alkyl, $C_1$-$C_6$-alkylthio, halo-$C_1$-$C_6$-alkylthio, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $SF_5$, $C_1$-$C_6$-alkoxy, $C_3$-$C_7$-cycloalkyloxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, $C_1$-$C_6$-alkylsulfonyl, amino, $C_1$-$C_6$-alkylamino, di($C_1$-$C_6$-alkyl)amino, unsubstituted or substituted aryl, unsubstituted or substituted arylthio, or unsubstituted or substituted aryloxy including phenoxy, whereby the substituents may each be independent of one another and are selected from the group consisting of cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $SF_5$, and methylthioamino;

$R_3$, $R_4$ and $R_6$ are H;
$R_5$ is methyl or $C_1$-$C_3$-alkyl; and
a is 1.

In still another embodiment, compounds of formula (IH) above are compounds wherein:
P is N;
Q is N or C—$R_2$;
V is C—$R_8$;
W is C—$R_9$;
X is C—$R_{10}$;
Y is C—$R_{11}$;
$R_2$, $R_8$, $R_9$, $R_{10}$ and $R_{11}$, independently of one another, is cyano, nitro, halogen, $C_1$-$C_6$-alkyl, $C_3$-$C_7$-cycloalkyl, halo-$C_1$-$C_6$-alkyl, $C_1$-$C_6$-alkylthio, halo-$C_1$-$C_6$-alkylthio, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $SF_5$, $C_1$-$C_6$-alkoxy, $C_3$-$C_7$-cycloalkyloxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, $C_1$-$C_6$-alkylamino, di($C_1$-$C_6$-alkyl)amino, unsubstituted or substituted aryl, unsubstituted or substituted arylthio, or unsubstituted or substituted aryloxy including phenoxy, whereby the substituents may each be independent of one another and are selected from the group consisting of cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $SF_5$, and methylthioamino;
$R_3$, $R_4$ and $R_6$ are H;
$R_5$ is methyl; and
a is 1.

In still another embodiment, compounds of formula (IH) above are compounds wherein:
$R_1$, $R_2$, $R_8$, $R_9$, $R_{10}$ and $R_{11}$, independently of one another, are hydrogen, cyano, halogen, halomethyl or methylthioamino;
$R_3$, $R_4$ and $R_6$ are H;
$R_5$ is methyl or $C_1$-$C_3$-alkyl;
P is C—$R_1$ or N;
Q is C—$R_2$ or N;
V is C—$R_8$ or N;
W is C—$R_9$ or N;
X is C—$R_{10}$ or N;
Y is C—$R_{11}$ or N; and
a is 1.

In still another embodiment, compounds of formula (IH) above are compounds wherein:
$R_1$, $R_2$, $R_8$, $R_9$, $R_{10}$ and $R_{11}$, independently of one another, are hydrogen, cyano, chloro or trifluoromethyl;
$R_3$, $R_4$ and $R_6$ is H;
$R_5$ is methyl;
P is C—$R_1$ or N;
Q is C—$R_2$ or N;
V is C—$R_8$ or N;
W is C—$R_9$ or N;
X is C—$R_{10}$ or N;
Y is C—$R_{11}$ or N; and
a is 1.

In still another embodiment, compounds of formula (IH) above are compounds wherein:
$R_2$, $R_8$, $R_9$, $R_{10}$ and $R_{11}$, independently of one another, are hydrogen, cyano, chloro or trifluoromethyl;
$R_3$, $R_4$ and $R_6$ is H;
$R_5$ is methyl;
P is N;
Q is C—$R_2$ or N;
V is C—$R_8$;
W is C—$R_9$;
X is C—$R_{10}$;
Y is C—$R_{11}$; and
a is 1.

In still another embodiment, compounds of formula (IH) above are compounds wherein:
$R_1$, $R_8$, $R_9$, $R_{10}$ and $R_{11}$, independently of one another, are hydrogen, cyano, chloro or trifluoromethyl;
$R_3$, $R_4$ and $R_6$ is H;
$R_5$ is methyl;
P is C—$R_1$;
Q is N;
V is C—$R_8$;
W is C—$R_9$;
X is C—$R_{10}$;
Y is C—$R_{11}$; and
a is 1.

In still another embodiment, compounds of formula (IH) above are compounds wherein:
$R_2$, $R_8$, $R_9$, $R_{10}$ and $R_{11}$, independently of one another, are hydrogen, cyano, chloro, trifluoromethyl or methylamino;
$R_3$, $R_4$ and $R_6$ is H;
$R_5$ is methyl;
P is N;
Q is C—$R_2$ or N;
V is C—$R_8$ or N;
W is C—$R_9$;
X is C—$R_{10}$;
Y is C—$R_{11}$ or N; and a is 1.

In an especially advantageous embodiment of the present invention, the compounds are (+)-N-[1-Cyano-1-methyl-2-(4,5,7-trichloro-2H-benzotriazol-2-yl)-ethyl]-4-trifluoromethoxybenzamide (compound No 1.096) and (+)-N-[2-(6-Bromo-2H-pyrazolo[4,3-b]pyridin-2-yl)-1-cyano-1-methylethyl]-4-trifluoromethoxybenzamide (compound No 3.024).

It is an object of the present invention to provide new paraciticidal compounds of the aryloazol-2-yl-cyanoethylamino family substantially enriched in an enantiomer, that exhibit significant in vitro and in vivo activity (the eutomer), together with processes for their preparation. It is surprising and unexpected that one enantiomer of the compounds would possess the desired biological activity of the racemic mixture while having a very favorable toxicity profile. For example, it has been found that the eutomer of some compounds of the invention are significantly more potent in the inhibition of motility of *Haemonchus contortus* (see Method A in Examples). The eutomer of compound 3.011 (compound 3.024) was found to be greater than 100 times more potent than the distomer (compound 3.025) at inhibiting the motility of *Haemonchus contortus* larvae. Similarly, compound 3.024 was also found to be greater than 100 times more potent than compound 3.025 at inhibiting the motility of *Caenorhabditis elegans*. This superior biological activity of the eutomer has been extended to sheep in vivo.

By the term "enriched" is meant when the weight:weight ratio is at least approximately 1.05 or higher in favor of the enantiomer that displays significant in vitro and in vivo activity (the eutomer)

Advantageously, the composition of the invention is substantially enriched in the enantiomer that displays significant in vitro and in vivo activity (the eutomer). By the term substantially enriched is meant wherein the weight:weight ratio is at least approximately 1.5 or higher in favor of the enantiomer that displays significant in vitro and in vivo activity (the eutomer)

In another embodiment of the invention, the weight:weight ratio is at least approximately 2 or greater, advantageously is at least approximately 5 or greater, most advantageously is at least approximately 10 or greater in favor of the enantiomer that displays significant in vitro and in vivo activity (the eutomer)

For the purposes of this application, unless otherwise stated in the specification, the following terms have the terminology cited below:

(1) Alkyl refers to both straight, branched carbon chains and cyclic hydrocarbon groups; references to individual alkyl groups are specific for the straight chain (e.g. butyl=n-butyl). In one embodiment of alkyl, the number of carbons atoms is 1-20, in other embodiments of alkyl, the number of carbon atoms is 1-12, 1-10 or 1-8 carbon atoms. In yet another embodiment of alkyl, the number of carbon atoms is 1-4 carbon atoms. Other ranges of carbon numbers are also contemplated depending on the location of the alkyl moiety on the molecule;

Examples of $C_1$-$C_{10}$ alkyl include, but are not limited to, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

Cyclic alkyl groups, which are encompassed by alkyls, may be referred to as "cycloalkyl" and include those with 3 to 10 carbon atoms having single or multiple fused rings. Non-limiting examples of cycloalkyl groups include adamantyl, cyclopropyl, cyclobutyl, cyclopentyl, cyclohexyl, cycloheptyl, cyclooctyl and the like.

The alkyl and cycloalkyl groups described herein can be unsubstituted or substituted with one or more moieties selected from the group consisting of alkyl, halo, haloalkyl, hydroxyl, carboxyl, acyl, acyloxy, amino, alkyl- or dialkylamino, amido, arylamino, alkoxy, aryloxy, nitro, cyano, azido, thiol, imino, sulfonic acid, sulfate, sulfonyl, sulfanyl, sulfinyl, sulfamonyl, ester, phosphonyl, phosphinyl, phosphoryl, phosphine, thioester, thioether, acid halide, anhydride, oxime, hydrozine, carbamate, phosphonic acid, phosphate, phosphonate, or any other viable functional group that does not inhibit the biological activity of the compounds of the invention, either unprotected, or protected as necessary, as known to those skilled in the art, for example, as taught in Greene, et al., Protective Groups in Organic Synthesis, John Wiley and Sons, Third Edition, 1999, hereby incorporated by reference.

(2) Alkenyl refers to both straight and branched carbon chains which have at least one carbon-carbon double bond. In one embodiment of alkenyl, the number of double bonds is 1-3, in another embodiment of alkenyl, the number of double bonds is one. In one embodiment of alkenyl, the number of carbons atoms is 2-20, in other embodiments of alkenyl, the number of carbon atoms is 2-12, 2-10 or 2-8. In yet another embodiment of alkenyl, the number of carbon atoms is 2-4. Other ranges of carbon-carbon double bonds and carbon numbers are also contemplated depending on the location of the alkenyl moiety on the molecule;

"$C_2$-$C_{10}$-alkenyl" groups may include more than one double bond in the chain. Examples include, but are not limited to, ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

(3) Alkynyl refers to both straight and branched carbon chains which have at least one carbon-carbon triple bond. In one embodiment of alkynyl, the number of triple bonds is 1-3; in another embodiment of alkynyl, the number of triple bonds is one. In one embodiment of alkynyl, the number of carbons atoms is 2-20, in other embodiments of alkynyl, the number of carbon atoms is 2-12, 2-10 or 2-8. In yet another embodiment of alkynyl, the number of carbon atoms is 2-4. Other ranges of carbon-carbon double bonds and carbon numbers are also contemplated depending on the location of the alkenyl moiety on the molecule;

For example, the term "$C_2$-$C_{10}$-alkynyl" as used herein refers to a straight-chain or branched unsaturated hydrocarbon group having 2 to 10 carbon atoms and containing at least one triple bond, such as ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex 1-yn-1-yl, n-hex 1-yn-3-yl, n-hex 1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl and the like.

(4) Aryl refers to a $C_6$-$C_{14}$ aromatic carbocyclic ring structure having a single ring or multiple fused rings. Aryl groups include, but are not limited to, phenyl, biphenyl, and naphthyl. In some embodiments aryl includes tetrahydronapthyl, phenylcyclopropyl and indanyl. Aryl groups may be unsubstituted or substituted by one or more moieties selected from halogen, cyano, nitro, hydroxy, mercapto, amino, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy, haloalkenyloxy, haloalkynyloxy, cycloalkoxy, cycloalkenyloxy, halocycloalkoxy, halocycloalkenyloxy, alkylthio, haloalkylthio, arylthio, cycloalkylthio, halocycloalkylthio, alkylsulfinyl, alkenylsulfinyl, alkynyl-sulfinyl, haloalkylsulfinyl, haloalkenylsulfinyl, haloalkynylsulfinyl, alkylsulfonyl, alkenylsulfonyl, alkynylsulfonyl, haloalkyl-sulfonyl, haloalkenylsulfonyl, haloalkynylsulfonyl, alkylcarbonyl, haloalkylcarbonyl, alkylamino, alkenylamino, alkynylamino, di(alkyl)amino, di(alkenyl)amino, di(alkynyl)amino, or $SF_5$. In one embodiment of aryl, the moiety is phenyl, naphthyl, tetrahydronapthyl, phenylcyclopropyl and indanyl; in another embodiment of aryl, the moiety is phenyl. Arylo refers to an aryl substituted at two adjacent sites.

(5) Alkoxy refers to —O-alkyl, wherein alkyl is as defined in (1);

(6) Alkoxycarbonyl refers to —C(=O)—O-alkyl, wherein alkoxy is as defined in (5);

(7) Cyclo as a prefix (e.g. cycloalkyl, cycloalkenyl, cycloalkynyl) refers to a saturated or unsaturated cyclic ring structure having from three to eight carbon atoms in the ring the scope of which is intended to be separate and distinct from the definition of aryl above. In one embodiment of cyclo, the range of ring sizes is 4-7 carbon atoms; in another embodiment of cyclo the range of ring sizes is 3-4. Other ranges of carbon numbers are also contemplated depending on the location of the cyclo-moiety on the molecule;

(8) Halogen means the atoms fluorine, chlorine, bromine and iodine. The designation of "halo" (e.g. as illustrated in the term haloalkyl) refers to all degrees of substitutions from a single substitution to a perhalo substitution (e.g. as illustrated with methyl as chloromethyl (—$CH_2Cl$), dichloromethyl (—$CHCl_2$), trichloromethyl (—$CCl_3$));

(9) Heterocycle, heterocyclic or heterocyclo refers to fully saturated or unsaturated cyclic groups, for example, 4 to 7 membered monocyclic, 7 to 11 membered bicyclic, or 10 to 15 membered tricyclic ring systems, which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system.

(10) Heteroaryl refers to a monovalent aromatic group of from 1 to 15 carbon atoms, preferably from 1 to 10 carbon atoms, having one or more oxygen, nitrogen, and sulfur heteroatoms within the ring, preferably 1 to 4 heteroatoms, or 1 to 3 heteroatoms. The nitrogen and sulfur heteroatoms may optionally be oxidized. Such heteroaryl groups can have a single ring (e.g., pyridyl or furyl) or multiple fused rings provided that the point of attachment is through a heteroaryl ring atom. Preferred heteroaryls include pyridyl, piridazinyl, pyrimidinyl, triazinyl, pyrrolyl, quinolinyl, isoquinolinyl, quinazolinyl, quinoxalinnyl, furanyl, thienyl, furyl, imidazolyl, oxazolyl, isoxazolyl, isothiazolyl, pyrazolyl, benzofuranyl, and benzothienyl. Heteroaryl rings may be unsubstituted or substituted by one or more moieties as described for aryl above.

Exemplary monocyclic heterocyclic or heteroaryl groups also include, but are not limited to, pyrrolidinyl, oxetanyl, pyrazolinyl, imidazolinyl, imidazolidinyl, oxazolidinyl, isoxazolinyl, thiazolyl, thiadiazolyl, thiazolidinyl, isothiazolidinyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, and the like.

Exemplary bicyclic heterocyclic groups include, but are not limited to, indolyl, benzothiazolyl, benzoxazolyl, benzodioxolyl, benzothienyl, quinuclidinyl, tetra-hydroisoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl and the like.

Exemplary tricyclic heterocyclic groups include, but are not limited to, carbazolyl, benzidolyl, phenanthrolinyl, acridinyl, phenanthridinyl, xanthenyl and the like.

Unless otherwise specifically noted or apparent by context, "active agent" or "active ingredient" or "therapeutic agent" as used in this specification, means an aryloazol-2-yl-cyanoethylamino compound of the invention.

Another aspect of the invention is the formation of parasiticidal compositions which comprise the aryloazol-2-yl-cyanoethylamino compounds of the invention. The composition of the invention can also be in a variety of forms which include, but are not limited to, oral formulations, injectable formulations, and topical, dermal or subdermal formulations. The formulations are intended to be administered to an animal which includes but is not limited to mammals, birds and fish. Examples of mammals include but are not limited to humans, cattle, sheep, goats, llamas, alpacas, pigs, horses, donkeys, dogs, cats and other livestock or domestic mammals. Examples of birds include turkeys, chickens, ostriches and other livestock or domestic birds.

The composition of the invention may be in a form suitable for oral use, for example, as baits (see, e.g., U.S. Pat. No. 4,564,631), dietary supplements, troches, lozenges, chewables, tablets, hard or soft capsules, emulsions, aqueous or oily suspensions, aqueous or oily solutions, oral drench formulations, dispersible powders or granules, premixes, syrups or elixirs, enteric formulations or pastes. Compositions intended for oral use may be prepared according to any method known in the art for the manufacture of pharmaceutical compositions and such compositions may contain one or more agents selected from the group consisting of sweetening agents, bittering agents, flavoring agents, coloring agents and preserving agents in order to provide pharmaceutically elegant and palatable preparations.

Tablets may contain the active ingredient in admixture with non-toxic, pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc, the tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in U.S. Pat. Nos. 4,256,108; 4,166,452; and 4,265,874 (incorporated herein by reference) to form osmotic therapeutic tablets for controlled release.

Formulations for oral use may be hard gelatin capsules, wherein the active ingredient is mixed with an inert solid diluent, for example, calcium carbonate, calcium phosphate or kaolin. Capsules may also be soft gelatin capsules, wherein the active ingredient is mixed with water or miscible solvents such as propylene glycol, PEGs and ethanol, or an oil medium, for example peanut oil, liquid paraffin, or olive oil.

The compositions of the invention may also be in the form of oil-in-water or water-in-oil emulsions. The oily phase may be a vegetable oil, for example, olive oil or arachis oil, or a mineral oil, for example, liquid paraffin or mixtures of these. Suitable emulsifying agents may be naturally-occurring phosphatides, for example, soybean, lecithin, and esters or partial esters derived from fatty acids and hexitol anhydrides, for example, sorbitan monoleate, and condensation products of the said partial esters with ethylene oxide, for example, polyoxyethylene sorbitan monooleate. The emulsions may also contain sweetening agents, bittering agents, flavoring agents, and/or preservatives.

In one embodiment of the formulation, the composition of the invention is in the form of a microemulsion. Microemulsions are well suited as the liquid carrier vehicle. Microemulsions are quaternary systems comprising an aqueous phase, an oily phase, a surfactant and a cosurfactant. They are translucent and isotropic liquids.

Microemulsions are composed of stable dispersions of microdroplets of the aqueous phase in the oily phase or conversely of microdroplets of the oily phase in the aqueous phase. The size of these microdroplets is less than 200 nm (1000 to 100,000 nm for emulsions). The interfacial film is composed of an alternation of surface-active (SA) and co-surface-active (Co-SA) molecules which, by lowering the interfacial tension, allows the microemulsion to be formed spontaneously.

In one embodiment of the oily phase, the oily phase can be formed from mineral or vegetable oils, from unsaturated polyglycosylated glycerides or from triglycerides, or alternatively from mixtures of such compounds. In one embodiment of the oily phase, the oily phase comprises of triglycerides; in another embodiment of the oily phase, the triglycerides are medium-chain triglycerides, for example $C_8$-$C_{10}$ caprylic/capric triglyceride. In another embodiment of the oily phase will represent a % v/v range selected from the group consisting of about 2 to about 15%; about 7 to about 10%; and about 8 to about 9% v/v of the microemulsion.

The aqueous phase includes, for example water or glycol derivatives, such as propylene glycol, glycol ethers, polyethylene glycols or glycerol. In one embodiment of the glycol derivatives, the glycol is selected from the group consisting of propylene glycol, diethylene glycol monoethyl ether, dipropylene glycol monoethyl ether and mixtures thereof. Generally, the aqueous phase will represent a proportion from about 1 to about 4% v/v in the microemulsion.

Surfactants for the microemulsion include diethylene glycol monoethyl ether, dipropyelene glycol monomethyl ether, polyglycolyzed $C_8$-$C_{10}$ glycerides or polyglyceryl-6 dioleate. In addition to these surfactants, the cosurfactants include short-chain alcohols, such as ethanol and propanol.

Some compounds are common to the three components discussed above, i.e., aqueous phase, surfactant and cosurfactant. However, it is well within the skill level of the practitioner to use different compounds for each component of the same formulation. In one embodiment for the amount of surfactant/cosurfactant, the cosurfactant to surfactant ratio will be from about 1/7 to about 1/2. In another embodiment for the amount of cosurfactant, there will be from about 25 to about 75% v/v of surfactant and from about 10 to about 55% v/v of cosurfactant in the microemulsion.

Oily suspensions may be formulated by suspending the active ingredient in a vegetable oil, for example, atachis oil, olive oil, sesame oil or coconut oil, or in mineral oil such as liquid paraffin. The oily suspensions may contain a thickening agent, for example, beeswax, hard paraffin or cetyl alcohol. Sweetening agents such as sucrose, saccharin or aspartame, bittering agents, and flavoring agents may be added to provide a palatable oral preparation. These compositions may be preserved by the addition of an anti-oxidant such as ascorbic acid, or other known preservatives.

Aqueous suspensions may contain the active material in admixture with excipients suitable for the manufacture of aqueous suspensions. Such excipients are suspending agents, for example, sodium carboxymethylcellulose, methylcellulose, hydroxy-propylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide, with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents and/or bittering agents, such as those set forth above.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, bittering, flavoring and coloring agents, may also be present.

Syrups and elixirs may be formulated with sweetening agents, for example, glycerol, propylene glycol, sorbitol or sucrose. Such formulations may also contain a demulcent, a preservative, flavoring agent(s) and/or coloring agent(s).

In another embodiment of the invention, the composition can be in paste form. Examples of embodiments in a paste form include but are not limited to those described in U.S. Pat. Nos. 6,787,342 and 7,001,889 (each of which are incorporated herein by reference). In addition to the aryloazol-2-yl cyanoethylamino compound of the invention, the paste can also contain fumed silica; a viscosity modifier; a carrier; optionally, an absorbent; and optionally, a colorant, stabilizer, surfactant, or preservative.

The process for preparing a paste formulation comprises the steps of:
(a) dissolving or dispersing the aryloazol-2-yl cyanoethylamino compound into the carrier by mixing;
(b) adding the fumed silica to the carrier containing the dissolved aryloazol-2-yl cyanoethylamino compound and mixing until the silica is dispersed in the carrier;
(c) allowing the intermediate formed in (b) to settle for a time sufficient in order to allow the air entrapped during step (b) to escape; and
(d) adding the viscosity modifier to the intermediate with mixing to produce a uniform paste.

The above steps are illustrative, but not limiting. For example, step (a) can be the last step.

In one embodiment of the formulation, the formulation is a paste containing aryloazol-2-yl cyanoethylamino compound, fumed silica, a viscosity modifier, an absorbent, a colorant; and a hydrophilic carrier which is triacetin, a monoglyceride, a diglyceride, or a triglyceride.

The paste may also include, but is not limited to, a viscosity modifier selected from the group consisting of PEG 200, PEG 300, PEG 400, PEG 600, monoethanolamine, triethanolamine, glycerol, propylene glycol, polyoxyethylene (20) sorbitan mono-oleate (POLYSORBATE 80 or TWEEN 80), and polyoxamers (e.g., PLURONIC L 81); an absorbent selected from the group consisting of magnesium carbonate, calcium carbonate, starch, and cellulose and its derivatives; and a colorant selected from the group consisting of titanium dioxide iron oxide, and FD&C Blue #1 ALUMINUM LAKE.

The compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol. Among the acceptable vehicles and solvents that may be employed are water, Ringer's solution and isotonic sodium chloride solution. Cosolvents such as ethanol, propylene glycol glycerol formal or polyethylene glycols may also be used. Preservatives, such as phenol or benzyl alcohol, may be used.

In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Topical, dermal and subdermal formulations can include emulsions, creams, ointments, gels, pastes, powders, shampoos, pour-on formulations, ready-to-use formulations, spot-on solutions and suspensions, dips and sprays. Topical application of an inventive compound or of a composition including at least one inventive compound among active agent(s) therein, a spot-on or pour-on composition, can allow for the inventive compound to be absorbed through the skin to achieve systemic levels, distributed through the sebaceous glands or on the surface of the skin achieving levels throughout the haircoat. When the compound is distributed through the sebaceous glands, they can act as a reservoir, whereby there can be a long-lasting effect (up to several months) effect. Spot-on formulations are typically applied in a localized region which refers to an area other than the entire animal. In one embodiment of a localized region, the location is between the shoulders. In another embodiment of a localized region it is a stripe, e.g. a stripe from head to tail of the animal. Pour-on formulations are described in U.S. Pat. No. 6,010,710, incorporated herein by reference. The pour-on formulations may be advantageously oily, and generally comprise a diluent or vehicle and also a solvent (e.g. an organic solvent) for the active ingredient if the latter is not soluble in the diluent.

Organic solvents that can be used in the invention include but are not limited to: acetyltributyl citrate, fatty acid esters such as the dimethyl ester, acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone including N-methylpyrrolidone, diethylene glycol monoethyl ether, propylene glycol monomethyl ether, propylene glycol monoethyl ether, ethylene glycol, diisobutyl adipate, diisopropyl adipate (also known as CERAPHYL 230), triacetin, butyl acetate, octyl acetate, propylene carbonate, butylene carbonate, dimethylsufoxide, organic amides including dimethylformamide and dimethylacetamide, and diethyl phthalate, or a mixture of at least two of these solvents.

In one embodiment of the invention, the pharmaceutically or veterinarily acceptable carrier of the formulation comprises $C_1$-$C_{10}$ alcohols or esters thereof (including acetates, such as ethyl acetate, butyl acetate and the like), $C_{10}$-$C_{18}$ saturated fatty acids or esters thereof, $C_{10}$-$C_{18}$ monounsaturated fatty acids or esters thereof, monoesters or diesters of aliphatic diacids, glycerol monoesters (e.g. monoglycerides), glycerol diesters (e.g. diglycerides), glycerol triesters (e.g. triglycerides such as triacetin), glycols, glycol ethers, glycol esters or glycol carbonates, polyethylene glycols of various grades (PEGs) or monoethers, diethers, monoesters or diesters thereof (e.g. diethylene glycol monoethyl ether), or mixtures thereof.

As vehicle or diluent, mention may be made of plant oils such as, but not limited to soybean oil, groundnut oil, castor oil, corn oil, cotton oil, olive oil, grape seed oil, sunflower oil, coconut oils etc.; mineral oils such as, but not limited to, petrolatum, paraffin, silicone, etc.; aliphatic or cyclic hydrocarbons or alternatively, for example, medium-chain (such as C8 to C12) triglycerides.

In another embodiment of the invention, an emollient and/or spreading and/or film-forming agent can be added. One embodiment of the emollient and/or spreading and/or film-forming agent are those agents selected from the group consisting of:

(a) polyvinylpyrrolidone, polyvinyl alcohols, copolymers of vinyl acetate and vinylpyrrolidone, polyethylene glycols, benzyl alcohol, 2-pyrrolidones including, but not limited to N-methylpyrrolidone, mannitol, glycerol, sorbitol, polyoxyethylenated sorbitan esters; lecithin, sodium carboxymethylcellulose, silicone oils, polydiorganosiloxane oils (such as polydimethylsiloxane (PDMS) oils), for example those containing silanol functionalities, or a 45V2 oil, (b) anionic surfactants such as alkaline stearates, sodium, potassium or ammonium stearates; calcium stearate, triethanolamine stearate; sodium abietate; alkyl sulphates (e.g. sodium lauryl sulphate and sodium cetyl sulphate); sodium dodecylbenzenesulphonate, sodium dioctylsulphosuccinate; fatty acids (e.g. those derived from coconut oil), (c) cationic surfactants such as water-soluble quaternary ammonium salts of formula N$^+$R'R''R'''R'''', Y$^-$ in which the radicals R are optionally hydroxylated hydrocarbon radicals and Y$^-$ is an anion of a strong acid such as the halide, sulphate and sulphonate anions; cetyltrimethylammonium bromide is among the cationic surfactants which can be used, (d) amine salts of formula N$^+$HR'R''R''' in which the radicals R are optionally hydroxylated hydrocarbon radicals; octadecylamine hydrochloride is among the cationic surfactants which can be used, (e) nonionic surfactants such as sorbitan esters, which are optionally polyoxyethylenated (e.g. POLYSORBATE 80), polyoxyethylenated alkyl ethers; polyoxypropylated fatty alcohols such as polyoxypropylene-styrol ether; polyethylene glycol stearate, polyoxyethylenated derivatives of castor oil, polyglycerol esters, polyoxyethylenated fatty alcohols, polyoxyethylenated fatty acids, copolymers of ethylene oxide and propylene oxide, (f) amphoteric surfactants such as the substituted lauryl compounds of betaine; or (g) a mixture of at least two of these agents.

The solvent will be used in proportion with the concentration of the aryloazol-2-yl cyanoethylamino compound and its solubility in this solvent. It will be sought to have the lowest possible volume. The vehicle makes up the difference to 100%.

In one embodiment of the amount of emollient, the emollient is used in a proportion of from 0.1 to 50% and 0.25 to 5%, by volume.

In another embodiment of the invention, the composition can be in ready-to-use solution form as is described in U.S. Pat. No. 6,395,765, incorporated herein by reference. In addition to the aryloazol-2-yl cyanoethylamino compound, the ready-to-use solution can contain a crystallization inhibitor, an organic solvent and an organic co-solvent.

In one embodiment of the amount of crystallization inhibitor, the crystallization inhibitor can be present in a proportion of about 1 to about 30% (w/v) in the composition. In other embodiments, the crystallization inhibitor may be present in a proportion of about 1 to about 20% (w/v) and about 5 to about 15%. Acceptable inhibitors are those whose addition to the formulation inhibits the formation of crystals when the formulation is applied. In some embodiments, formulations may include compounds that function as crystallization inhibitors other than those listed herein. In these embodiments, the suitability of a crystallization inhibitor may be determined by a the test in which 0.3 ml of a solution comprising 10% (w/v) of aryloazol-2-yl cyanoethylamino compound in the liquid carrier and 10% of the inhibitor are deposited on a glass slide at 20° C. and allowed to stand for 24 hours. The slide is then observed with the naked eye. Acceptable inhibitors are those whose addition provides for few (e.g. less than ten crystals) or no crystal.

In one embodiment, the organic solvent has a dielectric constant of a range selected from the group consisting of between about 2 to about 35, about 10 to about 35 or about 20 to about 30. In other embodiments, the solvent will have a dielectric constant of between about 2 and about 20, or between about 2 and about 10. The content of this organic solvent in the overall composition representing the complement to 100% of the composition.

As discussed above, the solvent may comprise a mixture of solvents including a mixture of an organic solvent and an organic co-solvent. In one embodiment, and the organic co-solvent has a boiling point of less than about 300° C. or less than about 250° C. In other embodiments, the co-solvent has a boiling point of below about 200° C., or below about 130° C. In still another embodiment of the invention, the organic co-solvent has a boiling point of below about 100° C., or below about 80° C. In still other embodiments, the organic co-solvent will have a dielectric constant of a range selected from the group consisting of about 2 to about 40, about 10 to about 40, or typically about 20 to about 30. In some embodiments of the invention, this co-solvent may be present in the composition in a organic co-solvent/organic solvent weight/weight (W/W) ratio of about 1/15 to about 1/2. In some embodiments, the co-solvent is volatile so as to act as a drying promoter, and is miscible with water and/or with the organic solvent.

The formulation can also comprise an antioxidizing agent intended to inhibit oxidation in air, this agent being present in a proportion selected from a range consisting of about 0.005 to about 1% (w/v) and about 0.01 to about 0.05%.

Crystallization inhibitors which are useful for the invention include but are not limited to:

(a) polyvinylpyrrolidone, polyvinyl alcohols, copolymers of vinyl acetate and of vinylpyrrolidone, polyethylene glycols of various grades, benzyl alcohol, 2-pyrrolidones including, but not limited to N-methylpyrrolidone, dimethylsufoxide, mannitol, glycerol, sorbitol or polyoxyethylenated esters of sorbitan; lecithin or sodium carboxymethylcellulose; a solvent as described herein that is capable of inhibiting crystal formation; acrylic derivatives, such as acrylates and methacrylates or other polymers derived from acrylic monomers, and others;

(b) anionic surfactants, such as alkaline stearates (e.g. sodium, potassium or ammonium stearate); calcium stearate or triethanolamine stearate; sodium abietate; alkyl sulphates, which include but are not limited to sodium lauryl sulphate and sodium cetyl sulphate; sodium dodecylbenzenesulphonate or sodium dioctyl sulphosuccinate; or fatty acids (e.g. coconut oil);

(c) cationic surfactants, such as water-soluble quaternary ammonium salts of formula $N^+R'R''R'''R''''Y^-$, in which the R radicals are identical or different optionally hydroxylated hydrocarbon radicals and $Y^-$ is an anion of a strong acid, such as halide, sulphate and sulphonate anions; cetyltrimethylammonium bromide is one of the cationic surfactants which can be used;

(d) amine salts of formula $N^+HR'R''R'''$, in which the R radicals are identical or different optionally hydroxylated hydrocarbon radicals; octadecylamine hydrochloride is one of the cationic surfactants which can be used;

(e) non-ionic surfactants, such as optionally polyoxyethylenated esters of sorbitan, e.g. POLYSORBATE 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide;

(f) amphoteric surfactants, such as substituted lauryl compounds of betaine; or (g) a mixture of at least two of the compounds listed in (a)-(f) above.

In one embodiment of the crystallization inhibitor, a crystallization inhibitor pair will be used. Such pairs include, for example, the combination of a film-forming agent of polymeric type and of a surface-active agent. These agents will be selected from the compounds mentioned above as crystallization inhibitor.

In one embodiment of the film-forming agent, the agents are of the polymeric type which include but are not limited to the various grades of polyvinylpyrrolidone, polyvinyl alcohols, and copolymers of vinyl acetate and of vinylpyrrolidone.

In one embodiment of the surface-active agents, the agents include but are not limited to those made of non-ionic surfactants; in another embodiment of the surface active agents, the agent is a polyoxyethylenated esters of sorbitan and in yet another embodiment of the surface-active agent, the agents include the various grades of POLYSORBATE, for example POLYSORBATE 80.

In another embodiment of the invention, the film-forming agent and the surface-active agent can be incorporated in similar or identical amounts within the limit of the total amounts of crystallization inhibitor mentioned elsewhere.

The pair thus constituted secures, in a noteworthy way, the objectives of absence of crystallization on the coat and of maintenance of the cosmetic appearance of the skin or fur, that is to say without a tendency towards sticking or towards a sticky appearance, despite the high concentration of active material.

In one embodiment of the antioxidizing agents, the agents are those conventional in the art and include but is not limited to butylated hydroxyanisole, butylated hydroxytoluene, ascorbic acid, sodium metabisulphite, propyl gallate, sodium thiosulphate or a mixture of not more than two of them.

The formulation adjuvants discussed above are well known to the practitioner in this art and may be obtained commercially or through known techniques. These concentrated compositions are generally prepared by simple mixing of the constituents as defined above; advantageously, the starting point is to mix the active material in the main solvent and then the other ingredients or adjuvants are added.

The volume applied is not restricted as long as the amount of substance administered is shown to be safe and efficacious. Typically, the volume applied depends on the size and weight of the animal as well as the concentration of active, the extent of infestation by parasites and the type of administration. In some embodiments, the volume applied can be of the order of about 0.3 to about 5 ml or about 0.3 ml to about 1 ml. In one embodiment for the volume, the volume is on the order of about 0.5 ml, for cats and on the order of about 0.3 to about 3 ml for dogs, depending on the weight of the animal.

In another embodiment of the invention, application of a spot-on formulation according to the present invention can also provide long-lasting and broad-spectrum efficacy when the solution is applied to the mammal or bird. The spot-on formulations provide for topical administration of a concentrated solution, suspension, microemulsion or emulsion for intermittent application to a spot on the animal, generally between the two shoulders (solution of spot-on type).

For spot-on formulations, the carrier can be a liquid carrier vehicle as described in U.S. Pat. No. 6,426,333 (incorporated herein by reference), which in one embodiment of the spot-on formulation comprises a solvent and a cosolvent wherein the solvent is selected from the group consisting of acetone, acetonitrile, benzyl alcohol, butyl diglycol, dimethylacetamide, dimethylformamide, dipropylene glycol n-butyl ether, propylene glycol monomethyl ether, propylene glycol monoethyl ether, diisobutyl adipate, diisopropyl adipate (also known as CERAPHYL 230), triacetin, butyl acetate, octyl acetate, propylene carbonate, butylene carbonate, dimethylsufoxide, organic amides including dimethylformamide and dimethylacetamide, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone including N-methylpyrrolidone, diethylene glycol monoethyl ether, ethylene glycol, diethyl phthalate fatty acid esters, such as the diethyl ester or diisobutyl adipate, and a mixture of at least two of these solvents and the cosolvent is selected from the group consisting of absolute ethanol, isopropanol or methanol.

In one embodiment of the invention, the pharmaceutically or veterinarily acceptable carrier of the formulation comprises $C_1$-$C_{10}$ alcohols or esters thereof (including acetates, such as ethyl acetate, butyl acetate and the like), $C_{10}$-$C_{18}$ saturated fatty acids or esters thereof, $C_{10}$-$C_{18}$ monounsaturated fatty acids or esters thereof, monoesters or diesters of aliphatic diacids, glycerol monoesters (e.g. monoglycerides), glycerol diesters (e.g. diglycerides), glycerol triesters (e.g. triglycerides such as triacetin), glycols, glycol ethers, glycol esters or glycol carbonates, polyethylene glycols of various grades (PEGs) or monoethers, diethers, monoesters or diesters thereof (e.g. diethylene glycol monoethyl ether), or mixtures thereof.

The liquid carrier vehicle can optionally contain a crystallization inhibitor including an anionic surfactant, a cationic surfactant, a non-ionic surfactant, an amine salt, an amphoteric surfactant or polyvinylpyrrolidone, polyvinyl alcohols, copolymers of vinyl acetate and vinylpyrrolidone, 2-pyrrolidone including N-methylpyrrolidone (NMP), dimethylsulfoxide, polyethylene glycols, benzyl alcohol, mannitol, glycerol, sorbitol, polyoxyethylenated sorbitan esters; lecithin, sodium carboxymethylcellulose, solvents as defined herein that can inhibit the formation of crystals, and acrylic derivatives such acrylates or methacrylates as well as other polymers derived from acrylic monomers, or a mixture of these crystallization inhibitors.

Spot-on formulations may be prepared by dissolving the active ingredients into the pharmaceutically or veterinary acceptable vehicle. Alternatively, the spot-on formulation can be prepared by encapsulation of the active ingredient to leave a residue of the therapeutic agent on the surface of the animal. These formulations will vary with regard to the weight of the therapeutic agent in the combination depending on the species of host animal to be treated, the severity and type of infection and the body weight of the host.

Dosage forms may contain from about 0.5 mg to about 5 g of an active agent. In one embodiment of the dosage form, the dosage is from about 1 mg to about 500 mg of an active agent, typically about 25 mg, about 50 mg, about 100 mg, about 200 mg, about 300 mg, about 400 mg, about 500 mg, about 600 mg, about 800 mg, or about 1000 mg.

In one embodiment of the invention, the active agent is present in the formulation at a concentration of about 0.05% to about 50% weight/volume. In other embodiments, the active agent may be present in the formulation at a concentration of about 0.1% to about 30%, about 0.5% to about 20% (w/v) or about 1% to about 10% (w/v). In another embodiment of the invention, the active agent is present in the formulation as a concentration from about 0.1 to 2% weight/volume. In yet another embodiment of the invention, the active agent is present in the formulation as a concentration from about 0.25 to about 1.5% weight/volume. In still another embodiment of the invention, the active agent is present in the formulation as a concentration about 1% weight/volume.

In a particular advantageous embodiment of the invention, the dose of the inventive compounds is about 0.1 mg/kg to about 100 mg/kg. In other embodiments, the dose of the inventive compounds is about 0.5 mg/kg to about 70 mg/kg, about 0.5 mg/kg to about 50 mg/kg or about 0.5 mg/kg to about 30 mg/kg. In other preferred embodiments, the dose is 0.5 mg/kg to about 30 mg/kg, 0.5 mg/kg to about 20 mg/kg or 0.5 mg/kg to about 10 mg/kg. More typically, in some embodiments the dose of the active compounds is about 0.1 mg/kg to 5 mg/kg, 0.1 mg/kg to about 3 mg/kg, or about 0.1 mg/kg to 1.5 mg/kg. In still other embodiments of the invention, the dose may be as low as 0.1 mg/kg (0.02 mg/ml), about 0.2 mg/kg (0.04 mg/ml), about 0.3 mg/kg (0.06 mg/ml), about 0.4 mg/kg (0.08 mg/ml), about 0.5 mg/kg (0.1 mg/ml), about 0.6 mg/kg (0.12 mg/ml), about 0.7 mg/kg (0.14 mg/ml), about 0.8 mg/kg (0.16 mg/ml), about 0.9 mg/kg (0.18 mg/ml), about 1.0 mg/kg (0.2 mg/ml).

Another embodiment of the invention is directed toward a method of treating endoparasitic infestation or infection in an animal, comprising administering an effective amount of the compound of the invention to the animal in need thereof. The compounds of the invention have been shown to have superior efficacy against endoparasites, and in particular against parasites that are resistant to active agents of the macrocyclic lactone class. For example, a compound of the invention has been shown to have superior efficacy against ivermectin-resistant endoparasites in sheep. FIG. 2 shows that a compound of the invention (compound 3.024) administered at a dosage of 1.5 mg/kg or 3 mg/kg orally had greater than 95% efficacy against ivermectin-resistant strains of *Haemonchus contortus, Ostertagia circumcincta* and *Trichostrongylus columbriformis*. In contrast, ivermectin administered orally at a dose of 0.2 mg/kg was almost completely inactive against *Haemonchus contortus*, less than 30% effective against *Ostertagia circumcincta* and less than 60% effective against *Trichostrongylus columbriformis*. It is surprising that the compounds of the invention have superior efficacy against endoparasites that are resistant to ivermectin, which is one of the most potent active agents known against endo- and ectoparasites.

Accordingly, in another embodiment, the invention provides a method for treating an endoparasitic infestation or infection in an animal, comprising administering an effective amount of an aryloazol-2-yl-cyanoethylamino compound of the invention in combination with an effective amount of activators of invertebrate GABA receptors including an avermectin or milbemycin to the animal in need thereof. Avermectins that may be used in combination with the compounds of the invention include, but are not limited to abamectin, dimadectin, doramectin, emamectin, eprinomectin, ivermectin, latidectin, lepimectin, and selamectin Milbemycins compounds that may be used in combination with the compounds of the invention include, but are not limited to, milbemectin, milbemycin D, moxidectin and nemadectin. Also included are the 5-oxo and 5-oxime derivatives of said avermectins and milbemycins.

In one embodiment, the compounds and compositions of the invention may be used for treating endoparasiticidal infection or infestation by helminth species including, but is not limited to, *Anaplocephala (Anoplocephala), Ancylostoma, Anecator, Ascaris, Brugia, Bunostomum, Capillaria, Chabertia, Cooperia, Cyathostomum, Cylicocyclus, Cylicodontophorus, Cylicostephanus, Craterostomum, Dictyocaulus, Dipetalonema, Dipylidium, Dirofilaria, Dracunculus, Echinococcus, Enterobius, Fasciola, Filaroides, Habronema, Haemonchus, Metastrongylus, Moniezia, Necator, Nematodirus, Nippostrongylus, Oesophagostumum, Onchocerca, Ostertagia, Oxyuris, Paracaris, Schistosoma, Strongylus, Taenia, Toxocara, Strongyloides, Toxascaris, Trichinella, Trichuris, Trichostrongylus, Triodontophorous, Uncinaria, Wuchereria*, and combinations thereof.

In another embodiment of the invention, the helminth is *Haemonchus contortus, Ostertagia circumcincta, Trichostrongylus axei, Trichostrongylus colubriformis, Cooperia curticei, Nematodirus battus* and combinations thereof.

Another embodiment of the invention is directed toward a method of treating ectoparasitic infestation or infection in an animal in need thereof which comprises administering an effective amount of the compound of the invention to the animal in need thereof.

In one embodiment, the infection or infestation is caused by fleas, ticks, mites, mosquitoes, flies, lice, blowfly and combinations thereof.

In still another embodiment, invention provides a method for treating an ectoparasitic infestation or infection in an animal, comprising administering an effective amount of an aryloazol-2-yl-cyanoethylamino compound of the invention in combination with an effective amount of an avermectin or milbemycin active agent to the animal in need thereof.

The compounds of formula (I) or their salts can be employed as such or in the form of their preparations (formulations) as combinations with other active substances, such as, for example, insecticides, attractants, sterilants, acaricides, nematicides, herbicides, fungicides, and with safeners, fertilizers and/or growth regulators, for example as a premix/readymix.

Classifications of fungicides are well-known in the art and include classifications by FRAC (Fungicide Resistance Action Committee). Fungicides which may optionally be admixed include, but are not limited to, methyl benzimidazole carbamates, such as benzimidazoles and thiophanates; dicarboximides; demethylation inhibitors, such as imidazoles, piperazines, pyridines, pyrimidines, and triazoles; phenylamides, such as acylalanines, oxazolidinones, and butyrolactones; amines, such as morpholines, piperidines, and spiroketalamines; phosphorothiolates; dithiolanes; carboxamides; hydroxy-(2-amino-)pyrimidines; anilino-pyrimidines; N-phenyl carbamates; quinone outside inhibitors; phenylpyrroles; quinolines; aromatic hydrocarbons; heteroaromatics; melanin biosynthesis inhibitors-reductase; melanin biosynthesis inhibitors-dehydratase; hydroxyanilides (SBI class III), such as fenhexamid; SBI class IV, such as thiocarbamates and allylamines; polyoxins; phenylureas; quinone inside inhibitors; benzamides; enopyranuronic acid antibiotic; hexopyranosyl antibiotic; glucopyranosyl antibiotic; glucopyranosyl antibiotic; cyanoacetamideoximes; carbamates; uncoupler of oxidative phosphorylation; organo tin compounds; carboxylic acids; heteroaromatics; phosphonates; phthalamic acids; benzotriazines; benzenesulfonamides; pyridazinones; carboxylic acid amides; tetracycline antibiotic; thiocarbamate; benzo-thiadiazole BTH; benzisothiazole; thiadiazolecarboxamide; thiazolecarboxamides; benzamidoxime; quinazolinone; benzophenone; acylpicolide; inorganic compounds, such as copper salts and sulphur; dithiocarbamates and relatives; phthalimides; chloronitriles; sulphamides; guanidines; triazines; quinones.

Other fungicides that may optionally be admixed may also be from the classes of compounds described in U.S. Pat. Nos. 7,001,903 and 7,420,062.

Herbicides that are known from the literature and classified by HRAC (Herbicide Resistance Action Committee) and may be combined with the compounds of the invention are, for example: aryloxyphenoxy-propionate; cyclohexanedione; phenylpyrazoline; sulfonylurea; imidazolinone, such as imazapic and imazethapyr; triazolopyrimidine; pyrimidinyl (thio)benzoate; sulfonylaminocarbonyl-triazolinone; triazine, such as atrazine; triazinone; triazolinone; uracil; pyridazinone; phenyl-carbamate; urea; amide; nitrile; benzothiadiazinone; phenyl-pyridazine; bipyridylium, such as paraquat; diphenylether; phenylpyrazole; N-phenylphthalimide; thiadiazole; thiadiazole; triazolinone; oxazolidinedione; pyrimidindione; pyridazinone; pyridinecarboxamide; triketone; isoxazole; pyrazole; triazole; isoxazolidinone; urea, such as linuron; diphenylether; glycine, such as glyphosate; phosphinic acid, such as glufosinate-ammonium; carbamate; dinitroaniline, such as pendimethalin; phosphoroamidate; pyridine; benzamide; benzoic acid; chloroacetamide; metolachlor; acetamide; oxyacetamide; tetrazolinone; nitrile; benzamide; triazolocarboxamide; quinoline carboxylic acid; dinitrophenol; thiocarbamate; phosphorodithioate; benzofuran; chloro-carbonic-acid; phenoxy-carboxylic-acid, such as 2,4-D; benzoic acid, such as dicamba; pyridine carboxylic acid, such as clopyralid, triclopyr, fluoroxypyr and picloram; quinoline carboxylic acid; phthalamate semicarbazone; qrylaminopropionic acid; qrylaminopropionic acid; organoarsenical.

Other herbicides that may optionally be admixed are compounds described in U.S. Pat. Nos. 7,432,226, 7,012,041, and 7,365,082.

Appropriate herbicide safeners include but are not limited to benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anyhydride and oxabetrinil.

Bactericides include, but are not limited to, bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

Insecticides/acaricides/nematicides include those compounds mentioned in U.S. Pat. Nos. 7,420,062 and 7,001,903, U.S. Patent publication 2008/0234331, each incorporated herein by reference, the literature known to the person skilled in the art, and the compounds classified by IRAC (Insecticide Resistance Action Committee). Examples of insecticides/acaricides/nematicides include, but are limited to, carbamates; triazemate; organophosphates; cyclodiene organochlorines; phenylpyrazoles; DDT; methoxychlor; pyrethroids; pyrethrins; neonicotinoids; nicotine; bensultap; cartap hydrochloride; nereistox analogues; spinosyns; avermectins and milbemycins; juvenile hormone analogues; fenoxycarb; fenoxycarb; alkyl halides; chloropicrin; sulfuryl fluoride; cryolite; pymetrozine; flonicamid; clofentezine; hexythiazox; etoxazole; *Bacillus sphaericus*; diafenthiuron; organotin miticides; propargite; tetradifon; chlorfenapyr; DNOC; benzoylureas; buprofezin; cyromazine; diacylhydrazines; azadirachtin; amitraz; hydramethylnon; acequinocyl; fluacrypyrim; METI acaricides; rotenone; indoxacarb; metaflumizone; tetronic acid derivatives; aluminium phosphide; cyanide; phosphine; bifenazate; fluoroacetate; P450-dependent monooxygenase inhibitors; esterase inhibitors; diamides; benzoximate; chinomethionat; dicofol; pyridalyl; borax; tartar emetic; fumigants, such as methyl bromide; ditera; clandosan; sincocin.

The compounds of formula (I) can be formulated in various ways, depending on the prevailing biological and/or chemico-physical parameters. Examples of possible formulations which are suitable are: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), dispersions on an oil or water basis, solutions which are miscible with oil, capsule suspensions (CS), dusts (DP), seed-dressing products, granules for broadcasting and soil application, granules (GR) in the form of microgranules, spray granules, coated granules and adsorption granules, water-dispersible granules (WG), water-soluble granules (SG), ULV formulations, microcapsules and waxes.

Solid state forms of the compounds of formula (I) can be prepared by methods known in the art, e.g. Byrn et al., "Solid-State Chemistry of Drugs", $2^{nd}$ Edition, SSCI Inc., (1999); Glusker et al., "Crystal Structure Analysis—A Primer", $2^{nd}$ Edition, Oxford University Press, (1985).

The formulations mentioned can be prepared in a manner known per se, for example by mixing the active compounds with at least one solvent or diluent, emulsifier, dispersant and/or binder or fixative, water repellent and optionally one or more of a desiccant, UV stabilizer, a colorant, a pigment and other processing auxiliaries.

These individual formulation types are known in principle and described, for example, in: Winnacker-Küchler, "Chemische Technologie" [Chemical Technology], Volume 7, C. Hauser Verlag, Munich, 4th Edition 1986; Wade van Valkenburg, "Pesticide Formulations", Marcel Dekker, N.Y., 1973; K. Martens, "Spray Drying Handbook", 3rd Ed. 1979, G. Goodwin Ltd. London.

The necessary formulation auxiliaries such as inert materials, surfactants, solvents and other additives are also known and described, for example, in: Watkins, "Handbook of Insecticide Dust Diluents and Carriers", 2nd Ed., Darland Books, Caldwell N.J.; H. v. Olphen, "Introduction to Clay Colloid Chemistry", 2nd Ed., J. Wiley & Sons, N.Y.; C. Marsden, "Solvents Guide", 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1976; Winnacker-Küchler, "Chemische Technologie" [Chemical Technology], Volume 7, C. Hauser Verlag, Munich, 4th Ed. 1986.

Wettable powders are preparations which are uniformly dispersible in water and which, besides the compounds of formula (I), also comprise ionic and/or nonionic surfactants (wetters, dispersants), for example, polyoxyethylated alkylphenols, polyoxyethylated fatty alcohols, polyoxyethylated fatty amines, fatty alcohol polyglycol ether sulfates, alkanesulfonates or alkylbenzenesulfonates, sodium lignosulfonate, sodium 2,2'-dinaphthylmethane-6,6'-disulfonate, sodium dibutylnaphthalenesulfonate or else sodium oleoylmethyltaurinate, in addition to a diluent or inert substance. To prepare the wettable powders, the compounds of formula (I) are, for example, ground finely in conventional apparatuses such as hammer mills, blower mills and air-jet mills and mixed with the formulation auxiliaries, either concomitantly or thereafter.

Emulsifiable concentrates are prepared, for example, by dissolving the compounds of formula (I) in an organic solvent, for example butanol, cyclohexanone, dimethylformamide, xylene or else higher-boiling aromatics or hydrocarbons or mixtures of these, with addition of one or more ionic and/or nonionic surfactants (emulsifiers). Emulsifiers which can be used are, for example: calcium salts of alkylarylsulfonic acids, such as calcium dodecylbenzenesulfonate or nonionic emulsifiers, such as fatty acid polyglycol esters, alkylaryl polyglycol ethers, fatty alcohol polyglycol ethers, propylene oxide/ethylene oxide condensates, alkyl polyethers, sorbitan esters such as sorbitan fatty acid esters or polyoxyethylene sorbitan esters such as polyoxyethylene sorbitan fatty acid esters.

Dusts are obtained by grinding the active substance with finely divided solid substances, for example talc or natural clays, such as kaolin, bentonite or pyrophyllite, or diatomaceous earth.

Suspension concentrates may be water- or oil-based. They can be prepared, for example, by wet grinding by means of commercially available bead mills, if appropriate with addition of surfactants, as they have already been mentioned above for example in the case of the other formulation types.

Emulsions, for example oil-in-water emulsions (EW), can be prepared for example by means of stirrers, colloid mills and/or static mixtures using aqueous organic solvents and, if appropriate, surfactants as they have already been mentioned above for example in the case of the other formulation types.

Granules can be prepared either by spraying the compounds of formula (I) onto adsorptive, granulated inert material or by applying active substance concentrates onto the surface of carriers such as sand, kaolinites or of granulated inert material, by means of binders, for example polyvinyl alcohol, sodium polyacrylate or alternatively mineral oils.

Suitable active substances can also be granulated in the manner which is conventional for the production of fertilizer granules, if desired in a mixture with fertilizers.

Water-dispersible granules are prepared, as a rule, by the customary processes such as spray-drying, fluidized-bed granulation, disk granulation, mixing in high-speed mixers and extrusion without solid inert material. To prepare disk, fluidized-bed, extruder and spray granules, see, for example, processes in "Spray-Drying Handbook" 3rd ed. 1979, G. Goodwin Ltd., London; J. E. Browning, "Agglomeration", Chemical and Engineering 1967, pages 147 et seq.; "Perry's Chemical Engineer's Handbook", 5th Ed., McGraw-Hill, New York 1973, p. 8-57. In general, the agrochemical preparations comprise a range selected from the group consisting of about 0.1 to about 99% by weight and about 0.1 to about 95% by weight, of compounds of formula (I).

The concentration of compounds of formula (I) in wettable powders is, for example, about 10 to about 90% by weight, the remainder to 100% by weight being composed of customary formulation components. In the case of emulsifiable concentrates, the concentration of compounds of formula (I) can amount to ranges selected from the group consisting of about 1% to about 90% and about 5% to about 80% by weight. Formulations in the form of dusts usually comprise in the range selected from the group consisting of about 1% to about 30% by weight of compounds of formula (I) and about 5% to about 20% by weight of compounds of formula (I). For sprayable solutions comprise a range selected from the group consisting of about 0.05% to about 80% by weight of compounds of formula (I) and about 2% to about 50% by weight of compounds of formula (I). In the case of water-dispersible granules, the content of compounds of formula (I) depends partly on whether the compounds of formula (I) are in liquid or solid form and on which granulation auxiliaries, fillers and the like are being used. The water-dispersible granules, for example, comprise a range selected from the group consisting of between about 1 and about 95% and between about 10% and about 80% by weight.

In addition, the formulations of compounds of formula (I) mentioned comprise, if appropriate, the adhesives, wetters, dispersants, emulsifiers, penetrants, preservatives, antifreeze agents, solvents, fillers, carriers, colorants, antifoams, evaporation inhibitors, pH regulators and viscosity regulators which are conventional in each case.

Additional pharmaceutically or veterinarily active ingredients may also be added to the compositions of the invention. In some embodiments, the additional active agents may be one or more parasiticidal compounds including acaricides, anthelmintics, endectocides and insecticides. Anti-parasitic agents can include both ectoparasiticisal and endoparasiticidal agents.

Veterinary pharmaceutical agents that may be included in the compositions of the invention are well-known in the art (see e.g. *Plumb' Veterinary Drug Handbook, 5th Edition*, ed. Donald C. Plumb, Blackwell Publishing, (2005) or *The Merck Veterinary Manual, 9th Edition*, (January 2005)) and include but are not limited to acarbose, acepromazine maleate, acetaminophen, acetazolamide, acetazolamide sodium, acetic acid, acetohydroxamic acid, acetylcysteine, acitretin, acyclovir, albendazole, albuterol sulfate, alfentanil, allopurinol, alprazolam, altrenogest, amantadine, amikacin sulfate, aminocaproic acid, aminopentamide hydrogen sulfate, aminophylline/theophylline, amiodarone, amitraz, amitriptyline, amlodipine besylate, ammonium chloride, ammonium molybdenate, amoxicillin, clavulanate potassium, amphotericin B desoxycholate, amphotericin B lipid-based, ampicillin, amprolium, antacids (oral), antivenin, apomorphine, apramycin sulfate, ascorbic acid, asparaginase, aspiring, atenolol, atipamezole, atracurium besylate, atropine sulfate, aurnofin, aurothioglucose, azaperone, azathioprine, azithromycin, baclofen, barbituates, benazepril, betamethasone, bethanechol chloride, bisacodyl, bismuth subsalicylate, bleomycin sulfate, boldenone undecylenate, bromides, bromocriptine mesylate, budenoside, buprenorphine, buspirone, busulfan, butorphanol tartrate, cabergoline, calcitonin salmon, calcitrol, calcium salts, captopril, carbenicillin indanyl sodium, carbimazole, carboplatin, carnitine, carprofen, carvedilol, cefadroxil, cefazolin sodium, cefixime, chlorsulon, cefoperazone sodium, cefotaxime sodium, cefotetan disodium, cefoxitin sodium, cefpodoxime proxetil, ceftazidime, ceftiofur sodium, ceftiofur, ceftiaxone sodium, cephalexin, cephalosporins, cephapirin, charcoal (activated), chlorambucil, chloramphenicol, chlordiazepoxide, chlordiazepoxide +/− clidinium bromide, chlorothiazide, chlorpheniramine maleate, chlorpromazine, chlorpropamide, chlortetracycline, chorionic gonadotropin (HCG), chromium, cimetidine, ciprofloxacin, cisapride, cisplatin, citrate salts, clarithromycin, clemastine fumarate, clenbuterol, clindamycin, clofazimine, clomipramine, claonazepam, clonidine, cloprostenol sodium, clorazepate dipotassium, clorsulon, cloxacillin, codeine phosphate, colchicine, corticotropin (ACTH), cosyntropin, cyclophosphamide, cyclosporine, cyproheptadine, cytarabine, dacarbazine, dactinomycin/actinomycin D, dalteparin sodium, danazol, dantrolene sodium, dapsone, decoquinate, deferoxamine mesylate, deracoxib, deslorelin acetate, desmopressin acetate, desoxycorticosterone pivalate, detomidine, dexamethasone, dexpanthenol, dexraazoxane, dextran, diazepam, diazoxide (oral), dichlorphenamide, diclofenac sodium, dicloxacillin, diethylcarbamazine citrate, diethylstilbestrol (DES), difloxacin, digoxin, dihydrotachysterol (DHT), diltiazem, dimenhydrinate, dimercaprol/BAL, dimethyl sulfoxide, dinoprost tromethamine, diphenylhydramine, disopyramide phosphate, dobutamine, docusate/DSS, dolasetron mesylate, domperidone, dopamine, doramectin, doxapram, doxepin, doxorubicin, doxycycline, edetate calcium disodium.calcium EDTA, edrophonium chloride, enalapril/enalaprilat, enoxaparin sodium, enrofloxacin, ephedrine sulfate, epinephrine, epoetin/erythropoietin, eprinomectin, epsiprantel, erythromycin, esmolol, estradiol cypionate, ethacrynic acid/ethacrynate sodium, ethanol (alcohol), etidronate sodium, etodolac, etomidate, euthanasia agents w/pentobarbital, famotidine, fatty acids (essential/omega), felbamate, fentanyl, ferrous sulfate, filgrastim, finasteride, fipronil, florfenicol, fluconazole, flucytosine, fludrocortisone acetate, flumazenil, flumethasone, flunixin meglumine, fluorouracil (5-FU), fluoxetine, fluticasone propionate, fluvoxamine maleate, fomepizole (4-MP), furazolidone, furosemide, gabapentin, gemcitabine, gentamicin sulfate, glimepiride, glipizide, glucagon, glucocorticoid agents, glucosamine/chondroitin sulfate, glutamine, glyburide, glycerine (oral), glycopyrrolate, gonadorelin, grisseofulvin, guaifenesin, halothane, hemoglobin glutamer-200 (oxyglobin®), heparin, hetastarch, hyaluronate sodium, hydrazaline, hydrochlorothiazide, hydrocodone bitartrate, hydrocortisone, hydromorphone, hydroxyurea, hydroxyzine, ifosfamide, imidacloprid, imidocarb dipropinate, impenem-cilastatin sodium, imipramine, inaminone lactate, insulin, interferon alfa-2a (human recombinant), iodide (sodium/potassium), ipecac (syrup), ipodate sodium, iron dextran, isoflurane, isoproterenol, isotretinoin, isoxsuprine, itraconazole, ivermectin, kaolin/pectin, ketamine, ketoconazole, ketoprofen, ketorolac tromethamine, lactulose, leuprolide, levamisole, levetiracetam, levothyroxine sodium, lidocaine, lincomycin, liothyronine sodium, lisinopril, lomustine (CCNU), lufenuron, lysine, magnesium, mannitol, marbofloxacin, mechlorethamine, meclizine, meclofenamic acid, medetomidine, medium chain triglycerides, medroxyprogesterone acetate, megestrol acetate, melarsomine, melatonin, meloxican, melphalan, meperidine, mercaptopurine, meropenem, metformin, methadone, methazolamide, methenamine mandelate/hippurate, methimazole, methionine, methocarbamol, methohexital sodium, methotrexate, methoxyflurane, methylene blue, methylphenidate, methylprednisolone, metoclopramide, metoprolol, metronidaxole, mexiletine, mibolerlone, midazolam milbemycin oxime, mineral oil, minocycline, misoprostol, mitotane, mitoxantrone, morphine sulfate, moxidectin, naloxone, mandrolone decanoate, naproxen, narcotic (opiate) agonist analgesics, neomycin sulfate, neostigmine, niacinamide, nitazoxanide, nitenpyram, nitrofurantoin, nitroglycerin, nitroprusside sodium, nizatidine, novobiocin sodium, nystatin, octreotide acetate, olsalazine sodium, omeprozole, ondansetron, opiate antidiarrheals, orbifloxacin, oxacillin sodium, oxazepam, oxibutynin chloride, oxymorphone, oxytretracycline, oxytocin, pamidronate disodium, pancreplipase, pancuronium bromide, paromomycin sulfate, parozetine, pencillamine, general information penicillins, penicillin G, penicillin V potassium, pentazocine, pentobarbital sodium, pentosan polysulfate sodium, pentoxifylline, pergolide mesylate, phenobarbital, phenoxybenzamine, pheylbutazone, phenylephrine, phenypropanolamine, phenyloin sodium, pheromones, parenteral phosphate, phytonadione/vitamin K-1, pimobendan, piperazine, pirlimycin, piroxicam, polysulfated glycosaminoglycan, ponazuril, potassium chloride, pralidoxime chloride, prazosin, prednisolone/prednisone, primidone, procainamide, procarbazine, prochlorperazine, propantheline bromide, *propionibacterium acnes* injection, propofol, propranolol, protamine sulfate, pseudoephedrine, psyllium hydrophilic mucilloid, pyridostigmine bromide, pyrilamine maleate, pyrimethamine, quinacrine, quinidine, ranitidine, rifampin, s-adenosyl-methionine (SAMe), saline/hyperosmotic laxative, selamectin, selegiline/I-deprenyl, sertraline, sevelamer, sevoflurane, silymarin/milk thistle, sodium bicarbonate, sodium polystyrene sulfonate, sodium stibogluconate, sodium sulfate, sodum thiosulfate, somatotropin, sotalol, spectinomycin, spironolactone, stanozolol, streptokinase, streptozocin, succimer, succinylcholine chloride, sucralfate, sufentanil citrate, sulfachlorpyridazine sodium, sulfadiazine/trimethroprim, sulfamethoxazole/trimethoprim, sulfadimentoxine, sulfadimethoxine/ormetoprim, sulfasalazine, taurine, tepoxaline, terbinafline, terbutaline sulfate, testosterone, tetracycline, thiacetarsamide sodium, thiamine, thioguanine, thiopental sodium, thiotepa, thyrotropin, tiamulin, ticarcilin disodium, tiletamine/zolazepam, tilmocsin, tiopronin, tobramycin sulfate, tocamide, tolazoline, telfenamic acid, topiramate, tramadol, trimcinolone acetonide, trientine, trilostane, trimepraxine tartrate w/prednisolone, tripelennamine, tylosin, urdosiol, valproic acid, vanadium, vancomycin, vasopressin, vecuronium bromide, verapamil, vinblastine sulfate, vincristine sulfate, vitamin E/selenium, warfarin sodium, xylazine, yohimbine, zafirlukast, zidovudine (AZT), zinc acetate/zinc sulfate, zonisamide and mixtures thereof.

In one embodiment of the invention, arylpyrazole compounds such as phenylpyrazoles (e.g. fipronil, pyriprole), may be suitable for combination with the aryloazol-2-yl cyanoethylamino compounds of the invention. Examples of such arylpyrazole compounds include but are not limited to those described in U.S. Pat. Nos. 6,001,384; 6,010,710; 6,083,519; 6,096,329; 6,174,540; 6,685,954 and 6,998,131—each assigned to Merial, Ltd., Duluth, Ga.

In another embodiment of the invention, nodulisporic acid and its derivatives (a class of known acaricidal, anthelminitic, anti-parasitic and insecticidal agents) can be added to the compositions of the invention. These compounds are used to treat or prevent infections in humans and animals and are described, for example, in U.S. Pat. Nos. 5,399,582, 5,962,499, 6,221,894 and 6,399,786. The composition can include one or more of the known nodulisporic acid derivatives in the art, including all stereoisomers, such as those described in the literature cited above.

In another embodiment, anthelmintic compounds of the amino acetonitrile class (AAD) of compounds such as monepantel (ZOLVIX) and the like may be added to the compositions of the invention. These compounds are described, for example, in WO 2004/024704; Sager et al., Veterinary Parasitology, 2009, 159, 49-54; Kaminsky et al., Nature vol. 452, 13 Mar. 2008, 176-181.

In another embodiment, the compositions of the invention may advantageously include one or more compounds of the isoxazoline class of compounds. These active agents are described in WO 2007/079162, WO 2007/075459 and US 2009/0133319, WO 2007/070606 and US 2009/0143410, WO 2009/003075, WO 2009/002809, WO 2009/024541, WO 2005/085216 and US 2007/0066617 and WO 2008/122375, all of which are incorporated herein by reference in their entirety.

The compositions of the invention may also be combined with paraherquamide compounds and derivatives of these compounds, including derquantel (see Ostlind et al., *Research in Veterinary Science,* 1990, 48, 260-61; and Ostlind et al., *Medical and Veterinary Entomology,* 1997, 11, 407-408). The paraherquamide family of compounds are known class of compounds that include a spirodioxepino indole core with activity against certain parasites (see *Tet. Lett.* 1981, 22, 135; *J. Antibiotics* 1990, 43, 1380, and *J. Antibiotics* 1991, 44, 492). In addition, the structurally related marcfortine family of compounds, such as marcfortines A-C, are also known and may be combined with the formulations of the invention (see *J. Chem. Soc.—Chem. Comm.* 1980, 601 and *Tet. Lett.* 1981, 22, 1977). Further references to the paraherquamide derivatives can be found, for example, in WO 91/09961, WO 92/22555, WO 97/03988, WO 01/076370, WO 09/004,432, U.S. Pat. No. 5,703,078 and U.S. Pat. No. 5,750,695, all of which are hereby incorporated by reference in their entirety.

In another embodiment, the compositions of the invention may be combined with cyclodepsipeptide anthelmintic compounds including emodepside (see Willson et al., *Parasitology,* January 2003, 126(Pt 1):79-86).

In some embodiments, the compositions of the invention may include one or more antinematodal agents including, but not limited to, active agents in the benzimidazoles, imidazothiazoles, tetrahydropyrimidines, organophosphates class of compounds. In some embodiments, benzimidazoles including, but not limited to, thiabendazole, cambendazole, parbendazole, oxibendazole, mebendazole, flubendazole, fenbendazole, oxfendazole, albendazole, cyclobendazole, febantel, thiophanate and its o,o-dimethyl analogue may be included in the compositions.

In other embodiments, the compositions may include an imidazothiazole compounds including, but not limited to, tetramisole, levamisole and butamisole. In still other embodiments, the compositions of the invention may include tetrahydropyrimidine active agents including, but not limited to, pyrantel, oxantel, and morantel. Suitable organophosphate active agents include, but are not limited to, coumaphos, trichlorfon, haloxon, naftalofos and dichlorvos.

In other embodiments, the compositions may include the antinematodal compounds phenothiazine, piperazine as the neutral compound and in various salt forms, diethylcarbamazine, phenols such as disophenol, arsenicals such as arsenamide, ethanolamines such as bephenium, thenium closylate, and methyridine; cyanine dyes including pyrvinium chloride, pyrvinium pamoate and dithiazanine iodide; isothiocyanates including bitoscanate, suramin sodium, phthalofyne, and various natural products including, but not limited to, hygromycin B, □-santonin and kainic acid.

In other embodiments, the compositions of the invention may include antitrematodal agents. Suitable antitrematodal agents include, but are not limited to, the miracils such as miracil D and mirasan; praziquantel, clonazepam and its 3-methyl derivative, oltipraz, lucanthone, hycanthone, oxamniquine, amoscanate, niridazole, nitroxynil, various bisphenol compounds known in the art including hexachlorophene, bithionol, bithionol sulfoxide and menichlopholan; various salicylanilide compounds including tribromsalan, oxyclozanide, clioxanide, rafoxanide, brotianide, bromoxanide and closantel; triclabendazole, diamfenetide, clorsulon, hetolin and emetine.

Anticestodal compounds may also be advantageously used in the compositions of the invention including, but not limited to, arecoline in various salt forms, bunamidine, niclosamide, nitroscanate, paromomycin and paromomycin II.

In yet other embodiments, the compositions of the invention may include other active agents that are effective against artropod parasites. Suitable active agents include, but are not limited to, bromocyclen, chlordane, DDT, endosulfan, lindane, methoxychlor, toxaphene, bromophos, bromophosethyl, carbophenothion, chlorfenvinphos, chlorpyrifos, crotoxyphos, cythioate, diazinon, dichlorenthion diemthoate, dioxathion, ethion, famphur, fenitrothion, fenthion, fospirate, iodofenphos, malathion, naled, phosalone, phosmet, phoxim, propetamphos, ronnel, stirofos, carbaryl, promacyl, propoxur, allethrin, cyhalothrin, cypermethrin, deltamethrin, fenvalerate, flucythrinate, permethrin, phenothrin, pyrethrins, resmethrin, amitraz, benzyl benzoate, carbon disulfide, crotamiton, diflubenzuron, diphenylamine, disulfuram, isobornyl thiocyanato acetate, methroprene, monosulfuram, pirenonylbutoxide, rotenone, triphenyltin acetate, triphenyltin hydroxide, deet, dimethyl phthalate, and the compounds 1,5a,6,9,9a,9b-hexahydro-4-a(4H)-dibenzofurancarboxaldehyde (MGK-11), 2-(2-ethyl hexyl)-3a,4,7,7a-tetrahydro-4,7-methano-1H-isoindole-1,3(2H)dione (MGK-264), dipropyl-2,5-pyridinedicarboxylate (MGK-326) and 2-(octylthio) ethanol (MGK-874).

In another embodiment of the invention, one or more macrocyclic lactones, which act as an acaricide, anthelmintic agent and insecticide, can be added to the compositions of the invention.

The macrocyclic lactones also include, but are not limited to, avermectins, such as abamectin, dimadectin, doramectin, emamectin, eprinomectin, ivermectin, latidectin, lepimectin, selamectin and milbemycins, such as milbemectin, milbemycin D, moxidectin and nemadectin. Also included are the 5-oxo and 5-oxime derivatives of said avermectins and milbemycins. Examples of combinations of macrocyclic lactones with other active agents are described in U.S. Pat. Nos. 6,426,333; 6,482,425; 6,962,713 and 6,998,131—each assigned to Merial, Ltd., Duluth, Ga., all incorporated herein by reference.

The macrocyclic lactone compounds are known in the art and can be obtained commercially or through synthesis techniques known in the art. Reference is made to the widely available technical and commercial literature. For avermectins, ivermectin and abamectin, reference may be made, for example, to the work "Ivermectin and Abamectin", 1989, by M. N. Fischer and H. Mrozik, William C. Campbell, published by Springer Verlag., "Macrocyclic Lactones in Antiparasitic Therapy", 2002, by J Vercruysse and R S Rew published by CABI Publishing or Albers-Schonberg et al. (1981), "Avermectins Structure Determination", J. Am. Chem. Soc., 103, 4216-4221. For doramectin, "Veterinary Parasitology", vol. 49, No. 1, July 1993, 5-15 may be consulted. For milbemycins, reference may be made, inter alia, to Davies H. G. et al., 1986, "Avermectins and Milbemycins", Nat. Prod. Rep., 3, 87-121, Mrozik H. et al., 1983, Synthesis of Milbemycins from Avermectins, *Tetrahedron Lett.*, 24, 5333-5336, U.S. Pat. No. 4,134,973 and EP 0 677 054.

Macrocyclic lactones are either natural products or are semi-synthetic derivatives thereof. The structures of the avermectins and milbemycins are closely related, e.g., by sharing a complex 16-membered macrocyclic lactone ring; milbemycins lack the glycosidic moiety of the avermectins. The natural products avermectins are disclosed in U.S. Pat. No. 4,310,519 to Albers-Schönberg et al., and the 22,23-dihydro avermectin compounds are disclosed in Chabala et al., U.S. Pat. No. 4,199,569. Mention is also made of Kitano, U.S. Pat. No. 4,468,390, Beuvry et al., U.S. Pat. No. 5,824,653, EP 0 007 812 A1, U.K. Patent Specification 1 390 336, EP 0 002 916, and Ancare New Zealand Patent No. 237 086, inter alia. Naturally occurring milbemycins are described in Aoki et al., U.S. Pat. No. 3,950,360 as well as in the various references cited in "The Merck Index" $12^{th}$ ed., S. Budavari, Ed., Merck & Co., Inc. Whitehouse Station, N.J. (1996). Latidectin is described in the "International Nonproprietary Names for Pharmaceutical Substances (INN)", WHO Drug Information, vol. 17, no. 4, pp. 263-286, (2003). Semisynthetic derivatives of these classes of compounds are well known in the art and are described, for example, in U.S. Pat. Nos. 5,077,308, 4,859,657, 4,963,582, 4,855,317, 4,871,719, 4,874,749, 4,427,663, 4,310,519, 4,199,569, 5,055,596, 4,973,711, 4,978,677, 4,920,148 and EP 0 667 054.

Combination of the compounds of the invention with an avermectin or milbemycin compound is particularly preferred. It has been surprisingly been discovered that combination of the compounds of the invention with an avermectin or a milbemycin compound results in unexpected superior efficacy against parasites that are resistant to macrocyclic lactones such as ivermectin, or parasites that are not well controlled by these potent anthelmintic agents. For example, it was found that a combination of a compound of the invention (compound 3.024) at a dose of 6 mg/kg with ivermectin at a dose of 50 µg/kg (0.05 mg/kg) administered subcutaneously to cattle infected by an ivermectin-resistant strain of *Haemonchus placei* and by *Nematodirus helvetianus*, a parasite that is not well controlled by ivermectin, resulted in an efficacy of greater than 95% for *Haemonchus placei* and *Nematodirus helvetianus*. In comparison, treatment with ivermectin alone at a dose of 0.2 mg/kg (200 µg/kg) administered subcutaneously resulted in less than 70% efficacy against *Haemonchus placei* and less than 30% efficacy against *Nematodirus helvetianus*. FIG. 2 shows the % efficacy of a combination of compound 3.024 (6 mg/kg subcutaneous) with ivermectin (50 µg/kg subcutaneous) for a variety of endoparasites in cattle. It is surprising that this combination achieves greater than 95% efficacy against a wide variety of endoparasites in cattle, including parasites that are not well controlled by ivermectin alone and including parasites that may not be adequately controlled by the suboptimal dose of ivermectin at 50 µg/kg In another embodiment of the invention, the class of acaricides or insecticides known as insect growth regulators (IGRs) can also be added to the compositions of the invention. Compounds belonging to this group are well known to the practitioner and represent a wide range of different chemical classes. These compounds all act by interfering with the development or growth of the insect pests. Insect growth regulators are described, for example, in U.S. Pat. Nos. 3,748, 356; 3,818,047; 4,225,598; 4,798,837; 4,751,225, EP 0 179 022 or U.K. 2 140 010 as well as U.S. Pat. Nos. 6,096,329 and 6,685,954 (both assigned to Merial Ltd., Duluth, Ga.). Examples of IGRs suitable for use include but are not limited to methoprene, pyriproxyfen, hydroprene, cyromazine, fluazuron, lufenuron, novaluron, pyrethroids, formamidines and 1-(2,6-difluorobenzoyl)-3-(2-fluoro-4-(trifluoromethyl)phenylurea.

A parasiticidal agent that can be combined with the compound of the invention to form a composition can be a biologically active peptide or protein including, but not limited to, depsipeptides, which act at the neuromuscular junction by stimulating presynaptic receptors belonging to the secretin receptor family resulting in the paralysis and death of parasites. In one embodiment of the depsipeptide, the depsipeptide is emodepside.

An insecticidal agent that can be combined with the compound of the invention to form a composition can be a spinosyn (e.g. spinosad) or a substituted pyridylmethyl derivative compound such as imidacloprid. Agents of this class are described above, and for example, in U.S. Pat. No. 4,742,060 or in EP 0 892 060. It would be well within the skill level of the practitioner to decide which individual compound can be used in the inventive formulation to treat a particular parasitic infection/infestation. For ectoparasites, active agents that can be combined also include but are not limited to pyrethoids, organophosphates and neonicotinoids such as imidacloprid, as well as compounds such as metaflumizone, amitraz and ryanodine receptor antagonists.

Where appropriate the anthelmintic, parasiticidal and insecticial agent may also be selected from the group of compounds described above as suitable for agrochemical use.

In general, the additional active agent is included in a dose of between about 0.1 μg and about 500 mg. In some embodiments, the additional active agent may be present in a dose of about 1 mg to about 500 mg, about 1 mg to about 300 mg, or about 1 mg to about 100 mg. In other embodiments, the additional active agent may be present in a dose of about 1 mg to about 50 mg or about 1 mg to about 20 mg. In other embodiment of the invention, the additional active agent is included in a dose of about 1 μg to about 10 mg.

In another embodiment of the invention, the additional active agent is included in a dose of about 5 μg/kg to about 50 mg/kg. In other embodiments, the additional active agent may be included in a dose of about 5 μg/kg to about 30 mg/kg, about 5 μg/kg to about 20 mg/kg or about 5 μg/kg to about 10 mg/kg.

In still other embodiments, the additional active agent may be included in a dose of about 10 μg/kg to about 1 mg/kg or about 50 μg/kg to about 500 μg/kg of weight of the animal. In yet another embodiment of the invention, the additional active agent is included in a dose between about 0.1 mg/kg to about 10 mg/kg of weight of animal. In still another embodiment of the invention, the additional active agent is included in a dose between about 0.5 mg/kg to 50 mg/kg.

The proportions, by weight, of the aryloazol-2-yl-cyanoethylamino compound and the additional active agent are for example between about 5/1 and about 10,000/1. However, one of ordinary skill in the art would be able to select the appropriate ratio of aryloazol-2-yl-cyanoethylamino compound and the additional active agent for the intended host and use thereof.

Another aspect of the invention is the process of making the aryloazol-2-yl-cyanoethylamino compounds of the invention.

The compounds of formula (I) may be prepared according to the processes described herein or by the application or adaptation of known methods (i.e. methods heretofore used or described in the chemical literature).

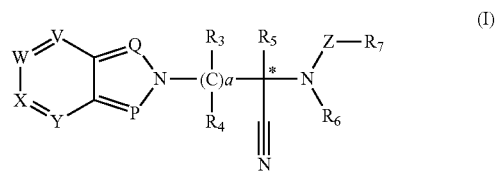

For example, compounds of formula (I) are obtainable by a process wherein compound (II) is reacted with compound (III) wherein $R_3$, $R_4$, $R_5$, $R_6$, $R_7$, P, Q, V, W, X, Y, Z, and a are as defined above for the compounds of formula (I) and T is a leaving group such as a halogen atom, methanesulfonyl, trifluoromethanesulfonyl, toluenesulfonyl and the like.

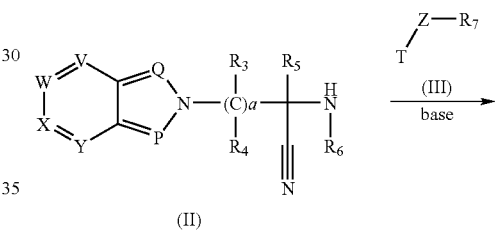

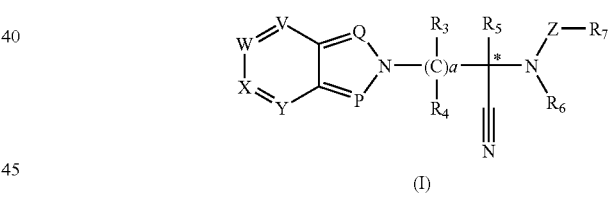

The reaction is generally carried out in the presence of a base in a solvent.

The base to be used in this reaction includes, for example but not limited to, inorganic bases such as sodium carbonate, potassium carbonate and the like, organic bases such as dimethylaminopyridine, triethylamine, diisopropylethylamine, 1,8-diazabicyclo [5.4.0]-7-undecene and the like.

The solvent to be used in the reaction includes, but is not limited to, ethers such as diethylether, tetrahydrofuran and the like, halogenated hydrocarbons such as methylene chloride, chloroform, 1,2-dichloroethane and the like, or other solvents known in the art that are suitable for nucleophilic substitution reactions.

The reaction temperature is usually in the range of −78° C. to 150° C., preferably in the range of −20° C. to 80° C. and the reaction time is usually in the range of 0.5 to 72 hours.

After completion of the reaction, the compounds of formula (I) can be isolated by employing conventional methods such as adding the reaction mixture to water, extracting with an organic solvent, concentrating the extract and the like.

Work-up methods are well known in the art, and variations or modifications of work-up procedures may be made depending on the specific characteristics of the reaction mixtures. The isolated compound of formula (I) can be purified by a technique such as chromatography, recrystallization and the like, or a combination of purification procedures, if necessary.

The compounds of formula (Ia) may be prepared by the application or adaptation of known methods of amide formation (i.e. methods heretofore used or described in the chemical literature).

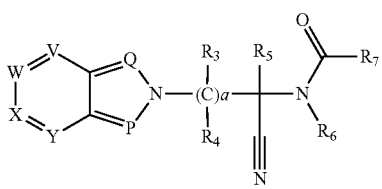

(Ia)

Many procedures are available for forming amide bonds between an amine derivative such as the α-amino nitrile derivatives of formula (II) and a carboxylic acid with the use of coupling agents. Procedures have been developed which use reagents such as carbodiimides as amide coupling agents. These carbodiimides include for example dicyclohexylcarbodiimide (DCC), diisopropylcarbodiimide (DIC), 1-(3-dimethylaminopropyl)-3-ethylcarbodiimide hydrochloride (EDC) and the like. Other amide coupling agents known in the art such as 1-ethoxycarbonyl-2-dihydroquinoline (EEDQ), phosphonium (e.g. phosphonium hexafluorophosphate (BOP), and others) or uronium-based reagents (e.g. TBTU, HATU and others) may also be used to form the amide bonds. In addition, anhydrides may also be utilized to form the desired amide bond. Catalysts such as 1-hydroxybenzotriazole (HOBT) and derivatives thereof have also been used. A summary of such methods is found in "*Comprehensive Organic Transformations*", R. C. Larock, VCH Publishers (1989) pp. 972-972. An overview of such transformations is also available in "*March's Advanced Organic Chemistry: Reactions, Mechanisms, and Structure* (Sixth Edition)", Michael B. Smith and Jerry March, Wiley-Interscience Publishers, (2007), pp 1431-1434.

Another general reaction for the preparation of amides is the treatment of acyl halides with amine. Such a transformation is well known to those skilled in the art and an overview of such transformations is available in "*March's Advanced Organic Chemistry: Reactions, Mechanisms, and Structure* (Sixth Edition)", Michael B. Smith and Jerry March, Wiley-Interscience Publishers, (2007), pp. 1427-1429.

The α-amino nitrile derivatives of formula (II) can be prepared in one step by the treatment of carbonyl compounds of general formula (IV) with a suitable cyanide source such as sodium cyanide, potassium cyanide, trimethylsilyl cyanide and the like, with amines of general formula $R_6$—$NH_2$ such as ammonia, methyl amine and the like and generally in presence of ammonium salt such as ammonium chloride and the like. Those skilled in the art will recognize this as the Strecker synthesis (see e.g. page 1391 in "*March's Advanced Organic Chemistry: Reactions, Mechanisms, and Structure* (Sixth Edition)", Michael B. Smith and Jerry March, Wiley-Interscience Publishers, (2007).

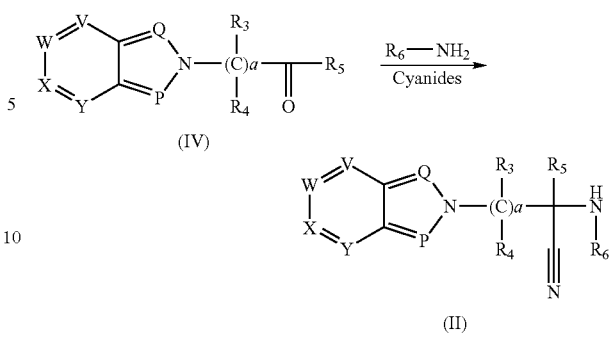

The carbonyl compounds of formula (IV) can be prepared by treatment of a NH-arylo-azole of general formula (V) with compound of general formula (VI) wherein, $R_1$, $R_2$, $R_3$, $R_4$, $R_5$, $R_7$, P, Q, V, W, X, Y, a, m and n are as defined above for the compounds of formula (I) and T is a leaving group such as a halogen atom, methanesulfonyl, trifluoromethanesulfonyl, toluenesulfonyl and the like.

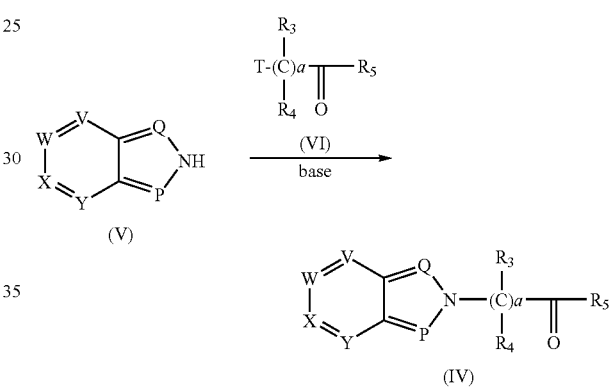

The reaction is generally carried out in the presence of a base in a solvent.

The base to be used in this reaction includes, for example but not limited to, inorganic bases such as sodium carbonate, potassium carbonate and the like, organic bases such as dimethylaminopyridine, triethylamine, diisopropylethylamine, 1,8-diazabicyclo [5.4.0]-7-undecene and the like.

The solvent to be used in the reaction includes, for example but not limited to, acetone, ethers such as diethylether, tetrahydrofuran and the like, halogenated hydrocarbon such as methylene chloride, chloroform, 1,2-dichloroethane and the like.

The reaction temperature is usually in the range of −78° C. to 150° C., preferably in the range of −20° C. to 80° C. and the reaction time is usually in the range of 0.5 to 72 hours.

After completion of the reaction, the compounds of formula (IV) can be isolated by employing conventional methods such as adding the reaction mixture to water, extracting with an organic solvent, concentrating the extract and the like. The isolated compound of formula (IV) can be purified by a technique such as chromatography, recrystallization and the like, if necessary.

The 2H—NH-arylo-azole of formula (Va), (formula (V) with P=N), are generally represented as their tautomeric structure 1H—NH-arylo-azole (Vb). Specifically, 2H-benzotriazole of formula (Vc) and 2H-indazole of formula (Ve) are generally represented as their alternative tautomeric forms, respectively 1H-benzotriazole of formulas (Vd) or (Ve) and 1H-indazole of formula (Vg).

A discussion on tautomerism of heterocycles can be found in "*The Tautomerism of Heterocycles, Advances in Heterocyclic Chemistry Supplement 1*", eds. José Elguero, Claude Marzin, Alan R. Katritzky and Paolo Linda, Academic Press Publishers, (1976).

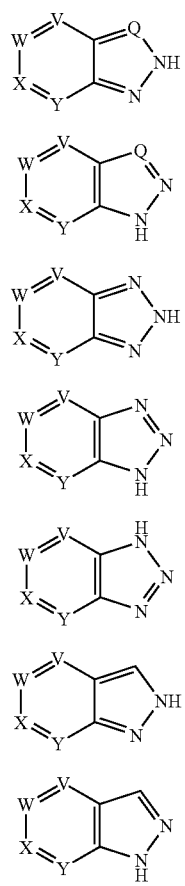

When carbonyl compounds of formula (IVa) were prepared by treatment of a 1H—NH-arylo-azole of general formula (Va) with compound of general formula (VI), regioisomer carbonyl compounds of formula (IVb) were also usually obtained. Those could be separated from desired carbonyl compounds of formula (IVa) by standard technique of purification known by persons skilled in the art such as, but not limited to, liquid chromatography using normal phase or reverse phase silica column and crystallization.

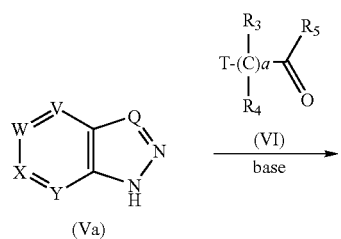

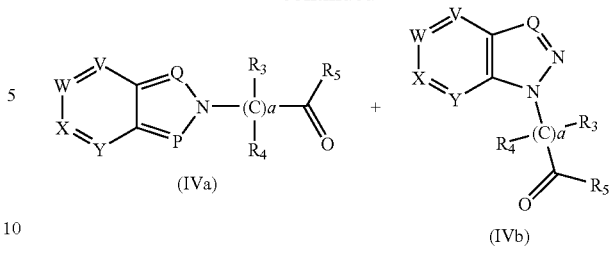

Those 1H—NH-arylo-azole compounds of general formula (Va) not commercially available can be prepared by the application or adaptation of known methods (i.e. methods heretofore used or described in the chemical literature).

For example, a general method of preparation of 1H-benzotriazole of formula (Vd) or (Ve) wherein, $R_1$, $R_2$, V, W, X, Y, m and n are as defined above for the compounds of formula (I) can be found in Organic Synthesis, Coll. Vol. 3, p. 106 (1955) and in *Journal of Heterocyclic Chemistry*, volume 22, (1985), pp. 1165-1167. Halogenation of 1H-benzotriazole of formula (Vd) or (Ve) can be achieved by adapting procedures described in the literature such as ones described by R. H. Wiley and K. F. Hussung in *Journal of the American Chemical Society*, (1957), pages 4395-4400 and by K. Kopanska et al. in *Bioorganic & Medicinal Chemistry*, volume 13 (2005) page 3601 and in *Bioorganic & Medicinal Chemistry*, volume 12 (2004), pages 2617-2624.

A general method of preparation of 1H-indazole of formula (Vg) wherein, $R_1$, $R_2$, V, W, X, Y, m and n are as defined above for the compounds of formula (I) was reported in the literature by R. A. Bartsch and II-Woo Yang in *Journal of Heterocyclic Chemistry*, volume 21, (1984), pp. 1063-1164 and recently by the team of Valerie Collot and Sylvain Rault in *Bioorganic & Medicinal Chemistry Letters*, volume 11 (2001), pages 1153-1156 and volume 17 (2007), pages 3177-3180.

In one embodiment of the invention, carbonyl compounds of formula (IVa), wherein Q is alkoxymethylene (Q=C—$OR_{13}$) or methylene (Q=CH), are formed by oxidation of the alcohol compounds of formula (VIIa).

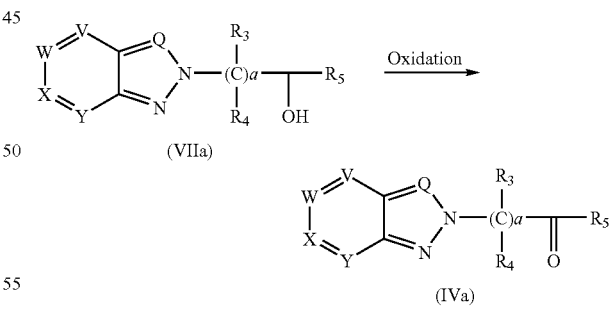

Such a transformation is well known to those skilled in the art, a summary of such methods is found in "*Comprehensive Organic Transformations*", VCH Publishers, (1989), R. C. Larock, pp. 604-614. For example, it can be realized with dimethylsufoxide-based reagents such as reacting oxalyl chloride with dimethylsufoxide at low temperature, those skilled in the art will recognize this as the Swern oxidation. It can also be realized by nitroxyl radical, 2,2,6,6-tetramethylpiperidine-1-oxyl free radical (TEMPO) and related reagents and with hypervalent iodine reagents such as the so called Dess-Martin Periodinane reagent (see e.g. page 1715-1728, "Oxidation or Dehydrogenation of Alcohols to Aldehydes and Ketones" in "March's Advanced Organic Chemistry: Reactions, Mechanisms, and Structure (Sixth Edition)", Michael B. Smith and Jerry March, Wiley-Interscience Publishers, (2007)). The solvent to be used in the reaction includes, for example but not limited to, ethers such as diethylether, tetrahydrofuran and the like, halogenated hydrocarbon such as such as methylene chloride, chloroform, 1,2-dichloroethane and the like. The reaction temperature is usually in the range of −78° C. to 150° C., preferably in the range of −78° C. to 50° C. and the reaction time is usually in the range of about 0.5 to 72 hours.

In another embodiment of the invention, carbonyl compounds of formula (IVa), wherein Q is alkoxymethylene (Q=C—OR$_{13}$) or methylene (Q=CH), are formed by oxidative cleavage of the alkene moiety of compound of formula (XVII) wherein R$_{17}$ and R$_{18}$ are independently selected from hydrogen, halogen, C1-C4 alkylcarbonyl or C1-C4 alkyl.

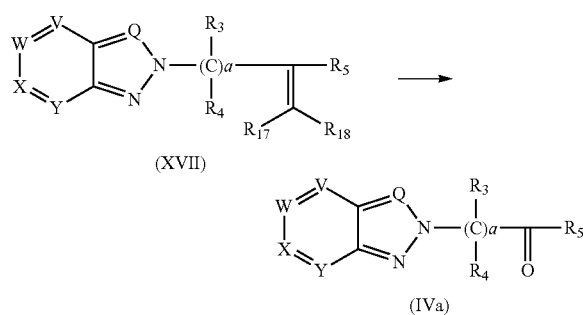

Such a transformation is well known to those skilled in the art and can be realized for example with ozone, potassium permanganate and sodium metaperiodate. The process may be carried out optionally in a solvent such as methylene chloride, diethylether, chloroform and generally at temperatures between about −100 and about 100° C. A summary of such methods is found in "Comprehensive Organic Transformations", VCH Publishers, (1989), R. C. Larock, pp. 595-596.

In another embodiment of the invention, free alcohol compounds of formula (VIIa), wherein Q is alkoxymethylene (Q=C—OR$_{13}$) or methylene (Q=CH), are formed by cleavage of a protecting group on the corresponding protected alcohol compounds of formula (VIIIa) wherein R$_{12}$ is a hydroxyl protecting group. Hydroxyl protecting group to be used in the reaction includes, for example but not limited to, ethers, such as para-methoxybenzyl ether, and silyl ethers, such as tert-butyldimethylsilyl ether, (see e.g. "Protection for the hydroxyl group" pages 16-299 in "Protective Groups in Organic Synthesis (Fourth Edition)", eds. Peter G. M. Wuts and Theodora W. Greene, Wiley-Interscience Publishers, (2007)).

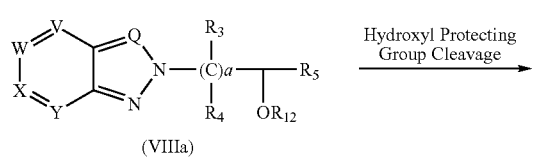

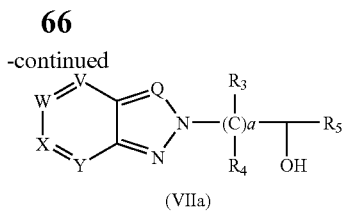

In another embodiment of the invention, compounds of formula (VIIIb) are formed by treating compounds of formula (IXa) with alcohol of formula R$_{13}$—OH and a base such as, but not limited to, potassium hydroxide, sodium hydroxide and the like.

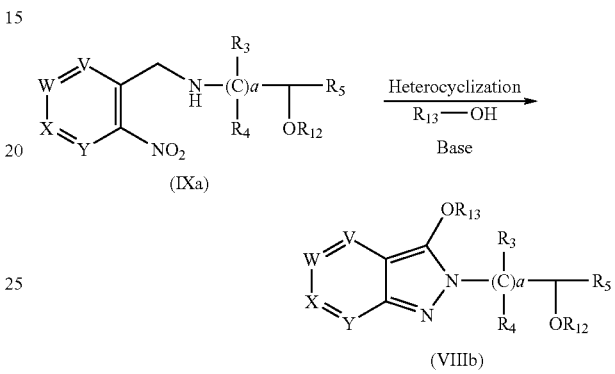

The synthesis of 3-alkoxy-2-substituted 2H-indazoles has been described in the chemical literature such as in Journal of Organic Chemistry, 2006, 71, 2687-2689 ("N,N-Bond-Forming Heterocyclization: Synthesis of 3-Alkoxy-2H-indazoles" by A. D. Mills, M. Z. Nazer, M. J. Haddadin and M. J. Kurth) and in Journal of Combinatorial Chemistry, 2007, 9, 171-177 ("Synthesis of a Library of 2-Alkyl-3-alkyloxy-2H-indazole-6-carboxamides" by A. D. Mills, P. Maloney, E. Hassanein, M. J. Haddadin and M. J. Kurth). However none of the foregoing publications describe the synthesis of compound of formula (VIIIb).

In another embodiment of the invention, compounds of formula (XVIIa) are formed by treating compounds of formula (XVIIIa) with alcohol of formula R$_{13}$—OH and a base such as, but not limited to, potassium hydroxide, sodium hydroxide and the like.

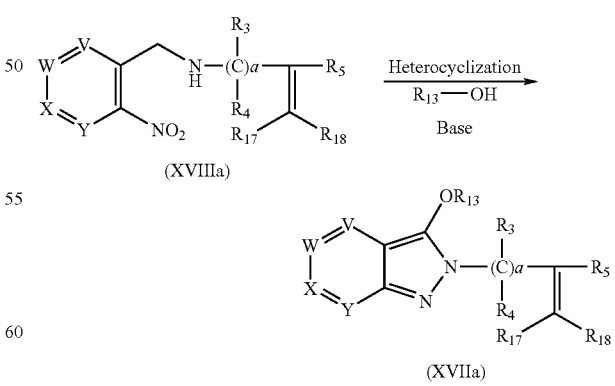

In another embodiment of the invention, compounds of formula (VIIIc) are formed by heterocyclization of compounds of formula (IXa) when treated with a reducing agent such as zinc.

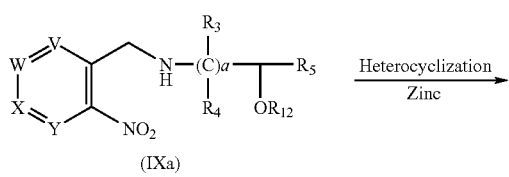

(IXa)

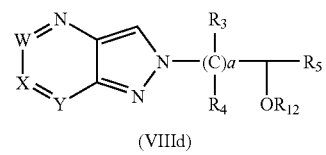

(VIIId)

The solvent to be used in the reaction includes, for example but not limited to, ethers such as diethylether, tetrahydrofuran, dioxane and the like, halogenated hydrocarbons such as such as methylene chloride, chloroform, 1,2-dichloroethane and the like. The reaction temperature is usually in the range of −78° C. to 150° C., preferably in the range of 0° C. to 120° C. and the reaction time is usually in the range of about 0.5 to 72 hours.

The synthesis of 2-substituted 2H-indazoles from 2-nitrobenzylamines derivatives has been described in the chemical literature such as in *Synlett,* 2007, 16, 2509-2512 ("A Novel and Efficient Synthesis of 2-Aryl-2H-indazoles via SnCl$_2$-Mediated Cyclization of 2-Nitrobenzylamines" by Da-Qing Shi et al), in *Journal of the Chemical Society,* Perkin Transactions 1, 1973, 3, 319-324 ("Pyrazolopyridines. Part II. Preparation of 3-Substituted 2-Aryl-2H-pyrazolo[4,3-b] pyridines. Acid-catalysed Cyclisation of 2-Arylamino-methyl-3-nitropyridines" by H. E. Foster and J. Hurst) and in *Tetrahedron,* 1998, 54, 3197-3206 ("2-Substituted Indazoles from Electrogenerated Ortho-nitrosobenzylamines" by B. A. Frontana-Uribe and C. Moinet). However none of the foregoing publications describe the synthesis of compound of formula (VIIIc).

In another embodiment of the invention, compounds of formula (XVIIb) are formed by heterocyclization of compounds of formula (XVIIIa) when treated with a reducing agent such as zinc.

In another embodiment of the invention, compounds of formula (XVIIc) are similarly formed by reacting aldehydes of formula (Xa) with amines of formula (XIX) in presence of a reducing agent such as, but not limited to, sodium cyanoborohydride, sodium borohydride, sodium triacetoxyborohydride, L-SELECTRIDE®(lithium tri-sec-butyl(hydrido)borate), decaborane and the like.

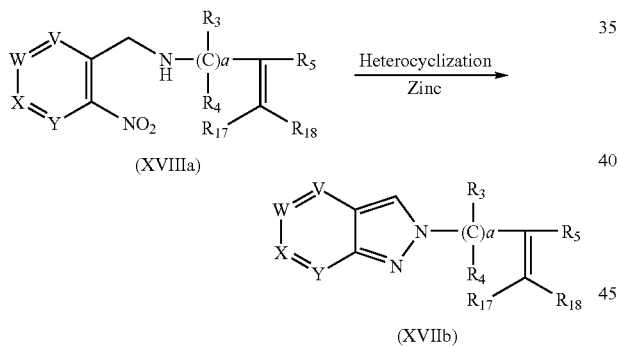

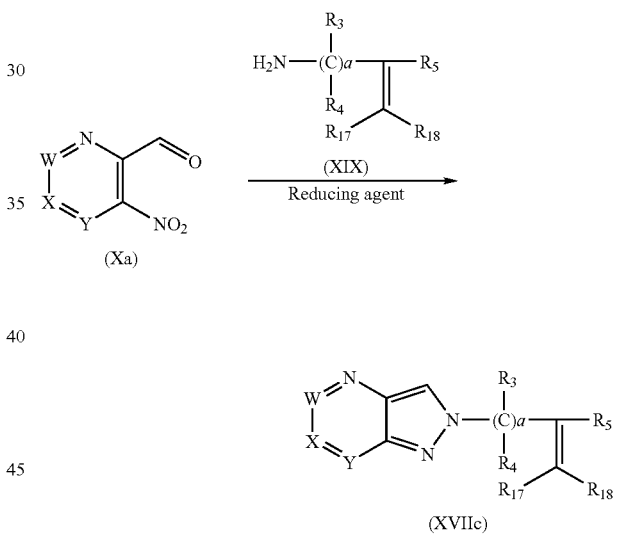

In another embodiment of the invention, compounds of formula (VIIId) are formed by reacting aldehydes of formula (Xa) with compounds of formula (XI) in presence of a reducing agent such as, but not limited to, sodium cyanoborohydride, sodium borohydride, sodium triacetoxyborohydride, L-SELECTRIDE®(lithium tri-sec-butyl(hydrido)borate), decaborane and the like.

The compounds of formula (IXa) can be prepared by treating aldehydes of formula (X) with compounds of formula (XI) and a reducing agent such as, but not limited to, sodium cyanoborohydride, sodium borohydride, sodium triacetoxyborohydride, L-SELECTRIDE® (lithium tri-sec-butyl(hydrido)borate), decaborane and the like.

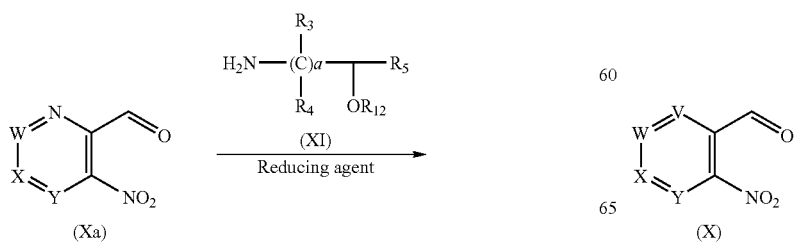

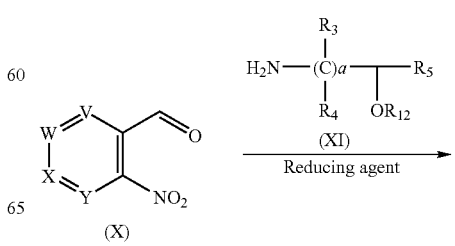

-continued

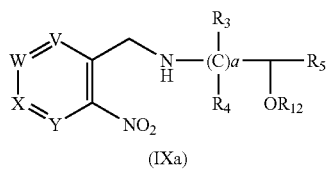

(IXa)

-continued

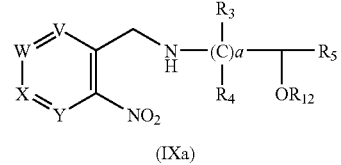

(IXa)

Such a transformation is well known to those skilled in the art and is known as reductive amination, a summary of such methods is found in "*Comprehensive Organic Transformations*", VCH Publishers, (1989), R. C. Larock, pp. 421-425. The solvent to be used in the reaction includes, for example but not limited to, ethers such as diethylether, tetrahydrofuran and the like, halogenated hydrocarbon such as such as methylene chloride, chloroform, 1,2-dichloroethane and the like. The reaction temperature is usually in the range of −78° C. to 150° C., preferably in the range of 0° C. to 80° C. and the reaction time is usually in the range of 1 to 72 hours.

Similarly, the compounds of formula (XVIIIa) can be prepared by treating aldehydes of formula (X) with compounds of formula (XIX) and a reducing agent such as, but not limited to, sodium cyanoborohydride, sodium borohydride, sodium triacetoxyborohydride, L-SELECTRIDE® (lithium tri-sec-butyl(hydrido)borate), decaborane and the like.

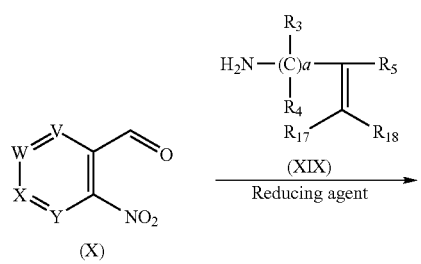

Alternatively, the compounds of formula (IXa) can be prepared by treating compounds of formula (XI) with compounds of formula (XII) where T is a leaving group such as a halogen atom, methanesulfonyl, trifluoromethanesulfonyl, toluenesulfonyl and the like.

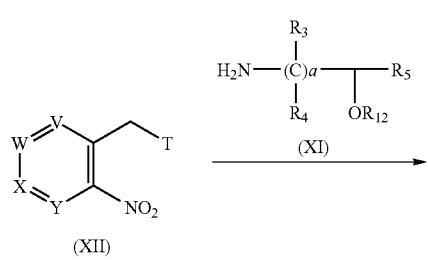

When not commercially available, the aldehydes of formula (X) can be prepared by oxidative cleavage of the alkene moiety of compound of formula (XIII) wherein $R_{14}$ and $R_{15}$ are independently selected from hydrogen, aminoalkyl, C1-C4 alkylcarbonyl or C1-C4 alkyl.

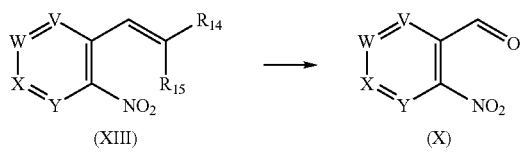

Such a transformation is well known to those skilled in the art and can be realized for example with ozone, potassium permanganate and sodium metaperiodate. The process may be carried out optionally in a solvent such as methylene chloride, diethylether, chloroform and generally at temperatures between about −100 and about 100° C. A summary of such methods is found in "*Comprehensive Organic Transformations*", VCH Publishers, (1989), R. C. Larock, pp. 595-596. The alkene compounds of formula (XIII), wherein $R_{14}$ and $R_{15}$ are independently selected from hydrogen, C1-C4 alkylcarbonyl or C1-C4 alkyl, can be prepared from coupling reactions of compound of formula (XIV), wherein $R_{16}$ is halogen atom or trifluoromethanesulfonyl and the like, with compound of formula (XV), wherein M is trialkyltin, boronic acid or boronate ester, and a palladium catalyst.

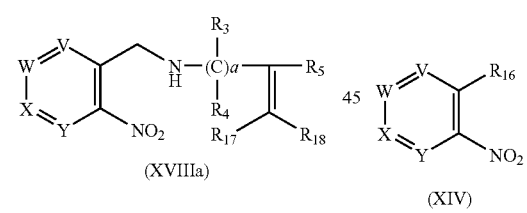

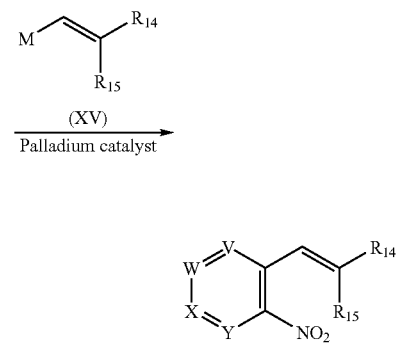

Such a transformation using compound of formula (XV), wherein M is trialkyltin, is known to those skilled in the art as the Stille coupling. A description of such methods is found in "*March's Advanced Organic Chemistry Reactions, Mechanisms, and Structure* (Sixth Edition)", Michael B. Smith and Jerry March, Wiley-Interscience Publishers, (2007) pp. 792-795.

The solvent to be used in the reaction includes, for example but not limited to, ethers such as tetrahydrofuran, dioxane and the like, halogenated hydrocarbons such as such as 1,2-dichloroethane and the like, aromatic solvent such as benzene, toluene, xylene and the like. The reaction temperature is usually in the range of 0° C. to 200° C., preferably in the range of 20° C. to 120° C. and the reaction time is usually in the range of about 0.5 to 72 hours.

Alternatively, the alkene compounds of formula (XIIIa), wherein $R_{14}$ and $R_{15}$ are independently selected from hydrogen, aminoalkyl, can be prepared by condensation with compounds of formula (XIVb) and dimethylformamide dimethyl acetal.

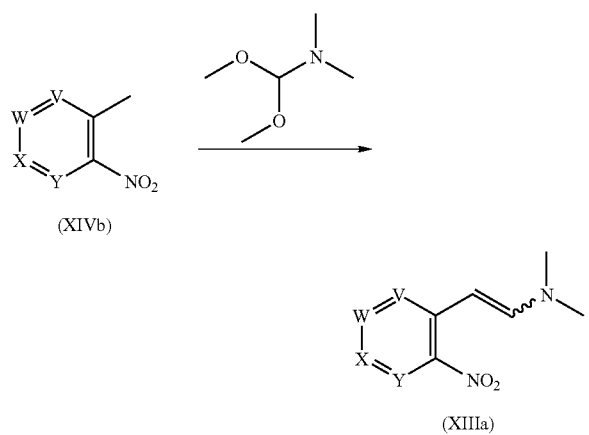

Example of such a transformation can be found in the literature such as *Tetrahedron Letters*, 1994, 35, 219-222 ("A mild method for the conversion of activated aryl methyl groups to carboxaldehydes via the uncatalyzed periodate cleavage of enamines" by M. G. Vetelino and J. W. Coe).

Compounds of formula (XIVb) can be prepared from coupling reactions of compound of formula (XIV), wherein $R_{16}$ is halogen atom or trifluoromethanesulfonyl and the like, with activated methylene compound of formula (XX) and subsequent acidic hydrolysis and decarboxylation of compound of formula (XXI),

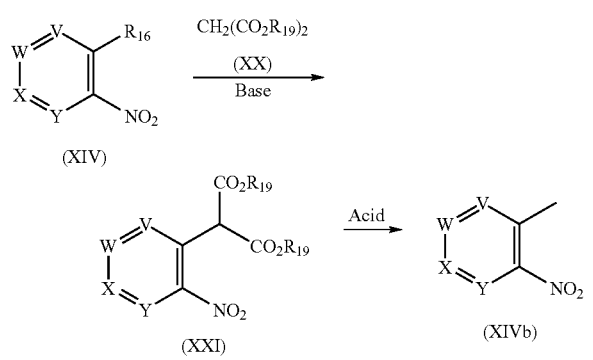

Example of such a transformation to yield compound of formula (XIVb), wherein V is Nitrogen, X is C—Br and W and Y are CH, can be found in WO 2006/103449 page 106.

The compounds of formula (XIVa), wherein $R_{16}$ is halogen atom, when not commercially available can be prepared from compounds of formula (XV) via formation of diazonium salt from corresponding aniline and treatment with cuprous halides.

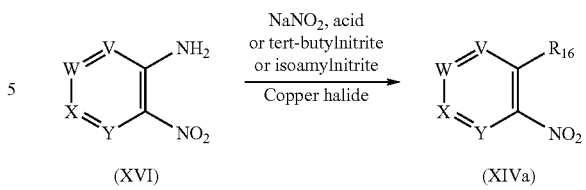

Such a transformation is known to those skilled in the art as the Sandmyer reaction (see e.g. "*March's Advanced Organic Chemistry: Reactions, Mechanisms, and Structure* (Sixth Edition)", Michael B. Smith and Jerry March, Wiley-Interscience Publishers, (2007) pp. 984-985).

The compounds of formula (Ii); wherein V is nitrogen or C—$R_8$, $R_{10}$ is halogen and $R_2$ and $R_{11}$ are either together or independently of each another, halogen or hydrogen; can be achieved by halogenation of the corresponding precursor compound of formula (Ih) using electrophilic halogenating agent known in the art such as, but not limited to, N-iodosuccinimide, N-bromosuccinimide, N-chlorosuccinimide, SELECTFLUOR® [1-chloromethyl-4-fluoro-1,4-diazoniabicyclo[2.2.2]octane bis-(tetrafluoroborate)] and the like.

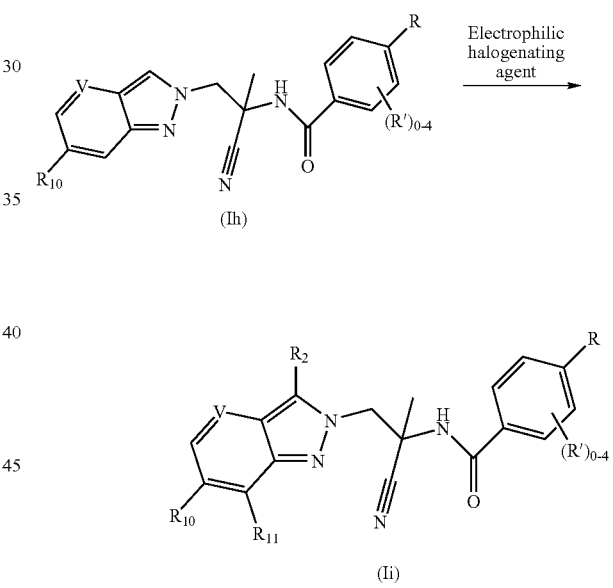

The compounds of formula (Ig) wherein p is 1 or 2 can be achieved by oxidation of the corresponding precursor compound of formula (If) using conventional oxidizers known in the art.

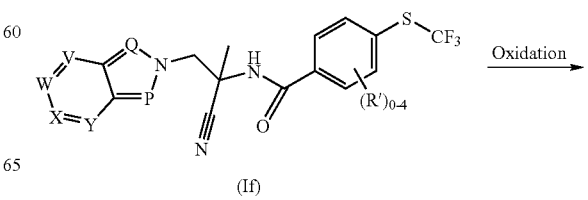

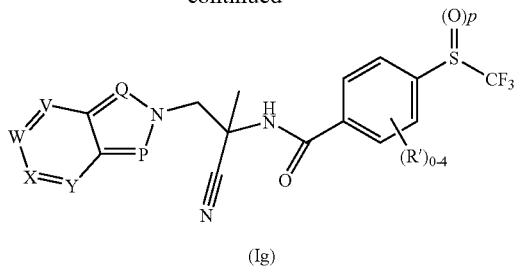

(Ig)

It will be appreciated by persons skilled in the art that, within aspect of the processes described above; the order of the synthetic steps employed may be varied and will depend inter alia on factors such as the nature of other functional groups present in a particular substrate, the availability of key intermediates, and the protecting group strategy (if any) to be adopted (see e.g. "*Protective Groups in Organic Synthesis* (Fourth Edition)", eds. Peter G. M. Wuts and Theodora W. Greene, Wiley-Interscience Publishers, (2007)). Clearly, such factors will also influence the choice of reagents for use in the said synthetic steps.

The invention further contemplates separating the enantioners in whole or in part of the present invention or synthesizing enantiomerically enriched compounds of the invention. The composition may be prepared by separating the enantioners in whole or in part by standard methods, for example by chemical resolution using optically active acid or by use of column chromatography or reverse-phase column chromatography using a substantially optically active (or "chiral") stationary phase as known to those skilled in the art. The formation and/or isolation of specific enantiomers of a compound is not routine, and there are no general methods that may be used to obtain specific enantiomers of all compounds. The methods and conditions used to obtain specific enantiomers of a compound must be determined for each specific compound.

Enantiomerically enriched compounds of the invention can also be obtained from enantiomerically enriched precursors. For example, enantiomerically enriched compounds of formula (I) can be obtained from enantiomerically enriched α-amino nitrile compounds of formula (IIa).

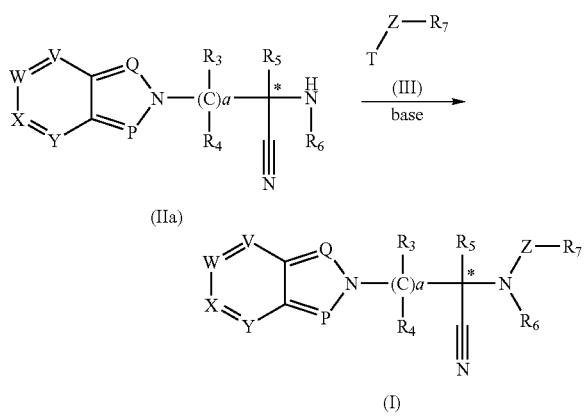

Examples for the resolution of racemic amino nitriles can be found in the literature such as in U.S. Pat. No. 4,683,324 ("Process for the resolution of certain racemic amino nitriles") and *Journal of Organic Chemistry*, 2007, 72, 7469-7472 ("A concise Synthesis of (S)—N-Ethoxycarbonyl-α-methylvaline" by J. T. Kuethe, D. R. Gauthier, Jr., G. L. Beutner and N. Yasuda). Literature reviews are also available such as in *Chemical Review*, 2006, 106, 2711-2733 ("Crystallization-Induced Diastereomer Transformations" by K. M. Jos Brands and A. J. Davies).

In another embodiment of the invention it was found that enantiomerically enriched α-amino nitrile compounds of formula (IIa) can be efficiently racemized back to a racemic mixture of formula (II) by submitting enriched α-amino nitrile compounds of formula (IIa) to a similar treatment that was used to obtained compound of formula (II) meaning treatment with a suitable cyanide source such as sodium cyanide, potassium cyanide, trimethylsilyl cyanide and the like, with amines of general formula $R_6$—$NH_2$ such as ammonia, methyl amine and the like and generally in presence of ammonium salt such as ammonium chloride and the like.

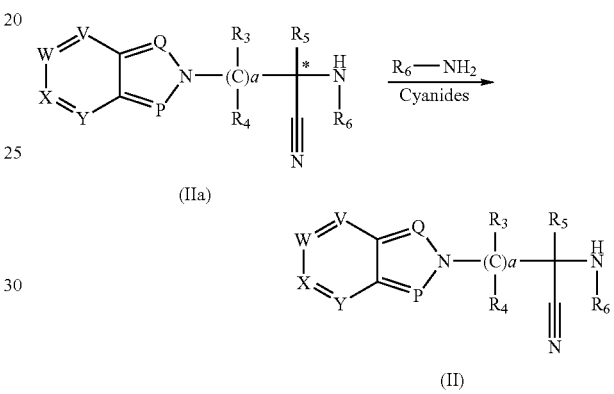

The reaction temperature is usually in the range of 0° C. to 50° C., preferably in the range of 10° C. to 30° C. and the reaction time is usually in the range of 1 to 72 hours.

The racemic mixture of formula (II) can be used again to prepared enantiomerically enriched α-amino nitrile compounds of formula (IIa) by separating the enantioners in whole or in part by standard methods, for example by chemical resolution using optically active acid or by use of column chromatography or reverse-phase column chromatography using a substantially optically active (or "chiral") stationary phase as known to those skilled in the art.

The invention will now be further described by way of the following non-limiting examples.

EXAMPLES

All temperatures are given in degrees Centigrade; room temperature means 20 to 25° C. Reagents were purchased from commercial sources or prepared following literature procedures.
DCM=dichloromethane
THF=tetrahydrofuran
MeOH=methanol
EtOH=ethanol
EA=ethyl acetate
DMF=dimethylformamide
AcOH=acetic acid
TFA=trifluoroacetic acid
TEA=triethylamine
DIEA=diisopropylethylamine Proton and fluorine magnetic resonance (respectively 1H NMR and 19F NMR) spectra were recorded on a Varian INOVA NMR spectrometer [400 MHz (1H) or 500 MHz (1H) and 377 MHz (19F)]. All spectra were determined in the solvents indicated. Chemical shifts are reported in ppm downfield of tetramethylsilane (TMS), referenced to the residual proton peak of the respective solvent peak for $^1$H NMR. Interproton coupling constants are reported in Hertz (Hz).

LC-MS spectra were either obtained using a Thermofinnigan AQA™ mass spectrometer operating with electrospray ionization, using a Phenomenex AQUA™ 5 micron C18 125A 50×4.60 mm column and a linear gradient from 55% methanol: 1% acetonitrile in water to 100% methanol over 3 minutes. 100% methanol was maintained for 2 minutes. In addition, LCMS spectra were also obtained using an Agilent 1200SL HPLC equipped with a 6130 mass spectrometer operating with electrospray ionization; chromatographic data were obtained using a Shimadzu Shim-pack XR-ODS, 3.0× 30 mm, 2.2 micron particle size column and a water:methanol gradient from 15% methanol to 95% methanol in 2.2 minutes under a 1.5 mL/min flow; a hold at 95% methanol was applied at the end of the gradient for 0.8 minutes; and both water and methanol mobile phases contained 0.1% formic acid. Finally when LCMS retention time are reported as RT, LCMS spectra were obtained using a Waters ACQUITY UPLC™ equipped with a Thermofinnigan AQA™ mass spectrometer operating with electrospray ionization; chromatographic data were obtained using a Supelco® Analytical Ascentis®Express, 2.1×50 mm, 2.7 micron particle size column ($C_{18}$) and a water:acetonitrile gradient from 5% acetonitrile to 100% acetonitrile in 0.8 minute under a 1.5 mL/min flow; a hold at 100% methanol was applied at the end of the gradient for 0.05 minutes; and water mobile phase was buffered with ammonium acetate (10 mmolar) and 0.1% v./v. acetic acid.

When semi-preparative HPLC was carried out to purify reaction mixture, a modified Gilson HPLC system was used with offline regeneration; chromatographic data were obtained using a Varian Pursuit™ XRS, 21.4×50 mm, 10 micron particle size column ($C_{18}$) and a water:methanol gradient from 40% methanol to 100% methanol in 5 minutes under a 28 mL/min flow; and water mobile phase was buffered with ammonium acetate (10 mmolar) and 0.1% v./v. ammonium hydroxide.

Compounds of Examples 1 to 10 and 52 to 58 were prepared according to the general reaction scheme:

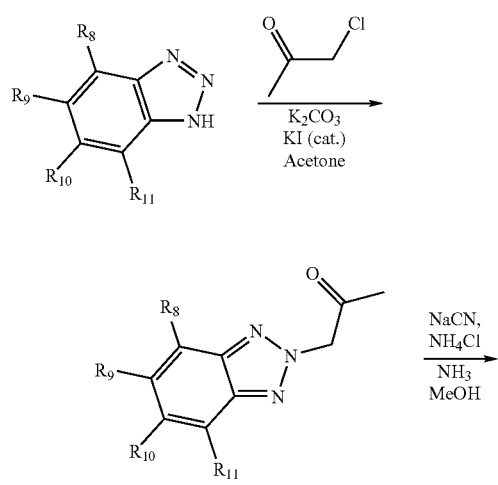

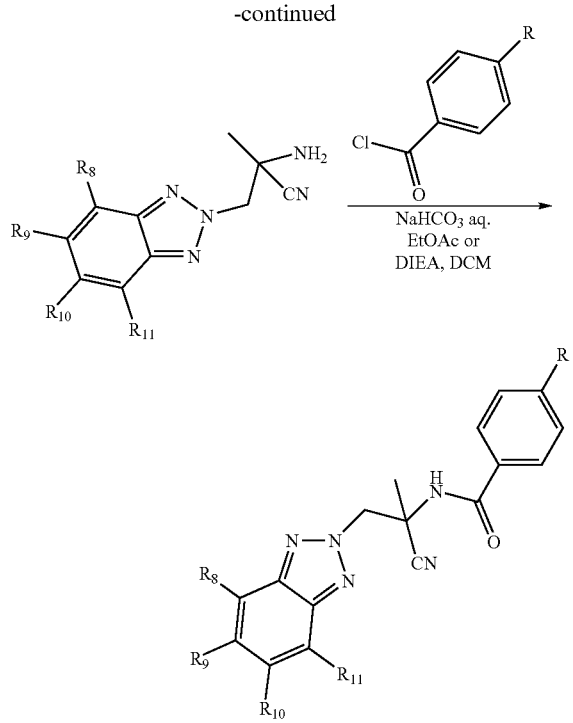

Final Product
V=C—$R_8$; W=C—$R_9$; X=C—$R_{10}$; Y=C—$R_{11}$;
Q=P=N;
$R_3$=$R_4$=H; a=1; $R_5$=methyl, butyl or $CH_2OH$; $R_6$=H
Z=C(O); $R_7$=p-phenyl-R.

Although the scheme above as well as other schemes below, describe the preparation of compounds of the invention with a para-substituted phenyl amide groups, it will be apparent to one of skill in the art that modified derivatives with variable substitution on the phenyl ring may also be made by starting the corresponding substituted benzoyl chloride. For example, an analogous compound with an ortho- or meta-substituted phenyl amide may be made with a suitably substituted acid chloride in the last step, which could be obtained from the corresponding benzoic acid by known methods. Furthermore, compounds with phenyl amide groups that have multiple substitution may be prepared using the same process with appropriately substituted benzoyl chloride reagents. Benzoic acid compounds with a variety of substitution patterns are commercially available or can be made by known processes.

Example 1

N-[2-(5-Chloro-2H-benzotriazol-2-yl)-1-cyano-1-methylethyl]-4-trifluoromethoxybenzamide (compound No 1.001)

4-trifluoromethoxybenzoyl chloride (0.34 g) was added to a solution of 2-amino-3-(5-chloro-2H-benzotriazol-2-yl)-2-methylpropionitrile (0.3 g) in dry DCM mixed with TEA (0.27 mL). The reaction mixture was stirred 48 hours at room temperature. Silica gel was added to the reaction mixture and solvent evaporated under reduced pressure. The resulting crude product loaded on silica gel was purified by chromatography ($SiO_2$, heptane/EA) to afford the title compound as a white solid (0.3 g, 54%). Rf=0.7 (1:1 EA/heptane). MS (ES): M/Z [M+H]=424. 1H NMR: (400 MHz, DMSO-$d_6$): 1.74 (s, 3H), 5.39-5.49 (m, 2H), 7.48 (dd, J=9.1, 1.9 Hz, 1H), 7.51 (br d, J=8.0 Hz, 2H), 7.93 (m, 2H), 8.01 (dd, J=9.1, 0.6 Hz, 1H), 8.13 (dd, J=1.9, 0.6 Hz, 1H) and 8.92 (s, 1H). 19F NMR (376 MHz, DMSO-$d_6$): −57.09 (s, 3F).

The starting material, 2-amino-3-(5-chloro-2H-benzotriazol-2-yl)-2-methylpropionitrile, was prepared as follows:

a. A mixture of 5-chloro-1H-benzotriazole (8 g), chloroacetone (6.5 mL), potassium carbonate (9.5 g) and potassium iodide (0.5 g) was stirred in acetone (90 mL) at room temperature for 48 hours. The reaction mixture was filtered and the filtrate concentrated under reduced pressure to give a residue that was purified by chromatography ($SiO_2$, heptane/EA) to afford 1-(5-chloro-2H-benzotriazol-2-yl)-propan-2-one as clear oil [1.8 g, 16%, Rf=0.6 (1:1 EA/heptane)]. The two other regioisomers were also isolated, 1-(6-chloro-1H-benzotriazol-1-yl)-propan-2-one [3.8 g, 35%, Rf=0.45 (1:1 EA/heptane)] and 1-(5-chloro-1H-benzotriazol-1-yl)-propan-2-one [3.2 g, 29%, Rf=0.35 (1:1 EA/heptane)].

b. Ammonia was charged into methanol (50 mL) at −78° C. for 5 min. The solution was allowed to warm to room temperature and was then treated with sodium cyanide (0.7 g), ammonium chloride (0.9 g) and 1-(5-chloro-2H-benzotriazol-2-yl)-propan-2-one (2.25 g). The reaction mixture was stirred for 6 days at room temperature before being concentrated under reduced pressure. The residue was taken into ethyl acetate, filtered and the filtrate concentrated under reduced pressure to give a residue that was purified by chromatography ($SiO_2$, heptane/EA) to afford 2-amino-3-(5-chloro-2H-benzotriazol-2-yl)-2-methylpropionitrile as a light yellow solid (2.0 g, 79%). Rf=0.25 (1:1 EA/heptane).

Example 2

N-[2-(5-Chloro-2H-benzotriazol-2-yl)-1-cyano-1-methylethyl]-4-trifluoromethylbenzamide (compound No 1.002)

Using a procedure similar to that described in Example 1, except using 4-trifluoromethylbenzoyl chloride, the title compound was isolated as a white solid (0.12 g, 71%). Rf=0.65 (1:1 EA/heptane). MS (ES): M/Z [M+H]=408. 1H NMR: (400 MHz, DMSO-$d_6$): 1.75 (s, 3H), 5.40-5.52 (m, 2H), 7.48 (dd, J=9.1, 1.9 Hz, 1H), 7.88-7.93 (m, 2H), 7.99 (br d, J=7.8 Hz, 1H), 8.03 (d, J=0.6 Hz, 1H), 8.13 (dd, J=1.9, 0.6 Hz, 1H) and 9.04 (s, 1H).

Example 3

N-[2-(5-Chloro-2H-benzotriazol-2-yl)-1-cyano-1-methylethyl]-4-trifluoromethylthiobenzamide (compound No 1.003)

Using a procedure similar to that described in Example 1, except using 4-trifluoromethylthiobenzoyl chloride, the title compound was isolated as a white solid (1.4 g, 75%). Rf=0.65 (1:1 EA/heptane). MS (ES): M/Z [M+H]=440. 1H NMR: (400 MHz, DMSO-$d_6$): 1.74 (s, 3H), 5.39-5.50 (m, 2H), 7.48 (dd, J=9.1, 1.9 Hz, 1H), 7.85-7.92 (m, 4H), 8.01 (dd, J=9.1, 0.7 Hz, 1H), 8.13 (dd, J=1.9, 0.6 Hz, 1H) and 9.01 (s, 1H). 19F NMR (376 MHz, DMSO-$d_6$): −41.93 (s, 3F).

Example 4

N-[2-(5-Chloro-2H-benzotriazol-2-yl)-1-cyano-1-methylethyl]-4-phenoxybenzamide (compound No 1.032)

Using a procedure similar to that described in Example 1, except using 4-phenoxybenzoyl chloride, the title compound was isolated as a white solid (57 mg, 65%). MS (ES): M/Z [M+H]=432. 1H NMR: (400 MHz, DMSO-$d_6$): 1.74 (s, 3H), 5.40-5.46 (m, 2H), 7.04-7.16 (m, 4H), 7.20-7.27 (m, 1H), 7.42-7.51 (m, 3H), 7.82-7.88 (m, 2H), 7.99-8.05 (m, 1H), 8.12-8.15 (m, 1H,) and 8.74 (s, 1H). 4-Phenoxybenzoyl chloride was prepared by reacting 4-phenoxybenzoic acid with oxalyl chloride.

Example 5

N-[2-(2H-Benzotriazol-2-yl)-1-cyano-1-methylethyl]-4-trifluoromethoxybenzamide (compound No 1.004)

Using a procedure similar to that described in Example 1, except using 2-amino-3-(2H-benzotriazol-2-yl)-2-methylpropionitrile, the title compound was isolated as a white solid (0.1 g, 51%). Rf=0.55 (1:1 EA/heptane). MS (ES): M/Z [M+H]=390. 1H NMR: (400 MHz, DMSO-$d_6$): 1.75 (s, 3H), 5.39-5.49 (m, 2H), 7.45 (br s, 2H), 7.51 (d, J=8.0 Hz, 2H), 7.94 (br d, J=7.5 Hz, 4H) and 8.93 (s, 1H). 2-Amino-3-(2H-benzotriazol-2-yl)-2-methylpropionitrile [1.9 g, 97%, Rf=0.2 (1:1 EA/heptane)] was prepared using a procedure similar to that described in Example 1, part a and b, except starting from 1H-benzotriazole.

Example 6

N-[2-(2H-Benzotriazol-2-yl)-1-cyano-1-methylethyl]-4-trifluoromethylthiobenzamide (compound No 1.005)

Using a procedure similar to that described in Example 1, except using 2-amino-3-(2H-benzotriazol-2-yl)-2-methylpropionitrile, described in Example 5, and 4-trifluoromethylthiobenzoyl chloride, the title compound was isolated as a white solid (0.12 g, 59%). Rf=0.6 (1:1 EA/heptane). MS (ES): M/Z [M+H]=406. 1H NMR: (400 MHz, DMSO-$d_6$): 1.75 (s, 3H), 5.39-5.50 (m, 2H), 7.46 (dd, J=6.6, 3.1 Hz, 2H), 7.85-7.95 (m, 6H) and 9.01 (s, 1H).

Example 7

N-[1-Cyano-1-methyl-2-(5-methyl-2H-benzotriazol-2-yl)ethyl]-4-trifluoromethoxybenzamide (compound No 1.006)

Using a procedure similar to that described in Example 1, except using 2-amino-2-methyl-3-(5-methyl-2H-benzotriazol-2-yl)propionitrile, the title compound was isolated as a white solid (0.09 g, 45%). Rf=0.6 (1:1 EA/heptane). MS (ES): M/Z [M+H]=404. 1H NMR: (400 MHz, DMSO-$d_6$): 1.73 (s, 3H), 2.45 (s, 3H), 5.34-5.43 (m, 2H), 7.30 (dd, J=8.8, 1.4 Hz, 1H), 7.52 (d, J=8.0 Hz, 2H), 7.68 (d, J=1.0 Hz, 1H), 7.82 (d, J=8.8 Hz, 1H), 7.90-7.97 (m, 2H) and 8.91 (s, 1H). 19F NMR (376 MHz, DMSO-$d_6$): −57.08 (s, 3F).

2-Amino-2-methyl-3-(5-methyl-2H-benzotriazol-2-yl)propionitrile [2.1 g, 92%, Rf=0.2 (1:1 EA/heptane)] was prepared using a procedure similar to that described in Example 1, part a and b, except starting from 5-methyl-1H-benzotriazole.

Example 8

N-[1-Cyano-1-methyl-2-(5-methyl-2H-benzotriazol-2-yl)ethyl]-4-trifluoromethylthiobenzamide (compound No 1.007)

Using a procedure similar to that described in Example 1, except using 2-amino-2-methyl-3-(5-methyl-2H-benzotriazol-2-yl)propionitrile, described in Example 7, and 4-trifluoromethylthiobenzoyl chloride, the title compound was isolated as a white solid (0.12 g, 57%). Rf=0.65 (1:1 EA/heptane). MS (ES): M/Z [M+H]=420. 1H NMR: (400 MHz, DMSO-$d_6$): 1.73 (s, 3H), 2.45 (s, 3H), 5.34-5.44 (m, 2H), 7.30 (dd, J=8.8, 1.4 Hz, 1H), 7.68 (d, J=1.0 Hz, 1H), 7.82 (d, J=8.8 Hz, 1H), 7.84-7.94 (m, 4H) and 8.91 (s, 1H). 19F NMR (376 MHz, DMSO-$d_6$): −41.94 (s, 3F).

Example 9

N-[2-(5-Chloro-6-methyl-2H-benzotriazol-2-yl)-1-cyano-1-methylethyl]-4-trifluoromethoxybenzamide (compound No 1.040)

Using a procedure similar to that described in Example 1, except using 2-amino-3-(5-chloro-6-methyl-2H-benzotriazol-2-yl)-2-methylpropionitrile (90 mg), the title compound was isolated as a white solid (125 mg, 79%). Rf=0.65 (1:1 EA/heptane). MS (ES): M/Z [M+H]=438. 1H NMR: (400 MHz, DMSO-$d_6$): 1.73 (s, 3H), 2.46 (s, 3H), 5.38 (d, J=13.4 Hz, 1H), 5.44 (d, J=13.3 Hz, 1H), 7.52 (d, J=8.0 Hz, 2H), 7.93 (d, J=8.8 Hz, 2H), 7.96 (s, 1H), 8.13 (s, 1H) and 8.92 (s, 1H). 19F NMR (376 MHz, DMSO-$d_6$): −57.08 (s, 3F).

2-Amino-3-(5-chloro-6-methyl-2H-benzotriazol-2-yl)-2-methylpropionitrile [2.1 g, 92%, Rf=0.2 (1:1 EA/heptane)] was prepared using a procedure similar to that described in Example 1, part a and b, except starting from 6-chloro-5-methyl-1H-benzotriazole.

Example 10

N-[2-(5-Chloro-6-methyl-2H-benzotriazol-2-yl)-1-cyano-1-methylethyl]-4-trifluoromethylthiobenzamide (compound No 1.041)

Using a procedure similar to that described in Example 1, except using 2-amino-3-(5-chloro-6-methyl-2H-benzotriazol-2-yl)-2-methylpropionitrile (90 mg, described in Example 9) and 4-trifluoromethylthiobenzoyl chloride (0.1 mL), the title compound was isolated as a white solid (152 mg, 93%). Rf=0.6 (1:1 EA/heptane). MS (ES): M/Z [M+H]=454. 1H NMR: (400 MHz, DMSO-$d_6$): 1.73 (s, 3H), 2.46 (s, 3H), 5.38 (d, J=13.4 Hz, 1H), 5.45 (d, J=13.4 Hz, 1H), 7.87 (d, J=8.5 Hz, 2H), 7.91 (d, J=8.6 Hz, 2H), 7.96 (s, 1H), 8.13 (s, 1H) and 9.00 (s, 1H). 19F NMR (376 MHz, DMSO-$d_6$): −41.93 (s, 3F).

Compounds of Examples 11 to 51, and 59 to 67 were prepared according to the general reaction scheme:

Final Product
V=C—$R_8$; W=C—$R_9$; X=C—$R_{10}$; Y=C—$R_{11}$;
Q=P=N;
$R_3$=$R_4$=H; a=1; $R_5$=$CH_3$, $R_6$=H;
Z=C(O); $R_7$=p-phenyl-R As discussed above, It will be apparent to one of skill in the art that modified derivatives with variable substitution on the phenyl ring may also be made by starting the corresponding substituted benzoic acid chloride.

Example 11

N-[1-Cyano-1-methyl-2-(5-trifluoromethyl-2H-benzotriazol-2-yl)ethyl]-4-trifluoromethoxybenzamide (compound No 1.008)

Using a procedure similar to that described in Example 1, except using 2-amino-2-methyl-3-(5-trifluoromethyl-2H-benzotriazol-2-yl)propionitrile, the title compound was isolated as a white solid (65 mg, 26%). Rf=0.6 (1:1 EA/heptane). MS (ES): M/Z [M+H]=458. 1H NMR: (400 MHz, DMSO-$d_6$): 1.76 (s, 3H), 5.47-5.57 (m, 2H), 7.50 (d, J=8.0 Hz, 2H), 7.71 (dd, J=9.0, 1.6 Hz, 1H), 7.93 (m, 2H), 8.20 (d, J=9.0 Hz, 1H), 8.50 (br s, 1H) and 8.91 (s, 1H). 19F NMR (376 MHz, DMSO-$d_6$): −61.17 (s, 3F) and −57.09 (s, 3F).

2-Amino-2-methyl-3-(5-trifluoromethyl-2H-benzotriazol-2-yl)propionitrile [1.2 g, 69%, Rf=0.35 (1:1 EA/heptane)] was prepared using a procedure similar to that described in Example 1, part a and b, except starting from 5-trifluoromethyl-1H-benzotriazole, that was prepared as follows:

a. A mixture of 2-nitro-4-trifluoromethylaniline (12 g) and activated palladium on charcoal (0.6 g) in methanol was hydrogenated with one atmosphere of hydrogen under stirring at room temperature for one hour. The reaction mixture was filtered through a pad of diatomaceous earth and the filtrate concentrated under reduced pressure to give a residue. This residue was then dissolved in acetic acid (100 mL) and water (15 mL) and cooled to 0° C. prior to adding hydrochloric acid (4 mL) and a solution of sodium nitrite (4.4 g) in water (10 mL). The

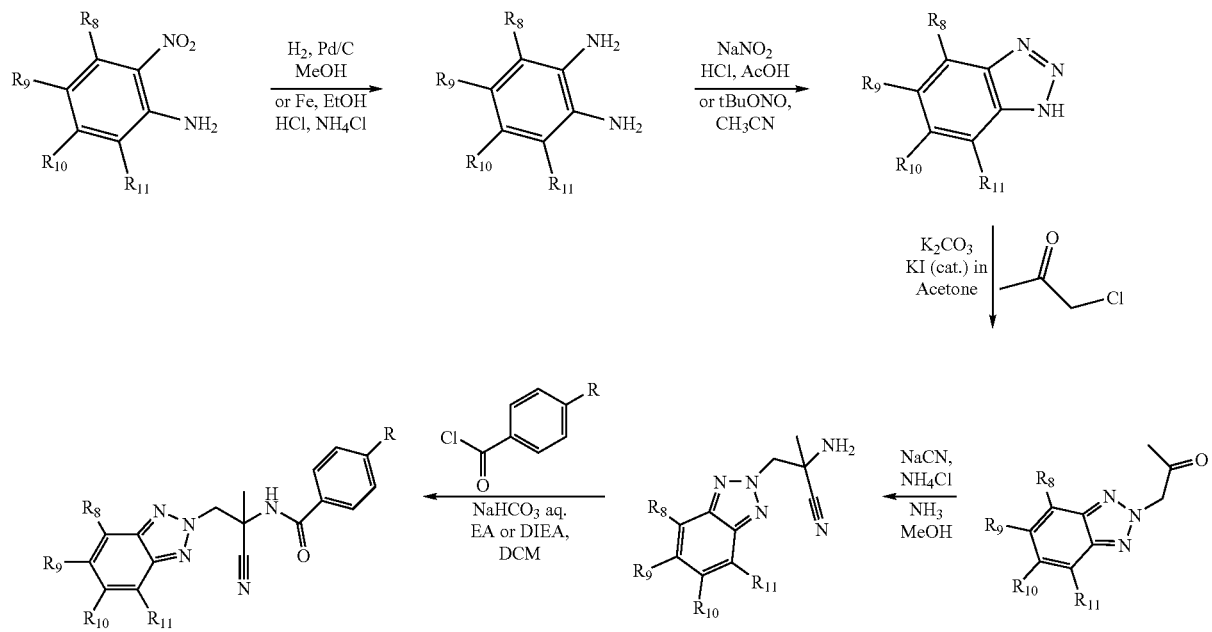

mixture was stirred at room temperature for two hours and then diluted with water. The resulting solid was filtered, washed with water and dried to obtain an off-white solid (8.0 g, 73%).

Example 12

N-[1-Cyano-1-methyl-2-(5-trifluoromethyl-2H-benzotriazol-2-yl)ethyl]-4-trifluoromethylthiobenzamide (compound No 1.009)

Using a procedure similar to that described in Example 1, except using 2-amino-2-methyl-3-(5-trifluoromethyl-2H-benzotriazol-2-yl)-propionitrile, described in Example 11, and 4-trifluoromethylthiobenzoyl chloride, the title compound was isolated as a white solid (0.16 g, 61%). Rf=0.65 (1:1 EA/heptane). MS (ES): M/Z [M+H]=474. 1H NMR: (400 MHz, CHLOROFORM-d): 1.88 (s, 3H), 5.39 (dd, J=112.8, 13.7 Hz, 2H), 7.38 (br s, 1H), 7.65 (d, J=9.1 Hz, 1H), 7.75-7.88 (m, 4H), 8.02 (d, J=9.0 Hz, 1H) and 8.25 (br s, 1H). 19F NMR (376 MHz, CHLOROFORM-d): −63.01 (s, 3F) and −42.23 (s, 3F).

Example 13

N-[1-Cyano-2-(5,6-dichloro-2H-benzotriazol-2-yl)-1-methylethyl]-4-trifluoromethoxybenzamide (compound No 1.010)

Using a procedure similar to that described in Example 1, except using 2-amino-3-(5,6-dichloro-2H-benzotriazol-2-yl)-2-methylpropionitrile, the title compound was isolated as a white solid (72 mg, 28%). Rf=0.6 (1:1 EA/heptane). MS (ES): M/Z [M+H]=458. 1H NMR: (400 MHz, DMSO-d$_6$): 1.74 (s, 3H), 5.41-5.51 (m, 2H), 7.51 (d, J=8.1 Hz, 2H), 7.93 (d, J=8.8 Hz, 2H), 8.43 (br s, 2H) and 8.92 (s, 1H). 19F NMR (376 MHz, DMSO-d$_6$): −57.10 (s, 3F).
2-Amino-3-(5,6-dichloro-2H-benzotriazol-2-yl)-2-methylpropionitrile [0.35 g, 79%, Rf=0.25 (1:1 EA/heptane)] was prepared using a procedure similar to that described in Example 1, part a and b, except starting from 5,6-dichloro-1H-benzotriazole, that was prepared as follows:
  a. 4,5-Dichlorobenzene-1,2-diamine (4.8 g) was dissolved in acetic acid (45 mL) and water (15 mL) and cooled to 0° C. prior to adding hydrochloric acid (2 mL) and a solution of sodium nitrite (2.8 g) in water (15 mL). The mixture was stirred at room temperature for 30 minutes and then diluted with water. The resulting solid was filtered, washed with water and dried. The resulting crude product was dissolved in hot ethanol. Any residual solid was filtered off and the filtrate let cooled down. Addition of water formed a solid that was filtered, washed with water and dried to give a tan solid (2.8 g, 55%).

Example 14

N-[1-Cyano-2-(5,6-dichloro-2H-benzotriazol-2-yl)-1-methylethyl]-4-trifluoromethylthiobenzamide (compound No 1.011)

Using a procedure similar to that described in Example 1, except using 2-amino-3-(5,6-dichloro-2H-benzotriazol-2-yl)-2-methylpropionitrile, described in Example 13, and 4-trifluoromethylthiobenzoyl chloride, the title compound was isolated as a white solid (90 mg, 34%). MS (ES): M/Z [M+H]=474. 1H NMR: (400 MHz, DMSO-d$_6$): 1.74 (s, 3H), 5.41-5.51 (m, 2H), 7.82-7.91 (m, 4H), 8.41 (br s, 2H) and 9.00 (s, 1H). 19F NMR (376 MHz, DMSO-d$_6$): −41.94 (s, 3F).

Example 15

N-[1-Cyano-2-(4,6-dichloro-2H-benzotriazol-2-yl)-1-methylethyl]-4-trifluoromethoxybenzamide (compound No 1.012)

Using a procedure similar to that described in Example 1, except using 2-amino-3-(4,6-dichloro-2H-benzotriazol-2-yl)-2-methylpropionitrile, the title compound was isolated as a white solid (83 mg, 33%). Rf=0.65 (1:1 EA/heptane). MS (ES): M/Z [M+H]=458. 1H NMR: (400 MHz, DMSO-d$_6$): 1.75 (s, 3H), 5.40-5.55 (m, 2H), 7.47 (d, J=8.25 Hz, 2H), 7.69 (dd, J=1.5, 0.8 Hz, 1H), 7.92 (d, J=8.8 Hz, 2H), 8.13 (d, J=1.6 Hz, 1H) and 8.87 (s, 1H). 19F NMR (376 MHz, DMSO-d$_6$): −57.19 (s, 3F).
2-Amino-3-(4,6-dichloro-2H-benzotriazol-2-yl)-2-methylpropionitrile [0.35 g, 63%, Rf=0.35 (1:1 EA/heptane)] was prepared using a procedure similar to that described in Example 1, part a and b, except starting from 5,7-dichloro-1H-benzotriazole. 5,7-Dichloro-1H-benzotriazole (11 g, 99%) was prepared using a procedure similar to that described in Example 11, part a, except starting from 2,4-dichloro-6-nitroaniline (12 g).

Example 16

N-[1-Cyano-2-(4,6-dichloro-2H-benzotriazol-2-yl)-1-methylethyl]-4-trifluoromethylthiobenzamide (compound No 1.013)

Using a procedure similar to that described in Example 1, except using 2-amino-3-(4,6-dichloro-2H-benzotriazol-2-yl)-2-methylpropionitrile, described in Example 15, and 4-trifluoromethylthiobenzoyl chloride, the title compound was isolated as a white solid (50 mg, 20%). Rf=0.7 (1:1 EA/heptane). MS (ES): M/Z [M+H]=475. NMR: (400 MHz, DMSO-d$_6$): 1.75 (s, 3H), 5.40-5.56 (m, 2H), 7.65 (m, 1H), 7.79-7.95 (m, 4H), 8.10 (m, 1H) and 8.95 (s, 1H). 19F NMR (376 MHz, DMSO-d$_6$): −42.05 (s, 3F).

Example 17

N-[1-Cyano-2-(4,6-dichloro-2H-benzotriazol-2-yl)-1-methylethyl]biphenyl-4-carboxamide (compound No 1.046)

Using a procedure similar to that described in Example 1, except using 2-amino-3-(4,6-dichloro-2H-benzotriazol-2-yl)-2-methylpropionitrile, described in Example 15, and 4-biphenyl carbonyl chloride, the title compound was isolated as a white solid (32 mg). MS (ES): M/Z [M+H]=450. NMR: (400 MHz, DMSO-d$_6$): 1.78 (s, 3H), 5.45 (d, J=13.3 Hz, 1H), 5.55 (d, J=13.3 Hz, 1H), 7.43 (m, 1H), 7.51 (t, J=7.5 Hz, 1H), 7.70-7.78 (m, 3H), 7.81 (d, J=8.4 Hz, 2H), 7.90 (d, J=8.5 Hz, 2H), 8.18 (d, J=1.6 Hz, 1H) and 8.83 (s, 1H).

Example 18

N-[1-Cyano-2-(4,6-dichloro-2H-benzotriazol-2-yl)-1-methylethyl]-4-tert-butylbenzamide (compound No 1.053)

Using a procedure similar to that described in Example 1, except using 2-amino-3-(4,6-dichloro-2H-benzotriazol-2- yl)-2-methylpropionitrile, described in Example 15, and 4-tert-butylbenzoyl chloride, the title compound was isolated as a white solid (80 mg). MS (ES): M/Z [M+H]=430. NMR: (400 MHz, DMSO-$d_6$): 1.30 (s, 9H), 1.75 (s, 3H), 5.47 (q, J=17.8 Hz, 2H), 5.51 (d, J=8.3 Hz, 2H), 7.70-7.76 (m, 3H), 8.18 (d, J=1.5 Hz, 1H) and 8.70 (br s, 1H).

Example 19

N-[2-(4-Chloro-6-trifluoromethyl-2H-benzotriazol-2-yl)-1-cyano-1-methylethyl]-4-trifluoromethoxy-benzamide (compound No 1.014)

Using a procedure similar to that described in Example 1, except using 2-amino-3-(4-chloro-6-trifluoromethyl-2H-benzotriazol-2-yl)-2-methylpropionitrile, the title compound was isolated as a white solid (0.66 g, 82%). Rf=0.7 (1:1 EA/heptane). MS (ES): M/Z [M+H]=492. 1H NMR: (400 MHz, DMSO-$d_6$): 1.77 (s, 3H), 5.46-5.67 (m, 2H), 7.50 (d, J=8.1 Hz, 2H), 7.89-7.96 (m, 2H), 8.56 (br s, 1H) and 8.87 (s, 1H). 19F NMR (376 MHz, DMSO-$d_6$): −61.07 (s, 3F) and −57.15 (s, 3F).
2-Amino-3-(4-chloro-6-trifluoromethyl-2H-benzotriazol-2-yl)-2-methylpropionitrile [1.7 g, 89%, Rf=0.35 (1:1 EA/heptane)] was prepared using a procedure similar to that described in Example 1, part a and b, except starting from 7-chloro-5-trifluoromethyl-1H-benzotriazole. 7-Chloro-5-trifluoromethyl-1H-benzotriazole (4.6 g, 99%) was prepared using a procedure similar to that described in Example 11, part a, except starting from 4-amino-3-chloro-5-nitrobenzotrifluoride (5 g).

Example 20

N-[2-(4-Chloro-6-trifluoromethyl-2H-benzotriazol-2-yl)-1-cyano-1-methylethyl]-4-trifluoromethylthiobenzamide (compound No 1.015)

Using a procedure similar to that described in Example 1, except using 2-amino-3-(4-chloro-6-trifluoromethyl-2H-benzotriazol-2-yl)-2-methylpropionitrile, described in Example 19, and 4-trifluoromethylthiobenzoyl chloride, the title compound was isolated as a white solid (0.45 g, 90%). Rf=0.6 (1:1 EA/heptane). MS (ES): M/Z [M+H]=508. 1H NMR: (400 MHz, DMSO-$d_6$): 1.77 (s, 3H), 5.49-5.65 (m, 2H), 7.84-7.93 (m, 5H), 8.56 (d, J=1.1 Hz, 1H) and 8.95 (s, 1H). 19F NMR (376 MHz, DMSO-$d_6$): −61.09 (s, 3F) and −42.03 (s, 3F).

Example 21

N-[1-Cyano-2-(5-cyano-2H-benzotriazol-2-yl)-1-methylethyl]-4-trifluoromethoxybenzamide (compound No 1.016)

Using a procedure similar to that described in Example 1, except using 2-amino-3-(5-cyano-2H-benzotriazol-2-yl)-2-methylpropionitrile, the title compound was isolated as a white solid (0.25 g, 45%). Rf=0.45 (1:1 EA/heptane). MS (ES): M/Z [M+H]=415. 1H NMR: (400 MHz, DMSO-$d_6$): 1.76 (s, 3H), 5.46-5.59 (m, 2H), 7.51 (d, J=8.0 Hz, 2H), 7.76 (dd, J=8.8, 1.4 Hz, 1H), 7.89-7.96 (m, 2H), 8.17 (dd, J=8.9, 0.9 Hz, 1H), 8.77 (m, 1H) and 8.93 (s, 1H). 19F NMR (376 MHz, DMSO-$d_6$): −57.11 (s, 3F).
2-Amino-3-(5-cyano-2H-benzotriazol-2-yl)-2-methylpropionitrile [0.85 g, 75%, Rf=0.15 (1:1 EA/heptane)] was prepared using a procedure similar to that described in Example 1, part a and b, except starting from 5-cyano-1H-benzotriazole. 5-Cyano-1H-benzotriazole (5.7 g, 65%) was prepared using a procedure similar to that described in Example 11, part a, except starting from 4-amino-3-nitrobenzonitrile (10 g).

Example 22

N-[1-Cyano-2-(5-cyano-2H-benzotriazol-2-yl)-1-methylethyl]-4-trifluoromethylthiobenzamide (compound No 1.017)

Using a procedure similar to that described in Example 1, except using 2-amino-3-(5-cyano-2H-benzotriazol-2-yl)-2-methylpropionitrile, described in Example 21, and 4-trifluoromethylthiobenzoyl chloride, the title compound was isolated as a white solid (0.46 g, 81%). Rf=0.45 (1:1 EA/heptane). MS (ES): M/Z [M+H]=431. 1H NMR: (400 MHz, DMSO-$d_6$): 1.76 (s, 3H), 5.46-5.59 (m, 2H), 7.76 (dd, J=8.9, 1.3 Hz, 1H), 7.84-7.93 (m, 4H), 8.18 (d, J=8.9 Hz, 1H), 8.78 (br s, 1H) and 9.01 (br s, 1H). 19F NMR (376 MHz, DMSO-$d_6$): −41.93 (s, 3F).

Example 23

N-[2-(4,6-Bis(trifluoromethyl)-2H-benzotriazol-2-yl)-1-cyano-1-methylethyl]-4-trifluoromethoxybenzamide (compound No 1.018)

Using a procedure similar to that described in Example 1, except using 2-amino-3-(4,6-bis(trifluoromethyl)-2H-benzotriazol-2-yl)-2-methylpropionitrile, the title compound was isolated as a white solid (0.41 g, 88%). Rf=0.6 (1:1 EA/heptane). MS (ES): M/Z [M+H]=526. 1H NMR: (400 MHz, DMSO-$d_6$): 1.79 (s, 3H), 5.61 (dd, J=55.9, 13.3 Hz, 2H), 7.48 (d, J=8.0 Hz, 2H), 7.88-7.91 (m, 2H), 8.13 (s, 1H), 8.83 (s, 1H) and 8.98 (s, 1H). 19F NMR (376 MHz, DMSO-$d_6$): −57.18 (s, 3F), −61.00 (s, 3F) and −61.59 (s, 3F).
2-Amino-3-(4,6-bis(trifluoromethyl)-2H-benzotriazol-2-yl)-2-methylpropionitrile [1.5 g, 77%, Rf=0.3 (1:1 EA/heptane)] was prepared using a procedure similar to that described in Example 1, part a and b, except starting from 5,7-bis(trifluoromethyl)-2H-benzotriazole. 5,7-Bis(trifluoromethyl)-1H-benzotriazole (5.2 g, 99%) was prepared using a procedure similar to that described in Example 13, part a, except starting from 3,5-bis(trifluoromethyl)-1,2-phenylenediamine (5 g).

Example 24

N-[2-(4,6-Bis(trifluoromethyl)-2H-benzotriazol-2-yl)-1-cyano-1-methylethyl]-4-trifluoromethylthiobenzamide (compound No 1.019)

Using a procedure similar to that described in Example 1, except using 2-amino-3-(4,6-bis(trifluoromethyl)-2H-benzotriazol-2-yl)-2-methylpropionitrile, described in Example 23, and 4-trifluoromethylthiobenzoyl chloride, the title compound was isolated as a white solid (0.40 g, 83%). Rf=0.7 (1:1 EA/heptane). MS (ES): M/Z [M+H]=542. 1H NMR: (400 MHz, DMSO-$d_6$): 1.79 (s, 3H), 5.62 (dd, J=60.6, 13.3 Hz, 2H), 7.76-7.97 (m, 4H), 8.13 (s, 1H), 8.92 (s, 1H) and 8.97 (s, 1H). 19F NMR (376 MHz, DMSO-$d_6$): −61.62 (s, 3F), −61.04 (s, 3F) and −42.10 (s, 3F).

Example 25

N-[2-(5-Bromo-2H-benzotriazol-2-yl)-1-cyano-1-methylethyl]-4-trifluoromethoxybenzamide (compound No 1.020)

Using a procedure similar to that described in Example 1, except using 2-amino-3-(5-bromo-2H-benzotriazol-2-yl)-2-methylpropionitrile, the title compound was isolated as a white solid (0.36 g, 72%). Rf=0.65 (1:1 EA/heptane). MS (ES): M/Z [M+H]=468. 1H NMR: (400 MHz, DMSO-$d_6$): 1.74 (s, 3H), 5.44 (dd, J=26.8, 13.3 Hz, 2H), 7.51 (d, J=8.0 Hz, 2H), 7.58 (dd, J=9.1, 1.8 Hz, 1H), 7.91-7.96 (m, 2H), 7.96 (dd, J=9.1, 0.5 Hz, 1H), 8.29 (dd, J=1.7, 0.5 Hz, 1H) and 8.92 (s, 1H). 19F NMR (376 MHz, DMSO-$d_6$): −57.09 (s, 3F).

2-Amino-3-(5-bromo-2H-benzotriazol-2-yl)-2-methylpropionitrile [1.7 g, 93%, Rf=0.35 (1:1 EA/heptane)] was prepared using a procedure similar to that described in Example 1, part a and b, except starting from 5-bromo-1H-benzotriazole. 5-bromo-1H-benzotriazole was prepared using a procedure similar to that described in Example 13, part a, except starting from 4-bromo-1,2-diamino benzene.

Example 26

N-[2-(5-Bromo-2H-benzotriazol-2-yl)-1-cyano-1-methylethyl]-4-trifluoromethylthiobenzamide (compound No 1.021)

Using a procedure similar to that described in Example 1, except using 2-amino-3-(5-bromo-2H-benzotriazol-2-yl)-2-methylpropionitrile, described in Example 25, and 4-trifluoromethylthiobenzoyl chloride, the title compound was isolated as a white solid (0.45 g, 87%). Rf=0.65 (1:1 EA/heptane). MS (ES): M/Z [M+H]=484. 1H NMR: (400 MHz, DMSO-$d_6$): 1.74 (s, 3H), 5.36-5.53 (m, 2H), 7.58 (dd, J=9.1, 1.8 Hz, 1H), 7.84-7.92 (m, 4H), 7.95 (dd, J=9.1, 0.5 Hz, 1H), 8.29 (dd, J=1.7, 0.6 Hz, 1H) and 9.00 (s, 1H). 19F NMR (376 MHz, DMSO-$d_6$): −41.93 (s, 3F).

Example 27

N-[2-(6-Chloro-4-methyl-2H-benzotriazol-2-yl)-1-cyano-1-methylethyl]-4-trifluoromethoxybenzamide (compound No 1.033)

Using a procedure similar to that described in Example 1, except using 2-amino-3-(6-chloro-4-methyl-2H-benzotriazol-2-yl)-2-methylpropionitrile, the title compound was isolated as a white solid (192 mg, 55%). MS (ES): M/Z [M+H]=438. 1H NMR: (400 MHz, DMSO-$d_6$): 1.74 (s, 3H), 2.47 (s, 3H), 5.35-5.51 (m, 2H), 7.27 (s, 1H), 7.52 (d, J=8.0 Hz, 2H), 7.88-7.95 (m, 3H) and 8.84 (s, 1H). 19F NMR (376 MHz, DMSO-$d_6$): −57.12 (s, 3F).

2-Amino-3-(6-chloro-4-methyl-2H-benzotriazol-2-yl)-2-methylpropionitrile (0.4 g, 67%) was prepared using a procedure similar to that described in Example 1, part a and b, except starting from 5-chloro-7-methyl-1H-benzotriazole. 5-Chloro-7-methyl-1H-benzotriazole (4.35 g, 97%) was prepared using a procedure similar to that described in Example 11, part a, except starting from 4-chloro-2-methyl-6-nitroaniline (5 g).

Example 28

N-[2-(6-Chloro-4-methyl-2H-benzotriazol-2-yl)-1-cyano-1-methylethyl]-4-trifluoromethylthiobenzamide (compound No 1.034)

Using a procedure similar to that described in Example 1, except using 2-amino-3-(6-chloro-4-methyl-2H-benzotriazol-2-yl)-2-methylpropionitrile, described in Example 27, and 4-trifluoromethylthiobenzoyl chloride, the title compound was isolated as a white solid (233 mg, 64%). MS (ES): M/Z [M+H]=454. NMR: (400 MHz, DMSO-$d_6$): 1.74 (s, 3H), 2.47 (s, 3H), 5.44 (dd, J=57.5, 13.3 Hz, 2H), 7.27 (s, 1H), 7.79-7.99 (m, 5H) and 8.92 (s, 1H). 19F NMR (376 MHz, DMSO-$d_6$): −42.01 (s, 3F).

Example 29

N-[2-(6-Chloro-4-methyl-2H-benzotriazol-2-yl)-1-cyano-1-methylethyl]-4-phenoxybenzamide (compound No 1.039)

Using a procedure similar to that described in Example 1, except using 2-amino-3-(6-chloro-4-methyl-2H-benzotriazol-2-yl)-2-methylpropionitrile (60 mg, described in Example 27) and 4-phenoxybenzoyl chloride (0.067 mL), the title compound was isolated as a white solid (90 mg, 84%). MS (ES): M/Z [M+H]=446. NMR: (400 MHz, DMSO-$d_6$): 1.73 (s, 3H), 2.47 (s, 3H), 5.38 (d, J=13.3 Hz, 1H), 5.45 (d, J=13.3 Hz, 1H), 7.08 (t, J=8.25 Hz, 4H), 7.23 (t, 1H), 7.28 (s, 1H), 7.45 (t, 2H), 7.84 (d, J=8.79 Hz, 2H), 7.91 (m, 1H) and 8.68 (s, 1H).

4-Phenoxybenzoyl chloride was prepared by reacting 4-phenoxybenzoic acid with oxalyl chloride.

Example 30

N-[1-Cyano-1-methyl-2-(5-trifluoromethoxy-2H-benzotriazol-2-yl)ethyl]-4-trifluoromethoxybenzamide (compound No 1.035)

Using a procedure similar to that described in Example 1, except using 2-amino-3-(5-trifluoromethoxy-2H-benzotriazol-2-yl)-2-methylpropionitrile (100 mg), the title compound was isolated as a white solid (140 mg, 85%). MS (ES): M/Z [M+H]=474. 1H NMR: (400 MHz, DMSO-$d_6$): 1.75 (s, 3H), 5.44 (d, J=13.3 Hz, 1H), 5.51 (d, J=13.4 Hz, 1H), 7.45-7.52 (m, 3H), 7.93 (d, J=8.8 Hz, 2H), 8.06 (br s, 1H), 8.12 (d, 1H, J=9.9 Hz) and 8.89 (s, 1H). 19F NMR (376 MHz, DMSO-$d_6$): −57.42 (s, 3F) and −57.11 (s, 3F).

2-Amino-3-(5-trifluoromethoxy-2H-benzotriazol-2-yl)-2-methylpropionitrile (0.24 g) was prepared using a procedure similar to that described in Example 1, part a and b, except starting from 5-trifluoromethoxy-1H-benzotriazole (3.2 g). 5-Trifluoromethoxy-1H-benzotriazole (3.4 g, 74%) was prepared using a procedure similar to that described in Example 11, part a, except starting from 2-nitro-4-trifluoromethoxyaniline (5 g).

Example 31

N-[1-Cyano-1-methyl-2-(5-trifluoromethoxy-2H-benzotriazol-2-yl)ethyl]-4-trifluoromethylthiobenzamide (compound No 1.036)

Using a procedure similar to that described in Example 1, except using 2-amino-3-(5-trifluoromethoxy-2H-benzotriazol-2-yl)-2-methylpropionitrile (100 mg, described in Example 30) and 4-trifluoromethylthiobenzoyl chloride (0.12 mL), the title compound was isolated as a white solid (142 mg, 83%). MS (ES): M/Z [M+H]=490. 1H NMR: (400 MHz, CHLOROFORM-d): 1.75 (s, 3H), 5.48 (d, J=13.4 Hz, 1H), 5.52 (d, J=13.3 Hz, 1H), 7.47 (d, J=10.6 Hz, 1H), 7.85-

7.91 (m, 4H), 8.05 (br s, 1H), 8.12 (d, 1H, J=9.3 Hz) and 8.98 (br s, 1H). 19F NMR (376 MHz, CHLOROFORM-d): −57.43 (s, 3F) and −41.96 (s, 3F).

Example 32

N-[2-(6-Chloro-4-trifluoromethyl-2H-benzotriazol-2-yl)-1-cyano-1-methylethyl]-4-trifluoromethoxybenzamide (compound No 1.037)

Using a procedure similar to that described in Example 1, except using 2-amino-3-(6-chloro-4-trifluoromethyl-2H-benzotriazol-2-yl)-2-methylpropionitrile (100 mg), the title compound was isolated as a white solid (148 mg, 91%). MS (ES): M/Z [M+H]=492. 1H NMR: (400 MHz, DMSO-$d_6$): 1.77 (s, 3H), 2.47 (s, 3H), 5.46 (d, J=13.2 Hz, 1H), 5.60 (d, J=13.4 Hz, 1H), 7.49 (d, J=8.0 Hz, 2H), 7.89 (d, J=8.8 Hz, 2H), 7.96 (s, 1H), 8.56 (s, 1H) and 8.85 (s, 1H). 19F NMR (376 MHz, DMSO-$d_6$): −61.51 (s, 3F) and −57.16 (s, 3F).

2-Amino-3-(6-chloro-4-trifluoromethyl-2H-benzotriazol-2-yl)-2-methylpropionitrile (0.82 g) was prepared using a procedure similar to that described in Example 1, part a and b, except starting from 5-chloro-7-trifluoromethyl-1H-benzotriazole (2.5 g). 5-Chloro-7-trifluoromethyl-1H-benzotriazole (2.5 g, 55%) was prepared using a procedure similar to that described in Example 11, part a, except starting from 2-amino-5-chloro-3-nitrobenzotrifluoride (5 g).

Example 33

N-[2-(6-Chloro-4-trifluoromethyl-2H-benzotriazol-2-yl)-1-cyano-1-methylethyl]-4-trifluoromethylthiobenzamide (compound No 1.038)

Using a procedure similar to that described in Example 1, except using 2-amino-3-(6-chloro-4-trifluoromethyl-2H-benzotriazol-2-yl)-2-methylpropionitrile (100 mg, described in Example 32) and 4-trifluoromethylthiobenzoyl chloride (0.12 mL), the title compound was isolated as a white solid (142 mg, 85%). MS (ES): M/Z [M+H]=508. NMR: (400 MHz, DMSO-$d_6$): 1.77 (s, 3H), 2.47 (s, 3H), 5.46 (d, J=13.3 Hz, 1H), 5.62 (d, J=13.3 Hz, 1H), 7.82-7.88 (m, 4H), 7.96 (s, 1H), 8.57 (s, 1H) and 8.93 (s, 1H). 19F NMR (376 MHz, DMSO-$d_6$): −42.05 (s, 3F) and −61.51 (s, 3F).

Example 34

N-[2-(6-Chloro-4-trifluoromethyl-2H-benzotriazol-2-yl)-1-cyano-1-methylethyl]-4-phenoxybenzamide (compound No 1.042)

Using a procedure similar to that described in Example 1, except using 2-amino-3-(6-chloro-4-trifluoromethyl-2H-benzotriazol-2-yl)-2-methylpropionitrile (100 mg, described in Example 32) and 4-phenoxybenzoyl chloride (0.10 mL), the title compound was isolated as a white solid (95 mg, 58%). Rf=0.75 (1:1 EA/heptane). MS (ES): M/Z [M+H]=500. NMR: (400 MHz, DMSO-$d_6$): 1.76 (s, 3H), 2.47 (s, 3H), 5.47 (d, J=13.3 Hz, 1H), 5.57 (d, J=13.3 Hz, 1H), 7.04-7.12 (m, 4H), 7.22 (t, J=7.4 Hz, 1H), 7.97 (s, 1H), 8.57 (s, 1H) and 8.69 (s, 1H). 19F NMR (376 MHz, DMSO-$d_6$): −61.41 (s, 3F).

4-Phenoxybenzoyl chloride was prepared by reacting 4-phenoxybenzoic acid with oxalyl chloride.

Example 35

N-[2-(4-Chloro-2H-benzotriazol-2-yl)-1-cyano-1-methylethyl]-4-trifluoromethoxybenzamide (compound No 1.043)

Using a procedure similar to that described in Example 1, except using 2-amino-3-(4-chloro-2H-benzotriazol-2-yl)-2-methylpropionitrile (100 mg), the title compound was isolated as a white solid (142 mg, 80%). Rf=0.65 (1:1 EA/heptane). MS (ES): M/Z [M+H]=424. 1H NMR: (400 MHz, DMSO-$d_6$): 1.77 (s, 3H), 5.43 (d, J=13.4 Hz, 1H), 5.54 (d, J=13.4 Hz, 1H), 7.46 (t, 1H), 7.50 (d, J=7.9 Hz, 2H), 7.59 (d, J=6.8 Hz, 1H), 7.91-7.97 (m, 3H) and 8.90 (s, 1H). 19F NMR (376 MHz, DMSO-$d_6$): −57.12 (s, 3F).

2-Amino-3-(4-chloro-2H-benzotriazol-2-yl)-2-methylpropionitrile (0.3 g) was prepared using a procedure similar to that described in Example 1, part a and b, except starting from 7-chloro-1H-benzotriazole (1.0 g). 7-chloro-1H-benzotriazole (1.0 g, 23%) was prepared using a procedure similar to that described in Example 11, part a, except starting from 3-chloro-2-nitroaniline (5 g).

Example 36

N-[2-(4-Chloro-2H-benzotriazol-2-yl)-1-cyano-1-methylethyl]-4-trifluoromethylthiobenzamide (compound No 1.044)

Using a procedure similar to that described in Example 1, except using 2-amino-3-(4-chloro-2H-benzotriazol-2-yl)-2-methylpropionitrile (100 mg, described in Example 35) and 4-trifluoromethylthiobenzoyl chloride (0.1 mL), the title compound was isolated as a white solid (130 mg, 70%). Rf=0.6 (1:1 EA/heptane). MS (ES): M/Z [M+H]=440. NMR: (400 MHz, DMSO-$d_6$): 1.75 (s, 3H), 5.43 (d, J=13.3 Hz, 1H), 5.55 (d, J=13.4 Hz, 1H), 7.46 (t, J=8.0 Hz, 1H), 7.59 (d, J=6.7 Hz, 1H), 7.75-7.95 (m, 5H) and 8.97 (s, 1H). 19F NMR (376 MHz, DMSO-$d_6$): −41.98 (s, 3F).

Example 37

N-[2-(4-Chloro-2H-benzotriazol-2-yl)-1-cyano-1-methylethyl]-4-phenoxybenzamide (compound No 1.045)

Using a procedure similar to that described in Example 1, except using 2-amino-3-(4-chloro-2H-benzotriazol-2-yl)-2-methylpropionitrile (100 mg, described in Example 35) and 4-phenoxybenzoyl chloride (0.10 mL), the title compound was isolated as a white solid (70 mg, 38%). Rf=0.7 (1:1 EA/heptane). MS (ES): M/Z [M+H]=432. NMR: (400 MHz, DMSO-$d_6$): 1.75 (s, 3H), 5.43 (d, J=13.3 Hz, 1H), 5.50 (d, J=13.3 Hz, 1H), 7.04-7.10 (m, 4H), 7.22 (t, J=7.4 Hz, 1H), 7.43-7.48 (m, 3H), 7.59 (d, J=6.6 Hz, 1H), 7.84 (d, J=8.9 Hz, 2H), 7.94 (d, J=8.0 Hz, 1H) and 8.73 (s, 1H).

4-Phenoxybenzoyl chloride was prepared by reacting 4-phenoxybenzoic acid with oxalyl chloride.

Example 38

N-[2-(4-Bromo-6-chloro-2H-benzotriazol-2-yl)-1-cyano-1-methylethyl]-4-trifluoromethoxybenzamide (compound No 1.060)

Using a procedure similar to that described in Example 1, except using 2-amino-3-(4-bromo-6-chloro-2H-benzotriazol-2-yl)-2-methylpropionitrile (1.0 g), the title compound was isolated as a white solid (1.5 g, 90%). Rf=0.6 (1:1 EA/heptane). MS (ES): M/Z [M+H]=502. 1H NMR: (400 MHz, DMSO-$d_6$): 1.75 (s, 3H), 5.42 (d, 1H), 5.53 (d, 1H), 7.51 (d, J=8.0 Hz, 2H), 7.86 (d, J=1.6 Hz, 1H), 7.92 (d, J=8.8 Hz, 2H), 8.20 (d, J=1.6 Hz, 1H) and 8.88 (s, 1H). 19F NMR (376 MHz, DMSO-$d_6$): −57.1 (s, 3F).

2-Amino-3-(4-bromo-6-chloro-2H-benzotriazol-2-yl)-2-methylpropionitrile was prepared using a procedure similar to that described in Example 1, part a and b, except starting from 7-bromo-5-chloro-1H-benzotriazole. 7-Bromo-5-chloro-1H-benzotriazole (7.6 g, 99%) was prepared using a procedure similar to that described in Example 13, part a, except starting from 3-bromo-5-chloro-1,2-diaminobenzene that was prepared as follows:
- a. A mixture of 4-chloro-2-nitroaniline (10 g) and N-bromosuccinimide (11.3 g) in acetonitrile (200 mL) was heated at 70° C. overnight. The mixture was concentrated under reduced pressure and then poured into water and let stirred at room temperature for one hour. The resulting solid was filtered, washed with water and dried. The resulting crude product loaded on silica gel was purified by chromatography ($SiO_2$, heptane/EA) to afford 2-bromo-4-chloro-6-nitroaniline as a yellow solid (11.5 g, 79%). Rf=0.6 (3:7 EA/heptane).
- b. To a rapidly stirred suspension of iron powder (1.1 g) in ethanol (10 mL) was added concentrated hydrochloric acid (2.5 ml) and the mixture heated at 65° C. After 4 hours, a 25% aqueous solution of ammonium chloride was added (4 mL) followed by slow addition of a solution of 2-bromo-4-chloro-6-nitroaniline (1 g) in ethanol. After 3 hours, the mixture was allowed to cool down to room temperature and Celite® filter agent was added directly to the mixture. The suspension was filtered through a plug of Celite® filter agent. The filtrate was concentrated under reduced pressure, dissolved in ethyl acetate and filtered through a plug of Celite® filter agent. The filtered solution was treated with a saturated solution of sodium bicarbonate, washed with brine, dried over anhydrous sodium sulfate, filtered and concentrated under reduced pressure to give 3-bromo-5-chloro-1,2-diaminobenzene as an off-white solid (0.86 g, 98%). Rf=0.25 (3:7 EA/heptane).

Example 39

N-[1-Cyano-1-methyl-2-(4,5,7-trichloro-2H-benzotriazol-2-yl)-ethyl]-4-trifluoromethoxybenzamide (compound No 1.064)

Using a procedure similar to that described in Example 1, except using 2-amino-2-methyl-3-(4,5,7-trichloro-2H-benzotriazol-2-yl)-propionitrile (150 mg), the title compound was isolated as a white solid (210 mg, 87%). Rf=0.6 (1:1 EA/heptane). MS (ES): M/Z [M+H]=492. 1H NMR: (400 MHz, DMSO-$d_6$): 1.76 (s, 3H), 5.45 (d, 1H), 5.59 (d, 1H), 7.47 (d, J=8.25 Hz, 2H), 7.69 (dd, J=1.5, 0.8 Hz, 1H), 7.81-8.04 (m, 3H) and 8.83 (s, 1H). 19F NMR (376 MHz, DMSO-$d_6$): −57.1 (s, 3F).

2-Amino-2-methyl-3-(4,5,7-trichloro-2H-benzotriazol-2-yl)-propionitrile [1.3 g, Rf=0.2 (1:1 EA/heptane)] was prepared using a procedure similar to that described in Example 1, part a and b, except starting from 4,5,7-trichloro-1H-benzotriazole. 4,5,7-Trichloro-1H-benzotriazole (4 g, 85%) was prepared using a procedure similar to that described in Example 11, part a, except starting from 2-nitro-3,4,6-trichloroaniline (6.1 g) that was prepared as follows:
- a. 2,4,5-trichloroaniline (10 g) was dissolved in acetic anhydride (50 mL) and stirred overnight at room temperature. The resulting solid was filtered and air dried to give N-(2,4,5-trichlorophenyl)acetamide as an off white solid (12 g, 99%). Rf=0.5 (1:1 EA/heptane).
- b. To a solution of N-(2,4,5-trichlorophenyl)acetamide (12 g) in concentrated sulfuric acid (50 mL) at 0° C., was added dropwise, concentrated nitric acid (8 mL). After addition was complete, the mixture was allowed to warm slowly to room temperature. After 5 hours, the mixture was poured into ice water (200 mL). The resulting solid was filtered, washed with water and crystallized from a mixture of water and ethanol. The resulting solid was filtered and dried to give N-(2-nitro-3,4,6-trichlorophenyl)-acetamide as a grey solid (12 g, 99%).
- c. A solution of N-(2-nitro-3,4,6-trichlorophenyl)acetamide (7 g) in dioxane and concentrated hydrochloric acid (70 mL) was heated at reflux overnight. The mixture was concentrated under reduced pressure to remove dioxane, diluted with water (150 mL), neutralized with a saturated solution of sodium bicarbonate and extracted with ethyl acetate. The organic phase was washed with brine, dried over anhydrous sodium sulfate, filtered and concentrated under reduced pressure to give 2-nitro-3,4,6-trichloroaniline as a grey solid (6.1 g, quantitative). Rf=0.6 (3:7 EA/heptane).

Example 40

N-[1-Cyano-1-methyl-2-(4,5,7-trichloro-2H-benzotriazol-2-yl)-ethyl]-4-trifluoromethylthiobenzamide (compound No 1.065)

Using a procedure similar to that described in Example 1, except using 2-amino-2-methyl-3-(4,5,7-trichloro-2H-benzotriazol-2-yl)-propionitrile (150 mg, described in Example 39) and 4-trifluoromethylthiobenzoyl chloride (0.1 mL), the title compound was isolated as a white solid (200 mg, 80%). Rf=0.55 (1:1 EA/heptane). MS (ES): M/Z [M+H]=508. NMR: (400 MHz, DMSO-$d_6$): 1.76 (s, 3H), 5.45 (d, J=13.3 Hz, 1H), 5.61 (d, J=13.3 Hz, 1H), 7.83-7.92 (m, 4H), 7.94 (s, 1H) and 8.91 (s, 1H). 19F NMR (376 MHz, DMSO-$d_6$): −42.0 (s, 3F).

Example 41

N-[1-Cyano-1-methyl-2-(4,5,7-trichloro-2H-benzotriazol-2-yl)-ethyl]-4-(1,2,2,2-tetrafluoroethyl)benzamide (compound No 1.069)

Using a procedure similar to that described in Example 1, except using 2-amino-2-methyl-3-(4,5,7-trichloro-2H-benzotriazol-2-yl)-propionitrile (35 mg, described in Example 39) and 4-(1,2,2,2-tetrafluoroethyl)benzoyl chloride, the title compound was isolated as a solid (6.2 mg, 11%). MS (ES): M/Z [M+H]=508. NMR: (400 MHz, CHLOROFORM-d): 1.90 (s, 3H), 5.20 (d, J=13.8 Hz, 1H), 5.53 (d, J=13.8 Hz, 1H), 5.69 (dq, J=44.3 Hz, 5.9 Hz, 1H), 7.54 (br.s, 1H), 7.58 (s, 1H), 7.60 (d, J=8.1 Hz, 2H) and 7.98 (d, J=8.2 Hz, 2H). 19F NMR (376 MHz, CHLOROFORM-d): −197.6--197.1 (m, 1F), −79.0 (q, J=5.9 Hz, 3F).

4-(1,2,2,2-Tetrafluoroethyl)benzoyl chloride was prepared as follows:
- a. To a solution of 4-formylbenzoic acid methyl ester (4 g) in THF (40 mL), was added a solution of tetrabutylammonium fluoride (1 molar in THF, 2.4 mL), followed by a solution of (trifluoromethyl)trimethylsilane (2 molar THF, 13.4 mL). Water was added to quench the reaction and the mixture was extracted with ethyl acetate. The organic phase was dried over anhydrous sodium sulfate, filtered and the filtrate concentrated under reduced pressure to give a residue that was purified by chromatography (SiO$_2$, heptane/EA) to afford methyl 4-(2,2,2-trifluoro-1-hydroxyethyl)benzoate (4.5 g, 78%). 1H NMR: (400 MHz, DMSO-d$_6$): 3.86 (s, 3H), 5.30 (m, 1H), 7.01 (d, J=5.7 Hz, 1H), 7.65 (d, J=8.2 Hz, 2H), 8.00 (d, J=8.4 Hz, 2H). 19F NMR (376 MHz, DMSO-d$_6$): −77.0 (d, J=7.3 Hz, 3F).

b. To a cooled solution of methyl 4-(2,2,2-trifluoro-1-hydroxyethyl)benzoate (0.94 g) in DCM (9 mL) was added of (diethylamino)sulfur trifluoride (1.2 mL). The mixture was allowed to warm slowly to room temperature overnight. Water was added and the mixture was extracted with more DCM. The organic phase was washed with water and brine, dried over anhydrous sodium sulfate, filtered and the filtrate concentrated under reduced pressure to afford methyl 4-(1,2,2,2-tetrafluoroethyl)benzoate (0.94 g, 99%). 1H NMR: (400 MHz, DMSO-d$_6$): 3.88 (s, 3H), 6.52 (m, 1H), 7.69 (d, J=8.2 Hz, 2H), 8.09 (d, J=8.1 Hz, 2H). 19F NMR (376 MHz, DMSO-d$_6$): −197.9 (m, 1F), −78.0 (m, 3F)

c. A mixture of methyl 4-(1,2,2,2-tetrafluoroethyl)benzoate (190 mg) and lithium hydroxide (19 mg) in methanol and water was stirred at room temperature overnight. The mixture was made slightly acidic with a solution of 6 N hydrochloric acid and then extracted with ethyl acetate. The organic phase was dried over anhydrous sodium sulfate, filtered and the filtrate concentrated under reduced pressure to afford 4-(1,2,2,2-tetrafluoroethyl)benzoic acid (86 mg, 48%). 1H NMR: (400 MHz, DMSO-d$_6$): 6.50 (m, 1H), 7.65 (d, J=8.2 Hz, 2H), 8.07 (d, J=8.0 Hz, 2H), 13.43 (br. s., 1H). 19F NMR (376 MHz, DMSO-d$_6$): −199.0–−196.4 (m, 1F), −78.0 (m, 3F)

d. Oxalyl chloride (0.13 mL) was added to 4-(1,2,2,2-tetrafluoroethyl)benzoic acid (96 mg) in DCM (5 mL) and dimethyl formamide (0.2 mL). After 4 hours at room temperature, the mixture was concentrated under reduced pressure to afford 4-(1,2,2,2-tetrafluoroethyl)benzoyl chloride.

Example 42

N-[2-(4-Chloro-6-methoxy-2H-benzotriazol-2-yl)-1-cyano-1-methylethyl]-4-trifluoromethoxybenzamide (compound No 1.070)

Using a procedure similar to that described in Example 1, except using 2-amino-3-(4-chloro-6-methoxy-2H-benzotriazol-2-yl)-2-methylpropionitrile (50 mg), the title compound was isolated as a white solid (87 mg, 88%). MS (ES): M/Z [M+H]=454. 1H NMR: (400 MHz, DICHLOROMETHANE-d$_2$): 1.86 (s, 3H), 3.88 (s, 3H), 5.11 (d, J=13.9 Hz, 1H), 5.35 (d, J=13.9 Hz, 1H), 7.05 (d, J=2.1 Hz, 1H), 7.20 (d, J=2.0 Hz, 1H), 7.34 (d, J=8.1 Hz, 2H), 7.67 (s, 1H) and 7.93 (d, J=8.8 Hz, 2H). 19F NMR (376 MHz, DICHLOROMETHANE-d$_2$): −58.5 (s, 3F).

2-amino-3-(4-chloro-6-methoxy-2H-benzotriazol-2-yl)-2-methylpropionitrile was prepared using a procedure similar to that described in Example 1, part a and b, except starting from 7-chloro-5-methoxy-1H-benzotriazole. 7-Chloro-5-methoxy-1H-benzotriazole (0.8 g) was prepared using a procedure similar to that described in Example 13, part a, except starting from 3-chloro-1,2-diamino-5-methoxybenzene. 3-Chloro-1,2-diamino-5-methoxybenzene (1.88 g, 75%) was prepared using a procedure similar to that described in Example 38, part a and b, except starting from 4-methoxy-2-nitroaniline (16.8 g) and N-chlorosuccinimide (15 g) in part a to yield 6-chloro-4-methoxy-2-nitroaniline (2.9 g, 14%) used in part b.

Example 43

N-[2-(4-Chloro-6-methoxy-2H-benzotriazol-2-yl)-1-cyano-1-methylethyl]-4-trifluoromethylthiobenzamide (compound No 1.071)

Using a procedure similar to that described in Example 1, except using 2-amino-3-(4-chloro-6-methoxy-2H-benzotriazol-2-yl)-2-methylpropionitrile (50 mg, described in Example 42) and 4-trifluoromethylthiobenzoyl chloride (0.04 mL), the title compound was isolated as a white solid (45 mg, 51%). MS (ES): M/Z [M+H]=470. 1H NMR: (400 MHz, DICHLOROMETHANE-d$_2$): 1.86 (s, 3H), 3.88 (s, 3H), 5.11 (d, J=13.9 Hz, 1H), 5.36 (d, J=13.9 Hz, 1H), 7.05 (d, J=2.1 Hz, 1H), 7.20 (d, J=2.0 Hz, 1H), 7.72 (s, 1H), 7.79 (d, J=8.2 Hz, 2H) and 7.92 (d, J=8.6 Hz, 2H). 19F NMR (376 MHz, DICHLOROMETHANE-d$_2$): −42.8 (s, 3F).

Example 44

N-[1-cyano-2-(5-methoxy-2H-benzotriazol-2-yl)-1-methylethyl]-4-trifluoromethoxybenzamide (compound No 1.072)

Using a procedure similar to that described in Example 1, except using 2-amino-3-(5-methoxy-2H-benzotriazol-2-yl)-2-methylpropionitrile (150 mg), the title compound was isolated as a white solid (190 mg, 70%). Rf=0.35 (1:1 EA/heptane). MS (ES): M/Z [M+H]=420. 1H NMR: (400 MHz, DMSO-d$_6$): 1.73 (s, 3H), 3.84 (s, 3H), 5.32 (d, J=13.4 Hz, 1H), 5.37 (d, J=13.4 Hz, 1H), 7.10 (dd, J=9.3, 2.1 Hz, 1H), 7.24 (d, J=2.1 Hz, 1H), 7.52 (d, J=8.1 Hz, 2H), 7.82 (dd, J=9.3, 0.4 Hz, 1H), 7.95 (d, J=8.9 Hz, 2H) and 8.92 (s, 1H). 19F NMR (376 MHz, DMSO-d$_6$): −57.1 (s, 3F).

2-amino-3-(5-methoxy-2H-benzotriazol-2-yl)-2-methylpropionitrile was prepared using a procedure similar to that described in Example 1, part a and b, except starting from 5-methoxy-1H-benzotriazole that was prepared as follows:

a. To a solution of 1,2-diamino-4-methoxybenzene hydrochloride (2 g) in acetonitrile (20 mL) was added dropwise tert-butylnitrite (1.35 mL) at 0° C. After 4 hours at room temperature, the mixture was concentrated under reduced pressure to a solid residue, which was then dissolved in water. The aqueous solution was neutralized with a saturated solution of sodium bicarbonate and extracted with ethyl acetate. The organic phase was washed with brine, dried over anhydrous sodium sulfate, filtered and the filtrate concentrated under reduced pressure to afford 5-methoxy-1H-benzotriazole as an off-white solid (1.2 g, 85%). MS (ES): M/Z [M+H]=150.

Example 45

N-[1-cyano-2-(5-methoxy-2H-benzotriazol-2-yl)-1-methylethyl]-4-trifluoromethylthiobenzamide (compound No 1.073)

Using a procedure similar to that described in Example 1, except using 2-amino-3-(5-methoxy-2H-benzotriazol-2-yl)-2-methylpropionitrile (120 mg, described in Example 44) and 4-trifluoromethylthiobenzoyl chloride (0.16 mL), the title compound was isolated as a white solid (150 mg, 66%). Rf=0.3 (1:1 EA/heptane). MS (ES): M/Z [M+H]=436. 1H NMR: (400 MHz, DMSO-d$_6$): 1.73 (s, 3H), 3.84 (s, 3H), 5.32 (d, J=13.4 Hz, 1H), 5.38 (d, J=13.4 Hz, 1H), 7.10 (dd, J=9.3, 2.3 Hz, 1H), 7.24 (d, J=2.1 Hz, 1H), 7.82 (dd, J=9.2, 0.4 Hz, 1H), 7.87 (d, J=8.6 Hz, 2H), 7.92 (d, J=8.6 Hz, 2H) and 9.00 (s, 1H). 19F NMR (376 MHz, DMSO-d$_6$): −41.9 (s, 3F).

Example 46

N-[1-Cyano-2-(5,7-dichloro-4-fluoro-2H-benzotriazol-2-yl)-1-methylethyl]-4-trifluoromethoxybenzamide (compound No 1.090)

Using a procedure similar to that described in Example 1, except using 2-amino-3-(5,7-dichloro-4-fluoro-2H-benzotriazol-2-yl)-2-methylpropionitrile (90 mg), the title compound was isolated as a white solid (65 mg, 44%). Rf=0.6 (1:1 EA/heptane). MS (ES): M/Z [M+H]=476. 1H NMR: (400 MHz, DMSO-d$_6$): 1.76 (s, 3H), 5.47 (d, J=13.3 Hz, 1H), 5.58 (d, J=13.4 Hz, 1H), 7.50 (d, J=8.1 Hz, 2H), 7.70-8.10 (m, 3H) and 8.86 (s, 1H). 19F NMR (376 MHz, DMSO-d$_6$): −127.6 (d, J=5.9 Hz, 1F) and −57.1 (s, 3F).

2-Amino-3-(5,7-dichloro-4-fluoro-2H-benzotriazol-2-yl)-2-methylpropionitrile [1.3 g, Rf=0.2 (1:1 EA/heptane)] was prepared using a procedure similar to that described in Example 1, part a and b, except starting from 5,7-dichloro-4-fluoro-1H-benzotriazole. 5,7-Dichloro-4-fluoro-1H-benzotriazole (4 g, 85%) was prepared using a procedure similar to that described in Example 11, part a, except starting from 4,6-dichloro-3-fluoro-2-nitroaniline. 4,6-Dichloro-3-fluoro-2-nitroaniline (6.1 g) was prepared using a procedure similar to that described in Example 39, part a, b and c, except starting from 2,4-dichloro-5-fluoroaniline (10 g).

Example 47

N-[1-Cyano-2-(5,7-dichloro-4-fluoro-2H-benzotriazol-2-yl)-1-methylethyl]-4-trifluoromethylthiobenzamide (compound No 1.091)

Using a procedure similar to that described in Example 1, except using 2-amino-3-(5,7-dichloro-4-fluoro-2H-benzotriazol-2-yl)-2-methylpropionitrile (90 mg, described in Example 46) and 4-trifluoromethylthiobenzoyl chloride (0.06 mL), the title compound was isolated as a white solid (95 mg, 62%). Rf=0.55 (1:1 EA/heptane). MS (ES): M/Z [M+H]=492. NMR: (400 MHz, DMSO-d$_6$): 1.76 (s, 3H), 5.47 (d, J=13.3 Hz, 1H), 5.60 (d, J=13.3 Hz, 1H), 7.58-8.22 (m, 5H) and 8.94 (s, 1H). 19F NMR (376 MHz, DMSO-d$_6$): −127.6 (d, J=5.3 Hz, 1F) and −42.0 (s, 3F).

Example 48

N-[2-(5-Chloro-4,7-dimethyl-2H-benzotriazol-2-yl)-1-cyano-1-methylethyl]-4-trifluoromethoxybenzamide (compound No 1.092)

Using a procedure similar to that described in Example 1, except using 2-amino-3-(5-chloro-4,7-dimethyl-2H-benzotriazol-2-yl)-2-methylpropionitrile (120 mg), the title compound was isolated as a white solid (85 mg, 41%). Rf=0.7 (1:1 EA/heptane). MS (ES): M/Z [M+H]=452. 1H NMR: (400 MHz, DMSO-d$_6$): 1.74 (s, 3H), 2.43 (s, 3H), 2.45 (s, 3H), 5.35 (d, J=13.3 Hz, 1H), 5.52 (d, J=13.3 Hz, 1H), 7.25 (d, J=0.6 Hz, 1H), 7.51 (d, J=8.1 Hz, 2H), 7.91 (d, J=8.8 Hz, 2H) and 8.78 (s, 1H). 19F NMR (376 MHz, DMSO-d$_6$): −57.2 (s, 3F).

2-Amino-3-(5-chloro-4,7-dimethyl-2H-benzotriazol-2-yl)-2-methylpropionitrile [1.3 g, Rf=0.2 (1:1 EA/heptane)] was prepared using a procedure similar to that described in Example 1, part a and b, except starting from 5-chloro-4,7-dimethyl-1H-benzotriazole. 5-Chloro-4,7-dimethyl-1H-benzotriazole (4 g, 85%) was prepared using a procedure similar to that described in Example 11, part a, except starting from 4-chloro-3,6-dimethyl-2-nitroaniline. 4-Chloro-3,6-dimethyl-2-nitroaniline (6.1 g) was prepared using a procedure similar to that described in Example 39, part a, b and c, except starting from 4-chloro-2,5-dimethylaniline (10 g).

Example 49

N-[2-(5-Chloro-4,7-dimethyl-2H-benzotriazol-2-yl)-1-cyano-1-methylethyl]-4-trifluoromethylthiobenzamide (compound No 1.093)

Using a procedure similar to that described in Example 1, except using 2-amino-3-(5-chloro-4,7-dimethyl-2H-benzotriazol-2-yl)-2-methylpropionitrile (120 mg, described in Example 48) and 4-trifluoromethylthiobenzoyl chloride (0.09 mL), the title compound was isolated as a white solid (180 mg, 85%). Rf=0.7 (1:1 EA/heptane). MS (ES): M/Z [M+H]=468. NMR: (400 MHz, DMSO-d$_6$): 1.74 (s, 3H), 2.43 (s, 3H), 2.44 (s, 3H), 5.34 (d, J=13.3 Hz, 1H), 5.54 (d, J=13.3 Hz, 1H), 7.24 (d, J=0.7 Hz, 1H), 7.81-7.93 (m, 4H) and 8.86 (s, 1H). 19F NMR (376 MHz, DMSO-d$_6$): −42.1 (s, 3F).

Example 50

N-[2-(5-bromo-4-fluoro-7-methyl-2H-benzotriazol-2-yl)-1-cyano-1-methylethyl]-4-trifluoromethoxybenzamide (compound No 1.094)

Using a procedure similar to that described in Example 1, except using 2-amino-3-(5-bromo-4-fluoro-7-methyl-2H-benzotriazol-2-yl)-2-methylpropionitrile (120 mg), the title compound was isolated as a white solid (130 mg, 68%). Rf=0.65 (1:1 EA/heptane). MS (ES): M/Z [M+H]=500. 1H NMR: (400 MHz, DMSO-d$_6$): 1.75 (s, 3H), 2.42 (s, 3H), 5.40 (d, J=13.3 Hz, 1H), 5.54 (d, J=13.4 Hz, 1H), 7.45 (d, J=5.7 Hz, 1H), 7.51 (d, J=8.3 Hz, 2H), 7.91 (d, J=8.7 Hz, 2H) and 8.82 (s, 1H). 19F NMR (376 MHz, DMSO-d$_6$): −122.4 (d, J=5.3 Hz, 1F) and −57.1 (s, 3F).

2-Amino-3-(5-bromo-4-fluoro-7-methyl-2H-benzotriazol-2-yl)-2-methylpropionitrile [1.3 g, Rf=0.2 (1:1 EA/heptane)] was prepared using a procedure similar to that described in Example 1, part a and b, except starting from 5-bromo-4-fluoro-7-methyl-1H-benzotriazole. 5-Bromo-4-fluoro-7-methyl-1H-benzotriazole (4 g, 85%) was prepared using a procedure similar to that described in Example 11, part a, except starting from 4-bromo-3-fluoro-6-methyl-2-nitroaniline. 4-Bromo-3-fluoro-6-methyl-2-nitroaniline (6.1 g) was prepared using a procedure similar to that described in Example 39, part a, b and c, except starting from 4-bromo-5-fluoro-2-methylaniline (10 g).

Example 51

N-[2-(5-bromo-4-fluoro-7-methyl-2H-benzotriazol-2-yl)-1-cyano-1-methylethyl]-4-trifluoromethylthiobenzamide (compound No 1.095)

Using a procedure similar to that described in Example 1, except using 2-amino-3-(5-bromo-4-fluoro-7-methyl-2H- benzotriazol-2-yl)-2-methylpropionitrile (120 mg, described in Example 50) and 4-trifluoromethylthiobenzoyl chloride (0.09 mL), the title compound was isolated as a white solid (175 mg, 88%). Rf=0.65 (1:1 EA/heptane). MS (ES): M/Z [M+H]=516. NMR: (400 MHz, DMSO-$d_6$): 1.75 (s, 3H), 2.41 (s, 3H), 5.41 (d, J=13.3 Hz, 1H), 5.56 (d, J=13.3 Hz, 1H), 7.45 (dd, J=5.9, 1.1 Hz, 1H), 7.85-7.90 (m, 4H), 8.90 (s, 1H). 19F NMR (376 MHz, DMSO-$d_6$): −122.4 (d, J=5.3 Hz, 1F), −42.0 (s, 3F).

Example 52

N-[2-(4-Bromo-5-chloro-2H-benzotriazol-2-yl)-1-cyano-1-methylethyl]-4-trifluoromethoxybenzamide (compound No 1.057)

Using a procedure similar to that described in Example 1, except using 2-amino-3-(4-bromo-5-chloro-2H-benzotriazol-2-yl)-2-methylpropionitrile (48 mg), the title compound was isolated as a white solid (43 mg, 56%). MS (ES): M/Z [M+H]=502. 1H NMR: (400 MHz, DMSO-$d_6$): 1.75 (s, 3H), 5.42 (d, J=13.4 Hz, 1H), 5.54 (d, J=13.4 Hz, 1H), 7.51 (d, J=8.1 Hz, 2H), 7.63 (d, J=9.0 Hz, 1H), 7.93 (d, J=8.8 Hz, 2H), 8.02 (d, J=9.0 Hz, 1H) and 8.88 (s, 1H). 19F NMR (376 MHz, DMSO-$d_6$): −57.1 (s, 3F).

2-amino-3-(4-bromo-5-chloro-2H-benzotriazol-2-yl)-2-methylpropionitrile (48 mg) was prepared using a procedure similar to that described in Example 1, part a and b, except starting from 4-bromo-5-chloro-1H-benzotriazole (213 mg) that was prepared as follows:
a. To a solution of 5-chloro-1H-benzotriazole (1 g) and sodium acetate (1 g) in acetic acid was added bromine (2 g). After 10 days at room temperature, the mixture was treated with a saturated solution sodium thiosulfate, neutralized with a saturated solution of sodium bicarbonate and extracted with ethyl acetate. The organic phase was washed with brine, dried over anhydrous sodium sulfate, filtered and the filtrate concentrated under reduced pressure to afford a residue that was purified by semi-preparative liquid chromatography to afford 4-bromo-5-chloro-1H-benzotriazole as an off-white solid (213 mg, 14%). MS (ES): M/Z [M+H]=232. 1H NMR: (400 MHz, DMSO-$d_6$): 7.58 (d, J=8.7 Hz, 2H) and 7.91 (d, J=8.7 Hz, 1H).

Example 53

N-[2-(5-Chloro-4,7-dibromo-2H-benzotriazol-2-yl)-1-cyano-1-methylethyl]-4-trifluoromethoxybenzamide (compound No 1.083)

Using a procedure similar to that described in Example 1, except using 2-amino-3-(5-chloro-4,7-dibromo-2H-benzotriazol-2-yl)-2-methylpropionitrile (390 mg), the title compound was isolated as a white solid (530 mg, 90%). MS (ES): M/Z [M+H]=580. 1H NMR: (400 MHz, DMSO-$d_6$): 1.75 (s, 3H), 5.43 (d, J=13.3 Hz, 1H), 5.59 (d, J=13.4 Hz, 1H), 7.51 (d, J=8.0 Hz, 2H), 7.84-7.96 (m, 2H), 8.04 (s, 1H) and 8.83 (s, 1H). 19F NMR (376 MHz, DMSO-$d_6$): −57.1 (s, 3F).

2-Amino-3-(5-chloro-4,7-dibromo-2H-benzotriazol-2-yl)-2-methylpropionitrile (440 mg) was prepared using a procedure similar to that described in Example 1, part a and b, except starting from 5-chloro-4,7-dibromo-1H-benzotriazole (4.2 g) that was prepared as follows by adapting a procedure described in the literature by K. Kopanska et al. in Bioorganic & Medicinal Chemistry, volume 13 (2005) page 3601 and in Bioorganic & Medicinal Chemistry, volume 12 (2004), pages 2617-2624:
a. To a solution of 5-chloro-1H-benzotriazole (7.7 g) and silver sulfate (19 g) in sulfuric acid (100 mL) was slowly added bromine (15 mL). After 2 days at room temperature, water was slowly added to the chilled mixture and the mixture stirred at room temperature for 3 days. The resulting solid was filtered, washed with water and triturated with ethyl acetate. The organic filtrate was collected and treated with a saturated solution of sodium bisulfite, a saturated solution of sodium bicarbonate, then water, dried over anhydrous sodium sulfate and filtered through a pad of Celite®. The filtrate was concentrated under reduced pressure to afford 5-chloro-4,7-dibromo-1H-benzotriazole as a solid (11.2 g, 71%). MS (ES): M/Z [M+H]=310. 1H NMR: (400 MHz, DMSO-$d_6$): 8.0 (s, 1H).

Example 54

N-[2-(5-Chloro-4,7-dibromo-2H-benzotriazol-2-yl)-1-cyano-1-methylethyl]-4-trifluoromethylthiobenzamide (compound No 1.085)

Using a procedure similar to that described in Example 1, except using 2-amino-3-(5-chloro-4,7-dibromo-2H-benzotriazol-2-yl)-2-methylpropionitrile (44 mg, described in Example 53) and 4-trifluoromethylthiobenzoyl chloride, the title compound was isolated as a white solid (15 mg, 22%). MS (ES): M/Z [M−H]=594. NMR: (400 MHz, DMSO-$d_6$): 1.75 (s, 3H), 5.43 (d, J=13.4 Hz, 1H), 5.61 (d, J=13.3 Hz, 1H), 7.88 (q, J=8.5 Hz, 4H), 8.04 (s, 1H) and 8.91 (s, 1H). 19F NMR (376 MHz, DMSO-$d_6$): −42.0 (s, 3F).

Example 55

N-[2-(4-Bromo-5,7-dichloro-2H-benzotriazol-2-yl)-1-cyano-1-methylethyl]-4-trifluoromethoxybenzamide (compound No 1.086)

Using a procedure similar to that described in Example 1, except using 2-amino-3-(4-bromo-5,7-dichloro-2H-benzotriazol-2-yl)-2-methylpropionitrile, the title compound was isolated as a white solid (260 mg). MS (ES): M/Z [M+H]=536. 1H NMR: (400 MHz, DMSO-$d_6$): 1.76 (s, 3H), 5.44 (d, J=13.2 Hz, 1H), 5.59 (d, J=13.4 Hz, 1H), 7.51 (d, J=8.1 Hz, 2H), 7.84-7.99 (m, 3H) and 8.83 (s, 1H). 19F NMR (376 MHz, DMSO-$d_6$): −57.1 (s, 3F).

2-Amino-3-(4-bromo-5,7-dichloro-2H-benzotriazol-2-yl)-2-methylpropionitrile was prepared using a procedure similar to that described in Example 1, part a and b, except starting from 4-bromo-5,7-dichloro-1H-benzotriazole that was prepared along with 4,6-dibromo-5,7-dichloro-1H-benzotriazole using a procedure similar to that described in Example 53 except using 5,7-dichloro-1H-benzotriazole described in Example 15.

Example 56

N-[2-(4-Bromo-5,7-dichloro-2H-benzotriazol-2-yl)-1-cyano-1-methylethyl]-4-trifluoromethylthiobenzamide (compound No 1.087)

Using a procedure similar to that described in Example 1, except using 2-amino-3-(4-bromo-5,7-dichloro-2H-benzotriazol-2-yl)-2-methylpropionitrile and 4-trifluoromethylthiobenzoyl chloride, the title compound was isolated as a white solid (110 mg, described in Example 55). MS (ES): M/Z [M+H]=552. NMR: (400 MHz, DMSO-$d_6$): 1.75 (s, 3H), 5.44 (d, J=13.3 Hz, 1H), 5.60 (d, J=13.7 Hz, 1H), 7.75-8.04 (m, 5H) and 8.91 (s, 1H). 19F NMR (376 MHz, DMSO-$d_6$): −42.0 (s, 3F).

Example 57

N-[1-Cyano-2-(4,6-dibromo-5,7-dichloro-2H-benzotriazol-2-yl)-1-methylethyl]-4-trifluoromethoxybenzamide (compound No 1.088)

Using a procedure similar to that described in Example 1, except using 2-amino-3-(4,6-dibromo-5,7-dichloro-2H-benzotriazol-2-yl)-2-methylpropionitrile, the title compound was isolated as a white solid (130 mg). MS (ES): M/Z [M+H]=614. 1H NMR: (400 MHz, DMSO-$d_6$): 1.75 (s, 3H), 5.45 (d, J=13.3 Hz, 1H), 5.59 (d, J=13.4 Hz, 1H), 7.51 (d, J=8.0 Hz, 2H), 7.91 (d, J=8.8 Hz, 2H) and 8.82 (s, 1H). 19F NMR (376 MHz, DMSO-$d_6$): −57.1 (s, 3F).

2-Amino-3-(4,6-dibromo-5,7-dichloro-2H-benzotriazol-2-yl)-2-methylpropionitrile was prepared using a procedure similar to that described in Example 1, part a and b, except starting from 4,6-dibromo-5,7-dichloro-1H-benzotriazole that was prepared along with 4-bromo-5,7-dichloro-1H-benzotriazole described in Example 55 using a procedure similar to that described in Example 53 except using 5,7-dichloro-1H-benzotriazole described in Example 15.

Example 58

N-[1-Cyano-2-(4,6-dibromo-5,7-dichloro-2H-benzotriazol-2-yl)-1-methylethyl]-4-trifluoromethylthiobenzamide (compound No 1.089)

Using a procedure similar to that described in Example 1, except using 2-amino-3-(4,6-dibromo-5,7-dichloro-2H-benzotriazol-2-yl)-2-methylpropionitrile, described in Example 57, and 4-trifluoromethylthiobenzoyl chloride, the title compound was isolated as a white solid (100 mg). MS (ES): M/Z [M+H]=630. NMR: (400 MHz, DMSO-$d_6$): 1.75 (s, 3H), 5.45 (d, J=13.3 Hz, 1H), 5.60 (d, J=13.0 Hz, 1H), 7.82-7.92 (m, 4H) and 8.90 (s, 1H). 19F NMR (376 MHz, DMSO-$d_6$): −42.0 (s, 3F).

Example 59

N-[1-Cyano-1-methyl-2-(4,5,7-trichloro-2H-benzotriazol-2-yl)-ethyl]-4-pentafluorothiobenzamide (compound No 1.104)

Using a procedure similar to that described in Example 1, except using 2-amino-2-methyl-3-(4,5,7-trichloro-2H-benzotriazol-2-yl)-propionitrile (105 mg, described in Example 39) and 4-pentafluorothiobenzoyl chloride (126 mg), the title compound was isolated as a white solid (210 mg). MS (ES): M/Z [M+Na]=556. 1H NMR: (400 MHz, CHLOROFORM-d): 1.89 (s, 3H), 5.20 (d, J=13.8 Hz, 1H), 5.53 (d, J=13.8 Hz, 1H), 7.59 (s, 2H), 7.88 (d, J=8.8 Hz, 2H) and 7.98 (d, J=8.4 Hz, 2H). 19F NMR (376 MHz, CHLOROFORM-d): −167.8 (d, J=150.4 Hz, 4F) and −147.8 (quin, J=150.4 Hz, 1F).

Example 60

N-[2-(5-Chloro-4,7-dibromo-2H-benzotriazol-2-yl)-1-cyano-1-methylethyl]-4-cyanobenzamide (compound No 1.098)

A solution of 4-cyanobenzoyl chloride (0.16 mmole) in THF was added to a solution of 2-amino-3-(5-chloro-4,7-dibromo-2H-benzotriazol-2-yl)-2-methylpropionitrile (0.075 mmole, described in Example 53) in THF mixed with TEA (3% v./v.). The reaction mixture was stirred 12 hours at room temperature then heated to 45° C. for 6 hours before solvent was evaporated under reduced pressure. The resulting crude product was dissolved in DMSO and purify by semi-preparative HPLC. The desired fractions were collected and evaporated under reduced pressure. The title compound was isolated as solid residue (10.8 mg) that was dissolved in DMSO for further biological evaluation and analyzed by LCMS. MS (ES): M/Z [M+H]=521, RT=0.66 min.

Example 61

N-[2-(5-Chloro-4,7-dibromo-2H-benzotriazol-2-yl)-1-cyano-1-methylethyl]-4-(1,1,2,2-tetrafluoroethoxy) benzamide (compound No 1.099)

Using a procedure similar to that described in Example 60, except using a solution of 4-(1,1,2,2-tetrafluoroethoxy)benzoyl chloride (0.16 mmole) in THF, the title compound was isolated as solid residue (5.9 mg). It was dissolved in DMSO for further biological evaluation and analyzed by LCMS. MS (ES): M/Z [M+H]=612, RT=0.72 min.

Example 62

N-[1-Cyano-1-methyl-2-(4,5,7-trichloro-2H-benzotriazol-2-yl)-ethyl]-4-iodobenzamide (compound No 1.100)

Using a procedure similar to that described in Example 60, except using a solution of 4-iodobenzoyl chloride (0.16 mmole) in THF and a solution of 2-amino-2-methyl-3-(4,5,7-trichloro-2H-benzotriazol-2-yl)-propionitrile (0.075 mmole, described in Example 39) in THF mixed with TEA (3% v./v.), the title compound was isolated as solid residue (3.9 mg). It was dissolved in DMSO for further biological evaluation and analyzed by LCMS. MS (ES): M/Z [M+H]=534, RT=0.73 min.

Example 63

N-[1-Cyano-1-methyl-2-(4,5,7-trichloro-2H-benzotriazol-2-yl)-ethyl]-4-trifluoromethylbenzamide (compound No 1.101)

Using a procedure similar to that described in Example 60, except using a solution of 4-trifluoromethylbenzoyl chloride (0.16 mmole) in THF and a solution of 2-amino-2-methyl-3-(4,5,7-trichloro-2H-benzotriazol-2-yl)-propionitrile (0.075 mmole, described in Example 39) in THF mixed with TEA (3% v./v.), the title compound was isolated as solid residue (13.9 mg). It was dissolved in DMSO for further biological evaluation and analyzed by LCMS. MS (ES): M/Z [M+H]=476, RT=0.72 min.

Example 64

N-[1-Cyano-1-methyl-2-(4,5,7-trichloro-2H-benzotriazol-2-yl)-ethyl]-4-cyanobenzamide (compound No 1.102)

Using a procedure similar to that described in Example 60, except using a solution of 4-cyanobenzoyl chloride (0.16 mmole) in THF and a solution of 2-amino-2-methyl-3-(4,5,7-trichloro-2H-benzotriazol-2-yl)-propionitrile (0.075 mmole, described in Example 39) in THF mixed with TEA (3% v./v.), the title compound was isolated as solid residue (4.2 mg). It was dissolved in DMSO for further biological evaluation and analyzed by LCMS. MS (ES): M/Z [M+H]=433, RT=0.64 min.

Example 65

N-[1-Cyano-1-methyl-2-(4,5,7-trichloro-2H-benzotriazol-2-yl)-ethyl]-4-(1,1,2,2-tetrafluoroethoxy)benzamide (compound No 1.103)

Using a procedure similar to that described in Example 169, except using a solution of 4-(1,1,2,2-tetrafluoroethoxy)benzoyl chloride (0.16 mmole) in THF and a solution of 2-amino-2-methyl-3-(4,5,7-trichloro-2H-benzotriazol-2-yl)-propionitrile (0.075 mmole, described in Example 39) in THF mixed with TEA (3% v./v.), the title compound was isolated as solid residue (4.2 mg). It was dissolved in DMSO for further biological evaluation and analyzed by LCMS. MS (ES): M/Z [M+H]=524, RT=0.72 min.

Example 66

N-[1-Cyano-1-methyl-2-(4,5,7-trichloro-2H-benzotriazol-2-yl)-ethyl]-3-fluoro-4-trifluoromethylbenzamide (compound No 1.146)

Using a procedure similar to that described in Example 60, except using a solution of 3-fluoro-4-trifluoromethylbenzoyl chloride (0.16 mmole) in THF and a solution of 2-amino-2-methyl-3-(4,5,7-trichloro-2H-benzotriazol-2-yl)-propionitrile (0.075 mmole, described in Example 39) in THF mixed with TEA (3% v./v.), the title compound was isolated as solid residue (13.9 mg). It was dissolved in DMSO for further biological evaluation and analyzed by LCMS. MS (ES): M/Z [M+H]=494, RT=0.73 min.

Example 67

N-[1-Cyano-1-methyl-2-(4,5,7-trichloro-2H-benzotriazol-2-yl)-ethyl]-2-fluoro-4-trifluoromethylbenzamide (compound No 1.143)

Using a procedure similar to that described in Example 60, except using a solution of 2-fluoro-4-trifluoromethylbenzoyl chloride (0.16 mmole) in THF and a solution of 2-amino-2-methyl-3-(4,5,7-trichloro-2H-benzotriazol-2-yl)-propionitrile (0.075 mmole, described in Example 39) in THF mixed with TEA (3% v./v.), the title compound was isolated as solid residue (13.9 mg). It was dissolved in DMSO for further biological evaluation and analyzed by LCMS. MS (ES): M/Z [M+H]=494, RT=0.73 min.

Compounds of Examples 68 and 69 were prepared according to the following general reaction scheme:

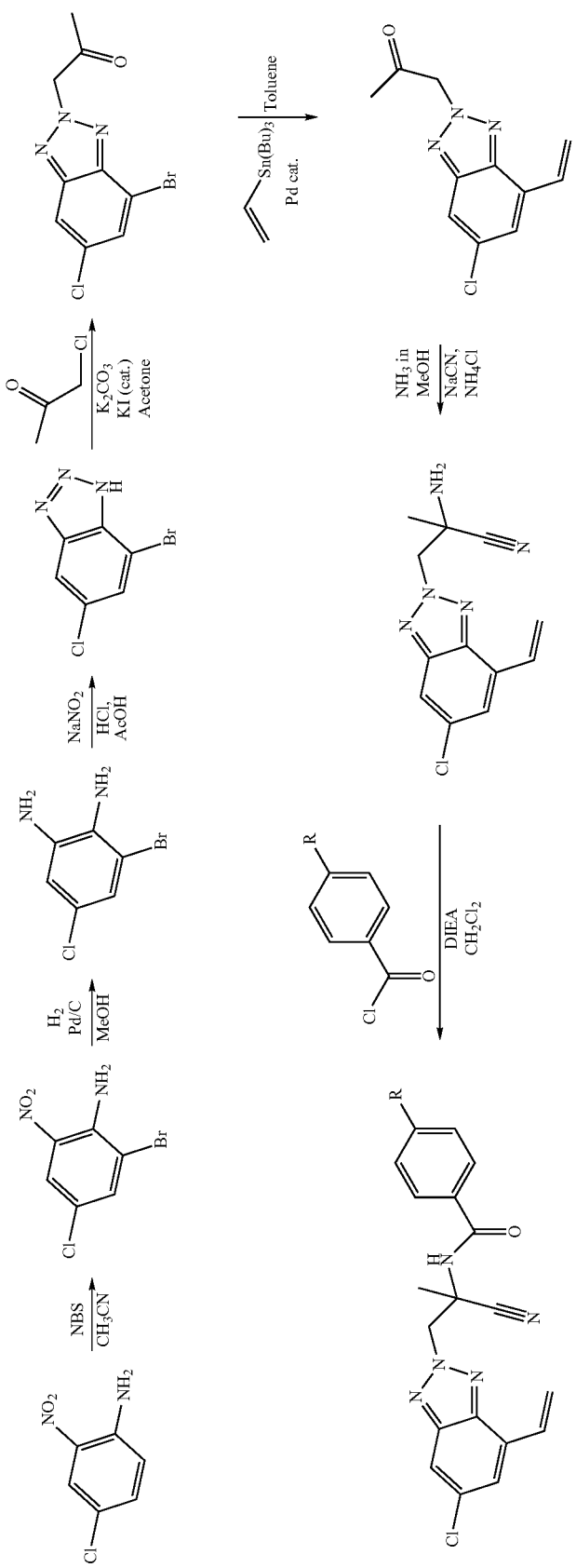

Final Product
V=C—H; W=C—Cl; X=C—H; Y=C—CH=CH$_2$;
Q=P=N;
R$_3$=R$_4$=H; a=1; R$_5$=CH$_3$, R$_6$=H;
Z=C(O); R$_7$=p-phenyl-R It will be apparent to one of skill in the art that modified derivatives with variable substitution on the phenyl ring may also be made by starting the corresponding substituted benzoic acid chloride.

Example 68

N-[2-(6-Chloro-4-vinyl-2H-benzotriazol-2-yl)-1-cyano-1-methylethyl]-4-trifluoromethoxybenzamide (compound No 1.075)

Using a procedure similar to that described in Example 1, except using 2-amino-3-(6-chloro-4-vinyl-2H-benzotriazol-2-yl)-2-methylpropionitrile (2.3 g), the title compound was isolated as a white solid (3.2 g, 80%). Rf=0.45 (1:1 EA/heptane). MS (ES): M/Z [M+H]=450. 1H NMR: (400 MHz, DMSO-d$_6$): 1.75 (s, 3H), 5.41 (d, J=13.3 Hz, 1H), 5.51 (dd, J=11.2, 1.2 Hz, 1H), 5.55 (d, J=13.4 Hz, 1H), 6.45 (dd, J=17.7, 1.2 Hz, 1H), 6.91 (dd, J=17.6, 11.3 Hz, 1H), 7.48-7.52 (m, 3H), 7.93 (d, J=8.8 Hz, 2H), 8.03 (d, J=1.8 Hz, 1H), and 8.87 (s, 1H). 19F NMR (376 MHz, DMSO-d$_6$): −57.1 (s, 3F).

2-Amino-3-(6-chloro-4-vinyl-2H-benzotriazol-2-yl)-2-methylpropionitrile [2.3 g, 97%, Rf=0.3 (1:1 EA/heptane)] was prepared using a procedure similar to that described in Example 1, part b, except starting from 1-(6-chloro-4-vinyl-2H-benzotriazol-2-yl)-propan-2-one. 1-(6-Chloro-4-vinyl-2H-benzotriazol-2-yl)-propan-2-one (4 g, 85%) was prepared as follows:

a. 1-(4-Bromo-6-chloro-2H-benzotriazol-2-yl)-propan-2-one (3 g), tributylvinyltin (3.5 g) and bis(tri-t-butylphosphine)palladium (0.5 g) were heated in toluene (20 mL) at 50° C. overnight. The mixture was concentrated under reduced pressure, taken up in ethyl acetate and filtered through a plug of Celite®. Filtrate was concentrated under reduced pressure to give a residue that was purified by chromatography (SiO$_2$, heptane/EA) to afford 1-(6-chloro-4-vinyl-2H-benzotriazol-2-yl)-propan-2-one as a white solid (2.2 g, 90%). Rf=0.5 (1:1 EA/heptane). 1-(4-Bromo-6-chloro-2H-benzotriazol-2-yl)-propan-2-one was prepared using a procedure similar to that described in Example 1, part a, except starting from 7-bromo-5-chloro-1H-benzotriazole described in Example 38, part a and b.

Example 69

N-[2-(6-Chloro-4-vinyl-2H-benzotriazol-2-yl)-1-cyano-1-methylethyl]-4-trifluoromethylthiobenzamide (compound No 1.076)

Using a procedure similar to that described in Example 1, except using 2-amino-3-(6-chloro-4-vinyl-2H-benzotriazol-2-yl)-2-methylpropionitrile (50 mg) described in Example 59 above and 4-trifluoromethylthiobenzoyl chloride (0.05 mL), the title compound was isolated as a white solid (65 mg, 73%). Rf=0.5 (1:1 EA/heptane). MS (ES): M/Z [M+H]=466. NMR: (400 MHz, DMSO-d$_6$): 1.75 (s, 3H), 5.41 (d, J=13.4 Hz, 1H), 5.50 (d, J=11.5 Hz, 1H), 5.57 (d, J=13.4 Hz, 1H), 6.45 (d, J=17.6 Hz, 1H), 6.91 (dd, J=17.6, 11.3 Hz, 1H), 7.51 (s, 1H), 7.84 (d, J=8.2 Hz, 2H), 7.91 (d, J=8.3 Hz, 2H), 8.03 (s, 1H) and 8.96 (s, 1H). 19F NMR (376 MHz, DMSO-d$_6$): −42.0 (s, 3F).

Compounds of Examples 70 to 76 were prepared according to the following general reaction scheme:

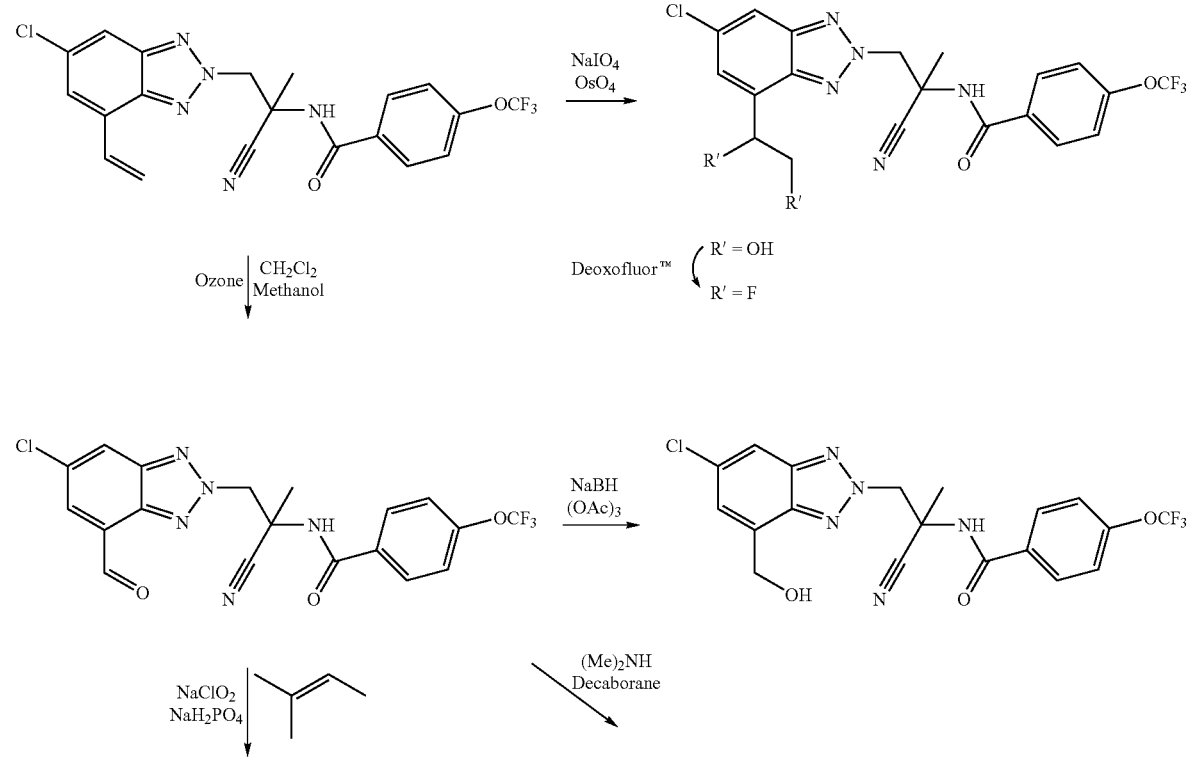

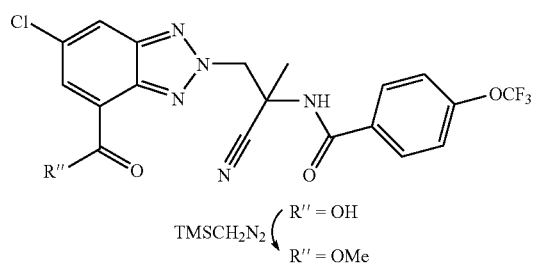 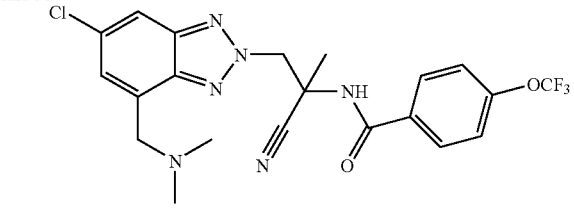

Final Product
V=C—H; W=C—Cl; X=C—H; Y=C—R$_{11}$;
R$_{11}$=CO$_2$H, CO$_2$Me, CH$_2$N(CH$_3$)$_2$, CH$_2$OH, CH(OH) CH$_2$OH, CHFCH$_2$F
Q=P=N;
R$_3$=R$_4$=H; a=1; R$_5$=CH$_3$, R$_6$=H;
Z=C(O); R$_7$=p-phenyl-OCF$_3$

Example 70

N-{2-[6-Chloro-4-(1,2-dihydroxyethyl)-2H-benzotriazol-2-yl]-1-cyano-1-methyl-ethyl}-4-trifluoromethoxybenzamide (compound No 1.077)

To a solution of N-[2-(6-Chloro-4-vinyl-2H-benzotriazol-2-yl)-1-cyano-1-methylethyl]-4-trifluoromethoxybenzamide (0.25 g) in 5 mL of a mixture of THF and water (10 to 1), was added sodium periodate (0.24 g, 2.1 equivalent) and a 4% osmium tetroxide solution in water (17 mL, 5 mole %). After 2 hours at room temperature, the mixture was quenched with a 10% solution of sodium thiosulfate, extracted with ethylacetate and washed with water. The organic layer was dried over sodium sulfate, filtered and concentrated under reduced pressure to give a residue that was purified by chromatography (SiO$_2$, heptane/EA) to afford the title compound as a white solid mixture of diastereoisomers (110 mg, 40%). Rf=0.35 (1:1 EA/heptane). MS (ES): M/Z [M+H]=484. 1H NMR: (400 MHz, DMSO-d$_6$): 1.74-1.75 (d, 3H), 3.40-3.56 (m, 1H), 3.67-3.82 (m, 1H), 4.78 (dt, J=17.3, 6.0 Hz, 1H), 5.01-5.12 (m, 1H), 5.35-5.43 (m, 1H), 5.43-5.51 (m, 1H), 5.61 (d, J=4.8 Hz, 1H), 7.42 (s, 1H), 7.51 (d, J=7.9 Hz, 2H), 7.93 (dd, J=8.7, 3.8 Hz, 2H), 7.98 (t, J=2.1 Hz, 1H) and 8.92 (d, 1H). 19F NMR (376 MHz, DMSO-d$_6$): −57.1 (s, 3F).

Example 71

N-{2-[6-Chloro-4-(1,2-difluoroethyl)-2H-benzotriazol-2-yl]-1-cyano-1-methyl-ethyl}-4-trifluoromethoxybenzamide (compound No 1.078)

To a solution of N-{2-[6-Chloro-4-(1,2-dihydroxyethyl)-2H-benzotriazol-2-yl]-1-cyano-1-methyl-ethyl}-4-trifluoromethoxybenzamide (50 mg) in DCM (3 mL), was added Deoxofluor™ [Bis(2-methoxyethyl)aminosulfur Trifluoride] (0.07 mL). After stirring overnight at room temperature, the mixture was concentrated under reduced pressure to give a residue that was purified by chromatography (SiO$_2$, heptane/EA) to afford the title compound as a white solid mixture of diastereoisomers (35 mg, 69%). Rf=0.7 (1:1 EA/heptane). MS (ES): M/Z [M+H]=488. 1H NMR: (400 MHz, CHLOROFORM-d): 1.88-1.89 (d, 3H), 4.71-5.00 (m, 2H), 5.19 (dd, J=13.7, 4.5 Hz, 1H), 5.47 (t, J=13.9 Hz, 1H), 5.99-6.25 (m, 1H), 7.20 (d, J=18.7 Hz, 1H), 7.33 (d, J=8.1 Hz, 2H), 7.53 (s, 1H), 7.86 (d, J=8.7 Hz, 2H) and 7.90 (s, 1H). 19F NMR (376 MHz, CHLOROFORM-d): −192.2 (s, 1F), −58.1 (s, 3F) and 3.1 (br. s., 1F).

Example 72

N-[2-(6-Chloro-4-formyl-2H-benzotriazol-2-yl)-1-cyano-1-methylethyl]-4-trifluoromethoxybenzamide (compound No 1.079)

A solution of N-[2-(6-Chloro-4-vinyl-2H-benzotriazol-2-yl)-1-cyano-1-methylethyl]-4-trifluoromethoxybenzamide (0.29 g) in 35 mL of a 3 to 1 mixture of DCM and methanol was treated with ozone gas for 15 minutes. After stirring one hour at −78° C., the mixture was purged 10 minutes with oxygen and then quenched with dimethyl sulfide followed by a 10% solution of sodium thiosulfate, then diluted with DCM (100 mL). The mixture was separated, and the organic layer was dried over sodium sulfate, filtered and concentrated under reduced pressure to give a residue that was purified by chromatography (SiO$_2$, heptane/EA) to afford the title compound as a white solid (0.23 g, 79%). Rf=0.6 (1:1 EA/heptane). MS (ES): M/Z [M+H]=452. 1H NMR: (400 MHz, CHLOROFORM-d): 1.58 (s, 3H), 5.24 (d, J=13.8 Hz, 1H), 5.47 (d, J=13.8 Hz, 1H), 7.37 (d, J=8.1 Hz, 2H), 7.94 (br. s, 1H), 8.00 (d, J=1.8 Hz, 1H), 8.05 (m, 2H), 8.22 (d, J=1.9 Hz, 1H) and 10.34 (s, 1H). 19F NMR (376 MHz, CHLOROFORM-d): −58.1 (s, 3F).

Example 73

N-[2-(6-Chloro-4-dimethylaminomethyl-2H-benzotriazol-2-yl)-1-cyano-1-methylethyl]-4-trifluoromethoxybenzamide (compound No 1.080)

To a solution of N-[2-(6-Chloro-4-formyl-2H-benzotriazol-2-yl)-1-cyano-1-methylethyl]-4-trifluoromethoxybenzamide (0.18 g) in methanol (3 mL) was added a 2 molar methanolic solution of dimethylamine (0.24 mL). After one hour stirring at room temperature, decaborane was added (15 mg) and the mixture stirred one more hour before being concentrated under reduced pressure. The residue was purified by chromatography (SiO$_2$, heptane/EA) to afford the title compound as a white solid (100 mg, 52%). Rf=0.2 (3:1 EA/heptane). MS (ES): M/Z [M+H]=481. 1H NMR: (400 MHz, CHLOROFORM-d): 1.81 (s, 3H), 2.31 (s, 6H), 3.75 (d, J=13.5 Hz, 1H), 3.92 (d, J=13.5 Hz, 1H), 5.12 (d, J=13.8 Hz, 1H), 5.52 (d, J=13.7 Hz, 1H), 7.32 (d, J=8.1 Hz, 2H), 7.36 (s, 1H), 7.81 (d, J=1.7 Hz, 1H) and 7.95 (br. d, J=8.7 Hz, 3H). 19F NMR (376 MHz, CHLOROFORM-d): −58.1 (s, 3F).

Example 74

N-[2-(6-Chloro-4-hydroxymethyl-2H-benzotriazol-2-yl)-1-cyano-1-methylethyl]-4-trifluoromethoxybenzamide (compound No 1.081)

To a solution of N-[2-(6-Chloro-4-formyl-2H-benzotriazol-2-yl)-1-cyano-1-methylethyl]-4-trifluoromethoxybenzamide (150 mg) in ethanol (2 mL) cooled in an ice bath was added sodium triacetoxyborohydride (0.22 g). After 6 hour at room temperature, more sodium triacetoxyborohydride (0.29 g) was added and the mixture stirred overnight at room temperature. The mixture was quenched with water, extracted with ethyl acetate. The organic layer was dried over sodium sulfate, filtered and concentrated under reduced pressure to give a residue that was purified by chromatography ($SiO_2$, heptane/EA) to afford the title compound as a white solid (100 mg, 67%). Rf=0.4 (3:1 EA/heptane). MS (ES): M/Z [M+H]=454. 1H NMR: (400 MHz, CHLOROFORM-d): 1.87 (s, 3H), 5.06 (s, 2H), 5.15 (d, J=13.8 Hz, 1H), 5.43 (d, J=13.8 Hz, 1H), 7.33 (d, J=8.8 Hz, 2H), 7.43 (dt, J=1.8, 1.0 Hz, 1H), 7.47 (s, 1H), 7.80 (d, J=1.8 Hz, 1H) and 7.88 (d, J=8.8 Hz, 2H). 19F NMR (376 MHz, CHLOROFORM-d): −58.1 (s, 3F).

Example 75

6-Chloro-2-[2-cyano-2-({[4-(trifluoromethoxy)phenyl]carbonyl}amino)-propyl]-2H-benzotriazole-4-carboxylic acid (compound No 1.082)

To a solution of N-[2-(6-Chloro-4-formyl-2H-benzotriazol-2-yl)-1-cyano-1-methylethyl]-4-trifluoromethoxybenzamide (1.5 g) in a mixture of THF (25 mL), t-butanol (10 mL) and 2-methyl-2-butene was added dropwise the solution of sodium hypochlorite (0.9 g) and sodium dihydrogen phosphate (1.15 g) in water (20 mL). After 4 hour at room temperature, the mixture was concentrated under reduced pressure, diluted with water (50 mL) and acidified to pH 2 with normal HCl. The white solid was filtered and washed with water and dried under vacuum to give the title compound (1.35 g, 87%). MS (ES): M/Z [M+H]=468. 1H NMR: (400 MHz, DMSO-$d_6$): 1.72 (s, 3H), 5.48-5.64 (m, 2H), 7.43 (d, J=8.2 Hz, 2H), 7.83 (d, J=2.0 Hz, 1H), 7.99 (d, J=8.8 Hz, 2H), 8.23 (d, J=1.8 Hz, 0H) and 9.41 (br. s., 1H). 19F NMR (376 MHz, DMSO-$d_6$): −57.1 (s, 3F).

Example 76

Methyl 6-chloro-2-[2-cyano-2-({[4-(trifluoromethoxy)phenyl]carbonyl}-amino)propyl]-2H-benzotriazole-4-carboxylate (compound No 1.084)

A 2 molar ether solution of trimethylsilyldiazomethane was added to 6-chloro-2-[2-cyano-2-({[4-(trifluoromethoxy)phenyl]carbonyl}amino)-propyl]-2H-benzotriazole-4-carboxylic acid (100 mg) dissolved in a ten to 1 one mixture of THF and methanol (2 mL). After overnight at room temperature, the mixture was concentrated under reduced pressure to give a residue that was purified by chromatography ($SiO_2$, heptane/EA) to afford the title compound as a white solid (42 mg, 40%). MS (ES): M/Z [M+H]=482. 1H NMR: (400 MHz, DMSO-$d_6$): 1.75 (s, 3H), 3.78 (s, 3H), 5.44 (d, J=13.3 Hz, 1H), 5.58 (d, J=13.3 Hz, 1H), 7.50 (d, J=8.1 Hz, 2H), 7.92 (d, J=8.8 Hz, 2H), 8.02 (d, J=1.9 Hz, 1H), 8.52 (d, J=1.9 Hz, 1H) and 8.87 (s, 1H). 19F NMR (376 MHz, DMSO-$d_6$): −57.1 (s, 3F).

The preparation of 6-chloro-2-[2-cyano-2-({[4-(trifluoromethoxy)phenyl]carbonyl}amino)-propyl]-2H-benzotriazole-4-carboxylic acid is described in Example 75 above.

Compound of Example 77 was prepared according to the following reaction scheme:

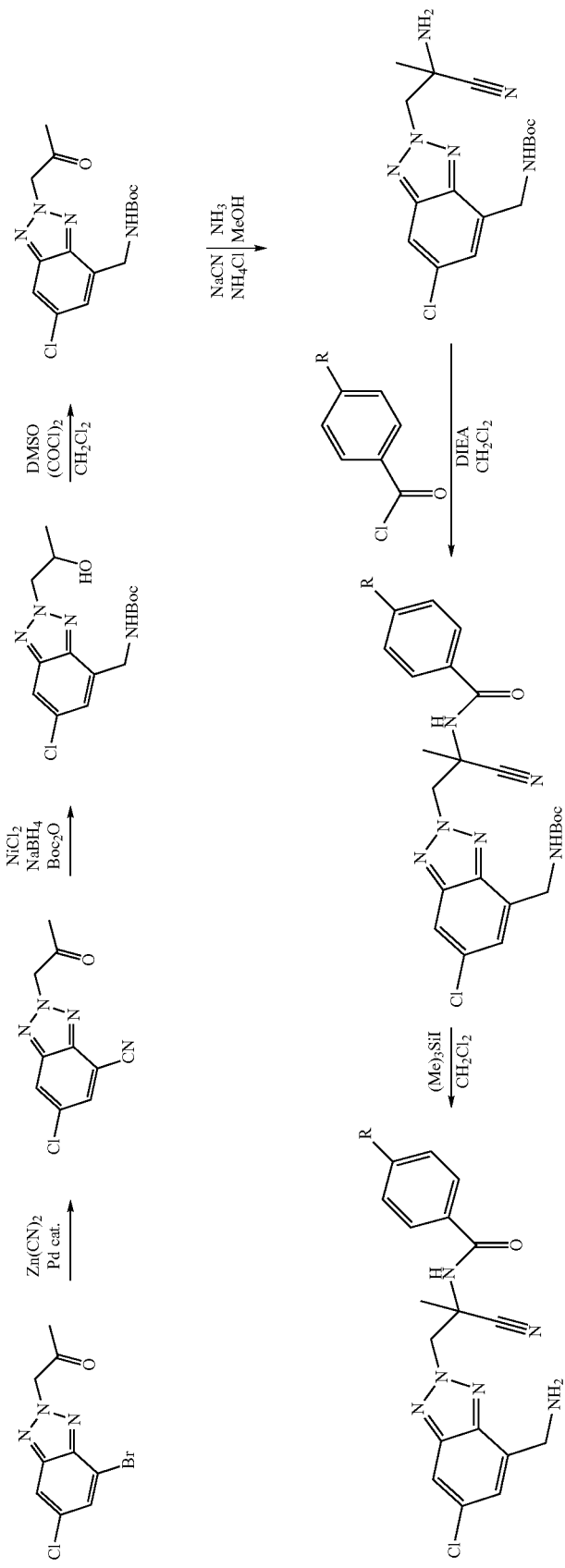

Final Product
V=C—H; W=C—Cl; X=C—H; Y=C—CH$_2$NH$_2$;
Q=P=N;
R$_3$=R$_4$=H; a=1; R$_5$=CH$_3$, R$_6$=H;
Z=C(O); R$_7$=p-phenyl-R It will be apparent to one of skill in the art that modified derivatives with variable substitution on the phenyl ring may also be made by starting the corresponding substituted benzoic acid chloride.

Example 77

N-[2-(4-Aminomethyl-6-chloro-2H-benzotriazol-2-yl)-1-cyano-1-methylethyl]-4-trifluoromethoxybenzamide (compound No 1.074)

To a solution of {6-chloro-2-[2-cyano-2-methyl-2-(4-trifluoromethoxy-benzoylamino)-ethyl]-2H-benzotriazol-4-ylmethyl}-carbamic acid tert-butyl ester (100 mg) in DCM (2 mL) was added trimethylsilyl iodide (0.05 mL). After 20 minutes, the mixture was quenched with methanol and concentrated under reduced pressure. The residue was taken up in ethyl acetate, washed with a saturated solution of sodium bicarbonate, dried over sodium sulfate, filtered and concentrated under reduced pressure to give the title compound as a white solid (70 mg, 87%). Rf=0.2 (1:1 EA/heptane). MS (ES): M/Z [M+H]=453. 1H NMR: (500 MHz, CHLOROFORM-d): 1.86 (s, 3H), 4.21 (d, J=3.4 Hz, 2H), 5.16 (d, J=13.7 Hz, 1H), 5.43 (d, J=13.8 Hz, 1H), 7.30 (d, J=8.4 Hz, 2H), 7.33 (d, J=0.7 Hz, 1H), 7.60 (s, 1H), 7.75 (d, J=1.5 Hz, 1H) and 7.88 (d, J=8.7 Hz, 2H). 19F NMR (376 MHz, DMSO-d$_6$): −57.1 (s, 3F).

The starting material {6-chloro-2-[2-cyano-2-methyl-2-(4-trifluoromethoxy-benzoylamino)-ethyl]-2H-benzotriazol-4-ylmethyl}-carbamic acid tert-butyl ester [0.25 g, 60%, MS (ES): M/Z [M+H]=553] was prepared using a procedure similar to that described in Example 1 except starting from [2-(2-amino-2-cyano-2-methylethyl)-6-chloro-2H-benzotriazol-4-ylmethyl]-carbamic acid tert-butyl ester (0.28 g) that was prepared using a procedure similar to that described in Example 1, part b, except starting from [6-chloro-2-(2-oxopropyl)-2H-benzotriazol-4-ylmethyl]-carbamic acid tert-butyl ester (0.4 g) that was prepared as follows:

a. 1-(4-Bromo-6-chloro-2H-benzotriazol-2-yl)-propan-2-one (3.5 g), zinc cyanide (2.8 g), zinc powder (0.4 g) and bis(tri-t-butylphosphine)palladium (0.62 g) were heated in degassed dimethylacetamide (60 mL) at 60° C. After stirring two hours, the mixture was diluted with water. A solid residue formed and was filtered, washed with water and taken up in ethyl acetate. Organic layer was filtered and concentrated under reduced pressure to give a residue that was purified by chromatography (SiO$_2$, heptane/EA) to afford 6-chloro-2-(2-oxopropyl)-2H-benzotriazole-4-carbonitrile as a white solid (2 g, 70%). Rf=0.55 (1:1 EA/heptane). 1-(4-Bromo-6-chloro-2H-benzotriazol-2-yl)-propan-2-one was prepared using a procedure similar to that described in Example 1, part a, except starting from 7-bromo-5-chloro-1H-benzotriazole described in Example 38, part a and b.

b. To a solution of 6-chloro-2-(2-oxopropyl)-2H-benzotriazole-4-carbonitrile in methanol (160 mL) at 0° C. was added di-tert-butyl dicarbonate (7.6 g) and nickel chloride hexahydrate (0.4 g) followed by slow addition over 1.5 hours of sodium borohydride (5.2). After stirring one additional hour, the mixture was treated with diethylenetriamine (1.8 mL), concentrated under reduced pressure, taken up in ethyl acetate and washed with a saturated solution of sodium bicarbonate. The organic layer was dried over sodium sulfate, filtered and concentrated under reduced pressure to give a brown residue (5.6 g) that contained [6-chloro-2-(2-hydroxypropyl)-2H-benzotriazol-4-ylmethyl]-carbamic acid tert-butyl ester and the des-halogeno analog [2-(2-hydroxypropyl)-2H-benzotriazol-4-ylmethyl]-carbamic acid tert-butyl ester. This residue was taken directly to the next step without further purification.

c. To a solution of oxalyl chloride (0.8 mL) in DCM (20 mL) was added dropwise at −78° C. under nitrogen a solution of DMSO (1.2 mL) in DCM (10 mL). After stirring 10 minutes, a solution of the crude residue containing [6-chloro-2-(2-hydroxypropyl)-2H-benzotriazol-4-ylmethyl]-carbamic acid tert-butyl ester (1.45 g) in DCM (5 mL) was added dropwise under nitrogen. After stirring 30 minutes, TEA (5 mL) was added under nitrogen and the mixture allowed warming to room temperature. The mixture was concentrated under reduced pressure to give a residue that was purified by chromatography (SiO$_2$, heptane/EA) to afford [6-chloro-2-(2-oxopropyl)-2H-benzotriazol-4-ylmethyl]-carbamic acid tert-butyl ester as a yellow solid (0.4 g, 30%). Rf=0.45 (1:1 EA/heptane). 1H NMR: (400 MHz, CHLOROFORM-d): 1.47 (s, 9H), 2.19 (s, 3H), 4.71 (d, J=5.3 Hz, 2H), 5.21 (br. s., 1H), 5.50 (s, 2H), 7.30 (d, J=0.8 Hz, 1H) and 7.78 (d, J=1.3 Hz, 1H).

Compounds of Examples 78 to 83 were prepared according to the following general reaction scheme:

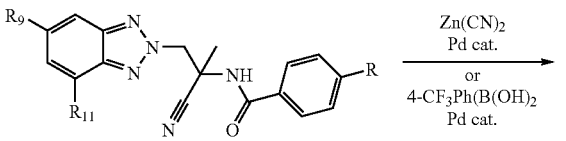

R$_{11}$ = CF$_3$, R$_9$ = Cl, R = OCF$_3$ or SCF$_3$
R$_{11}$ = Cl, R$_9$ = CF$_3$, R = OCF$_3$ or SCF$_3$
R$_{11}$ = Br, R$_9$ = Cl, R = OCF$_3$ or SCF$_3$
R$_{11}$ = Br, R$_9$ = Cl, R = OCF$_3$ or SCF$_3$

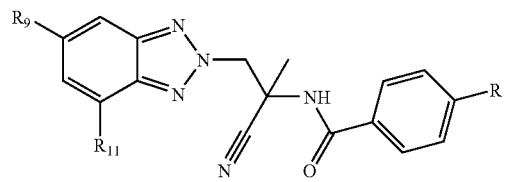

R$_{11}$ = CF$_3$, R$_9$ = CN, R = OCF$_3$ or SCF$_3$
R$_{11}$ = CN, R$_9$ = CF$_3$, R = OCF$_3$ or SCF$_3$
R$_{11}$ = CN, R$_9$ = Cl, R = OCF$_3$
R$_{11}$ = 4-CF$_3$Ph, R$_9$ = Cl, R = OCF$_3$

Final Product
V=C—H; W=C—R$_9$; X=C—H; Y=C—R$_{11}$;
Q=P=N;
R$_3$=R$_4$=H; a=1; R$_5$=CH$_3$, R$_6$=H;
Z=C(O); R$_7$=p-phenyl-R It will be apparent to one of skill in the art that modified derivatives with variable substitution on the phenyl ring may also be made by starting the corresponding substituted benzoic acid chloride.

Example 78

N-[1-Cyano-2-(4-cyano-6-trifluoromethyl-2H-benzotriazol-2-yl)-1-methylethyl]-4-trifluoromethoxybenzamide (compound No 1.054)

N-[2-(4-Chloro-6-trifluoromethyl-2H-benzotriazol-2-yl)-1-cyano-1-methylethyl]-4-trifluoromethoxybenzamide (100 mg, described in Example 19), zinc cyanide (50 mg), zinc powder (10 mg), 2-di-t-butylphosphino-1,1'-binaphthyl (40 mg) and palladium trifluoroacetate (34 mg) were heated under nitrogen in degassed dimethylacetamide (1 mL) at 100° C. overnight. The mixture was concentrated under reduced pressure to give a residue that was purified by chromatography (SiO$_2$, heptane/EA) to afford the title compound as a white solid (62 mg, 63%). Rf=0.6 (1:1 EA/heptane). MS (ES): M/Z [M+H]=483. NMR: (400 MHz, DMSO-d$_6$): 1.77 (s, 3H), 5.56 (d, J=13.3 Hz, 1H), 5.66 (d, J=13.3 Hz, 1H), 7.49 (d, J=8.2 Hz, 2H), 7.92 (d, J=8.6 Hz, 2H), 8.59 (s, 1H), 8.90 (s, 1H) and 9.02 (s, 1H). 19F NMR (376 MHz, DMSO-d$_6$): −61.0 (s, 3F) and −57.1 (s, 3F).

Example 79

N-[1-Cyano-2-(4-cyano-6-trifluoromethyl-2H-benzotriazol-2-yl)-1-methylethyl]-4-trifluoromethylthiobenzamide (compound No 1.055)

Using a procedure similar to that described in Example 78, except using N-[2-(4-chloro-6-trifluoromethyl-2H-benzotriazol-2-yl)-1-cyano-1-methylethyl]-4-trifluoromethylthiobenzamide (100 mg, described in Example 20), the title compound was isolated as a white solid (52 mg, 53%). Rf=0.5 (1:1 EA/heptane). MS (ES): M/Z [M+H]=499. NMR: (400 MHz, DMSO-d$_6$): 1.77 (s, 3H), 5.57 (d, J=13.2 Hz, 1H), 5.67 (d, J=13.3 Hz, 1H), 7.84 (d, J=8.3 Hz, 2H), 7.90 (d, J=8.4 Hz, 2H), 8.60 (d, J=1.1 Hz, 1H), 8.99 (s, 1H) and 9.01 (s, 1H). 19F NMR (376 MHz, DMSO-d$_6$): −42.0 (s, 3F) and −61.0 (s, 3F).

Example 80

N-[1-Cyano-2-(6-cyano-4-trifluoromethyl-2H-benzotriazol-2-yl)-1-methylethyl]-4-trifluoromethoxybenzamide (compound No 1.056)

Using a procedure similar to that described in Example 78, except using N-[2-(6-chloro-4-trifluoromethyl-2H-benzotriazol-2-yl)-1-cyano-1-methylethyl]-4-trifluoromethoxybenzamide (100 mg, described in Example 32), the title compound was isolated as a white solid (44 mg, 45%). Rf=0.55 (1:1 EA/heptane). MS (ES): M/Z [M+H]=483. NMR: (400 MHz, DMSO-d$_6$): 1.78 (s, 3H), 5.53 (d, J=13.2 Hz, 1H), 5.68 (d, J=13.3 Hz, 1H), 7.48 (d, J=8.1 Hz, 2H), 7.89 (d, J=8.8 Hz, 2H), 8.32 (s, 1H), 8.85 (s, 1H) and 9.18 (s, 1H). 19F NMR (376 MHz, DMSO-d$_6$): −61.7 (s, 3F) and −57.2 (s, 3F).

Example 81

N-[1-Cyano-2-(6-cyano-4-trifluoromethyl-2H-benzotriazol-2-yl)-1-methylethyl]-4-trifluoromethylthiobenzamide (compound No 1.066)

Using a procedure similar to that described in Example 78, except using N-[2-(6-chloro-4-trifluoromethyl-2H-benzotriazol-2-yl)-1-cyano-1-methylethyl]-4-trifluoromethylthiobenzamide (590 mg, described in Example 33), the title compound was isolated as a white solid (320 mg, 55%). Rf=0.5 (1:1 EA/heptane). MS (ES): M/Z [M+H]=499. NMR: (400 MHz, DMSO-d$_6$): 1.78 (s, 3H), 5.53 (d, J=13.2 Hz, 1H), 5.69 (d, J=13.3 Hz, 1H), 7.79-7.91 (m, 4H), 8.31 (s, 1H), 8.94 (s, 1H) and 9.18 (s, 1H). 19F NMR (376 MHz, DMSO-d$_6$): −42.1 (s, 3F) and −61.7 (s, 3F).

Example 82

N-[2-(6-Chloro-4-cyano-2H-benzotriazol-2-yl)-1-cyano-1-methylethyl]-4-trifluoromethoxybenzamide (compound No 1.067)

Using a procedure similar to that described in Example 78, except using N-[2-(4-bromo-6-chloro-2H-benzotriazol-2-yl)-1-cyano-1-methylethyl]-4-trifluoromethoxybenzamide (100 mg) described in Example 38 and bis(tri-t-butylphosphine)palladium (20 mg) as palladium catalyst with no additional phosphine ligand and heating the reaction mixture at 60° C. for one hour; the title compound was isolated as a white solid (70 mg, 79%). Rf=0.6 (1:1 EA/heptane). MS (ES): M/Z [M+H]=449. NMR: (400 MHz, DICHLOROMETHANE-d$_2$): 1.87 (s, 3H), 5.28 (d, J=13.7 Hz, 1H), 5.52 (d, J=13.7 Hz, 1H), 7.29-7.43 (m, 3H), 7.85 (d, J=1.8 Hz, 1H), 7.87-7.95 (m, 2H) and 8.20 (d, J=1.7 Hz, 1H). 19F NMR (376 MHz, DICHLOROMETHANE-d$_2$): −58.5 (s, 3F).

Example 83

N-{2-[6-Chloro-4-(4-trifluoromethylphenyl)-2H-benzotriazol-2-yl]-1-cyano-1-methylethyl}-4-trifluoromethoxybenzamide (compound No 1.068)

N-[2-(4-Bromo-6-chloro-2H-benzotriazol-2-yl)-1-cyano-1-methylethyl]-4-trifluoromethoxybenzamide (120 mg) described in Example 38, bis(tri-t-butylphosphine)palladium (20 mg), bis(dibenzylideneacetone)palladium (20 mg), potassium fluoride (42 mg) and 4-trifluoromethylphenyl boronic acid (45 mg) in THF were stirred at room temperature for 3 days. The mixture was concentrated under reduced pressure to give a residue that was purified by chromatography (SiO$_2$, heptane/EA) to afford a one to one mixture of title compound and starting material [110 mg, Rf=0.3 (3:7 EA/heptane)]. This mixture was further purified by semi-preparative liquid chromatography (methanol/water) to afford the title compound as pure solid (35 mg, 26%). MS (ES): M/Z [M+H]=568. NMR: (400 MHz, DMSO-d$_6$): 1.74 (s, 3H), 1.84 (s, 1H), 5.39 (d, J=13.3 Hz, 1H), 5.64 (d, J=13.3 Hz, 1H), 7.41 (d, J=8.0 Hz, 2H), 7.60 (d, J=8.3 Hz, 2H), 7.84 (d, J=1.8 Hz, 1H), 7.93 (d, J=8.9 Hz, 2H), 8.12 (d, J=8.1 Hz, 2H) and 8.23 (d, J=1.8 Hz, 1H). 19F NMR (376 MHz, DMSO-d$_6$): −61.8 (s, 3F) and −57.3 (s, 3F).

Compounds of Examples 84 to 95 were prepared according to the following general reaction scheme:
52
Final Product
W=C—R$_9$; X=C—R$_{10}$; Y=C—R$_{11}$;
P=N;
R$_3$=R$_4$=H; a=1; R$_5$=CH$_3$; R$_6$=H;
Z=C(O); R$_7$=p-phenyl-R; R=S(O)$_n$CF$_3$; n=0, 1, or 2

Example 84

N-[1-Cyano-2-(5-cyano-2H-benzotriazol-2-yl)-1-methylethyl]-4-trifluoromethylsulfinylbenzamide (compound No 1.022)

3-Chloroperbenzoic acid (77% pure, 0.13 g) was added at 0° C. to a DCM solution of N-[1-cyano-2-(5-cyano-2H-benzotriazol-2-yl)-1-methylethyl]-4-trifluoromethylthiobenzamide (0.11 g, described in Example 22). The reaction mixture was stirred 72 hours at room temperature. The reaction mixture was diluted with DCM then washed with saturated aqueous sodium bicarbonate solution. The organic phase was dried over anhydrous sodium sulfate, filtered and concentrated under reduced pressure to give a residue that was purified by chromatography (SiO$_2$, heptane/EA) to afford the title compound as a white solid (60 mg, 53%). MS (ES): M/Z [M+H]=447. 1H NMR: (400 MHz, DMSO-d$_6$): 1.77 (s, 3H), 5.44-5.65 (m, 2H), 7.76 (d, J=8.8 Hz, 1H), 8.02-8.07 (m, 4H), 7.94 (d, J=8.9 Hz, 1H), 8.78 (s, 1H) and 9.10 (s, 1H). 19F NMR (376 MHz, DMSO-d$_6$): −74.20 (s, 3F).

Example 85

N-[2-(4-Chloro-6-trifluoromethyl-2H-benzotriazol-2-yl)-1-cyano-1-methylethyl]-4-trifluoromethylsulfinylbenzamide (compound No 1.023)

Using a procedure similar to that described in Example 84, except using N-[1-cyano-1-methyl-2-(4-chloro-6-trifluoromethylbenzotriazol-2-yl)-ethyl]-4-trifluoromethylthiobenzamide described in Example 20, the title compound was isolated as a white solid (60 mg, 53%). MS (ES): M/Z [M+H]=524. 1H NMR: (400 MHz, DMSO-d$_6$): 1.78 (s, 3H), 5.46-5.56 (m, 2H), 7.94 (d, 1H, J=0.7 Hz), 8.01-8.07 (m, 4H), 8.56 (d, J=0.8 Hz, 1H) and 9.02 (s, 1H). 19F NMR (376 MHz, DMSO-d$_6$): −74.27 (s, 3F) and −61.08 (s, 3F).

Example 86

N-[1-Cyano-2-(4,6-dichloro-2H-benzotriazol-2-yl)-1-methylethyl]-4-trifluoromethylsulfinylbenzamide (compound No 1.024)

3-Chloroperbenzoic acid (77% pure, 0.57 g) was added at 0° C. to a DCM solution of N-[1-cyano-2-(4,6-dichloro-2H-benzotriazol-2-yl)-1-methylethyl]-4-trifluoromethylthiobenzamide (0.3 g, described in Example 16). The reaction mixture was stirred over night at room temperature. The reaction mixture was diluted with DCM, washed with saturated aqueous sodium bicarbonate solution. The organic phase was dried over anhydrous sodium sulfate, filtered and concentrated under reduced pressure to give a residue that was purified by chromatography (SiO$_2$, heptane/EA) to afford the title compound as a white solid (100 mg, 32%). Rf=0.6 (1:1 EA/heptane). MS (ES): M/Z [M+H]=490. NMR: (400 MHz, DMSO-d$_6$): 1.76 (s, 3H), 5.39-5.60 (m, 2H), 7.74 (d, J=1.6 Hz, 1H), 7.99-8.08 (m, 4H), 8.18 (dd, J=1.5, 0.9 Hz, 1H), and 9.04 (s, 1H). 19F NMR (376 MHz, DMSO-d$_6$): −74.24 (s, 3F).

Example 87

N-[1-Cyano-2-(4,6-dichloro-2H-benzotriazol-2-yl)-1-methylethyl]-4-trifluoromethylsulfonylbenzamide (compound No 1.025)

The crude residue described in Experimental 86 that was purified by chromatography (SiO$_2$, heptane/EA) also provided the sulfone title compound as a white solid (100 mg, 31%). Rf=0.65 (1:1 EA/heptane). MS (ES): M/Z [M+H]=506. NMR: (400 MHz, DMSO-d$_6$): 1.76 (s, 3H), 5.51 (dd, J=60.1, 13.4 Hz, 1H), 7.73 (d, J=1.6 Hz, 1H), 8.12-8.17 (m, 2H), 8.19 (d, J=1.6 Hz, 1H), 8.31 (d, J=8.4 Hz, 2H) and 9.19 (s, 1H). 19F NMR (376 MHz, DMSO-d$_6$): −78.70 (s, 3F).

Example 88

N-[1-Cyano-1-methyl-2-(5-trifluoromethyl-2H-benzotriazol-2-yl)ethyl]-4-trifluoromethylsulfonylbenzamide (compound No 1.026)

3-Chloroperbenzoic acid (60 mg) was added at 0° C. to a DCM solution of N-[1-cyano-1-methyl-2-(5-trifluoromethyl-2H-benzotriazol-2-yl)ethyl]-4-trifluoromethylthiobenzamide (50 mg, described in Example 11). The reaction mixture was stirred 48 hours at room temperature then more 3-chloroperbenzoic acid (60 mg) was added and the reaction mixture was stirred 48 additional hours at room temperature. The reaction mixture was diluted with DCM, washed with saturated aqueous sodium bicarbonate solution. The organic phase was dried over anhydrous sodium sulfate, filtered and concentrated under reduced pressure to give a residue that was purified by chromatography (SiO$_2$, heptane/EA) to afford the title compound as a white solid (42 mg, 79%). Rf=0.5 (1:1 EA/heptane). MS (ES): M/Z [M+H]=506. 1H NMR: (400 MHz, CHLOROFORM-d): 1.90 (s, 3H), 5.40 (dd, J=120.3, 13.8 Hz, 2H), 7.38 (br s, 1H), 7.66 (dd, J=9.1, 1.5 Hz, 1H), 8.07-8.14 (m, 2H), 8.16-8.23 (m, 2H) and 8.26 (br s, 1H). 19F NMR (376 MHz, CHLOROFORM-d): −78.33 (s, 3F) and −63.04 (s, 3F).

Example 89

N-[1-Cyano-1-methyl-2-(5-cyano-2H-benzotriazol-2-yl)-ethyl]-4-trifluoromethylsulfonylbenzamide (compound No 1.027)

Using a procedure similar to that described in Example 88, except using N-[1-cyano-2-(5-cyano-2H-benzotriazol-2-yl)-1-methylethyl]-4-trifluoromethylthiobenzamide (50 mg, described in Example 22), the title compound was isolated as a white solid (35 mg, 65%). Rf=0.4 (1:1 EA/heptane). MS (ES): M/Z [M+H]=463. 1H NMR: (400 MHz, DMSO-d$_6$): 1.76 (s, 3H), 5.44-5.65 (m, 2H), 7.77 (d, J=8.8 Hz, 1H), 8.15 (d, J=8.6 Hz, 2H), 8.19 (d, J=8.8 Hz, 1H), 8.32 (d, J=8.4 Hz, 2H), 8.79 (s, 1H) and 9.26 (s, 1H). 19F NMR (376 MHz, DMSO-d$_6$): −78.67 (s, 3F).

Example 90

N-[2-(4-Chloro-6-trifluoromethyl-2H-benzotriazol-2-yl)-1-cyano-1-methylethyl]-4-trifluoromethylsulfonylbenzamide (compound No 1.028)

Using a procedure similar to that described in Example 86, except using N-[2-(4-chloro-6-trifluoromethyl-2H-benzotriazol-2-yl)-1-cyano-1-methylethyl]-4-trifluoromethylthiobenzamide (50 mg, described in Example 20) and a 6 fold excess of 3-chloroperbenzoic acid (77% pure, 130 mg), the title compound was isolated as a white solid (35 mg, 66%). Rf=0.65 (1:1 EA/heptane). MS (ES): M/Z [M+H]=540. 1H NMR: (400 MHz, DMSO-d$_6$): 1.78 (s, 3H), 5.59 (dd, J=58.3, 13.3 Hz, 2H), 7.93 (s, 1H), 8.16 (d, J=8.58 Hz, 2H), 8.57 (s, 1H) and 9.17 (s, 1H). 19F NMR (376 MHz, DMSO-d$_6$): −78.73 (s, 3F) and −61.08 (s, 3F).

Example 91

N-[2-(2H-Benzotriazol-2-yl)-1-cyano-1-methylethyl]-4-trifluoromethylsulfonylbenzamide (compound No 1.029)

Sodium periodate (200 mg) and ruthenium chloride (10 mg) were added to a solution of N-[2-(2H-benzotriazol-2-yl)-1-cyano-1-methylethyl]-4-trifluoromethylthiobenzamide (100 mg, described in Example 6), in a mixture of acetonitrile-water (2:1). The reaction mixture was stirred 48 hours whereupon the mixture was diluted with ethyl acetate and washed with saturated aqueous sodium bicarbonate solution. The organic filtrate was dried over anhydrous magnesium sulfate, filtered and concentrated under reduced pressure to give to give a residue that was purified by chromatography (SiO$_2$, heptane/EA) to afford the title compound as a white solid (50 mg, 46%). Rf=0.6 (1:1 EA/heptane). MS (ES): M/Z [M+H]=438. 1H NMR: (400 MHz, DMSO-d$_6$): 1.75 (s, 3H), 5.39-5.53 (m, 2H), 7.47 (dd, J=6.6, 3.1 Hz, 2H), 7.95 (dd, J=6.6, 3.1 Hz, 2H), 8.17 (d, J=8.6 Hz, 2H), 8.31 (d, J=8.4 Hz, 2H) and 9.25 (s, 1H). 19F NMR (376 MHz, DMSO-d$_6$): −78.66 (s, 3F).

Example 92

N-[1-Cyano-1-methyl-2-(5-methyl-2H-benzotriazol-2-yl)ethyl]-4-trifluoromethylsulfonylbenzamide (compound No 1.030)

Using a procedure similar to that described in Example 88, except using N-[1-cyano-1-methyl-2-(5-methyl-2H-benzotriazol-2-yl)ethyl]-4-trifluoromethylthiobenzamide (50 mg, described in Example 8), the title compound was isolated as a white solid (40 mg, 37%). Rf=0.6 (1:1 EA/heptane). MS (ES): M/Z [M+H]=452. 1H NMR: (400 MHz, DMSO-d$_6$): 1.73 (s, 3H), 5.34-5.47 (m, 2H), 7.30 (dd, J=8.8, 1.4 Hz, 1H), 7.69 (s, 1H), 7.83 (d, J=8.8 Hz, 1H), 8.17 (d, J=8.5 Hz, 2H), 8.32 (d, J=8.4 Hz, 2H) and 9.24 (s, 1H). 19F NMR (376 MHz, DMSO-d$_6$): −78.67 (s, 3F).

Example 93

N-[2-(5-Chloro-2H-benzotriazol-2-yl)-1-cyano-1-methylethyl]-4-trifluoromethylsulfonylbenzamide (compound No 1.031)

Using a procedure similar to that described in Example 88, except using N-[2-(5-chloro-2H-benzotriazol-2-yl)-1-cyano-1-methylethyl]-4-trifluoromethylthiobenzamide (50 mg, described in Example 3), the title compound was isolated as a white solid (120 mg, 45%). Rf=0.6 (1:1 EA/heptane). MS (ES): M/Z [M+H]=472. 1H NMR: (400 MHz, DMSO-d$_6$): 1.75 (s, 3H), 5.41-5.52 (m, 2H), 7.49 (m, 1H), 8.02 (m, 1H), 8.14-8.32 (m, 4H) and 9.25 (s, 1H). 19F NMR (376 MHz, DMSO-d$_6$): −78.67 (s, 3F).

Example 94

N-[2-(6-Chloro-2H-pyrazolo[4,3-b]pyridin-2-yl)-1-cyano-1-methylethyl]-4-trifluoromethylsulfonylbenzamide (compound No 3.032)

Using a procedure similar to that described in Example 91, except using N-[2-(6-chloro-2H-pyrazolo[4,3-b]pyridin-2-yl)-1-cyano-1-methylethyl]-4-trifluoromethylthiobenzamide (25 mg, described in Example 181), the title compound was isolated as a white solid (6.9 mg). MS (ES): M/Z [M+H]=472. 1H NMR: (400 MHz, CHLOROFORM-d): 1.98 (s, 3H), 4.82-4.89 (m, 1H), 4.97-5.03 (m, 1H), 8.11-8.15 (m, 2H), 8.21 (d, J=8.4 Hz, 2H), 8.44-8.47 (m, 1H), 8.49-8.53 (m, 1H) and 8.58 (d, J=2.0 Hz, 1H). 19F NMR (376 MHz, CHLOROFORM-d): −78.3 (s, 3F).

Example 95

N-[2-(6-Bromo-2H-pyrazolo[4,3-b]pyridin-2-yl)-1-cyano-1-methylethyl]-4-trifluoromethylsulfonylbenzamide (compound No 3.033)

Using a procedure similar to that described in Example 91, except using N-[2-(6-bromo-2H-pyrazolo[4,3-b]pyridin-2-yl)-1-cyano-1-methylethyl]-4-trifluoromethylthiobenzamide (17 mg described in Example 183), the title compound was isolated as a white solid (7.4 mg). MS (ES): M/Z [M+H]=516. 1H NMR: (400 MHz, CHLOROFORM-d): 1.98 (s, 3H), 4.81-4.89 (m, 1H), 4.97-5.04 (m, 1H), 8.10-8.15 (m, 2H), 8.21 (d, J=8.3 Hz, 2H), 8.42-8.51 (m, 2H) and 8.66 (d, J=1.7 Hz, 1H). 19F NMR (376 MHz, CHLOROFORM-d): −78.3 (s, 3F).

Compounds of Examples 96 to 99 were prepared according to the following general reaction scheme:

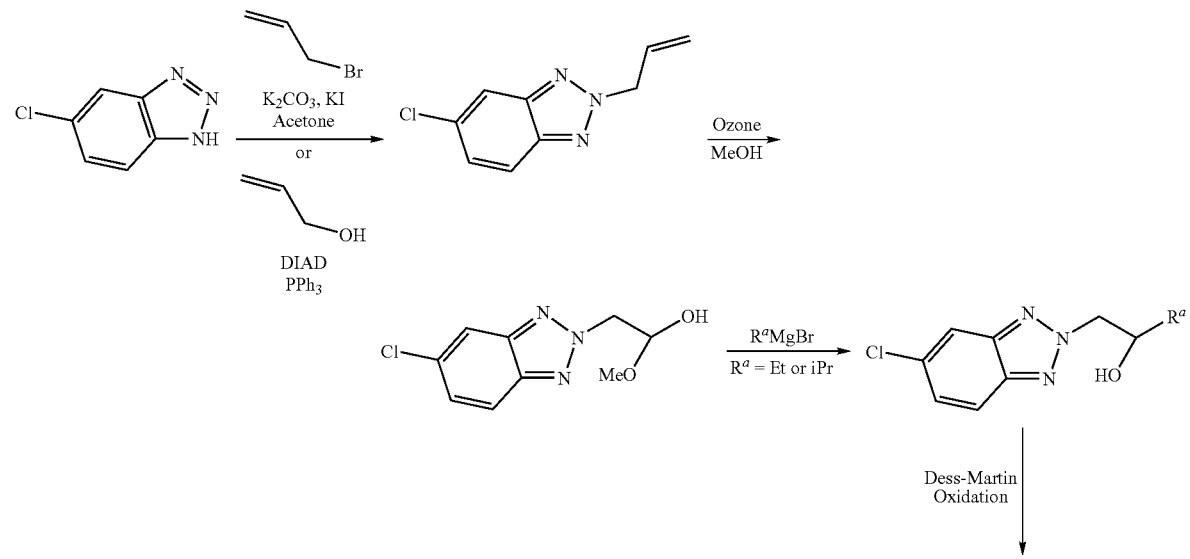

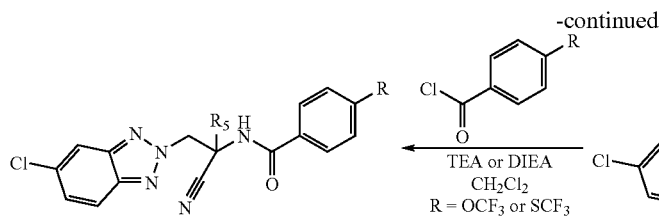
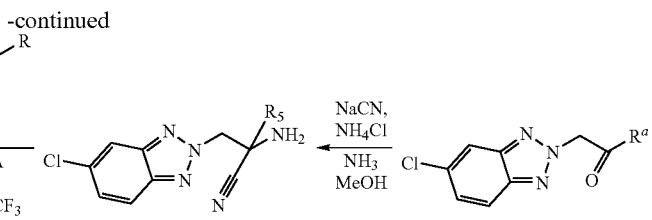

Final Product
V=C—H; W=C—Cl; X=C—H; Y=C—H;
Q=P=N;
R$_3$=R$_4$=H; a=1; R$_6$=H;
Z=C(O); R$_7$=p-phenyl-R; R=OCF$_3$ or SCF$_3$ It will be apparent to one of skill in the art that modified derivatives with variable substitution on the phenyl ring may also be made by starting the corresponding substituted benzoic acid chloride.

Example 96

N-{1-[(5-Chloro-2H-benzotriazol-2-yl)methyl]-1-cyanopropyl}-4-trifluoromethoxybenzamide (compound No 1.047)

Using a procedure similar to that described in Example 1, except using 2-amino-2-[(5-chloro-2H-benzotriazol-2-yl)methyl]butyronitrile, the title compound was isolated as a solid. MS (ES): M/Z [M+H]=438. 1H NMR: (400 MHz, CHLOROFORM-0:1.29 (t, J=7.4 Hz, 3H), 1.72-1.94 (m, J=14.4, 7.4 Hz, 1H), 2.29 (m, J=14.3, 7.4 Hz, 1H), 5.23 (d, J=13.9 Hz, 1H), 5.47 (d, J=13.8 Hz, 1H), 7.15 (s, 1H), 7.33 (d, J=8.2 Hz, 2H), 7.40 (dd, J=9.1, 1.8 Hz, 1H), 7.82 (d, J=9.1 Hz, 1H), 7.85 (d, J=8.7 Hz, 2H) and 7.87 (d, J=1.2 Hz, 1H). 19F NMR (376 MHz, CHLOROFORM-d): −58.1 (s, 3F).

2-Amino-2-[(5-chloro-2H-benzotriazol-2-yl)methyl]butyronitrile was prepared using a procedure similar to that described in Example 1, part b, except starting from 1-(5-chloro-2H-benzotriazol-2-yl)butan-2-one that was prepared as follows:

a. A solution of 5-chloro-1H-benzotriazole (1.53 g) in THF was added at 0° C. to a mixture of diisopropylic azodicarboxylate (2 mL), triphenyl phosphine (2.9 g) and allyl alcohol (1.4 mL) in THF. After stirring one hour at 0° C., the mixture was concentrated under reduced pressure to give a residue that was purified by chromatography (SiO$_2$, heptane/EA) to afford 2-allyl-5-chloro-2H-benzotriazole (1.02 g, 53%). A mixture of 1-allyl-5-chloro-1H-benzotriazole and 1-allyl-6-chloro-1H-benzotriazole was also recovered (0.9 g, 47%). Alternatively, 2-allyl-5-chloro-2H-benzotriazole [4.87 g, 25%, Rf=0.4 (1:3 EA/heptane)] was obtained using a procedure similar to that described in Example 1, part a, except using 3-bromopropene. Similarly, a mixture of 1-allyl-5-chloro-1H-benzotriazole and 1-allyl-6-chloro-1H-benzotriazole was also recovered [10.81 g, 56%, Rf=0.2 (1:3 EA/heptane)].

b. 2-Allyl-5-chloro-2H-benzotriazole dissolved in a mixture of DCM and methanol was treated with ozone gas for 30 minutes. After stirring one hour at −78° C., the mixture was purged 10 minutes with oxygen and then quenched with dimethyl sulfide followed by a 10% solution of sodium thiosulfate and diluted with DCM (100 mL). The organic layer was dried over sodium sulfate, filtered and concentrated under reduced pressure to give quantitatively 2-(5-chloro-2H-benzotriazol-2-yl)-1-methoxyethanol c. To a solution of 2-(5-chloro-2H-benzotriazol-2-yl)-1-methoxyethanol (300 mg) in THF was added a 2 molar solution of ethyl magnesium bromide Grignard reagent (1.6 mL) at −78° C. under nitrogen and the mixture let warm slowly to room temperature. The mixture was quenched with a saturated solution of ammonium chloride, followed by magnesium sulfate. The resulted solids were filtered off and the organic layer concentrated under reduced pressure to give a residue that was purified by chromatography (SiO$_2$, heptane/EA) to afford 1-(5-chloro-2H-benzotriazol-2-yl)butan-2-ol (107 mg). Rf=0.7 (2:1 EA/heptane).

d. 1-(5-Chloro-2H-benzotriazol-2-yl)butan-2-ol in DCM was reacted with Dess-Martin periodinane. After stirring at room temperature, the mixture was concentrated under reduced pressure and purified by chromatography (SiO$_2$, heptane/EA) to afford 1-(5-chloro-2H-benzotriazol-2-yl)butan-2-one.

Example 97

N-{1-[(5-Chloro-2H-benzotriazol-2-yl)methyl]-1-cyanopropyl}-4-trifluoromethylthiobenzamide (compound No 1.048)

Using a procedure similar to that described in Example 1, except using 2-amino-2-[(5-chloro-2H-benzotriazol-2-yl)methyl]butyronitrile described in Example 96 and 4-trifluoromethylbenzoyl chloride, the title compound was isolated as a solid. MS (ES): M/Z [M+H]=454. 1H NMR: (400 MHz, CHLOROFORM-d): 1.29 (t, J=7.4 Hz, 3H), 1.77-1.94 (m, J=14.4, 7.4, 7.4, 7.3 Hz, 1H), 2.16-2.36 (m, J=14.4, 7.4, 7.4, 7.3 Hz, 1H), 5.23 (d, J=13.9 Hz, 1H), 5.47 (d, J=13.8 Hz, 1H), 7.21 (s, 1H), 7.39 (dd, J=9.1, 1.9 Hz, 1H), 7.73-7.79 (m, 2H), 7.79-7.85 (m, 3H) and 7.87 (dd, J=1.8, 0.7 Hz, 1H). 19F NMR (376 MHz, CHLOROFORM-d): −42.3 (s, 3F).

Example 98

N-{1-[(5-Chloro-2H-benzotriazol-2-yl)methyl]-1-cyano-3-methylbutyl}-4-trifluoromethoxybenzamide (compound No 1.049)

Using a procedure similar to that described in Example 1, except using 2-amino-2-[(5-chloro-2H-benzotriazol-2-yl)methyl]-4-methylpentanenitrile, the title compound was isolated as a solid. MS (ES): M/Z [M+H]=466. 1H NMR: (400 MHz, CHLOROFORM-d): 1.11 (d, J=6.4 Hz, 3H), 1.14 (d, J=6.3 Hz, 3H), 1.79-1.90 (m, 1H), 2.05-2.21 (m, 2H), 5.27 (d, J=13.8 Hz, 1H), 5.48 (d, J=13.8 Hz, 1H), 7.27 (s, 1H), 7.32 (d, J=8.5 Hz, 2H), 7.39 (dd, J=9.1, 1.7 Hz, 1H), 7.78-7.86 (m, 3H) and 7.87 (d, J=1.8 Hz, 1H). 19F NMR (376 MHz, CHLOROFORM-d): −58.1 (s, 3F).

2-Amino-2-[(5-chloro-2H-benzotriazol-2-yl)methyl]-4-methylpentanenitrile was prepared using a procedure similar to that described in Example 1, part b, except starting from 1-(5-chloro-2H-benzotriazol-2-yl)-4-methylpentan-2-one. 1-(5-Chloro-2H-benzotriazol-2-yl)-4-methylpentan-2-one was prepared using a procedure similar to that described in Example 96, part a to d, except using isopropyl magnesium bromide Grignard reagent in part c.

Example 99

N-{1-[(5-Chloro-2H-benzotriazol-2-yl)methyl]-1-cyano-3-methylbutyl}-4-trifluoromethylthiobenzamide (compound No 1.050)

Using a procedure similar to that described in Example 1, except using 2-amino-2-[(5-chloro-2H-benzotriazol-2-yl)methyl]-4-methylpentanenitrile described in Example 98 and 4-trifluoromethylbenzoyl chloride, the title compound was isolated as a solid. 1H NMR: (400 MHz, CHLOROFORM-d): 1.11 (d, J=6.5 Hz, 3H), 1.15 (d, J=6.4 Hz, 3H), 1.78-1.91 (m, 1H), 2.06-2.21 (m, 2H), 5.27 (d, J=13.8 Hz, 1H), 5.49 (d, J=13.8 Hz, 1H), 7.16 (s, 1H), 7.40 (dd, J=9.1, 1.8 Hz, 1H), 7.75-7.80 (m, 2H), 7.80-7.86 (m, 3H) and 7.87 (dd, J=1.8, 0.5 Hz, 1H). 19F NMR (376 MHz, CHLOROFORM-d): −42.2 (s, 3F).

Compounds of Examples 100 and 101 were prepared according to the following reaction scheme:

Example 100

N-{1-[(5-Chloro-2H-benzotriazol-2-yl)methyl]-1-cyano-2,2-dimethylpropyl}-4-trifluoromethoxybenzamide (compound No 1.051)

Using a procedure similar to that described in Example 1, except using 2-amino-2-[(5-chloro-2H-benzotriazol-2-yl)methyl]-3,3-dimethylbutyronitrile, the bis-amide derivative N-{1-[(5-chloro-2H-benzotriazol-2-yl)methyl]-1-cyano-2,2-dimethylpropyl}-4-trifluoromethoxy-N-(4-trifluoromethoxybenzoyl)-benzamide was isolated instead of the title compound. MS (ES): M/Z [M+H]=654. Subsequent treatment with lithium hydroxide in methanol and purification by chromatography (SiO$_2$, heptane/EA) afforded the title compound as a solid. MS (ES): M/Z [M+H]=466. 1H NMR: (400 MHz, CHLOROFORM-d): 0.17 (s, 9H), 5.34 (d, J=14.1 Hz, 1H), 5.51 (d, J=14.1 Hz, 1H), 7.02 (s, 1H), 7.35 (d, J=8.0 Hz, 2H), 7.38 (dd, J=9.1, 1.9 Hz, 1H), 7.79 (dd, J=9.1, 0.6 Hz, 1H), 7.84 (dd, J=1.8, 0.6 Hz, 1H) and 7.89 (d, J=8.8 Hz, 2H). 19F NMR (376 MHz, CHLOROFORM-d): −58.1 (s, 3F).

2-Amino-2-[(5-chloro-2H-benzotriazol-2-yl)methyl]-3,3-dimethylbutyronitrile was prepared using a procedure similar to that described in Example 1, part a and b, except using 1-chloro-3,3-dimethylbutan-2-one instead of chloroacetone in part a.

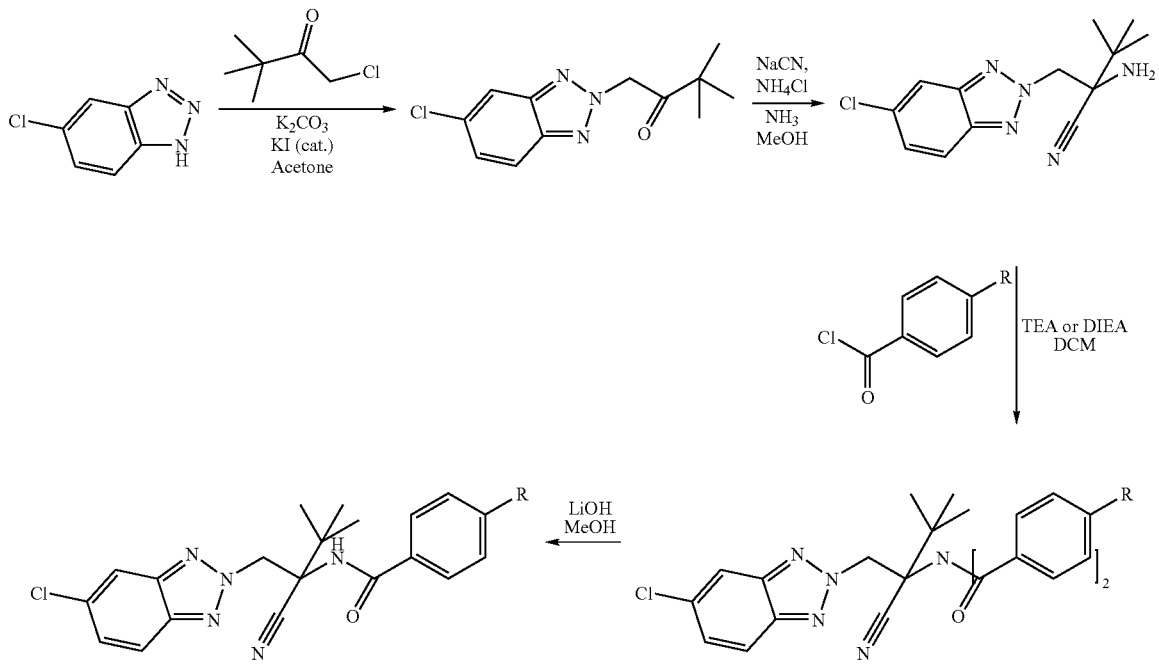

Final Product
V=C—H; W=C—Cl; X=C—H; Y=C—H;
Q=P=N;
R$_3$=R$_4$=H; a=1; R$_5$=t-butyl; R$_6$=H;
Z=C(O); R$_7$=p-phenyl-R It will be apparent to one of skill in the art that modified derivatives with variable substitution on the phenyl ring may also be made by starting the corresponding substituted benzoic acid chloride.

Example 101

N-{1-[(5-Chloro-2H-benzotriazol-2-yl)methyl]-1-cyano-2,2-dimethylpropyl}-4-trifluoromethylthiobenzamide (compound No 1.052)

Using a procedure similar to that described in Example 1, except using 2-amino-2-[(5-chloro-2H-benzotriazol-2-yl)methyl]-3,3-dimethylbutyronitrile described in Example 100 and 4-trifluoromethylbenzoyl chloride, the bis-amide derivative N-{1-[(5-chloro-2H-benzotriazol-2-yl)methyl]-1-cyano-2,2-dimethylpropyl}-4-trifluoromethylthio-N-(4-trifluoromethylthiobenzoyl)-benzamide was isolated instead of the title compound. MS (ES): M/Z [M+H]=686. Subsequent treatment with lithium hydroxide in methanol and purification by chromatography (SiO$_2$, heptane/EA) afforded the title compound as a solid. MS (ES): M/Z [M+H]=482. 1H NMR: (400 MHz, CHLOROFORM-d): 1.17 (s, 9H), 5.35 (d, J=14.1 Hz, 1H), 5.51 (d, J=14.1 Hz, 1H), 7.06 (s, 1H), 7.38 (dd, J=9.1, 1.9 Hz, 1H), 7.75-7.82 (m, 3H), 7.84 (dd, J=1.8, 0.6 Hz, 1H) and 7.85-7.91 (m, 2H). 19F NMR (376 MHz, CHLOROFORM-d): −42.3 (s, 3F).

Compounds of Examples 102 and 103 were prepared according to the following general reaction scheme:

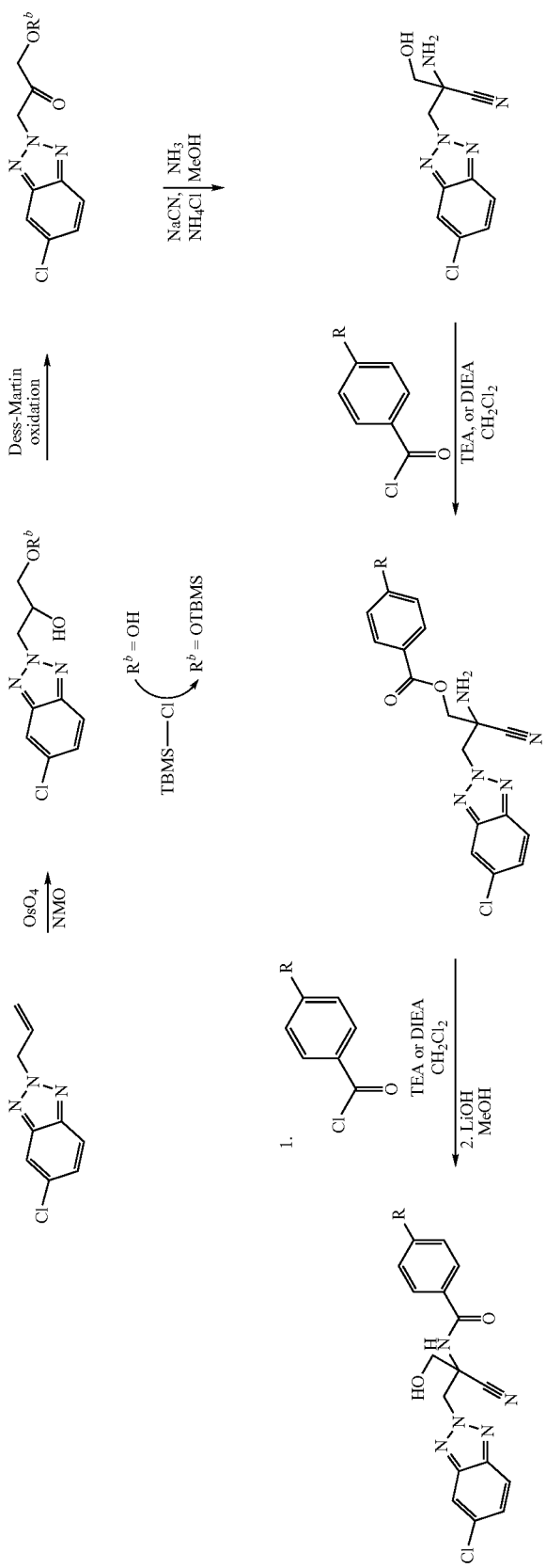

Final Product
V=C—H; W=C—Cl; X=C—H; Y=C—H;
Q=P=N;
R$_3$=R$_4$=H; a=1 R$_5$=CH$_2$OH, R$_6$=H;
Z=C(O); R$_7$=p-phenyl-R It will be apparent to one of skill in the art that modified derivatives with variable substitution on the phenyl ring may also be made by starting the corresponding substituted benzoic acid chloride.

Example 102

N-[2-(5-Chloro-2H-benzotriazol-2-yl)-1-cyano-1-(hydroxymethyl)ethyl]-4-trifluoromethoxybenzamide (compound No 1.058)

Using a procedure similar to that described in Example 1, except using 2-amino-3-(5-chloro-2H-benzotriazol-2-yl)-2-(hydroxymethyl)propionitrile, the ester derivative 4-trifluoromethoxybenzoic acid 2-amino-3-(5-chloro-2H-benzotriazol-2-yl)-2-cyanopropyl ester was isolated instead of the title compound. This ester was reacted with more 4-trifluoromethoxybenzoyl chloride, subsequently treated with lithium hydroxide in methanol and purified by chromatography (SiO$_2$, heptane/EA) to afford the title compound as a solid. MS (ES): M/Z [M+H]=440. 1H NMR: (400 MHz, CHLOROFORM-d): 3.27 (t, J=7.3 Hz, 1H), 3.94 (dd, J=11.9, 7.3 Hz, 1H), 4.30 (dd, J=11.9, 5.9 Hz, 1H), 5.43 (d, J=13.9 Hz, 1H), 5.48 (, J=14.0 Hz, 1H), 7.33 (d, J=8.1 Hz, 2H), 7.43 (dd, J=9.1, 1.9 Hz, 1H), 7.45 (s, 1H), 7.82-7.89 (m, 3H) and 7.90 (dd, J=1.8, 0.6 Hz, 1H). 19F NMR (376 MHz, CHLOROFORM-d): −58.1 (s, 3F).

2-Amino-3-(5-chloro-2H-benzotriazol-2-yl)-2-(hydroxymethyl)propionitrile was prepared using a procedure similar to that described in Example 1, part b, except starting from 1-(tert-butyldimethylsilyloxy)-3-(5-chloro-2H-benzotriazol-2-yl)-propan-2-one that was prepared as follows (the tert-butyldimethylsilyl protecting group was removed under the Strecker reaction conditions):

a. To a solution of 2-allyl-5-chloro-2H-benzotriazole (5.2 g), described in Example 85 part a, in a 10 to 1 mixture of THF and water (45 mL), was added a 50% solution of 4-methylmorpholine-N-oxide in water (7 mL) followed by a 4% solution of osmium tetroxide in water (2 mL). After stirring overnight at room temperature, the mixture was quenched with a 10% solution of sodium thiosulfate, extracted with ethyl acetate. The organic layer was dried over magnesium sulfate, filtered and concentrated under reduced pressure to give 3-(5-chloro-2H-benzotriazol-2-yl)-propane-1,2-diol (4.8 g, 79%) that was used directly into the next step without further purification.

b. To a solution of 3-(5-chloro-2H-benzotriazol-2-yl)-propane-1,2-diol (1.09 g) in DCM at 0° C. was added imidazole (0.65 g) and tert-butyldimethylsilyl chloride (0.8 g). After stirring overnight at room temperature, the mixture was diluted with DCM, washed with water, dried over magnesium sulfate, filtered and concentrated under reduced pressure to give a residue that was purified by chromatography (SiO$_2$, heptane/EA) to afford 1-(tert-butyldimethylsilyloxy)-3-(5-chloro-2H-benzotriazol-2-yl)-propan-2-ol (1.5 g, 85%). Rf=0.55 (1:1 EA/heptane).

c. 1-(tert-Butyldimethylsilyloxy)-3-(5-chloro-2H-benzotriazol-2-yl)-propan-2-ol (1.5 g) in DCM (20 mL) was reacted with Dess-Martin periodinane (2.1 g). After stirring overnight at room temperature, the mixture was concentrated under reduced pressure and purified by chromatography (SiO$_2$, heptane/EA) to afford 1-(tert-butyldimethylsilyloxy)-3-(5-chloro-2H-benzotriazol-2-yl)-propan-2-one (1.2 g).

Example 103

N-[2-(5-Chloro-2H-benzotriazol-2-yl)-1-cyano-1-(hydroxymethyl)ethyl]-4-trifluoromethylthiobenzamide (compound No 1.059)

Using a procedure similar to that described in Example 1, except using 2-amino-3-(5-chloro-2H-benzotriazol-2-yl)-2-(hydroxymethyl)propionitrile, described in Example 102, and 4-trifluoromethylbenzoyl chloride, the ester derivative 4-trifluoromethylbenzoic acid 2-amino-3-(5-chloro-2H-benzotriazol-2-yl)-2-cyanopropyl ester was isolated instead of the title compound. This ester was reacted with more 4-trifluoromethylbenzoyl chloride, subsequently treated with lithium hydroxide in methanol and purified by chromatography (SiO$_2$, heptane/EA) to afford the title compound as a solid. MS (ES): M/Z [M+H]=456. 1H NMR: (400 MHz, CHLOROFORM-d): 3.31 (br. s., 1H), 3.94 (d, J=11.8 Hz, 1H), 4.31 (d, J=11.7 Hz, 1H), 5.43 (d, J=14.0 Hz, 1H), 5.49 (d, J=13.9 Hz, 1H), 7.43 (dd, J=9.1, 1.9 Hz, 1H), 7.51 (s, 1H), 7.78 (d, J=8.3 Hz, 2H), 7.84-7.87 (m, 3H) and 7.90 (dd, J=1.8, 0.6 Hz, 1H). 19F NMR (376 MHz, CHLOROFORM-d): −42.2 (s, 3F).

Compounds of Examples 104 to 106 were prepared according to the following general reaction scheme:

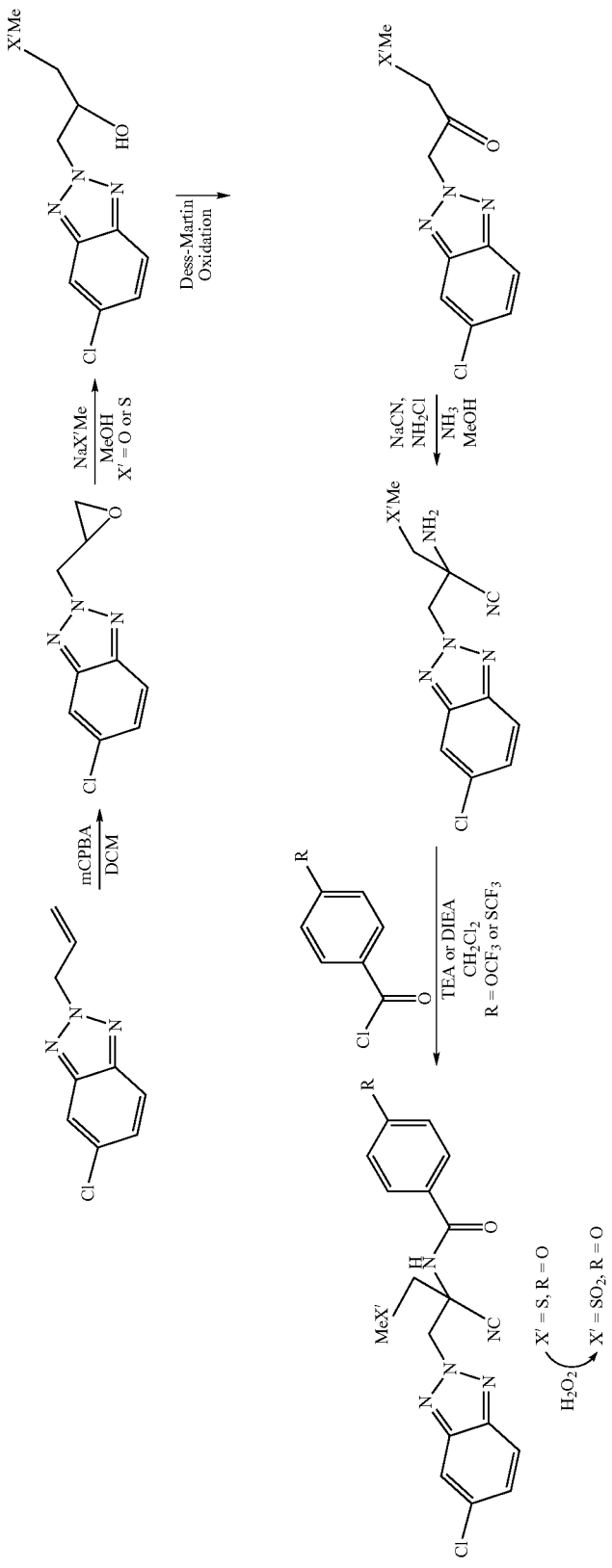

Final Product
V=C—H; W=C—Cl; X=C—H; Y=C—H;
Q=P=N;
R$_3$=R$_4$=H; a=1; R$_5$=CH$_2$X'Me; R$_6$=H;
Z=C(O); R$_7$=p-phenyl-R; R=OCF$_3$ or SCF$_3$ It will be apparent to one of skill in the art that modified derivatives with variable substitution on the phenyl ring may also be made by starting the corresponding substituted benzoic acid chloride.

Example 104

N-[2-(5-Chloro-2H-benzotriazol-2-yl)-1-cyano-1-(methylthiomethyl)ethyl]-4-trifluoromethoxybenzamide (compound No 1.061)

Using a procedure similar to that described in Example 1, except using 2-amino-3-(5-chloro-2H-benzotriazol-2-yl)-2-(methylthiomethyl)propionitrile, the title compound was isolated as a solid. MS (ES): M/Z [M+H]=470. 1H NMR: (400 MHz, CHLOROFORM-d): 2.41 (s, 3H), 3.07 (d, J=14.7 Hz, 1H), 3.52 (d, J=14.6 Hz, 1H), 5.47 (dd, 2H), 7.34 (d, J=8.5 Hz, 2H), 7.41 (dd, J=9.1, 1.8 Hz, 2H) and 7.79-7.94 (m, 5H). 19F NMR (376 MHz, CHLOROFORM-d): −58.1 (s, 3F).

2-Amino-3-(5-chloro-2H-benzotriazol-2-yl)-2-(methylthiomethyl)propionitrile was prepared using a procedure similar to that described in Example 1, part b, except starting from 1-(5-chloro-2H-benzotriazol-2-yl)-3-(methylthio)propan-2-one that was prepared as follows:

a. To a solution of 2-allyl-5-chloro-2H-benzotriazole (5.0 g), described in Example 85 part a, in DCM (50 mL), was added meta-chloroperbenzoic acid (8.5 g, 55% pure). After stirring at room temperature for 24 hours, the mixture was filtered through a plug of basic alumina. The filtrate was concentrated under reduced pressure to give a residue that was purified by chromatography (SiO$_2$, heptane/EA) to afford 5-chloro-2-oxiranylmethyl-2H-benzotriazole (0.7 g). Rf=0.55 (2:1 EA/heptane).

b. To a solution of 5-chloro-2-oxiranylmethyl-2H-benzotriazole (306 mg) in methanol (5 mL) was added sodium thiomethoxide (307 mg). After stirring overnight at room temperature, the mixture was extracted with ethyl acetate. The organic layer was washed with water, dried over magnesium sulfate, filtered and concentrated under reduced pressure to give 1-(5-chloro-2H-benzotriazol-2-yl)-3-(methylthio)propan-2-ol that was used directly into the next oxidation step.

c. 1-(5-Chloro-2H-benzotriazol-2-yl)-3-(methylthio)propan-2-ol in DCM (5 mL) was reacted with Dess-Martin periodinane (720 mg). After stirring overnight at room temperature, the mixture was concentrated under reduced pressure and purified by chromatography (SiO$_2$, heptane/EA) to afford 1-(5-chloro-2H-benzotriazol-2-yl)-3-(methylthio)propan-2-one (149 mg, 40% in two steps).

Example 105

N-[2-(5-Chloro-2H-benzotriazol-2-yl)-1-cyano-1-(methoxymethyl)ethyl]-4-trifluoromethoxybenzamide (compound No 1.062)

Using a procedure similar to that described in Example 1, except using 2-amino-3-(5-chloro-2H-benzotriazol-2-yl)-2-(methoxymethyl)propionitrile, the title compound was isolated as a solid. MS (ES): M/Z [M+H]=454. 1H NMR: (400 MHz, CHLOROFORM-d): 3.52 (s, 3H), 3.71 (d, J=9.8 Hz, 1H), 4.12 (d, J=9.7 Hz, 1H), 5.37-5.47 (m, 2H), 7.33 (d, 2H), 7.40 (dd, J=9.1, 1.9 Hz, 1H), 7.48 (s, 1H) and 7.81-7.90 (m, 4H). 19F NMR (376 MHz, CHLOROFORM-d): −58.1 (s, 3F).

2-Amino-3-(5-chloro-2H-benzotriazol-2-yl)-2-(methoxymethyl)propionitrile was prepared using a procedure similar to that described in Example 1, part b, except starting from 1-(5-chloro-2H-benzotriazol-2-yl)-3-methoxypropan-2-one. 1-(5-Chloro-2H-benzotriazol-2-yl)-3-methoxypropan-2-one was prepared using a procedure similar to that described in Example 104, part a to c, except using sodium methoxide in part b.

Example 106

N-[2-(5-Chloro-2H-benzotriazol-2-yl)-1-cyano-1-(methanesulfonylmethyl)ethyl]-4-trifluoromethoxybenzamide (compound No 1.063)

To a solution of N-[2-(5-Chloro-2H-benzotriazol-2-yl)-1-cyano-1-(methylthiomethyl)ethyl]-4-trifluoromethoxybenzamide (36 mg) in a mixture of DCM and TFA was added 3 drops of hydrogen peroxide (30% weight in water). After stirring overnight at room temperature, the mixture was concentrated under reduced pressure to give the title compound as a solid. MS (ES): M/Z [M+H]=502. 1H NMR: (400 MHz, DMSO-d$_6$): 3.03 (s, 3H), 4.13 (d, J=5.0 Hz, 1H), 4.20 (d, J=5.1 Hz, 1H), 5.54 (s, 2H), 7.43 (dd, J=9.1, 1.9 Hz, H), 7.50 (d, J=8.7, 0.8 Hz, 2H), 7.68 (s, 1H), 7.81-7.90 (m, 2H), 7.91-8.00 (m, 2H), 8.05 (dd, J=1.9, 0.6 Hz, 1H) and 8.29 (s, 1H). 19F NMR (376 MHz, DMSO-d$_6$): −57.1 (s, 3F).

Compounds of Examples 107 to 115 were prepared according to the following general reaction scheme:

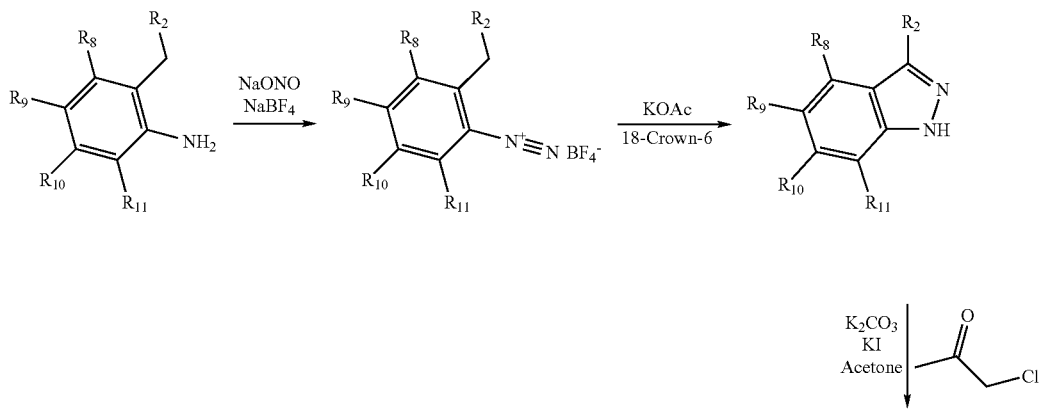

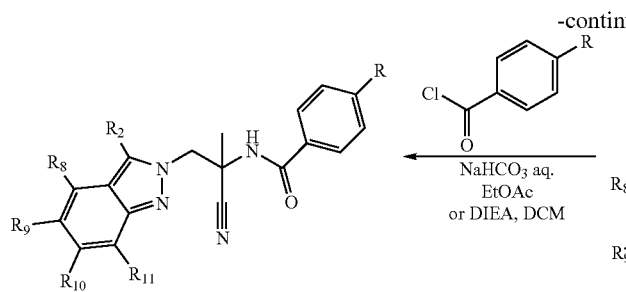
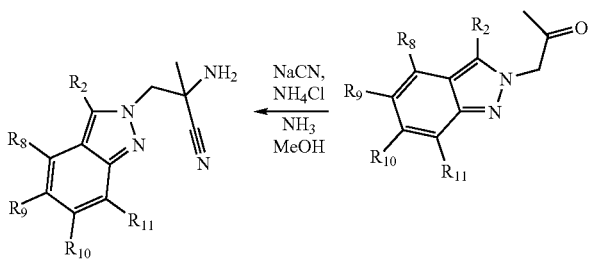

Final Product
V=C—R$_8$; W=C—R$_9$; X=C—R$_{10}$; Y=C—R$_{11}$;
Q=C—R$_2$; P=N;
R$_3$=R$_4$=H; a=1; R$_5$=CH$_3$, R$_6$=H;
Z=C(O); R$_7$=p-phenyl-R It will be apparent to one of skill in the art that modified derivatives with variable substitution on the phenyl ring may also be made by starting the corresponding substituted benzoic acid chloride.

Example 107

N-[1-Cyano-1-methyl-2-(5-nitro-2H-indazol-2-yl) ethyl]-4-trifluoromethoxybenzamide (compound No 2.001)

Using a procedure similar to that described in Example 1, except using 2-amino-2-methyl-3-(5-nitro-2H-indazol-2-yl) propionitrile (62 mg), the title compound was isolated as a white solid (100 mg, 91%). MS (ES): M/Z [M+H]=434. 1H NMR: (400 MHz, DMSO-d$_6$): 1.72 (s, 3H), 5.21 (q, J=13.7 Hz, 2H), 7.53 (d, J=8.2 Hz, 2H), 7.81 (d, J=9.5 Hz, 1H), 7.97 (d, J=8.8 Hz, 2H), 8.01 (dd, J=2.2 Hz, 1H), 8.82 (s, 1H), 8.94 (d, J=2.0 Hz, 1H) and 8.99 (s, 1H). 19F NMR (376 MHz, DMSO-d$_6$): −57.1 (s, 3F).

2-Amino-2-methyl-3-(5-nitro-2H-indazol-2-yl)propionitrile (444 mg) was prepared using a procedure similar to that described in Example 1, part a and b, except starting from commercially available 5-nitro-1H-indazole (7 g), one-half molar equivalent of potassium carbonate (3.1 g), one equivalent of potassium iodide (9.2 g) and heating the reaction mixture to reflux in acetone to isolate desired 1-(5-nitro-2H-indazol-2-yl)propan-2-one (890 mg, 9.5%) along with 1-(5-nitro-1H-indazol-1-yl)propan-2-one in part a.

Example 108

N-[1-Cyano-1-methyl-2-(5-nitro-2H-indazol-2-yl) ethyl]-4-trifluoromethylthiobenzamide (compound No 2.002)

Using a procedure similar to that described in Example 1, except using 2-amino-2-methyl-3-(5-nitro-2H-indazol-2-yl) propionitrile (62 mg, described in Example 107) and 4-trifluoromethylthiobenzoyl chloride, the title compound was isolated as a white solid (96 mg, 84%). MS (ES): M/Z [M+H]=450. 1H NMR: (400 MHz, DMSO-d$_6$): 1.72 (s, 3H), 5.22 (q, 2H), 7.81 (d, J=9.5 Hz, 1H), 7.86-7.90 (m, 2H), 7.92-7.97 (m, 2H), 8.00-8.05 (m, 1H), 8.83 (s, 1H), 8.95 (d, J=1.9 Hz, 1H) and 9.07 (s, 1H). 19F NMR (376 MHz, DMSO-d$_6$): −41.9 (s, 3F).

Example 109

N-[1-Cyano-2-(5,7-dichloro-2H-indazol-2-yl)-1-methylethyl]-4-trifluoromethoxybenzamide (compound No 2.003)

Using a procedure similar to that described in Example 1, except using 2-amino-3-(5,7-dichloro-2H-indazol-2-yl)-2-methylpropionitrile (60 mg), the title compound was isolated as a white solid (80 mg, 78%). MS (ES): M/Z [M+H]=457. 1H NMR: (400 MHz, DMSO-d$_6$): 1.70 (s, 3H), 5.11 (d, 1H), 5.23 (d, 1H), 7.51 (d, J=8.3 Hz, 2H), 7.89 (d, J=1.6 Hz, 1H), 7.97 (d, J=8.8 Hz, 2H), 8.53 (s, 1H), 8.94 (d, J=2.0 Hz, 1H) and 8.95 (s, 1H). 19F NMR (376 MHz, DMSO-d$_6$): −57.1 (s, 3F).

2-Amino-3-(5,7-dichloro-2H-indazol-2-yl)-2-methylpropionitrile was prepared using a procedure similar to that described in Example 1, part a and b, except starting from 5,7-dichloro-1H-indazole (3 g) and heating the reaction mixture to reflux in acetone to isolate desired 1-(5,7-dichloro-2H-indazol-2-yl)propan-2-one (1.7 g, 44%) along with 1-(5,7-dichloro-1H-indazol-1-yl)propan-2-one (1.2 g, 30%) in part a.

5,7-Dichloro-1H-indazole was prepared as follows by adapting procedures described in the literature for the preparation of indazoles substituted on the six-membered ring. See for example, R. A. Bartsch, et al. *J. Heterocycl. Chem.* 1984, 21, 1063 and P. Schumann et al, *Bioorganic & Medicinal Chemistry Letters*, 2001, 11, 1153.

a. To a suspension of 2,4-dichloro-6-methylaniline (5 g) in a mixture of hydrochloric acid (7.5 mL) and water (7.5 mL), was slowly added at 0° C. a solution of sodium nitrite (2 g) in a minimal amount of water. After all solid starting materials disappeared to yield a yellow mixture; a solution of sodium tetrafluoroborate (4.4 g) in water (10 mL) was added. After stirring 45 minutes at 0° C., the solids that formed were filtered, washed with chilled methanol, washed with diethyl ether and dried under vacuum to yield 2,4-dichloro-6-methylbenzenediazonium tetrafluoroborate (5.7 g).

b. A mixture of 2,4-dichloro-6-methylbenzenediazonium tetrafluoroborate (5.5 g), 18-crown-6 (271 mg) and potassium acetate (4 g) were stirred in chloroform (60 mL) for 1.5 hours at room temperature. The resulting crude mixture was extracted with ethyl acetate, washed with brine, dried over anhydrous sodium sulfate, filtered and concentrated under reduced pressure to give 5,7-dichloro-1H-indazole as a pale brown solid (3 g).

Example 110

N-[1-Cyano-2-(5,7-dichloro-2H-indazol-2-yl)-1-methylethyl]-4-trifluoromethylthiobenzamide (compound No 2.005)

Using a procedure similar to that described in Example 1, except using 2-amino-2-methyl-3-(5,7-dichloro-2H-indazol-2-yl)propionitrile (60 mg, described in Example 109) and 4-trifluoromethylthiobenzoyl chloride, the title compound was isolated as a white solid (80 mg, 76%). MS (ES): M/Z [M+H]=473. 1H NMR: (400 MHz, DMSO-$d_6$): 1.70 (s, 3H), 5.11 (d, 1H), 5.25 (d, 1H), 7.48 (s, 1H), 7.84-7.91 (m, 3H), 7.95 (d, 2H), 8.54 (s, 1H) and 9.03 (s, 1H). 19F NMR (376 MHz, DMSO-$d_6$): −42.0 (s, 3F).

Example 111

N-[1-Cyano-2-(5,7-dichloro-2H-indazol-2-yl)-1-methylethyl]-4-phenoxybenzamide (compound No 2.004)

Using a procedure similar to that described in Example 1, except using 2-amino-2-methyl-3-(5,7-dichloro-2H-indazol-2-yl)propionitrile (60 mg, described in Example 109) and 4-phenoxybenzoyl chloride, the title compound was isolated as a white solid (90 mg, 87%). MS (ES): M/Z [M+H]=465. 1H NMR: (400 MHz, DMSO-$d_6$): 1.71 (s, 3H), 5.12 (d, 1H), 5.21 (d, 1H), 7.04-7.13 (m, 4H), 7.23 (t, J=7.4 Hz, 1H), 7.41-7.51 (m, 3H), 7.85-7.92 (m, 3H), 8.52 (s, 1H) and 8.80 (s, 1H).

Example 112

N-[2-(5-Chloro-7-methyl-2H-indazol-2-yl)-1-cyano-1-methylethyl]-4-trifluoromethoxybenzamide (compound No 2.006)

Using a procedure similar to that described in Example 1, except using 2-amino-3-(5-chloro-7-methyl-2H-indazol-2-yl)-2-methylpropionitrile (58 mg), the title compound was isolated as a white solid (73 mg, 72%). MS (ES): M/Z [M+H]=437. 1H NMR: (400 MHz, DMSO-$d_6$): 1.69 (s, 3H), 2.39 (s, 3H), 5.05 (d, 1H), 5.19 (d, J=13.7 Hz, 1H), 7.03 (s, 1H), 7.52 (d, J=8.2 Hz, 2H), 7.65 (d, J=0.8 Hz, 1H), 7.97 (d, J=8.7 Hz, 2H), 8.36 (s, 1H) and 8.89 (s, 1H). 19F NMR (376 MHz, DMSO-$d_6$): −57.1 (s, 3F).

2-Amino-3-(5-chloro-7-methyl-2H-indazol-2-yl)-2-methylpropionitrile was prepared using a procedure similar to that described in Example 1, part a and b, except starting from 5-chloro-7-methyl-1H-indazole (6.9 g) and heating the reaction mixture to reflux in acetone for 1.5 days to afford 1-(5-chloro-7-methyl-2H-indazol-2-yl)propan-2-one (1.9 g) in part a.

5-Chloro-7-methyl-1H-indazole was prepared using a procedure similar to that described in Example 109, part a and b, except starting from 4-chloro-2,6-dimethylaniline (5 g).

Example 113

N-[2-(5-Chloro-7-methyl-2H-indazol-2-yl)-1-cyano-1-methylethyl]-4-trifluoromethylthiobenzamide (compound No 2.007)

Using a procedure similar to that described in Example 1, except using 2-amino-2-methyl-3-(5-chloro-7-methyl-2H-indazol-2-yl)propionitrile (58 mg, described in Example 101) and 4-trifluoromethylthiobenzoyl chloride, the title compound was isolated as a white solid (77 mg, 73%). MS (ES): M/Z [M+H]=453. 1H NMR: (400 MHz, DMSO-$d_6$): 1.69 (s, 3H), 2.38 (s, 3H), 5.05 (d, 1H), 5.21 (d, 1H), 7.03 (s, 1H), 7.66 (s, 1H), 7.87 (d, 2H), 7.94 (d, 2H), 8.37 (s, 1H) and 8.97 (s, 1H). 19F NMR (376 MHz, DMSO-$d_6$): −42.0 (s, 3F).

Example 114

N-[1-Cyano-2-(5,7-dichloro-3-methyl-2H-indazol-2-yl)-1-methylethyl]-4-trifluoromethoxybenzamide (compound No 2.010)

Using a procedure similar to that described in Example 1, except using 2-amino-3-(5,7-dichloro-3-methyl-2H-indazol-2-yl)-2-methylpropionitrile (40 mg), the title compound was isolated as a white solid (60 mg, 90%). MS (ES): M/Z [M+H]=471. 1H NMR: (400 MHz, DMSO-$d_6$): 1.82 (s, 3H), 2.73 (s, 3H), 4.98 (d, 1H), 5.08 (d, J=13.7 Hz, 1H), 7.45 (dd, 1H), 7.52 (d, 2H), 7.91 (d, 1H), 8.00-8.04 (m, 2H) and 9.09 (s, 1H). 19F NMR (376 MHz, DMSO-$d_6$): −57.1 (s, 3F).

2-Amino-3-(5,7-dichloro-3-methyl-2H-indazol-2-yl)-2-methylpropionitrile was prepared using a procedure similar to that described in Example 1, part a and b, except starting from 5,7-dichloro-3-methyl-1H-indazole (400 mg) and heating the reaction mixture to reflux in acetone to afford 1-(5,7-dichloro-3-methyl-2H-indazol-2-yl)propan-2-one (140 mg) in part a.

5,7-Dichloro-3-methyl-1H-indazole was prepared using a procedure similar to that described in Example 109, part a and b, except starting from 2,4-dichloro-6-ethylaniline (2.9 g) that was prepared by chlorination of 6-ethylaniline (10 g) with N-chlorosuccinimide (22 g) in acetonitrile (80 mL).

Example 115

N-[2-(5,7-Dichloro-3-methyl-2H-indazol-2-yl)-1-cyano-1-methylethyl]-4-trifluoromethylthiobenzamide (compound No 2.011)

Using a procedure similar to that described in Example 1, except using 2-amino-2-methyl-3-(5,7-dichloro-3-methyl-2H-indazol-2-yl)propionitrile (40 mg, described in Example 114) and 4-trifluoromethylthiobenzoyl chloride, the title compound was isolated as a white solid (64 mg, 92%). MS (ES): M/Z [M+H]=487. 1H NMR: (400 MHz, DMSO-$d_6$): 1.83 (s, 3H), 2.73 (s, 3H), 5.00 (d, 1H), 5.06 (d, 1H), 7.45 (dd, J=1.6 Hz, 1H), 7.87 (d, J=8.2 Hz, 2H), 7.91 (dd, J=1.6 Hz, 1H), 8.00 (d, J=8.4 Hz, 2H) and 9.16 (s, 1H). 19F NMR (376 MHz, DMSO-$d_6$): −42.0 (s, 3F).

Compounds of Examples 116 to 142 were prepared according to the following general reaction scheme:

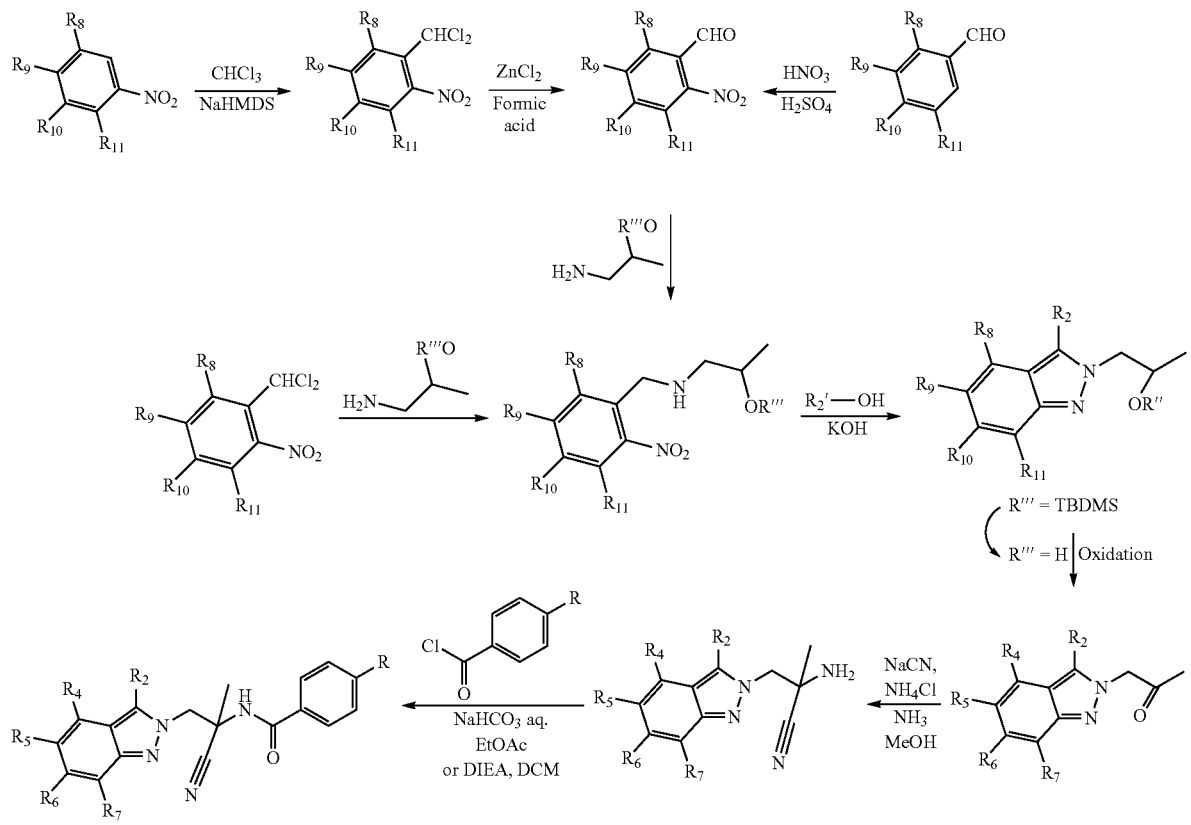

Final Product
V=C—R$_8$; W=C—R$_9$; X=C—R$_{10}$; Y=C—R$_{11}$;
Q=C—R$_2$; P=N;
R$_2$=O—C$_1$-C$_4$ alkyl, O—C$_1$-C$_4$-alkyl-O—C$_1$-C$_4$-alkyl, O—C$_1$-C$_4$—NH—C$_1$-C$_4$-alkyl, O—C$_1$-C$_4$—N(C$_1$-C$_4$-alkyl)$_2$;
R$_3$=R$_4$=H; a=1; R$_5$=CH$_3$, R$_6$=H;
Z=C(O); R$_7$=p-phenyl-R
It will be apparent to one of skill in the art that modified derivatives with variable substitution on the phenyl ring may also be made by starting the corresponding substituted benzoic acid chloride.

Example 116

N-[2-(6-Chloro-3-methoxy-2H-indazol-2-yl)-1-cyano-1-methylethyl]-4-trifluoromethoxybenzamide (compound No 2.008)

Using a procedure similar to that described in Example 1, except using 2-amino-3-(6-chloro-3-methoxy-2H-indazol-2-yl)-2-methylpropionitrile (40 mg), the title compound was isolated as a white solid (60 mg, 88%). MS (ES): M/Z [M+H]=453. 1H NMR: (400 MHz, DMSO-d$_6$): 1.71 (s, 3H), 4.19 (s, 3H), 4.76 (d, 1H), 4.88 (d, 1H), 6.87 (dd, J=9.0, 1.7 Hz, 1H), 7.50-7.55 (m, 3H), 7.89 (d, J=9.1 Hz, 1H), 7.97 (d, J=8.8 Hz, 2H) and 8.92 (s, 1H). 19F NMR (376 MHz, DMSO-d$_6$): −57.1 (s, 3F).
2-Amino-3-(6-chloro-3-methoxy-2H-indazol-2-yl)-2-methylpropionitrile (475 mg, 93%) was prepared using a procedure similar to that described in Example 1, part b, except starting from 1-(6-chloro-3-methoxy-2H-indazol-2-yl)propan-2-one (462 mg) that was prepared as follows:
a. To a solution of 4-chloro-2-nitrobenzaldehyde (4 g) in dioxane (35 mL), was added 2-(tert-butyldimethylsilanyloxy)propylamine (6.1 g, 1.5 equivalent) in methanol (15 mL) followed by acid acetic (1.9 mL) in methanol (15 mL). After overnight stirring at room temperature, a molar solution of sodium cyanoborohydride in THF (22 mL) was added. After 30 minutes, the reaction mixture was quenched with water and extracted with ethyl acetate. The organic phase was dried over anhydrous magnesium sulfate, filtered and concentrated under reduced pressure to yield a residue that was purified by chromatography (SiO$_2$, heptane/EA) to afford [2-(tert-butyldimethylsilanyloxy)propyl]-(4-chloro-2-nitrobenzyl)amine (5.9 g, 77%). 2-(tert-Butyldimethylsilanyloxy)propylamine was obtained by reacting 1-aminopropan-2-ol with 2-tert-butyldimethylsilyl chloride and imidazole in DCM for two hours at room temperature followed by an aqueous work-up.
b. Potassium hydroxide (0.72 g) was added to a stirred solution of [2-(tert-butyldimethylsilanyloxy)propyl]-(4-chloro-2-nitrobenzyl)amine (3 g) in methanol (30 mL). After overnight stirring at 60° C., the reaction mixture was quenched with water and extracted with ethyl acetate. The organic phase was dried over anhydrous magnesium sulfate, filtered and concentrated under reduced pressure to yield a residue that was purified by chromatography (SiO$_2$, heptane/EA) to afford 2-[2-(tert-butyldimethylsilanyloxy)propyl]-6-chloro-3-methoxy-2H-indazole (2.2 g, 87%).

c. To a solution of 2-[2-(tert-butyldimethylsilanyloxy)propyl]-6-chloro-3-methoxy-2H-indazole (1 g) in THF (35 mL), was added a solution of tert-butylammonium fluoride (1 M in THF, 3 mL). After stirring at room temperature for 1.5 hours, the reaction mixture was quenched with water and extracted with ethyl acetate. The organic phase was dried over anhydrous magnesium sulfate, filtered and concentrated under reduced pressure to afford quantitatively 1-(6-chloro-3-methoxy-2H-indazol-2-yl)-propan-2-ol as a solid (0.85 g).

d. A solution of dimethyl sulfoxide (1 mL) in DCM was added at −78° C. to a solution of oxalyl chloride (0.6 mL) in DCM. After stirring for 30 minutes at −78° C., a solution of 1-(6-chloro-3-methoxy-2H-indazol-2-yl)-propan-2-ol (0.85 g) in DCM was added. After stirring for 30 minutes at −78° C., diisopropylethylamine (3.4 mL) was added and after 30 additional minutes, the reaction mixture was allowed to warm to room temperature over 1.5 hours before being concentrated down under reduced pressure. The reaction mixture residue was taken into a mixture of ethyl acetate and brine. The organic phase was dried over anhydrous magnesium sulfate, filtered and concentrated under reduced pressure to yield a residue that was purified by chromatography ($SiO_2$, heptane/EA) to afford 1-(6-chloro-3-methoxy-2H-indazol-2-yl)-propan-2-one as a solid (0.46 g, 55%).

Alternatively, [2-(tert-butyldimethylsilanyloxy)propyl]-(4-chloro-2-nitrobenzyl)amine described in part a, was prepared as follows:

e. To a suspension of 2-(tert-butyldimethylsilanyloxy)propylamine (9 equivalents) in THF was slowly added 4-chloro-2-nitrobenzyl chloride in THF under vigorous stirring. After overnight stirring at room temperature, the mixture was concentrated under reduced pressure to give a residue that was triturated in diethyl ether and filtered. The ether fractions were collected and concentrated under reduced pressure to yield a residue that was purified by chromatography ($SiO_2$, heptane/EA) to afford [2-(tert-butyldimethylsilanyloxy)propyl]-(4-chloro-2-nitrobenzyl)amine.

Example 117

N-[2-(6-Chloro-3-methoxy-2H-indazol-2-yl)-1-cyano-1-methylethyl]-4-trifluoromethylthiobenzamide (compound No 2.009)

Using a procedure similar to that described in Example 1, except using 2-amino-3-(6-chloro-3-methoxy-2H-indazol-2-yl)-2-methylpropionitrile (40 mg, described in Example 116) and 4-trifluoromethylthiobenzoyl chloride, the title compound was isolated as a white solid (65 mg, 91%). MS (ES): M/Z [M+H]=469. 1H NMR: (400 MHz, DMSO-$d_6$): 1.71 (s, 3H), 4.20 (s, 3H), 4.76 (d, 1H), 4.89 (d, 1H), 6.87 (dd, J=9.0, 1.7 Hz, 1H), 7.51 (s, 1H), 7.86-7.91 (m, 3H), 7.97 (d, 2H) and 9.01 (s, 1H). 19F NMR (376 MHz, DMSO-$d_6$): −41.9 (s, 3F).

Example 118

N-[2-(5-Chloro-3-methoxy-2H-indazol-2-yl)-1-cyano-1-methylethyl]-4-trifluoromethoxybenzamide (compound No 2.012)

Using a procedure similar to that described in Example 1, except using 2-amino-3-(5-chloro-3-methoxy-2H-indazol-2-yl)-2-methylpropionitrile (57 mg), the title compound was isolated as a white solid (84 mg, 86%). MS (ES): M/Z [M+H]=453. 1H NMR: (400 MHz, DMSO-$d_6$): 1.70 (s, 3H), 4.18 (s, 3H), 4.77 (d, 1H), 4.90 (d, 1H), 7.16 (dd, J=9.3, 1.6 Hz, 1H), 7.46 (d, J=9.2 Hz, 1H), 7.52 (d, J=8.3 Hz, 2H), 7.94 (d, J=0.9 Hz, 1H), 7.98 (d, J=8.7 Hz, 2H) and 8.92 (s, 1H). 19F NMR (376 MHz, DMSO-$d_6$): −57.1 (s, 3F).

2-Amino-3-(5-chloro-3-methoxy-2H-indazol-2-yl)-2-methylpropionitrile (114 mg, 73%) was prepared using a procedure similar to that described in Example 1, part b, except starting from 1-(5-chloro-3-methoxy-2H-indazol-2-yl)propan-2-one (140 mg). 1-(5-chloro-3-methoxy-2H-indazol-2-yl)propan-2-one was prepared using a procedure similar to that described in Example 116 part a to d except using 5-chloro-2-nitrobenzaldehyde (2 g) and sodium triacetoxyborohydride (3.4 g) in part a to yield [2-(tert-butyldimethylsilanyloxy)propyl]-(5-chloro-2-nitrobenzyl)amine (2.2 g, 56%).

Example 119

N-[2-(5-Chloro-3-methoxy-2H-indazol-2-yl)-1-cyano-1-methylethyl]-4-trifluoromethylthiobenzamide (compound No 2.013)

Using a procedure similar to that described in Example 1, except using 2-amino-3-(5-chloro-3-methoxy-2H-indazol-2-yl)-2-methylpropionitrile (57 mg, described in Example 118) and 4-trifluoromethylthiobenzoyl chloride, the title compound was isolated as a white solid (96 mg, 95%). MS (ES): M/Z [M+H]=469. 1H NMR: (400 MHz, DMSO-$d_6$): 1.70 (s, 3H), 4.19 (s, 3H), 4.77 (d, 1H), 4.90 (d, 1H), 7.16 (d, J=9.2 Hz, 1H), 7.46 (d, J=9.4 Hz, 1H), 7.87 (d, J=8.0 Hz, 2H), 7.92-8.01 (m, 3H) and 9.00 (s, 1H). 19F NMR (376 MHz, DMSO-$d_6$): −41.9 (s, 3F).

Example 120

N-[2-(5-Chloro-3-ethoxy-2H-indazol-2-yl)-1-cyano-1-methylethyl]-4-trifluoromethoxybenzamide (compound No 2.014)

Using a procedure similar to that described in Example 1, except using 2-amino-3-(5-chloro-3-ethoxy-2H-indazol-2-yl)-2-methylpropionitrile (52 mg), the title compound was isolated as a white solid (85 mg, 97%). MS (ES): M/Z [M+H]=467. 1H NMR: (400 MHz, DMSO-$d_6$): 1.27 (t, J=7.0 Hz, 3H), 1.71 (s, 3H), 4.52 (q, J=6.9 Hz, 2H), 4.78 (d, 1H), 4.92 (d, 1H), 7.16 (dd, J=9.3, 2.0 Hz, 1H), 7.47 (d, J=9.3 Hz, 1H), 7.52 (d, J=8.2 Hz, 2H), 7.87 (d, J=1.5 Hz, 1H), 7.98 (d, J=8.8 Hz, 2H) and 8.91 (s, 1H). 19F NMR (376 MHz, DMSO-$d_6$): −57.1 (s, 3F).

2-Amino-3-(5-chloro-3-ethoxy-2H-indazol-2-yl)-2-methylpropionitrile (104 mg, 72%) was prepared using a procedure similar to that described in Example 1, part b, except starting from 1-(5-chloro-3-ethoxy-2H-indazol-2-yl)propan-2-one (131 mg). 1-(5-chloro-3-ethoxy-2H-indazol-2-yl)propan-2-one was prepared using a procedure similar to that described in Example 116 part a to d except using 5-chloro-2-nitrobenzaldehyde (2 g) and sodium triacetoxyborohydride (3.4 g) in part a and using ethanol instead of methanol in part b.

Example 121

N-[2-(5-Chloro-3-ethoxy-2H-indazol-2-yl)-1-cyano-1-methylethyl]-4-trifluoromethylthiobenzamide (compound No 2.015)

Using a procedure similar to that described in Example 1, except using 2-amino-3-(5-chloro-3-ethoxy-2H-indazol-2- yl)-2-methylpropionitrile (52 mg, described in Example 120) and 4-trifluoromethylthiobenzoyl chloride, the title compound was isolated as a white solid (83 mg, 93%). MS (ES): M/Z [M+H]=483. 1H NMR: (400 MHz, DMSO-d$_6$): 1.26 (t, J=7.0 Hz, 3H), 1.71 (s, 3H), 4.52 (q, J=7.0 Hz, 2H), 4.78 (d, 1H), 4.93 (d, 1H), 7.16 (dd, J=9.3, 1.9 Hz, 1H), 7.47 (d, J=9.3 Hz, 1H), 7.85-7.89 (m, 3H), 7.96 (d, J=8.8 Hz, 2H) and 8.99 (s, 1H). 19F NMR (376 MHz, DMSO-d$_6$): −42.0 (s, 3F).

Example 122

N-[1-Cyano-2-(3-methoxy-2H-indazol-2-yl)-1-methylethyl]-4-trifluoromethoxybenzamide (compound No 2.016)

Using a procedure similar to that described in Example 1, except using 2-amino-3-(3-methoxy-2H-indazol-2-yl)-2-methylpropionitrile (52 mg), the title compound was isolated as a white solid (140 mg, 77%). MS (ES): M/Z [M+H]=419. 1H NMR: (400 MHz, DMSO-d$_6$): 1.72 (s, 3H), 4.19 (s, 3H), 4.77 (d, 1H), 4.90 (d, 1H), 6.88 (d, J=1.2 Hz, 1H), 7.19 (d, J=6.7 Hz, 1H), 7.41 (d, J=8.9 Hz, 1H), 7.53 (d, J=8.2 Hz, 2H), 7.82 (d, J=8.6 Hz, 1H), 8.00 (d, J=8.7 Hz, 2H) and 8.95 (s, 1H). 19F NMR (376 MHz, DMSO-d$_6$): −57.1 (s, 3F).

2-Amino-3-(3-methoxy-2H-indazol-2-yl)-2-methylpropionitrile (130 mg, 83%) was prepared using a procedure similar to that described in Example 1, part b, except starting from 1-(3-methoxy-2H-indazol-2-yl)propan-2-one (138 mg). 1-(3-methoxy-2H-indazol-2-yl)propan-2-one was prepared using a procedure similar to that described in Example 116 part a to d except starting from 2-nitrobenzaldehyde (2.5 g) in part a.

Example 123

N-{2-[6-Chloro-3-(2-methoxyethoxy)-2H-indazol-2-yl]-1-cyano-1-methylethyl}-4-trifluoromethoxybenzamide (compound No 2.017)

Using a procedure similar to that described in Example 1, except using 2-amino-3-[6-chloro-3-(2-methoxyethoxy)-2H-indazol-2-yl]-2-methylpropionitrile (60 mg), the title compound was isolated as a white solid (41 mg, 43%). MS (ES): M/Z [M+H]=497. 1H NMR: (400 MHz, DMSO-d$_6$): 1.70 (s, 3H), 3.27 (s, 3H), 3.61 (dd, J=5.2, 3.7 Hz, 2H), 4.58 (dd, J=4.9, 3.9 Hz, 2H), 4.79 (d, 1H), 4.92 (d, 1H), 6.90 (dd, J=9.0, 1.8 Hz, 1H), 7.53-7.55 (m, 3H), 7.82 (d, J=9.1 Hz, 1H), 7.98 (d, 2H) and 8.93 (s, 1H). 19F NMR (376 MHz, DMSO-d$_6$): −57.1 (s, 3F).

2-Amino-3-[6-chloro-3-(2-methoxyethoxy)-2H-indazol-2-yl]-2-methylpropionitrile (60 mg, 61%) was prepared using a procedure similar to that described in Example 1, part b, except starting from 1-[6-chloro-3-(2-methoxyethoxy)-2H-indazol-2-yl]propan-2-one (90 mg). 1-[6-Chloro-3-(2-methoxyethoxy)-2H-indazol-2-yl]propan-2-one was prepared using a procedure similar to that described in Example 116 part a to d except using 2-methoxyethanol instead of methanol in part b.

Example 124

N-{2-[6-Chloro-3-(2-dimethylaminoethoxy)-2H-indazol-2-yl]-1-cyano-1-methylethyl}-4-trifluoromethoxybenzamide (compound No 2.018)

Using a procedure similar to that described in Example 1, except using 2-amino-3-[6-chloro-3-(2-dimethylaminoethoxy)-2H-indazol-2-yl]-2-methylpropionitrile (60 mg), the title compound was isolated as a white solid (44 mg, 46%). MS (ES): M/Z [M+H]=510. 1H NMR: (400 MHz, CHLOROFORM-d): 1.90 (s, 3H), 2.43 (s, 6H), 2.85 (dd, J=5.8, 4.8 Hz, 1H), 2.95 (dd, J=6.9, 4.8 Hz, 1H), 4.52 (d, J=14.2 Hz, 1H), 4.69 (ddd, J=10.3, 5.7, 4.9 Hz, 1H), 4.80 (ddd, J=10.2, 6.9, 4.7 Hz, 1H), 4.90 (d, J=14.2 Hz, 1H), 6.92 (dd, J=9.1, 1.7 Hz, 1H), 7.32 (d, J=8.0 Hz, 2H), 7.47 (dd, J=1.6, 0.6 Hz, 1H), 7.64 (dd, J=9.0, 0.6 Hz, 1H) and 9.00 (s, 1H). 19F NMR (376 MHz, CHLOROFORM-d): −58.1 (s, 3F).

2-Amino-3-[6-chloro-3-(2-dimethylaminoethoxy)-2H-indazol-2-yl]-2-methylpropionitrile (127 mg, 78%) was prepared using a procedure similar to that described in Example 1, part b, except starting from 1-[6-chloro-3-(2-dimethylaminoethoxy)-2H-indazol-2-yl]propan-2-one (150 mg). 1-[6-Chloro-3-(2-dimethylaminoethoxy)-2H-indazol-2-yl]propan-2-one was prepared using a procedure similar to that described in Example 116 part a to d except using 2-dimethylaminoethanol instead of methanol in part b.

Example 125

N-[1-Cyano-2-(5,7-dichloro-3-methoxy-2H-indazol-2-yl)-1-methylethyl]-4-trifluoromethoxybenzamide (compound No 2.020)

Using a procedure similar to that described in Example 1, except using 2-amino-3-(5,7-dichloro-3-methoxy-2H-indazol-2-yl)-2-methylpropionitrile (196 mg), the title compound was isolated as a white solid (147 mg, 46%). MS (ES): M/Z [M+H]=487. 1H NMR: (400 MHz, CHLOROFORM-d): 1.96 (s, 3H), 4.42 (s, 3H), 4.53 (d, J=14.2 Hz, 1H), 4.88 (d, J=14.2 Hz, 1H), 7.31 (d, 2H), 7.35 (d, J=1.7 Hz, 1H), 7.68 (d, J=1.7 Hz, 1H), 8.01-8.10 (m, 2H) and 9.13 (s, 1H). 19F NMR (376 MHz, CHLOROFORM-d): −58.1 (s, 3F).

2-Amino-3-(5,7-dichloro-3-methoxy-2H-indazol-2-yl)-2-methylpropionitrile was prepared using a procedure similar to that described in Example 1, part b, except starting from 1-(5,7-dichloro-3-methoxy-2H-indazol-2-yl)propan-2-one. 1-(4,6-dichloro-3-methoxy-2H-indazol-2-yl)propan-2-one was prepared using a procedure similar to that described in Example 116 part a to d except using 3,5-dichloro-2-nitrobenzaldehyde (2.1 g) and decaborane (0.41 g) in part a to yield [2-(tert-butyldimethylsilanyloxy)propyl]-(3,5-dichloro-2-nitrobenzyl)amine (1.2 g, 32%). 3,5-Dichloro-2-nitrobenzaldehyde (2.2 g, 79%) was prepared by nitration of 3,5-dichlorobenzaldehyde (2.2 g) in a mixture of nitric acid (1.5 mL) and sulfuric acid (8 mL) at 0° C. for 30 minutes.

Example 126

N-[1-Cyano-2-(5,7-dichloro-3-methoxy-2H-indazol-2-yl)-1-methylethyl]-4-trifluoromethylthiobenzamide (compound No 2.019)

Using a procedure similar to that described in Example 1, except using 2-amino-3-(5,7-dichloro-3-methoxy-2H-indazol-2-yl)-2-methylpropionitrile (181 mg, described in Example 125) and 4-trifluoromethylthiobenzoyl chloride, the title compound was isolated as a white solid (161 mg, 51%). MS (ES): M/Z [M+H]=503. 1H NMR: (400 MHz, CHLOROFORM-d): 1.96 (s, 3H), 4.42 (s, 3H), 4.53 (d, J=14.2 Hz, 1H), 4.88 (d, J=14.2 Hz, 1H), 7.35 (d, J=1.7 Hz, 1H), 7.68 (d, J=1.7 Hz, 1H), 7.75 (d, J=8.2 Hz, 2H), 8.02-8.09 (m, 2H) and 9.21 (s, 1H). 19F NMR (376 MHz, CHLOROFORM-d): −42.4 (s, 3F).

Example 127

N-[1-Cyano-2-(4,6-dichloro-3-methoxy-2H-indazol-2-yl)-1-methylethyl]-4-trifluoromethoxybenzamide (compound No 2.021)

Using a procedure similar to that described in Example 1, except using 2-amino-3-(4,6-dichloro-3-methoxy-2H-indazol-2-yl)-2-methylpropionitrile (30 mg), the title compound was isolated as a white solid (45 mg, 92%). MS (ES): M/Z [M+H]=487. 1H NMR: (400 MHz, DMSO-$d_6$): 1.75 (s, 3H), 4.12 (s, 3H), 4.94 (s, 2H), 7.17 (d, J=1.3 Hz, 1H), 7.53 (d, J=8.2 Hz, 2H), 7.63 (d, J=1.2 Hz, 1H), 7.98 (d, J=8.7 Hz, 2H) and 8.95 (s, 1H). 19F NMR (376 MHz, DMSO-$d_6$): −57.1 (s, 3F).

2-Amino-3-(4,6-dichloro-3-methoxy-2H-indazol-2-yl)-2-methylpropionitrile (60 mg, 32%) was prepared using a procedure similar to that described in Example 1, part b, except starting from 1-(4,6-dichloro-3-methoxy-2H-indazol-2-yl)propan-2-one (170 mg). 1-(4,6-dichloro-3-methoxy-2H-indazol-2-yl)propan-2-one was prepared using a procedure similar to that described in Example 116 part a to d except using 2,4-dichloro-6-nitrobenzaldehyde (1 g) in part a to yield [2-(tert-butyldimethylsilanyloxy)propyl]-(2,4-dichloro-6-nitrobenzyl)amine (0.6 g, 37%). 2,4-Dichloro-6-nitrobenzaldehyde was prepared as follows:

a. To a solution of 1,3-dichloro-5-nitrobenzene (7.7 g) and chloroform (4 mL) in a mixture of THF and DMF (1:1.5, 100 mL), was slowly added at −78° C. a one molar solution of sodium hexamethyldisilazane (NaHMDS) in THF (7.7 mL). After stirring for 30 minutes, the reaction was quenched at −78° C. with a methanolic solution of hydrochloric acid and let warm to room temperature. The reaction mixture was extracted with ethyl acetate. The organic phase was dried over anhydrous magnesium sulfate, filtered and concentrated under reduced pressure to yield a residue that contained 70% of 1,5-dichloro-2-dichloromethyl-3-nitrobenzene.

b. A mixture of 1,5-dichloro-2-dichloromethyl-3-nitrobenzene (5.8 g, 70% pure) and zinc dichloride in formic acid (85%) was heated under reflux for 14 hours. The reaction mixture was concentrated under reduced pressure to yield a residue that was poured into water and extracted with ethyl acetate. The organic phase was dried over anhydrous magnesium sulfate, filtered and concentrated under reduced pressure to yield a residue that was purified by chromatography (SiO$_2$, heptane/EA) to afford 2,4-dichloro-6-nitrobenzaldehyde as a solid (2.9 g, 87% pure). 1H NMR: (400 MHz, CHLOROFORM-d): 7.76 (d, J=1.9 Hz, 1H), 7.93 (d, J=1.9 Hz, 1H) and 10.32 (s, 1H).

Example 128

N-[1-Cyano-2-(4,6-dichloro-3-methoxy-2H-indazol-2-yl)-1-methylethyl]-4-trifluoromethylthiobenzamide (compound No 2.022)

Using a procedure similar to that described in Example 1, except using 2-amino-3-(4,6-dichloro-3-methoxy-2H-indazol-2-yl)-2-methylpropionitrile (30 mg, described in Example 127) and 4-trifluoromethylthiobenzoyl chloride, the title compound was isolated as a white solid (42 mg, 83%). MS (ES): M/Z [M+H]=503. 1H NMR: (400 MHz, DMSO-$d_6$): 1.75 (s, 3H), 4.12 (s, 3H), 4.94 (d, J=6.5 Hz, 2H), 7.17 (d, J=1.2 Hz, 1H), 7.62 (d, J=1.1 Hz, 1H), 7.86-7.91 (m, 2H), 7.93-7.99 (m, 2H) and 9.03 (s, 1H). 19F NMR (376 MHz, DMSO-$d_6$): −41.9 (s, 3F).

Example 129

N-[2-(6-Bromo-3-methoxy-2H-indazol-2-yl)-1-cyano-1-methylethyl]-4-trifluoromethoxybenzamide (compound No 2.023)

Using a procedure similar to that described in Example 1, except using 2-amino-3-(6-bromo-3-methoxy-2H-indazol-2-yl)-2-methylpropionitrile (50 mg), the title compound was isolated as a white solid (73 mg, 90%). MS (ES): M/Z [M+H]=497. 1H NMR: (400 MHz, DMSO-$d_6$): 1.71 (s, 3H), 4.19 (s, 3H), 4.76 (d, 1H), 4.88 (d, 1H), 6.97 (dd, J=9.0, 1.4 Hz, 1H), 7.53 (d, J=8.3 Hz, 2H), 7.68 (d, J=0.8 Hz, 1H), 7.83 (d, J=9.1 Hz, 1H), 7.98 (d, J=8.7 Hz, 2H) and 8.92 (s, 1H). 19F NMR (376 MHz, DMSO-$d_6$): −57.1 (s, 3F).

2-Amino-3-(6-bromo-3-methoxy-2H-indazol-2-yl)-2-methylpropionitrile was prepared using a procedure similar to that described in Example 1, part b, except starting from 1-(6-bromo-3-methoxy-2H-indazol-2-yl)propan-2-one. 1-(6-bromo-3-methoxy-2H-indazol-2-yl)propan-2-one was prepared using a procedure similar to that described in Example 116 part a to d except using 4-bromo-2-nitrobenzaldehyde (5.1 g) and decaborane (0.81 g) in part a to yield [2-(tert-butyldimethylsilanyloxy)propyl]-(4-bromo-2-nitrobenzyl)amine (3.4 g).

Example 130

N-[2-(6-Bromo-3-methoxy-2H-indazol-2-yl)-1-cyano-1-methylethyl]-4-trifluoromethylthiobenzamide (compound No 2.024)

Using a procedure similar to that described in Example 1, except using 2-amino-3-(6-bromo-3-methoxy-2H-indazol-2-yl)-2-methylpropionitrile (50 mg, described in Example 129) and 4-trifluoromethylthiobenzoyl chloride, the title compound was isolated as a white solid (80 mg, 96%). MS (ES): M/Z [M+H]=513. 1H NMR: (400 MHz, DMSO-$d_6$): 1.71 (s, 3H), 4.19 (s, 3H), 4.77 (d, 1H), 4.89 (d, 1H), 6.97 (dd, J=9.1, 1.5 Hz, 1H), 7.68 (d, J=0.9 Hz, 1H), 7.83 (d, J=9.1 Hz, 1H), 7.86-7.91 (m, 2H), 7.94-7.99 (m, 2H) and 9.00 (s, 1H). 19F NMR (376 MHz, DMSO-$d_6$): −41.9 (s, 3F).

Example 131

N-[1-Cyano-2-(3-methoxy-6-trifluoromethyl-2H-indazol-2-yl)-1-methylethyl]-4-trifluoromethoxybenzamide (compound No 2.025)

Using a procedure similar to that described in Example 1, except using 2-amino-3-(3-methoxy-6-trifluoromethyl-2H-indazol-2-yl)-2-methylpropionitrile (50 mg), the title compound was isolated as a white solid (62 mg, 77%). MS (ES): M/Z [M+H]=487. 1H NMR: (400 MHz, DMSO-$d_6$): 1.72 (s, 3H), 4.23 (s, 3H), 4.85 (d, 1H), 4.97 (d, 1H), 7.08 (dd, J=9.0, 1.1 Hz, 1H), 7.53 (d, J=8.2 Hz, 2H), 7.86 (s, 1H), 7.99 (d, J=8.8 Hz, 2H), 8.09 (d, J=9.0 Hz, 1H) and 8.92 (s, 1H). 19F NMR (376 MHz, DMSO-$d_6$): −61.8 (s, 3F) and −57.1 (s, 3F).

2-Amino-3-(3-methoxy-6-trifluoromethyl-2H-indazol-2-yl)-2-methylpropionitrile was prepared using a procedure similar to that described in Example 1, part b, except starting from 1-(3-methoxy-6-trifluoromethyl-2H-indazol-2-yl)propan-2-one. 1-(3-methoxy-6-trifluoromethyl-2H-indazol-2- yl)propan-2-one was prepared using a procedure similar to that described in Example 116 part a to d except using 2-nitro-4-(trifluoromethyl)benzaldehyde (1 g) in part a to yield [2-(tert-butyldimethylsilanyloxy)propyl]-[2-nitro-4-(trifluoromethyl)benzyl]amine (0.6 g, 33%).

Example 132

N N-[1-Cyano-2-(3-methoxy-6-trifluoromethyl-2H-indazol-2-yl)-1-methylethyl]-4-trifluoromethylthiobenzamide (compound No 2.026)

Using a procedure similar to that described in Example 1, except using 2-amino-3-(3-methoxy-6-trifluoromethyl-2H-indazol-2-yl)-2-methylpropionitrile (50 mg, described in Example 131) and 4-trifluoromethylthiobenzoyl chloride, the title compound was isolated as a white solid (66 mg, 78%). MS (ES): M/Z [M+H]=503. 1H NMR: (400 MHz, DMSO-d$_6$): 1.72 (s, 3H), 4.24 (s, 3H), 4.84 (d, J=13.8 Hz, 1H), 4.96 (d, J=13.9 Hz, 1H), 7.08 (dd, J=9.0, 1.4 Hz, 1H), 7.85 (s, 1H), 7.88 (d, J=8.2 Hz, 2H), 7.94-7.99 (m, 2H), 8.09 (d, J=9.0 Hz, 1H) and 8.99 (s, 1H). 19F NMR (376 MHz, DMSO-d$_6$): −42.0 (s, 3F) and −61.8 (s, 3F).

Example 133

N-[2-(6-Chloro-3-ethoxy-2H-indazol-2-yl)-1-cyano-1-methylethyl]-4-trifluoromethoxybenzamide (compound No 2.027)

Using a procedure similar to that described in Example 1, except using 2-amino-3-(6-chloro-3-ethoxy-2H-indazol-2-yl)-2-methylpropionitrile (113 mg), the title compound was isolated as a white solid (95 mg, 50%). MS (ES): M/Z [M+H]=467. 1H NMR: (400 MHz, CHLOROFORM-d): 1.58 (t, J=7.1 Hz, 3H), 1.91 (s, 3H), 4.50 (d, J=14.2 Hz, 1H), 4.63-4.81 (m, 2H), 4.83 (d, J=14.1 Hz, 1H), 6.92 (dd, J=9.1, 1.7 Hz, 1H), 7.34 (d, J=8.1 Hz, 2H), 7.46 (d, J=1.1 Hz, 1H), 7.62 (d, J=9.1 Hz, 1H), 7.89-8.02 (m, 2H) and 9.07 (s, 1H). 19F NMR (376 MHz, CHLOROFORM-d): −58.1 (s, 3F).

2-Amino-3-(6-chloro-3-ethoxy-2H-indazol-2-yl)-2-methylpropionitrile (221 mg, 95%) was prepared using a procedure similar to that described in Example 1, part b, except starting from 1-(6-chloro-3-ethoxy-2H-indazol-2-yl)propan-2-one (210 mg). 1-(6-chloro-3-ethoxy-2H-indazol-2-yl)propan-2-one was prepared using a procedure similar to that described in Example 116 part a to d except using 4-chloro-2-nitrobenzaldehyde (21.7 g) and decaborane (4.2 g) in part a and using ethanol instead of methanol in part b.

Example 134

N-[2-(6-Chloro-3-ethoxy-2H-indazol-2-yl)-1-cyano-1-methylethyl]-4-trifluoromethylthiobenzamide (compound No 2.028)

Using a procedure similar to that described in Example 1, except using 2-amino-3-(6-chloro-3-ethoxy-2H-indazol-2-yl)-2-methylpropionitrile (108 mg, described in Example 133) and 4-trifluoromethylthiobenzoyl chloride, the title compound was isolated as a white solid (96 mg, 51%). MS (ES): M/Z [M+H]=483. 1H NMR: (400 MHz, CHLOROFORM-d): 1.59 (t, J=7.0 Hz, 3H), 1.91 (s, 3H), 4.50 (d, J=14.2 Hz, 1H), 4.63-4.81 (m, 2H), 4.83 (d, J=14.2 Hz, 1H), 6.92 (dd, J=9.1, 1.7 Hz, 1H), 7.47 (d, J=1.2 Hz, 1H), 7.62 (d, J=9.0 Hz, 1H), 7.79 (d, J=8.3 Hz, 2H), 7.90-7.99 (m, 2H) and 9.15 (s, 1H). 19F NMR (376 MHz, CHLOROFORM-d): −42.3 (s, 3F).

Example 135

N-[2-(6-Chloro-3-propoxy-2H-indazol-2-yl)-1-cyano-1-methylethyl]-4-trifluoromethoxybenzamide (compound No 2.029)

Using a procedure similar to that described in Example 1, except using 2-amino-3-(6-chloro-3-propoxy-2H-indazol-2-yl)-2-methylpropionitrile (103 mg), the title compound was isolated as a white solid (104 mg, 54%). MS (ES): M/Z [M+H]=481. 1H NMR: (400 MHz, CHLOROFORM-d): 1.14 (t, J=7.4 Hz, 3H), 1.90 (s, 3H), 1.92-2.03 (m, 2H), 4.51 (d, J=14.1 Hz, 1H), 4.55-4.69 (m, 2H), 4.81 (d, J=14.1 Hz, 1H), 6.91 (dd, J=9.1, 1.7 Hz, 1H), 7.34 (dd, J=8.8, 0.8 Hz, 2H), 7.46 (dd, J=1.7, 0.6 Hz, 1H), 7.62 (dd, J=9.1, 0.6 Hz, 1H), 7.90-8.01 (m, 2H) and 9.10 (s, 1H). 19F NMR (376 MHz, CHLOROFORM-d): −58.1 (s, 3F).

2-Amino-3-(6-chloro-3-propoxy-2H-indazol-2-yl)-2-methylpropionitrile (207 mg, 92%) was prepared using a procedure similar to that described in Example 1, part b, except starting from 1-(6-chloro-3-propoxy-2H-indazol-2-yl)propan-2-one (205 mg). 1-(6-chloro-3-propoxy-2H-indazol-2-yl)propan-2-one was prepared using a procedure similar to that described in Example 116 part a to d except using 4-chloro-2-nitrobenzaldehyde (21.7 g) and decaborane (4.2 g) in part a and using n-propanol instead of methanol in part b.

Example 136

N-[2-(6-Chloro-3-propoxy-2H-indazol-2-yl)-1-cyano-1-methylethyl]-4-trifluoromethylthiobenzamide (compound No 2.030)

Using a procedure similar to that described in Example 1, except using 2-amino-3-(6-chloro-3-propoxy-2H-indazol-2-yl)-2-methylpropionitrile (104 mg, described in Example 135) and 4-trifluoromethylthiobenzoyl chloride, the title compound was isolated as a white solid (88 mg, 46%). MS (ES): M/Z [M+H]=497. 1H NMR: (400 MHz, CHLOROFORM-d): 1.14 (t, J=7.4 Hz, 3H), 1.90 (s, 3H), 1.92-2.04 (m, 2H), 4.51 (d, J=14.2 Hz, 1H), 4.56-4.70 (m, 2H), 4.82 (d, J=14.2 Hz, 1H), 6.92 (dd, J=9.1, 1.7 Hz, 1H), 7.47 (d, J=1.7 Hz, 1H), 7.62 (dd, J=9.1, 0.5 Hz, 1H), 7.79 (dd, J=8.3 Hz, 2H), 7.91-7.99 (m, 2H) and 9.17 (s, 1H). 19F NMR (376 MHz, CHLOROFORM-d): −42.3 (s, 3F).

Example 137

N-[2-(6-Chloro-3-butoxy-2H-indazol-2-yl)-1-cyano-1-methylethyl]-4-trifluoromethoxybenzamide (compound No 2.031)

Using a procedure similar to that described in Example 1, except using 2-amino-3-(6-chloro-3-butoxy-2H-indazol-2-yl)-2-methylpropionitrile (88 mg), the title compound was isolated as a white solid (60 mg, 43%). MS (ES): M/Z [M+H]=495. 1H NMR: (400 MHz, CHLOROFORM-d): 1.04 (t, J=7.4 Hz, 3H), 1.51-1.65 (m, 2H), 1.89 (s, 3H), 1.89-1.98 (m, 2H), 4.51 (d, J=14.2 Hz, 1H), 4.57-4.73 (m, 2H), 4.81 (d, J=14.2 Hz, 1H), 6.91 (dd, J=9.1, 1.7 Hz, 1H), 7.34 (d, J=8.0 Hz, 2H), 7.46 (d, J=1.1 Hz, 1H), 7.62 (dd, J=9.1, 0.5 Hz, 1H), 7.91-8.00 (m, 2H) and 9.09 (s, 1H). 19F NMR (376 MHz, CHLOROFORM-d): −58.1 (s, 3F).

2-Amino-3-(6-chloro-3-butoxy-2H-indazol-2-yl)-2-methylpropionitrile (88 mg) was prepared using a procedure similar to that described in Example 1, part b, except starting from 1-(6-chloro-3-butoxy-2H-indazol-2-yl)propan-2-one (79 mg). 1-(6-chloro-3-butoxy-2H-indazol-2-yl)propan-2-one was prepared using a procedure similar to that described in Example 116 part a to d except using 4-chloro-2-nitrobenzaldehyde (21.7 g) and decaborane (4.2 g) in part a and using n-butanol instead of methanol in part b.

Example 138

Methyl 2-[2-cyano-2-methyl-2-(4-trifluoromethoxybenzoylamino)ethyl]-3-methoxy-2H-indazole-6-carboxylate (compound No 2.032)

Using a procedure similar to that described in Example 1, except using methyl 2-(2-amino-2-cyano-2-methylethyl)-3-methoxy-2H-indazole-6-carboxylate (88 mg), the title compound was isolated as a white solid (126 mg, 86%). MS (ES): M/Z [M+H]=477. 1H NMR: (400 MHz, DMSO-$d_6$): 1.72 (s, 3H), 3.87 (s, 3H), 4.21 (s, 3H), 4.83 (d, 1H), 4.97 (d, 1H), 7.37 (d, J=8.9 Hz, 1H), 7.53 (d, J=8.3 Hz, 2H), 7.93-8.03 (m, 3H), 8.07 (s, 1H) and 8.92 (s, 1H). 19F NMR (376 MHz, DMSO-$d_6$): −57.1 (s, 3F).

Methyl 2-(2-amino-2-cyano-2-methylethyl)-3-methoxy-2H-indazole-6-carboxylate was prepared using a procedure similar to that described in Example 1, part b, except starting from methyl 3-methoxy-2-(2-oxo-propyl)-2H-indazole-6-carboxylate. 1 Methyl 3-methoxy-2-(2-oxo-propyl)-2H-indazole-6-carboxylate was prepared using a procedure similar to that described in Example 116 part a to d except using methyl 4-formyl-3-nitrobenzoate (2 g) in part a to yield methyl 4-{[2-(tert-butyldimethylsilanyloxy)propylamino]-methyl}-3-nitrobenzoate (2.83 g, 77%). In the basic cyclisation step in part b, desired methyl 2-[2-(tert-butyldimethylsilanyloxy)-propyl]-3-methoxy-2H-indazole-6-carboxylate (230 mg) was isolated along with 2-[2-(tert-butyldimethylsilanyloxy)propyl]-3-hydroxy-2H-indazole-6-carboxylic acid (781 mg).

Example 139

N-[1-Cyano-2-(3-methoxy-6-nitro-2H-indazol-2-yl)-1-methylethyl]-4-trifluoromethoxybenzamide (compound No 2.033)

Using a procedure similar to that described in Example 1, except using 2-amino-3-(3-methoxy-6-nitro-2H-indazol-2-yl)-2-methylpropionitrile (63 mg), the title compound was isolated as a white solid (84 mg, 79%). MS (ES): M/Z [M+H]=464. 1H NMR: (400 MHz, DMSO-$d_6$): 1.73 (s, 3H), 4.25 (s, 3H), 4.88 (d, 1H), 5.00 (d, 1H), 7.53 (d, J=8.3 Hz, 2H), 7.61 (dd, J=9.3, 1.9 Hz, 1H), 7.99 (d, J=8.7 Hz, 2H), 8.12 (d, J=9.3 Hz, 1H), 8.42 (d, J=1.6 Hz, 1H) and 8.93 (s, 1H). 19F NMR (376 MHz, DMSO-$d_6$): −57.1 (s, 3F).

2-Amino-3-(3-methoxy-6-nitro-2H-indazol-2-yl)-2-methylpropionitrile was prepared using a procedure similar to that described in Example 1, part b, except starting from 1-(3-methoxy-6-nitro-2H-indazol-2-yl)propan-2-one. 1-(3-Methoxy-6-nitro-2H-indazol-2-yl)propan-2-one was prepared using a procedure similar to that described in Example 116 part a to d except using 2,4-dinitrobenzaldehyde (2 g) in part a to yield [2-(tert-butyldimethylsilanyloxy)propyl]-(2,4-dinitrobenzyl)amine (2.6 g, 64%).

Example 140

N-[2-(6-Amino-3-methoxy-2H-indazol-2-yl)-1-cyano-1-methylethyl]-4-trifluoromethoxybenzamide (compound No 2.034)

A mixture of N-[1-cyano-2-(3-methoxy-6-nitro-2H-indazol-2-yl)-1-methylethyl]-4-trifluoromethoxybenzamide (30 mg) described in Example 139 and palladium on charcoal in methanol (2 mL) were stirred at room temperature under hydrogen for 2.5 hours. The reaction mixture was filtered through a plug of Celite® and concentrated under reduced pressure to yield a residue that was purified by chromatography (SiO$_2$, heptane/EA) to afford the title compound as a white solid (18 mg, 64%). MS (ES): M/Z [M+H]=434. 1H NMR: (400 MHz, CHLOROFORM-d): 1.88 (s, 3H), 4.38 (s, 3H), 4.41 (d, 1H), 4.72 (d, J=14.2 Hz, 1H), 6.48 (dd, J=9.0, 1.8 Hz, 1H), 6.53 (d, J=1.2 Hz, 1H), 7.31 (d, J=8.3 Hz, 2H), 7.55 (d, J=9.0 Hz, 1H), 7.98 (d, J=8.8 Hz, 2H) and 9.43 (s, 1H). 19F NMR (376 MHz, CHLOROFORM-d): −58.0 (s, 3F).

Example 141

N-[2-(6-Acetylamino-3-methoxy-2H-indazol-2-yl)-1-cyano-1-methylethyl]-4-trifluoromethoxybenzamide (compound No 2.035)

Using a procedure similar to that described in Example 1, except using N-[2-(6-amino-3-methoxy-2H-indazol-2-yl)-1-cyano-1-methylethyl]-4-trifluoromethoxybenzamide (23 mg, described in Example 140) and acetyl chloride, the title compound was isolated as a white solid (8 mg, 32%). MS (ES): M/Z [M+H]=476. 1H NMR: (400 MHz, DMSO-$d_6$): 1.71 (s, 3H), 2.05 (s, 3H), 4.16 (s, 3H), 4.71 (d, 1H), 4.82 (d, 1H), 6.88 (dd, J=9.2, 1.6 Hz, 1H), 7.52 (d, J=8.0 Hz, 2H), 7.74 (d, J=9.1 Hz, 1H), 7.86 (s, 1H), 7.99 (d, J=8.8 Hz, 2H), 8.95 (s, 1H) and 9.89 (s, 1H). 19F NMR (376 MHz, DMSO-$d_6$): −57.1 (s, 3F).

Example 142

Methyl 2-[2-cyano-2-methyl-2-(4-trifluoromethoxybenzoylamino)ethyl]-3-methoxy-2H-indazole-6-carboxamide (compound No 2.036)

A solution of methyl 2-[2-cyano-2-methyl-2-(4-trifluoromethoxybenzoylamino)ethyl]-3-methoxy-2H-indazole-6-carboxylate (50 mg, described in Example 138) in methanol (3 mL) was stirred with ammonium hydroxide (1.5 mL) at room temperature for 8 days. The reaction mixture was concentrated under reduced pressure to yield a residue that was purified by chromatography (SiO$_2$, heptane/EA) to afford the title compound as a white solid (3 mg). MS (ES): M/Z [M+H]=462. 1H NMR: (400 MHz, METHANOL-$d_4$): 1.81 (s, 3H), 4.32 (s, 3H), 4.82 (d, 1H), 5.08 (d, J=14.0 Hz, 1H), 7.38 (dd, J=9.0, 1.4 Hz, 1H), 7.42 (d, J=8.6 Hz, 2H), 7.90 (d, J=9.0 Hz, 1H), 7.97 (d, J=8.9 Hz, 2H) and 7.99 (s, 1H). 19F NMR (376 MHz, METHANOL-$d_4$): −59.8 (s, 3F).

Compounds of Examples 143 to 156 were prepared according to the following general reaction scheme:

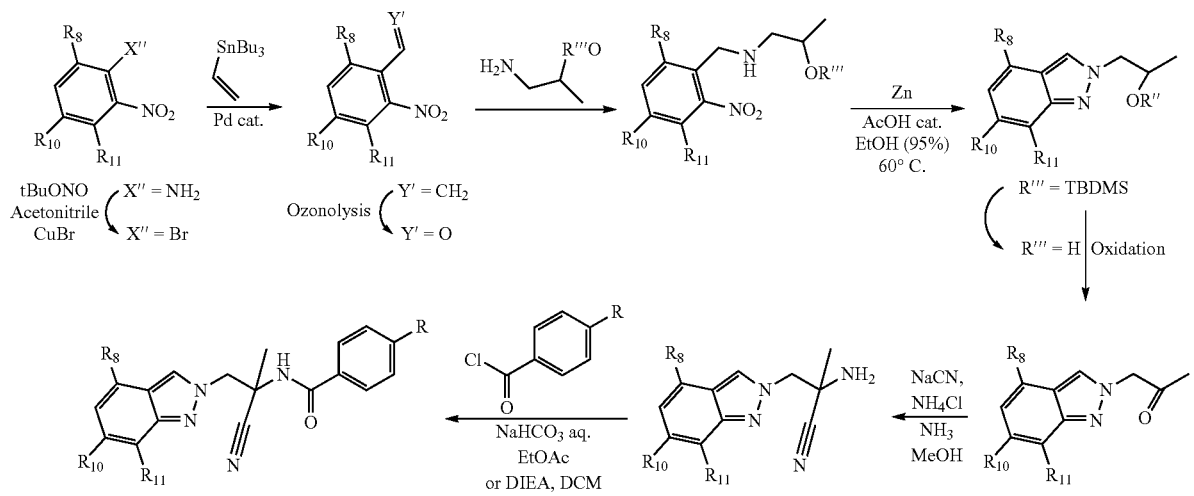

Final Product
V=C—R$_8$; W=C—H; X=C—R$_{10}$; Y C—R$_{11}$;
Q=C—H; P=N;
R$_3$=R$_4$=H; a=1; R$_5$=CH$_3$, R$_6$=H;
Z=C(O); R$_7$=p-phenyl-R It will be apparent to one of skill in the art that modified derivatives with variable substitution on the phenyl ring may also be made by starting the corresponding substituted benzoic acid chloride.

Example 143

N-[2-(6-Chloro-2H-indazol-2-yl)-1-cyano-1-methylethyl]-4-trifluoromethoxybenzamide (compound No 2.037)

Using a procedure similar to that described in Example 1, except using 2-amino-3-(6-chloro-2H-indazol-2-yl)-2-methylpropionitrile (20 mg), the title compound was isolated as a white solid (34 mg, 93%). MS (ES): M/Z [M+H]=423. 1H NMR: (400 MHz, CHLOROFORM-d): 1.95 (s, 3H), 4.81 (d, 1H), 4.89 (d, 1H), 7.11 (dd, J=8.9, 1.7 Hz, 1H), 7.33 (d, J=8.4 Hz, 2H), 7.65 (d, J=8.9 Hz, 1H), 7.69 (s, 1H), 7.90 (d, J=8.7 Hz, 2H), 8.17 (s, 1H) and 8.49 (s, 1H). 19F NMR (376 MHz, CHLOROFORM-d): −58.1 (s, 3F).

2-Amino-3-(6-chloro-2H-indazol-2-yl)-2-methylpropionitrile (54 mg, 79%) was prepared using a procedure similar to that described in Example 1, part b, except starting from 1-(6-chloro-2H-indazol-2-yl)propan-2-one (68 mg). 1-(6-Chloro-2H-indazol-2-yl)propan-2-one was prepared using a procedure similar to that described in Example 116 part c and d except starting from 2-[2-(tert-butyldimethylsilanyloxy)propyl]-6-chloro-2H-indazole that was prepared as follows:

a. A mixture of [2-(tert-butyldimethylsilanyloxy)propyl]-(4-chloro-2-nitrobenzyl)amine (4.6 g, described in Example 116 part a), and zinc (2 g) in ethanol (95%, 20 mL) and one drop of acetic acid was heated to 60° C. for 24 hours. The reaction mixture was filtered through a plug of Celite® and concentrated under reduced pressure to yield a residue that was purified by chromatography (SiO$_2$, heptane/EA) to afford 2-[2-(tert-butyldimethylsilanyloxy)propyl]-6-chloro-2H-indazole as a white solid (0.9 g, 22%) along with recovered starting material (2.2 g, 48%).

Example 144

N-[2-(6-Chloro-2H-indazol-2-yl)-1-cyano-1-methylethyl]-4-trifluoromethylthiobenzamide (compound No 2.038)

Using a procedure similar to that described in Example 1, except using 2-amino-3-(6-chloro-2H-indazol-2-yl)-2-methylpropionitrile (20 mg, described in Example 143) and 4-trifluoromethylthiobenzoyl chloride, the title compound was isolated as a white solid (37 mg, 98%). MS (ES): M/Z [M+H]=439. 1H NMR: (400 MHz, CHLOROFORM-d): 1.95 (s, 3H), 4.81 (d, 1H), 4.89 (d, 1H), 7.12 (dd, J=9.0, 1.6 Hz, 1H), 7.65 (d, J=9.0, 1H), 7.69 (s, 1H), 7.78 (d, J=8.3 Hz, 2H), 7.89 (d, J=8.3 Hz, 2H), 8.18 (s, 1H) and 8.58 (s, 1H). 19F NMR (376 MHz, CHLOROFORM-d): −42.2 (s, 3F).

Example 145

N-[1-Cyano-2-(4,6-dichloro-2H-indazol-2-yl)-1-methylethyl]-4-trifluoromethoxybenzamide (compound No 2.040)

Using a procedure similar to that described in Example 1, except using 2-amino-3-(4,6-dichloro-2H-indazol-2-yl)-2-methylpropionitrile (20 mg), the title compound was isolated as a white solid (31 mg, 91%). MS (ES): M/Z [M+H]=457. 1H NMR: (400 MHz, CHLOROFORM-d): 1.96 (s, 3H), 4.82 (d, 1H), 4.92 (d, 1H), 7.15 (d, J=1.3 Hz, 1H), 7.34 (d, J=8.2 Hz, 2H), 7.60 (s, 1H), 7.89 (d, J=8.8 Hz, 2H) and 8.22 (s, 2H). 19F NMR (376 MHz, CHLOROFORM-d): −58.1 (s, 3F).

2-Amino-3-(4,6-dichloro-2H-indazol-2-yl)-2-methylpropionitrile (88 mg, 54%) was prepared using a procedure similar to that described in Example 1, part b, except starting from 1-(4,6-dichloro-2H-indazol-2-yl)propan-2-one (146 mg). 1-(4,6-Dichloro-2H-indazol-2-yl)propan-2-one was prepared using a procedure similar to that described in Example 116 part c and d except starting from 2-[2-(tert-butyldimethylsilanyloxy)propyl]-4,6-dichloro-2H-indazole that was prepared using a procedure similar to that described in Example 143 part a except starting from [2-(tert-butyldimethylsilanyloxy)propyl]-(2,4-dichloro-6-nitrobenzyl)amine described in Example 127.

Example 146

N-[1-Cyano-2-(4,6-dichloro-2H-indazol-2-yl)-1-methylethyl]-4-trifluoromethylthiobenzamide (compound No 2.041)

Using a procedure similar to that described in Example 1, except using 2-amino-3-(4,6-dichloro-2H-indazol-2-yl)-2-methylpropionitrile (20 mg, described in Example 145) and 4-trifluoromethylthiobenzoyl chloride, the title compound was isolated as a white solid (34 mg, 97%). MS (ES): M/Z [M+H]=473. 1H NMR: (400 MHz, CHLOROFORM-d): 1.96 (s, 3H), 4.82 (d, 1H), 4.93 (d, 1H), 7.15 (d, J=0.9 Hz, 1H), 7.60 (s, 1H), 7.79 (d, 2H), 7.88 (d, 2H), 8.22 (s, 1H) and 8.32 (s, 1H). 19F NMR (376 MHz, CHLOROFORM-d): −42.2 (s, 3F).

Example 147

N-[1-Cyano-1-methyl-2-(4,6,7-trichloro-2H-indazol-2-yl)ethyl]-4-trifluoromethoxybenzamide (compound No 2.048)

Using a procedure similar to that described in Example 1, except using 2-amino-2-methyl-3-(4,6,7-trichloro-2H-indazol-2-yl)propionitrile (60 mg), the title compound was isolated as a white solid (34 mg, 35%). Rf=0.65 (1:1 EA/heptane). $^1$H NMR: (400 MHz, DMSO-$d_6$): 1.70 (s, 3H), 5.12 (d, 1H), 5.24 (d, 1H), 7.47 (s, 1H), 7.52 (d, J=8.1 Hz, 2H), 7.97 (d, J=8.8 Hz, 2H), 8.72 (s, 1H) and 8.92 (s, 1H). 19F NMR (376 MHz, DMSO-$d_6$): −57.1 (s, 3F).

2-Amino-2-methyl-3-(4,6,7-trichloro-2H-indazol-2-yl)propionitrile (0.16 g, 60%) was prepared using a procedure similar to that described in Example 1, part b, except starting from 1-(4,6,7-trichloro-2H-indazol-2-yl)propan-2-one (0.25 g). 1-(4,6,7-Trichloro-2H-indazol-2-yl)propan-2-one was prepared using a procedure similar to that described in Example 116 part c and d except starting from 2-[2-(tert-butyldimethylsilanyloxy)propyl]-4,6,7-trichloro-2H-indazole (1.4 g, 69%) that was prepared using a procedure similar to that described in Example 143 part a except starting from [2-(tert-butyldimethylsilanyloxy)propyl]-(2-nitro-3,4,6-trichlorobenzyl)amine (2.2 g). [2-(tert-Butyldimethylsilanyloxy)propyl]-(2-nitro-3,4,6-trichlorobenzyl)amine (2.2 g, 44%) was prepared using a procedure similar to that described in Example 116 part a except starting from 2-nitro-3,4,6-trichlorobenzaldehyde (3 g) that was prepared as follows:

a. To a mixture of 2-nitro-3,4,6-trichloroaniline (57 g), described in Example 39 part a to c, and copper (II) bromide (105 g) in acetonitrile (1 L) was added tert-butyl nitrite (90%, 37 mL) and the mixture heated to 60° C. overnight. The reaction mixture was filtered a plug of Celite®, rinsed with ethyl acetate and the filtrates concentrated under reduced pressure to yield a residue that was purified by chromatography (SiO$_2$, heptane/EA) to afford 2-bromo-3-nitro-1,4,5-trichlorobenzene (53 g, 74%). Rf=0.8 (1:4 EA/heptane).

b. 2-Bromo-3-nitro-1,4,5-trichlorobenzene (53 g), tributylvinyltin (58 mL, 62 g) and [1,1'-bis(diphenylphosphino)ferrocene]dichloropalladium (II), complex with dichloromethane (1:1) (14 g) were heated in toluene (400 mL) at 100° C. for 24 hours. The mixture was concentrated under reduced pressure, taken up in ethyl acetate (1 L) and treated with a saturated solution of potassium fluoride (300 mL) overnight. The mixture was filtered through a plug of Celite®, the organic layer was separated and dried over sodium sulfate, filtered and concentrated under reduced pressure to give a residue that was purified by chromatography (SiO$_2$, heptane/EA) to afford 3-nitro-1,2,5-trichloro-4-vinylbenzene as an of white solid (34 g, 78%). Rf=0.75 (1:4 EA/heptane).

c. A solution of 3-nitro-1,4,5-trichloro-2-vinylbenzene (27 g) in a mixture of DCM and methanol (3:1, 300 mL) was treated with ozone gas for 2 hours at −78° C. The mixture was purged 10 minutes with oxygen and then quenched with dimethyl sulfide (2 mL) at −78° C. The mixture was allowed to warm to 0° C., treated with a 10% solution of sodium thiosulfate (200 mL) then diluted with more DCM. The organic layer was collected, dried over sodium sulfate, filtered and concentrated under reduced pressure to give a residue that was purified by chromatography (SiO$_2$, heptane/EA) to afford 2-nitro-3,4,6-trichlorobenzaldehyde as a white solid (20 g, 74%). Rf=0.5 (3:8 EA/heptane). 1H NMR: (400 MHz, DMSO-$d_6$): 8.44 (s, 1H) and 10.17 (s, 1H).

Example 148

N-[1-Cyano-1-methyl-2-(4,6,7-trichloro-2H-indazol-2-yl)ethyl]-4-trifluoromethylthiobenzamide (compound No 2.049)

Using a procedure similar to that described in Example 1, except using 2-amino-2-methyl-3-(4,6,7-trichloro-2H-indazol-2-yl)propionitrile (60 mg, described in Example 147) and 4-trifluoromethylthiobenzoyl chloride, the title compound was isolated as a white solid (40 mg, 40%). Rf=0.65 (1:1 EA/heptane). 1H NMR: (400 MHz, DMSO-$d_6$): 1.70 (s, 3H), 5.11 (d, 1H), 5.25 (d, 1H), 7.47 (s, 1H), 7.79-7.80 (m, 4H), 8.73 (s, 1H) and 9.00 (s, 1H). 19F NMR (376 MHz, DMSO-$d_6$): −42.0 (s, 3F).

Example 149

N-[1-Cyano-1-methyl-2-(4,6,7-trichloro-2H-indazol-2-yl)ethyl]-4-pentafluorothiobenzamide (compound No 2.058)

Using a procedure similar to that described in Example 1, except using 2-amino-2-methyl-3-(4,6,7-trichloro-2H-indazol-2-yl)propionitrile (105 mg, described in Example 147) and 4-pentafluorothiobenzoyl chloride (111 mg), the title compound was isolated as a white solid (152 mg, 82%). MS (ES): M/Z [M+Na]=555. 1H NMR (400 MHz, CHLOROFORM-d): 2.00 (s, 3H), 4.86 (d, J=14.1 Hz, 1H), 4.92 (d, J=14.1 Hz, 1H), 7.26 (s, 1H), 7.82-7.90 (m, 2H), 8.05 (d, J=8.6 Hz, 2H), 8.31 (s, 1H) and 8.80 (s, 1H). 19F NMR (376 MHz, CHLOROFORM-d): −167.8 (d, J=150.4 Hz, 4F) and −147.6 (quin, J=150.4 Hz, 1F).

Example 150

N-[1-Cyano-1-methyl-2-(4,6,7-trichloro-2H-indazol-2-yl)ethyl]-4-chlorobenzamide (compound No 2.061)

Using a procedure similar to that described in Example 60, except using a solution of 4-chlorobenzoyl chloride (0.16 mmole) in THF and a solution of 2-amino-2-methyl-3-(4,6,7-trichloro-2H-indazol-2-yl)propionitrile (0.075 mmole, described in Example 147) in THF mixed with TEA (3% v./v.), the title compound was isolated as solid residue (13.9 mg). It was dissolved in DMSO for further biological evaluation and analyzed by LCMS. MS (ES): M/Z [M+H]=441, RT=0.74 min.

Example 151

N-[1-Cyano-1-methyl-2-(4,6,7-trichloro-2H-indazol-2-yl)ethyl]-4-trifluoromethylbenzamide (compound No 2.062)

Using a procedure similar to that described in Example 60, except using a solution of 4-trifluoromethylbenzoyl chloride (0.16 mmole) in THF and a solution of 2-amino-2-methyl-3-(4,6,7-trichloro-2H-indazol-2-yl)propionitrile (0.075 mmole, described in Example 147) in THF mixed with TEA (3% v./v.), the title compound was isolated as solid residue (13.9 mg). It was dissolved in DMSO for further biological evaluation and analyzed by LCMS. MS (ES): M/Z [M+H]=475, RT=0.75 min.

Example 152

N-[1-Cyano-1-methyl-2-(4,6,7-trichloro-2H-indazol-2-yl)ethyl]-4-cyanobenzamide (compound No 2.063)

Using a procedure similar to that described in Example 60, except using a solution of 4-cyanobenzoyl chloride (0.16 mmole) in THF and a solution of 2-amino-2-methyl-3-(4,6,7-trichloro-2H-indazol-2-yl)propionitrile (0.075 mmole, described in Example 147) in THF mixed with TEA (3% v./v.), the title compound was isolated as solid residue (10.5 mg). It was dissolved in DMSO for further biological evaluation and analyzed by LCMS. MS (ES): M/Z [M+H]=432, RT=0.66 min.

Example 153

N-[1-Cyano-1-methyl-2-(4,6,7-trichloro-2H-indazol-2-yl)ethyl]-4-(1,1,2,2-tetrafluoroethoxy)benzamide (compound No 2.066)

Using a procedure similar to that described in Example 60, except using a solution of 4-(1,1,2,2-tetrafluoroethoxy)benzoyl chloride (0.16 mmole) in THF and a solution of 2-amino-2-methyl-3-(4,6,7-trichloro-2H-indazol-2-yl)propionitrile (0.075 mmole, described in Example 147) in THF mixed with TEA (3% v./v.), the title compound was isolated as solid residue (6 mg). It was dissolved in DMSO for further biological evaluation and analyzed by LCMS. MS (ES): M/Z [M+H]=523, RT=0.73 min.

Example 154

N-[1-Cyano-1-methyl-2-(4,6,7-trichloro-2H-indazol-2-yl)ethyl]-4-phenoxybenzamide (compound No 2.067)

Using a procedure similar to that described in Example 60, except using a solution of 4-phenoxybenzoyl chloride (0.16 mmole) in THF and a solution of 2-amino-2-methyl-3-(4,6,7-trichloro-2H-indazol-2-yl)propionitrile (0.075 mmole, described in Example 147) in THF mixed with TEA (3% v./v.), the title compound was isolated as solid residue (13 mg). It was dissolved in DMSO for further biological evaluation and analyzed by LCMS. MS (ES): M/Z [M+H]=499, RT=0.79 min.

Example 155

N-[1-Cyano-1-methyl-2-(4,6,7-trichloro-2H-indazol-2-yl)ethyl]-4-iodobenzamide (compound No 2.068)

Using a procedure similar to that described in Example 60, except using a solution of 4-iodobenzoyl chloride (0.16 mmole) in THF and a solution of 2-amino-2-methyl-3-(4,6,7-trichloro-2H-indazol-2-yl)propionitrile (0.075 mmole, described in Example 147) in THF mixed with TEA (3% v./v.), the title compound was isolated as solid residue (13.9 mg). It was dissolved in DMSO for further biological evaluation and analyzed by LCMS. MS (ES): M/Z [M+H]=533, RT=0.77 min.

Example 156

N-[1-Cyano-1-methyl-2-(4,6,7-trichloro-2H-indazol-2-yl)ethyl]-4-nitrobenzamide (compound No 2.069)

Using a procedure similar to that described in Example 60, except using a solution of 4-nitrobenzoyl chloride (0.16 mmole) in THF and a solution of 2-amino-2-methyl-3-(4,6,7-trichloro-2H-indazol-2-yl)propionitrile (0.075 mmole, described in Example 147) in THF mixed with TEA (3% v./v.), the title compound was isolated as solid residue (6.7 mg). It was dissolved in DMSO for further biological evaluation and analyzed by LCMS. MS (ES): M/Z [M+H]=452, RT=0.69 min.

Example 157

N-[1-Cyano-1-methyl-2-(4,6,7-trichloro-2H-indazol-2-yl)ethyl]-3-fluoro-4-trifluoromethylbenzamide (compound No 2.190)

Using a procedure similar to that described in Example 60, except using a solution of 3-fluoro-4-trifluoromethylbenzoyl chloride (0.16 mmole) in THF and a solution of 2-amino-2-methyl-3-(4,6,7-trichloro-2H-indazol-2-yl)propionitrile (0.075 mmole, described in Example 147) in THF mixed with TEA (3% v./v.), the title compound was isolated as solid residue (13.9 mg). It was dissolved in DMSO for further biological evaluation and analyzed by LCMS. MS (ES): M/Z [M+H]=493, RT=0.76 min.

Example 158

N-[1-Cyano-1-methyl-2-(4,6,7-trichloro-2H-indazol-2-yl)ethyl]-2-fluoro-4-trifluoromethylbenzamide (compound No 2.187)

Using a procedure similar to that described in Example 60, except using a solution of 2-fluoro-4-trifluoromethylbenzoyl chloride (0.16 mmole) in THF and a solution of 2-amino-2-methyl-3-(4,6,7-trichloro-2H-indazol-2-yl)propionitrile (0.075 mmole, described in Example 147) in THF mixed with TEA (3% v./v.), the title compound was isolated as solid residue (13.9 mg). It was dissolved in DMSO for further biological evaluation and analyzed by LCMS. MS (ES): M/Z [M+H]=493, RT=0.75 min.

Example 159

N-[1-Cyano-1-methyl-2-(4,6,7-trichloro-2H-indazol-2-yl)ethyl]-3-fluoro-4-methoxybenzamide (compound No 2.227)

Using a procedure similar to that described in Example 60, except using a solution of 3-fluoro-4-methoxybenzoyl chloride (0.16 mmole) in THF and a solution of 2-amino-2-methyl-3-(4,6,7-trichloro-2H-indazol-2-yl)propionitrile (0.075 mmole, described in Example 147) in THF mixed with TEA (3% v./v.), the title compound was isolated as solid residue (6.6 mg). It was dissolved in DMSO for further biological evaluation and analyzed by LCMS. MS (ES): M/Z [M+H]=455, RT=0.69 min.

Example 160

2,4-Dichloro-N-[1-cyano-1-methyl-2-(4,6,7-trichloro-2H-indazol-2-yl)ethyl]benzamide (compound No 2.230)

Using a procedure similar to that described in Example 60, except using a solution of 2,4-dichlorobenzoyl chloride (0.16 mmole) in THF and a solution of 2-amino-2-methyl-3-(4,6,7-trichloro-2H-indazol-2-yl)propionitrile (0.075 mmole, described in Example 147) in THF mixed with TEA (3% v./v.), the title compound was isolated as solid residue (4.2 mg). It was dissolved in DMSO for further biological evaluation and analyzed by LCMS. MS (ES): M/Z [M+H]=475, RT=0.74 min.

Example 161

N-[1-Cyano-1-methyl-2-(4,6,7-trichloro-2H-indazol-2-yl)ethyl]-2,4-difluorobenzamide (compound No 2.228)

Using a procedure similar to that described in Example 60, except using a solution of 2,4-difluorobenzoyl chloride (0.16 mmole) in THF and a solution of 2-amino-2-methyl-3-(4,6,7-trichloro-2H-indazol-2-yl)propionitrile (0.075 mmole, described in Example 147) in THF mixed with TEA (3% v./v.), the title compound was isolated as solid residue (13.9 mg). It was dissolved in DMSO for further biological evaluation and analyzed by LCMS. MS (ES): M/Z [M+H]=443, RT=0.71 min.

Example 162

3-Bromo-N-[1-cyano-1-methyl-2-(4,6,7-trichloro-2H-indazol-2-yl)ethyl]benzamide (compound No 2.229)

Using a procedure similar to that described in Example 60, except using a solution of 3-bromobenzoyl chloride (0.16 mmole) in THF and a solution of 2-amino-2-methyl-3-(4,6,7-trichloro-2H-indazol-2-yl)propionitrile (0.075 mmole, described in Example 147) in THF mixed with TEA (3% v./v.), the title compound was isolated as solid residue (13.9 mg). It was dissolved in DMSO for further biological evaluation and analyzed by LCMS. MS (ES): M/Z [M+H]=485, RT=0.75 min.

Compounds of Examples 163 to 169 were prepared according to the following general reaction scheme:

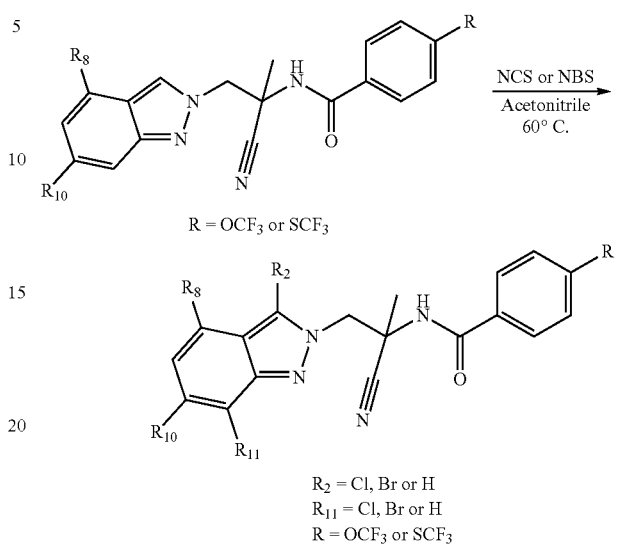

Final Product
V=C—$R_8$; W=C—H; X=C—$R_{10}$; Y=C—$R_{11}$;
Q=C—$R_2$; P=N;
$R_3$=$R_4$=H; a=1; $R_5$=$CH_3$, $R_6$=H;
Z=C(O); $R_7$=p-phenyl-R

Example 163

N-[1-Cyano-1-methyl-2-(3,6,7-trichloro-2H-indazol-2-yl)ethyl]-4-trifluoromethoxybenzamide (compound No 2.039)

A mixture of N-[2-(6-chloro-2H-indazol-2-yl)-1-cyano-1-methylethyl]-4-trifluoromethoxybenzamide (25 mg, described in Example 143), and N-chlorosuccinimide (50 mg) in acetonitrile (2 mL) was heated to 60° C. overnight. The mixture was concentrated under reduced pressure to yield a residue that was purified by chromatography (SiO$_2$, heptane/EA) to afford the title compound (22 mg, 75%) with 70% purity along with 30% of another isomer. MS (ES): M/Z [M+H]=491. 1H NMR: (400 MHz, CHLOROFORM-d): 1.96 (s, 3H), 4.81 (d, J=14.3 Hz, 1H), 5.06 (d, J=14.3 Hz, 1H), 7.25 (d, J=8.9 Hz, 1H), 7.32 (dd, J=8.1, 0.9 Hz, 2H), 7.51 (d, J=8.9 Hz, 1H), 8.05 (d, J=8.9 Hz, 2H) and 8.92 (s, 1H). 19F NMR (376 MHz, CHLOROFORM-d): −58.1 (s, 3F).

Example 164

N-[2-(3-Bromo-6-chloro-2H-indazol-2-yl)-1-cyano-1-methylethyl]-4-trifluoromethoxybenzamide (compound No 2.042)

A mixture of N-[2-(6-chloro-2H-indazol-2-yl)-1-cyano-1-methylethyl]-4-trifluoromethoxybenzamide (25 mg, described in Example 143), and N-bromosuccinimide (10 mg) in acetonitrile (1 mL) was heated to 60° C. for 3.5 hours. The mixture was cooled to room temperature, diluted with water and extracted with ethyl acetate. The organic layer was collected, dried over sodium sulfate, filtered and concentrated under reduced pressure to give a residue that was purified by chromatography (SiO$_2$, heptane/EA) to afford the title compound (12.5 mg, 42%). MS (ES): M/Z [M+H]=501. 1H NMR: (400 MHz, CHLOROFORM-d): 1.90 (s, 3H), 4.82 (d, J=14.3 Hz, 1H), 5.05 (d, J=14.3 Hz, 1H), 7.14 (dd, J=9.0, 1.6 Hz, 1H), 7.34 (d, J=8.2 Hz, 2H), 7.50 (d, J=8.9 Hz, 1H), 7.63 (d, J=0.9 Hz, 1H), 7.93 (d, J=8.8 Hz, 2H) and 8.71 (s, 1H). 19F NMR (376 MHz, CHLOROFORM-d): −58.1 (s, 3F).

Example 165

N-[2-(7-Bromo-6-chloro-2H-indazol-2-yl)-1-cyano-1-methylethyl]-4-trifluoromethoxybenzamide (compound No 2.043)

From the same reaction mixture described in Example 164 was also isolated the title compound (5 mg, 17%). MS (ES): M/Z [M+H]=501. 1H NMR: (400 MHz, CHLOROFORM-d): 1.99 (s, 3H), 4.87 (s, 2H), 7.22 (d, J=8.8 Hz, 1H), 7.31 (d, J=8.5 Hz, 2H), 7.63 (d, J=8.9 Hz, 1H), 8.04 (d, J=8.8 Hz, 2H), 8.31 (s, 1H) and 8.75 (s, 1H). 19F NMR (376 MHz, CHLOROFORM-d): −58.1 (s, 3F).

Example 166

N-[1-Cyano-2-(3,6-dichloro-2H-indazol-2-yl)-1-methylethyl]-4-trifluoromethoxybenzamide (compound No 2.044)

A mixture of N-[2-(6-chloro-2H-indazol-2-yl)-1-cyano-1-methylethyl]-4-trifluoromethoxybenzamide (50 mg, described in Example 143), and N-chlorosuccinimide (16 mg) in acetonitrile (1 mL) was heated to 60° C. for 3.5 hours. The mixture was cooled to room temperature, diluted with water and extracted with ethyl acetate. The organic layer was collected, dried over sodium sulfate, filtered and concentrated under reduced pressure to give a residue that was purified by chromatography (SiO$_2$, heptane/EA) to afford the title compound (46 mg, 85%). MS (ES): M/Z [M+H]=457. 1H NMR: (400 MHz, CHLOROFORM-d): 1.92 (s, 3H), 4.80 (d, J=14.3 Hz, 1H), 5.03 (d, J=14.3 Hz, 1H), 7.15 (dd, J=9.0, 1.4 Hz, 1H), 7.35 (d, J=8.5 Hz, 2H), 7.57 (d, J=9.0 Hz, 1H), 7.63 (s, 1H), 7.93 (d, J=8.7 Hz, 2H) and 8.65 (s, 1H). 19F NMR (376 MHz, CHLOROFORM-d): −58.1 (s, 3F).

Example 167

N-[1-Cyano-2-(6,7-dichloro-2H-indazol-2-yl)-1-methylethyl]-4-trifluoromethoxybenzamide (compound No 2.045)

From the same reaction mixture described in Example 166 was also isolated the title compound (6 mg, 11%). MS (ES): M/Z [M+H]=457. 1H NMR: (400 MHz, CHLOROFORM-0: 1.99 (s, 3H), 4.87 (s, 2H), 7.22 (d, J=8.8 Hz, 1H), 7.31 (d, J=8.2 Hz, 2H), 7.59 (d, J=8.9 Hz, 1H), 8.02 (d, J=8.8 Hz, 2H), 8.26 (s, 1H) and 8.81 (s, 1H). 19F NMR (376 MHz, CHLOROFORM-d): −58.1 (s, 3F).

Example 168

N-[1-Cyano-2-(3,7-dibromo-4,6-dichloro-2H-indazol-2-yl)-1-methylethyl]-4-trifluoromethoxybenzamide (compound No 2.046)

A mixture of N-[2-(4,6-dichloro-2H-indazol-2-yl)-1-cyano-1-methylethyl]-4-trifluoromethoxybenzamide, described in Example 145, and excess N-bromosuccinimide in acetonitrile was heated to 60° C. overnight. The mixture was cooled to room temperature, diluted with water and extracted with ethyl acetate. The organic layer was collected, dried over sodium sulfate, filtered and concentrated under reduced pressure to give a residue that was purified by chromatography (SiO$_2$, heptane/EA) to afford the title compound (13 mg). MS (ES): M/Z [M+H]=613. 1H NMR: (400 MHz, CHLOROFORM-d): 1.97 (s, 3H), 4.75 (br. s, 1H), 4.88 (d, J=14.3 Hz, 1H), 5.14 (d, J=14.3 Hz, 1H), 7.31 (d, J=8.3 Hz, 2H), 8.05 (d, J=8.8 Hz, 2H) and 8.65 (s, 1H). 19F NMR (376 MHz, CHLOROFORM-d): −58.1 (s, 3F).

Example 169

N-[2-(7-Bromo-6,7-dichloro-2H-indazol-2-yl)-1-cyano-1-methylethyl]-4-trifluoromethoxybenzamide (compound No 2.047)

From the same reaction mixture described in Example 168 was also isolated the title compound (18 mg). MS (ES): M/Z [M+Na]=557. 1H NMR: (400 MHz, CHLOROFORM-d): 2.00 (s, 3H), 4.84-4.93 (m, 2H), 7.25 (s, 1H), 7.31 (d, J=8.4 Hz, 2H), 8.02 (d, J=8.8 Hz, 2H), 8.35 (s, 1H) and 8.57 (s, 1H). 19F NMR (376 MHz, CHLOROFORM-d): −58.1 (s, 3F).

Example 170

N-[2-(6-Chloro-3-methyl-2H-indazol-2-yl)-1-cyano-1-methylethyl]-4-trifluoromethoxybenzamide (compound No 2.050)

The compound of Example 170 was prepared according to the following general reaction scheme:

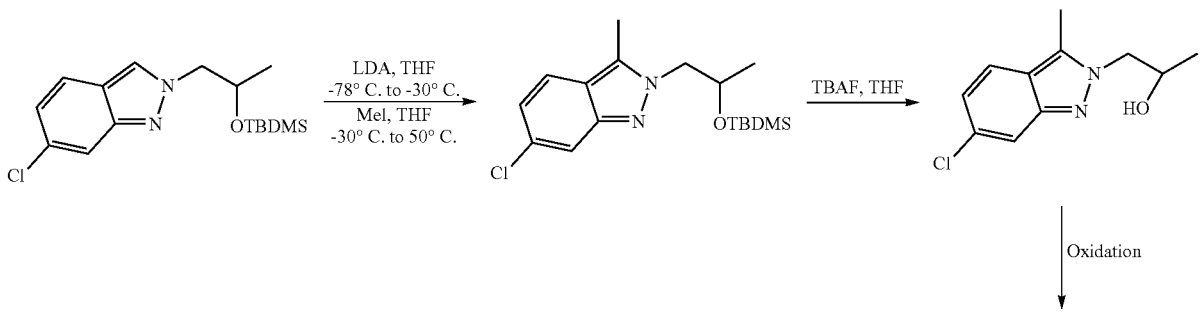

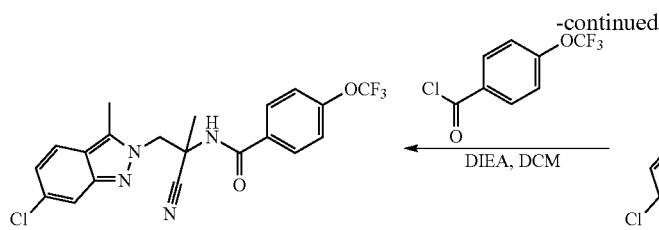
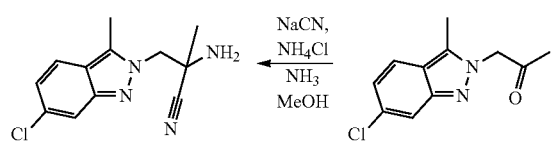

Using a procedure similar to that described in Example 1, except using 2-amino-3-(6-chloro-3-methyl-2H-indazol-2-yl)-2-methylpropionitrile (33 mg), the title compound was isolated as a white solid (31 mg, 52%). 1H NMR: (400 MHz, CHLOROFORM-d): 1.98 (s, 3H), 2.79 (s, 3H), 4.69 (d, 1H), 4.83 (d, 1H), 7.05 (dd, J=8.9, 1.6 Hz, 1H), 7.34 (d, J=8.2 Hz, 2-[2-(tert-butyldimethylsilanyloxy)propyl]-6-chloro-3-methyl-2H-indazole and starting material 2-[2-(tert-butyldimethylsilanyloxy)propyl]-6-chloro-2H-indazole.

Compounds of Examples 171 to 174 were prepared according to the following general reaction scheme:

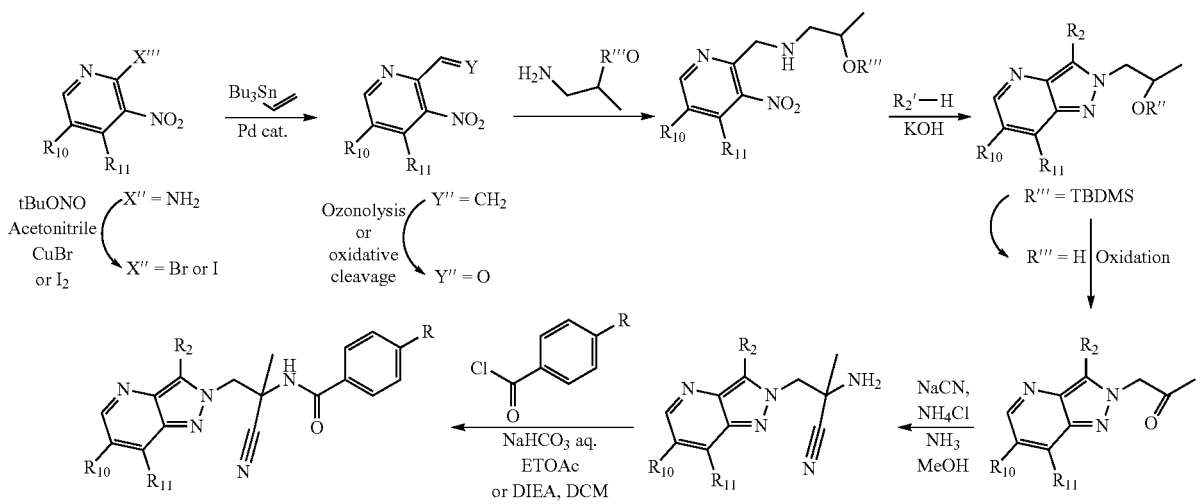

2H), 7.55 (d, J=9.0 Hz, 1H), 7.60 (d, J=0.9 Hz, 1H), 7.96 (d, J=8.8 Hz, 2H) and 9.19 (s, 1H). 19F NMR (376 MHz, CHLOROFORM-d): −58.1 (s, 3F).

2-Amino-3-(6-chloro-3-methyl-2H-indazol-2-yl)-2-methylpropionitrile was prepared using a procedure similar to that described in Example 1, part b, except starting from 1-(6-chloro-3-methyl-2H-indazol-2-yl)propan-2-one. 1-(6-Chloro-3-methyl-2H-indazol-2-yl)propan-2-one was prepared using a procedure similar to that described in Example 116 part c and d except starting from 2-[2-(tert-butyldimethylsilanyloxy)propyl]-6-chloro-3-methyl-2H-indazole that was prepared as follows:

a. To a solution of diisopropylamine (0.31 mL) in THF (3 mL) was added a solution of n-butyl lithium (1.6 molar in hexanes, 1.26 ml) at −78° C. After stirring 30 minutes at −78° C., a solution of 2-[2-(tert-butyldimethylsilanyloxy)propyl]-6-chloro-2H-indazole (469 g), described in Example 143 part a, in THF (3 mL) was added and the mixture let warm to −30° C. over one hour. Methyl iodide (0.126 mL) was added at −30° C. and the mixture let warm to room temperature and then heated to 50° C. for 24 hours. The reaction mixture was quenched with water and extracted with ethyl acetate. The organic layer was collected, dried over magnesium sulfate, filtered and concentrated under reduced pressure to yield a residue that was purified by chromatography (SiO$_2$, heptane/EA) to afford a mixture (1.3:1, 408 mg) of desired Final Product
V=N; W=C—H; X=C—R$_{10}$; Y=C—R$_{11}$;
Q=C—R$_2$; P=N;
R$_3$=R$_4$=H; a=1; R$_5$=CH$_3$, R$_6$=H;
Z=C(O); R$_7$=p-phenyl-R It will be apparent to one of skill in the art that modified derivatives with variable substitution on the phenyl ring may also be made by starting the corresponding substituted benzoic acid chloride.

Example 171

N-[2-(6-Chloro-3-methoxy-2H-pyrazolo[4,3-b]pyridin-2-yl)-1-cyano-1-methylethyl]-4-trifluoromethoxybenzamide (compound No 3.001)

Using a procedure similar to that described in Example 1, except using 2-amino-3-(6-chloro-3-methoxy-2H-pyrazolo[4,3-b]pyridin-2-yl)-2-methylpropionitrile (15 mg), the title compound was isolated as a white solid (24 mg, 82%). MS (ES): M/Z [M+H]=454. 1H NMR: (400 MHz, CHLOROFORM-d): 1.91 (s, 3H), 4.52 (d, J=14.2 Hz, 1H), 4.66 (s, 3H), 4.85 (d, J=14.2 Hz, 1H), 7.33 (d, J=8.2 Hz, 2H), 7.77 (d, J=2.0 Hz, 1H), 7.94 (d, J=8.8 Hz, 2H), 8.31 (d, J=2.0 Hz, 1H) and 8.74 (s, 1H). 19F NMR (376 MHz, CHLOROFORM-d): −58.1 (s, 3F).

2-Amino-3-(6-chloro-3-methoxy-2H-pyrazolo[4,3-b]pyridin-2-yl)-2-methylpropionitrile (39 mg) was prepared quantitatively using a procedure similar to that described in Example 1, part b, except starting from 1-(6-chloro-3-methoxy-2H-pyrazolo[4,3-b]pyridin-2-yl)propan-2-one (32 mg). 1-(6-Chloro-3-methoxy-2H-pyrazolo[4,3-b]pyridin-2-yl)propan-2-one was prepared using a procedure similar to that described in Example 116 part a to d except using 5-chloro-3-nitropyridine-2-carboxaldehyde (1.2 g) and decaborane in part a to yield [2-(tert-butyldimethylsilanyloxy)propyl]-(5-chloro-3-nitropyridin-2-yl-methyl)amine (0.4 g, 17%). 5-Chloro-3-nitropyridine-2-carboxaldehyde was prepared using a procedure similar to that described in Example 147 part a to c except starting from 2-amino-5-chloro-3-nitropyridine in part a or using commercially available 2-bromo-5-chloro-3-nitropyridine in part b. Alternatively, oxidative cleavage using a 4% solution of osmium tetroxide in water (2 mL) and sodium periodate (1.2 g) was carried out in a mixture of THF and water (10:1, 20 mL) in part c instead of ozonolysis following a procedure similar to that described in Example 70 to afford 5-chloro-3-nitropyridine-2-carboxaldehyde (0.72 g, 72%) from 5-chloro-3-nitro-2-vinylpyridine (1 g).

Example 172

N-[2-(6-Chloro-3-methoxy-2H-pyrazolo[4,3-b]pyridin-2-yl)-1-cyano-1-methylethyl]-4-trifluoromethylthiobenzamide (compound No 3.002)

Using a procedure similar to that described in Example 1, except using 2-amino-3-(6-chloro-3-methoxy-2H-pyrazolo[4,3-b]pyridin-2-yl)-2-methylpropionitrile (15 mg, described in Example 171) and 4-trifluoromethylthiobenzoyl chloride, the title compound was isolated as a white solid (20 mg, 67%). MS (ES): M/Z [M+H]=470. 1H NMR: (400 MHz, CHLOROFORM-d): 1.92 (s, 3H), 4.53 (d, J=14.2 Hz, 1H), 4.67 (s, 3H), 4.86 (d, J=14.2 Hz, 1H), 7.77-7.82 (m, 3H), 7.93 (d, J=8.2 Hz, 2H), 8.31 (d, J=1.9 Hz, 1H) and 8.82 (s, 1H). 19F NMR (376 MHz, CHLOROFORM-d): −42.3 (s, 3F).

Example 173

N-[2-(6-Bromo-3-methoxy-7-methyl-2H-pyrazolo[4,3-b]pyridin-2-yl)-1-cyano-1-methylethyl]-4-trifluoromethoxybenzamide (compound No 3.007)

Using a procedure similar to that described in Example 1, except using 2-amino-3-(6-bromo-3-methoxy-7-methyl-2H-pyrazolo[4,3-b]pyridin-2-yl)-2-methylpropionitrile (20 mg), the title compound was isolated as a white solid (21 mg, 66%). 1H NMR: (400 MHz, CHLOROFORM-d): 1.93 (s, 3H), 2.57 (s, 3H), 4.51 (d, J=14.2 Hz, 1H), 4.66 (s, 3H), 4.85 (d, J=14.2 Hz, 1H), 7.31 (d, J=8.3 Hz, 2H), 7.97 (d, J=8.7 Hz, 2H), 8.39 (s, 1H) and 9.03 (s, 1H). 19F NMR (376 MHz, CHLOROFORM-d): −58.1 (s, 3F).

2-Amino-3-(6-bromo-3-methoxy-7-methyl-2H-pyrazolo[4,3-b]pyridin-2-yl)-2-methylpropionitrile (20 mg) was prepared using a procedure similar to that described in Example 1, part b, except starting from 1-(6-bromo-3-methoxy-7-methyl-2H-pyrazolo[4,3-b]pyridin-2-yl)propan-2-one (117 mg). 1-(6-Bromo-3-methoxy-7-methyl-2H-pyrazolo[4,3-b]pyridin-2-yl)propan-2-one was prepared using a procedure similar to that described in Example 116 part a to d except using 5-bromo-4-methyl-3-nitropyridine-2-carboxaldehyde (5.5 g) in part a to yield [2-(tert-butyldimethylsilanyloxy)propyl]-(5-bromo-4-methyl-3-nitropyridin-2-yl-methyl)amine (6 g, 67%). 5-Bromo-4-methyl-3-nitro-pyridine-2-carboxaldehyde was prepared using a procedure similar to that described in Example 147 part a to c except starting from 2-amino-5-bromo-4-methyl-3-nitropyridine (58.6 g) and using iodine (64 g) in part a instead of copper bromide to generate 5-bromo-2-iodo-4-methyl-3-nitropyridine (28.7 g, 33%). Oxidative cleavage using a 4% solution of osmium tetroxide in water (3 mL) and sodium periodate (23.1 g) was carried out in a mixture of THF and water (10:1, 330 mL) in part c instead of ozonolysis following a procedure similar to that described in Example 70 to afford 5-bromo-4-methyl-3-nitropyridine-2-carboxaldehyde (11.7 g, 59%) from 5-bromo-4-methyl-3-nitro-2-vinylpyridine (18.8 g). 2-Amino-5-bromo-4-methyl-3-nitropyridine (120.2 g, 85%) was prepared using a procedure similar to that described in Example 38 part a except starting from 2-amino-4-methyl-3-nitropyridine (101.5 g).

Example 174

N-[2-(6-Chloro-3-methoxy-7-methyl-2H-pyrazolo[4,3-b]pyridin-2-yl)-1-cyano-1-methylethyl]-4-trifluoromethoxybenzamide (compound No 3.008)

Using a procedure similar to that described in Example 1, except using 2-amino-3-(6-chloro-3-methoxy-7-methyl-2H-pyrazolo[4,3-b]pyridin-2-yl)-2-methylpropionitrile (26 mg), the title compound was isolated as a white solid (17 mg, 38%). 1H NMR: (400 MHz, CHLOROFORM-d): 1.93 (s, 3H), 2.56 (s, 3H), 4.51 (d, J=14.2 Hz, 1H), 4.66 (s, 3H), 4.86 (d, J=14.2 Hz, 1H), 7.31 (d, J=8.4 Hz, 2H), 7.98 (d, J=8.7 Hz, 2H), 8.28 (s, 1H) and 9.05 (s, 1H). 19F NMR (376 MHz, CHLOROFORM-d): −58.1 (s, 3F).

2-Amino-3-(6-chloro-3-methoxy-7-methyl-2H-pyrazolo[4,3-b]pyridin-2-yl)-2-methylpropionitrile (26 mg) was prepared using a procedure similar to that described in Example 1, part b, except starting from 1-(6-chloro-3-methoxy-7-methyl-2H-pyrazolo[4,3-b]pyridin-2-yl)propan-2-one (78 mg). 1-(6-Chloro-3-methoxy-7-methyl-2H-pyrazolo[4,3-b]pyridin-2-yl)propan-2-one was prepared using a procedure similar to that described in Example 116 part a to d except using 5-chloro-4-methyl-3-nitropyridine-2-carboxaldehyde (1.3 g) in part a to yield [2-(tert-butyldimethylsilanyloxy)propyl]-(5-chloro-4-methyl-3-nitropyridin-2-yl-methyl)amine (1.4 g, 57%). 5-Chloro-4-methyl-3-nitro-pyridine-2-carboxaldehyde was prepared using a procedure similar to that described in Example 147 part a to c except starting from 2-amino-5-chloro-4-methyl-3-nitropyridine (32 g) in part a to generate 2-bromo-5-chloro-4-methyl-3-nitropyridine (25.2 g, 59%). Oxidative cleavage using a 4% solution of osmium tetroxide in water (1.5 mL) and sodium periodate (2.5 g) was carried out in a mixture of THF and water (10:1, 60 mL) in part c instead of ozonolysis following a procedure similar to that described in Example 70 to afford 5-chloro-4-methyl-3-nitropyridine-2-carboxaldehyde (1.3 g, 56%) from 5-chloro-4-methyl-3-nitro-2-vinylpyridine (2.3 g). 2-Amino-5-chloro-4-methyl-3-nitropyridine (4.6 g, 75%) was prepared using a procedure similar to that described in Example 38 part a except starting from 2-amino-4-methyl-3-nitropyridine (5 g) and using N-chlorosuccinimide (5.8 g) instead of N-bromosuccinimide.

Compounds of Examples 175 to 177 were prepared according to the following general reaction scheme:

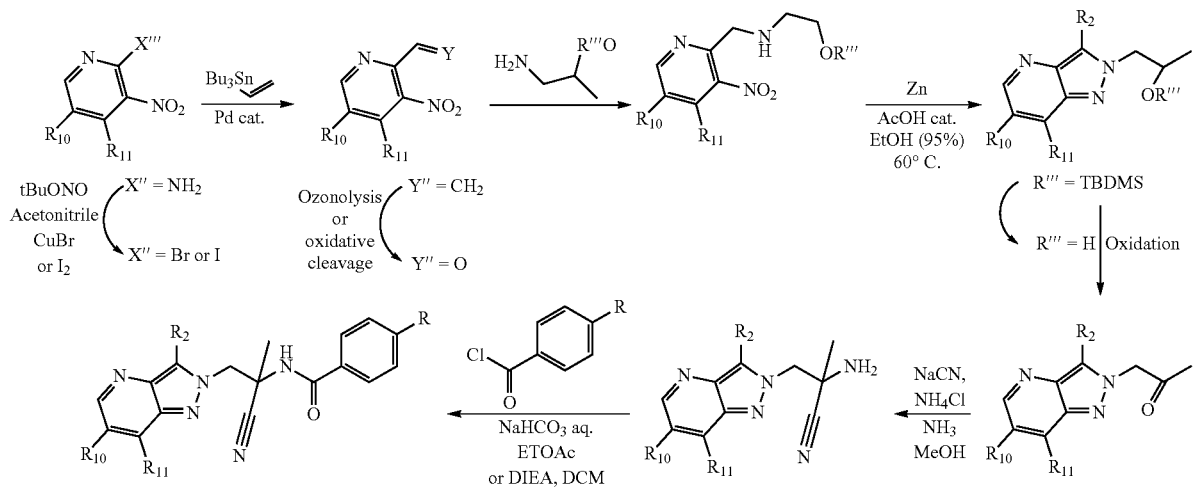

Final Product
V=N; W=C—H; X=C—R$_{10}$; Y=C—R$_{11}$;
Q=C—R$_2$; P=N;
R$_3$=R$_4$=H; a=1;
R$_5$=CH$_3$, R$_6$=H;
Z=C(O); R$_7$=p-phenyl-R It will be apparent to one of skill in the art that modified derivatives with variable substitution on the phenyl ring may also be made by starting the corresponding substituted benzoic acid chloride.

Example 175

N-[2-(6-Bromo-7-methyl-2H-pyrazolo[4,3-b]pyridin-2-yl)-1-cyano-1-methylethyl]-4-trifluoromethoxybenzamide (compound No 3.009)

Using a procedure adapted from that described in Example 1, using 2-amino-3-(6-bromo-7-methyl-2H-pyrazolo[4,3-b]pyridin-2-yl)-2-methylpropionitrile (27 mg), the title compound was isolated as a white solid (5 mg, 11%). MS (ES): M/Z [M+H]=482. 1H NMR: (400 MHz, CHLOROFORM-d): 1.97 (s, 3H), 2.68 (s, 3H), 4.82 (d, 1H), 4.98 (d, 1H), 7.32 (d, J=8.3 Hz, 2H), 7.93 (d, J=8.7 Hz, 2H), 8.38 (s, 1H), 8.41 (s, 1H) and 8.61 (s, 1H). 19F NMR (376 MHz, CHLOROFORM-d): −58.1 (s, 3F).

2-Amino-3-(6-bromo-7-methyl-2H-pyrazolo[4,3-b]pyridin-2-yl)-2-methylpropionitrile (33 mg) was prepared using a procedure similar to that described in Example 1, part b, except starting from 1-(6-bromo-7-methyl-2H-pyrazolo[4,3-b]pyridin-2-yl)propan-2-one (27 mg). 1-(6-Bromo-7-methyl-2H-pyrazolo[4,3-b]pyridin-2-yl)propan-2-one was prepared using a procedure similar to that described in Example 116 part c and d except starting from 2-[2-(tert-butyldimethylsilanyloxy)propyl]-6-bromo-7-methyl-2H-pyrazolo[4,3-b]pyridine. 2-[2-(tert-Butyldimethylsilanyloxy)propyl]-6-bromo-7-methyl-2H-pyrazolo[4,3-b]pyridine (0.15 g, 9%) was isolated along with 1-(6-bromo-7-methyl-2H-pyrazolo[4,3-b]pyridin-2-yl)propan-2-ol (0.14 g, 12%) using a procedure similar to that described in Example 143 part a except using [2-(tert-butyldimethylsilanyloxy)propyl]-(5-bromo-4-methyl-3-nitropyridin-2-yl-methyl)amine (1.9 g) described in Example 173.

Example 176

N-[2-(6-Bromo-7-methyl-2H-pyrazolo[4,3-b]pyridin-2-yl)-1-cyano-1-methylethyl]-4-trifluoromethylthiobenzamide (compound No 3.023)

Using a procedure adapted from that described in Example 1, using 2-amino-3-(6-bromo-7-methyl-2H-pyrazolo[4,3-b]pyridin-2-yl)-2-methylpropionitrile (56.7 mg, described in Example 175) and 4-trifluoromethylthiobenzoyl chloride, the title compound was isolated as a white solid (26 mg, 27%). MS (ES): M/Z [M+H]=498. 1H NMR: (400 MHz, CHLOROFORM-d): 1.97 (s, 3H), 2.67 (s, 3H), 4.82 (d, 1H), 4.97 (d, 1H), 7.77 (d, J=8.2 Hz, 2H), 7.92 (d, J=8.3 Hz, 2H), 8.38 (s, 1H), 8.54 (s, 1H) and 8.61 (s, 1H). 19F NMR (376 MHz, CHLOROFORM-d): −42.3 (s, 3F).

Example 177

N-[2-(6-Chloro-7-methyl-2H-pyrazolo[4,3-b]pyridin-2-yl)-1-cyano-1-methylethyl]-4-trifluoromethoxybenzamide (compound No 3.010)

Using a procedure similar to that described in Example 1, except using 2-amino-3-(6-chloro-7-methyl-2H-pyrazolo[4,3-b]pyridin-2-yl)-2-methylpropionitrile (32 mg), the title compound was isolated as a white solid (4 mg, 9%). 1H NMR: (400 MHz, CHLOROFORM-d): 1.97 (s, 3H), 2.67 (s, 3H), 4.83 (d, 1H), 4.97 (d, 1H), 7.32 (d, J=8.2 Hz, 2H), 7.93 (d, J=8.7 Hz, 2H), 8.39 (s, 1H), 8.44 (s, 1H) and 8.51 (s, 1H). 19F NMR (376 MHz, CHLOROFORM-d): −58.1 (s, 3F).

2-Amino-3-(6-chloro-7-methyl-2H-pyrazolo[4,3-b]pyridin-2-yl)-2-methylpropionitrile (33 mg) was prepared using a procedure similar to that described in Example 1, part b, except starting from 1-(6-chloro-7-methyl-2H-pyrazolo[4,3-b]pyridin-2-yl)propan-2-one (35 mg). 1-(6-Chloro-7-methyl-2H-pyrazolo[4,3-b]pyridin-2-yl)propan-2-one was prepared using a procedure similar to that described in Example 116 part c and d except starting from 2-[2-(tert-butyldimethylsilanyloxy)propyl]-6-chloro-7-methyl-2H-pyrazolo[4,3-b]pyridine. 2-[2-(tert-Butyldimethylsilanyloxy)propyl]-6-chloro-7-methyl-2H-pyrazolo[4,3-b]pyridine (0.13 g, 13%) was isolated along with 1-(6-chloro-7-methyl-2H-pyrazolo[4,3-b]pyridin-2-yl)propan-2-ol (0.13 mg, 21%) using a procedure similar to that described in Example 143 part a except using [2-(tert-butyldimethylsilanyloxy)propyl]-(5-chloro-4-methyl-3-nitropyridin-2-yl-methyl)amine (1.1 g) described in Example 174.

Compounds of Examples 178 to 179 were prepared according to the following general reaction scheme:

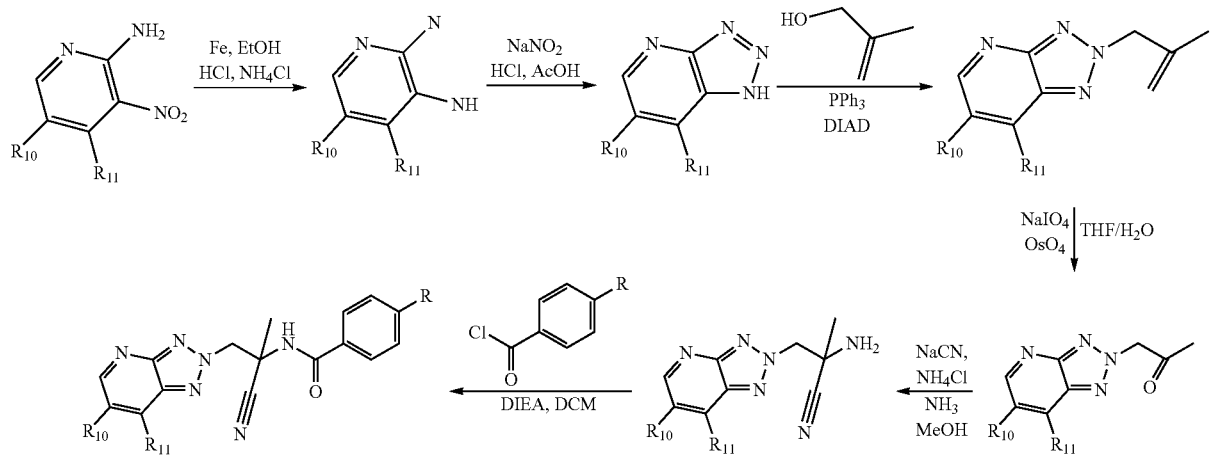

Final Product
V=N; W=C—H; X=C—R$_{10}$; Y=C—R$_{11}$;
Q=P=N;
R$_3$=R$_4$=H; a=1; R$_5$=CH$_3$, R$_6$=H;
Z=C(O); R$_7$=p-phenyl-R It will be apparent to one of skill in the art that modified derivatives with variable substitution on the phenyl ring may also be made by starting the corresponding substituted benzoic acid chloride.

Example 178

N-[2-(6-Bromo-7-methyl-2H-[1,2,3]triazolo[4,5-b]pyridin-2-yl)-1-cyano-1-methylethyl]-4-trifluoromethoxybenzamide (compound No 3.003)

Using a procedure similar to that described in Example 1, except using 2-amino-3-(6-bromo-7-methyl-2H-[1,2,3]triazolo[4,5-b]pyridin-2-yl)-2-methylpropionitrile (60 mg), the title compound was isolated as a white solid (60 mg, 61%). Rf=0.4 (1:1 EA/heptane). MS (ES): M/Z [M−H]=481. 1H NMR: (400 MHz, DMSO-d$_6$): 1.76 (s, 3H), 2.56 (s, 3H), 5.41 (d, 1H), 5.54 (d, 1H), 7.52 (d, J=8.2 Hz, 2H), 7.92 (d, J=8.6 Hz, 2H) and 8.85 (s, 2H). 19F NMR (376 MHz, DMSO-d$_6$): −57.1 (s, 3F).

2-Amino-3-(6-bromo-7-methyl-2H-[1,2,3]triazolo[4,5-b]pyridin-2-yl)-2-methylpropionitrile (0.15 g, 55%) was prepared using a procedure similar to that described in Example 1, part b, except starting from 1-(6-bromo-7-methyl-2H-[1,2,3]triazolo[4,5-b]pyridin-2-yl)propan-2-one (0.25 g) that was prepared as follows:

a. To a mixture of 2-methyl-2-propen-1-ol (1.4 mL) and triphenylphosphine (3.7 g) in THF (80 mL) was added dropwise diisopropyl azodicarboxylate (DIAD, 2.7 mL). After stirring for 15 minutes, 6-bromo-7-methyl-2H-[1,2,3]triazolo[4,5-b]pyridine (2.3 g) was added and the mixture stirred for 3 hours at room temperature. The mixture was poured into water and extracted with ethyl acetate and washed with water. The organic layer was dried over sodium sulfate, filtered and concentrated under reduced pressure to give a residue that was purified by chromatography (SiO$_2$, heptane/EA) to afford 6-bromo-7-methyl-2-(2-methyl-allyl)-2H-[1,2,3]triazolo[4,5-b]pyridine. 6-Bromo-7-methyl-2H-[1,2,3]triazolo[4,5-b]pyridine (2.4 g, 74%) was prepared using a procedure similar to that described in Example 13 part a except starting from 5-bromo-4-methylpyridine-2,3-diamine (3.5 g, 80%) that was prepared using a procedure similar to that described in Example 38 part b except starting from 2-amino-5-bromo-4-methyl-3-nitropyridine (5 g) described in Example 173.

b. To a solution of 6-bromo-7-methyl-2-(2-methyl-allyl)-2H-[1,2,3]triazolo[4,5-b]pyridine (0.9 g) in a mixture of THF and water (8:1, 18 mL), was added sodium periodate (2 g) and a 4% osmium tetroxide solution in water (2 mL, 5 mole %). After stirring overnight at room temperature, the mixture was quenched with a 10% solution of sodium thiosulfate, extracted with ethyl acetate and washed with water. The organic layer was dried over sodium sulfate, filtered and concentrated under reduced pressure to give a residue that was purified by chromatography (SiO$_2$, heptane/EA) to afford 1-(6-bromo-7-methyl-2H-[1,2,3]triazolo[4,5-b]pyridin-2-yl)propan-2-one (0.3 g, 33%).

Example 179

N-[2-(6-Bromo-7-methyl-2H-[1,2,3]triazolo[4,5-b]pyridin-2-yl)-1-cyano-1-methylethyl]-4-trifluoromethylthiobenzamide (compound No 3.004)

Using a procedure similar to that described in Example 1, except using 2-amino-3-(6-bromo-7-methyl-2H-[1,2,3]triazolo[4,5-b]pyridin-2-yl)-2-methylpropionitrile (90 mg, described in Example 178) and 4-trifluoromethylthiobenzoyl chloride, the title compound was isolated as a white solid (65 mg, 43%). Rf=0.4 (1:1 EA/heptane). MS (ES): M/Z [M−H]=497. 1H NMR: (400 MHz, DMSO-d$_6$): 1.76 (s, 3H), 2.56 (s, 3H), 5.40 (d, 1H), 5.54 (d, 1H), 7.82-7.94 (m, 4H), 8.86 (s, 1H) and 8.93 (s, 1H). 19F NMR (376 MHz, DMSO-d$_6$): −42.0 (s, 3F).

Compounds of Examples 180 to 198 were prepared according to the following general reaction scheme:
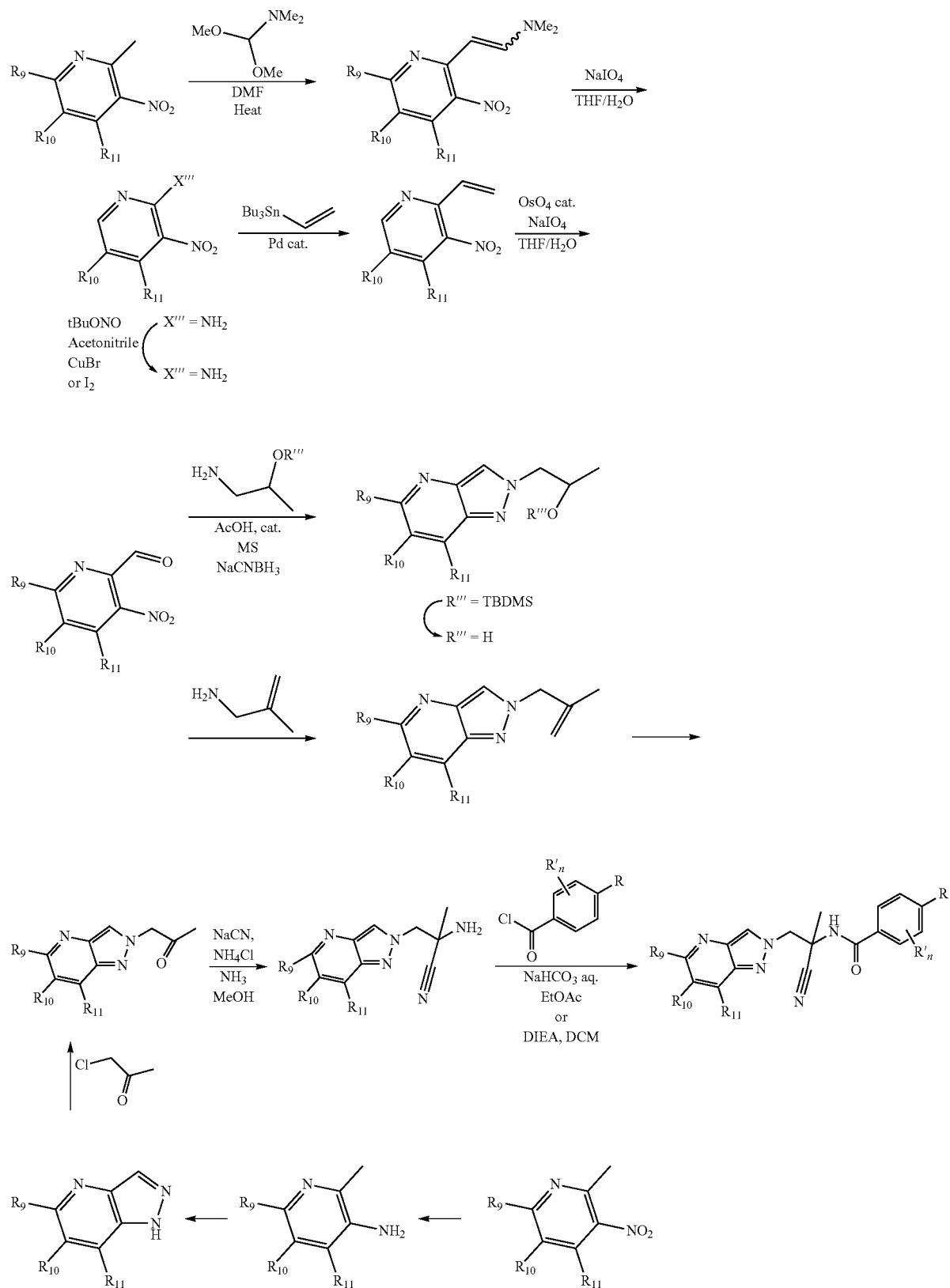

Final Product
V=N; W=C—H; X=C—R$_{10}$; Y=C—R$_{11}$;
Q=C—H; P=N;
R$_3$=R$_4$=H; a=1; R$_5$=CH$_3$, R$_6$=H;
Z=C(O); R$_7$=p-phenyl-R It will be apparent to one of skill in the art that modified derivatives with variable position of the pyridine nitrogen on the pyrazolopyridine ring may also be made by starting with the corresponding substituted ortho-nitromethylpyridine as it is the case for compounds of Examples 199 to 205.

Example 180

N-[2-(6-Chloro-2H-pyrazolo[4,3-b]pyridin-2-yl)-1-cyano-1-methylethyl]-4-trifluoromethoxybenzamide (compound No 3.005)

Using a procedure similar to that described in Example 1, except using 2-amino-3-(6-chloro-2H-pyrazolo[4,3-b]pyridin-2-yl)-2-methylpropionitrile (1.1 g), the title compound was isolated as a white solid (1 g, 49%). MS (ES): M/Z [M+H]=424. 1H NMR: (400 MHz, CHLOROFORM-d): 1.95 (s, 3H), 4.86 (d, J=14.0 Hz, 1H), 5.02 (d, J=14.0 Hz, 1H), 7.33 (d, J=8.1 Hz, 2H), 7.88 (d, J=8.7 Hz, 2H), 8.02 (dd, J=2.1, 0.9 Hz, 1H), 8.03 (s, 1H), 8.42 (d, J=0.8 Hz, 1H) and 8.55 (d, J=2.1 Hz, 1H). 19F NMR (376 MHz, CHLOROFORM-d): −58.1 (s, 3F).

2-Amino-3-(6-chloro-2H-pyrazolo[4,3-b]pyridin-2-yl)-2-methylpropionitrile (1.1 g, 97%) was prepared using a procedure similar to that described in Example 1, part b, except starting from 1-(6-chloro-2H-pyrazolo[4,3-b]pyridin-2-yl)propan-2-one (1 g). 1-(6-Chloro-3-methoxy-2H-pyrazolo[4,3-b]pyridin-2-yl)propan-2-one was prepared using a procedure similar to that described in Example 116 part c and d except starting from 2-[2-(tert-butyldimethylsilanyloxy)propyl]-6-chloro-2H-pyrazolo[4,3-b]pyridine that was prepared as follows:
  a. To a solution of 5-chloro-3-nitropyridine-2-carboxaldehyde (1 g), described in Example 171, in 1,2-dichloroethane (20 mL) was added 4 Å molecular sieves powder and 2-(tert-butyldimethylsilanyloxy)propylamine (1.22 g) described in Example 116 part a. After stirring overnight at room temperature, sodium cyanoborohydride (0.4 g) and acetic acid (0.33 mL) were added at 0° C. After stirring for one hour at 0° C., the reaction mixture was heated to 65° C. overnight. The reaction mixture was filtered through a plug of Celite® and concentrated under reduced pressure to yield a residue that was purified by chromatography (SiO$_2$, heptane/EA) to afford 2-[2-(tert-butyldimethylsilanyloxy)propyl]-6-chloro-2H-pyrazolo[4,3-b]pyridine (0.6 g, 37%). MS (ES): M/Z [M+H]=326. 1H NMR: (400 MHz, CHLOROFORM-d): −0.37 (s, 3H), −0.09 (s, 3H), 0.79 (s, 9H), 1.24 (d, J=6.1 Hz, 3H), 4.21-4.31 (m, 1H), 4.33-4.38 (m, 1H), 4.40-4.47 (m, 1H), 8.00 (dd, J=2.1, 0.9 Hz, 1H), 8.22 (d, J=0.7 Hz, 1H) and 8.48 (d, J=2.1 Hz, 1H).

Example 181

N-[2-(6-Chloro-2H-pyrazolo[4,3-b]pyridin-2-yl)-1-cyano-1-methylethyl]-4-trifluoromethylthiobenzamide (compound No 3.006)

Using a procedure similar to that described in Example 1, except using 2-amino-3-(6-chloro-2H-pyrazolo[4,3-b]pyridin-2-yl)-2-methylpropionitrile (35 mg, described in Example 180) and 4-trifluoromethylthiobenzoyl chloride, the title compound was isolated as a white solid (13 mg, 20%). MS (ES): M/Z [M+H]=440. 1H NMR: (400 MHz, CHLOROFORM-0:1.96 (s, 3H), 4.86 (d, J=14.0 Hz, 1H), 5.01 (d, J=14.0 Hz, 1H), 7.71-7.83 (m, 2H), 7.83-7.92 (m, 2H), 8.02 (dd, J=2.1, 0.9 Hz, 1H), 8.12 (s, 1H), 8.43 (d, J=0.7 Hz, 1H) and 8.56 (d, J=2.1 Hz, 1H). 19F NMR (376 MHz, CHLOROFORM-d): −42.2 (s, 3F).

Example 182

N-[2-(6-Bromo-2H-pyrazolo[4,3-b]pyridin-2-yl)-1-cyano-1-methylethyl]-4-trifluoromethoxybenzamide (compound No 3.011)

Using a procedure similar to that described in Example 1, except using 2-amino-3-(6-bromo-2H-pyrazolo[4,3-b]pyridin-2-yl)-2-methylpropionitrile (156 mg), the title compound was isolated as a white solid (133 mg, 48%). MS (ES): M/Z [M+H]=468. 1H NMR: (400 MHz, CHLOROFORM-d): 1.93 (s, 3H), 4.84 (d, J=14.0 Hz, 1H), 5.00 (d, J=14.1 Hz, 1H), 7.31 (d, J=8.1 Hz, 2H), 7.82-7.90 (m, 2H), 7.99 (s, 1H), 8.20 (dd, J=1.9, 0.8 Hz, 1H), 8.39 (s, 1H) and 8.61 (d, J=2.0 Hz, 1H). 19F NMR (376 MHz, CHLOROFORM-d): −58.1 (s, 3F).

2-Amino-3-(6-bromo-2H-pyrazolo[4,3-b]pyridin-2-yl)-2-methylpropionitrile (416 mg, 80%) was prepared using a procedure similar to that described in Example 1, part b, except starting from 1-(6-bromo-2H-pyrazolo[4,3-b]pyridin-2-yl)propan-2-one (471 mg). 1-(6-Bromo-2H-pyrazolo[4,3-b]pyridin-2-yl)propan-2-one was prepared using a procedure similar to that described in Example 116 part c and d except starting from 2-[2-(tert-butyldimethylsilanyloxy)propyl]-6-bromo-2H-pyrazolo[4,3-b]pyridine (289 mg, 39%) that was prepared using a procedure similar to that described in Example 180 except starting from 5-bromo-3-nitropyridine-2-carboxaldehyde (462 mg). 5-Bromo-3-nitropyridine-2-carboxaldehyde was prepared using a procedure similar to that described in Example 147 part a to c except starting from 2-amino-5-bromo-3-nitropyridine (50 g) and using iodine (69.9 g) in part a instead of copper bromide to generate 5-bromo-2-iodo-3-nitropyridine as a yellow solid (27.4 g, 36%). Oxidative cleavage using a 4% solution of osmium tetroxide in water (4 mL) and sodium periodate (6.7 g) was carried out in a mixture of THF and water (10:1, 390 mL) in part c instead of ozonolysis following a procedure similar to that described in Example 70 to afford 5-bromo-3-nitropyridine-2-carboxaldehyde as a tan solid (3.8 g, 62%) from 5-bromo-3-nitro-2-vinylpyridine (6 g). 1-(6-Bromo-2H-pyrazolo[4,3-b]pyridin-2-yl)propan-2-one was also prepared as follows:
  a. To a solution of 5-bromo-2-methyl-3-nitropyridine (243 g, described in WO 2006/103449 page 106), in DMF (240 mL) was added dimethylformamide dimethylacetal (240 mL). and 2-(tert-butyldimethylsilanyloxy)propylamine (1.22 g) described in Example 116 part a. After heating at 10° C. for 5 hours, the mixture was concentrated under reduced pressure to yield nearly quantitatively a dark purple residue of 2-(5-bromo-3-nitropyridin-2-yl)-vinyl]-dimethylamine that was used directly into the next step.
  b. To a solution of 2-(5-bromo-3-nitropyridin-2-yl)-vinyl]-dimethylamine (110 g) in a mixture of THF and water (1:1, 150 mL), was added portion wise sodium periodate (260 g) while cooling the mixture around 25° C. whenever necessary with an ice bath. After 3 hours, the reaction was quenched with a 10% solution of sodium sulfite (250 mL). After stirring one hour at room temperature, the reaction mixture was as concentrated under reduced pressure to give a residue that was taken in EA and washed with water. The organic layer was dried over sodium sulfate, filtered and concentrated under reduced pressure to give a residue that was purified by chromatography (SiO$_2$, heptane/EA) to afford 5-bromo-3-nitropyridine-2-carboxaldehyde as a tan solid (74.9 g, 80%). 1H NMR: (400 MHz, CHLOROFORM-d): 8.38 (d, J=1.9 Hz, 1H), 9.03 (d, J=1.9 Hz, 1H) and 10.21 (s, 1H).

c. To a suspension of 5-bromo-3-nitropyridine-2-carboxaldehyde (0.5 g) and 4 Å molecular sieves powder (1 g) in anhydrous dioxane (20 mL) was added 2-methylallylamine (0.23 mL). After stirring at room temperature for two hours, sodium cyanoborohydride (0.17 g) and acetic acid (0.2 mL) were added at 0° C. After stirring for one hour at 0° C., the reaction mixture was warmed to room temperature for one hour and then heated to 110° C. for 5 hours. The reaction mixture was cooled, filtered through a plug of Celite® and concentrated under reduced pressure to yield a residue that was purified by chromatography (SiO$_2$, heptane/EA) to afford 6-bromo-2-(2-methylallyl)-2H-pyrazolo[4,3-b]pyridine (0.23 g, 42%). 1H NMR: (400 MHz, CHLOROFORM-d): 1.71 (s, 3H), 4.96 (br. s, 1H), 4.98 (s, 2H), 5.09 (br. s, 1H), 8.20 (d, J=0.6 Hz, 1H), 8.23 (dd, J=2.0, 1.0 Hz, 1H) and 8.58 (d, J=2.0 Hz, 1H)

d. A solution of 6-bromo-2-(2-methylallyl)-2H-pyrazolo[4,3-b]pyridine (1.9 g) in a mixture of DCM and methanol (1:2, 3150 mL) was treated with ozone gas for 30 minutes at −78° C. The mixture was purged 20 minutes with oxygen and then quenched with dimethyl sulfide (10 mL) at −78° C. The mixture was allowed to slowly warm to room temperature then concentrated under reduced pressure to give a residue that was purified by chromatography (SiO$_2$, heptane/EA) to afford 1-(6-bromo-2H-pyrazolo[4,3-b]pyridin-2-yl)propan-2-one (1.35 g, 69%). 1H NMR: (400 MHz, DMSO-d$_6$): 2.21 (s, 3H), 5.54 (s, 2H), 8.45 (dd, J=2.1, 0.9 Hz, 1H), 8.56 (d, J=2.0 Hz, 1H) and 8.65 (d, J=0.7 Hz, 1H).

Alternatively, 1-(6-Bromo-2H-pyrazolo[4,3-b]pyridin-2-yl)propan-2-one was also prepared as follows:

e. To the suspension of iron (13 g) in ethanol (110 mL) was added HCl (12N, 10 mL) at room temperature. After heating the mixture at 65° C. for 30 minutes, a saturated solution of ammonium chloride in water (25%, 35 mL) was added followed by a suspension of 5-bromo-2-methyl-3-nitropyridine (10 g, described in WO 2006/103449) in ethanol. After heating the mixture at 65° C. for 4 hours, the mixture was allowed to cool to room temperature and was filtered through a plug of Celite® that was rinsed with more ethanol. The filtrate was concentrated under reduced pressure to yield a residue that was taken in EA and washed with water. The organic layer was dried over sodium sulfate, filtered and concentrated under reduced pressure to give 3-amino-5-bromo-2-methylpyridine (8.3 g) that was used directly into the next step.

f. To a mixture of 3-amino-5-bromo-2-methylpyridine (8.3 g) and potassium acetate (5.2 g) in chloroform (200 mL) was added acetic anhydride (16.7 mL) at room temperature and the mixture let stirred at room temperature for 3 hours and then heated to reflux for an additional 2 hours, After cooling the mixture to room temperature, was added isoamylnitrite (11.9 mL) and 18-crown-6-ether (1 g) and the mixture heated to reflux for 26 hours. After cooling to room temperature, the mixture was filtered through a plug of Celite®. The filtrate was concentrated under reduced pressure to yield a residue that was treated with a suspension of potassium carbonate (10 g) in a mixture of methanol (150 mL) and water (10 mL) at 0° C. for 2 hours. The mixture was concentrated under reduced pressure to yield a residue that was extracted with EA and washed with water. The organic layer was dried over sodium sulfate, filtered and concentrated under reduced pressure to give a residue that was triturated with a mixture of DCM and heptane to give 6-bromo-1H-pyrazolo[4,3-b]pyridine (6.85 g, 75% overall yield from 10 g of 5-bromo-2-methyl-3-nitropyridine). MS (ES): M/Z [M+H]=198. 1H NMR: (400 MHz, DMSO-d$_6$): 8.33 (br. s, 2H), 8.57 (d, J=1.7 Hz, 1H), 13.47 (br. s, 1H)

g. To a mixture of 6-bromo-1H-pyrazolo[4,3-b]pyridine (1.6 g) and potassium carbonate (637 mg) in acetone was added chloroacetone at room temperature. After heating the mixture to reflux for 4 hours, the mixture was concentrated under reduced pressure to give a residue that was purified by chromatography (SiO$_2$, heptane/EA) to afford 1-(6-bromo-2H-pyrazolo[4,3-b]pyridin-2-yl)propan-2-one (0.43 g, 21%) along with 1-(6-bromo-1H-pyrazolo[4,3-b]pyridin-1-yl)propan-2-one (1.46 g, 71%).

Example 183

N-[2-(6-Bromo-2H-pyrazolo[4,3-b]pyridin-2-yl)-1-cyano-1-methylethyl]-4-trifluoromethylthiobenzamide (compound No 3.012)

Using a procedure similar to that described in Example 1, except using 2-amino-3-(6-bromo-2H-pyrazolo[4,3-b]pyridin-2-yl)-2-methylpropionitrile (223 mg described in Example 182) and 4-trifluoromethylthiobenzoyl chloride, the title compound was isolated as a white solid (145 mg, 38%). MS (ES): M/Z [M+H]=484. 1H NMR: (400 MHz, CHLOROFORM-d): 1.95 (s, 3H), 4.86 (d, J=14.0 Hz, 1H), 5.01 (d, J=14.1 Hz, 1H), 7.78 (d, J=8.3 Hz, 2H), 7.84-7.90 (m, 2H), 8.11 (s, 1H), 8.22 (dd, J=2.0, 1.0 Hz, 1H), 8.42 (d, J=0.8 Hz, 1H) and 8.64 (d, J=2.0 Hz, 1H). 19F NMR (376 MHz, CHLOROFORM-d): −42.2 (s, 3F).

Example 184

N-[1-Cyano-2-(6-iodo-2H-pyrazolo[4,3-b]pyridin-2-yl)-1-methylethyl]-4-trifluoromethoxybenzamide (compound No 3.026).

Using a procedure similar to that described in Example 1, except using 2-amino-3-(6-iodo-2H-pyrazolo[4,3-b]pyridin-2-yl)-2-methylpropionitrile (25 mg), the title compound was isolated as a white solid (17 mg, 43%). MS (ES): M/Z [M+H]=516. 1H NMR: (400 MHz, CHLOROFORM-d): 1.94 (s, 3H), 4.85 (d, J=14.1 Hz, 1H), 5.03 (d, J=13.9 Hz, 1H), 7.33 (d, J=8.4 Hz, 2H), 7.88 (d, J=8.6 Hz, 2H), 8.01 (s, 1H), 8.39 (s, 1H), 8.46 (s, 1H) and 8.75 (d, J=1.6 Hz, 1H). 19F NMR (376 MHz, CHLOROFORM-d): −58.1 (s, 3F). 2-Amino-3-(6-iodo-2H-pyrazolo[4,3-b]pyridin-2-yl)-2-methylpropionitrile (25 mg, 66%; MS (ES): M/Z [M+H]=328) was prepared using a procedure similar to that described in Example 1, part b, except starting from 1-(6-iodo-2H-pyrazolo[4,3-b]pyridin-2-yl)propan-2-one (35 mg; MS (ES): M/Z [M+H]=302). 1-(6-Iodo-2H-pyrazolo[4,3-b]pyridin-2-yl)propan-2-one was prepared using a procedure similar to that described in Example 182 part g using chloroacetone and potassium carbonate except starting from 6-iodo-1H-pyrazolo[4,3-b]pyridine. 6-Iodo-1H-pyrazolo[4,3-b]pyridine was prepared as follows:

a. A solution of n-butyllithium in hexane (2.2 molar equivalent) was added at low temperature to a solution of 6-bromo-1H-pyrazolo[4,3-b]pyridine (0.5 g) in dry THF (20 mL) cooled with a dry ice actone bath. After stirring the mixture at low temperature for 90 minutes, iodine was added (703 mg, 1.1 molar equivalent) and the mixture stirred for another hour before let rise to around 5° C. and quenched with a saturated solution of ammonium chloride. The mixture was extracted with EA and washed with water. The organic layer was dried over magnesium sulfate, filtered and concentrated under reduced pressure to give a residue that was purified by chromatography ($SiO_2$, heptane/EA) to afford 6-iodo-1H-pyrazolo[4,3-b]pyridine. MS (ES): M/Z [M+H]=246. The synthesis of 6-bromo-1H-pyrazolo[4,3-b]pyridine is described in Example 182 part f.

Example 185

N-[2-(6-Bromo-2H-pyrazolo[4,3-b]pyridin-2-yl)-1-cyano-1-methylethyl]-4-pentafluorothiobenzamide (compound No 3.029)

Using a procedure similar to that described in Example 1, except using 2-amino-3-(6-bromo-2H-pyrazolo[4,3-b]pyridin-2-yl)-2-methylpropionitrile (110 mg described in Example 182) and 4-pentafluorothiobenzoyl chloride (126 mg), the title compound was isolated as a white solid (146 mg, 73%). MS (ES): M/Z [M+H]=510. 1H NMR: (400 MHz, CHLOROFORM-d): 1.96 (s, 3H), 4.86 (d, J=14.1 Hz, 1H), 5.00 (d, J=14.1 Hz, 1H), 7.85-7.95 (m, 4H), 8.23 (dd, J=2.0, 0.8 Hz, 1H), 8.25 (s, 1H), 8.43 (d, J=0.7 Hz, 1H) and 8.64 (d, J=2.0 Hz, 1H). 19F NMR (376 MHz, CHLOROFORM-d): −167.8 (d, J=150 Hz, 4F) and −147.7 (quin, J=150 Hz, 1F).

Example 186

N-[2-(6-Bromo-2H-pyrazolo[4,3-b]pyridin-2-yl)-1-cyano-1-methylethyl]-4-chlorobenzamide (compound No 3.046)

Using a procedure similar to that described in Example 60, except using a solution of 4-chlorobenzoyl chloride (0.16 mmole) in THF and a solution of 2-amino-3-(6-bromo-2H-pyrazolo[4,3-b]pyridin-2-yl)-2-methylpropionitrile (0.075 mmole, described in Example 182) in THF mixed with TEA (3% v./v.), the title compound was isolated as solid residue (13.9 mg). It was dissolved in DMSO for further biological evaluation and analyzed by LCMS. MS (ES): M/Z [M+H]=418, RT=0.56 min.

Example 187

N-[2-(6-Bromo-2H-pyrazolo[4,3-b]pyridin-2-yl)-1-cyano-1-methylethyl]-4-trifluoromethylbenzamide (compound No 3.047)

Using a procedure similar to that described in Example 60, except using a solution of 4-trifluoromethylbenzoyl chloride (0.16 mmole) in THF and a solution of 2-amino-3-(6-bromo-2H-pyrazolo[4,3-b]pyridin-2-yl)-2-methylpropionitrile (0.075 mmole, described in Example 182) in THF mixed with TEA (3% v./v.), the title compound was isolated as solid residue (13.9 mg). It was dissolved in DMSO for further biological evaluation and analyzed by LCMS. MS (ES): M/Z [M+H]=452, RT=0.59 min.

Example 188

N-[2-(6-Bromo-2H-pyrazolo[4,3-b]pyridin-2-yl)-1-cyano-1-methylethyl]-4-phenoxybenzamide (compound No 3.048)

Using a procedure similar to that described in Example 60, except using a solution of 4-phenoxybenzoyl chloride (0.16 mmole) in THF and a solution of 2-amino-3-(6-bromo-2H-pyrazolo[4,3-b]pyridin-2-yl)-2-methylpropionitrile (0.075 mmole, described in Example 182) in THF mixed with TEA (3% v./v.), the title compound was isolated as solid residue (6.7 mg). It was dissolved in DMSO for further biological evaluation and analyzed by LCMS. MS (ES): M/Z [M+H]=476, RT=0.63 min.

Example 189

N-[2-(6-Bromo-2H-pyrazolo[4,3-b]pyridin-2-yl)-1-cyano-1-methylethyl]-4-iodobenzamide (compound No 3.049)

Using a procedure similar to that described in Example 60, except using a solution of 4-iodobenzoyl chloride (0.16 mmole) in THF and a solution of 2-amino-3-(6-bromo-2H-pyrazolo[4,3-b]pyridin-2-yl)-2-methylpropionitrile (0.075 mmole, described in Example 182) in THF mixed with TEA (3% v./v.), the title compound was isolated as solid residue (8.3 mg). It was dissolved in DMSO for further biological evaluation and analyzed by LCMS. MS (ES): M/Z [M+H]=510, RT=0.59 min.

Example 190

N-[2-(6-Bromo-2H-pyrazolo[4,3-b]pyridin-2-yl)-1-cyano-1-methylethyl]-biphenyl-4-carboxamide (compound No 3.050)

Using a procedure similar to that described in Example 60, except using a solution of biphenyl-4-carbonyl chloride (0.16 mmole) in THF and a solution of 2-amino-3-(6-bromo-2H-pyrazolo[4,3-b]pyridin-2-yl)-2-methylpropionitrile (0.075 mmole, described in Example 182) in THF mixed with TEA (3% v./v.), the title compound was isolated as solid residue (6.3 mg). It was dissolved in DMSO for further biological evaluation and analyzed by LCMS. MS (ES): M/Z [M+H]=460, RT=0.63 min.

Example 191

N-[2-(6-Bromo-2H-pyrazolo[4,3-b]pyridin-2-yl)-1-cyano-1-methylethyl]-4-hexylbenzamide (compound No 3.051)

Using a procedure similar to that described in Example 60, except using a solution of 4-hexylbenzoyl chloride (0.16 mmole) in THF and a solution of 2-amino-3-(6-bromo-2H-pyrazolo[4,3-b]pyridin-2-yl)-2-methylpropionitrile (0.075 mmole, described in Example 182) in THF mixed with TEA (3% v./v.), the title compound was isolated as solid residue (13.9 mg). It was dissolved in DMSO for further biological evaluation and analyzed by LCMS. MS (ES): M/Z [M+H]=468, RT=0.76 min.

Example 192

N-[1-Cyano-1-methyl-2-(2H-pyrazolo[4,3-b]pyridin-2-yl)ethyl]-4-trifluoromethoxybenzamide (compound No 3.045)

Using a procedure similar to that described in Example 1, except using 2-amino-2-methyl-3-(2H-pyrazolo[4,3-b]pyridin-2-yl)-propionitrile (27 mg), the title compound was isolated as a white solid (8 mg). MS (ES): M/Z [M+H]=390. 1H NMR: (400 MHz, CHLOROFORM-d): 1.94 (s, 3H), 4.87 (d, J=14.1 Hz, 1H), 5.04 (d, J=14.1 Hz, 1H), 7.31 (d, J=7.6 Hz, 3H), 7.90 (d, J=8.8 Hz, 2H), 8.05 (d, J=8.8 Hz, 1H), 8.30 (s, 1H), 8.43 (s, 1H) and 8.65 (d, J=2.9 Hz, 1H). 19F NMR (376 MHz, CHLOROFORM-d): −58.1 (s, 3F). 2-Amino-2-methyl-3-(2H-pyrazolo[4,3-b]pyridin-2-yl)-propionitrile (37 mg) was prepared using a procedure similar to that described in Example 1, part b, except starting from 1-(2H-pyrazolo[4,3-b]pyridin-2-yl)propan-2-one (37 mg). 1-(2H-Pyrazolo[4,3-b]pyridin-2-yl)propan-2-one (37 mg, 6.6%; MS (ES): M/Z [M+H]=176) was prepared using a procedure similar to that described in Example 182 part g using chloroacetone and potassium carbonate except starting from 1H-pyrazolo[4,3-b]pyridine (380 mg). 1H-pyrazolo[4,3-b]pyridine (380 mg, 34%) was prepared using a procedure similar to that described in Example 182 part f except starting from 3-amino-2-methylpyridine (1 g).

Example 193

N-[2-(6-Bromo-5-methoxy-2H-pyrazolo[4,3-b]pyridin-2-yl)-1-cyano-1-methylethyl]-4-trifluoromethoxybenzamide (compound No 3.052)

Using a procedure similar to that described in Example 1, except using 2-amino-3-(6-bromo-5-methoxy-2H-pyrazolo[4,3-b]pyridin-2-yl)-2-methylpropionitrile (100 mg), the title compound was isolated as a white solid (76 mg, 47%). MS (ES): M/Z [M+H]=498. 1H NMR: (400 MHz, CHLOROFORM-d): 1.93 (s, 3H), 4.05 (s, 3H), 4.76 (d, J=14.3 Hz, 1H), 4.90 (d, J=14.3 Hz, 1H), 7.33 (d, J=8.2 Hz, 2H), 7.88 (d, J=8.8 Hz, 2H), 8.11 (s, 2H) and 8.20 (s, 1H). 19F NMR (376 MHz, CHLOROFORM-d): −58.1 (s, 3F). 2-Amino-3-(6-bromo-5-methoxy-2H-pyrazolo[4,3-b]pyridin-2-yl)-2-methylpropionitrile (230 mg) was prepared using a procedure similar to that described in Example 1, part b, except starting from 1-(6-bromo-5-methoxy-2H-pyrazolo[4,3-b]pyridin-2-yl)propan-2-one (230 mg). 1-(6-Bromo-5-methoxy-2H-pyrazolo[4,3-b]pyridin-2-yl)propan-2-one (230 mg, 15%) was prepared using a procedure similar to that described in Example 182 part g using chloroacetone and potassium carbonate except starting from 1-(6-bromo-5-methoxy-2H-pyrazolo[4,3-b]pyridine (1.2 g). 1-(6-Bromo-5-methoxy-2H-pyrazolo[4,3-b]pyridine (2.05 g, 60%) was prepared using a procedure similar to that described in Example 182 part f except starting from N-(5-bromo-6-methoxy-2-methylpyridin-3-yl)acetamide (3.89 g) and using toluene instead of chloroform. N-(5-Bromo-6-methoxy-2-methylpyridin-3-yl)acetamide (3.89 g, 87%)) was prepared by bromination of N-(6-methoxy-2-methylpyridin-3-yl)acetamide (3.1 g) with bromine (2.2 mL) in acetic acid (20 mL). N-(6-Methoxy-2-methylpyridin-3-yl)acetamide was prepared by acetylation of 3-amino-6-methoxy-2-methylpyridine in acetic anhydride. 3-Amino-6-methoxy-2-methylpyridine was prepared by iron reduction of 6-methoxy-2-methyl-3-nitropyridine. 6-Methoxy-2-methyl-3-nitropyridine (5 g, 93%) was prepared by methanolic displacement of 6-fluoro-2-methyl-3-nitropyridine (5 g) with potassium carbonate (13.3 g) in methanol (60 mL) at 45° C. overnight.

Example 194

N-[2-(6-Bromo-5-methoxy-2H-pyrazolo[4,3-b]pyridin-2-yl)-1-cyano-1-methylethyl]-4-trifluoromethylthiobenzamide (compound No 3.053).

Using a procedure similar to that described in Example 1, except using 2-amino-3-(6-bromo-5-methoxy-2H-pyrazolo[4,3-b]pyridin-2-yl)-2-methylpropionitrile (100 mg described in Example 193) and 4-trifluoromethylthiobenzoyl chloride, the title compound was isolated as a white solid (67.5 mg, 41%). MS (ES): M/Z [M+H]=514. 1H NMR: (400 MHz, CHLOROFORM-d): 1.93 (s, 3H), 4.05 (s, 3H), 4.76 (d, J=14.4 Hz, 1H), 4.90 (d, J=14.4 Hz, 1H), 7.78 (d, J=8.6 Hz, 2H), 7.87 (d, J=8.6 Hz, 2H), 8.12 (s, 1H) and 8.20 (s, 2H). 19F NMR (376 MHz, CHLOROFORM-d): −42.2 (s, 3F).

Example 195

N-[1-Cyano-2-(5,6-dibromo-2H-pyrazolo[4,3-b]pyridin-2-yl)-1-methylethyl]-4-trifluoromethoxybenzamide (compound No 3.042)

Using a procedure similar to that described in Example 1, except using 2-amino-3-(5,6-dibromo-2H-pyrazolo[4,3-b]pyridin-2-yl)-2-methylpropionitrile (60 mg), the title compound was isolated as a white solid (51 mg, 56%). MS (ES): M/Z [M+H]=546. 1H NMR: (400 MHz, DMSO-$d_6$): 1.68 (s, 3H), 5.15 (d, J=13.6 Hz, 1H), 5.16 (d, J=13.6 Hz, 1H), 7.53 (d, J=8.4 Hz, 2H), 7.97 (d, J=8.8 Hz, 2H), 8.74 (s, 1H), 8.78 (s, 1H) and 8.96 (s, 1H). 19F NMR (376 MHz, DMSO-$d_6$): −57.1 (s, 3F). 2-Amino-3-(5,6-dibromo-2H-pyrazolo[4,3-b]pyridin-2-yl)-2-methylpropionitrile (260 mg, 86%; MS (ES): M/Z [M+H]=360) was prepared using a procedure similar to that described in Example 1, part b, except starting from 1-(5,6-dibromo-2H-pyrazolo[4,3-b]pyridin-2-yl)propan-2-one (280 mg). 1-(5,6-Dibromo-2H-pyrazolo[4,3-b]pyridin-2-yl)propan-2-one (300 mg) was prepared using a procedure similar to that described in Example 182 part g using chloroacetone and potassium carbonate except starting from 5,6-dibromo-1H-pyrazolo[4,3-b]pyridine (1.18 g). 5,6-Dibromo-1H-pyrazolo[4,3-b]pyridine (1.18 g, 75%) was prepared using a procedure similar to that described in Example 182 part f except starting from 3-amino-5,6-dibromo-2-methylpyridine (1.5 g) and using toluene instead of chloroform. 3-Amino-5,6-dibromo-2-methylpyridine (2.53 g, 89%) was prepared by bromination of 3-amino-5-bromo-2-methylpyridine (2 g, described in Example 182) with N-bromosuccinimide (2.1 g) in acetonitrile (80 mL) at 50° C.

Example 196

N-[1-Cyano-2-(5,6-dibromo-2H-pyrazolo[4,3-b]pyridin-2-yl)-1-methylethyl]-4-trifluoromethylthiobenzamide (compound No 3.043)

Using a procedure similar to that described in Example 1, except using 2-amino-3-(5,6-dibromo-2H-pyrazolo[4,3-b]pyridin-2-yl)-2-methylpropionitrile (60 mg, described in Example 195) and 4-trifluoromethylthiobenzoyl chloride (28 μL), the title compound was isolated as a white solid (44 mg, 47%). MS (ES): M/Z [M+H]=562. 1H NMR: (400 MHz, DMSO-$d_6$): 1.68 (s, 3H), 5.13 (d, J=13.2 Hz, 1H), 5.18 (d, J=13.2 Hz, 1H), 7.88 (d, J=8.4 Hz, 2H), 7.94 (d, J=8.4 Hz, 2H), 8.74 (s, 1H), 8.79 (s, 1H) and 9.04 (s, 1H). 19F NMR (376 MHz, DMSO-$d_6$): −41.9 (s, 3F).

Example 197

N-[1-Cyano-2-(5-bromo-2H-pyrazolo[4,3-b]pyridin-2-yl)-1-methylethyl]-4-trifluoromethoxybenzamide (compound No 3.044)

Using a procedure similar to that described in Example 1, except using 2-amino-3-(5-bromo-2H-pyrazolo[4,3-b]pyridin-2-yl)-2-methylpropionitrile (33 mg), the title compound was isolated as a white solid (46 mg, 84%). Rf=0.4 (1:1 EA/heptane). MS (ES): M/Z [M+H]=468. 1H NMR: (400 MHz, DMSO-$d_6$): 1.69 (s, 3H), 5.06-5.24 (m, 2H), 7.44 (d, J=9.0 Hz, 1H), 7.53 (d, J=8.1 Hz, 2H), 7.97 (d, J=8.8 Hz, 2H), 8.12 (d, J=9.0 Hz, 1H), 8.69 (s, 1H) and 8.96 (s, 1H). 19F NMR (376 MHz, DMSO-$d_6$): −57.1 (s, 3F). 2-Amino-3-(5-bromo-2H-pyrazolo[4,3-b]pyridin-2-yl)-2-methylpropionitrile [40 mg, 73%; Rf=0.35 (EA)] was prepared using a procedure similar to that described in Example 1, part b, except starting from 1-(5-bromo-2H-pyrazolo[4,3-b]pyridin-2-yl)propan-2-one (50 mg). 1-(5-Bromo-2H-pyrazolo[4,3-b]pyridin-2-yl)propan-2-one [80 mg, 12%; Rf=0.25 (2:1 EA/heptane)] was prepared using a procedure similar to that described in Example 182 part g using chloroacetone and potassium carbonate except starting from 5-bromo-1H-pyrazolo[4,3-b]pyridine (0.5 g). 5-Bromo-1H-pyrazolo[4,3-b]pyridine (0.5 g, 24%) was prepared using a procedure similar to that described in Example 182 part f except starting from 3-amino-6-bromo-2-methylpyridine (2 g). 3-Amino-6-bromo-2-methylpyridine [3.2 g, 93%; Rf=0.75 (1:1 EA/heptane)] was prepared using a procedure similar to that described in Example 182 part e except starting from 6-bromo-2-methyl-3-nitropyridine (4 g).

Example 198

N-[2-(6-Bromo-2H-pyrazolo[4,3-b]pyridin-2-yl)-1-cyano-1-methylethyl]-2-fluoro-4-trifluoromethoxybenzamide (compound No 3.056)

2-Fluoro-4-trifluoromethoxybenzoic acid (80 mg, 0.357 mmole), 1-ethyl-(3-dimethylaminopropyl)carbodiimide hydrochloride (EDAC.HCl, 78 mg, 0.4 mmole), 1-hydroxybenzotriazole monohydrate (HOBt.H$_2$O, 69 mg, 0.45 mmole) and N-methylmorpholine (71 μL) were stirred in DMF (2 mL) for 20 minutes at room temperature prior to adding 2-amino-3-(6-bromo-2H-pyrazolo[4,3-b]pyridin-2-yl)-2-methylpropionitrile (100 mg, 0.357 mmole, described in Example 182). The mixture was stirred overnight at room temperature, quenched with a saturated solution of ammonium chloride and extracted with EA. The organic layer was washed with water, dried over magnesium sulfate, filtered and concentrated under reduced pressure to give a residue that was purified by chromatography (SiO$_2$, heptane/EA) to afford the title compound as a white solid (17 mg, 9%). MS (ES): M/Z [M+H]=486. 1H NMR: (400 MHz, CHLOROFORM-d): 1.91 (s, 3H), 4.90 (d, J=14.1 Hz, 1H), 5.08 (d, J=14.1 Hz, 1H), 7.07 (d, J=12.1 Hz, 1H), 7.17 (d, J=8.4 Hz, 1H), 8.02 (d, J=12.1 Hz, 1H), 8.15-8.28 (m, 2H), 8.38 (s, 1H) and 8.62 (d, J=2.0 Hz, 1H). 19F NMR (376 MHz, CHLOROFORM-d): −108.6 (td, J=11.9, 9.2 Hz, 1F) and −58.3 (s, 3F). 2-fluoro-4-trifluoromethoxybenzoic acid was prepared as follows:

a. 1-Bromo-2-fluoro-4-trifluoromethoxybenzene (0.9 g), tributyl(vinyl)tin (1.32 g) and [1,1'-bis(diphenylphosphino)ferrocene] dichloropalladium (0.127 mg) were heated to reflux in toluene (30 mL). Upon completion of the reaction monitored by TLC, the mixture was let cool to room temperature and then stirred with a saturated aqueous solution of potassium fluoride overnight. The mixture was diluted with EA, filtered over a plug of Celite® that was rinsed with more EA. The filtrate was washed with brine, dried over magnesium sulfate, filtered and concentrated under reduced pressure to give a residue that was purified by chromatography (SiO$_2$, heptane/EA) to afford 2-fluoro-4-trifluoromethoxy-1-vinylbenzene that was used directly into the next step.

b. 2-Fluoro-4-trifluoromethoxy-1-vinylbenzene dissolved in a mixture of DCM (38 mL) and methanol (12 mL) was treated with ozone gas for 10 minutes. After stirring 1000 minute at −78° C., the mixture was purged 2 minutes with oxygen and 20 minute with nitrogen and then quenched with dimethyl sulfide (0.5 mL) followed by a 10% solution of sodium thiosulfate (10 mL) and diluted with DCM. The organic layer was dried over sodium sulfate, filtered and concentrated under reduced pressure to give 2-fluoro-4-trifluoromethoxybenzaldehyde that was engaged directly in the next step.

c. A solution of sodium chlorite (510 mg) and sodium phosphate monobasic (810 mg) in water (6 mL) was added to a mixture of 2-methyl-2-butene (2 mL) and 2-fluoro-4-trifluoromethoxybenzaldehyde and the mixture stirred for 30 minute at room temperature. The mixture was diluted with an aqueous solution of sodium hydroxide and washed with diethyl ether. Aqueous layer was acidified and extracted with EA. The organic layer was washed with brine, dried over magnesium sulfate, filtered and concentrated under reduced pressure to afford 2-fluoro-4-trifluoromethoxybenzoic acid as a solid (290 mg, 37% over three steps). 1H NMR: (400 MHz, CHLOROFORM-d): 7.06 (d, J=10.9 Hz, 1H), 7.11 (dd, J=8.8, 0.9 Hz, 1H) and 8.10 (t, J=8.4 Hz, 1H). 19F NMR (376 MHz, CHLOROFORM-d): −103.6 (dd, J=10.6, 8.6 Hz, 1F) and −58.2 (s, 3F).

Example 199

N-[2-(5-Bromo-2H-pyrazolo[3,4-c]pyridin-2-yl)-1-cyano-1-methylethyl]-4-trifluoromethoxybenzamide (compound No 4.001)

Using a procedure similar to that described in Example 1, except using 2-amino-3-(5-bromo-2H-pyrazolo[3,4-c]pyridin-2-yl)-2-methylpropionitrile (100 mg), the title compound was isolated as a white solid (140 mg, 84%). Rf=0.55 (1:1 EA/heptane). MS (ES): M/Z [M+H]=468. 1H NMR: (400 MHz, DMSO-$d_6$): 1.69 (s, 3H), 5.20 (d, J=13.5 Hz, 1H), 5.23 (d, J=13.4 Hz, 1H), 7.53 (d, J=8.2 Hz, 2H), 7.96 (d, J=8.7 Hz, 2H), 8.04 (d, J=0.9 Hz, 1H), 8.52 (s, 1H), 8.96 (s, 1H) and 9.05 (s, 1H). 19F NMR (376 MHz, DMSO-$d_6$): −57.1 (s, 3F).

2-Amino-3-(5-bromo-2H-pyrazolo[3,4-c]pyridin-2-yl)-2-methylpropionitrile [0.35 g, 79%, Rf=0.3 (100% EA)] was prepared using a procedure similar to that described in Example 1, part b, except starting from 1-(5-bromo-2H-pyrazolo[3,4-c]pyridin-2-yl)propan-2-one (0.4 g). $^1$H NMR: (400 MHz, CHLOROFORM-d): 1.65 (s, 3H), 2.22 (s, 2H), 4.59 (d, J=13.6 Hz, 1H), 4.65 (d, J=13.6 Hz, 1H), 7.79 (d, J=1.3 Hz, 1H), 8.14 (s, 1H) and 9.09 (t, J=1.0 Hz, 1H).

1-(5-Bromo-2H-pyrazolo[3,4-c]pyridin-2-yl)propan-2-one was prepared as follows:
  a. To the suspension of iron (6.4 g) in ethanol (60 mL) was added HCl (12N, 1 mL) at room temperature. After heating the mixture at 65° C. for 2 hours, a saturated solution of ammonium chloride in water (25%, 20 mL) was added followed by a suspension of 2-bromo-4-methyl-5-nitropyridine (5 g) in ethanol. After heating the mixture at 65° C. for 3 hours, the mixture was allowed to cool to room temperature and was filtered through a plug of Celite® that was rinsed with more ethanol. The filtrate was concentrated under reduced pressure to yield a residue that was taken in EA and washed with water. The organic layer was dried over sodium sulfate, filtered and concentrated under reduced pressure to give 5-amino-2-bromo-4-methylpyridine (4.4 g) that was used directly into the next step.
  b. To a mixture of 5-amino-2-bromo-4-methylpyridine (4.4 g) and potassium acetate (1.8 g) in chloroform (125 mL) was added acetic anhydride (3.5 mL) at room temperature and the mixture heated to reflux for 2 hours, After cooling the mixture to room temperature, was added isoamylnitrite (2.5 mL) and 18-crown-6-ether (0.5 g) and the mixture heated to reflux for 26 hours. After cooling to room temperature, the mixture was filtered through a plug of Celite®. The filtrate was concentrated under reduced pressure to yield a residue that was treated with a suspension of potassium carbonate in methanol (125 mL) at room temperature overnight. The mixture was concentrated under reduced pressure to yield a residue that was extracted with EA and washed with brine. The organic layer was dried over sodium sulfate, filtered and concentrated under reduced pressure to give a residue that was triturated with a mixture of DCM and heptane to give 5-bromo-1H-pyrazolo[3,4-c]pyridine [1.35 g, 30% overall yield from 5 g of 2-bromo-4-methyl-5-nitropyridine; also recovered N-(6-bromo-4-methyl-pyridin-3-yl)-acetamide (3.2 g)]. 1H NMR: (400 MHz, DMSO-d$_6$): 8.05 (s, 1H), 8.20 (s, 1H), 8.88 (s, 1H) and 13.81 (br. s, 1H).
  c. To a mixture of 5-bromo-1H-pyrazolo[3,4-c]pyridine (1.6 g) and potassium carbonate (637 mg) in acetone was added chloroacetone at room temperature. After heating the mixture to reflux for 4 hours, the mixture was concentrated under reduced pressure to give a residue that was purified by chromatography (SiO$_2$, heptane/EA) to afford 1-(5-bromo-2H-pyrazolo[3,4-c]pyridin-2-yl)propan-2-one [0.4 g, 23%, Rf=0.25 (2:1 EA/heptane)] along with 1-(5-bromo-1H-pyrazolo[3,4-c]pyridin-1-yl)propan-2-one [1 g, 58%, Rf=0.45 (1:1 EA/heptane)]. 1H NMR: (400 MHz, CHLOROFORM-d): 2.28 (s, 3H), 5.31 (s, 2H), 7.79 (s, 1H), 7.98 (s, 1H) and 9.06 (s, 1H).

Example 200

N-[2-(5-Bromo-2H-pyrazolo[3,4-c]pyridin-2-yl)-1-cyano-1-methylethyl]-4-trifluoromethylthiobenzamide (compound No 4.002)

Using a procedure similar to that described in Example 1, except using 2-amino-3-(5-bromo-2H-pyrazolo[3,4-c]pyridin-2-yl)-2-methylpropionitrile (100 mg, described in Example 199) and 4-trifluoromethylthiobenzoyl chloride (92 mg), the title compound was isolated as a white solid (150 mg, 87%). MS (ES): M/Z [M+H]=484. 1H NMR: (400 MHz, DMSO-d$_6$): 1.69 (s, 3H), 5.20 (d, J=13.5 Hz, 1H), 5.27 (d, J=13.5 Hz, 1H), 7.88 (d, J=8.4 Hz, 2H), 7.93 (d, J=8.4 Hz, 2H), 8.04 (d, J=1.2 Hz, 1H), 8.54 (d, J=0.6 Hz, 1H) and 9.05 (d, J=1.1 Hz, 1H). 19F NMR (376 MHz, DMSO-d$_6$): −41.9 (s, 3F).

Example 201

N-[2-(4-Bromo-2H-pyrazolo[3,4-c]pyridin-2-yl)-1-cyano-1-methylethyl]-4-trifluoromethoxybenzamide (compound No 4.003)

Using a procedure similar to that described in Example 1, except using a one to one mixture of 2-amino-3-(4-bromo-2H-pyrazolo[3,4-c]pyridin-2-yl)-2-methylpropionitrile and 2-amino-3-(4-bromo-1H-pyrazolo[3,4-c]pyridin-1-yl)-2-methylpropionitrile (100 mg), the title compound was isolated after purification by semi-prep HPLC as a white solid (50 mg). Rf=0.5 (1:1 EA/heptane). MS (ES): M/Z [M+H]=468. 1H NMR: (500 MHz, DMSO-d$_6$): 1.70 (s, 3H), 5.21 (br. s., 2H), 7.45 (d, J=8.4 Hz, 2H), 7.93 (d, J=8.6 Hz, 2H), 8.32 (s, 1H), 8.39 (s, 1H), 8.93 (br. s., 1H) and 9.24 (s, 1H).

The mixture of 2-amino-3-(4-bromo-2H-pyrazolo[3,4-c]pyridin-2-yl)-2-methylpropionitrile and 2-amino-3-(4-bromo-1H-pyrazolo[3,4-c]pyridin-1-yl)-2-methylpropionitrile [0.4 g, 77%, Rf=0.3 (100% EA)] was prepared using a procedure similar to that described in Example 1, part b, except starting from a one to one mixture of 1-(4-bromo-2H-pyrazolo[3,4-c]pyridin-2-yl)propan-2-one and 1-(4-bromo-1H-pyrazolo[3,4-c]pyridin-1-yl)propan-2-one (0.47 g) that was prepared as follows:
  a. Isoamylnitrite (4.4 mL, 1.5 molar equivalent) was added dropwise to a solution of 2-amino-5-bromo-4-methyl-3-nitropyridine (5 g) in acetontirile (120 mL) at 0° C. and then let warm-up to room temperature overnight. The mixture was cooled back to 0° C. prior to adding more isoamylnitrite added (4.4 mL) and mixture stirred at room temperature for 24 hours. The mixture was concentrated under reduced pressure to yield a residue that purified by chromatography (SiO$_2$, heptane/EA) to afford 3-bromo-4-methyl-5-nitropyridine as a white solid [Rf=0.75 (3:7 EA/heptane)].
  b. To the suspension of iron (4.3 g) in ethanol (70 mL) was added HCl (12N, 0.7 mL) at room temperature. After heating the mixture at 65° C. for 2 hours, a saturated solution of ammonium chloride in water (25%, 14 mL) was added followed by a suspension of 3-bromo-4-methyl-5-nitropyridine (3.34 g) in ethanol. After heating the mixture at 65° C. for 3 hours, the mixture was allowed to cool to room temperature and was filtered through a plug of Celite® that was rinsed with more ethanol. The filtrate was concentrated under reduced pressure to yield a residue that was taken in EA and washed with water. The organic layer was dried over sodium sulfate, filtered and concentrated under reduced pressure to give 3-amino-5-bromo-4-methylpyridine [2.8 g, 97%, Rf=0.75 (1:1 EA/heptane)]
  c. To a mixture of 3-amino-5-bromo-4-methylpyridine (2.8 g) and potassium acetate (1.2 g) in chloroform (125 mL) was added acetic anhydride (2.2 mL) at room temperature and the mixture heated to reflux for 2 hours, After cooling the mixture to room temperature, was added isoamylnitrite (1.6 mL) and 18-crown-6-ether (0.5 g) and the mixture heated to reflux for 26 hours. After cooling to room temperature, the mixture was filtered through a plug of Celite®. The filtrate was concentrated under reduced pressure to yield a residue that was treated with a suspension of potassium carbonate in methanol (125 mL) at room temperature overnight. The mixture was concentrated under reduced pressure to yield a residue that was extracted with EA and washed with brine. The organic layer was dried over sodium sulfate, filtered and concentrated under reduced pressure to give a residue that was triturated with a mixture of DCM and heptane to give 4-bromo-1H-pyrazolo[3,4-c]pyridine [1 g, 34%, Rf=0.4 (1:1 EA/heptane)]. 1H NMR: (400 MHz, DMSO-$d_6$): 8.25 (s, 1H), 8.36 (s, 1H), 9.06 (s, 1H) and 14.02 (br. s, 1H).

d. To a mixture of 4-bromo-1H-pyrazolo[3,4-c]pyridine (1 g) and potassium carbonate (0.39 g) in acetone was added chloroacetone (0.5 g) at room temperature. After heating the mixture to reflux for 5 hours, the mixture was concentrated under reduced pressure to give a residue that was purified by chromatography (SiO$_2$, heptane/EA) to afford a one to one mixture of 1-(4-bromo-2H-pyrazolo[3,4-c]pyridin-2-yl)propan-2-one and 1-(4-bromo-1H-pyrazolo[3,4-c]pyridin-1-yl)propan-2-one [0.85 g, 66%, Rf=0.2 (1:1 EA/heptane)].

Example 202

N-[2-(7-Bromo-2H-pyrazolo[3,4-c]pyridin-2-yl)-1-cyano-1-methylethyl]-4-trifluoromethoxybenzamide (compound No 4.005)

Using a procedure similar to that described in Example 1, except using 2-amino-3-(7-bromo-2H-pyrazolo[3,4-c]pyridin-2-yl)-2-methylpropionitrile (100 mg), the title compound was isolated as a white solid (151 mg, 90%). Rf=0.25 (1:1 EA/heptane). MS (ES): M/Z [M+H]=468. 1H NMR: (400 MHz, DMSO-$d_6$): 1.71 (s, 3H), 5.09-5.41 (m, 2H), 7.52 (d, J=8.2 Hz, 2H), 7.76 (d, J=5.8 Hz, 1H), 7.87 (d, J=5.8 Hz, 1H), 7.98 (d, J=8.8 Hz, 2H), 8.70 (s, 1H) and 8.93 (s, 1H). 19F NMR (376 MHz, DMSO-$d_6$): −57.1 (s, 3F).

2-Amino-3-(7-bromo-2H-pyrazolo[3,4-c]pyridin-2-yl)-2-methylpropionitrile [0.84 g, 85%, Rf=0.3 (100% EA)] was prepared using a procedure similar to that described in Example 1, part b, except starting from 1-(7-bromo-2H-pyrazolo[3,4-c]pyridin-2-yl)propan-2-one (0.9 g) that was prepared as follows:

a. To the suspension of iron (12.8 g) in ethanol (120 mL) was added HCl (12N, 2 mL) at room temperature. After heating the mixture at 65° C. for 2 hours, a saturated solution of ammonium chloride in water (25%, 40 mL) was added followed by a suspension of 2-bromo-4-methyl-3-nitropyridine (10 g) in ethanol. After heating the mixture at 65° C. for 3 hours, the mixture was allowed to cool to room temperature and was filtered through a plug of Celite® that was rinsed with more ethanol. The filtrate was concentrated under reduced pressure to yield a residue that was taken in EA and washed with water. The organic layer was dried over sodium sulfate, filtered and concentrated under reduced pressure to give 3-amino-2-bromo-4-methylpyridine as a light brown solid (7.3 g, 85%).

b. To a mixture of 3-amino-2-bromo-4-methylpyridine (4.5 g) and potassium acetate (2.84 g) in acetic acid (100 mL) at 10° C. was added a solution of sodium nitrite (1.9 g) in water (5 mL) and the mixture heated to 60° C. overnight, After cooling to room temperature, the mixture was concentrated under reduced pressure to yield a residue that was extracted with EA and washed with water and brine. The organic layer was dried over sodium sulfate, filtered and concentrated under reduced pressure to give a residue that was purified by chromatography (SiO$_2$, heptane/EA) to afford 7-bromo-1H-pyrazolo[3,4-c]pyridine (1.2 g, 25%])

c. To a mixture of 7-bromo-1H-pyrazolo[3,4-c]pyridine (1 g) and potassium carbonate (0.39 g) in acetone was added chloroacetone (0.5 g) at room temperature. After heating the mixture to reflux for 5 hours, the mixture was concentrated under reduced pressure to give a residue that was purified by chromatography (SiO$_2$, heptane/EA) to afford 1-(7-bromo-2H-pyrazolo[3,4-c]pyridin-2-yl)propan-2-one [0.93 g, 72%, Rf=0.25 (2:1 EA/heptane)] along with 1-(7-bromo-1H-pyrazolo[3,4-c]pyridin-1-yl)propan-2-one [0.25 g, 19%, Rf=0.5 (2:1 EA/heptane)].

Example 203

N-[2-(7-Bromo-2H-pyrazolo[3,4-c]pyridin-2-yl)-1-cyano-1-methylethyl]-4-trifluoromethylthiobenzamide (compound No 4.006)

Using a procedure similar to that described in Example 1, except using 2-amino-3-(7-bromo-2H-pyrazolo[3,4-c]pyridin-2-yl)-2-methylpropionitrile (100 mg, described in Example 202) and 4-trifluoromethylthiobenzoyl chloride (93 mg), the title compound was isolated as a white solid (153 mg, 89%). Rf=0.25 (1:1 EA/heptane). MS (ES): M/Z [M+H]=484. 1H NMR: (400 MHz, DMSO-$d_6$): 1.70 (s, 3H), 5.18 (d, J=13.5 Hz, 1H), 5.33 (d, J=13.5 Hz, 1H), 7.76 (d, J=5.8 Hz, 1H), 7.87-7.90 (m, 3H), 7.96 (d, J=8.4 Hz, 1H), 8.71 (s 1H) and 9.01 (d, J=1.1 Hz, 1H). 19F NMR (376 MHz, DMSO-$d_6$): −42.0 (s, 3F).

Example 204

N-[2-(5-Bromo-2H-pyrazolo[3,4-b]pyridin-2-yl)-1-cyano-1-methylethyl]-4-trifluoromethoxybenzamide (compound No 5.001)

Using a procedure similar to that described in Example 1, except using 2-amino-3-(5-bromo-2H-pyrazolo[3,4-b]pyridin-2-yl)-2-methylpropionitrile (35 mg), the title compound was isolated as a white solid (28 mg, 48%). MS (ES): M/Z [M+H]=468. 1H NMR: (400 MHz, CHLOROFORM-d): 1.99 (s, 3H), 4.93 (d, J=2.1 Hz, 2H), 7.31 (d, J=8.4 Hz, 2H), 7.91 (d, J=8.8 Hz, 2H), 8.20 (s, 1H), 8.25 (d, J=2.1 Hz, 1H), 8.28 (s, 1H) and 8.73 (d, J=2.3 Hz, 1H). 19F NMR (376 MHz, CHLOROFORM-d): −58.1 (s, 3F).

2-Amino-3-(5-bromo-2H-pyrazolo[3,4-b]pyridin-2-yl)-2-methylpropionitrile (70 mg, 80%) was prepared using a procedure similar to that described in Example 1, part b, except starting from 1-(5-bromo-2H-pyrazolo[3,4-b]pyridin-2-yl)propan-2-one (79 mg) that was prepared as follows:

a. To a mixture of 5-bromo-1H-pyrazolo[3,4-b]pyridine (0.5 g, Synthonix Corporation, Wake Forest, N.C.-USA) and potassium carbonate (0.19 g) in acetone (20 mL) was added chloroacetone (0.26 mL) at room temperature. After heating the mixture to reflux for 6 hours, the mixture was concentrated under reduced pressure to give a residue that was purified by chromatography (SiO$_2$, heptane/EA) to afford 1-(5-bromo-2H-pyrazolo[3,4-b]pyridin-2-yl)propan-2-one (85 mg, 13%,) along with 1-(5-bromo-1H-pyrazolo[3,4-b]pyridin-1-yl)propan-2-one (0.37 g, 58%).

Example 205

N-[2-(5-Bromo-2H-pyrazolo[3,4-b]pyridin-2-yl)-1-cyano-1-methylethyl]-4-trifluoromethylthiobenzamide (compound No 5.002)

Using a procedure similar to that described in Example 1, except using 2-amino-3-(5-bromo-2H-pyrazolo[3,4-b]pyridin-2-yl)-2-methylpropionitrile (35 mg, described in Example 204) and 4-trifluoromethylthiobenzoyl chloride, the title compound was isolated as a white solid (30.7 mg, 50%). MS (ES): M/Z [M+H]=484. 1H NMR: (400 MHz, CHLOROFORM-d): 1.99 (s, 3H), 4.94 (d, J=1.6 Hz, 2H), 7.76 (d, J=8.2 Hz, 1H), 7.90 (d, J=8.4 Hz, 2H), 8.20 (s 1H), 8.26 (d, J=2.1 Hz, 1H), 8.37 (s 1H) and 8.74 (d, J=2.1 Hz, 1H). 19F NMR (376 MHz, CHLOROFORM-d): −42.2 (s, 3F).

Compounds of Examples 206 and 207 were prepared according to the following general reaction scheme:

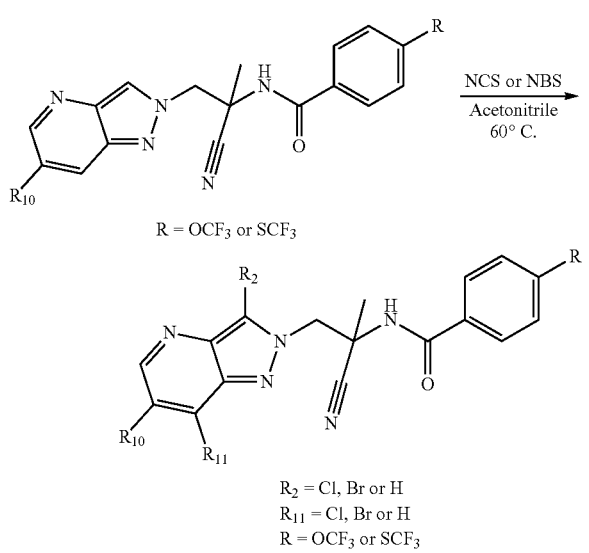

Final Product
V=N; W=C—H; X=C—$R_{10}$; Y=C—$R_{11}$;
Q=C—$R_2$; P=N;
$R_3$=$R_4$=H; a=1; $R_5$=$CH_3$, $R_6$=H;
Z=C(O); $R_n$=p-phenyl-R

Example 206

N-[1-Cyano-2-(3,6-dichloro-2H-pyrazolo[4,3-b]pyridin-2-yl)-1-methylethyl]-4-trifluoromethoxybenzamide (compound No 3.017)

A mixture of N-[2-(6-Chloro-2H-pyrazolo[4,3-b]pyridin-2-yl)-1-cyano-1-methylethyl]-4-trifluoromethoxybenzamide (134 mg described in Example 180), and N-chlorosuccinimide (51 mg) in acetonitrile (3.5 mL) was heated to 60° C. overnight. The mixture was concentrated under reduced pressure to yield a residue that was purified by chromatography ($SiO_2$, heptane/EA) to afford the title compound as white solid (129 mg, 89%). MS (ES): M/Z [M+H]=458. 1H NMR: (400 MHz, DMSO-$d_6$): 1.78 (s, 3H), 5.10-5.20 (m, 2H), 7.53 (d, J=8.3 Hz, 2H), 7.97 (d, J=8.8 Hz, 2H), 8.43 (d, J=2.0 Hz, 1H), 8.59 (d, J=2.0 Hz, 1H) and 8.99 (s, 1H). 19F NMR (376 MHz, DMSO-$d_6$): −57.1 (s, 3F).

Example 207

N-[2-(3-Bromo-6-chloro-2H-pyrazolo[4,3-b]pyridin-2-yl)-1-cyano-1-methylethyl]-4-trifluoromethoxybenzamide (compound No 3.019)

A mixture of N-[2-(6-Chloro-2H-pyrazolo[4,3-b]pyridin-2-yl)-1-cyano-1-methylethyl]-4-trifluoromethoxybenzamide (134 mg described in Example 180) and N-bromosuccinimide (68 mg) in acetonitrile (3.5 mL) was heated to 60° C. overnight. The mixture was concentrated under reduced pressure to yield a residue that was purified by chromatography ($SiO_2$, heptane/EA) to afford the title compound as a white solid (125 mg, 80%). MS (ES): M/Z [M+H]=502. 1H NMR: (400 MHz, DMSO-$d_6$): 1.78 (s, 3H), 5.10-5.22 (m, 2H), 7.52 (d, J=8.2 Hz, 2H), 7.98 (d, J=8.7 Hz, 2H), 8.43 (d, J=2.0 Hz, 1H), 8.58 (d, J=1.9 Hz, 1H) and 9.00 (s, 1H). 19F NMR (376 MHz, DMSO-$d_6$): −57.1 (s, 3F).

Table 1 below shows specific compounds encompased by formula (I), which have the structure (IJ):

TABLE 1

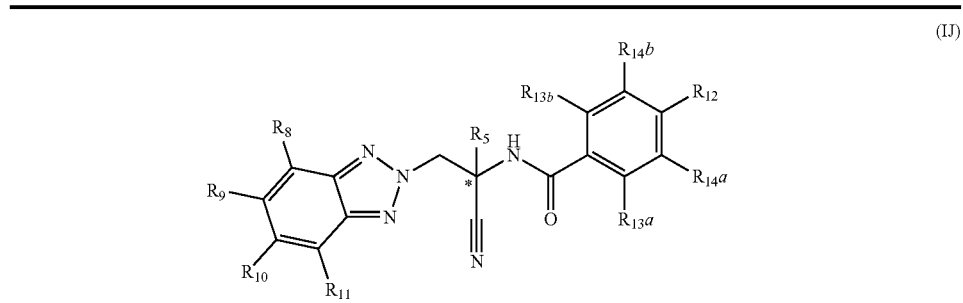

| Cmpd N | $R_{12}$ | $R_{13a}$ | $R_{13b}$ | $R_{14a}$ | $R_{14b}$ | $R_5$ | $R_8$ | $R_9$ | $R_{10}$ | $R_{11}$ | Optical Rotation |
|---|---|---|---|---|---|---|---|---|---|---|---|
| 1.001 | $OCF_3$ | H | H | H | H | Me | H | Cl | H | H | (+)/(−) |
| 1.002 | $CF_3$ | H | H | H | H | Me | H | Cl | H | H | (+)/(−) |
| 1.003 | $SCF_3$ | H | H | H | H | Me | H | Cl | H | H | (+)/(−) |
| 1.004 | $OCF_3$ | H | H | H | H | Me | H | H | H | H | (+)/(−) |
| 1.005 | $SCF_3$ | H | H | H | H | Me | H | H | H | H | (+)/(−) |
| 1.006 | $OCF_3$ | H | H | H | H | Me | H | Me | H | H | (+)/(−) |
| 1.007 | $SCF_3$ | H | H | H | H | Me | H | Me | H | H | (+)/(−) |

TABLE 1-continued (IJ)

| Cmpd N | $R_{12}$ | $R_{13a}$ | $R_{13b}$ | $R_{14a}$ | $R_{14b}$ | $R_5$ | $R_8$ | $R_9$ | $R_{10}$ | $R_{11}$ | Optical Rotation |
|---|---|---|---|---|---|---|---|---|---|---|---|
| 1.008 | $OCF_3$ | H | H | H | H | Me | H | $CF_3$ | H | H | (+)/(−) |
| 1.009 | $SCF_3$ | H | H | H | H | Me | H | $CF_3$ | H | H | (+)/(−) |
| 1.010 | $OCF_3$ | H | H | H | H | Me | H | Cl | Cl | H | (+)/(−) |
| 1.011 | $SCF_3$ | H | H | H | H | Me | H | Cl | Cl | H | (+)/(−) |
| 1.012 | $OCF_3$ | H | H | H | H | Me | Cl | H | Cl | H | (+)/(−) |
| 1.013 | $SCF_3$ | H | H | H | H | Me | Cl | H | Cl | H | (+)/(−) |
| 1.014 | $OCF_3$ | H | H | H | H | Me | Cl | H | $CF_3$ | H | (+)/(−) |
| 1.015 | $SCF_3$ | H | H | H | H | Me | Cl | H | $CF_3$ | H | (+)/(−) |
| 1.016 | $OCF_3$ | H | H | H | H | Me | H | CN | H | H | (+)/(−) |
| 1.017 | $SCF_3$ | H | H | H | H | Me | H | CN | H | H | (+)/(−) |
| 1.018 | $OCF_3$ | H | H | H | H | Me | $CF_3$ | H | $CF_3$ | H | (+)/(−) |
| 1.019 | $SCF_3$ | H | H | H | H | Me | $CF_3$ | H | $CF_3$ | H | (+)/(−) |
| 1.020 | $OCF_3$ | H | H | H | H | Me | H | Br | H | H | (+)/(−) |
| 1.021 | $SCF_3$ | H | H | H | H | Me | H | Br | H | H | (+)/(−) |
| 1.022 | $SOCF_3$ | H | H | H | H | Me | H | CN | H | H | (+)/(−) |
| 1.023 | $SOCF_3$ | H | H | H | H | Me | Cl | H | $CF_3$ | H | (+)/(−) |
| 1.024 | $SOCF_3$ | H | H | H | H | Me | Cl | H | Cl | H | (+)/(−) |
| 1.025 | $SO_2CF_3$ | H | H | H | H | Me | Cl | H | Cl | H | (+)/(−) |
| 1.026 | $SO_2CF_3$ | H | H | H | H | Me | H | $CF_3$ | H | H | (+)/(−) |
| 1.027 | $SO_2CF_3$ | H | H | H | H | Me | H | CN | H | H | (+)/(−) |
| 1.028 | $SO_2CF_3$ | H | H | H | H | Me | Cl | H | $CF_3$ | H | (+)/(−) |
| 1.029 | $SO_2CF_3$ | H | H | H | H | Me | H | H | H | H | (+)/(−) |
| 1.030 | $SO_2CF_3$ | H | H | H | H | Me | H | Me | H | H | (+)/(−) |
| 1.031 | $SO_2CF_3$ | H | H | H | H | Me | H | Cl | H | H | (+)/(−) |
| 1.032 | OPh | H | H | H | H | Me | H | Cl | H | H | (+)/(−) |
| 1.033 | $OCF_3$ | H | H | H | H | Me | Me | H | Cl | H | (+)/(−) |
| 1.034 | $SCF_3$ | H | H | H | H | Me | Me | H | Cl | H | (+)/(−) |
| 1.035 | $OCF_3$ | H | H | H | H | Me | H | $OCF_3$ | H | H | (+)/(−) |
| 1.036 | $SCF_3$ | H | H | H | H | Me | H | $OCF_3$ | H | H | (+)/(−) |
| 1.037 | $OCF_3$ | H | H | H | H | Me | $CF_3$ | H | Cl | H | (+)/(−) |
| 1.038 | $SCF_3$ | H | H | H | H | Me | $CF_3$ | H | Cl | H | (+)/(−) |
| 1.039 | OPh | H | H | H | H | Me | Me | H | Cl | H | (+)/(−) |
| 1.040 | $OCF_3$ | H | H | H | H | Me | H | Cl | Me | H | (+)/(−) |
| 1.041 | $SCF_3$ | H | H | H | H | Me | H | Cl | Me | H | (+)/(−) |
| 1.042 | OPh | H | H | H | H | Me | $CF_3$ | H | Cl | H | (+)/(−) |
| 1.043 | $OCF_3$ | H | H | H | H | Me | Cl | H | H | H | (+)/(−) |
| 1.044 | $SCF_3$ | H | H | H | H | Me | Cl | H | H | H | (+)/(−) |
| 1.045 | OPh | H | H | H | H | Me | Cl | H | H | H | (+)/(−) |
| 1.046 | Ph | H | H | H | H | Me | Cl | H | Cl | H | (+)/(−) |
| 1.047 | $OCF_3$ | H | H | H | H | Et | H | Cl | H | H | (+)/(−) |
| 1.048 | $SCF_3$ | H | H | H | H | Et | H | Cl | H | H | (+)/(−) |
| 1.049 | $OCF_3$ | H | H | H | H | $CH_2CH(CH_3)_2$ | H | Cl | H | H | (+)/(−) |
| 1.050 | $SCF_3$ | H | H | H | H | $CH_2CH(CH_3)_2$ | H | Cl | H | H | (+)/(−) |
| 1.051 | $OCF_3$ | H | H | H | H | t-Bu | H | Cl | H | H | (+)/(−) |
| 1.052 | $SCF_3$ | H | H | H | H | t-Bu | H | Cl | H | H | (+)/(−) |
| 1.053 | t-Bu | H | H | H | H | Me | Cl | H | Cl | H | (+)/(−) |
| 1.054 | $OCF_3$ | H | H | H | H | Me | CN | H | $CF_3$ | H | (+)/(−) |
| 1.055 | $SCF_3$ | H | H | H | H | Me | CN | H | $CF_3$ | H | (+)/(−) |
| 1.056 | $OCF_3$ | H | H | H | H | Me | $CF_3$ | H | CN | H | (+)/(−) |
| 1.057 | $OCF_3$ | H | H | H | H | Me | Br | Cl | H | H | (+)/(−) |
| 1.058 | $OCF_3$ | H | H | H | H | $CH_2OH$ | H | Cl | H | H | (+)/(−) |
| 1.059 | $SCF_3$ | H | H | H | H | $CH_2OH$ | H | Cl | H | H | (+)/(−) |
| 1.060 | $OCF_3$ | H | H | H | H | Me | Br | H | Cl | H | (+)/(−) |
| 1.061 | $OCF_3$ | H | H | H | H | $CH_2SMe$ | H | Cl | H | H | (+)/(−) |
| 1.062 | $OCF_3$ | H | H | H | H | $CH_2OMe$ | H | Cl | H | H | (+)/(−) |
| 1.063 | $OCF_3$ | H | H | H | H | $CHOSO_2Me$ | H | Cl | H | H | (+)/(−) |
| 1.064 | $OCF_3$ | H | H | H | H | Me | Cl | Cl | H | Cl | (+)/(−) |
| 1.065 | $SCF_3$ | H | H | H | H | Me | Cl | Cl | H | Cl | (+)/(−) |
| 1.066 | $SCF_3$ | H | H | H | H | Me | $CF_3$ | H | CN | H | (+)/(−) |
| 1.067 | $OCF_3$ | H | H | H | H | Me | CN | H | Cl | H | (+)/(−) |
| 1.068 | $OCF_3$ | H | H | H | H | Me | p-Ph-$CF_3$ | H | Cl | H | (+)/(−) |
| 1.069 | $CHFCF_3$ | H | H | H | H | Me | Cl | Cl | H | Cl | (+)/(−) |

TABLE 1-continued

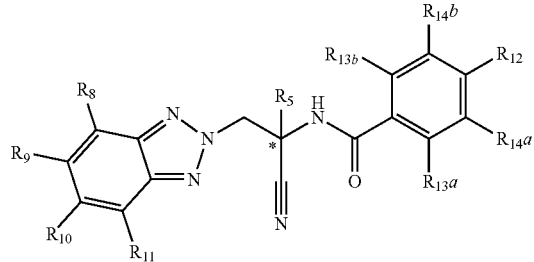

(IJ)

| Cmpd N | $R_{12}$ | $R_{13a}$ | $R_{13b}$ | $R_{14a}$ | $R_{14b}$ | $R_5$ | $R_8$ | $R_9$ | $R_{10}$ | $R_{11}$ | Optical Rotation |
|---|---|---|---|---|---|---|---|---|---|---|---|
| 1.070 | $OCF_3$ | H | H | H | H | Me | Cl | H | OMe | H | (+)/(−) |
| 1.071 | $SCF_3$ | H | H | H | H | Me | Cl | H | OMe | H | (+)/(−) |
| 1.072 | $OCF_3$ | H | H | H | H | Me | H | OMe | H | H | (+)/(−) |
| 1.073 | $SCF_3$ | H | H | H | H | Me | H | OMe | H | H | (+)/(−) |
| 1.074 | $OCF_3$ | H | H | H | H | Me | $CH_2NH_2$ | H | Cl | H | (+)/(−) |
| 1.075 | $OCF_3$ | H | H | H | H | Me | Vinyl | H | Cl | H | (+)/(−) |
| 1.076 | $SCF_3$ | H | H | H | H | Me | Vinyl | H | Cl | H | (+)/(−) |
| 1.077 | $OCF_3$ | H | H | H | H | Me | $CH(OH)CH_2OH$ | H | Cl | H | (+)/(−) |
| 1.078 | $OCF_3$ | H | H | H | H | Me | $CH(F)CH_2F$ | H | Cl | H | (+)/(−) |
| 1.079 | $OCF_3$ | H | H | H | H | Me | Formyl | H | Cl | H | (+)/(−) |
| 1.080 | $OCF_3$ | H | H | H | H | Me | $CH_2NMe_2$ | H | Cl | H | (+)/(−) |
| 1.081 | $OCF_3$ | H | H | H | H | Me | $CH_2OH$ | H | Cl | H | (+)/(−) |
| 1.082 | $OCF_3$ | H | H | H | H | Me | $CO_2H$ | H | Cl | H | (+)/(−) |
| 1.083 | $OCF_3$ | H | H | H | H | Me | Br | Cl | H | Br | (+)/(−) |
| 1.084 | $OCF_3$ | H | H | H | H | Me | $CO_2Me$ | H | Cl | H | (+)/(−) |
| 1.085 | $SCF_3$ | H | H | H | H | Me | Br | Cl | H | Br | (+)/(−) |
| 1.086 | $OCF_3$ | H | H | H | H | Me | Br | Cl | H | Cl | (+)/(−) |
| 1.087 | $SCF_3$ | H | H | H | H | Me | Br | Cl | H | Cl | (+)/(−) |
| 1.088 | $OCF_3$ | H | H | H | H | Me | Br | Cl | Br | Cl | (+)/(−) |
| 1.089 | $SCF_3$ | H | H | H | H | Me | Br | Cl | Br | Cl | (+)/(−) |
| 1.090 | $OCF_3$ | H | H | H | H | Me | F | Cl | H | Cl | (+)/(−) |
| 1.091 | $SCF_3$ | H | H | H | H | Me | F | Cl | H | Cl | (+)/(−) |
| 1.092 | $OCF_3$ | H | H | H | H | Me | Me | Cl | H | Me | (+)/(−) |
| 1.093 | $SCF_3$ | H | H | H | H | Me | Me | Cl | H | Me | (+)/(−) |
| 1.094 | $OCF_3$ | H | H | H | H | Me | F | Br | H | Me | (+)/(−) |
| 1.095 | $SCF_3$ | H | H | H | H | Me | F | Br | H | Me | (+)/(−) |
| 1.096 | $OCF_3$ | H | H | H | H | Me | Cl | Cl | H | Cl | (+) |
| 1.097 | $OCF_3$ | H | H | H | H | Me | Cl | Cl | H | Cl | (−) |
| 1.098 | CN | H | H | H | H | Me | Br | Cl | H | Br | (+)/(−) |
| 1.099 | $OCH_2CHF_2$ | H | H | H | H | Me | Br | Cl | H | Br | (+)/(−) |
| 1.100 | I | H | H | H | H | Me | Cl | Cl | H | Cl | (+)/(−) |
| 1.101 | $CF_3$ | H | H | H | H | Me | Cl | Cl | H | Cl | (+)/(−) |
| 1.102 | CN | H | H | H | H | Me | Cl | Cl | H | Cl | (+)/(−) |
| 1.103 | $OCH_2CHF_2$ | H | H | H | H | Me | Cl | Cl | H | Cl | (+)/(−) |
| 1.104 | $SF_5$ | H | H | H | H | Me | Cl | Cl | H | Cl | (+)/(−) |
| 1.105 | $SF_5$ | H | H | H | H | Me | Cl | Cl | H | Cl | (+) |
| 1.106 | $SF_5$ | H | H | H | H | Me | Cl | Cl | H | Cl | (−) |
| 1.107 | $SF_5$ | Br | H | H | H | Me | Cl | Cl | H | Cl | (+)/(−) |
| 1.108 | $SF_5$ | Cl | H | H | H | Me | Cl | Cl | H | Cl | (+)/(−) |
| 1.109 | $SF_5$ | F | H | H | H | Me | Cl | Cl | H | Cl | (+)/(−) |
| 1.110 | $SF_5$ | H | H | Br | H | Me | Cl | Cl | H | Cl | (+)/(−) |
| 1.111 | $SF_5$ | H | H | Cl | H | Me | Cl | Cl | H | Cl | (+)/(−) |
| 1.112 | $SF_5$ | H | H | F | H | Me | Cl | Cl | H | Cl | (+)/(−) |
| 1.113 | $SF_5$ | Cl | H | F | H | Me | Cl | Cl | H | Cl | (+)/(−) |
| 1.114 | $SF_5$ | F | H | Cl | H | Me | Cl | Cl | H | Cl | (+)/(−) |
| 1.115 | $SF_5$ | F | H | F | H | Me | Cl | Cl | H | Cl | (+)/(−) |
| 1.116 | $SF_5$ | Br | H | H | F | Me | Cl | Cl | H | Cl | (+)/(−) |
| 1.117 | $SF_5$ | Cl | H | H | F | Me | Cl | Cl | H | Cl | (+)/(−) |
| 1.118 | $SF_5$ | F | H | H | F | Me | Cl | Cl | H | Cl | (+)/(−) |
| 1.119 | $SF_5$ | F | F | H | H | Me | Cl | Cl | H | Cl | (+)/(−) |
| 1.120 | $SF_5$ | H | H | F | F | Me | Cl | Cl | H | Cl | (+)/(−) |
| 1.121 | $SF_5$ | F | F | F | F | Me | Cl | Cl | H | Cl | (+)/(−) |
| 1.122 | $SF_5$ | Me | H | H | H | Me | Cl | Cl | H | Cl | (+)/(−) |
| 1.123 | $SF_5$ | Me | H | H | F | Me | Cl | Cl | H | Cl | (+)/(−) |
| 1.124 | $OCF_3$ | Br | H | H | H | Me | Cl | Cl | H | Cl | (+)/(−) |
| 1.125 | $OCF_3$ | Cl | H | H | H | Me | Cl | Cl | H | Cl | (+)/(−) |
| 1.126 | $OCF_3$ | F | H | H | H | Me | Cl | Cl | H | Cl | (+)/(−) |
| 1.127 | $OCF_3$ | H | H | Br | H | Me | Cl | Cl | H | Cl | (+)/(−) |
| 1.128 | $OCF_3$ | H | H | Cl | H | Me | Cl | Cl | H | Cl | (+)/(−) |
| 1.129 | $OCF_3$ | H | H | F | H | Me | Cl | Cl | H | Cl | (+)/(−) |
| 1.130 | $OCF_3$ | Cl | H | F | H | Me | Cl | Cl | H | Cl | (+)/(−) |
| 1.131 | $OCF_3$ | F | H | Cl | H | Me | Cl | Cl | H | Cl | (+)/(−) |

TABLE 1-continued

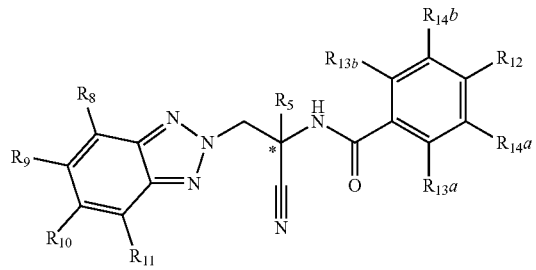

(IJ)

| Cmpd N | $R_{12}$ | $R_{13a}$ | $R_{13b}$ | $R_{14a}$ | $R_{14b}$ | $R_5$ | $R_8$ | $R_9$ | $R_{10}$ | $R_{11}$ | Optical Rotation |
|---|---|---|---|---|---|---|---|---|---|---|---|
| 1.132 | OCF$_3$ | F | H | F | H | Me | Cl | Cl | H | Cl | (+)/(−) |
| 1.133 | OCF$_3$ | Br | H | H | F | Me | Cl | Cl | H | Cl | (+)/(−) |
| 1.134 | OCF$_3$ | Cl | H | H | F | Me | Cl | Cl | H | Cl | (+)/(−) |
| 1.135 | OCF$_3$ | F | H | H | F | Me | Cl | Cl | H | Cl | (+)/(−) |
| 1.136 | OCF$_3$ | F | F | H | H | Me | Cl | Cl | H | Cl | (+)/(−) |
| 1.137 | OCF$_3$ | H | H | F | F | Me | Cl | Cl | H | Cl | (+)/(−) |
| 1.138 | OCF$_3$ | F | F | F | F | Me | Cl | Cl | H | Cl | (+)/(−) |
| 1.139 | OCF$_3$ | Me | H | H | H | Me | Cl | Cl | H | Cl | (+)/(−) |
| 1.140 | OCF$_3$ | Me | H | H | F | Me | Cl | Cl | H | Cl | (+)/(−) |
| 1.141 | CF$_3$ | Br | H | H | H | Me | Cl | Cl | H | Cl | (+)/(−) |
| 1.142 | CF$_3$ | Cl | H | H | H | Me | Cl | Cl | H | Cl | (+)/(−) |
| 1.143 | CF$_3$ | F | H | H | H | Me | Cl | Cl | H | Cl | (+)/(−) |
| 1.144 | CF$_3$ | H | H | Br | H | Me | Cl | Cl | H | Cl | (+)/(−) |
| 1.145 | CF$_3$ | H | H | Cl | H | Me | Cl | Cl | H | Cl | (+)/(−) |
| 1.146 | CF$_3$ | H | H | F | H | Me | Cl | Cl | H | Cl | (+)/(−) |
| 1.147 | CF$_3$ | Cl | H | F | H | Me | Cl | Cl | H | Cl | (+)/(−) |
| 1.148 | CF$_3$ | F | H | Cl | H | Me | Cl | Cl | H | Cl | (+)/(−) |
| 1.149 | CF$_3$ | F | H | F | H | Me | Cl | Cl | H | Cl | (+)/(−) |
| 1.150 | CF$_3$ | Br | H | H | F | Me | Cl | Cl | H | Cl | (+)/(−) |
| 1.151 | CF$_3$ | Cl | H | H | F | Me | Cl | Cl | H | Cl | (+)/(−) |
| 1.152 | CF$_3$ | F | H | H | F | Me | Cl | Cl | H | Cl | (+)/(−) |
| 1.153 | CF$_3$ | F | F | H | H | Me | Cl | Cl | H | Cl | (+)/(−) |
| 1.154 | CF$_3$ | H | H | F | F | Me | Cl | Cl | H | Cl | (+)/(−) |
| 1.155 | CF$_3$ | F | F | F | F | Me | Cl | Cl | H | Cl | (+)/(−) |
| 1.156 | CF$_3$ | Me | H | H | H | Me | Cl | Cl | H | Cl | (+)/(−) |
| 1.157 | CF$_3$ | Me | H | H | F | Me | Cl | Cl | H | Cl | (+)/(−) |

Compounds of general formula (IJ) which are of particular interest include, but are not limited to, N-[2-(5-Chloro-2H-benzotriazol-2-yl)-1-cyano-1-methylethyl]-4-trifluoromethoxybenzamide (compound No 1.001)

N-[2-(5-Chloro-2H-benzotriazol-2-yl)-1-cyano-1-methylethyl]-4-trifluoromethylbenzamide (compound No 1.002)

N-[2-(5-Chloro-2H-benzotriazol-2-yl)-1-cyano-1-methylethyl]-4-trifluoromethylthiobenzamide (compound No 1.003)

N-[2-(2H-Benzotriazol-2-yl)-1-cyano-1-methylethyl]-4-trifluoromethoxybenzamide (compound No 1.004)

N-[2-(2H-Benzotriazol-2-yl)-1-cyano-1-methylethyl]-4-trifluoromethylthiobenzamide (compound No 1.005)

N-[1-Cyano-1-methyl-2-(5-methyl-2H-benzotriazol-2-yl)ethyl]-4-trifluoromethoxybenzamide (compound No 1.006)

N-[1-Cyano-1-methyl-2-(5-methyl-2H-benzotriazol-2-yl)ethyl]-4-trifluoromethylthiobenzamide (compound No 1.007)

N-[1-Cyano-1-methyl-2-(5-trifluoromethyl-2H-benzotriazol-2-yl)ethyl]-4-trifluoromethoxybenzamide (compound No 1.008)

N-[1-Cyano-1-methyl-2-(5-trifluoromethyl-2H-benzotriazol-2-yl)ethyl]-4-trifluoromethylthiobenzamide (compound No 1.009)

N-[1-Cyano-2-(5,6-dichloro-2H-benzotriazol-2-yl)-1-methylethyl]-4-trifluoromethoxybenzamide (compound No 1.010)

N-[1-Cyano-2-(5,6-dichloro-2H-benzotriazol-2-yl)-1-methylethyl]-4-trifluoromethylthiobenzamide (compound No 1.011)

N-[1-Cyano-2-(4,6-dichloro-2H-benzotriazol-2-yl)-1-methylethyl]-4-trifluoromethoxybenzamide (compound No 1.012)

N-[1-Cyano-2-(4,6-dichloro-2H-benzotriazol-2-yl)-1-methylethyl]-4-trifluoromethylthiobenzamide (compound No 1.013)

N-[2-(4-Chloro-6-trifluoromethyl-2H-benzotriazol-2-yl)-1-cyano-1-methylethyl]-4-trifluoromethoxybenzamide (compound No 1.014)

N-[2-(4-Chloro-6-trifluoromethyl-2H-benzotriazol-2-yl)-1-cyano-1-methylethyl]-4-trifluoromethylthiobenzamide (compound No 1.015)

N-[1-Cyano-2-(5-cyano-2H-benzotriazol-2-yl)-1-methylethyl]-4-trifluoromethoxybenzamide (compound No 1.016)

N-[1-Cyano-2-(5-cyano-2H-benzotriazol-2-yl)-1-methylethyl]-4-trifluoromethylthiobenzamide (compound No 1.017)

N-[2-(4,6-Bis(trifluoromethyl)-2H-benzotriazol-2-yl)-1-cyano-1-methylethyl]-4-trifluoromethoxybenzamide (compound No 1.018)

N-[2-(4,6-Bis(trifluoromethyl)-2H-benzotriazol-2-yl)-1-cyano-1-methylethyl]-4-trifluoromethylthiobenzamide (compound No 1.019)

N-[2-(5-Bromo-2H-benzotriazol-2-yl)-1-cyano-1-methylethyl]-4-trifluoromethoxybenzamide (compound No 1.020)
N-[2-(5-Bromo-2H-benzotriazol-2-yl)-1-cyano-1-methylethyl]-4-trifluoromethylthiobenzamide (compound No 1.021)
N-[1-Cyano-2-(5-cyano-2H-benzotriazol-2-yl)-1-methylethyl]-4-trifluoromethylsulfinylbenzamide (compound No 1.022)
N-[2-(4-Chloro-6-trifluoromethyl-2H-benzotriazol-2-yl)-1-cyano-1-methylethyl]-4-trifluoromethylsulfinylbenzamide (compound No 1.023)
N-[1-Cyano-2-(4,6-dichloro-2H-benzotriazol-2-yl)-1-methylethyl]-4-trifluoromethylsulfinylbenzamide (compound No 1.024)
N-[1-Cyano-2-(4,6-dichloro-2H-benzotriazol-2-yl)-1-methylethyl]-4-trifluoromethylsulfonylbenzamide (compound No 1.025)
N-[1-Cyano-1-methyl-2-(5-trifluoromethyl-2H-benzotriazol-2-yl)ethyl]-4-trifluoromethylsulfonylbenzamide (compound No 1.026)
N-[1-Cyano-1-methyl-2-(5-cyano-2H-benzotriazol-2-yl)ethyl]-4-trifluoromethylsulfonylbenzamide (compound No 1.027)
N-[2-(4-Chloro-6-trifluoromethyl-2H-benzotriazol-2-yl)-1-cyano-1-methylethyl]-4-trifluoromethylsulfonylbenzamide (compound No 1.028)
N-[2-(2H-Benzotriazol-2-yl)-1-cyano-1-methylethyl]-4-trifluoromethylsulfonylbenzamide (compound No 1.029)
N-[1-Cyano-1-methyl-2-(5-methyl-2H-benzotriazol-2-yl)ethyl]-4-trifluoromethylsulfonylbenzamide (compound No 1.030)
N-[2-(5-Chloro-2H-benzotriazol-2-yl)-1-cyano-1-methylethyl]-4-trifluoromethylsulfonylbenzamide (compound No 1.031)
N-[2-(5-Chloro-2H-benzotriazol-2-yl)-1-cyano-1-methylethyl]-4-phenoxybenzamide (compound No 1.032)
N-[2-(6-Chloro-4-methyl-2H-benzotriazol-2-yl)-1-cyano-1-methylethyl]-4-trifluoromethoxybenzamide (compound No 1.033)
N-[2-(6-Chloro-4-methyl-2H-benzotriazol-2-yl)-1-cyano-1-methylethyl]-4-trifluoromethylthiobenzamide (compound No 1.034)
N-[1-Cyano-1-methyl-2-(5-trifluoromethoxy-2H-benzotriazol-2-yl)ethyl]-4-trifluoromethoxybenzamide (compound No 1.035)
N-[1-Cyano-1-methyl-2-(5-trifluoromethoxy-2H-benzotriazol-2-yl)ethyl]-4-trifluoromethylthiobenzamide (compound No 1.036)
N-[2-(6-Chloro-4-trifluoromethyl-2H-benzotriazol-2-yl)-1-cyano-1-methylethyl]-4-trifluoromethoxybenzamide (compound No 1.037)
N-[2-(6-Chloro-4-trifluoromethyl-2H-benzotriazol-2-yl)-1-cyano-1-methylethyl]-4-trifluoromethylthiobenzamide (compound No 1.038)
N-[2-(6-Chloro-4-methyl-2H-benzotriazol-2-yl)-1-cyano-1-methylethyl]-4-phenoxybenzamide (compound No 1.039)
N-[2-(5-Chloro-6-methyl-2H-benzotriazol-2-yl)-1-cyano-1-methylethyl]-4-trifluoromethoxybenzamide (compound No 1.040)
N-[1-Cyano-1-methyl-2-(5-methyl-2H-benzotriazol-2-yl)ethyl]-4-trifluoromethylthiobenzamide (compound No 1.041)
N-[2-(6-Chloro-4-trifluoromethyl-2H-benzotriazol-2-yl)-1-cyano-1-methylethyl]-4-phenoxybenzamide (compound No 1.042)
N-[2-(4-Chloro-2H-benzotriazol-2-yl)-1-cyano-1-methylethyl]-4-trifluoromethoxybenzamide (compound No 1.043)
N-[2-(4-Chloro-2H-benzotriazol-2-yl)-1-cyano-1-methylethyl]-4-trifluoromethylthiobenzamide (compound No 1.044)
N-[2-(4-Chloro-2H-benzotriazol-2-yl)-1-cyano-1-methylethyl]-4-phenoxybenzamide (compound No 1.045)
N-[1-Cyano-2-(4,6-dichloro-2H-benzotriazol-2-yl)-1-methylethyl]biphenyl-4-carboxamide (compound No 1.046)
N-{1-[(5-Chloro-2H-benzotriazol-2-yl)methyl]-1-cyanopropyl}-4-trifluoromethoxybenzamide (compound No 1.047)
N-{1-[(5-Chloro-2H-benzotriazol-2-yl)methyl]-1-cyanopropyl}-4-trifluoromethylthiobenzamide (compound No 1.048)
N-{1-[(5-Chloro-2H-benzotriazol-2-yl)methyl]-1-cyano-3-methylbutyl}-4-trifluoromethoxybenzamide (compound No 1.049)
N-{1-[(5-Chloro-2H-benzotriazol-2-yl)methyl]-1-cyano-3-methylbutyl}-4-trifluoromethylthiobenzamide (compound No 1.050)
N-{1-[(5-Chloro-2H-benzotriazol-2-yl)methyl]-1-cyano-2,2-dimethylpropyl}-4-trifluoromethoxybenzamide (compound No 1.051)
N-{1-[(5-Chloro-2H-benzotriazol-2-yl)methyl]-1-cyano-2,2-dimethylpropyl}-4-trifluoromethylthiobenzamide (compound No 1.052)
N-[1-Cyano-2-(4,6-dichloro-2H-benzotriazol-2-yl)-1-methylethyl]-4-tert-butylbenzamide (compound No 1.053)
N-[1-Cyano-2-(4-cyano-6-trifluoromethyl-2H-benzotriazol-2-yl)-1-methylethyl]-4-trifluoromethoxybenzamide (compound No 1.054)
N-[1-Cyano-2-(4-cyano-6-trifluoromethyl-2H-benzotriazol-2-yl)-1-methylethyl]-4-trifluoromethylthiobenzamide (compound No 1.055)
N-[1-Cyano-2-(6-cyano-4-trifluoromethyl-2H-benzotriazol-2-yl)-1-methylethyl]-4-trifluoromethoxybenzamide (compound No 1.056)
N-[2-(4-Bromo-5-chloro-2H-benzotriazol-2-yl)-1-cyano-1-methylethyl]-4-trifluoromethoxybenzamide (compound No 1.057)
N-[2-(5-Chloro-2H-benzotriazol-2-yl)-1-cyano-1-(hydroxymethyl)ethyl]-4-trifluoromethoxybenzamide (compound No 1.058)
N-[2-(5-Chloro-2H-benzotriazol-2-yl)-1-cyano-1-(hydroxymethyl)ethyl]-4-trifluoromethylthiobenzamide (compound No 1.059)
N-[2-(4-Bromo-6-chloro-2H-benzotriazol-2-yl)-1-cyano-1-methylethyl]-4-trifluoromethoxybenzamide (compound No 1.060)
N-[2-(5-Chloro-2H-benzotriazol-2-yl)-1-cyano-1-(methylthiomethyl)ethyl]-4-trifluoromethoxybenzamide (compound No 1.061)
N-[2-(5-Chloro-2H-benzotriazol-2-yl)-1-cyano-1-(methoxymethyl)ethyl]-4-trifluoromethoxybenzamide (compound No 1.062)
N-[2-(5-Chloro-2H-benzotriazol-2-yl)-1-cyano-1-(methanesulfonylmethyl)ethyl]-4-trifluoromethoxybenzamide (compound No 1.063)
N-[1-Cyano-1-methyl-2-(4,5,7-trichloro-2H-benzotriazol-2-yl)-ethyl]-4-trifluoromethoxybenzamide (compound No 1.064)
(+)-N-[1-Cyano-1-methyl-2-(4,5,7-trichloro-2H-benzotriazol-2-yl)-ethyl]-4-trifluoromethoxybenzamide (compound No 1.096)

(−)-N-[1-Cyano-1-methyl-2-(4,5,7-trichloro-2H-benzotriazol-2-yl)-ethyl]-4-trifluoromethoxybenzamide (compound No 1.097)
N-[1-Cyano-1-methyl-2-(4,5,7-trichloro-2H-benzotriazol-2-yl)-ethyl]-4-trifluoromethylthiobenzamide (compound No 1.065)
N-[1-Cyano-2-(6-cyano-4-trifluoromethyl-2H-benzotriazol-2-yl)-1-methylethyl]-4-trifluoromethylthiobenzamide (compound No 1.066)
N-[2-(6-Chloro-4-cyano-2H-benzotriazol-2-yl)-1-cyano-1-methylethyl]-4-trifluoromethoxybenzamide (compound No 1.067)
N-{2-[6-Chloro-4-(4-trifluoromethylphenyl)-2H-benzotriazol-2-yl]-1-cyano-1-methylethyl}-4-trifluoromethoxybenzamide (compound No 1.068)
N-[1-Cyano-1-methyl-2-(4,5,7-trichloro-2H-benzotriazol-2-yl)-ethyl]-4-(1,2,2,2-tetrafluoroethyl)benzamide (compound No 1.069)
N-[2-(4-Chloro-6-methoxy-2H-benzotriazol-2-yl)-1-cyano-1-methylethyl]-4-trifluoromethoxybenzamide (compound No 1.070)
N-[2-(4-Chloro-6-methoxy-2H-benzotriazol-2-yl)-1-cyano-1-methylethyl]-4-trifluoromethylthiobenzamide (compound No 1.071)
N-[1-cyano-2-(5-methoxy-2H-benzotriazol-2-yl)-1-methylethyl]-4-trifluoromethoxybenzamide (compound No 1.072)
N-[1-cyano-2-(5-methoxy-2H-benzotriazol-2-yl)-1-methylethyl]-4-trifluoromethylthiobenzamide (compound No 1.073)
N-[2-(4-Aminomethyl-6-chloro-2H-benzotriazol-2-yl)-1-cyano-1-methylethyl]-4-trifluoromethoxybenzamide (compound No 1.074)
N-[2-(6-Chloro-4-vinyl-2H-benzotriazol-2-yl)-1-cyano-1-methylethyl]-4-trifluoromethoxybenzamide (compound No 1.075)
N-[2-(6-Chloro-4-vinyl-2H-benzotriazol-2-yl)-1-cyano-1-methylethyl]-4-trifluoromethylthiobenzamide (compound No 1.076)
N-{2-[6-Chloro-4-(1,2-dihydroxyethyl)-2H-benzotriazol-2-yl]-1-cyano-1-methyl-ethyl}-4-trifluoromethoxybenzamide (compound No 1.077)
N-{2-[6-Chloro-4-(1,2-difluoroethyl)-2H-benzotriazol-2-yl]-1-cyano-1-methyl-ethyl}-4-trifluoromethoxybenzamide (compound No 1.078)
N-[2-(6-Chloro-4-formyl-2H-benzotriazol-2-yl)-1-cyano-1-methylethyl]-4-trifluoromethoxybenzamide (compound No 1.079)
N-[2-(6-Chloro-4-dimethylaminomethyl-2H-benzotriazol-2-yl)-1-cyano-1-methylethyl]-4-trifluoromethoxybenzamide (compound No 1.080)
N-[2-(6-Chloro-4-hydroxymethyl-2H-benzotriazol-2-yl)-1-cyano-1-methylethyl]-4-trifluoromethoxybenzamide (compound No 1.081)
6-Chloro-2-[2-cyano-2-({[4-(trifluoromethoxy)phenyl]carbonyl}amino)-propyl]-2H-benzotriazole-4-carboxylic acid (compound No 1.082)
Methyl 6-chloro-2-[2-cyano-2-({[4-(trifluoromethoxy)phenyl]carbonyl}-amino)propyl]-2H-benzotriazole-4-carboxylate (compound No 1.084)
N-[2-(5-Chloro-4,7-dibromo-2H-benzotriazol-2-yl)-1-cyano-1-methylethyl]-4-trifluoromethylthiobenzamide (compound No 1.085)
N-[2-(4-Bromo-5,7-dichloro-2H-benzotriazol-2-yl)-1-cyano-1-methylethyl]-4-trifluoromethoxybenzamide (compound No 1.086)
N-[2-(4-Bromo-5,7-dichloro-2H-benzotriazol-2-yl)-1-cyano-1-methylethyl]-4-trifluoromethylthiobenzamide (compound No 1.087)
N-[1-Cyano-2-(4,6-dibromo-5,7-dichloro-2H-benzotriazol-2-yl)-1-methylethyl]-4-trifluoromethoxybenzamide (compound No 1.088)
N-[1-Cyano-2-(4,6-dibromo-5,7-dichloro-2H-benzotriazol-2-yl)-1-methylethyl]-4-trifluoromethylthiobenzamide (compound No 1.089)
N-[1-Cyano-2-(5,7-dichloro-4-fluoro-2H-benzotriazol-2-yl)-1-methylethyl]-4-trifluoromethoxybenzamide (compound No 1.090)
N-[1-Cyano-2-(5,7-dichloro-4-fluoro-2H-benzotriazol-2-yl)-1-methylethyl]-4-trifluoromethylthiobenzamide (compound No 1.091)
N-[2-(5-Chloro-4,7-dimethyl-2H-benzotriazol-2-yl)-1-cyano-1-methylethyl]-4-trifluoromethoxybenzamide (compound No 1.092)
N-[2-(5-Chloro-4,7-dimethyl-2H-benzotriazol-2-yl)-1-cyano-1-methylethyl]-4-trifluoromethylthiobenzamide (compound No 1.093)
N-[2-(5-bromo-4-fluoro-7-methyl-2H-benzotriazol-2-yl)-1-cyano-1-methylethyl]-4-trifluoromethoxybenzamide (compound No 1.094)
N-[2-(5-bromo-4-fluoro-7-methyl-2H-benzotriazol-2-yl)-1-cyano-1-methylethyl]-4-trifluoromethylthiobenzamide (compound No 1.095)
(+)-N-[1-Cyano-1-methyl-2-(4,5,7-trichloro-2H-benzotriazol-2-yl)-ethyl]-4-trifluoromethoxybenzamide (compound No 1.096)
(−)-N-[1-Cyano-1-methyl-2-(4,5,7-trichloro-2H-benzotriazol-2-yl)-ethyl]-4-trifluoromethoxybenzamide (compound No 1.097)
N-[2-(5-Chloro-4,7-dibromo-2H-benzotriazol-2-yl)-1-cyano-1-methylethyl]-4-cyanobenzamide (compound No 1.098)
N-[2-(5-Chloro-4,7-dibromo-2H-benzotriazol-2-yl)-1-cyano-1-methylethyl]-4-(1,1,2,2-tetrafluoroethoxy)benzamide (compound No 1.099)
N-[1-Cyano-1-methyl-2-(4,5,7-trichloro-2H-benzotriazol-2-yl)-ethyl]-4-iodobenzamide (compound No 1.100)
N-[1-Cyano-1-methyl-2-(4,5,7-trichloro-2H-benzotriazol-2-yl)-ethyl]-4-trifluoromethylbenzamide (compound No 1.101)
N-[1-Cyano-1-methyl-2-(4,5,7-trichloro-2H-benzotriazol-2-yl)-ethyl]-4-cyanobenzamide (compound No 1.102)
N-[1-Cyano-1-methyl-2-(4,5,7-trichloro-2H-benzotriazol-2-yl)-ethyl]-4-(1,1,2,2-tetrafluoroethoxy)benzamide (compound No 1.103)
N-[1-Cyano-1-methyl-2-(4,5,7-trichloro-2H-benzotriazol-2-yl)-ethyl]-4-pentafluorothiobenzamide (compound No 1.104)
(+)-N-[1-Cyano-1-methyl-2-(4,5,7-trichloro-2H-benzotriazol-2-yl)-ethyl]-4-pentafluorothiobenzamide (compound No 1.105)
(−)-N-[1-Cyano-1-methyl-2-(4,5,7-trichloro-2H-benzotriazol-2-yl)-ethyl]-4-pentafluorothiobenzamide (compound No 1.106)
N-[1-Cyano-1-methyl-2-(4,5,7-trichloro-2H-benzotriazol-2-yl)-ethyl]-3-fluoro-4-trifluoromethylbenzamide (compound No 1.146)
N-[1-Cyano-1-methyl-2-(4,5,7-trichloro-2H-benzotriazol-2-yl)-ethyl]-2-fluoro-4-trifluoromethylbenzamide (compound No 1.143)
The numbers 1.001 to 1.157 are assigned to the above compounds for identification and reference hereinafter.

Table 2 below shows specific compounds encompased by formula (I), which have the structure (IK):

TABLE 2

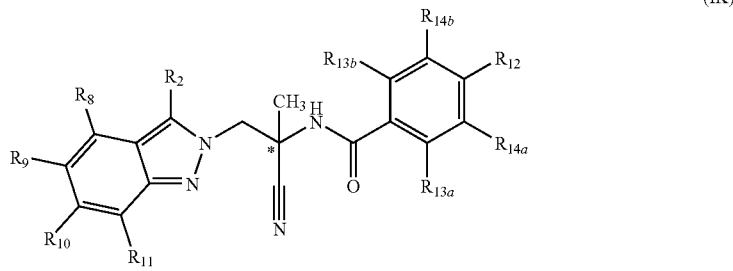

(IK)

| Compound No. | $R_{12}$ | $R_{13a}$ | $R_{13b}$ | $R_{14a}$ | $R_{14b}$ | $R_2$ | $R_8$ | $R_9$ | $R_{10}$ | $R_{11}$ | Optical rotation |
|---|---|---|---|---|---|---|---|---|---|---|---|
| 2.001 | $OCF_3$ | H | H | H | H | H | H | $NO_2$ | H | H | (+)/(−) |
| 2.002 | $SCF_3$ | H | H | H | H | H | H | $NO_2$ | H | H | (+)/(−) |
| 2.003 | $OCF_3$ | H | H | H | H | H | H | Cl | H | Cl | (+)/(−) |
| 2.004 | OPh | H | H | H | H | H | H | Cl | H | Cl | (+)/(−) |
| 2.005 | $SCF_3$ | H | H | H | H | H | H | Cl | H | Cl | (+)/(−) |
| 2.006 | $OCF_3$ | H | H | H | H | H | H | Cl | H | Me | (+)/(−) |
| 2.007 | $SCF_3$ | H | H | H | H | H | H | Cl | H | Me | (+)/(−) |
| 2.008 | $OCF_3$ | H | H | H | H | OMe | H | H | Cl | H | (+)/(−) |
| 2.009 | $SCF_3$ | H | H | H | H | OMe | H | H | Cl | H | (+)/(−) |
| 2.010 | $OCF_3$ | H | H | H | H | Me | H | Cl | H | Cl | (+)/(−) |
| 2.011 | $SCF_3$ | H | H | H | H | Me | H | Cl | H | Cl | (+)/(−) |
| 2.012 | $OCF_3$ | H | H | H | H | OMe | H | Cl | H | H | (+)/(−) |
| 2.013 | $SCF_3$ | H | H | H | H | OMe | H | Cl | H | H | (+)/(−) |
| 2.014 | $OCF_3$ | H | H | H | H | OEt | H | Cl | H | H | (+)/(−) |
| 2.015 | $SCF_3$ | H | H | H | H | OEt | H | Cl | H | H | (+)/(−) |
| 2.016 | $OCF_3$ | H | H | H | H | OMe | H | H | H | H | (+)/(−) |
| 2.017 | $OCF_3$ | H | H | H | H | $O(CH_2)_2OMe$ | H | H | Cl | H | (+)/(−) |
| 2.018 | $OCF_3$ | H | H | H | H | $O(CH_2)_2NMe_2$ | H | H | Cl | H | (+)/(−) |
| 2.019 | $SCF_3$ | H | H | H | H | OMe | H | Cl | H | Cl | (+)/(−) |
| 2.020 | $OCF_3$ | H | H | H | H | OMe | H | Cl | H | Cl | (+)/(−) |
| 2.021 | $OCF_3$ | H | H | H | H | OMe | Cl | H | Cl | H | (+)/(−) |
| 2.022 | $SCF_3$ | H | H | H | H | OMe | Cl | H | Cl | H | (+)/(−) |
| 2.023 | $OCF_3$ | H | H | H | H | OMe | H | H | Br | H | (+)/(−) |
| 2.024 | $SCF_3$ | H | H | H | H | OMe | H | H | Br | H | (+)/(−) |
| 2.025 | $OCF_3$ | H | H | H | H | OMe | H | H | $CF_3$ | H | (+)/(−) |
| 2.026 | $SCF_3$ | H | H | H | H | OMe | H | H | $CF_3$ | H | (+)/(−) |
| 2.027 | $OCF_3$ | H | H | H | H | OEt | H | H | Cl | H | (+)/(−) |
| 2.028 | $SCF_3$ | H | H | H | H | OEt | H | H | Cl | H | (+)/(−) |
| 2.029 | $OCF_3$ | H | H | H | H | O-n-Pr | H | H | Cl | H | (+)/(−) |
| 2.030 | $SCF_3$ | H | H | H | H | O-n-Pr | H | H | Cl | H | (+)/(−) |
| 2.031 | $OCF_3$ | H | H | H | H | O-n-Bu | H | H | Cl | H | (+)/(−) |
| 2.032 | $OCF_3$ | H | H | H | H | OMe | H | H | $CO_2Me$ | H | (+)/(−) |
| 2.033 | $OCF_3$ | H | H | H | H | OMe | H | H | $NO_2$ | H | (+)/(−) |
| 2.034 | $OCF_3$ | H | H | H | H | OMe | H | H | $NH_2$ | H | (+)/(−) |
| 2.035 | $OCF_3$ | H | H | H | H | OMe | H | H | NHAc | H | (+)/(−) |
| 2.036 | $OCF_3$ | H | H | H | H | OMe | H | H | $CONH_2$ | H | (+)/(−) |
| 2.037 | $OCF_3$ | H | H | H | H | H | H | H | Cl | H | (+)/(−) |
| 2.038 | $SCF_3$ | H | H | H | H | H | H | H | Cl | H | (+)/(−) |
| 2.039 | $OCF_3$ | H | H | H | H | Cl | H | H | Cl | Cl | (+)/(−) |
| 2.040 | $OCF_3$ | H | H | H | H | H | Cl | H | Cl | H | (+)/(−) |
| 2.041 | $SCF_3$ | H | H | H | H | H | Cl | H | Cl | H | (+)/(−) |
| 2.042 | $OCF_3$ | H | H | H | H | Br | H | H | Cl | H | (+)/(−) |
| 2.043 | $OCF_3$ | H | H | H | H | H | H | H | Cl | Br | (+)/(−) |
| 2.044 | $OCF_3$ | H | H | H | H | Cl | H | H | Cl | H | (+)/(−) |
| 2.045 | $OCF_3$ | H | H | H | H | H | H | H | Cl | Cl | (+)/(−) |
| 2.046 | $OCF_3$ | H | H | H | H | Br | Cl | H | Cl | Br | (+)/(−) |
| 2.047 | $OCF_3$ | H | H | H | H | H | Cl | H | Cl | Br | (+)/(−) |
| 2.048 | $OCF_3$ | H | H | H | H | H | Cl | H | Cl | Cl | (+)/(−) |
| 2.049 | $SCF_3$ | H | H | H | H | H | Cl | H | Cl | Cl | (+)/(−) |
| 2.050 | $OCF_3$ | H | H | H | H | Me | H | H | Cl | H | (+)/(−) |
| 2.051 | $SCF_3$ | H | H | H | H | H | Cl | H | Cl | Br | (+)/(−) |
| 2.052 | $OCF_3$ | H | H | H | H | H | Cl | H | Cl | Br | (+) |
| 2.053 | $OCF_3$ | H | H | H | H | H | Cl | H | Cl | Br | (−) |
| 2.054 | $OCF_3$ | H | H | H | H | H | Cl | H | Cl | Cl | (+) |
| 2.055 | $OCF_3$ | H | H | H | H | H | Cl | H | Cl | Cl | (−) |
| 2.056 | $SCF_3$ | H | H | H | H | H | Cl | H | Cl | Cl | (+) |
| 2.057 | $SCF_3$ | H | H | H | H | H | Cl | H | Cl | Cl | (−) |
| 2.058 | $SF_5$ | H | H | H | H | H | Cl | H | Cl | Cl | (+)/(−) |
| 2.059 | $SF_5$ | H | H | H | H | H | Cl | H | Cl | Cl | (+) |

TABLE 2-continued

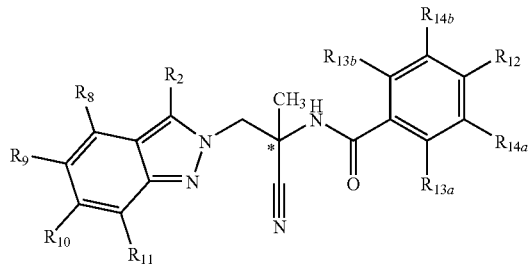

(IK)

| Compound No. | $R_{12}$ | $R_{13a}$ | R13b | $R_{14a}$ | $R_{14b}$ | $R_2$ | $R_8$ | $R_9$ | $R_{10}$ | $R_{11}$ | Optical rotation |
|---|---|---|---|---|---|---|---|---|---|---|---|
| 2.060 | SF$_5$ | H | H | H | H | H | Cl | H | Cl | Cl | (−) |
| 2.061 | Cl | H | H | H | H | H | Cl | H | Cl | Cl | (+)/(−) |
| 2.062 | CF$_3$ | H | H | H | H | H | Cl | H | Cl | Cl | (+)/(−) |
| 2.063 | CN | H | H | H | H | H | Cl | H | Cl | Cl | (+)/(−) |
| 2.064 | CN | H | H | H | H | H | Cl | H | Cl | Cl | (+) |
| 2.065 | CN | H | H | H | H | H | Cl | H | Cl | Cl | (−) |
| 2.066 | CF$_2$CHF$_2$ | H | H | H | H | H | Cl | H | Cl | Cl | (+)/(−) |
| 2.067 | OPh | H | H | H | H | H | Cl | H | Cl | Cl | (+)/(−) |
| 2.068 | I | H | H | H | H | H | Cl | H | Cl | Cl | (+)/(−) |
| 2.069 | NO$_2$ | H | H | H | H | H | Cl | H | Cl | Cl | (+)/(−) |
| 2.070 | OCF$_3$ | H | H | H | H | H | Cl | H | Br | Cl | (+)/(−) |
| 2.071 | OCF$_3$ | H | H | H | H | H | Cl | H | Br | Cl | (+) |
| 2.072 | OCF$_3$ | H | H | H | H | H | Cl | H | Br | Cl | (−) |
| 2.073 | SCF$_3$ | H | H | H | H | H | Cl | H | Br | Cl | (+)/(−) |
| 2.074 | SCF$_3$ | H | H | H | H | H | Cl | H | Br | Cl | (+) |
| 2.075 | SCF$_3$ | H | H | H | H | H | Cl | H | Br | Cl | (−) |
| 2.076 | CN | H | H | H | H | H | Cl | H | Br | Cl | (+)/(−) |
| 2.077 | CN | H | H | H | H | H | Cl | H | Br | Cl | (+) |
| 2.078 | CN | H | H | H | H | H | Cl | H | Br | Cl | (−) |
| 2.079 | OCF$_3$ | H | H | H | H | H | Me | H | Br | H | (+)/(−) |
| 2.080 | OCF$_3$ | H | H | H | H | H | Me | H | Br | H | (+) |
| 2.081 | OCF$_3$ | H | H | H | H | H | Me | H | Br | H | (−) |
| 2.082 | SCF$_3$ | H | H | H | H | H | Me | H | Br | H | (+)/(−) |
| 2.083 | SCF$_3$ | H | H | H | H | H | Me | H | Br | H | (+) |
| 2.084 | SCF$_3$ | H | H | H | H | H | Me | H | Br | H | (−) |
| 2.085 | CN | H | H | H | H | H | Me | H | Br | H | (+)/(−) |
| 2.086 | CN | H | H | H | H | H | Me | H | Br | H | (+) |
| 2.087 | CN | H | H | H | H | H | Me | H | Br | H | (−) |
| 2.088 | OCF$_3$ | H | H | H | H | H | Me | H | Br | Cl | (+)/(−) |
| 2.089 | OCF$_3$ | H | H | H | H | H | Me | H | Br | Cl | (+) |
| 2.090 | OCF$_3$ | H | H | H | H | H | Me | H | Br | Cl | (−) |
| 2.091 | SCF$_3$ | H | H | H | H | H | Me | H | Br | Cl | (+)/(−) |
| 2.092 | SCF$_3$ | H | H | H | H | H | Me | H | Br | Cl | (+) |
| 2.093 | SCF$_3$ | H | H | H | H | H | Me | H | Br | Cl | (−) |
| 2.094 | CN | H | H | H | H | H | Me | H | Br | Cl | (+)/(−) |
| 2.095 | CN | H | H | H | H | H | Me | H | Br | Cl | (+) |
| 2.096 | CN | H | H | H | H | H | Me | H | Br | Cl | (−) |
| 2.097 | OCF$_3$ | H | H | H | H | H | H | H | Br | Cl | (+)/(−) |
| 2.098 | OCF$_3$ | H | H | H | H | H | H | H | Br | Cl | (+) |
| 2.099 | OCF$_3$ | H | H | H | H | H | H | H | Br | Cl | (−) |
| 2.100 | SCF$_3$ | H | H | H | H | H | H | H | Br | Cl | (+)/(−) |
| 2.101 | SCF$_3$ | H | H | H | H | H | H | H | Br | Cl | (+) |
| 2.102 | SCF$_3$ | H | H | H | H | H | H | H | Br | Cl | (−) |
| 2.103 | CN | H | H | H | H | H | H | H | Br | Cl | (+)/(−) |
| 2.104 | CN | H | H | H | H | H | H | H | Br | Cl | (+) |
| 2.105 | CN | H | H | H | H | H | H | H | Br | Cl | (−) |
| 2.106 | OCF$_3$ | H | H | H | H | H | Cl | H | I | Cl | (+)/(−) |
| 2.107 | OCF$_3$ | H | H | H | H | H | Cl | H | I | Cl | (+) |
| 2.108 | OCF$_3$ | H | H | H | H | H | Cl | H | I | Cl | (−) |
| 2.109 | SCF$_3$ | H | H | H | H | H | Cl | H | I | Cl | (+)/(−) |
| 2.110 | SCF$_3$ | H | H | H | H | H | Cl | H | I | Cl | (+) |
| 2.111 | SCF$_3$ | H | H | H | H | H | Cl | H | I | Cl | (−) |
| 2.112 | CN | H | H | H | H | H | Cl | H | I | Cl | (+)/(−) |
| 2.113 | CN | H | H | H | H | H | Cl | H | I | Cl | (+) |
| 2.114 | CN | H | H | H | H | H | Cl | H | I | Cl | (−) |
| 2.115 | OCF$_3$ | H | H | H | H | H | Me | H | I | H | (+)/(−) |
| 2.116 | OCF$_3$ | H | H | H | H | H | Me | H | I | H | (+) |
| 2.117 | OCF$_3$ | H | H | H | H | H | Me | H | I | H | (−) |
| 2.118 | SCF$_3$ | H | H | H | H | H | Me | H | I | H | (+)/(−) |
| 2.119 | SCF$_3$ | H | H | H | H | H | Me | H | I | H | (+) |
| 2.120 | SCF$_3$ | H | H | H | H | H | Me | H | I | H | (−) |
| 2.121 | CN | H | H | H | H | H | Me | H | I | H | (+)/(−) |

TABLE 2-continued (IK)

| Compound No. | R$_{12}$ | R$_{13a}$ | R13b | R$_{14a}$ | R$_{14b}$ | R$_2$ | R$_8$ | R$_9$ | R$_{10}$ | R$_{11}$ | Optical rotation |
|---|---|---|---|---|---|---|---|---|---|---|---|
| 2.122 | CN | H | H | H | H | H | Me | H | I | H | (+) |
| 2.123 | CN | H | H | H | H | H | Me | H | I | H | (−) |
| 2.124 | OCF$_3$ | H | H | H | H | H | Me | H | I | Cl | (+)/(−) |
| 2.125 | OCF$_3$ | H | H | H | H | H | Me | H | I | Cl | (+) |
| 2.126 | OCF$_3$ | H | H | H | H | H | Me | H | I | Cl | (−) |
| 2.127 | SCF$_3$ | H | H | H | H | H | Me | H | I | Cl | (+)/(−) |
| 2.128 | SCF$_3$ | H | H | H | H | H | Me | H | I | Cl | (+) |
| 2.129 | SCF$_3$ | H | H | H | H | H | Me | H | I | Cl | (−) |
| 2.130 | CN | H | H | H | H | H | Me | H | I | Cl | (+)/(−) |
| 2.131 | CN | H | H | H | H | H | Me | H | I | Cl | (+) |
| 2.132 | CN | H | H | H | H | H | Me | H | I | Cl | (−) |
| 2.133 | OCF$_3$ | H | H | H | H | H | Me | H | Cl | H | (+)/(−) |
| 2.134 | OCF$_3$ | H | H | H | H | H | Me | H | Cl | H | (+) |
| 2.135 | OCF$_3$ | H | H | H | H | H | Me | H | Cl | H | (−) |
| 2.136 | SCF$_3$ | H | H | H | H | H | Me | H | Cl | H | (+)/(−) |
| 2.137 | SCF$_3$ | H | H | H | H | H | Me | H | Cl | H | (+) |
| 2.138 | SCF$_3$ | H | H | H | H | H | Me | H | Cl | H | (−) |
| 2.139 | CN | H | H | H | H | H | Me | H | Cl | H | (+)/(−) |
| 2.140 | CN | H | H | H | H | H | Me | H | Cl | H | (+) |
| 2.141 | CN | H | H | H | H | H | Me | H | Cl | H | (−) |
| 2.142 | OCF$_3$ | H | H | H | H | H | Me | H | Cl | Cl | (+)/(−) |
| 2.143 | OCF$_3$ | H | H | H | H | H | Me | H | Cl | Cl | (+) |
| 2.144 | OCF$_3$ | H | H | H | H | H | Me | H | Cl | Cl | (−) |
| 2.145 | SCF$_3$ | H | H | H | H | H | Me | H | Cl | Cl | (+)/(−) |
| 2.146 | SCF$_3$ | H | H | H | H | H | Me | H | Cl | Cl | (+) |
| 2.147 | SCF$_3$ | H | H | H | H | H | Me | H | Cl | Cl | (−) |
| 2.148 | CN | H | H | H | H | H | Me | H | Cl | Cl | (+)/(−) |
| 2.149 | CN | H | H | H | H | H | Me | H | Cl | Cl | (+) |
| 2.150 | CN | H | H | H | H | H | Me | H | Cl | Cl | (−) |
| 2.151 | SF$_5$ | Br | H | H | H | Me | Cl | H | Cl | Cl | (+)/(−) |
| 2.152 | SF$_5$ | Cl | H | H | H | Me | Cl | H | Cl | Cl | (+)/(−) |
| 2.153 | SF$_5$ | F | H | H | H | Me | Cl | H | Cl | Cl | (+)/(−) |
| 2.154 | SF$_5$ | H | H | Br | H | Me | Cl | H | Cl | Cl | (+)/(−) |
| 2.155 | SF$_5$ | H | H | Cl | H | Me | Cl | H | Cl | Cl | (+)/(−) |
| 2.156 | SF$_5$ | H | H | F | H | Me | Cl | H | Cl | Cl | (+)/(−) |
| 2.157 | SF$_5$ | Cl | H | F | H | Me | Cl | H | Cl | Cl | (+)/(−) |
| 2.158 | SF$_5$ | F | H | Cl | H | Me | Cl | H | Cl | Cl | (+)/(−) |
| 2.159 | SF$_5$ | F | H | F | H | Me | Cl | H | Cl | Cl | (+)/(−) |
| 2.160 | SF$_5$ | Br | H | H | F | Me | Cl | H | Cl | Cl | (+)/(−) |
| 2.161 | SF$_5$ | Cl | H | H | F | Me | Cl | H | Cl | Cl | (+)/(−) |
| 2.162 | SF$_5$ | F | H | H | F | Me | Cl | H | Cl | Cl | (+)/(−) |
| 2.163 | SF$_5$ | F | F | H | H | Me | Cl | H | Cl | Cl | (+)/(−) |
| 2.164 | SF$_5$ | H | H | F | F | Me | Cl | H | Cl | Cl | (+)/(−) |
| 2.165 | SF$_5$ | F | F | F | F | Me | Cl | H | Cl | Cl | (+)/(−) |
| 2.166 | SF$_5$ | Me | H | H | H | Me | Cl | H | Cl | Cl | (+)/(−) |
| 2.167 | SF$_5$ | Me | H | H | F | Me | Cl | H | Cl | Cl | (+)/(−) |
| 2.168 | OCF$_3$ | Br | H | H | H | Me | Cl | H | Cl | Cl | (+)/(−) |
| 2.169 | OCF$_3$ | Cl | H | H | H | Me | Cl | H | Cl | Cl | (+)/(−) |
| 2.170 | OCF$_3$ | F | H | H | H | Me | Cl | H | Cl | Cl | (+)/(−) |
| 2.171 | OCF$_3$ | H | H | Br | H | Me | Cl | H | Cl | Cl | (+)/(−) |
| 2.172 | OCF$_3$ | H | H | Cl | H | Me | Cl | H | Cl | Cl | (+)/(−) |
| 2.173 | OCF$_3$ | H | H | F | H | Me | Cl | H | Cl | Cl | (+)/(−) |
| 2.174 | OCF$_3$ | Cl | H | F | H | Me | Cl | H | Cl | Cl | (+)/(−) |
| 2.175 | OCF$_3$ | F | H | Cl | H | Me | Cl | H | Cl | Cl | (+)/(−) |
| 2.176 | OCF$_3$ | F | H | F | H | Me | Cl | H | Cl | Cl | (+)/(−) |
| 2.177 | OCF$_3$ | Br | H | H | F | Me | Cl | H | Cl | Cl | (+)/(−) |
| 2.178 | OCF$_3$ | Cl | H | H | F | Me | Cl | H | Cl | Cl | (+)/(−) |
| 2.179 | OCF$_3$ | F | H | H | F | Me | Cl | H | Cl | Cl | (+)/(−) |
| 2.180 | OCF$_3$ | F | F | H | H | Me | Cl | H | Cl | Cl | (+)/(−) |
| 2.181 | OCF$_3$ | H | H | F | F | Me | Cl | H | Cl | Cl | (+)/(−) |
| 2.182 | OCF$_3$ | F | F | F | F | Me | Cl | H | Cl | Cl | (+)/(−) |
| 2.183 | OCF$_3$ | Me | H | H | H | Me | Cl | H | Cl | Cl | (+)/(−) |

TABLE 2-continued

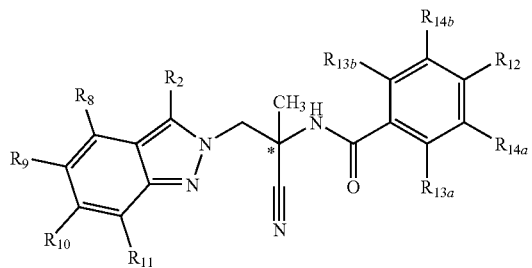

(IK)

| Compound No. | $R_{12}$ | $R_{13a}$ | R13b | $R_{14a}$ | $R_{14b}$ | $R_2$ | $R_8$ | $R_9$ | $R_{10}$ | $R_{11}$ | Optical rotation |
|---|---|---|---|---|---|---|---|---|---|---|---|
| 2.184 | $OCF_3$ | Me | H | H | F | Me | Cl | H | Cl | Cl | (+)/(−) |
| 2.185 | $CF_3$ | Br | H | H | H | Me | Cl | H | Cl | Cl | (+)/(−) |
| 2.186 | $CF_3$ | Cl | H | H | H | Me | Cl | H | Cl | Cl | (+)/(−) |
| 2.187 | $CF_3$ | F | H | H | H | Me | Cl | H | Cl | Cl | (+)/(−) |
| 2.188 | $CF_3$ | H | H | Br | H | Me | Cl | H | Cl | Cl | (+)/(−) |
| 2.189 | $CF_3$ | H | H | Cl | H | Me | Cl | H | Cl | Cl | (+)/(−) |
| 2.190 | $CF_3$ | H | H | F | H | Me | Cl | H | Cl | Cl | (+)/(−) |
| 2.191 | $CF_3$ | Cl | H | F | H | Me | Cl | H | Cl | Cl | (+)/(−) |
| 2.192 | $CF_3$ | F | H | Cl | H | Me | Cl | H | Cl | Cl | (+)/(−) |
| 2.193 | $CF_3$ | F | H | F | H | Me | Cl | H | Cl | Cl | (+)/(−) |
| 2.194 | $CF_3$ | Br | H | H | F | Me | Cl | H | Cl | Cl | (+)/(−) |
| 2.195 | $CF_3$ | Cl | H | H | F | Me | Cl | H | Cl | Cl | (+)/(−) |
| 2.196 | $CF_3$ | F | H | H | F | Me | Cl | H | Cl | Cl | (+)/(−) |
| 2.197 | $CF_3$ | F | F | H | H | Me | Cl | H | Cl | Cl | (+)/(−) |
| 2.198 | $CF_3$ | H | H | F | F | Me | Cl | H | Cl | Cl | (+)/(−) |
| 2.199 | $CF_3$ | F | F | F | F | Me | Cl | H | Cl | Cl | (+)/(−) |
| 2.200 | $CF_3$ | Me | H | H | H | Me | Cl | H | Cl | Cl | (+)/(−) |
| 2.201 | $CF_3$ | Me | H | H | F | Me | Cl | H | Cl | Cl | (+)/(−) |
| 2.202 | CN | Br | H | H | H | Me | Cl | H | Cl | Cl | (+)/(−) |
| 2.203 | CN | Cl | H | H | H | Me | Cl | H | Cl | Cl | (+)/(−) |
| 2.204 | CN | F | H | H | H | Me | Cl | H | Cl | Cl | (+)/(−) |
| 2.205 | CN | H | H | Br | H | Me | Cl | H | Cl | Cl | (+)/(−) |
| 2.206 | CN | H | H | Cl | H | Me | Cl | H | Cl | Cl | (+)/(−) |
| 2.207 | CN | H | H | F | H | Me | Cl | H | Cl | Cl | (+)/(−) |
| 2.208 | CN | Cl | H | F | H | Me | Cl | H | Cl | Cl | (+)/(−) |
| 2.209 | CN | F | H | Cl | H | Me | Cl | H | Cl | Cl | (+)/(−) |
| 2.210 | CN | F | H | F | H | Me | Cl | H | Cl | Cl | (+)/(−) |
| 2.211 | CN | Br | H | H | F | Me | Cl | H | Cl | Cl | (+)/(−) |
| 2.212 | CN | Cl | H | H | F | Me | Cl | H | Cl | Cl | (+)/(−) |
| 2.213 | CN | F | H | H | F | Me | Cl | H | Cl | Cl | (+)/(−) |
| 2.214 | CN | F | F | H | H | Me | Cl | H | Cl | Cl | (+)/(−) |
| 2.215 | CN | H | H | F | F | Me | Cl | H | Cl | Cl | (+)/(−) |
| 2.216 | CN | F | F | F | F | Me | Cl | H | Cl | Cl | (+)/(−) |
| 2.217 | CN | Me | H | H | H | Me | Cl | H | Cl | Cl | (+)/(−) |
| 2.218 | CN | Me | H | H | F | Me | Cl | H | Cl | Cl | (+)/(−) |
| 2.219 | $OCF_3$ | H | H | CN | H | Me | Cl | H | Cl | Cl | (+)/(−) |
| 2.220 | $OCF_3$ | CN | H | H | H | Me | Cl | H | Cl | Cl | (+)/(−) |
| 2.221 | $OCF_3$ | H | H | CN | H | Me | Me | H | Br | Cl | (+)/(−) |
| 2.222 | $OCF_3$ | CN | H | H | H | Me | Me | H | Br | Cl | (+)/(−) |
| 2.223 | $OCF_3$ | H | H | CN | H | Me | H | H | Br | Cl | (+)/(−) |
| 2.224 | $OCF_3$ | CN | H | H | H | Me | H | H | Br | Cl | (+)/(−) |
| 2.225 | $OCF_3$ | H | H | CN | H | Me | H | H | Cl | Br | (+)/(−) |
| 2.226 | $OCF_3$ | CN | H | H | H | Me | H | H | Cl | Br | (+)/(−) |
| 2.227 | $OCH_3$ | H | H | F | H | Me | Cl | H | Cl | Cl | (+)/(−) |
| 2.228 | F | F | H | H | H | Me | Cl | H | Cl | Cl | (+)/(−) |
| 2.229 | H | H | H | Br | H | Me | Cl | H | Cl | Cl | (+)/(−) |
| 2.230 | Cl | Cl | H | H | H | Me | Cl | H | Cl | Cl | (+)/(−) |

Compounds of general formula (IK) which are of particular interest include, but are not limited to, N-[1-Cyano-1-methyl-2-(5-nitro-2H-indazol-2-yl)ethyl]-4-trifluoromethoxybenzamide (compound No 2.001)
N-[1-Cyano-1-methyl-2-(5-nitro-2H-indazol-2-yl)ethyl]-4-trifluoromethylthiobenzamide (compound No 2.002)
N-[1-Cyano-2-(5,7-dichloro-2H-indazol-2-yl)-1-methylethyl]-4-trifluoromethoxybenzamide (compound No 2.003)
N-[1-Cyano-2-(5,7-dichloro-2H-indazol-2-yl)-1-methylethyl]-4-phenoxybenzamide (compound No 2.004)
N-[1-Cyano-2-(5,7-dichloro-2H-indazol-2-yl)-1-methylethyl]-4-trifluoromethylthiobenzamide (compound No 2.005)
N-[2-(5-Chloro-7-methyl-2H-indazol-2-yl)-1-cyano-1-methylethyl]-4-trifluoromethoxybenzamide (compound No 2.006)
N-[2-(5-Chloro-7-methyl-2H-indazol-2-yl)-1-cyano-1-methylethyl]-4-trifluoromethylthiobenzamide (compound No 2.007)
N-[2-(6-Chloro-3-methoxy-2H-indazol-2-yl)-1-cyano-1-methylethyl]-4-trifluoromethoxybenzamide (compound No 2.008)
N-[2-(6-Chloro-3-methoxy-2H-indazol-2-yl)-1-cyano-1-methylethyl]-4-trifluoromethylthiobenzamide (compound No 2.009)
N-[1-Cyano-2-(5,7-dichloro-3-methyl-2H-indazol-2-yl)-1-methylethyl]-4-trifluoromethoxybenzamide (compound No 2.010)
N-[2-(5,7-Dichloro-3-methyl-2H-indazol-2-yl)-1-cyano-1-methylethyl]-4-trifluoromethylthiobenzamide (compound No 2.011)
N-[2-(5-Chloro-3-methoxy-2H-indazol-2-yl)-1-cyano-1-methylethyl]-4-trifluoromethoxybenzamide (compound No 2.012)
N-[2-(5-Chloro-3-methoxy-2H-indazol-2-yl)-1-cyano-1-methylethyl]-4-trifluoromethylthiobenzamide (compound No 2.013)
N-[2-(5-Chloro-3-ethoxy-2H-indazol-2-yl)-1-cyano-1-methylethyl]-4-trifluoromethoxybenzamide (compound No 2.014)
N-[2-(5-Chloro-3-ethoxy-2H-indazol-2-yl)-1-cyano-1-methylethyl]-4-trifluoromethylthiobenzamide (compound No 2.015)
N-[1-Cyano-2-(3-methoxy-2H-indazol-2-yl)-1-methylethyl]-4-trifluoromethoxybenzamide (compound No 2.016)
N-{2-[6-Chloro-3-(2-methoxyethoxy)-2H-indazol-2-yl]-1-cyano-1-methylethyl}-4-trifluoromethoxybenzamide (compound No 2.017)
N-{2-[6-Chloro-3-(2-dimethylaminoethoxy)-2H-indazol-2-yl]-1-cyano-1-methylethyl}-4-trifluoromethoxybenzamide (compound No 2.018)
N-[1-Cyano-2-(5,7-dichloro-3-methoxy-2H-indazol-2-yl)-1-methylethyl]-4-trifluoromethylthiobenzamide (compound No 2.019)
N-[1-Cyano-2-(5,7-dichloro-3-methoxy-2H-indazol-2-yl)-1-methylethyl]-4-trifluoromethoxybenzamide (compound No 2.020)
N-[1-Cyano-2-(4,6-dichloro-3-methoxy-2H-indazol-2-yl)-1-methylethyl]-4-trifluoromethoxybenzamide (compound No 2.021)
N-[1-Cyano-2-(4,6-dichloro-3-methoxy-2H-indazol-2-yl)-1-methylethyl]-4-trifluoromethylthiobenzamide (compound No 2.022)
N-[2-(6-Bromo-3-methoxy-2H-indazol-2-yl)-1-cyano-1-methylethyl]-4-trifluoromethoxybenzamide (compound No 2.023)
N-[2-(6-Bromo-3-methoxy-2H-indazol-2-yl)-1-cyano-1-methylethyl]-4-trifluoromethylthiobenzamide (compound No 2.024)
N-[1-Cyano-2-(3-methoxy-6-trifluoromethyl-2H-indazol-2-yl)-1-methylethyl]-4-trifluoromethoxybenzamide (compound No 2.025)
N-[1-Cyano-2-(3-methoxy-6-trifluoromethyl-2H-indazol-2-yl)-1-methylethyl]-4-trifluoromethylthiobenzamide (compound No 2.026)
N-[2-(6-Chloro-3-ethoxy-2H-indazol-2-yl)-1-cyano-1-methylethyl]-4-trifluoromethoxybenzamide (compound No 2.027)
N-[2-(6-Chloro-3-ethoxy-2H-indazol-2-yl)-1-cyano-1-methylethyl]-4-trifluoromethylthiobenzamide (compound No 2.028)
N-[2-(6-Chloro-3-propoxy-2H-indazol-2-yl)-1-cyano-1-methylethyl]-4-trifluoromethoxybenzamide (compound No 2.029)
N-[2-(6-Chloro-3-propoxy-2H-indazol-2-yl)-1-cyano-1-methylethyl]-4-trifluoromethylthiobenzamide (compound No 2.030)
N-[2-(6-Chloro-3-butoxy-2H-indazol-2-yl)-1-cyano-1-methylethyl]-4-trifluoromethoxybenzamide (compound No 2.031)
Methyl 2-[2-cyano-2-methyl-2-(4-trifluoromethoxybenzoylamino)ethyl]-3-methoxy-2H-indazole-6-carboxylate (compound No 2.032)
N-[1-Cyano-2-(3-methoxy-6-nitro-2H-indazol-2-yl)-1-methylethyl]-4-trifluoromethoxybenzamide (compound No 2.033)
N-[2-(6-Amino-3-methoxy-2H-indazol-2-yl)-1-cyano-1-methylethyl]-4-trifluoromethoxybenzamide (compound No 2.034)
N-[2-(6-Acetylamino-3-methoxy-2H-indazol-2-yl)-1-cyano-1-methylethyl]-4-trifluoromethoxybenzamide (compound No 2.035)
Methyl 2-[2-cyano-2-methyl-2-(4-trifluoromethoxybenzoylamino)ethyl]-3-methoxy-2H-indazole-6-carboxamide (compound No 2.036)
N-[2-(6-Chloro-2H-indazol-2-yl)-1-cyano-1-methylethyl]-4-trifluoromethoxybenzamide (compound No 2.037)
N-[2-(6-Chloro-2H-indazol-2-yl)-1-cyano-1-methylethyl]-4-trifluoromethylthiobenzamide (compound No 2.038)
N-[1-Cyano-1-methyl-2-(3,6,7-trichloro-2H-indazol-2-yl)ethyl]-4-trifluoromethoxybenzamide (compound No 2.039)
N-[1-Cyano-2-(4,6-dichloro-2H-indazol-2-yl)-1-methylethyl]-4-trifluoromethoxybenzamide (compound No 2.040)
N-[1-Cyano-2-(4,6-dichloro-2H-indazol-2-yl)-1-methylethyl]-4-trifluoromethylthiobenzamide (compound No 2.041)
N-[2-(3-Bromo-6-chloro-2H-indazol-2-yl)-1-cyano-1-methylethyl]-4-trifluoromethoxybenzamide (compound No 2.042)
N-[2-(7-Bromo-6-chloro-2H-indazol-2-yl)-1-cyano-1-methylethyl]-4-trifluoromethoxybenzamide (compound No 2.043)
N-[1-Cyano-2-(3,6-dichloro-2H-indazol-2-yl)-1-methylethyl]-4-trifluoromethoxybenzamide (compound No 2.044)
N-[1-Cyano-2-(6,7-dichloro-2H-indazol-2-yl)-1-methylethyl]-4-trifluoromethoxybenzamide (compound No 2.045)

N-[1-Cyano-2-(3,7-dibromo-4,6-dichloro-2H-indazol-2-yl)-1-methylethyl]-4-trifluoromethoxybenzamide (compound No 2.046)

N-[2-(7-Bromo-6,7-dichloro-2H-indazol-2-yl)-1-cyano-1-methylethyl]-4-trifluoromethoxybenzamide (compound No 2.047)

N-[1-Cyano-1-methyl-2-(4,6,7-trichloro-2H-indazol-2-yl)ethyl]-4-trifluoromethoxybenzamide (compound No 2.048)

N-[1-Cyano-1-methyl-2-(4,6,7-trichloro-2H-indazol-2-yl)ethyl]-4-trifluoromethylthiobenzamide (compound No 2.049)

N-[2-(6-Chloro-3-methyl-2H-indazol-2-yl)-1-cyano-1-methylethyl]-4-trifluoromethoxybenzamide (compound No 2.050)

N-[1-Cyano-1-methyl-2-(4,6,7-trichloro-2H-indazol-2-yl)ethyl]-4-pentafluorothiobenzamide (compound No 2.058)

(+)-N-[1-Cyano-1-methyl-2-(4,6,7-trichloro-2H-indazol-2-yl)ethyl]-4-pentafluorothiobenzamide (compound No 2.059)

(−)-N-[1-Cyano-1-methyl-2-(4,6,7-trichloro-2H-indazol-2-yl)ethyl]-4-pentafluorothiobenzamide (compound No 2.060)

N-[1-Cyano-1-methyl-2-(4,6,7-trichloro-2H-indazol-2-yl)ethyl]-4-chlorobenzamide (compound No 2.061)

N-[1-Cyano-1-methyl-2-(4,6,7-trichloro-2H-indazol-2-yl)ethyl]-4-trifluoromethylbenzamide (compound No 2.062)

N-[1-Cyano-1-methyl-2-(4,6,7-trichloro-2H-indazol-2-yl)ethyl]-4-cyanobenzamide (compound No 2.063)

(+)-N-[1-Cyano-1-methyl-2-(4,6,7-trichloro-2H-indazol-2-yl)ethyl]-4-cyanobenzamide (compound No 2.064)

(−)-N-[1-Cyano-1-methyl-2-(4,6,7-trichloro-2H-indazol-2-yl)ethyl]-4-cyanobenzamide (compound No 2.065)

N-[1-Cyano-1-methyl-2-(4,6,7-trichloro-2H-indazol-2-yl)ethyl]-4-(1,1,2,2-tetrafluoroethoxy)benzamide (compound No 2.066)

N-[1-Cyano-1-methyl-2-(4,6,7-trichloro-2H-indazol-2-yl)ethyl]-4-phenoxybenzamide (compound No 2.067)

N-[1-Cyano-1-methyl-2-(4,6,7-trichloro-2H-indazol-2-yl)ethyl]-4-iodobenzamide (compound No 2.068)

N-[1-Cyano-1-methyl-2-(4,6,7-trichloro-2H-indazol-2-yl)ethyl]-4-nitrobenzamide (compound No 2.069)

N-[1-Cyano-1-methyl-2-(4,6,7-trichloro-2H-indazol-2-yl)ethyl]-2-fluoro-4-trifluoromethylbenzamide (compound No 2.187)

N-[1-Cyano-1-methyl-2-(4,6,7-trichloro-2H-indazol-2-yl)ethyl]-3-fluoro-4-trifluoromethylbenzamide (compound No 2.190)

N-[1-Cyano-1-methyl-2-(4,6,7-trichloro-2H-indazol-2-yl)ethyl]-3-fluoro-4-methoxybenzamide (compound No 2.227)

N-[1-Cyano-1-methyl-2-(4,6,7-trichloro-2H-indazol-2-yl)ethyl]-2,4-difluorobenzamide (compound No 2.228)

3-Bromo-N-[1-cyano-1-methyl-2-(4,6,7-trichloro-2H-indazol-2-yl)ethyl]benzamide (compound No 2.229)

2,4-Dichloro-N-[1-cyano-1-methyl-2-(4,6,7-trichloro-2H-indazol-2-yl)ethyl]benzamide (compound No 2.230)

The numbers 2.001 to 2.230 are assigned to the above compounds for identification and reference hereinafter.

Table 3 below shows specific compounds encompassed by formula (ID):

TABLE 3

(ID)

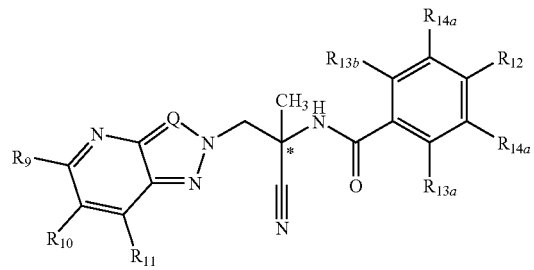

| Compound No. | $R_{12}$ | $R_{13a}$ | $R_{13b}$ | $R_{14a}$ | $R_{14b}$ | Q | $R_9$ | $R_{10}$ | $R_{11}$ | Optical Rotation |
|---|---|---|---|---|---|---|---|---|---|---|
| 3.001 | $OCF_3$ | H | H | H | H | C-OMe | H | Cl | H | (+)/(−) |
| 3.002 | $SCF_3$ | H | H | H | H | C-OMe | H | Cl | H | (+)/(−) |
| 3.003 | $OCF_3$ | H | H | H | H | N | H | Br | Me | (+)/(−) |
| 3.004 | $SCF_3$ | H | H | H | H | N | H | Br | Me | (+)/(−) |
| 3.005 | $OCF_3$ | H | H | H | H | C—H | H | Cl | H | (+)/(−) |
| 3.006 | $SCF_3$ | H | H | H | H | C—H | H | Cl | H | (+)/(−) |
| 3.007 | $OCF_3$ | H | H | H | H | C-OMe | H | Br | Me | (+)/(−) |
| 3.008 | $OCF_3$ | H | H | H | H | C-OMe | H | Cl | Me | (+)/(−) |
| 3.009 | $OCF_3$ | H | H | H | H | C—H | H | Br | Me | (+)/(−) |
| 3.010 | $OCF_3$ | H | H | H | H | C—H | H | Cl | Me | (+)/(−) |
| 3.011 | $OCF_3$ | H | H | H | H | C—H | H | Br | H | (+)/(−) |
| 3.012 | $SCF_3$ | H | H | H | H | C—H | H | Br | H | (+)/(−) |
| 3.013 | $OCF_3$ | H | H | H | H | C—H | H | Cl | Cl | (+)/(−) |
| 3.014 | $SCF_3$ | H | H | H | H | C—H | H | Cl | Cl | (+)/(−) |
| 3.015 | $OCF_3$ | H | H | H | H | C—H | H | Br | Cl | (+)/(−) |
| 3.016 | $SCF_3$ | H | H | H | H | C—H | H | Br | Cl | (+)/(−) |
| 3.017 | $OCF_3$ | H | H | H | H | C—Cl | H | Cl | H | (+)/(−) |
| 3.018 | $SCF_3$ | H | H | H | H | C—Cl | H | Cl | H | (+)/(−) |
| 3.019 | $OCF_3$ | H | H | H | H | C—Br | H | Cl | H | (+)/(−) |
| 3.020 | $SCF_3$ | H | H | H | H | C—Br | H | Cl | H | (+)/(−) |
| 3.021 | $OCF_3$ | H | H | H | H | C—H | H | Cl | Br | (+)/(−) |
| 3.022 | $SCF_3$ | H | H | H | H | C—H | H | Cl | Br | (+)/(−) |
| 3.023 | $SCF_3$ | H | H | H | H | C—H | H | Br | Me | (+)/(−) |

TABLE 3-continued (ID)

| Compound No. | $R_{12}$ | $R_{13a}$ | $R_{13b}$ | $R_{14a}$ | $R_{14b}$ | Q | $R_9$ | $R_{10}$ | $R_{11}$ | Optical Rotation |
|---|---|---|---|---|---|---|---|---|---|---|
| 3.024 | OCF₃ | H | H | H | H | C—H | H | Br | H | (+) |
| 3.025 | OCF₃ | H | H | H | H | C—H | H | Br | H | (−) |
| 3.026 | OCF₃ | H | H | H | H | C—H | H | I | H | (+)/(−) |
| 3.027 | OCF₃ | H | H | H | H | C—H | H | I | H | (+) |
| 3.028 | OCF₃ | H | H | H | H | C—H | H | I | H | (−) |
| 3.029 | SF₅ | H | H | H | H | C—H | H | Br | H | (+)/(−) |
| 3.030 | SF₅ | H | H | H | H | C—H | H | Br | H | (+) |
| 3.031 | SF₅ | H | H | H | H | C—H | H | Br | H | (−) |
| 3.032 | SO₂CF₃ | H | H | H | H | C—H | H | Cl | H | (+)/(−) |
| 3.033 | SO₂CF₃ | H | H | H | H | C—H | H | Br | H | (+)/(−) |
| 3.034 | SCF₃ | H | H | H | H | C—H | H | Br | H | (+) |
| 3.035 | SCF₃ | H | H | H | H | C—H | H | Br | H | (−) |
| 3.036 | OCF₃ | H | H | H | H | C-Me | H | I | H | (+)/(−) |
| 3.037 | OCF₃ | H | H | H | H | C-Me | H | I | H | (+) |
| 3.038 | OCF₃ | H | H | H | H | C-Me | H | I | H | (−) |
| 3.039 | OCF₃ | H | H | H | H | C—H | H | I | Me | (+)/(−) |
| 3.040 | OCF₃ | H | H | H | H | C—H | H | I | Me | (+) |
| 3.041 | OCF₃ | H | H | H | H | C—H | H | I | Me | (−) |
| 3.042 | OCF₃ | H | H | H | H | C—H | Br | Br | H | (+)/(−) |
| 3.043 | SCF₃ | H | H | H | H | C—H | Br | Br | H | (+)/(−) |
| 3.044 | OCF₃ | H | H | H | H | C—H | Br | H | H | (+)/(−) |
| 3.045 | OCF₃ | H | H | H | H | C—H | H | H | H | (+)/(−) |
| 3.046 | Cl | H | H | H | H | C—H | H | Br | H | (+)/(−) |
| 3.047 | CF₃ | H | H | H | H | C—H | H | Br | H | (+)/(−) |
| 3.048 | OPh | H | H | H | H | C—H | H | Br | H | (+)/(−) |
| 3.049 | I | H | H | H | H | C—H | H | Br | H | (+)/(−) |
| 3.050 | Ph | H | H | H | H | C—H | H | Br | H | (+)/(−) |
| 3.051 | n-hexyl | H | H | H | H | C—H | H | Br | H | (+)/(−) |
| 3.052 | OCF₃ | H | H | H | H | C—H | OMe | Br | H | (+)/(−) |
| 3.053 | SCF₃ | H | H | H | H | C—H | OMe | Br | H | (+)/(−) |
| 3.054 | OCF₃ | Br | H | H | H | C—H | H | Br | H | (+)/(−) |
| 3.055 | OCF₃ | Cl | H | H | H | C—H | H | Br | H | (+)/(−) |
| 3.056 | OCF₃ | F | H | H | H | C—H | H | Br | H | (+)/(−) |
| 3.057 | OCF₃ | H | H | Br | H | C—H | H | Br | H | (+)/(−) |
| 3.058 | OCF₃ | H | H | Cl | H | C—H | H | Br | H | (+)/(−) |
| 3.059 | OCF₃ | H | H | F | H | C—H | H | Br | H | (+)/(−) |
| 3.060 | OCF₃ | Cl | H | F | H | C—H | H | Br | H | (+)/(−) |
| 3.061 | OCF₃ | F | H | Cl | H | C—H | H | Br | H | (+)/(−) |
| 3.062 | OCF₃ | F | H | F | H | C—H | H | Br | H | (+)/(−) |
| 3.063 | OCF₃ | Br | H | H | F | C—H | H | Br | H | (+)/(−) |
| 3.064 | OCF₃ | Cl | H | H | F | C—H | H | Br | H | (+)/(−) |
| 3.065 | OCF₃ | F | H | H | F | C—H | H | Br | H | (+)/(−) |
| 3.066 | OCF₃ | F | F | H | H | C—H | H | Br | H | (+)/(−) |
| 3.067 | OCF₃ | H | H | F | F | C—H | H | Br | H | (+)/(−) |
| 3.068 | OCF₃ | F | F | F | F | C—H | H | Br | H | (+)/(−) |
| 3.069 | OCF₃ | Me | H | H | H | C—H | H | Br | H | (+)/(−) |
| 3.070 | OCF₃ | Me | H | H | F | C—H | H | Br | H | (+)/(−) |
| 3.071 | SCF₃ | Br | H | H | H | C—H | H | Br | H | (+)/(−) |
| 3.072 | SCF₃ | Cl | H | H | H | C—H | H | Br | H | (+)/(−) |
| 3.073 | SCF₃ | F | H | H | H | C—H | H | Br | H | (+)/(−) |
| 3.074 | SCF₃ | H | H | Br | H | C—H | H | Br | H | (+)/(−) |
| 3.075 | SCF₃ | H | H | Cl | H | C—H | H | Br | H | (+)/(−) |
| 3.076 | SCF₃ | H | H | F | H | C—H | H | Br | H | (+)/(−) |
| 3.077 | SCF₃ | Cl | H | F | H | C—H | H | Br | H | (+)/(−) |
| 3.078 | SCF₃ | F | H | Cl | H | C—H | H | Br | H | (+)/(−) |
| 3.079 | SCF₃ | F | H | F | H | C—H | H | Br | H | (+)/(−) |
| 3.080 | SCF₃ | Br | H | H | F | C—H | H | Br | H | (+)/(−) |
| 3.081 | SCF₃ | Cl | H | H | F | C—H | H | Br | H | (+)/(−) |
| 3.082 | SCF₃ | F | H | H | F | C—H | H | Br | H | (+)/(−) |
| 3.083 | SCF₃ | F | F | H | H | C—H | H | Br | H | (+)/(−) |
| 3.084 | SCF₃ | H | H | F | F | C—H | H | Br | H | (+)/(−) |
| 3.085 | SCF₃ | F | F | F | F | C—H | H | Br | H | (+)/(−) |

TABLE 3-continued

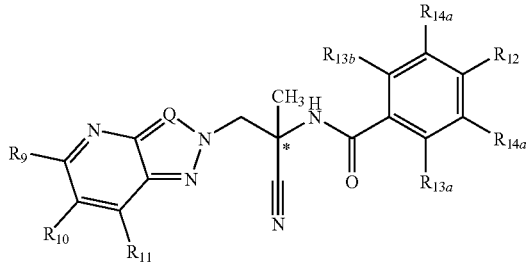

(ID)

| Compound No. | $R_{12}$ | $R_{13a}$ | $R_{13b}$ | $R_{14a}$ | $R_{14b}$ | Q | $R_9$ | $R_{10}$ | $R_{11}$ | Optical Rotation |
|---|---|---|---|---|---|---|---|---|---|---|
| 3.086 | SCF$_3$ | Me | H | H | H | C—H | H | Br | H | (+)/(−) |
| 3.087 | SCF$_3$ | Me | H | H | F | C—H | H | Br | H | (+)/(−) |
| 3.088 | SF$_5$ | Br | H | H | H | C—H | H | Br | H | (+)/(−) |
| 3.089 | SF$_5$ | Cl | H | H | H | C—H | H | Br | H | (+)/(−) |
| 3.090 | SF$_5$ | F | H | H | H | C—H | H | Br | H | (+)/(−) |
| 3.091 | SF$_5$ | H | H | Br | H | C—H | H | Br | H | (+)/(−) |
| 3.092 | SF$_5$ | H | H | Cl | H | C—H | H | Br | H | (+)/(−) |
| 3.093 | SF$_5$ | H | H | F | H | C—H | H | Br | H | (+)/(−) |
| 3.094 | SF$_5$ | Cl | H | F | H | C—H | H | Br | H | (+)/(−) |
| 3.095 | SF$_5$ | F | H | Cl | H | C—H | H | Br | H | (+)/(−) |
| 3.096 | SF$_5$ | F | H | F | H | C—H | H | Br | H | (+)/(−) |
| 3.097 | SF$_5$ | Br | H | H | F | C—H | H | Br | H | (+)/(−) |
| 3.098 | SF$_5$ | Cl | H | H | F | C—H | H | Br | H | (+)/(−) |
| 3.099 | SF$_5$ | F | H | H | F | C—H | H | Br | H | (+)/(−) |
| 3.100 | SF$_5$ | F | F | H | H | C—H | H | Br | H | (+)/(−) |
| 3.101 | SF$_5$ | H | H | F | F | C—H | H | Br | H | (+)/(−) |
| 3.102 | SF$_5$ | F | F | F | F | C—H | H | Br | H | (+)/(−) |
| 3.103 | SF$_5$ | Me | H | H | H | C—H | H | Br | H | (+)/(−) |
| 3.104 | SF$_5$ | Me | H | H | F | C—H | H | Br | H | (+)/(−) |

Compounds of general formula (ID) which are of particular interest include, but are not limited to, N-[2-(6-Chloro-3-methoxy-2H-pyrazolo[4,3-b]pyridin-2-yl)-1-cyano-1-methylethyl]-4-trifluoromethoxybenzamide (compound No 3.001)

N-[2-(6-Chloro-3-methoxy-2H-pyrazolo[4,3-b]pyridin-2-yl)-1-cyano-1-methylethyl]-4-trifluoromethylthiobenzamide (compound No 3.002)

N-[2-(6-Bromo-7-methyl-2H-[1,2,3]triazolo[4,5-b]pyridin-2-yl)-1-cyano-1-methylethyl]-4-trifluoromethoxybenzamide (compound No 3.003)

N-[2-(6-Bromo-7-methyl-2H-[1,2,3]triazolo[4,5-b]pyridin-2-yl)-1-cyano-1-methylethyl]-4-trifluoromethylthiobenzamide (compound No 3.004)

N-[2-(6-Chloro-2H-pyrazolo[4,3-b]pyridin-2-yl)-1-cyano-1-methylethyl]-4-trifluoromethoxybenzamide (compound No 3.005)

N-[2-(6-Chloro-2H-pyrazolo[4,3-b]pyridin-2-yl)-1-cyano-1-methylethyl]-4-trifluoromethylthiobenzamide (compound No 3.006)

N-[2-(6-Bromo-3-methoxy-7-methyl-2H-pyrazolo[4,3-b]pyridin-2-yl)-1-cyano-1-methylethyl]-4-trifluoromethoxybenzamide (compound No 3.007)

N-[2-(6-Chloro-3-methoxy-7-methyl-2H-pyrazolo[4,3-b]pyridin-2-yl)-1-cyano-1-methylethyl]-4-trifluoromethoxybenzamide (compound No 3.008)

N-[2-(6-Bromo-7-methyl-2H-pyrazolo[4,3-b]pyridin-2-yl)-1-cyano-1-methylethyl]-4-trifluoromethoxybenzamide (compound No 3.009)

N-[2-(6-Chloro-7-methyl-2H-pyrazolo[4,3-b]pyridin-2-yl)-1-cyano-1-methylethyl]-4-trifluoromethoxybenzamide (compound No 3.010)

N-[2-(6-Bromo-2H-pyrazolo[4,3-b]pyridin-2-yl)-1-cyano-1-methylethyl]-4-trifluoromethoxybenzamide (compound No 3.011)

N-[2-(6-Bromo-2H-pyrazolo[4,3-b]pyridin-2-yl)-1-cyano-1-methylethyl]-4-trifluoromethylthiobenzamide (compound No 3.012)

N-[1-Cyano-2-(3,6-dichloro-2H-pyrazolo[4,3-b]pyridin-2-yl)-1-methylethyl]-4-trifluoromethoxybenzamide (compound No 3.017)

N-[2-(3-Bromo-6-chloro-2H-pyrazolo[4,3-b]pyridin-2-yl)-1-cyano-1-methylethyl]-4-trifluoromethoxybenzamide (compound No 3.019)

N-[2-(6-Bromo-7-methyl-2H-pyrazolo[4,3-b]pyridin-2-yl)-1-cyano-1-methylethyl]-4-trifluoromethylthiobenzamide (compound No 3.023)

(+)-N-[2-(6-Bromo-2H-pyrazolo[4,3-b]pyridin-2-yl)-1-cyano-1-methylethyl]-4-trifluoromethoxybenzamide (compound No 3.024)

(−)-N-[2-(6-Bromo-2H-pyrazolo[4,3-b]pyridin-2-yl)-1-cyano-1-methylethyl]-4-trifluoromethoxybenzamide (compound No 3.025)

N-[1-Cyano-2-(6-iodo-2H-pyrazolo[4,3-b]pyridin-2-yl)-1-methylethyl]-4-trifluoromethoxybenzamide (compound No 3.026)

(+)-N-[1-Cyano-2-(6-iodo-2H-pyrazolo[4,3-b]pyridin-2-yl)-1-methylethyl]-4-trifluoromethoxybenzamide (compound No 3.027)

(−)-N-[1-Cyano-2-(6-iodo-2H-pyrazolo[4,3-b]pyridin-2-yl)-1-methylethyl]-4-trifluoromethoxybenzamide (compound No 3.027)

N-[2-(6-Bromo-2H-pyrazolo[4,3-b]pyridin-2-yl)-1-cyano-1-methylethyl]-4-pentafluorothiobenzamide (compound No 3.029)

(+)-N-[2-(6-Bromo-2H-pyrazolo[4,3-b]pyridin-2-yl)-1-cyano-1-methylethyl]-4-pentafluorothiobenzamide (compound No 3.030)

(−)-N-[2-(6-Bromo-2H-pyrazolo[4,3-b]pyridin-2-yl)-1-cyano-1-methylethyl]-4-pentafluorothiobenzamide (compound No 3.030)

N-[2-(6-Chloro-2H-pyrazolo[4,3-b]pyridin-2-yl)-1-cyano-1-methylethyl]-4-trifluoromethylsulfonylbenzamide (compound No 3.032)

N-[2-(6-Bromo-2H-pyrazolo[4,3-b]pyridin-2-yl)-1-cyano-1-methylethyl]-4-trifluoromethylsulfonylbenzamide (compound No 3.033)

(+)-N-[2-(6-Bromo-2H-pyrazolo[4,3-b]pyridin-2-yl)-1-cyano-1-methylethyl]-4-trifluoromethylthiobenzamide (compound No 3.034)

(−)-N-[2-(6-Bromo-2H-pyrazolo[4,3-b]pyridin-2-yl)-1-cyano-1-methylethyl]-4-trifluoromethylthiobenzamide (compound No 3.035)

N-[2-(6-Iodo-7-methyl-2H-pyrazolo[4,3-b]pyridin-2-yl)-1-cyano-1-methylethyl]-4-trifluoromethoxybenzamide (compound No 3.039)

(+)-N-[2-(6-Iodo-7-methyl-2H-pyrazolo[4,3-b]pyridin-2-yl)-1-cyano-1-methylethyl]-4-trifluoromethoxybenzamide (compound No 3.040)

(−)-N-[2-(6-Iodo-7-methyl-2H-pyrazolo[4,3-b]pyridin-2-yl)-1-cyano-1-methylethyl]-4-trifluoromethoxybenzamide (compound No 3.041)

N-[1-Cyano-2-(5,6-dibromo-2H-pyrazolo[4,3-b]pyridin-2-yl)-1-methylethyl]-4-trifluoromethoxybenzamide (compound No 3.042)

N-[1-Cyano-2-(5,6-dibromo-2H-pyrazolo[4,3-b]pyridin-2-yl)-1-methylethyl]-4-trifluoromethylthiobenzamide (compound No 3.043)

N-[1-Cyano-2-(5-bromo-2H-pyrazolo[4,3-b]pyridin-2-yl)-1-methylethyl]-4-trifluoromethoxybenzamide (compound No 3.044)

N-[1-Cyano-1-methyl-2-(2H-pyrazolo[4,3-b]pyridin-2-yl)ethyl]-4-trifluoromethoxybenzamide (compound No 3.045)

N-[2-(6-Bromo-2H-pyrazolo[4,3-b]pyridin-2-yl)-1-cyano-1-methylethyl]-4-chlorobenzamide (compound No 3.046)

N-[2-(6-Bromo-2H-pyrazolo[4,3-b]pyridin-2-yl)-1-cyano-1-methylethyl]-4-trifluoromethylbenzamide (compound No 3.047)

N-[2-(6-Bromo-2H-pyrazolo[4,3-b]pyridin-2-yl)-1-cyano-1-methylethyl]-4-phenoxybenzamide (compound No 3.048)

N-[2-(6-Bromo-2H-pyrazolo[4,3-b]pyridin-2-yl)-1-cyano-1-methylethyl]-4-iodobenzamide (compound No 3.049)

N-[2-(6-Bromo-2H-pyrazolo[4,3-b]pyridin-2-yl)-1-cyano-1-methylethyl]-biphenyl-4-carboxamide (compound No 3.050)

N-[2-(6-Bromo-2H-pyrazolo[4,3-b]pyridin-2-yl)-1-cyano-1-methylethyl]-4-hexylbenzamide (compound No 3.051)

N-[2-(6-Bromo-2H-pyrazolo[4,3-b]pyridin-2-yl)-1-cyano-1-methylethyl]-2-fluoro-4-trifluoromethoxybenzamide (compound No 3.056)

The numbers 3.001 to 3.104 are assigned to the above compounds for identification and reference hereinafter.

Table 4 below shows specific compounds encompassed by formula (IF):

TABLE 4

(IF)

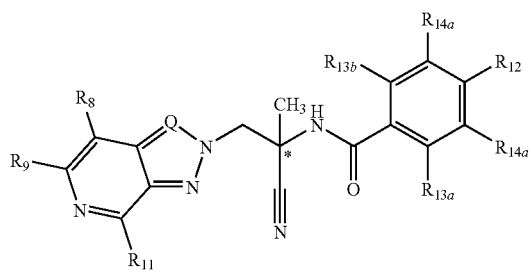

| Compound No. | $R_{12}$ | $R_{13a}$ | $R_{13b}$ | $R_{14a}$ | $R_{14b}$ | Q | $R_8$ | $R_9$ | $R_{11}$ | Optical Rotation |
|---|---|---|---|---|---|---|---|---|---|---|
| 4.001 | $OCF_3$ | H | H | H | H | C—H | H | Br | H | (+)/(−) |
| 4.002 | $SCF_3$ | H | H | H | H | C—H | H | Br | H | (+)/(−) |
| 4.003 | $OCF_3$ | H | H | H | H | C—H | Br | H | H | (+)/(−) |
| 4.004 | $SCF_3$ | H | H | H | H | C—H | Br | H | H | (+)/(−) |
| 4.005 | $OCF_3$ | H | H | H | H | C—H | H | H | Br | (+)/(−) |
| 4.006 | $SCF_3$ | H | H | H | H | C—H | H | H | Br | (+)/(−) |
| 4.007 | $OCF_3$ | H | H | H | H | C—H | Br | H | Br | (+)/(−) |
| 4.008 | $SCF_3$ | H | H | H | H | C—H | Br | H | Br | (+)/(−) |
| 4.009 | $SF_5$ | H | H | H | H | C—H | H | Br | H | (+)/(−) |
| 4.010 | $SF_5$ | H | H | H | H | C—H | Br | H | H | (+)/(−) |
| 4.011 | $SF_5$ | H | H | H | H | C—H | H | H | Br | (+)/(−) |
| 4.012 | $SF_5$ | H | H | H | H | C—H | Br | H | Br | (+)/(−) |
| 4.013 | $OCF_3$ | H | H | H | H | C—H | H | Br | H | (+) |
| 4.014 | $OCF_3$ | H | H | H | H | C—H | H | Br | H | (−) |
| 4.015 | $OCF_3$ | H | H | H | H | C—H | Br | H | H | (+) |
| 4.016 | $OCF_3$ | H | H | H | H | C—H | Br | H | H | (−) |
| 4.017 | $OCF_3$ | H | H | H | H | C—H | H | H | Br | (+) |
| 4.018 | $OCF_3$ | H | H | H | H | C—H | H | H | Br | (−) |
| 4.019 | $OCF_3$ | H | H | H | H | C—H | Br | H | Br | (+) |
| 4.020 | $OCF_3$ | H | H | H | H | C—H | Br | H | Br | (−) |
| 4.021 | $SCF_3$ | H | H | H | H | C—H | H | Br | H | (+) |
| 4.022 | $SCF_3$ | H | H | H | H | C—H | H | Br | H | (−) |
| 4.023 | $SCF_3$ | H | H | H | H | C—H | Br | H | H | (+) |

TABLE 4-continued

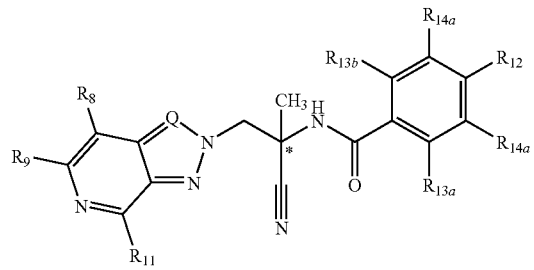

(IF)

| Compound No. | $R_{12}$ | $R_{13a}$ | $R_{13b}$ | $R_{14a}$ | $R_{14b}$ | Q | $R_8$ | $R_9$ | $R_{11}$ | Optical Rotation |
|---|---|---|---|---|---|---|---|---|---|---|
| 4.024 | SCF$_3$ | H | H | H | H | C—H | Br | H | H | (−) |
| 4.025 | SCF$_3$ | H | H | H | H | C—H | H | H | Br | (+) |
| 4.026 | SCF$_3$ | H | H | H | H | C—H | H | H | Br | (−) |
| 4.027 | SCF$_3$ | H | H | H | H | C—H | Br | H | Br | (+) |
| 4.028 | SCF$_3$ | H | H | H | H | C—H | Br | H | Br | (−) |
| 4.029 | SF$_5$ | H | H | H | H | C—H | H | Br | H | (+) |
| 4.030 | SF$_5$ | H | H | H | H | C—H | H | Br | H | (−) |
| 4.031 | SF$_5$ | H | H | H | H | C—H | Br | H | H | (+) |
| 4.032 | SF$_5$ | H | H | H | H | C—H | Br | H | H | (−) |
| 4.033 | SF$_5$ | H | H | H | H | C—H | H | H | Br | (+) |
| 4.034 | SF$_5$ | H | H | H | H | C—H | H | H | Br | (−) |
| 4.035 | SF$_5$ | H | H | H | H | C—H | Br | H | Br | (+) |
| 4.036 | SF$_5$ | H | H | H | H | C—H | Br | H | Br | (−) |

Compounds of general formula (IF) which are of particular interest include, but are not limited to, N-[2-(5-Bromo-2H-pyrazolo[3,4-c]pyridin-2-yl)-1-cyano-1-methylethyl]-4-trifluoromethoxybenzamide (compound No 4.001)

N-[2-(5-Bromo-2H-pyrazolo[3,4-c]pyridin-2-yl)-1-cyano-1-methylethyl]-4-trifluoromethylthiobenzamide (compound No 4.002)

N-[2-(4-Bromo-2H-pyrazolo[3,4-c]pyridin-2-yl)-1-cyano-1-methylethyl]-4-trifluoromethoxybenzamide (compound No 4.003)

N-[2-(7-Bromo-2H-pyrazolo[3,4-c]pyridin-2-yl)-1-cyano-1-methylethyl]-4-trifluoromethoxybenzamide (compound No 4.005)

N-[2-(7-Bromo-2H-pyrazolo[3,4-c]pyridin-2-yl)-1-cyano-1-methylethyl]-4-trifluoromethylthiobenzamide (compound No 4.006)

Table 5 below shows specific compounds of the invention encompased by formula (IG):

TABLE 5

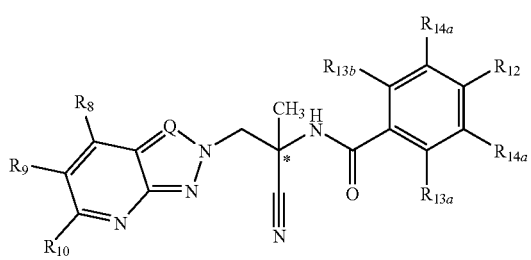

(IG)

| Compound No. | $R_{12}$ | $R_{13a}$ | $R_{13b}$ | $R_{14a}$ | $R_{14b}$ | Q | $R_8$ | $R_9$ | $R_{10}$ | Optical Rotation |
|---|---|---|---|---|---|---|---|---|---|---|
| 5.001 | OCF$_3$ | H | H | H | H | C—H | H | Br | H | (+)/(−) |
| 5.002 | SCF$_3$ | H | H | H | H | C—H | H | Br | H | (+)/(−) |
| 5.003 | OCF$_3$ | H | H | H | H | C—H | Br | H | H | (+)/(−) |
| 5.004 | SCF$_3$ | H | H | H | H | C—H | Br | H | H | (+)/(−) |
| 5.005 | OCF$_3$ | H | H | H | H | C—H | H | H | Br | (+)/(−) |
| 5.006 | SCF$_3$ | H | H | H | H | C—H | H | H | Br | (+)/(−) |
| 5.007 | OCF$_3$ | H | H | H | H | C—H | Br | H | Br | (+)/(−) |

TABLE 5-continued

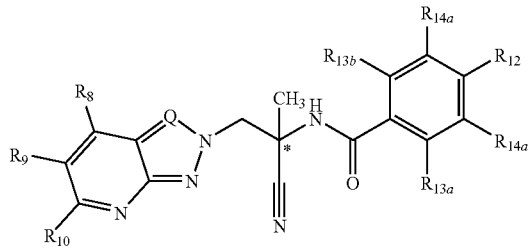

(IG)

| Compound No. | $R_{12}$ | $R_{13a}$ | $R_{13b}$ | $R_{14a}$ | $R_{14b}$ | Q | $R_8$ | $R_9$ | $R_{10}$ | Optical Rotation |
|---|---|---|---|---|---|---|---|---|---|---|
| 5.008 | $SCF_3$ | H | H | H | H | C—H | Br | H | Br | (+)/(−) |
| 5.009 | $SF_5$ | H | H | H | H | C—H | H | Br | H | (+)/(−) |
| 5.010 | $SF_5$ | H | H | H | H | C—H | Br | H | H | (+)/(−) |
| 5.011 | $SF_5$ | H | H | H | H | C—H | H | H | Br | (+)/(−) |
| 5.012 | $SF_5$ | H | H | H | H | C—H | Br | H | Br | (+)/(−) |
| 5.013 | $OCF_3$ | H | H | H | H | C—H | H | Br | H | (+) |
| 5.014 | $OCF_3$ | H | H | H | H | C—H | H | Br | H | (−) |
| 5.015 | $OCF_3$ | H | H | H | H | C—H | Br | H | Br | (+) |
| 5.016 | $OCF_3$ | H | H | H | H | C—H | Br | H | Br | (−) |
| 5.017 | $SCF_3$ | H | H | H | H | C—H | H | Br | H | (+) |
| 5.018 | $SCF_3$ | H | H | H | H | C—H | H | Br | H | (−) |
| 5.019 | $SCF_3$ | H | H | H | H | C—H | Br | H | H | (+) |
| 5.020 | $SCF_3$ | H | H | H | H | C—H | Br | H | H | (−) |
| 5.021 | $SCF_3$ | H | H | H | H | C—H | Br | H | Br | (+) |
| 5.022 | $SCF_3$ | H | H | H | H | C—H | Br | H | Br | (−) |
| 5.023 | $SF_5$ | H | H | H | H | C—H | H | Br | H | (+) |
| 5.024 | $SF_5$ | H | H | H | H | C—H | H | Br | H | (−) |
| 5.025 | $SF_5$ | H | H | H | H | C—H | Br | H | H | (+) |
| 5.026 | $SF_5$ | H | H | H | H | C—H | Br | H | H | (−) |
| 5.027 | $SF_5$ | H | H | H | H | C—H | Br | H | Br | (+) |
| 5.028 | $SF_5$ | H | H | H | H | C—H | Br | H | Br | (−) |

Compounds of general formula (IG) which are of particular interest include, but are not limited to, N-[2-(5-Bromo-2H-pyrazolo[3,4-b]pyridin-2-yl)-1-cyano-1-methylethyl]-4-trifluoromethoxybenzamide (compound No 5.001)

N-[2-(5-Bromo-2H-pyrazolo[3,4-b]pyridin-2-yl)-1-cyano-1-methylethyl]-4-trifluoromethylthiobenzamide (compound No 5.002)

Example 208

Separation of Enantiomers of N-[1-Cyano-1-methyl-2-(4,5,7-trichloro-2H-benzotriazol-2-yl)-ethyl]-4-trifluoromethoxybenzamide (compound No 1.064) to yield (+)-N-[1-Cyano-1-methyl-2-(4,5,7-trichloro-2H-benzotriazol-2-yl)-ethyl]-4-trifluoromethoxybenzamide (compound No 1.096) and (−)-N-[1-Cyano-1-methyl-2-(4,5,7-trichloro-2H-benzotriazol-2-yl)-ethyl]-4-trifluoromethoxybenzamide (compound No 1.097)

A feed solution of N-[1-Cyano-1-methyl-2-(4,5,7-trichloro-2H-benzotriazol-2-yl)-ethyl]-4-trifluoromethoxybenzamide (1.135 g, compound No 1.064 described above) is prepared in ethanol with stirring and heating until complete dissolution is achieved. The feed solution was filtered through a 0.2 μm filter before use. The enantiomers were separated using a CHIRALPAK®AD® column (CHIRAL Technologies Inc., 20 μm particle size of amylose tris(3,5-dimethylphenylcarbamate) polysaccharide CHIRALPAK®AD® stationary phase, 5 cm internal diameter, 50 cm length at 25° C. and flow rate of 120 mL/min). The fractions collected from the chromatographic process for each of the two chromatographic eluting peaks were concentrated using a bench top rotary evaporators at 40° C. and 50 mbar. After solvent removal, the products were dried to constant weight in a vacuum oven at 40° C. The target eutomer (+)-N-[1-Cyano-1-methyl-2-(4,5,7-trichloro-2H-benzotriazol-2-yl)-ethyl]-4-trifluoromethoxybenzamide was isolated from the first eluting peak with a recovery yield of 97.5% (0.554 g). The percent enantiomeric excess of the eutomer is superior to 99.9% with a specific optical rotation average of +12.1° at a concentration of 10.4 mg/mL in $CH_2Cl_2$ at 22° C. using 589 nm wavelength with a cell path of 100 mm (measured on a Perkin-Elmer Polarimeter 341 at Robertson Microlit Laboratories Inc. Madison, N.J.-USA). The distomer (−)-N-[1-Cyano-1-methyl-2-(4,5,7-trichloro-2H-benzotriazol-2-yl)-ethyl]-4-trifluoromethoxybenzamide was isolated from the second eluting peak with a recovery yield of 96.6% (0.548 g). The percent enantiomeric excess of the distomer is superior to 99.9% with an optical rotation average of −12.7° at a concentration of 10.2 mg/mL in $CH_2Cl_2$ at 22° C. using 589 nm wavelength and a cell path of 100 mm (measured on a Perkin-Elmer Polarimeter 341 at Robertson Microlit Laboratories Inc. Madison, N.J.-USA).

Example 209

Separation of Enantiomers of N-[2-(6-Bromo-2H-pyrazolo[4,3-b]pyridin-2-yl)-1-cyano-1-methylethyl]-4-trifluoromethoxybenzamide (compound No 3.011) to yield (+)-N-[2-(6-Bromo-2H-pyrazolo[4,3-b]pyridin-2-yl)-1-cyano-1-methylethyl]-4-trifluoromethoxybenzamide (compound No 3.024) and (−)-N-[2-(6-Bromo-2H-pyrazolo[4,3-b]pyridin-2-yl)-1-cyano-1-methylethyl]-4-trifluoromethoxybenzamide (compound No 3.025)

A feed solution of N-[2-(6-Bromo-2H-pyrazolo[4,3-b]pyridin-2-yl)-1-cyano-1-methylethyl]-4-trifluoromethoxybenzamide (1.95 g, compound No 3.011 described above) is prepared in ethanol (220 mL) with stirring and heating until complete dissolution is achieved. The feed solution was filtered through a 0.2 μm filter before use. The enantiomers were separated using a CHIRALPAK®AD® column (CHIRAL Technologies Inc., 20 μm particle size of amylose tris(3,5-dimethylphenylcarbamate) polysaccharide CHIRALPAK®AD® stationary phase, 5 cm internal diameter, 50 cm length at 25° C. and flow rate of 120 mL/min) with injection volume of 65 mL every 9 min. The fractions collected from the chromatographic process for each of the two chromatographic eluting peaks were concentrated using a bench top rotary evaporators at 40° C. and 50 mbar. After solvent removal, the products were dried to constant weight in a vacuum oven at 40° C. The target eutomer (+)-N-[2-(6-Bromo-2H-pyrazolo[4,3-b]pyridin-2-yl)-1-cyano-1-methylethyl]-4-trifluoromethoxybenzamide was isolated from the first eluting peak with a recovery yield of 77.9% (0.76 g). The percent enantiomeric excess of the eutomer is superior to 99.9% with an optical rotation average of +48.6° at a concentration of 10.1 mg/mL in $CH_2Cl_2$ at 22° C. using a 589 nm wavelength (measured on a Perkin-Elmer Polarimeter 341 at Robertson Microlit Laboratories Inc. Madison, N.J.-USA). The distomer (−)-N-[2-(6-Bromo-2H-pyrazolo[4,3-b]pyridin-2-yl)-1-cyano-1-methylethyl]-4-trifluoromethoxybenzamide was isolated from the second eluting peak with a recovery yield of 84.1% (0.82 g). The percent enantiomeric excess of the distomer is 99.2% with an optical rotation average of −49.0° at a concentration of 10.2 mg/mL in $CH_2Cl_2$ at 22° C. using a 589 nm wavelength (measured on a Perkin-Elmer Polarimeter 341 at Robertson Microlit Laboratories Inc. Madison, N.J.-USA).

Example 210

Preparative Scale Separation of Enantiomers of N-[2-(6-Bromo-2H-pyrazolo[4,3-b]pyridin-2-yl)-1-cyano-1-methylethyl]-4-trifluoromethoxybenzamide (compound No 3.011) to yield (+)-N-[2-(6-Bromo-2H-pyrazolo[4,3-b]pyridin-2-yl)-1-cyano-1-methylethyl]-4-trifluoromethoxybenzamide (compound No 3.024) and (−)-N-[2-(6-Bromo-2H-pyrazolo[4,3-b]pyridin-2-yl)-1-cyano-1-methylethyl]-4-trifluoromethoxybenzamide (compound No 3.025)

A feed solution of racemic N-[2-(6-Bromo-2H-pyrazolo[4,3-b]pyridin-2-yl)-1-cyano-1-methylethyl]-4-trifluoromethoxybenzamide (43.39 g, in two batches of 43.0 g and 0.39 g, compound No 3.011 described above) is prepared in ethanol (feed solubility was 8.6 g/L) with stirring and heating until complete dissolution is achieved. The feed solution was filtered through a 0.2 μm filter before use. The enantiomers were separated using a CHIRALPAK®AD® column (CHIRAL Technologies Inc., 20 μm particle size of amylose tris(3,5-dimethylphenylcarbamate) polysaccharide CHIRALPAK®AD® stationary phase, 5 cm internal diameter, 50 cm length at 25° C. and flow rate of 110 mL/min) with injection volume of 65 mL every 11 min. The fractions collected from the chromatographic process for each of the two chromatographic eluting peaks were concentrated using a a 20 L rotary evaporator at 40° C. and 50 mbar. After solvent removal, the products were dried to constant weight in a vacuum oven at 40° C. The target eutomer (+)-N-[2-(6-Bromo-2H-pyrazolo[4,3-b]pyridin-2-yl)-1-cyano-1-methylethyl]-4-trifluoromethoxybenzamide was isolated from the first eluting peak with a recovery yield of 89.0% (19.3 g). The percent enantiomeric excess of the eutomer is superior to 99.8% as measured via analytical chiral HPLC using a CHIRALPAK®AD® column (CHIRAL Technologies Inc., 4.6×250 mm, at 30° C., flow rate of 0.7 mL/min of EtOH mobile phase, retention time=8.16 min) with an optical rotation average of +51.6° at a concentration of 10.06 mg/mL in $CH_2Cl_2$ at 22° C. using a 589 nm wavelength (measured on a Perkin-Elmer Polarimeter 341 at Robertson Microlit Laboratories Inc. Madison, N.J.-USA). The distomer (−)-N-[2-(6-Bromo-2H-pyrazolo[4,3-b]pyridin-2-yl)-1-cyano-1-methylethyl]-4-trifluoromethoxybenzamide was isolated from the second eluting peak with a recovery yield of 94.5% (20.5 g). The percent enantiomeric excess of the distomer is 98.8% as measured via analytical chiral HPLC using a CHIRALPAK®AD® column (CHIRAL Technologies Inc., 4.6×250 mm, at 30° C., flow rate of 0.7 mL/min of EtOH mobile phase, retention time=12.5 min).

The distomer was analyzed via single crystal X-Ray diffraction analysis using A clear colourless needle-like specimen of $C_{18}H_{12}BrF_3N_5O_2$, approximate dimensions 0.05 mm×0.05 mm×0.20 mm, was used for the X-ray crystallographic analysis. The X-ray intensity data were measured.

The integration of the data using a triclinic unit cell yielded a total of 14077 reflections to a maximum θ angle of 65.99° (0.84 Å resolution), of which 5635 were independent (average redundancy 2.498, completeness=95.0%, $R_{int}$=4.46%, $R_{sig}$=5.47%) and 5472 (97.11%) were greater than $2\sigma(F^2)$. The final cell constants of a=6.116(2) Å, b=10.630(2) Å, c=15.171(4) Å, α=107.99(2)°, β=95.65(2)°, γ=90.94(2)°, volume=932.4(4) Å$^3$, are based upon the refinement of the XYZ-centroids of reflections above 20σ(I). The calculated minimum and maximum transmission coefficients (based on crystal size) are 0.5398 and 0.8438.

The structure was solved and refined using the Bruker SHELXTL Software Package, using the space group P 1, with Z=2 for the formula unit, $C_{18}H_{12}BrF_3N_5O_2$. The final anisotropic full-matrix least-squares refinement on $F^2$ with 525 variables converged at R1=7.32%, for the observed data and wR2=19.23% for all data. The goodness-of-fit was 1.067. The largest peak in the final difference electron density synthesis was 1.912 e$^-$/Å$^3$ and the largest hole was −0.662 e$^-$/Å$^3$ with an RMS deviation of 0.155 e$^-$/Å$^3$. On the basis of the final model, the calculated density was 1.664 g/cm$^3$ and F(000), 466 e$^-$.

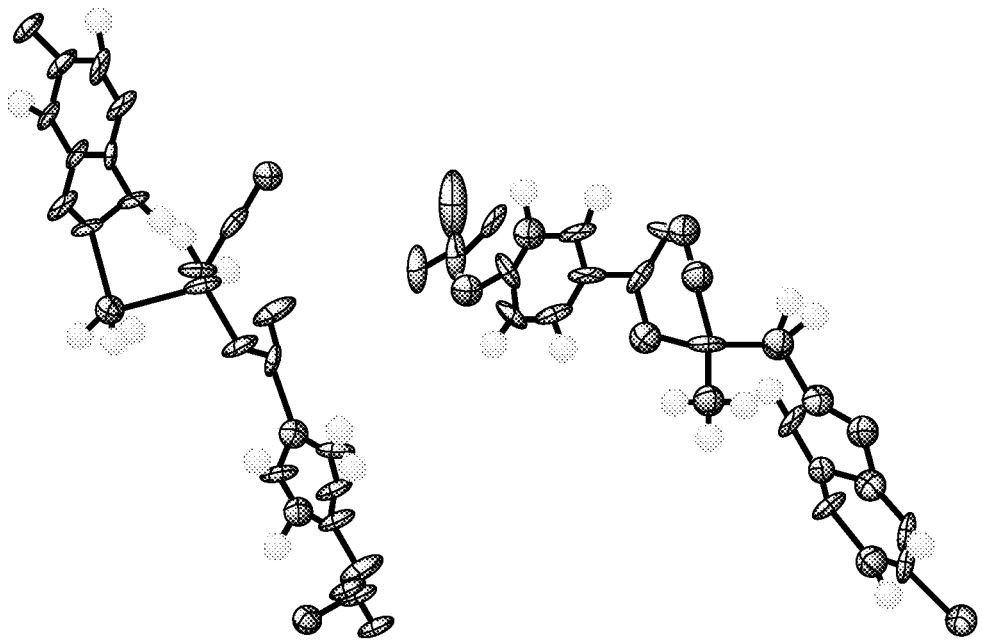

Modern X-ray techniques have enabled the elucidation of absolute stereochemical configuration for molecules, see Ladd, M. and Palmer, R. in "Structure Determination by X-Ray Crystallography, $4^{th}$ ed." Springer, 2003; Flack, H. D. "On Enantiomorph Polarity Estimation," *Acta. Cryst.* 1983, A39: 876-881; Flack, H. D. "The use of X-ray Crystallography to Determine Absolute Configuration," *Chirality* 2008, 20, 681-690; and Flack, H. D. "The use of X-ray Crystallography to Determine Absolute Configuration (II)," *Acta. Chim. Slov.* 2008, 55, 689-691; and references contained therein. The absolute stereochemical configuration was elucidated based on the Flack parameter (Table 5). The X-ray crystallographic analysis unambiguously gave the (S)-absolute configuration for the distomer (−)-N-[2-(6-Bromo-2H-pyrazolo[4,3-b]pyridin-2-yl)-1-cyano-1-methylethyl]-4-trifluoromethoxybenzamide (compound No 3.025) using the Cahn-Ingold-Prelog system in which the four groups on an asymmetric carbon are ranked according to a set of sequence rules. For a description of the Cahn-Ingold-Prelog system see "*March's Advanced Organic Chemistry: Reactions, Mechanisms, and Structure* (Sixth Edition)", Michael B. Smith and Jerry March, Wiley-Interscience Publishers, (2007) pp. 155-158 and references cited therein. The eutomer (+)-N-[2-(6-Bromo-2H-pyrazolo[4,3-b]pyridin-2-yl)-1-cyano-1-methylethyl]-4-trifluoromethoxybenzamide (compound No 3.024) has then the (R)-absolute configuration. As expected for an enantiomer, the $^1$H NMR and $^{19}$F NMR data for the eutomer is well correlated with that of the racemic mixture and the distomer.

Molecular depictions drawn below follow standard conventions for depicting stereochemistry. To indicate stereoconfiguration, bonds rising from the plane of the drawing and towards the viewer are denoted by solid wedges wherein the broad end of the wedge is attached to the atom rising from the plane of the drawing towards the viewer. Bonds going below the plane of the drawing and away from the viewer are denoted by dashed wedges wherein the narrow end of the wedge is attached to the atom further away from the viewer. Constant width lines indicate bonds with a direction opposite or neutral relative to bonds shown with solid or dashed wedges; constant width lines also depict bonds in molecules or parts of molecules in which no particular stereoconfiguration is intended to be specified.

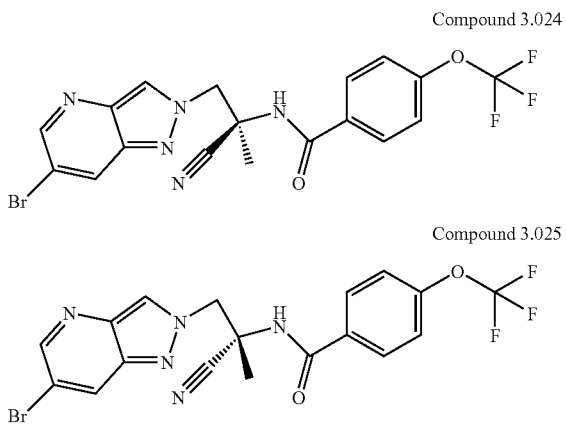

Compound 3.024

Compound 3.025

TABLE 4

Sample and Crystal Data for Compound 3.025.

| | |
|---|---|
| Chemical formula | $C_{18}H_{12}BrF_3N_5O_2$ |
| Formula weight | 467.24 |
| Temperature | 100(2) K |
| Wavelength | 1.54178 Å |
| Crystal size | 0.05 × 0.05 × 0.20 mm |
| Crystal habit | clear colourless needle |
| Crystal system | triclinic |
| Space group | P 1 |
| Unit cell dimensions | a = 6.116(2) Å   α = 107.99(2)° |
| | b = 10.630(2) Å   β = 95.65(2)° |
| | c = 15.171(4) Å   γ = 90.94(2)° |

TABLE 4-continued

Sample and Crystal Data for Compound 3.025.

| | |
|---|---|
| Volume | 932.4(4) Å$^3$ |
| Z | 2 |
| Density (calculated) | 1.664 Mg/cm$^3$ |
| Absorption coefficient | 3.516 mm$^{-1}$ |
| F(000) | 466 |

TABLE 5

Data Collection and Structure Refinement for Compound 3.025.

| | |
|---|---|
| Theta range for data collection | 3.08 to 65.99° |
| Index ranges | −7 <= h <= 7, −11 <= k <= 12, −17 <= l <= 17 |
| Reflections collected | 14077 |
| Independent reflections | 5635 [R(int) = 0.0446] |
| Max. and min. transmission | 0.8438 and 0.5398 |
| Structure solution technique | direct methods |
| Structure solution program | SHELXS-97 (Sheldrick, 2008) |
| Refinement method | Full-matrix least-squares on F$^2$ |
| Refinement program | SHELXL-97 (Sheldrick, 2008) |
| Function minimized | $\Sigma$ w(F$_o^2$ − F$_c^2$)$^2$ |
| Data/restraints/parameters | 5635/75/525 |
| Goodness-of-fit on F$^2$ | 1.067 |
| $\Delta/\sigma_{max}$ | 0.001 |
| Final R indices | 5472 data; R1 = 0.0732, wR2 = 0.1909 I > 2σ(I) all data R1 = 0.0746, wR2 = 0.1923 |
| Weighting scheme | w = 1/[σ$^2$(F$_o^2$) + (0.1113P)$^2$ + 4.5631P] where P = (F$_o^2$ + 2F$_c^2$)/3 |
| Absolute structure parameter (estimated standard deviation) | 0.029(29) |
| Largest diff. peak and hole | 1.912 and −0.662 eÅ$^{-3}$ |
| R.M.S. deviation from mean | 0.155 eÅ$^{-3}$ |

TABLE 6

Atomic Coordinates and Equivalent Isotropic Atomic Displacement Parameters (Å$^2$) for Compound 3.025.

| | x/a | y/b | z/c | U(eq) |
|---|---|---|---|---|
| Br1 | 0.16677(12) | 0.96665(8) | 0.12535(6) | 0.0374(2) |
| C1 | 0.995(2) | 0.0633(11) | 0.0600(7) | 0.035(3) |
| C2 | 0.0857(17) | 0.1815(11) | 0.0539(7) | 0.037(2) |
| N3 | 0.9969(13) | 0.2523(8) | 0.0074(5) | 0.0299(18) |
| C4 | 0.7960(13) | 0.2056(9) | 0.9591(5) | 0.024(2) |
| C5 | 0.6470(18) | 0.2596(10) | 0.9041(5) | 0.033(2) |
| N6 | 0.4699(11) | 0.1712(9) | 0.8775(5) | 0.0313(17) |
| N7 | 0.4816(11) | 0.0660(7) | 0.9105(5) | 0.0280(16) |
| C8 | 0.6840(17) | 0.0865(9) | 0.9623(5) | 0.031(2) |
| C9 | 0.2658(14) | 0.1815(9) | 0.8206(5) | 0.030(2) |
| C10 | 0.7917(17) | 0.0092(10) | 0.0120(5) | 0.030(2) |
| C11 | 0.2869(14) | 0.1316(9) | 0.7149(5) | 0.0270(18) |
| C12 | 0.3787(15) | 0.9903(9) | 0.6868(5) | 0.030(2) |
| C13 | 0.0539(14) | 0.1166(9) | 0.6701(5) | 0.0263(18) |
| N14 | 0.8725(14) | 0.1008(9) | 0.6392(5) | 0.038(2) |
| N15 | 0.4138(11) | 0.2192(8) | 0.6829(5) | 0.0305(17) |
| C16 | 0.3375(15) | 0.3379(9) | 0.6786(5) | 0.025(2) |
| O17 | 0.1677(10) | 0.3793(7) | 0.7109(5) | 0.0357(15) |
| C18 | 0.4689(14) | 0.4129(9) | 0.6310(5) | 0.030(2) |
| C19 | 0.3808(18) | 0.5300(10) | 0.6202(8) | 0.041(2) |
| C20 | 0.481(3) | 0.5991(11) | 0.5728(11) | 0.070(4) |
| C21 | 0.678(3) | 0.5567(13) | 0.5382(11) | 0.072(3) |
| C22 | 0.770(2) | 0.4461(14) | 0.5485(9) | 0.053(3) |
| C23 | 0.6651(15) | 0.3699(11) | 0.5929(7) | 0.036(2) |
| O24 | 0.824(2) | 0.6213(10) | 0.4995(8) | 0.077(2) |
| C25 | 0.792(3) | 0.7235(15) | 0.4808(11) | 0.069(2) |
| F26 | 0.576(2) | 0.6858(13) | 0.4197(8) | 0.118(4) |
| F27 | 0.9090(11) | 0.7608(5) | 0.4249(4) | 0.0510(16) |
| F28 | 0.7211(11) | 0.8294(5) | 0.5437(4) | 0.0483(15) |

TABLE 6-continued

Atomic Coordinates and Equivalent Isotropic Atomic Displacement Parameters (Å$^2$) for Compound 3.025.

| | x/a | y/b | z/c | U(eq) |
|---|---|---|---|---|
| Br2 | 0.87382(13) | 0.83636(10) | 0.76229(6) | 0.0431(2) |
| C31 | 0.0027(15) | 0.7358(10) | 0.8387(5) | 0.0257(16) |
| C32 | 0.2048(16) | 0.7632(11) | 0.8809(7) | 0.0304(18) |
| C33 | 0.2838(14) | 0.6810(10) | 0.9328(5) | 0.025(2) |
| N34 | 0.4749(11) | 0.6830(9) | 0.9828(5) | 0.0305(18) |
| N35 | 0.4515(11) | 0.5790(8) | 0.0147(5) | 0.0250(16) |
| C36 | 0.2585(16) | 0.5108(10) | 0.9898(5) | 0.033(2) |
| C37 | 0.1335(15) | 0.5744(9) | 0.9325(5) | 0.027(2) |
| N38 | 0.9269(13) | 0.5451(8) | 0.8878(5) | 0.0294(17) |
| C39 | 0.8663(15) | 0.6261(10) | 0.8393(5) | 0.0281(18) |
| C40 | 0.6379(14) | 0.5463(11) | 0.0725(5) | 0.033(2) |
| C41 | 0.6504(14) | 0.6185(9) | 0.1767(7) | 0.028(2) |
| C42 | 0.7495(15) | 0.7598(10) | 0.1974(7) | 0.031(2) |
| C43 | 0.4317(15) | 0.6288(9) | 0.2102(5) | 0.029(2) |
| N44 | 0.2590(14) | 0.6482(9) | 0.2365(5) | 0.036(2) |
| N45 | 0.7928(11) | 0.5448(8) | 0.2254(5) | 0.0278(16) |
| C46 | 0.7193(15) | 0.4240(10) | 0.2281(5) | 0.028(2) |
| O47 | 0.5366(11) | 0.3793(7) | 0.1935(5) | 0.0351(15) |
| C48 | 0.8774(15) | 0.3530(10) | 0.2802(5) | 0.029(2) |
| C49 | 0.0901(18) | 0.4015(11) | 0.3185(8) | 0.045(3) |
| C50 | 0.2178(16) | 0.3341(13) | 0.3663(7) | 0.040(3) |
| C51 | 0.126(3) | 0.2209(14) | 0.3780(8) | 0.065(3) |
| C52 | 0.917(2) | 0.1697(11) | 0.3409(9) | 0.057(3) |
| C53 | 0.784(2) | 0.2390(11) | 0.2899(8) | 0.050(3) |
| O54 | 0.2606(18) | 0.1602(9) | 0.4375(5) | 0.069(2) |
| C55 | 0.307(3) | 0.0390(14) | 0.4080(9) | 0.066(2) |
| F56 | 0.1697(16) | 0.9408(8) | 0.3552(5) | 0.081(2) |
| F57 | 0.4472(14) | 0.0065(8) | 0.4646(4) | 0.064(2) |
| F58 | 0.429(2) | 0.0344(10) | 0.3332(5) | 0.090(3) |

U(eq) is defined as one third of the trace of the orthogonalized U$_{ij}$ tensor.

TABLE 7

Bond Lengths (Å) for Compound 3.025.

| | | | |
|---|---|---|---|
| Br1—C1 | 1.897(12) | C1—C10 | 1.395(16) |
| C1—C2 | 1.398(16) | C2—N3 | 1.276(14) |
| N3—C4 | 1.367(12) | C4—C5 | 1.422(14) |
| C4—C8 | 1.446(12) | C5—N6 | 1.366(13) |
| N6—N7 | 1.359(12) | N6—C9 | 1.472(12) |
| N7—C8 | 1.375(13) | C8—C10 | 1.407(15) |
| C9—C11 | 1.545(12) | C11—N15 | 1.427(13) |
| C11—C13 | 1.501(12) | C11—C12 | 1.559(12) |
| C13—N14 | 1.149(12) | N15—C16 | 1.371(14) |
| C16—O17 | 1.223(11) | C16—C18 | 1.501(13) |
| C18—C23 | 1.405(12) | C18—C19 | 1.414(15) |
| C19—C20 | 1.354(17) | C20—C21 | 1.39(2) |
| C21—C22 | 1.36(2) | C21—O24 | 1.395(14) |
| C22—C23 | 1.386(16) | O24—C25 | 1.22(2) |
| C25—F27 | 1.306(14) | C25—F28 | 1.343(16) |
| C25—F26 | 1.51(2) | Br2—C31 | 1.929(9) |
| C31—C32 | 1.319(14) | C31—C39 | 1.426(14) |
| C32—C33 | 1.408(15) | C33—N34 | 1.325(12) |
| C33—C37 | 1.446(13) | N34—N35 | 1.348(12) |
| N35—C36 | 1.333(13) | N35—C40 | 1.481(12) |
| C36—C37 | 1.431(14) | C37—N38 | 1.357(12) |
| N38—C39 | 1.329(13) | C40—C41 | 1.523(13) |
| C41—C43 | 1.471(12) | C41—N45 | 1.473(11) |
| C41—C42 | 1.537(12) | C43—N44 | 1.165(12) |
| N45—C46 | 1.368(13) | C46—O47 | 1.210(11) |
| C46—C48 | 1.540(13) | C48—C53 | 1.385(17) |
| C48—C50 | 1.393(15) | C49—C50 | 1.371(16) |
| C50—C51 | 1.39(2) | C51—C52 | 1.38(2) |
| C51—O54 | 1.463(13) | C52—C53 | 1.429(17) |
| O54—C55 | 1.272(16) | C55—F57 | 1.282(14) |
| C55—F56 | 1.325(17) | C55—F58 | 1.41(2) |

TABLE 8

Bond Angles (°) for Compound 3.025.

| | | | |
|---|---|---|---|
| C10—C1—C2 | 121.5(10) | C10—C1—Br1 | 119.6(8) |
| C2—C1—Br1 | 118.6(9) | N3—C2—C1 | 125.8(10) |
| C2—N3—C4 | 115.8(9) | N3—C4—C5 | 131.4(9) |
| N3—C4—C8 | 123.2(9) | C5—C4—C8 | 105.3(8) |
| N6—C5—C4 | 104.4(8) | N7—N6—C5 | 116.1(8) |
| N7—N6—C9 | 117.2(7) | C5—N6—C9 | 126.7(9) |
| N6—N7—C8 | 103.4(7) | N7—C8—C10 | 130.2(8) |
| N7—C8—C4 | 110.8(9) | C10—C8—C4 | 118.9(9) |
| N6—C9—C11 | 112.8(7) | C1—C10—C8 | 114.7(9) |
| N15—C11—C13 | 110.3(8) | N15—C11—C9 | 114.1(8) |
| C13—C11—C9 | 104.3(7) | N15—C11—C12 | 110.7(7) |
| C13—C11—C12 | 106.5(7) | C9—C11—C12 | 110.5(7) |
| N14—C13—C11 | 175.8(9) | C16—N15—C11 | 121.7(8) |
| O17—C16—N15 | 121.1(9) | O17—C16—C18 | 121.8(9) |
| N15—C16—C18 | 117.1(8) | C23—C18—C19 | 119.0(9) |
| C23—C18—C16 | 124.0(9) | C19—C18—C16 | 116.9(8) |
| C20—C19—C18 | 120.8(10) | C19—C20—C21 | 119.1(12) |
| C22—C21—C20 | 121.8(11) | C22—C21—O24 | 109.0(13) |
| C20—C21—O24 | 128.8(13) | C21—C22—C23 | 120.4(11) |
| C22—C23—C18 | 118.9(11) | C25—O24—C21 | 125.9(14) |
| O24—C25—F27 | 122.0(14) | O24—C25—F28 | 120.6(12) |
| F27—C25—F28 | 110.4(11) | O24—C25—F26 | 100.3(13) |
| F27—C25—F26 | 100.0(12) | F28—C25—F26 | 96.0(12) |
| C32—C31—C39 | 124.2(9) | C32—C31—Br2 | 121.7(8) |
| C39—C31—Br2 | 113.9(7) | C31—C32—C33 | 116.8(9) |
| N34—C33—C32 | 131.4(9) | N34—C33—C37 | 112.8(9) |
| C32—C33—C37 | 115.8(8) | C33—N34—N35 | 103.3(7) |
| C36—N35—N34 | 116.2(8) | C36—N35—C40 | 124.5(8) |
| N34—N35—C40 | 119.2(7) | N35—C36—C37 | 105.2(8) |
| N38—C37—C36 | 130.2(9) | N38—C37—C33 | 127.3(9) |
| C36—C37—C33 | 102.5(8) | C39—N38—C37 | 113.1(8) |
| N38—C39—C31 | 122.7(8) | N35—C40—C41 | 115.5(7) |
| C43—C41—N45 | 110.0(7) | C43—C41—C40 | 111.8(7) |
| N45—C41—C40 | 107.9(8) | C43—C41—C42 | 107.8(8) |
| N45—C41—C42 | 109.8(7) | C40—C41—C42 | 109.5(8) |
| N44—C43—C41 | 174.1(10) | C46—N45—C41 | 119.4(7) |
| O47—C46—N45 | 120.7(8) | O47—C46—C48 | 122.9(8) |
| N45—C46—C48 | 116.4(8) | C53—C48—C49 | 122.7(10) |
| C53—C48—C46 | 113.6(8) | C49—C48—C46 | 123.7(9) |
| C50—C49—C48 | 119.9(10) | C49—C50—C51 | 118.1(10) |
| C52—C51—C50 | 123.6(11) | C52—C51—O54 | 120.3(14) |
| C50—C51—O54 | 116.0(12) | C51—C52—C53 | 118.3(12) |
| C48—C53—C52 | 117.4(11) | C55—O54—C51 | 121.1(9) |
| O54—C55—F57 | 112.8(11) | O54—C55—F56 | 125.4(12) |
| F57—C55—F56 | 114.6(13) | O54—C55—F58 | 103.0(13) |
| F57—C55—F58 | 102.3(12) | F56—C55—F58 | 92.1(10) |

TABLE 9

Torsion Angles (°) for Compound 3.025.

| | | | |
|---|---|---|---|
| C10—C1—C2—N3 | 1.2(15) | Br1—C1—C2—N3 | 175.0(8) |
| C1—C2—N3—C4 | −0.6(14) | C2—N3—C4—C5 | 177.0(9) |
| C2—N3—C4—C8 | 2.3(13) | N3—C4—C5—N6 | −177.2(9) |
| C8—C4—C5—N6 | −1.8(10) | C4—C5—N6—N7 | 1.5(10) |
| C4—C5—N6—C9 | 178.8(8) | C5—N6—N7—C8 | −0.5(10) |
| C9—N6—N7—C8 | −178.0(7) | N6—N7—C8—C10 | −178.4(9) |
| N6—N7—C8—C4 | −0.7(9) | N3—C4—C8—N7 | 177.5(8) |
| C5—C4—C8—N7 | 1.6(10) | N3—C4—C8—C10 | −4.5(13) |
| C5—C4—C8—C10 | 179.6(8) | N7—N6—C9—C11 | −99.8(9) |
| C5—N6—C9—C11 | 83.0(11) | C2—C1—C10—C8 | −3.2(13) |
| Br1—C1—C10—C8 | −177.0(7) | N7—C8—C10—C1 | −177.8(9) |
| C4—C8—C10—C1 | 4.7(13) | N6—C9—C11—N15 | −73.8(10) |
| N6—C9—C11—C13 | 165.7(8) | N6—C9—C11—C12 | 51.7(10) |
| C13—C11—N15—C16 | 46.3(11) | C9—C11—N15—C16 | −70.7(10) |
| C12—C11—N15—C16 | 163.9(8) | C11—N15—C16—O17 | 7.6(13) |
| C11—N15—C16—C18 | −171.3(8) | O17—C16—C18—C23 | 179.8(9) |
| N15—C16—C18—C23 | −1.3(12) | O17—C16—C18—C19 | −3.7(13) |
| N15—C16—C18—C19 | 175.2(8) | C23—C18—C19—C20 | 1.0(16) |
| C16—C18—C19—C20 | −175.6(11) | C18—C19—C20—C21 | −3.(2) |
| C19—C20—C21—C22 | 2.(3) | C19—C20—C21—O24 | −170.0(15) |
| C20—C21—C22—C23 | 1.(2) | O24—C21—C22—C23 | 174.6(12) |
| C21—C22—C23—C18 | −3.2(18) | C19—C18—C23—C22 | 2.0(14) |
| C16—C18—C23—C22 | 178.5(9) | C22—C21—O24—C25 | 179.7(15) |
| C20—C21—O24—C25 | −8.(3) | C21—O24—C25—F27 | −162.9(14) |
| C21—O24—C25—F28 | 49.(2) | C21—O24—C25—F26 | −54.2(18) |
| C39—C31—C32—C33 | −2.9(15) | Br2—C31—C32—C33 | −178.3(7) |
| C31—C32—C33—N34 | −179.4(9) | C31—C32—C33—C37 | 0.8(13) |
| C32—C33—N34—N35 | −179.6(10) | C37—C33—N34—N35 | 0.3(9) |
| C33—N34—N35—C36 | −0.7(10) | C33—N34—N35—C40 | 178.2(7) |
| N34—N35—C36—C37 | 0.8(11) | C40—N35—C36—C37 | −178.0(8) |
| N35—C36—C37—N38 | 179.2(9) | N35—C36—C37—C33 | −0.6(9) |
| N34—C33—C37—N38 | −179.6(8) | C32—C33—C37—N38 | 0.3(13) |
| N34—C33—C37—C36 | 0.2(10) | C32—C33—C37—C36 | −180.0(8) |
| C36—C37—N38—C39 | −179.0(9) | C33—C37—N38—C39 | 0.8(13) |
| C37—N38—C39—C31 | −2.8(13) | C32—C31—C39—N38 | 4.2(15) |
| Br2—C31—C39—N38 | 179.9(7) | C36—N35—C40—C41 | −94.0(11) |
| N34—N35—C40—C41 | 87.2(10) | N35—C40—C41—C43 | 40.3(11) |
| N35—C40—C41—N45 | 161.4(7) | N35—C40—C41—C42 | −79.1(10) |
| C43—C41—N45—C46 | 51.7(11) | C40—C41—N45—C46 | −70.5(10) |
| C42—C41—N45—C46 | 170.2(8) | C41—N45—C46—O47 | −2.3(13) |
| C41—N45—C46—C48 | 180.0(7) | O47—C46—C48—C53 | −4.8(13) |
| N45—C46—C48—C53 | 172.9(8) | O47—C46—C48—C49 | 178.4(9) |
| N45—C46—C48—C49 | −3.9(13) | C53—C48—C49—C50 | 1.5(16) |
| C46—C48—C49—C50 | 178.0(9) | C48—C49—C50—C51 | −2.4(16) |
| C49—C50—C51—C52 | 3.(2) | C49—C50—C51—O54 | −173.9(10) |
| C50—C51—C52—C53 | −2.(2) | O54—C51—C52—C53 | 174.7(11) |
| C49—C48—C53—C52 | −0.6(16) | C46—C48—C53—C52 | −177.4(10) |

TABLE 9-continued

Torsion Angles (°) for Compound 3.025.

| | | | |
|---|---|---|---|
| C51—C52—C53—C48 | 0.7(18) | C52—C51—O54—C55 | 58.(2) |
| C50—C51—O54—C55 | −125.1(15) | C51—O54—C55—F57 | 172.0(14) |
| C51—O54—C55—F56 | −40.(2) | C51—O54—C55—F58 | 62.5(17) |

TABLE 10

Anisotropic Atomic Displacement Parameters (Å$^2$) for Compound 3.025. The anisotropic atomic displacement factor exponent takes the form: $-2\pi^2[h^2 a^{*2} U_{11} + \ldots + 2 h k a^* b^* U_{12}]$

| | $U_{11}$ | $U_{22}$ | $U_{33}$ | $U_{23}$ | $U_{13}$ | $U_{12}$ |
|---|---|---|---|---|---|---|
| Br1 | 0.0434(5) | 0.0352(5) | 0.0380(5) | 0.0204(4) | −0.0031(4) | −0.0037(4) |
| C1 | 0.059(7) | 0.033(6) | 0.019(4) | 0.013(4) | 0.015(4) | 0.000(5) |
| C2 | 0.040(5) | 0.042(6) | 0.025(4) | 0.007(4) | 0.001(4) | 0.000(4) |
| N3 | 0.030(4) | 0.028(4) | 0.035(4) | 0.016(3) | −0.003(3) | −0.009(3) |
| C4 | 0.022(4) | 0.027(5) | 0.026(4) | 0.012(4) | 0.005(3) | −0.009(4) |
| C5 | 0.053(6) | 0.025(5) | 0.025(5) | 0.012(4) | 0.008(4) | −0.006(4) |
| N6 | 0.025(4) | 0.043(5) | 0.026(4) | 0.013(3) | −0.001(3) | −0.001(3) |
| N7 | 0.031(4) | 0.020(4) | 0.036(4) | 0.015(3) | 0.002(3) | −0.006(3) |
| C8 | 0.046(5) | 0.021(5) | 0.026(4) | 0.009(4) | 0.006(4) | −0.014(4) |
| C9 | 0.030(4) | 0.021(5) | 0.039(5) | 0.011(4) | 0.006(4) | 0.002(3) |
| C10 | 0.043(5) | 0.025(5) | 0.028(4) | 0.017(4) | 0.007(4) | −0.003(4) |
| C11 | 0.027(4) | 0.024(5) | 0.032(4) | 0.010(4) | 0.007(3) | 0.012(4) |
| C12 | 0.032(5) | 0.026(5) | 0.033(5) | 0.012(4) | 0.003(4) | 0.004(4) |
| C13 | 0.025(5) | 0.023(5) | 0.035(4) | 0.014(4) | 0.004(3) | 0.003(3) |
| N14 | 0.033(5) | 0.030(5) | 0.053(5) | 0.014(4) | 0.008(4) | 0.002(4) |
| N15 | 0.033(4) | 0.028(5) | 0.036(4) | 0.019(3) | 0.005(3) | 0.003(3) |
| C16 | 0.038(5) | 0.019(5) | 0.020(4) | 0.010(3) | −0.006(3) | −0.004(4) |
| O17 | 0.030(3) | 0.034(4) | 0.049(4) | 0.018(3) | 0.011(3) | 0.012(3) |
| C18 | 0.029(4) | 0.027(5) | 0.029(4) | 0.005(4) | −0.006(3) | −0.005(3) |
| C19 | 0.050(6) | 0.018(5) | 0.052(6) | 0.004(4) | 0.015(5) | −0.001(4) |
| C20 | 0.100(11) | 0.023(6) | 0.110(11) | 0.040(7) | 0.056(9) | 0.025(6) |
| C21 | 0.106(6) | 0.029(5) | 0.092(6) | 0.024(4) | 0.053(5) | −0.010(5) |
| C22 | 0.041(6) | 0.057(8) | 0.063(8) | 0.016(6) | 0.024(5) | −0.005(5) |
| C23 | 0.030(5) | 0.037(6) | 0.044(5) | 0.017(4) | 0.002(4) | −0.002(4) |
| O24 | 0.113(5) | 0.037(4) | 0.095(5) | 0.029(4) | 0.047(4) | −0.007(4) |
| C25 | 0.107(5) | 0.041(4) | 0.071(4) | 0.026(4) | 0.037(4) | −0.012(4) |
| F26 | 0.157(8) | 0.114(7) | 0.081(6) | 0.021(5) | 0.033(6) | −0.029(7) |
| F27 | 0.082(4) | 0.040(3) | 0.040(3) | 0.023(3) | 0.019(3) | −0.011(3) |
| F28 | 0.075(4) | 0.023(3) | 0.052(3) | 0.018(3) | 0.016(3) | 0.002(3) |
| Br2 | 0.0542(5) | 0.0435(7) | 0.0346(5) | 0.0198(5) | −0.0067(4) | 0.0096(5) |
| C31 | 0.031(3) | 0.027(4) | 0.026(3) | 0.018(3) | 0.005(3) | 0.005(3) |
| C32 | 0.036(4) | 0.031(4) | 0.028(4) | 0.016(3) | 0.005(3) | −0.008(3) |
| C33 | 0.026(4) | 0.029(5) | 0.023(4) | 0.013(4) | 0.004(3) | −0.003(4) |
| N34 | 0.023(4) | 0.040(5) | 0.029(4) | 0.013(4) | 0.000(3) | −0.008(3) |
| N35 | 0.030(4) | 0.019(4) | 0.028(4) | 0.012(3) | −0.002(3) | 0.003(3) |
| C36 | 0.040(5) | 0.032(6) | 0.035(5) | 0.023(4) | 0.005(4) | −0.002(4) |
| C37 | 0.029(5) | 0.026(5) | 0.024(4) | 0.005(4) | 0.005(3) | −0.002(4) |
| N38 | 0.033(4) | 0.030(4) | 0.025(3) | 0.010(3) | −0.002(3) | −0.008(3) |
| C39 | 0.029(4) | 0.031(4) | 0.026(4) | 0.011(3) | 0.000(3) | 0.001(3) |
| C40 | 0.024(4) | 0.039(6) | 0.038(5) | 0.017(4) | 0.002(3) | 0.002(4) |
| C41 | 0.020(4) | 0.023(5) | 0.052(6) | 0.028(4) | 0.002(4) | −0.002(3) |
| C42 | 0.028(4) | 0.023(5) | 0.051(6) | 0.024(4) | 0.001(4) | 0.006(4) |
| C43 | 0.036(5) | 0.022(5) | 0.033(4) | 0.017(4) | −0.001(4) | 0.006(4) |
| N44 | 0.035(5) | 0.032(5) | 0.046(5) | 0.020(4) | 0.007(4) | 0.000(3) |
| N45 | 0.029(4) | 0.027(4) | 0.032(4) | 0.019(3) | −0.004(3) | 0.001(3) |
| C46 | 0.033(5) | 0.029(6) | 0.029(5) | 0.020(4) | 0.005(4) | 0.001(4) |
| O47 | 0.038(4) | 0.028(4) | 0.039(4) | 0.016(3) | −0.008(3) | −0.009(3) |
| C48 | 0.032(4) | 0.036(6) | 0.023(4) | 0.013(4) | 0.005(3) | 0.000(4) |
| C49 | 0.051(6) | 0.048(7) | 0.050(6) | 0.036(5) | 0.008(5) | −0.007(5) |
| C50 | 0.030(5) | 0.060(8) | 0.032(5) | 0.016(5) | 0.002(4) | 0.001(5) |
| C51 | 0.103(6) | 0.041(5) | 0.042(4) | 0.011(4) | −0.027(5) | 0.031(5) |
| C52 | 0.074(8) | 0.029(6) | 0.061(7) | 0.015(5) | −0.026(6) | −0.005(5) |
| C53 | 0.052(7) | 0.042(7) | 0.045(6) | 0.005(5) | −0.015(5) | 0.007(5) |
| O54 | 0.109(5) | 0.047(3) | 0.042(3) | 0.014(3) | −0.033(3) | 0.035(3) |
| C55 | 0.103(5) | 0.047(4) | 0.042(4) | 0.017(3) | −0.023(4) | 0.026(4) |
| F56 | 0.104(6) | 0.035(4) | 0.096(5) | 0.019(4) | −0.023(5) | 0.006(4) |
| F57 | 0.107(5) | 0.045(4) | 0.043(3) | 0.025(3) | −0.009(3) | 0.026(4) |
| F58 | 0.127(7) | 0.083(6) | 0.069(5) | 0.036(4) | 0.013(5) | 0.038(5) |

TABLE 11

Hydrogen Atomic Coordinates and Isotropic Atomic Displacement Parameters (Å²) for Compound 3.025.

|       | x/a     | y/b     | z/c     | U(eq) |
|-------|---------|---------|---------|-------|
| H2    | 1.2260  | 0.2118  | 1.0875  | 0.044 |
| H5    | 0.6664  | 0.3392  | 0.8891  | 0.04  |
| H9A   | 0.2254  | 0.2751  | 0.8383  | 0.036 |
| H9B   | 0.1456  | 0.1292  | 0.8343  | 0.036 |
| H10   | 0.7309  | −0.0732 | 1.0128  | 0.036 |
| H12A  | 0.3567  | −0.0489 | 0.6188  | 0.045 |
| H12B  | 0.3010  | −0.0654 | 0.7156  | 0.045 |
| H12C  | 0.5362  | −0.0036 | 0.7081  | 0.045 |
| H19   | 0.2495  | 0.5607  | 0.6467  | 0.049 |
| H20   | 0.4176  | 0.6754  | 0.5633  | 0.084 |
| H22   | 0.9063  | 0.4207  | 0.5253  | 0.064 |
| H23   | 0.7251  | 0.2899  | 0.5974  | 0.043 |
| H32   | 0.2928  | 0.8351  | −0.1236 | 0.037 |
| H36   | 0.2136  | 0.4360  | 0.0065  | 0.039 |
| H39   | −0.2737 | 0.6102  | −0.1964 | 0.034 |
| H40A  | 0.7766  | 0.5665  | 0.0499  | 0.039 |
| H40B  | 0.6283  | 0.4498  | 0.0628  | 0.039 |
| H42A  | 0.7627  | 0.8051  | 0.2647  | 0.047 |
| H42B  | 0.6536  | 0.8085  | 0.1652  | 0.047 |
| H42C  | 0.8954  | 0.7558  | 0.1754  | 0.047 |
| H49   | 1.1466  | 0.4812  | 0.3115  | 0.054 |
| H50   | 1.3651  | 0.3640  | 0.3908  | 0.048 |
| H52   | 0.8615  | 0.0905  | 0.3491  | 0.068 |
| H53   | 0.6385  | 0.2080  | 0.2637  | 0.06  |

Example 211

Preparation of Enantiomer (R)-(+)-N-[2-(6-Bromo-2H-pyrazolo[4,3-b]pyridin-2-yl)-1-cyano-1-methyl-ethyl]-4-trifluoromethoxybenzamide (compound No 3.024)

4-Trifluoromethoxybenzoyl chloride (14.5 mL) was added at around 0° C. to a cold solution of (R)-2-amino-3-(6-bromo-pyrazolo[4,3-b]pyridin-2-yl)-2-methyl-propionitrile (23.4 g, 95% ee) in dry THF (600 mL) mixed with TEA (13.4 mL). The reaction mixture was stirred for around 4 hours at around 0° C. The cold reaction mixture was then filtered through a short plug of Celite® and basic alumina and solvent evaporated under reduced pressure. The resulting residue was triturated with DCM to afford a solid that was isolated by filtration to give the title compound as a white solid (28.6 g, 73.1%, 99.6% analytical purity, 99% ee). The filtrate was collected and solvent evaporated under reduced pressure. The residue was loaded on silica gel and purified by chromatography (SiO$_2$, heptane/EA) to afford a second crop of title compound as a white solid (4.1 g, 10.5%). MS (ES): M/Z [M+H]=468. 1H NMR: (400 MHz, CHLOROFORM-d): 1.94 (s, 3H), 4.86 (d, J=14.0 Hz, 1H), 5.02 (d, J=14.0 Hz, 1H), 7.33 (d, J=8.1 Hz, 2H), 7.83-7.92 (m, 2H), 8.02 (s, 1H), 8.21 (dd, J=2.0, 0.7 Hz, 1H), 8.40 (d, J=0.7 Hz, 1H) and 8.62 (d, J=2.0 Hz, 1H). 19F NMR (376 MHz, CHLOROFORM-d): −58.1 (s, 3F). The starting material (R)-2-amino-3-(6-bromo-pyrazolo[4,3-b]pyridin-2-yl)-2-methyl-propionitrile was prepared as follows:

a. To a cold solution of (+)-di-p-toluoyl-D-tartaric acid (47.5 g) in methanol (150 mL) was added at around 8° C. a solution of 2-amino-3-(6-bromo-pyrazolo[4,3-b]pyridin-2-yl)-2-methyl-propionitrile (35.5 g, described in Example 182) in methanol (200 mL). After a very thick suspension formed, mixture was triturated with a spatula rinsed with additional methanol (50 mL) to allow the stirring to continue for 2 hours at around 15° C. The solid salt was then collected by filtration and dried overnight under vacuum at room temperature. The filtrate was collected and solvent evaporated under reduced pressure to give a residue that was kept aside.

b. The solid salt (30.2 g) was neutralized by addition to a cold solution of concentrated aqueous ammonia (50 mL) at around 5° C. The mixture was extracted twice with DCM (250 mL and 50 mL). The organic phases were dried over anhydrous sodium sulfate, filtered and concentrated under reduced pressure to give (R)-2-amino-3-(6-bromo-pyrazolo[4,3-b]pyridin-2-yl)-2-methyl-propionitrile as a pale yellow solid foam (12.2 g, 34%, 84% ee).

c. To a cold solution of (+)-di-p-toluoyl-D-tartaric acid (47.5 g) in methanol (60 mL) was added at around 8° C. a solution of enantiomerically enriched (R)-2-amino-3-(6-bromo-pyrazolo[4,3-b]pyridin-2-yl)-2-methyl-propionitrile (29.7 g, 82% ee) in methanol (90 mL). A very thick suspension formed, and additional methanol (50 mL) was added and stirred in with a spatula, after which magnetic stirring was continued for 2 hours at around 15° C. The solid salt was collected by filtration and dried overnight under vacuum at room temperature. The filtrate was collected and solvent evaporated under reduced pressure to give a residue that was kept aside.

d. The solid salt was neutralized using a procedure similar to that described above part b to give (R)-2-amino-3-(6-bromo-pyrazolo[4,3-b]pyridin-2-yl)-2-methyl-propionitrile as a pale yellow solid foam (23.4 g, 79%, 95.7% ee).

e. Both filtrate residues kept aside in part a and c above were neutralized following a procedure similar to that described above part b to give a residue containing principally enantiomerically enriched (S)-2-amino-3-(6-bromo-pyrazolo[4,3-b]pyridin-2-yl)-2-methylpropionitrile. This material was racemized nearly quantitatively to (+/−)-2-amino-3-(6-bromo-pyrazolo[4,3-b]pyridin-2-yl)-2-methyl-propionitrile by treatment with ammonia, ammonium chloride, and sodium cyanide in methanol following a procedure similar to that described in Example 1, part b.

Method A: Screening Method to Test Activity of Compounds Against *Haemonchus contortus*.

Twenty L1 *Haemonchus contortus* larvae were added to wells of a microtitre plate containing a nutrient medium and the test compound in DMSO. The microtitre plate was then held at 27° C. where the L1 larvae were allowed to develop. An analysis was conducted at 4 days to determine successful development to the L3 stage. Larvae exposed to DMSO and no test compound served as controls. Compounds numbers 1.010, 2.029, 2.031, 3.042, 3.043, 3.044, 3.045, 3.051, 4.002, 4.005, 4.006, 5.001 and 5.002 gave at least 90% motility inhibition at a test concentration of 0.6 ppm at the 4 days assessment. Compounds numbers 1.002, 1.005, 1.006, 1.008, 1.009, 1.010, 1.011, 1.014, 1.017, 1.018, 1.025, 1.031, 1.045, 1.054, 1.055, 1.061, 1.075, 1.076, 1.079, 1.081, 1.084, 1.146, 2.004, 2.010, 2.014, 2.015, 2.016, 2.020, 2.022, 2.027, 2.033, 2.227, 2.229, 3.003, 3.004, 3.046 and 3.050 gave at least 90% motility inhibition at a test concentration of 0.15 ppm at the 4 days assessment. Compounds numbers 1.003, 1.007, 1.011, 1.015, 1.032, 1.038, 1.042, 1.043, 1.047, 1.048, 1.056, 1.057, 1.060, 1.066, 1.067, 1.070, 1.071, 1.078, 1.100, 1.102, 1.143, 2.001, 2002, 2.003, 2.005, 2.006, 2.007, 2.013, 2.021, 2.067, 2.228, 2.230, 3.010, 3.047, 3.049 and 3.056 gave at least 90% motility inhibition at a test concentration of 0.04 ppm at the 4 days assessment. Compounds numbers 1.001, 1.012, 1.020, 1.021, 1.033, 1.034, 1.037, 1.039, 1.044, 1.085, 1.089, 1.091, 1.092, 1.093, 1.098, 1.099, 1.103, 1.104, 2.012, 2.028, 2.039, 2.069, 2.187, 2.190, 3.005, 3.007, 3.008, 3.017, 3.019, 3.029, 3.048, 3.052 and 3.053 gave at least 90% motility inhibition at a test concentration of 0.01 ppm at the 4 days assessment. Compounds numbers 1.064, 1.065, 1.069, 1.083, 1.086, 1.087, 1.088, 1.090, 1.094, 1.095, 1.096, 1.101, 2.008, 2.009, 2.023, 2.024, 2.025, 2.026, 2.037, 2.038, 2.040, 2.041, 2.042, 2.043, 2.044, 2.045, 2.046, 2.047, 2.048, 2.049, 2.050, 2.058, 2.061, 2.062, 2.063, 2.066, 2.068, 3.001, 3.002, 3.006, 3.009, 3.011, 3.012, 3.023, 3.024 and 3.026 gave at least 90% motility inhibition at a test concentration of 0.0025 ppm at the 4 days assessment. The distomers, compounds number 1.097 and 3.025 did not give at least 90% motility inhibition at a test concentration of 0.3 ppm at the 4 days assessment.

Method B: Screening Method to Test Activity of Compounds Against *Haemonchus contortus* In Vivo in Mongolian Gerbil (*Meriones unguiculatus*).

Mongolian gerbils, at least five weeks old, were immunosuppressed and artificially infected with ca. 1000 ensheathed *Haemonchus contortus* third instar larvae. Six days after infection, the Mongolian gerbils were treated by oral gavage with the test compounds, dissolved in a mixture of 2 parts DMSO and 1 part polyethylene glycol (PEG400), at doses of 100 mg/kg and dissolved in pure polyethylene glycol (PEG400) at doses of 10 and 1 mg/kg. Mongolian gerbils treated only with the placebo (2 parts DMSO and 1 part PEG400 or pure PEG400) served as controls. On day 9 (3 days after treatment) the jirds were euthanized and necropsied for recovery of parasites from the stomach. Efficacy was calculated as the average % reduction in the number of worms in each test group compared with the average number of worms from the control group. In this screen, a vast reduction in nematode was achieved with compounds of formula (I), especially from table 1, 2 and 3. Compound numbers 1.001, 1.008, 1.012, 1.013 and 1.014 provided at least 95% reduction in nematode in Mongolian gerbils treated by oral gavage with test article at a dose of 100 mg/kg. Compound numbers 1.012, 1.033, 1.064, 2.008, 2.037, 2.038, 2.040, 2.041, 3.001 provided at least 95% reduction in nematode infection at a dose of 10 mg/kg. Compound numbers 1.094, 1.096, 2.048, 3.001, 3.007 and 3.009, provided at least 95% reduction in nematode infection at a dose of 1 mg/kg. Compound numbers 3.006, 3.017 and 3.019 provided at least 95% reduction in nematode infection at a dose of 0.5 mg/kg. Compound numbers 3.005, 3.011 and 3.012 provided at least 95% reduction in nematode infection at a dose of 0.3 mg/kg. The eutomer compound number 3.024 provided at least 95% reduction in nematode infection at a dose of 0.1 mg/kg. The distomer compound number 1.097 did not provide at least 95% reduction in nematode infection at a dose of 1 mg/kg and the distomer compound number 3.025 did not provide at least 95% reduction in nematode infection at a dose of 0.3 mg/kg.

Method C: Screening Method to Test Activity of Compounds Against *Ctenocephalides felis*.

Three to five day old *Ctenocephalides felis* adults (50) were aspirated into a test cage. A separate glass cylinder closed on one end with a self-sealing flexible film was placed on top of the test cage in such a position that the fleas could pierce the film and feed on the contents of the glass cylinder. The test compound was dissolved in DMSO and added to bovine blood which was then placed in the glass cylinder. DMSO treated blood served as the control. The fleas were held at 20-22° C., 40-60% relative humidity while the treated blood was held at 37° C. and 40-60% relative humidity. The treated blood was changed daily for six days during which time eggs and fecal material were allowed to accumulate in the flea cage. On day 6, the contents of each cage were inspected and placed in a dish containing larval diet consisting of sand, ground cat food and dried cow blood. The dishes were held at 28° C. and 82% relative humidity for 11 days. Pupae were then sieved, weighed and returned to the controlled conditions for an additional 5 days, after which adult emergence was assessed. Pupal weights and adult emergence were then compared to the controls. Compounds numbers 1.012, 1.013, 1.020, 1.034, 1.064 and 3.005 gave at least 80% reduction in pupal weights at a test concentration of 100 ppm. Compounds numbers 2.048, 3.011 and 3.024 gave at least 95% reduction in pupal weights at a test concentration of 50 ppm.

Method D: Screening Method to Test Activity of Compounds Against *Trichostrongylus colubriformis*.

Twenty L1 *Trichostrongylus colubriformis* larvae were added to wells of a microtitre plate containing a nutrient medium and the test compound in DMSO. The microtitre plate was then held at 27° C. where the L1 larvae were allowed to develop. An analysis was conducted at 4 days to determine successful development to the L3 stage. Larvae exposed to DMSO and no test compound served as controls. Compounds numbers 1.008, 1.014, 1.042, 1.047, 1.048, 1.073, 2.001, 2.003 and 2.020, gave at least 90% motility inhibition at a test concentration of 0.15 ppm at the 4 days assessment. Compounds numbers 1.001, 1.003, 1.007, 1.011, 1.037, 1.038, 1.043, 1.056, 1.066, 1.070, 1.071, 2.012 and 2.016, gave at least 90% motility inhibition at a test concentration of 0.04 ppm at the 4 days assessment. Compounds numbers 1.012, 1.020, 1.021, 1.033, 1.034, 1.039, 1.064, 1.065, 2.008, 2.009 and 3.005 gave at least 90% motility inhibition at a test concentration of 0.01 ppm at the 4 days assessment. Compounds numbers 1.094, 2.040, 2.048, 2.049, 3.006, 3.009, 3.011 and 3.012 gave at least 90% motility inhibition at a test concentration of 0.0025 ppm at the 4 days assessment.

Method E: Screening Method to Test Activity of Compounds Against *Haemonchus contortus, Ostertagia circumcincta, Trichostrongylus axei, Trichostrongylus colubriformis, Cooperia curticei* and *Nematodirus battus* In Vivo in Sheep.

Sheep were challenged orally with infective $3^{rd}$ stage larvae (L3) of Ostertagia circumcincta (~3,000 infective L3 per animal) on Dat −28, *Haemonchus contortus* (~2,000 infective L3 per animal) on Dat −25, *Nematodirus battus* (~3,000 infective L3 per animal) and *Trichostrongylus axei* (~3,000 infective L3 per animal) on Dat −23 and *Cooperia curticei* (~3,000 infective L3 per animal) and *Trichostrongylus colubriformis* (~3,000 infective L3 per species per animal) on Dat −21. The inoculation schedule was designed so that nematodes were expected to be in the adult stage on Day 0. Test compounds were dissolved in a mixture of DMSO/Corn oil (1:1) at a concentration of 100 mg/mL. All treatments were administered orally once on Day 0. At necropsy on Day 15 the abomasum, small intestine and large intestine (including cecum) were removed. Nematode counts were conducted on 10% (abomasal and small intestinal content, abomasal soak) or 20% aliquots (large intestinal content). All nematodes were speciated, or assigned to species based on location of recovery (adult females, fourth-stage larvae) for a total count per species. Efficacy was calculated as the % reduction in the mean number of worms in each test group compared with the mean number of worms recovered from the control group. In this screen, a significant reduction in nematode infection was achieved with compounds of formula (I), especially from table 1, 2 and 3. Compound numbers 1.012 and 1.013 provided at least 90% reduction in nematode infection at a dose of 30 mg/kg.

In addition, compound numbers 1.064, 1.094, 2.048, 3.005, 3.006, 3.009, 3.011, 3.012 and 3.024 provided >90% efficacy against one or more species of the nematodes tested, at doses as low as 1 or 3 mg/kg. For example, compound 3.009 provided >95% efficacy against *Trichostrongylus* at a dose of 3 mg/kg and compound numbers 1.064, 1.094, 2.048, 3.006 and 3.012 provided >95% efficacy against *Haemonchus, Ostertagia*, and *Trichostrongylus* at a dose of 3 mg/kg, and compound numbers 3.005 and 3.011 were more than 95% effective against these parasites at doses as low as 1 mg/kg.

Method F: Screening Method to Test Activity of Compounds Against Microfilaria of *Dirofilaria immitis*.

Four hundred to six hundred microfilaria of *Dirofilaria immitis* were added to wells of a microtitre plate containing buffer and the test compound in DMSO. The microtitre plate was then held at 37° C. in an environment containing 5% $CO_2$. An assessment was conducted at 24 hours to determine survival of the microfilaria. Microfilaria exposed to DMSO and no test compound served as controls. Compounds numbers 1.003, 1.012, 1.013, 1.064, 1.086, 1.087, 1.090, 1.094, 2.043, 2.046, 2.047, 2.048, 2.049, 3.005, 3.006, 3.009, 3.011, 3.012, 3.017, 3.019 and 3.023 gave at least 90% motility inhibition at a test concentration of 50 ppm.

Method G: Evaluation of Anthelmintic Efficacy Against Induced Infections of Adult Nematodes in Cats Cats were inoculated on three consecutive days with an aliquot of infective eggs of *Toxocara cati* (days −63, −62, −61) and *Ancylostoma tubaeforme* (days −28, −27, −26) from one bulk solution each. The inoculation schedule was designed such that nematodes were adult on day 0. The approximate number of infective eggs/larvae given was recorded. Fecal samples were collected between day −7 and day −1 and examined to confirm the presence of infections, and are reported as eggs/gram of feces. Each formulation was orally administered once on day 0. On day 8, the cats were humanely euthanized. The stomach, cecum, small and large intestines were removed and the total content was retained for parasite recovery. Parasites were collected and identified. Efficacy was determined for each nematode species by calculating the percent efficacy as 100[(C−T)/C], where C is the mean count among untreated controls and T is the count of the treated animals. Compound 3.024 demonstrated >94% efficacy in companion animals against *Toxocara cati* and *Ancylostoma tubaeforme* at doses as low as 1 mg/kg.

Method H: Screening Method to Test Activity of Compounds Against *Haemonchus placei, Ostertagia ostertagi, Trichostrongylus axei, Cooperia punctata, Bunostomum phlebotomum, Oesophagostomum radiatum, Dictyocaulus viviparus*, and *Nematodirus helvetianus* In Vivo in Cattle.

Calves were challenged intra-aurally with larvae from Bunostomum phlebotomum (500-1000 L3 per animal) on Dat −56; and orally with larvae from *Oesophagostomum radiatum* (1,000-2,000 infective L3 per animal) on Dat −49, *Nematodirus helvetianus* (3,000-6,000 infective L3 per animal) on Dat −28, *Haemonchus placei* (5,000-7,000 infective L3 per animal) on Dat −28, *Dictyocaulus viviparus* (1,000-2,000 infective L3 per animal) on Dat −28, *Ostertagia ostertagi* (10,000-20,000 infective L3 per animal) on Dat −21, *Trichostrongylus axei* (10,000-20,000 infective L3 per animal) on Dat −21, *Cooperia punctata* (10,000-20,000 infective L3 per animal) on Dat −28, and *Cooperia oncophora* (10,000-20,000 infective L3 per animal) on Dat −21. The test compound was administered alone at a dose of 3 or 6 mg/kg orally or subcutaneously or subcutaneously at a dose of 6 mg/kg in combination with ivermectin at a dose of 50 mcg/kg. For oral administration, test compounds were formulated at a concentration of 10 mg/mL in DMSO/Corn oil (1:1). For subcutaneous administration, test compounds were formulated in propylene glycol/glycerol formal (60:40). All treatments were administered at Day 0. At necropsy on Day 14/15, the abomasa, small intestine and large intestine were removed and processed for parasite recovery. Nematode counts were conducted on appropriate aliquots. Efficacy was calculated for each nematode species by calculating the percent efficacy as 100[(C−T)/C], where C is the mean count among untreated controls and T is the count of the treated animals. Compound number 3.024 provided >95% efficacy against *Haemonchus placei, Ostertagia ostertagi, Trichostrongylus axei, Cooperia punctata, Oesophagostomum radiatum* and *Nematodirus helvetianus* at a dose as low as 3 mg/kg administered orally. Compound number 3.024 administered subcutaneously provided >95% efficacy against all nematode species tested at a dose of 6 mg/kg in combination with ivermectin at a dose of 50 mcg/kg.

Method I: Screening Method to Test Activity of Compounds Against Ivermectin-Resistant *Haemonchus contortus, Ostertagia circumcincta*, and *Trichostrongylus colubriformis* In Vivo in Sheep.

Sheep were challenged orally with infective $3^{rd}$ stage larvae (L3) of *Ostertagia circumcincta* (~3,000-6,000 infective L3 per animal) on Dat −28, *Haemonchus contortus* (~2,000-4,000 infective L3 per animal) on Dat −25, and *Trichostrongylus colubriformis* (~3,000-6,000 infective L3 per species per animal) on Dat −23. The inoculation schedule was designed so that nematodes were expected to be in the adult stage on Day 0. Test compounds were dissolved in a mixture of DMSO/Corn oil (1:1) at a concentration of 10 mg/mL. All treatments were administered orally once on Day 0. At sacrifice on Day 14 the abomasum, small intestine and large intestine (including cecum) were removed. Nematode counts were conducted on 10% (abomasal and small intestinal content, abomasal soak) or 20% aliquots (large intestinal content). All nematodes were speciated, or assigned to species based on location of recovery (adult females, fourth-stage larvae) for a total count per species. Efficacy was calculated as the % reduction in the mean number of worms in each test group compared with the mean number of worms recovered from the control group. In this screen, compound 3.024 provided >95% efficacy against all species of the nematodes tested, at doses as low as 1.5 mg/kg.

FIG. 2 shows the % efficacy of compound 3.024 against *Haemonchus contortus, Ostertagia circumcincta*, and *Trichostrongylus colubriformis* at 1.5 mg/kg and 3 mg/kg administered orally to sheep compared with ivermectin at a dosage of 0.2 mg/kg. Thus, it is clear from the study that the compounds of the invention are surprisingly effective against ivermectin-resistant endoparasites in sheep.

The invention is further described by the following numbered paragraphs:

1. An aryloazol-2-yl-cyanoethylamine compound of formula (I) that is substantially enriched in an enantiomer, or a salt thereof:

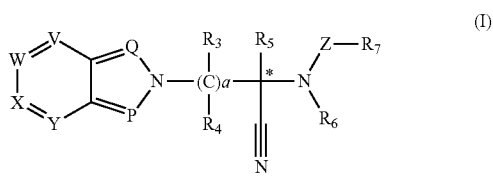

P is C—$R_1$ or N;
Q is C—$R_2$ or N;
V is C—$R_8$ or N;
W is C—$R_9$ or N;
X is C—$R_{10}$ or N;
Y is C—$R_{11}$ or N;

$R_1$, $R_2$, $R_8$, $R_9$, $R_{10}$ and $R_{11}$ are independently of one another hydrogen, amino, amido, cyano, nitro, halogen, alkyl, alkenyl, alkynyl, cycloalkyl, hydroxyalkyl, haloalkyl, alkylthio, haloalkylthio, arylthio, alkoxy, phenoxy, alkoxyalkoxy, cycloalkyloxy, haloalkoxy, alkylcarbonyl, haloalkylcarbonyl, alkoxycarbonyl, haloalkoxycarbonyl, alkylsulfinyl, haloalkylsulfinyl, $SF_5$, alkylsulfonyl, haloalkylsulfonyl, alkylamino, di(alkyl)amino, alkylcarbonylamino, alkylaminoalkoxy, dialkylaminoalkoxy, alkylaminoalkyl, dialkylaminoalkyl, aminoalkyl, formyl, —C(O)OH, unsubstituted or substituted aryl, unsubstituted or substituted arylthio, unsubstituted or substituted aryloxy, or unsubstituted or substituted heteroaryl, wherein the substituents, independent of one another, may be one or more of cyano, nitro, halogen, alkyl, haloalkyl, alkylthio, haloalkylthio, arylthio, alkoxy, haloalkoxy, alkylcarbonyl, haloalkylcarbonyl, alkoxycarbonyl, haloalkoxycarbonyl, alkylsulfinyl, haloalkylsulfinyl, alkylsulfonyl, haloalkylsulfonyl, $SF_5$ or methylthioamino;

$R_3$, $R_4$ and $R_5$ are independently of one another hydrogen, halogen, alkyl, hydroxyalkyl, alkylthioalkyl, haloalkyl, alkyloxyalkyl, alkylsulfinylalkyl, alkylsulfonylalkyl, alkylsulfonyloxyalkyl; unsubstituted or substituted cycloalkyl, wherein the substituents may each be independently halogen and alkyl; unsubstituted or substituted aryl, unsubstituted or substituted heteroaryl, wherein the substituents may each be independent of one another cyano, nitro, halogen, alkyl, haloalkyl, alkylthio, haloalkylthio, arylthio, alkoxy, haloalkoxy, alkylcarbonyl, haloalkylcarbonyl, alkoxycarbonyl, haloalkoxycarbonyl, alkylsulfinyl, haloalkylsulfinyl, alkylsulfonyl, haloalkylsulfonyl, $SF_5$, alkylamino, or di(alkyl)amino; or $R_4$ and $R_5$ together with the carbon to which they are attached form a cycloalkyl ring;

$R_6$ is hydrogen, alkyl, alkoxyalkyl, alkylcarbonyl, haloalkylcarbonyl, alkoxycarbonyl, haloalkoxycarbonyl, alkylthiocarbonyl or unsubstituted or substituted benzyl, wherein the substituents may each be independent of one another cyano, nitro, halogen, alkyl, haloalkyl, alkylthio, haloalkylthio, arylthio, alkoxy, haloalkoxy, alkylcarbonyl, haloalkylcarbonyl, alkoxycarbonyl, haloalkoxycarbonyl, alkylsulfinyl, haloalkylsulfinyl, alkylsulfonyl, haloalkylsulfonyl, SF5, alkylamino, or di(alkyl)amino;

$R_7$ is hydrogen, alkyl, cylcoalkyl, haloalkyl, alkoxyalkyl, alkylcarbonyl, haloalkylcarbonyl, alkoxycarbonyl, haloalkoxycarbonyl, alkylthiocarbonyl, heterocyclyl; unsubstituted or substituted aryl, wherein the substituents may each be independent of one another cyano, nitro, halogen, alkyl, cycloalkyl, haloalkyl, unsubstituted or substituted aryl, unsubstituted or substituted aryloxy, unsubstituted or substituted heteroaryl, unsubstituted or substituted arylthio, alkylthio, haloalkylthio, alkoxy, cycloalkyloxy, haloalkoxy, alkylcarbonyl, haloalkylcarbonyl, alkoxycarbonyl, haloalkoxycarbonyl, alkylsulfinyl, haloalkylsulfinyl, alkylsulfonyl, haloalkylsulfonyl, amino, alkylamino, di(alkyl)amino, $SF_5$, methylthioamino; or unsubstituted or substituted heteroaryl, wherein the substituents may each be independent of one another cyano, nitro, halogen, alkyl, cycloalkyl, haloalkyl, unsubstituted or substituted aryl, unsubstituted or substituted aryloxy, unsubstituted or substituted heteroaryl, unsubstituted or substituted arylthio, alkylthio, haloalkylthio, alkoxy, cycloalkyloxy, haloalkoxy, alkylcarbonyl, haloalkylcarbonyl, alkoxycarbonyl, haloalkoxycarbonyl, alkylsulfinyl, haloalkylsulfinyl, alkylsulfonyl, haloalkylsulfonyl, amino, alkylamino, di(alkyl)amino, $SF_5$, methylthioamino;

Z is a direct bond, C(O), C(S) or $S(O)_p$;
a is 1, 2 or 3; and
p is 0, 1 or 2.

2. The compound of paragraph 1, wherein:
$R_5$ is hydrogen, alkyl, or haloalkyl; and
$R_7$ is unsubstituted or substituted phenyl.

3. The compound of paragraph 1, wherein:
$R_3$ and $R_4$ are hydrogen;
$R_5$ is hydrogen, $C_1$-$C_6$-alkyl or halo-$C_1$-$C_6$-alkyl;
$R_6$ is hydrogen, $C_1$-$C_6$-alkyl, unsubstituted or substituted benzyl, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, or halo-$C_1$-$C_6$-alkylsulfonyl;
$R_7$ is unsubstituted or substituted phenyl, wherein the substituents may each be independently cyano, nitro, halogen, $C_1$-$C_6$-alkyl, $C_3$-$C_7$-cycloalkyl, halo-$C_1$-$C_6$-alkyl, $C_1$-$C_6$-alkylthio, halo-$C_1$-$C_6$-arylthio, $C_1$-$C_6$-alkoxy, $C_3$-$C_7$-cycloalkyloxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, amino, $C_1$-$C_6$-alkylamino, di($C_1$-$C_6$-alkyl)amino or $SF_5$; or unsubstituted or substituted heteroaryl, wherein the substituents may each be independently cyano, nitro, halogen, $C_1$-$C_6$-alkyl, $C_3$-$C_7$-cycloalkyl, halo-$C_1$-$C_6$-alkyl, $C_1$-$C_6$-alkylthio, halo-$C_1$-$C_6$-alkylthio, arylthio, $C_1$-$C_6$-alkoxy, $C_3$-$C_7$-cycloalkyloxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, amino, $C_1$-$C_6$-alkylamino, di($C_1$-$C_6$-alkyl)amino, or $SF_5$;
Z is C(O); and
a is 1.

4. The aryloazol-2-yl-cyanoethylamine of paragraph 1, wherein
P is N;
Q is C—$R_2$ or N;
V is C—$R_8$;
W is C—$R_9$;
X is C—$R_{10}$;
Y is C—$R_{11}$;
$R_2$, $R_8$, $R_9$, $R_{10}$ and $R_{11}$ are, independently of one another, hydrogen, amino, amido, cyano, nitro, halogen, $C_1$-$C_6$-alkyl, $C_2$-$C_6$-alkenyl, $C_2$-$C_6$-akynyl, $C_3$-$C_7$-cycloalkyl, hydroxy-$C_1$-$C_6$-alkyl, halo-$C_1$-$C_6$-alkyl, $C_1$-$C_6$-alkylthio, halo-$C_1$-$C_6$-alkylthio, $C_1$-$C_6$-alkoxy, $C_3$-$C_7$-cycloalkyloxy, phenoxy, $C_1$-$C_6$-alkoxy-$C_1$-$C_6$-alkoxy, $C_3$-$C_7$-cycloalkyloxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $C_1$-$C_6$-alkylamino, di($C_1$-$C_6$-alkyl)amino, $C_1$-$C_6$-alkylcarboxylamino, $C_1$-$C_6$-alkylamino-$C_1$-$C_6$-alkoxy, di-$C_1$-$C_6$-alkylamino-$C_1$-$C_6$-alkoxy, $C_1$-$C_6$-alkylamino $C_1$-$C_6$-alkyl, di-$C_1$-$C_6$-alkylamino $C_1$-$C_6$-alkyl, amino-$C_1$-$C_6$-alkyl, formyl, —C(O)OH; unsubstituted or substituted aryl, unsubstituted or substituted arylthio, unsubstituted or substituted heteroaryl, or unsubstituted or substituted aryloxy, whereby the substituents may each be independent of one another and are selected from the group consisting of cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl;
$R_3$ and, $R_4$ are each independently H, $C_1$-$C_6$-alkyl, or halo-$C_1$-$C_6$-alkyl;

$R_5$ is hydrogen, $C_1$-$C_6$-alkyl or halo-$C_1$-$C_6$-alkyl;

$R_6$ is hydrogen, $C_1$-$C_6$-alkyl, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, or halo-$C_1$-$C_6$-alkylsulfonyl;

$R_7$ is unsubstituted or substituted phenyl, wherein the substituents may each be independently cyano, nitro, halogen, $C_1$-$C_6$-alkyl, $C_3$-$C_7$-cycloalkyl, halo-$C_1$-$C_6$-alkyl, $C_1$-$C_6$-alkylthio, halo-$C_1$-$C_6$-arylthio, $C_1$-$C_6$-alkoxy, $C_3$-$C_7$-cycloalkyl, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $C_1$-$C_6$-alkylamino, di($C_1$-$C_6$-alkyl)amino or $SF_5$; or unsubstituted or substituted heteroaryl, wherein the substituents may each be independently cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, amino, $C_1$-$C_6$-alkylamino, di($C_1$-$C_6$-alkyl)amino, or $SF_5$;

Z is C(O); and a is 1; and salts thereof.

5. The aryloazol-2-yl-cyanoethylamine of paragraph 1, wherein

P is N;

Q is C—$R_2$ or N;

V is N;

W is C—$R_9$;

X is C—$R_{10}$;

Y is C—$R_{11}$;

$R_2$, $R_9$, $R_{10}$ and $R_{11}$ are, independently of one another, hydrogen, amino, amido, cyano, nitro, halogen, $C_1$-$C_6$-alkyl, $C_2$-$C_6$-alkenyl, $C_2$-$C_6$-akynyl, $C_3$-$C_7$-cycloalkyl, hydroxy-$C_1$-$C_6$-alkyl, halo-$C_1$-$C_6$-alkyl, $C_1$-$C_6$-alkylthio, halo-$C_1$-$C_6$-alkylthio, $C_1$-$C_6$-alkoxy, $C_3$-$C_7$-cycloalkyloxy, phenoxy, $C_1$-$C_6$-alkoxy-$C_1$-$C_6$-alkoxy, $C_3$-$C_7$-cycloalkyloxy, halo-$C_1$-$C_6$-alkoxy, $C_1$-$C_6$-alkylcarbonyl, halo-$C_1$-$C_6$-alkylcarbonyl, alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $C_1$-$C_6$-alkylamino, di($C_1$-$C_6$-alkyl)amino, $C_1$-$C_6$-alkylcarboxylamino, $C_1$-$C_6$-alkylamino-$C_1$-$C_6$-alkoxy, di-$C_1$-$C_6$-alkylamino-$C_1$-$C_6$-alkoxy, $C_1$-$C_6$-alkylamino $C_1$-$C_6$-alkyl, di-$C_1$-$C_6$-alkylamino $C_1$-$C_6$-alkyl, amino-$C_1$-$C_6$-alkyl, formyl, —C(O)OH; unsubstituted or substituted aryl, unsubstituted or substituted arylthio, unsubstituted or substituted heteroaryl, or unsubstituted or substituted aryloxy, whereby the substituents may each be independent of one another and are selected from the group consisting of cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl;

$R_3$, $R_4$ are each independently H, $C_1$-$C_6$-alkyl, or halo-$C_1$-$C_6$-alkyl;

$R_5$ is hydrogen, $C_1$-$C_6$-alkyl or halo-$C_1$-$C_6$-alkyl;

$R_6$ is hydrogen, $C_1$-$C_6$-alkyl, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, or halo-$C_1$-$C_6$-alkylsulfonyl;

$R_7$ is unsubstituted or substituted phenyl, wherein the substituents may each be independently cyano, nitro, halogen, $C_1$-$C_6$-alkyl, $C_3$-$C_7$-cycloalkyl, halo-$C_1$-$C_6$-alkyl, $C_1$-$C_6$-alkylthio, halo-$C_1$-$C_6$-arylthio, $C_1$-$C_6$-alkoxy, $C_3$-$C_7$-cycloalkyl, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $C_1$-$C_6$-alkylamino, di($C_1$-$C_6$-alkyl)amino or $SF_5$; or unsubstituted or substituted heteroaryl, wherein the substituents may each be independently cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, amino, $C_1$-$C_6$-alkylamino, di($C_1$-$C_6$-alkyl)amino, or $SF_5$;

Z is C(O); and a is 1.

6. The compound of paragraph 1, wherein

P is N;

Q is C—$R_2$ or N;

V is C—$R_8$;

W is C—$R_8$;

X is N;

Y is C—$R_{11}$;

$R_2$, $R_8$, $R_9$, and $R_{11}$ are, independently of one another, hydrogen, amino, amido, cyano, nitro, halogen, $C_1$-$C_6$-alkyl, $C_2$-$C_6$-alkenyl, $C_2$-$C_6$-akynyl, $C_3$-$C_7$-cycloalkyl, hydroxy-$C_1$-$C_6$-alkyl, halo-$C_1$-$C_6$-alkyl, $C_1$-$C_6$-alkylthio, halo-$C_1$-$C_6$-alkylthio, $C_1$-$C_6$-alkoxy, $C_3$-$C_7$-cycloalkyloxy, phenoxy, $C_1$-$C_6$-alkoxy-$C_1$-$C_6$-alkoxy, $C_3$-$C_7$-cycloalkyloxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $C_1$-$C_6$-alkylamino, di($C_1$-$C_6$-alkyl)amino, $C_1$-$C_6$-alkylcarboxylamino, $C_1$-$C_6$-alkylamino-$C_1$-$C_6$-alkoxy, di-$C_1$-$C_6$-alkylamino-$C_1$-$C_6$-alkoxy, $C_1$-$C_6$-alkylamino $C_1$-$C_6$-alkyl, di-$C_1$-$C_6$-alkylamino $C_1$-$C_6$-alkyl, amino-$C_1$-$C_6$-alkyl, formyl, —C(O)OH; unsubstituted or substituted aryl, unsubstituted or substituted arylthio, unsubstituted or substituted heteroaryl, or unsubstituted or substituted aryloxy, whereby the substituents may each be independent of one another and are selected from the group consisting of cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl;

$R_3$, $R_4$ are each independently H, $C_1$-$C_6$-alkyl, or halo-$C_1$-$C_6$-alkyl;

$R_5$ is hydrogen, $C_1$-$C_6$-alkyl or halo-$C_1$-$C_6$-alkyl;

$R_6$ is hydrogen, $C_1$-$C_6$-alkyl, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, or halo-$C_1$-$C_6$-alkylsulfonyl;

$R_7$ is unsubstituted or substituted phenyl, wherein the substituents may each be independently cyano, nitro, halogen, $C_1$-$C_6$-alkyl, $C_3$-$C_7$-cycloalkyl, halo-$C_1$-$C_6$-alkyl, $C_1$-$C_6$-alkylthio, halo-$C_1$-$C_6$-arylthio, $C_1$-$C_6$-alkoxy, $C_3$-$C_7$-cycloalkyl, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, $C_1$-$C_6$-alkylamino, di($C_1$-$C_6$-alkyl)amino or $SF_5$; or unsubstituted or substituted heteroaryl, wherein the substituents may each be independently cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, amino, $C_1$-$C_6$-alkylamino, di($C_1$-$C_6$-alkyl)amino, or $SF_5$;
Z is C(O); and
a is 1.

7. The aryloazol-2-yl-cyanoethylamine of paragraph 1, wherein
P is N;
Q is C—$R_2$ or N;
V is C—$R_8$;
W is C—$R_8$;
X is C—$R_{10}$;
Y is N;
$R_2$, $R_8$, $R_9$, and $R_{10}$ are, independently of one another, hydrogen, amino, amido, cyano, nitro, halogen, $C_1$-$C_6$-alkyl, $C_2$-$C_6$-alkenyl, $C_2$-$C_6$-akynyl, $C_3$-$C_7$-cycloalkyl, hydroxy-$C_1$-$C_6$-alkyl, halo-$C_1$-$C_6$-alkyl, $C_1$-$C_6$-alkylthio, halo-$C_1$-$C_6$-alkylthio, $C_1$-$C_6$-alkoxy, $C_3$-$C_7$-cycloalkyloxy, phenoxy, $C_1$-$C_6$-alkoxy-$C_1$-$C_6$-alkoxy, $C_3$-$C_7$-cycloalkyloxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $C_1$-$C_6$-alkylamino, di($C_1$-$C_6$-alkyl)amino, $C_1$-$C_6$-alkylcarboxyamino, $C_1$-$C_6$-alkylamino-$C_1$-$C_6$-alkoxy, di-$C_1$-$C_6$-alkylamino-$C_1$-$C_6$-alkoxy, $C_1$-$C_6$-alkylamino $C_1$-$C_6$-alkyl, di-$C_1$-$C_6$-alkylamino $C_1$-$C_6$-alkyl, amino-$C_1$-$C_6$-alkyl, formyl, —C(O)OH; unsubstituted or substituted aryl, unsubstituted or substituted arylthio, unsubstituted or substituted heteroaryl, or unsubstituted or substituted aryloxy, whereby the substituents may each be independent of one another and are selected from the group consisting of cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl;
$R_3$, $R_4$ are each independently H, $C_1$-$C_6$-alkyl, or halo-$C_1$-$C_6$-alkyl;
$R_5$ is hydrogen, $C_1$-$C_6$-alkyl or halo-$C_1$-$C_6$-alkyl;
$R_6$ is hydrogen, $C_1$-$C_6$-alkyl, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, or halo-$C_1$-$C_6$-alkylsulfonyl;
$R_7$ is unsubstituted or substituted phenyl, wherein the substituents may each be independently cyano, nitro, halogen, $C_1$-$C_6$-alkyl, $C_3$-$C_7$-cycloalkyl, halo-$C_1$-$C_6$-alkyl, $C_1$-$C_6$-alkylthio, halo-$C_1$-$C_6$-arylthio, $C_1$-$C_6$-alkoxy, $C_3$-$C_7$-cycloalkyl, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $C_1$-$C_6$-alkylamino, di($C_1$-$C_6$-alkyl)amino or $SF_5$; or unsubstituted or substituted heteroaryl, wherein the substituents may each be independently cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, amino, $C_1$-$C_6$-alkylamino, di($C_1$-$C_6$-alkyl)amino, or $SF_5$;
Z is C(O); and
a is 1.

8. The aryloazol-2-yl-cyanoethylamine of paragraph 1, wherein
P is N;
Q is C—$R_2$ or N;
V is N;
W is C—$R_9$;
X is C—$R_{10}$;
Y is C—$R_{11}$;
$R_2$ is hydrogen, Cl, Br, methoxy;
$R_3$, $R_4$ and $R_6$ are hydrogen;
$R_5$ is methyl;
$R_7$ is phenyl substituted by one or more of cyano, halogen, $SF_5$, $OCF_3$ or $SCF_3$;
$R_9$, $R_{10}$ and $R_{11}$ are, independently of one another, hydrogen, Cl, Br, I or methyl;
Z is C(O); and
a is 1.

9. The aryloazol-2-yl-cyanoethylamine of paragraph 1, wherein
P and Q are N;
V is N or C—$R_8$;
W is C—$R_8$;
X is C—$R_{10}$;
Y is C—$R_{11}$;
$R_2$ is hydrogen, Cl, Br, methoxy;
$R_3$, $R_4$ and $R_6$ are hydrogen;
$R_5$ is methyl;
$R_7$ is phenyl substituted by one or more of cyano, halogen, $SF_5$, $OCF_3$ or $SCF_3$;
$R_8$, $R_9$, $R_{10}$ and $R_{11}$ are, independently of one another, hydrogen, Cl, Br, I or methyl;
Z is C(O); and
a is 1.

10. The aryloazol-2-yl-cyanoethylamine of paragraph 8, wherein:
Q is C—$R_2$;
$R_2$ is hydrogen or methoxy;
$R_3$, $R_4$ and $R_6$ are hydrogen;
$R_5$ is methyl;
$R_7$ is phenyl substituted by one or more of cyano, $OCF_3$ or $SCF_3$,
$R_9$, $R_{10}$ and $R_{11}$ are, independently of one another, hydrogen, Cl, Br, I or methyl;
Z is C(O); and
a is 1.

11. The arylozaol-2-yl-cyanoethylamine of paragraph 1, wherein the arylozaol-2-yl-cyanoethylamine is:
(+)-N-[1-Cyano-1-methyl-2-(4,5,7-trichloro-2H-benzotriazol-2-yl)-ethyl]-4-trifluoromethoxybenzamide, or (−)-N-[1-cyano-1-methyl-2-(4,5,7-trichloro-2H-benzotriazol-2-yl)-ethyl]-4-trifluoromethoxybenzamide 12. The arylozaol-2-yl-cyanoethylamine of paragraph 1, wherein the arylozaol-2-yl-cyanoethylamine is:
(+)-N-[2-(6-Bromo-2H-pyrazolo[4,3-b]pyridin-2-yl)-1-cyano-1-methylethyl]-4-trifluoromethoxybenzamide, or (−)-N-[2-(6-bromo-2H-pyrazolo[4,3-b]pyridin-2-yl)-1-cyano-1-methylethyl]-4-trifluoromethoxybenzamide.

13. An aryloazol-2-yl-cyanoethylamino pentafluorothiobenzamide derivatives of formula (IH):

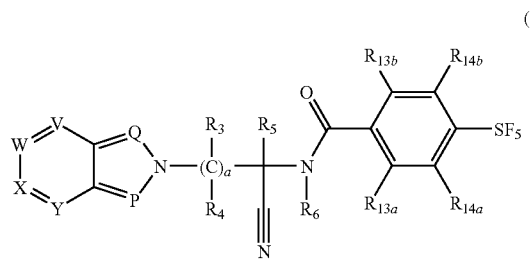

Wherein:
P is C—$R_1$ or N;
Q is C—$R_2$ or N;
V is C—$R_8$ or N;
W is C—$R_9$ or N;
X is C—$R_{10}$ or N;
Y is C—$R_{11}$ or N;
$R_1$, $R_2$, $R_5$, $R_9$, $R_{10}$ and $R_{11}$ are independently of one another hydrogen, amino, amido, cyano, nitro, halogen, alkyl, alkenyl, alkynyl, cycloalkyl, hydroxyalkyl, haloalkyl, alkylthio, haloalkylthio, arylthio, alkoxy, phenoxy, alkoxyalkoxy, cycloalkyloxy, haloalkoxy, alkylcarbonyl, haloalkylcarbonyl, alkoxycarbonyl, haloalkoxycarbonyl, alkylsulfinyl, haloalkylsulfinyl, $SF_5$, alkylsulfonyl, haloalkylsulfonyl, alkylamino, di(alkyl)amino, alkylcarbonylamino, alkylaminoalkoxy, dialkylaminoalkoxy, alkylaminoalkyl, dialkylaminoalkyl, aminoalkyl, formyl, —C(O)OH, unsubstituted or substituted aryl, unsubstituted or substituted arylthio, unsubstituted or substituted aryloxy, or unsubstituted or substituted heteroaryl, wherein the substituents, independent of one another, may be one or more of cyano, nitro, halogen, alkyl, haloalkyl, alkylthio, haloalkylthio, arylthio, alkoxy, haloalkoxy, alkylcarbonyl, haloalkylcarbonyl, alkoxycarbonyl, haloalkoxycarbonyl, alkylsulfinyl, haloalkylsulfinyl, alkylsulfonyl, haloalkylsulfonyl, $SF_5$ or methylthioamino;

$R_3$, $R_4$ and $R_5$ are independently of one another hydrogen, halogen, alkyl, hydroxyalkyl, alkylthioalkyl, haloalkyl, alkyloxyalkyl, alkylsulfinylalkyl, alkylsulfonylalkyl, alkylsulfonyloxyalkyl; unsubstituted or substituted cycloalkyl, wherein the substituents may each be independently halogen and alkyl; unsubstituted or substituted aryl, unsubstituted or substituted heteroaryl, wherein the substituents may each be independent of one another cyano, nitro, halogen, alkyl, haloalkyl, alkylthio, haloalkylthio, arylthio, alkoxy, haloalkoxy, alkylcarbonyl, haloalkylcarbonyl, alkoxycarbonyl, haloalkoxycarbonyl, alkylsulfinyl, haloalkylsulfinyl, alkylsulfonyl, haloalkylsulfonyl, $SF_5$, alkylamino, or di(alkyl)amino; or $R_4$ and $R_5$ together with the carbon to which they are attached form a cycloalkyl ring;

$R_6$ is hydrogen, alkyl, alkoxyalkyl, alkylcarbonyl, haloalkylcarbonyl, alkoxycarbonyl, haloalkoxycarbonyl, alkylthiocarbonyl or unsubstituted or substituted benzyl, wherein the substituents may each be independent of one another cyano, nitro, halogen, alkyl, haloalkyl, alkylthio, haloalkylthio, arylthio, alkoxy, haloalkoxy, alkylcarbonyl, haloalkylcarbonyl, alkoxycarbonyl, haloalkoxycarbonyl, alkylsulfinyl, haloalkylsulfinyl, alkylsulfonyl, haloalkylsulfonyl, SF5, alkylamino, or di(alkyl)amino; a is 1, 2 or 3;

$R_{13a}$, $R_{13b}$, $R_{14a}$ and $R_{14b}$ are each independently of one another cyano, nitro, halogen, alkyl, cycloalkyl, haloalkyl, unsubstituted or substituted aryl, unsubstituted or substituted heteroaryl, unsubstituted or substituted phenoxy, alkylthio, haloalkylthio, arylthio, alkoxy, cycloalkyloxy, haloalkoxy, alkylcarbonyl, haloalkylcarbonyl, alkoxycarbonyl, haloalkoxycarbonyl, alkylsulfinyl, haloalkylsulfinyl, alkylsulfonyl, haloalkylsulfonyl, $SF_5$, alkylamino, di(alkyl)amino, or methylthioamino; and
a is 1, 2 or 3.

14. The compound of paragraph 13, wherein P is N and Q is N or C—$R_2$.

15. The compound of paragraph 13, wherein P is N, Q is N or C—$R_2$, and V is N.

16. The compound of paragraph 13, wherein P is N, Q is N or C—$R_2$, and X is N.

17. The compound of paragraph 13, wherein P is N, Q is N or C—$R_2$, and Y is N.

18. The compound of paragraph 13, wherein:
P is N;
Q is N or C—$R_2$;
$R_3$ and $R_4$ are hydrogen;
$R_5$ is hydrogen, $C_1$-$C_3$-alkyl, or halo-$C_1$-$C_3$-alkyl;
$R_6$ is hydrogen, $C_1$-$C_6$-alkyl, $C_1$-$C_6$-alkylcarbonyl, halo-$C_1$-$C_6$-alkylcarbonyl, $C_1$-$C_6$-alkoxycarbonyl, halo-$C_1$-$C_6$-alkoxycarbonyl, $C_1$-$C_6$-alkylsulfinyl, halo-$C_1$-$C_6$-alkylsulfinyl, $C_1$-$C_6$-alkylsulfonyl, or halo-$C_1$-$C_6$-alkylsulfonyl; and
a is 1.

19. The compound of paragraph 13, wherein:
P is N;
Q is N or C—$R_2$;
$R_3$, $R_4$, $R_6$ are hydrogen;
$R_5$ is methyl; and
a is 1.

20. The compound of paragraph 13, wherein the compound is enriched in an enantiomer.

21. A paraciticidal composition comprising a compound of paragraph 1 or paragraph 13 and a pharmaceutically acceptable carrier.

22. The composition of paragraph 21 which further comprises one or more additional active agents.

23. The composition of paragraph 21, wherein the additional active agent is an avermectin or milbemycin.

24. The composition of paragraph 23, wherein the avermectin or milbemycin is abamectin, dimadectin, doramectin, emamectin, eprinomectin, ivermectin, latidectin, lepimectin, selamectin, milbemectin, milbemycin D, moxidectin, nemadectin, a 5-oxo avermectin or milbemycin derivative, a 5-oxime avermectins or milbemycin derivative, or a combination thereof.

25. A method for treating or preventing parasitic infection or infestation in an animal comprising administering an effective amount of the compound of paragraph 1 or paragraph 13 to the animal in need thereof.

26. The method of paragraph 25, wherein the parasite is *Anaplocephala, Ancylostoma, Anecator, Ascaris, Brugia, Bunostomum, Capillaria, Chabertia, Cooperia, Cyathostomum, Cylicocyclus, Cylicodontophorus, Cylicostephanus, Craterostomum, Dictyocaulus, Dipetalonema, Dipylidium, Dirofilaria, Dracunculus, Echinococcus, Enterobius, Fasciola, Filaroides, Habronema, Haemonchus, Metastrongylus, Moniezia, Necator, Nematodirus, Nippostrongylus, Oesophagostumum, Onchocerca, Ostertagia, Oxyuris, Paracaris, Schistosoma, Strongylus, Taenia, Toxocara, Strongyloides, Toxascaris, Trichinella, Trichuris, Trichostrongylus, Triodontophorous, Uncinaria, Wuchereria*, or combinations thereof.

27. The method of paragraph 25, wherein the parasite is *Haemonchus contortus, Ostertagia circumcincta, Tricho-* strongylus axei, Trichostrongylus colubriformis, Cooperia curticei, Nematodirus battus or combinations thereof.

28. The method of paragraph 25, wherein the parasites are fleas, ticks, mites, mosquitoes, flies, fly larvae, lice, or combinations thereof.

29. The method of paragraph 25, wherein the parasites are fleas or ticks.

30. The method of paragraph 25, wherein the compound is administered in combination with an effective amount of an avermectin or milbemycin compound.

31. The method of paragraph 30, wherein the avermectin or milbemycin compound is abamectin, dimadectin, doramectin, emamectin, eprinomectin, ivermectin, latidectin, lepimectin, selamectin, milbemectin, milbemycin D, moxidectin, nemadectin, a 5-oxo avermectin or milbemycin derivative, a 5-oxime avermectins or milbemycin derivative, or a combination thereof.

32. The compound of formula (I) wherein the compound is (+)-N-[2-(6-Bromo-2H-pyrazolo[4,3-b]pyridin-2-yl)-1-cyano-1-methylethyl]-4-trifluoromethoxybenzamide.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. An aryloazol-2-yl-cyanoethylamine compound of formula (I) that is enriched in an enantiomer that is significantly more active in vitro and in vivo compared with the other enantiomer, wherein the weight:weight ratio is at least 1.5 or higher in favor of the enantiomer that is significantly more active in vitro and in vivo, or a salt thereof:

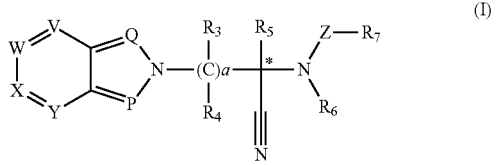

P is N;
Q is C—$R_2$ or N;
V is N;
W is C—$R_9$;
X is C—$R_{10}$;
Y is C—$R_{11}$;
$R_2$ is hydrogen;
$R_9$, $R_{10}$ and $R_{11}$ are independently of one another hydrogen, halogen, $C_1$-$C_6$-alkyl or halo-$C_1$-$C_6$-alkyl;
$R_3$ and $R_4$ are hydrogen;
$R_5$ is $C_1$-$C_6$-alkyl;
$R_6$ is hydrogen or $C_1$-$C_6$-alkyl;
$R_7$ is unsubstituted or substituted phenyl, wherein the substituents may each be independent of one another alkylthio, haloalkylthio, alkoxy, or haloalkoxy;
Z is C(O); and
a is 1.

2. The compound of claim 1, wherein:
$R_5$ is methyl.

3. The compound of claim 1, wherein:
$R_5$ is methyl; and
$R_6$ is hydrogen.

4. The aryloazol-2-yl-cyanoethylamine of claim 1, wherein
Q is C—$R_2$;
$R_5$ is methyl;
$R_6$ is hydrogen;
$R_7$ is substituted phenyl, wherein the substituents may each be independently halo-$C_1$-$C_6$-alkylthio or halo-$C_1$-$C_6$-alkoxy.

5. The aryloazol-2-yl-cyanoethylamine of claim 1, wherein
$R_5$ is methyl;
$R_7$ is phenyl substituted by one or more of $OCF_3$ or $SCF_3$; and
$R_9$, $R_{10}$ and $R_{11}$ are, independently of one another, hydrogen, Cl, Br, I or methyl.

6. The aryloazol-2-yl-cyanoethylamine of claim 1, wherein
Q is N;
$R_6$ is hydrogen;
$R_5$ is methyl;
$R_7$ is phenyl substituted by one or more of $OCF_3$ or $SCF_3$; and
$R_9$, $R_{10}$ and $R_{11}$ are, independently of one another, hydrogen, Cl, Br, I or methyl.

7. The aryloazol-2-yl-cyanoethylamine of claim 5, wherein:
Q is C—$R_2$;
$R_6$ is hydrogen;
$R_5$ is methyl;
$R_7$ is phenyl substituted by one or more of $OCF_3$ or $SCF_3$; and
$R_9$, $R_{10}$ and $R_{11}$ are, independently of one another, hydrogen, Cl, Br, I or methyl.

8. The arylozaol-2-yl-cyanoethylamine of claim 1, wherein the arylozaol-2-yl -cyanoethylamine is:
(+)-N-[2-(6-Bromo-2H-pyrazolo[4,3-b]pyridin-2-yl)-1-cyano-1-methylethyl]-4-trifluoromethoxybenzamide, or (−)-N-[2-(6-bromo-2H-pyrazolo[4,3-b]pyridin-2-yl)-1-cyano-1-methylethyl]-4-trifluoromethoxybenzamide.

9. An aryloazol-2-yl-cyanoethylamino pentafluorothiobenzamide derivatives of formula (IH):

(IH)

Wherein:
P is C—$R_1$ or N;
Q is C—$R_2$ or N;
V is N;
W is C—$R_9$;
X is C—$R_{10}$;
Y is C—$R_{11}$;
$R_1$, $R_2$ $R_9$, $R_{10}$ and $R_{11}$ are independently of one another hydrogen, amino, amido, cyano, nitro, halogen, alkyl, alkenyl, alkynyl, cycloalkyl, hydroxyalkyl, haloalkyl, alkylthio, haloalkylthio, arylthio, alkoxy, phenoxy, alkoxyalkoxy, cycloalkyloxy, haloalkoxy, alkylcarbonyl, haloalkylcarbonyl, alkoxycarbonyl, haloalkoxycarbonyl, alkylsulfinyl, haloalkylsulfinyl, SF$_5$, alkylsulfonyl, haloalkylsulfonyl, alkylamino, di(alkyl)amino, alkylcarbonylamino, alkylaminoalkoxy, dialkylaminoalkoxy, alkylaminoalkyl, dialkylaminoalkyl, aminoalkyl, formyl, —C(O)OH, unsubstituted or substituted aryl, unsubstituted or substituted arylthio, unsubstituted or substituted aryloxy, or unsubstituted or substituted heteroaryl, wherein the substituents, independent of one another, may be one or more of cyano, nitro, halogen, alkyl, haloalkyl, alkylthio, haloalkylthio, arylthio, alkoxy, haloalkoxy, alkylcarbonyl, haloalkylcarbonyl, alkoxycarbonyl, haloalkoxycarbonyl, alkylsulfinyl, haloalkylsulfinyl, alkylsulfonyl, haloalkylsulfonyl, SF$_5$ or methylthioamino;

R$_3$, R$_4$ and R$_5$ are independently of one another hydrogen, halogen, alkyl, hydroxyalkyl, alkylthioalkyl, haloalkyl, alkyloxyalkyl, alkylsulfinylalkyl, alkylsulfonylalkyl, alkylsulfonyloxyalkyl; unsubstituted or substituted cycloalkyl, wherein the substituents may each be independently halogen and alkyl; unsubstituted or substituted aryl, unsubstituted or substituted heteroaryl, wherein the substituents may each be independent of one another cyano, nitro, halogen, alkyl, haloalkyl, alkylthio, haloalkylthio, arylthio, alkoxy, haloalkoxy, alkylcarbonyl, haloalkylcarbonyl, alkoxycarbonyl, haloalkoxycarbonyl, alkylsulfinyl, haloalkylsulfinyl, alkylsulfonyl, haloalkylsulfonyl, SF$_5$, alkylamino, or di(alkyl)amino; or R$_4$ and R$_5$ together with the carbon to which they are attached form a cycloalkyl ring;

R$_6$ is hydrogen, alkyl, alkoxyalkyl, alkylcarbonyl, haloalkylcarbonyl, alkoxycarbonyl, haloalkoxycarbonyl, alkylthiocarbonyl or unsubstituted or substituted benzyl, wherein the substituents may each be independent of one another cyano, nitro, halogen, alkyl, haloalkyl, alkylthio, haloalkylthio, arylthio, alkoxy, haloalkoxy, alkylcarbonyl, haloalkylcarbonyl, alkoxycarbonyl, haloalkoxycarbonyl, alkylsulfinyl, haloalkylsulfinyl, alkylsulfonyl, haloalkylsulfonyl, SF$_5$, alkylamino, or di(alkyl)amino;

R$_{13a}$, R$_{13b}$, R$_{14a}$ and R$_{14b}$ are each independently of one another cyano, nitro, halogen, alkyl, cycloalkyl, haloalkyl, unsubstituted or substituted aryl, unsubstituted or substituted heteroaryl, unsubstituted or substituted phenoxy, alkylthio, haloalkylthio, arylthio, alkoxy, cycloalkyloxy, haloalkoxy, alkylcarbonyl, haloalkylcarbonyl, alkoxycarbonyl, haloalkoxycarbonyl, alkylsulfinyl, haloalkylsulfinyl, alkylsulfonyl, haloalkylsulfonyl, SF$_5$, alkylamino, di(alkyl)amino, or methylthioamino; and a is 1, 2 or 3.

10. The compound of claim 9, wherein P is N and Q is N or C—R$_2$.

11. The compound of claim 9, wherein P is N, Q is N or C—R$_2$, and R$_3$ and R$_4$ are hydrogen.

12. The compound of claim 9, wherein P is N, Q is N or C—R$_2$, R$_3$ and R$_4$ are hydrogen;
R$_5$ is alkyl or haloalkyl; and
R$_6$ is H or alkyl.

13. The compound of claim 9, wherein P is N, Q is N or C—R$_2$;
R$_3$, R$_4$ and R$_6$ are hydrogen; and
R$_5$ is C$_1$-C$_3$-alkyl.

14. The compound of claim 9, wherein:
P is N;
Q is N or C—R$_2$;
R$_3$ and R$_4$ are hydrogen;
R$_5$ is hydrogen, C$_1$-C$_3$-alkyl, or halo- C$_1$-C$_3$-alkyl;
R$_6$ is hydrogen, C$_1$-C$_6$-alkyl, C$_1$-C$_6$-alkylcarbonyl, halo-C$_1$-C$_6$-alkylcarbonyl, C$_1$-C$_6$-alkoxycarbonyl or halo-C$_1$-C$_6$-alkoxycarbonyl; and
a is 1.

15. The compound of claim 9, wherein:
P is N;
Q is N or C—R$_2$;
R$_3$, R$_4$, R$_6$ are hydrogen;
R$_5$ is methyl; and
a is 1.

16. The compound of claim 9, wherein the compound is enriched in an enantiomer.

17. A parasiticidal composition comprising an effective amount of a compound of claim 1 or claim 9 and a pharmaceutically acceptable carrier.

18. The composition of claim 17 which further comprises one or more additional active agents.

19. The composition of claim 17, wherein the additional active agent is an avermectin or milbemycin.

20. The composition of claim 19, wherein the avermectin or milbemycin is abamectin, dimadectin, doramectin, emamectin, eprinomectin, ivermectin, latidectin, lepimectin, selamectin, milbemectin, milbemycin D, moxidectin, nemadectin, a 5-oxo avermectin or milbemycin derivative, a 5-oxime avermectin or milbemycin derivative, or a combination thereof.

21. A method for treating a parasitic infection or infestation in an animal comprising administering an effective amount of the compound of claim 1 or claim 9 to the animal in need thereof.

22. The method of claim 21, wherein the parasite is *Anaplocephala, Ancylostoma, Anecator, Ascaris, Brugia, Bunostomum, Capillaria, Chabertia, Cooperia, Cyathostomum, Cylicocyclus, Cylicodontophorus, Cylicostephanus, Craterostomum, Dictyocaulus, Dipetalonema, Dipylidium, Dirofilaria, Dracunculus, Echinococcus, Enterobius, Fasciola, Filaroides, Habronema, Haemonchus, Metastrongylus, Moniezia, Necator, Nematodirus, Nippostrongylus, Oesophagostumum, Onchocerca, Ostertagia, Oxyuris, Paracaris, Schistosoma, Strongylus, Taenia, Toxocara, Strongyloides, Toxascaris, Trichinella, Trichuris, Trichostrongylus, Triodontophorous, Uncinaria* or *Wuchereria*, or combinations thereof.

23. The method of claim 21, wherein the parasite is *Haemonchus contortus, Ostertagia circumcincta, Trichostrongylus axei, Trichostrongylus colubriformis, Cooperia curticet* or *Nematodirus battus*, or combinations thereof.

24. The method of claim 21, wherein the parasites are fleas, ticks, mites, mosquitoes, flies, fly larvae or lice, or combinations thereof.

25. The method of claim 21, wherein the parasites are fleas or ticks.

26. The method of claim 21, wherein the compound is administered in combination with an effective amount of an avermectin or milbemycin compound.

27. The method of claim 26, wherein the avermectin or milbemycin compound is abamectin, dimadectin, doramectin, emamectin, eprinomectin, ivermectin, latidectin, lepimectin, selamectin, milbemectin, milbemycin D, moxidectin, nemadectin, a 5-oxo avermectin or milbemycin derivative, a 5-oxime avermectins or milbemycin derivative, or a combination thereof.

28. The compound of formula (I) of claim 1 wherein the compound is (+)-N-[2-(6-Bromo-2H-pyrazolo[4,3-b]pyridin-2-yl)-1-cyano-1-methylethyl]-4-trifluoromethoxybenzamide.

29. The composition of claim 17, wherein the composition is a pour-on, spot-on, oral drench or injectable composition.

30. The composition of claim 29, wherein the composition is a pour-on or oral drench composition.

* * * * *